US012479833B2

(12) United States Patent
Flynn et al.

(10) Patent No.: US 12,479,833 B2
(45) Date of Patent: Nov. 25, 2025

(54) HETEROARYLAMINOPYRIMIDINE AMIDE AUTOPHAGY INHIBITORS AND METHODS OF USE THEREOF

(71) Applicant: Deciphera Pharmaceuticals, LLC, Waltham, MA (US)

(72) Inventors: Daniel L. Flynn, Waltham, MA (US); Yu Mi Ahn, Waltham, MA (US); Timothy Caldwell, Lawrence, KS (US); Lakshminarayana Vogeti, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 567 days.

(21) Appl. No.: 17/832,224

(22) Filed: Jun. 3, 2022

(65) Prior Publication Data

US 2023/0047915 A1 Feb. 16, 2023

Related U.S. Application Data

(63) Continuation of application No. 16/870,418, filed on May 8, 2020, now Pat. No. 11,518,758.

(60) Provisional application No. 62/911,733, filed on Oct. 7, 2019, provisional application No. 62/911,736, filed on Oct. 7, 2019, provisional application No. 62/846,264, filed on May 10, 2019, provisional application No. 62/846,260, filed on May 10, 2019.

(51) Int. Cl.

| | |
|---|---|
| ***C07D 403/14*** | (2006.01) |
| ***A61K 31/519*** | (2006.01) |
| ***A61K 45/06*** | (2006.01) |
| ***A61P 35/04*** | (2006.01) |
| ***C07D 401/14*** | (2006.01) |
| ***C07D 405/14*** | (2006.01) |
| ***C07D 413/14*** | (2006.01) |

(52) U.S. Cl.

CPC ............ *C07D 403/14* (2013.01); *A61P 35/04* (2018.01); *C07D 401/14* (2013.01); *C07D 405/14* (2013.01); *C07D 413/14* (2013.01); *A61K 31/519* (2013.01); *A61K 45/06* (2013.01)

(58) Field of Classification Search

CPC ................ C07D 403/14; C07D 401/14; C07D 401/405; C07D 413/14; A61P 35/04; A61K 31/519; A61K 45/06

See application file for complete search history.

(56) References Cited

U.S. PATENT DOCUMENTS

| | | | |
|---|---|---|---|
| 6,262,088 | B1 | 7/2001 | Phillips |
| 6,492,376 | B2 | 12/2002 | Phillips |
| 6,495,574 | B2 | 12/2002 | Phillips |
| 6,495,684 | B2 | 12/2002 | Phillips |
| 6,552,030 | B2 | 4/2003 | Phillips |
| 6,559,147 | B2 | 5/2003 | Phillips |
| 6,686,367 | B2 | 2/2004 | Phillips |
| 6,773,599 | B1 | 8/2004 | Lowe et al. |
| 6,906,067 | B2 | 6/2005 | Moriarty et al. |
| 7,087,614 | B2 | 8/2006 | Guo et al. |
| 7,122,542 | B2 | 10/2006 | Singh et al. |
| 7,144,911 | B2 | 12/2006 | Flynn et al. |
| 7,166,599 | B2 | 1/2007 | Bornemann et al. |
| 7,173,028 | B2 | 2/2007 | Dahmann et al. |
| 7,202,257 | B2 | 4/2007 | Flynn et al. |
| 7,253,174 | B2 | 8/2007 | Ahmed et al. |
| 7,276,510 | B2 | 10/2007 | Kukla et al. |
| 7,279,576 | B2 | 10/2007 | Flynn et al. |
| 7,342,037 | B2 | 3/2008 | Flynn et al. |
| 7,364,656 | B1 | 4/2008 | Lowe et al. |
| 7,442,705 | B2 | 10/2008 | Guillemont et al. |
| 7,449,465 | B2 | 11/2008 | Freyne et al. |
| 7,452,879 | B2 | 11/2008 | Singh et al. |
| 7,479,495 | B2 | 1/2009 | Moriarty et al. |
| 7,504,410 | B2 | 3/2009 | Bryant et al. |
| 7,531,566 | B2 | 5/2009 | Flynn et al. |
| 7,560,466 | B2 | 7/2009 | Singh et al. |
| 7,582,648 | B2 | 9/2009 | Singh et al. |
| 7,601,836 | B2 | 10/2009 | Pitts et al. |
| 7,666,895 | B2 | 2/2010 | Flynn et al. |
| 7,709,480 | B2 | 5/2010 | Dahmann et al. |
| 7,737,283 | B2 | 6/2010 | Flynn et al. |
| 7,790,756 | B2 | 9/2010 | Flynn et al. |
| 7,858,633 | B2 | 12/2010 | Li et al. |
| 7,868,013 | B2 | 1/2011 | Li et al. |
| 7,884,111 | B2 | 2/2011 | Argade et al. |
| 7,897,762 | B2 | 3/2011 | Flynn et al. |
| 8,044,040 | B2 | 10/2011 | Ahmed et al. |
| 8,143,293 | B2 | 3/2012 | Flynn et al. |
| 8,163,756 | B2 | 4/2012 | Flynn et al. |
| 8,178,671 | B2 | 5/2012 | Singh et al. |
| 8,188,113 | B2 | 5/2012 | Flynn et al. |

(Continued)

FOREIGN PATENT DOCUMENTS

| | | |
|---|---|---|
| CN | 102574816 A | 7/2012 |
| CN | 103159736 A | 6/2013 |

(Continued)

OTHER PUBLICATIONS

U.S. Appl. No. 11/963,740, filed Dec. 21, 2007, Patented, U.S. Pat. No. 8,163,756.
U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented, U.S. Pat. No. 8,188,113.

(Continued)

*Primary Examiner* — Erich A Leeser
(74) *Attorney, Agent, or Firm* — Goodwin Procter LLP

(57) ABSTRACT

Described herein are compounds that are inhibitors of autophagy and their use in the treatment of disorders such as cancers.

30 Claims, No Drawings

Specification includes a Sequence Listing.

(56) References Cited

U.S. PATENT DOCUMENTS

| | | | |
|---|---|---|---|
| 8,193,206 | B2 | 6/2012 | Yen et al. |
| 8,278,331 | B2 | 10/2012 | Flynn et al. |
| 8,338,439 | B2 | 12/2012 | Singh et al. |
| 8,354,407 | B2 | 1/2013 | Djung et al. |
| 8,399,433 | B2 | 3/2013 | Appari et al. |
| 8,410,093 | B2 | 4/2013 | Li et al. |
| 8,410,126 | B2 | 4/2013 | Sapountzis et al. |
| 8,420,630 | B2 | 4/2013 | Dahmann et al. |
| 8,450,335 | B2 | 5/2013 | Singh et al. |
| 8,461,179 | B1 | 6/2013 | Flynn et al. |
| 8,486,951 | B2 | 7/2013 | Flynn et al. |
| 8,519,129 | B2 | 8/2013 | Marsilje, III et al. |
| 8,552,002 | B2 | 10/2013 | Ding et al. |
| 8,569,319 | B2 | 10/2013 | Flynn et al. |
| 8,586,565 | B2 | 11/2013 | Flynn et al. |
| 8,609,679 | B2 | 12/2013 | Singh et al. |
| 8,637,672 | B2 | 1/2014 | Flynn et al. |
| 8,710,222 | B2 | 4/2014 | Singh et al. |
| 8,741,911 | B2 | 6/2014 | Allgeier et al. |
| 8,748,627 | B2 | 6/2014 | Gu et al. |
| 8,791,130 | B2 | 7/2014 | Baker-Glenn et al. |
| 8,809,341 | B2 | 8/2014 | Argade et al. |
| 8,907,095 | B2 | 12/2014 | Xia et al. |
| 8,921,565 | B2 | 12/2014 | Flynn et al. |
| 8,940,756 | B2 | 1/2015 | Flynn et al. |
| 9,012,635 | B2 | 4/2015 | Flynn et al. |
| 9,096,624 | B2 | 8/2015 | Crew et al. |
| 9,133,183 | B2 | 9/2015 | Flynn et al. |
| 9,139,566 | B2 | 9/2015 | Marik et al. |
| 9,145,402 | B2 | 9/2015 | Baker-Glenn et al. |
| 9,181,223 | B2 | 11/2015 | Kaufman et al. |
| 9,187,474 | B2 | 11/2015 | Flynn et al. |
| 9,193,719 | B2 | 11/2015 | Flynn et al. |
| 9,212,181 | B2 | 12/2015 | Singh et al. |
| 9,296,737 | B2 | 3/2016 | Singh et al. |
| 9,309,224 | B2 | 4/2016 | Flynn et al. |
| 9,334,267 | B2 | 5/2016 | Flynn et al. |
| 9,382,228 | B2 | 7/2016 | Flynn et al. |
| 9,387,202 | B2 | 7/2016 | Flynn et al. |
| 9,409,921 | B2 | 8/2016 | Singh et al. |
| 9,457,019 | B2 | 10/2016 | Flynn et al. |
| 9,598,432 | B2 | 3/2017 | Argade et al. |
| 9,725,419 | B2 | 8/2017 | Li et al. |
| 9,751,893 | B2 | 9/2017 | Singh et al. |
| 9,783,504 | B2 | 10/2017 | Gray et al. |
| 9,840,517 | B2 | 12/2017 | Liu et al. |
| 9,987,276 | B2 | 6/2018 | Singh et al. |
| 10,010,548 | B2 | 7/2018 | Singh et al. |
| 10,259,826 | B2 | 4/2019 | Singh et al. |
| 10,273,242 | B2 | 4/2019 | Liu et al. |
| 10,316,002 | B2 | 6/2019 | Gray et al. |
| 10,329,270 | B2 | 6/2019 | Qiu et al. |
| 10,336,734 | B2 | 7/2019 | Mahajan et al. |
| 11,161,826 | B2 | 11/2021 | Dax |
| 11,512,065 | B2 | 11/2022 | Sebhat et al. |
| 11,530,206 | B2 | 12/2022 | Flynn et al. |
| 11,576,986 | B2 | 2/2023 | Salter et al. |
| 11,590,134 | B2 | 2/2023 | Flynn et al. |
| 2003/0171359 | A1 | 9/2003 | Dahmann et al. |
| 2009/0036434 | A1 | 2/2009 | Jones et al. |
| 2009/0312321 | A1 | 12/2009 | Ren et al. |
| 2010/0298557 | A1 | 11/2010 | Yagi et al. |
| 2012/0122840 | A1 | 5/2012 | Kumar et al. |
| 2014/0073634 | A1 | 3/2014 | Jones et al. |
| 2015/0045370 | A1 | 2/2015 | Cohen et al. |
| 2015/0174132 | A1 | 6/2015 | Foley et al. |
| 2018/0290984 | A1 | 10/2018 | Schonbrunn et al. |
| 2019/0091217 | A1 | 3/2019 | Flynn et al. |
| 2019/0117650 | A1 | 4/2019 | Singh et al. |
| 2019/0192512 | A1 | 6/2019 | Singh et al. |
| 2020/0129489 | A1 | 4/2020 | Flynn et al. |
| 2020/0253973 | A1 | 8/2020 | Flynn et al. |
| 2020/0253981 | A1 | 8/2020 | Fisher et al. |
| 2020/0352920 | A1 | 11/2020 | Flynn et al. |
| 2020/0354346 | A1 | 11/2020 | Flynn et al. |
| 2020/0354352 | A1 | 11/2020 | Flynn et al. |
| 2021/0015801 | A1 | 1/2021 | Flynn et al. |
| 2021/0128556 | A1 | 5/2021 | Flynn et al. |

FOREIGN PATENT DOCUMENTS

| | | | | |
|---|---|---|---|---|
| CN | 103242341 A | | 8/2013 | |
| CN | 103781780 A | | 5/2014 | |
| CN | 108239069 A | | 7/2018 | |
| CN | 109535132 A | | 3/2019 | |
| EP | 3075730 A1 | | 10/2016 | |
| JP | 4072615 B2 | | 4/2008 | |
| WO | WO-1999/62882 A1 | | 12/1999 | |
| WO | WO-2003/30909 A1 | | 4/2003 | |
| WO | WO-2003/032997 A1 | | 4/2003 | |
| WO | WO-2004/048343 A1 | | 6/2004 | |
| WO | WO-2006/128129 | | 11/2006 | |
| WO | WO-2009/122180 A1 | | 10/2009 | |
| WO | WO-2010/002655 A2 | | 1/2010 | |
| WO | WO-2010/136559 A1 | | 12/2010 | |
| WO | WO-2011/075515 A1 | | 6/2011 | |
| WO | WO-2011/082285 A1 | | 7/2011 | |
| WO | WO-2012/062783 A1 | | 5/2012 | |
| WO | WO-2012/110773 A1 | | 8/2012 | |
| WO | WO-2013/134252 A1 | | 9/2013 | |
| WO | WO-2013/136070 A1 | | 9/2013 | |
| WO | WO-2014/086102 A1 | | 6/2014 | |
| WO | WO-2014/145025 A2 | | 9/2014 | |
| WO | WO-2015/039613 A1 | | 3/2015 | |
| WO | WO-2015/057963 A1 | | 4/2015 | |
| WO | WO-2015/123722 A1 | | 8/2015 | |
| WO | WO-2016/033100 A1 | | 3/2016 | |
| WO | WO-2016/131789 A1 | | 8/2016 | |
| WO | WO-2017/156493 A1 | | 9/2017 | |
| WO | WO-2018/160774 A1 | | 9/2018 | |
| WO | WO-2019/191189 A1 | | 10/2019 | |
| WO | WO-2019/199864 A1 | | 10/2019 | |
| WO | WO-2020/229974 A1 | | 11/2020 | |
| WO | WO-2020/231496 A1 | | 11/2020 | |
| WO | WO 2020/231808 | * | 11/2020 | ........... C07D 403/12 |
| WO | WO-2020/231808 A1 | | 11/2020 | |
| WO | WO-2021/071837 A1 | | 4/2021 | |
| WO | WO-2021/146258 A1 | | 7/2021 | |
| WO | WO-2023/108110 A2 | | 6/2023 | |

OTHER PUBLICATIONS

U.S. Appl. No. 10/746,460, filed Dec. 24, 2003, Patented, U.S. Pat. No. 7,144,911.

U.S. Appl. No. 10/886,329, filed Jul. 6, 2004, Patented, U.S. Pat. No. 7,202,257.

U.S. Appl. No. 11,450,840, filed Jun. 9, 2006, Patented, U.S. Pat. No. 7,342,037.

U.S. Appl. No. 11/336,708, filed Jan. 20, 20067, Patented, U.S. Pat. No. 7,531,566.

U.S. Appl. No. 11/450,850, filed Jun. 9, 2006, Patented, U.S. Pat. No. 7,666,895.

U.S. Appl. No. 10/746,607, filed Dec. 24, 2003, Patented, U.S. Pat. No. 7,279,576.

U.S. Appl. No. 11/854,293, filed Sep. 12, 2007, Patented, U.S. Pat. No. 7,897,762.

U.S. Appl. No. 12/105,408, filed Apr. 18, 2008, Patented, U.S. Pat. No. 8,143,293.

U.S. Appl. No. 13/590,955, filed Aug. 21, 2012, Patented, U.S. Pat. No. 8,486,951.

U.S. Appl. No. 11/450,849, filed Jun. 9, 2006, Patented, U.S. Pat. No. 7,737,283.

U.S. Appl. No. 13/785,575, filed Mar. 5, 2013, Patented, U.S. Pat. No. 8,741,911.

U.S. Appl. No. 12/608,578, filed Oct. 29, 2009, Patented, U.S. Pat. No. 8,278,331.

U.S. Appl. No. 13/098,247, filed Apr. 29, 2011, Patented, U.S. Pat. No. 8,569,319.

U.S. Appl. No. 13/559,170, filed Jul. 26, 2012, Patented, U.S. Pat. No. 8,637,672.

(56) References Cited

OTHER PUBLICATIONS

U.S. Appl. No. 14/214,134, filed Mar. 14, 2014, Patented, U.S. Pat. No. 9,133,183.
U.S. Appl. No. 14/383,803, filed Mar. 5, 2013, Patented, U.S. Pat. No. 9,187,474.
U.S. Appl. No. 13/491,394, filed Jun. 7, 2012, Patented, U.S. Pat. No. 8,461,179.
U.S. Appl. No. 13/801,753, filed Mar. 13, 2013, Patented, U.S. Pat. No. 8,940,756.
U.S. Appl. No. 16/387,315, filed Apr. 17, 2019, Patented, RE48,731.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,171, filed Mar. 14, 2014, Patented, U.S. Pat. No. 9,181,223.
U.S. Appl. No. 14/214,185, filed Mar. 14, 2014, Patented, U.S. Pat. No. 9,382,228.
U.S. Appl. No. 14/214,179, filed Mar. 14, 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.
U.S. Appl. No. 17/028,591, filed Sep. 22, 2019, Pending, US 2021-0015801 A1.
U.S. Appl. No. 17/506,772, filed Oct. 21, 2021, Pending, US 2022-0031678 A1.
U.S. Appl. No. 17/845,275, filed Jun. 21, 2022, Pending.
U.S. Appl. No. 17/845,278, filed Jun. 21, 2022, Pending.
U.S. Appl. No. 16/943,821, filed Jul. 30, 2020, Pending, US 2021-0145805 A1.
U.S. Appl. No. 16/943,871, filed Jul. 30, 2020, Pending, US 2020-0352920 A1.
U.S. Appl. No. 16/725,282, filed Dec. 23, 2019, Patented, U.S. Pat. No. 11,103,507.
U.S. Appl. No. 17/358,137, filed Jun. 25, 2021, Pending, US 2022-0143018 A1.
U.S. Appl. No. 16/870,384, filed May 8, 2020, Pending, US 2020-0354352 A1.
U.S. Appl. No. 17/833,272, filed Jun. 6, 2022, Pending.
U.S. Appl. No. 16/870,418, filed May 8, 2020, Pending, US 2020-0354346 A1.
U.S. Appl. No. 17/832,224, filed Jun. 3, 2022, Pending.
U.S. Appl. No. 16/902,989, filed Jun. 16, 2020, Pending, US 2021-0128556 A1.
U.S. Appl. No. 16/991,644, filed Aug. 12, 2020, Pending, US 2022-0047573 A1.
U.S. Appl. No. 17/028,640, filed Sep. 22, 2020, Patented, U.S. Pat. No. 10,966,966.
U.S. Appl. No. 17/180,218, filed Feb. 19, 2021, Patented, U.S. Pat. No. 11,266,635.
U.S. Appl. No. 17/583,977, filed Jan. 25, 2022, Pending, US 2022-0142997 A1.
U.S. Appl. No. 17/583,985, filed Jan. 25, 2022, Patented, U.S. Pat. No. 11,344,536.
U.S. Appl. No. 17/727,307, filed Apr. 22, 2022, Pending.
U.S. Appl. No. 17/735,678, filed May 3, 2022, Pending.
U.S. Appl. No. 17/735,682, filed May 3, 2022, Pending.
U.S. Appl. No. 17/735,862, filed May 3, 2022, Pending.
U.S. Appl. No. 17/180,234, filed Feb. 19, 2021, Patented, U.S. Pat. No. 11,185,535.
U.S. Appl. No. 17/504,133, filed Oct. 18, 2021, Pending, US 2022-0031677 A1.
U.S. Appl. No. 17/735,741, filed May 3, 2022, Pending.
U.S. Appl. No. 17/735,784, filed May 3, 2022, Pending.
U.S. Appl. No. 17/180,241 filed Feb. 19, 2021, Patented, U.S. Pat. No. 11,395,818.
U.S. Appl. No. 17/735,820, filed May 3, 2022, Pending.
U.S. Appl. No. 17/193,707, filed Mar. 5, 2021, Pending, US 2021-0275518 A1.
U.S. Appl. No. 17/528,478, filed Nov. 17, 2021, Pending.
International Search Report and Written Opinion for International Application No. PCT/US2020/032087 dated Jul. 2, 2020.
International Search Report and Written Opinion for International Application No. PCT/US2020/032090 dated Jun. 29, 2020.
International Search Report and Written Opinion for International Application No. PCT/US2020/037906 dated Aug. 7, 2020.
Lazarus et al., "Discovery and Structure of a New Inhibitor Scaffold of the Autophagy Initiating Kinase ULK1," Bioorg Med Chem., 2015, 23(17): 5483-5488.
McIver et al., "Synthesis and Structure-Activity Relationships of a Novel Series of Pyrimidines as Potent Inhibitors of TBK1/IKK Kinases," Biorganic & Medicinal Chemistry Letters, 2012, 22: 7169-7173.
U.S. Appl. No. 17/869,108, filed Jul. 20, 2022, Patented, U.S. Pat. No. 11,969,414.
U.S. Appl. No. 17/938,353, filed Oct. 6, 2022, Patented, U.S. Pat. No. 11,779,572.
U.S. Appl. No. 18/073,886, filed Dec. 2, 2022, Pending, US 2023-0382915 A1.
U.S. Appl. No. 18/073,721, filed Dec. 2, 2022, Pending, US 2023-0257352 A1.
U.S. Appl. No. 18/078,271, filed Dec. 9, 2022, Pending, US 2023-0257352 A1.
U.S. Appl. No. 18/078,269, filed Dec. 9, 2022, Pending, US 2023-0357179 A1.
U.S. Appl. No. 18/148,766, filed Dec. 30, 2022, Patented, U.S. Pat. No. 11,896,585.
U.S. Appl. No. 18/091,743, filed Dec. 30, 2022, Patented, U.S. Pat. No. 11,813,251.
U.S. Appl. No. 18/152,993, filed Jan. 11, 2023, Pending, US 2023-0338376 A1.
U.S. Appl. No. 18/178,789, filed Mar. 6, 2023, Patented, U.S. Pat. No. 11,793,795.
U.S. Appl. No. 18/140,942, filed Apr. 28, 2023, Pending, US 2023-0414614 A1.
U.S. Appl. No. 18/314,348, filed May 9, 2023, Patented, U.S. Pat. No. 11,801,237.
U.S. Appl. No. 18/448,333, filed Aug. 11, 2023, Patented, U.S. Pat. No. 11,850,241.
U.S. Appl. No. 18/448,347, filed Aug. 11, 2023, Patented, U.S. Pat. No. 11,844,788.
U.S. Appl. No. 18/448,312, filed Aug. 11, 2023, Patented, U.S. Pat. No. 11,903,933.
U.S. Appl. No. 18/448,309, filed Aug. 11, 2023, Patented, U.S. Pat. No. 11,850,240.
U.S. Appl. No. 18/456,831, filed Aug. 28, 2023, Pending, US 2024-0150368 A1.
U.S. Appl. No. 18/457,825, filed Aug. 29, 2023, Pending, US 2024-0180923 A1.
U.S. Appl. No. 18/463,498, filed Sep. 8, 2023, Pending, US 2024-0197696 A1.
U.S. Appl. No. 18/464,519, filed Sep. 11, 2023, Pending, US 2024-0261270 A1.
U.S. Appl. No. 18/490,197, filed Oct. 19, 2023, Patented, U.S. Pat. No. 11,918,564.
U.S. Appl. No. 18/490,188, filed Oct. 19, 2023, Patented, U.S. Pat. No. 11,911,370.
U.S. Appl. No. 18/500,686, filed Nov. 2, 2023, Patented, U.S. Pat. No. 12,023,326.
U.S. Appl. No. 18/500,792, filed Nov. 2, 2023, Patented, U.S. Pat. No. 12,059,411.
U.S. Appl. No. 18/500,730, filed Nov. 2, 2023, Patented, U.S. Pat. No. 12,023,327.
U.S. Appl. No. 18/500,650, filed Nov. 2, 2023, Patented, U.S. Pat. No. 12,023,325.
U.S. Appl. No. 18/500,549, filed Nov. 2, 2023, Patented, U.S. Pat. No. 12,059,410.

(56) References Cited

OTHER PUBLICATIONS

U.S. Appl. No. 18/505,396, filed Nov. 9, 2023, Pending, US 2024-0122906 A1.
U.S. Appl. No. 18/512,447, filed Nov. 17, 2023, Pending.
U.S. Appl. No. 18/518,110, filed Nov. 2, 2023, Patented, U.S. Pat. No. 12,023,328.
U.S. Appl. No. 18/518,100, filed Nov. 22, 2023, Patented, U.S. Pat. No. 11,969,415.
U.S. Appl. No. 18/518,093, filed Nov. 22, 2023, Patented, U.S. Pat. No. 12,064,422.
U.S. Appl. No. 18/389,888, filed Dec. 20, 2023, Pending, US 2024-0245660 A1.
U.S. Appl. No. 18/408,956, filed Jan. 10, 2024, Pending, US 2024-0376058 A1.
U.S. Appl. No. 18/683,078, filed Feb. 12, 2024, Pending.
U.S. Appl. No. 18/631,891, filed Apr. 10, 2024, Pending.
U.S. Appl. No. 18/750,032, filed Jun. 21, 2024, Pending, US 2024-0342145 A1.
U.S. Appl. No. 18/750,014, filed Jun. 21, 2024, Pending, US 2024-0342144 A1.
U.S. Appl. No. 18/758,007, filed Jun. 28, 2024, Pending, US 2024-0350466 A1.
U.S. Appl. No. 18/770,318, filed Jul. 11, 2024, Pending.
U.S. Appl. No. 18/795,731, filed Aug. 6, 2024, Pending.
U.S. Appl. No. 18/795,683, filed Aug. 6, 2024, Pending.
U.S. Appl. No. 18/795,711, filed Aug. 6, 2024, Pending.
U.S. Appl. No. 18/815,054, finding Aug. 26, 2024, Pending.
"A Phase 1/2 Study of DCC-3116 as Monotherapy and Combination Therapy in Patients With MAPK Pathway Mutant Solid Tumors", May 25, 2022 (May 25, 2022), XP093101834.
"Deciphera Pharmaceuticals, Inc. Expands Pipeline with Potential First-in-Class Autophagy Inhibitor to Treat Mutant RAS Cancers", M2 Pharma, Jun. 10, 2019, XP093101838.
Bogdan, M. et al., "DCC-3116, a first-in-class selective inhibitor of ULK1/2 kinases and autophagy, synergizes with encorafenib and cetuximab in BRAFV600E-mutant colorectal cancer models", The American Association for Cancer Research (AACR) Annual Meeting Orlando, FL, Apr. 14, 2023, XP093101803.
Dhillon, S.,"Ripretinib: First Approval", Drugs, vol. 80, No. 11, Jul. 1, 2020, pp. 1133-1138.
International Search Report and Written Opinion of PCT/US2023/072978 dated Dec. 1, 2023, 11 pages.
International Search Report and Written Opinion of PCT/US2023/073071 dated Nov. 28, 2023, 15 pages.
Tabernero, J. et al., "Encorafenib Plus Cetuximab as a New Standard of Care for Previously Treated BRAF VGOOE1\Ilutant Metastatic Colorectal Cancer: Updated Survival Results and Subgroup Analyses from the BEACON Study", Journal of Clinical Oncology, vol. 39, No. 4, Jan. 1, 2021, pp. 273-285.
Tolcher, A. et al., "Initial monotherapy results of a phase I first-in-human study of ULK1/2 inhibitor DCC-3116 alone and in combination with MAPK pathway inhibition", Paris ESMO Congress, Sep. 10, 2022, XP093101825.

* cited by examiner

HETEROARYLAMINOPYRIMIDINE AMIDE AUTOPHAGY INHIBITORS AND METHODS OF USE THEREOF

CROSS-REFERENCE TO RELATED APPLICATIONS

This application is a continuation of U.S. Ser. No. 16/870,418 filed May 8, 2020, which claims priority to U.S. Ser. No. 62/846,260 filed May 10, 2019, U.S. Ser. No. 62/846,264 filed May 10, 2019, U.S. Ser. No. 62/911,733 filed Oct. 7, 2019, and U.S. Ser. No. 62/911,736 filed Oct. 7, 2019, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 3, 2022, is named DCP_080_SEQ_LIST.txt and is 26.5 KB in size.

BACKGROUND

Autophagy (literally meaning "self eating") is a process that enables cells to recycle cellular organelles, proteins, stored lipids, glucagon, and other materials for the purpose of generating nutrients under periods of stress. These cellular contents are recycled by engulfment in vesicles called autophagosomes. Autophagosomes subsequently merge with lysosomes that degrade the autophagosomal contents for recycling of nutrients to the cell. Tumor cells are prone to activate autophagy, as these cells have a high metabolic demand, experience cellular stress, and frequently are in hypoxic environments with limited blood flow and nutrient supply. Moreover, chemotherapy and targeted therapies have been shown to induce autophagy as a treatment resistance mechanism, and combination of autophagy inhibition (by genetic loss of function mutations in autophagy genes or by pharmacologic means) with chemotherapeutic regimens has been shown to suppress tumor growth and trigger tumor cell apoptosis to a greater extent than single agent chemotherapy.

Mutant Ras proteins drive approximately 30 percent of all human cancers—including 95 percent of pancreatic cancers and 45 percent of colorectal cancers, and treatment of these mutant Ras cancers is currently an area of high unmet medical need. Mutant Ras cancers are highly proliferative and depend on basal levels of autophagy for survival, suggesting that inhibition of autophagy in these "autophagy addicted" cancers is a viable therapeutic approach.

Currently, the most widely used autophagy inhibitors are chloroquine and hydroxychloroquine, which are well-known anti-malarial agents. These anti-malarials have been thought to block autophagy by being sequestered in the lysosomal compartment, raising the pH of these lysomes and thereby inactivating proteases that degrade and recycle nutrients. These anti-malarial agents have multiple mechanisms of action beyond inhibiting lysosomes and are known to induce retinopathies in patients. Hence there is a need for more targeted agents which selectively block autophagy and do not exhibit the toxicities of these anti-malarial agents. ULK1 kinase is the initiating protein of autophagy and is a serine/threonine kinase. The ULK1 kinase complex is activated in response to cellular stress including nutrient deprivation and energy depletion. Nutrient deprivation activates ULK kinase activity through inhibition of mTORC1, and energy depletion activates ULK kinase activity through activation by AMP-activated protein kinase AMPK. Importantly, kinase dead mutants of ULK kinase block initiation of canonical autophagy, suggesting that small molecule inhibitors of ULK kinase activity would be able to block autophagy.

Further mechanistic studies have shown that genetic deletion of ULK1 inhibits autophagy in cancer cells, relieving FOX3A turn-over and upregulation of the pro-apoptotic protein PUMA. In addition to classical activation of canonical autophagy, ULK1 kinase activity has been shown to be required for Bcl-2-L-13 mediated mitophagy (autophagy of damaged mitochondria). ULK1 and ULK2 kinases have also been demonstrated to rewire cancer cell glucose metabolism. ULK inhibitors may also find utility in blocking these noncanonical protumoral activities of ULK.

Autophagy is also upregulated in host cells and tissues in cancer. Autophagy in pancreatic tissue stellate cells was demonstrated to support tumor growth. Pancreatic stellate cells were shown to support pancreatic cancer tumor metabolism through autophagic alanine secretion. Inhibition of host tissue autophagy was demonstrated to lead to a depletion in circulating arginine (a required amino acid for tumor metabolism and growth) through liver-mediated increases in arginase secretion. Activation of ULK1 kinase was also shown to inactivate the STING pathway in immune cells through inhibitory phosphorylation of STING, mediating a negative feedback mechanism for limiting an innate immune cell response mediated by interferons. Thus, not only is autophagy activated in tumor cells (cancer cell autonomous), but also in other cells in the tumor microenvironment or host tissues (cancer call nonautonomous) to support tumor survival and growth.

Mutant Ras cancers are addicted to autophagy. In pancreatic cancer, mutant Ras signals predominantly through the MAPKAP pathway. Mutant Ras activates RAF kinases, which in turn activate MEK kinases, which finally activate ERK kinases: mutant Ras→RAF→MEK→ERK. Despite mutant Ras signaling through the MAPKAP pathway, inhibitors of this pathway have provided no or little clinical benefit in clinical trials when used as single agents. It has been recently reported that inhibition of the MAPKAP pathway induces autophagy as a compensatory survival mechanism. When MEK inhibitors were combined with the autophagy inhibitor hydroxychloroquine, there was synergistic activity leading to regression of a number of mutant Ras or mutant BRAF cancers. Similarly, when ERK inhibitors were combined with the autophagy inhibitor hydroxychloroquine or chloroquine, there was synergistic activity leading to inhibition of mutant Ras pancreatic cancers. It has been demonstrated that genetic depletion of RAF kinases (CRAF and BRAF) led to synergistic anti-tumor activity in mutant Ras cancer cell lines when autophagy was also genetically depleted. In composite, recent publications highlight that dual inhibition of the MAPKAP pathway and the autophagy pathway in mutant Ras cancers is a promising treatment regimen for patients with mutant Ras cancers. It has also been demonstrated that other targeted therapies and chemotherapeutic agents activate tumor autophagy as a resistance mechanism; hence there is rationale for combining such targeted therapeutics or chemotherapeutic agents with inhibitors of autophagy.

Mutations in the gene encoding LRRK2 kinase are causative of Parkinson's disease. LRRK2 point mutations are found in both familial (inherited) as well as sporadic Parkinson's disease patients. The most common mutation of LRRK2 in Parkinson's disease is LRRK2 G2019S. These mutations in LRRK2 are gain-of-function mutations that cause overactivation of LRRK2 signaling. Ongoing autophagy is a process that is used by brain neuronal cells to maintain health and homeostasis. Autophagy is a process by which cells identify, localize, and destroy aged organelles and structural elements within cells, and particularly in the case of proteins known to aggregate in neurons, autophagy eliminates such toxic protein aggregates to maintain neuronal health. LRRK2 activity suppresses autophagy, and the LRRK2 G2019S gain-of-function mutant even more so suppresses autophagy and has been linked to aggressive forms of Parkinson's disease.

Increased LRRK2 kinase activity has also been linked to immunoinflammatory diseases including colitis and Crohn's disease and inflammatory bowel disease. In the gastrointestinal tract, LRRK2 is present in antigen-presenting cells including dendritic cells. LRRK2 activity has been shown to be important in Dectin-1 mediated innate immune responses, including an activation of the NFkB pathway and increased TNF-alpha production in dendritic cells of patients with Crohn's disease.

Inhibitors of LRRK2 are sought for the treatment of neurodegenerative diseases including Parkinson's disease, and also are sought for the treatment of gastrointestinal diseases including Crohn's disease, ulcerative colitis, and inflammatory bowel disease.

There is a need for new targeted therapies which inhibit autophagy and can be used in combination with MAPKAP pathway inhibitors, chemotherapeutic agents, and/or other targeted therapeutics.

SUMMARY

Described herein are compounds that are inhibitors of autophagy, pharmaceutical compositions, and their use as agents in the treatment of disorders such as cancer, processes for their preparation, and pharmaceutical compositions containing them as an active ingredient. Such pharmaceutical compositions may comprise the compound as the sole active agent or in combination with other active agents in the presence of a pharmaceutically acceptable excipient. In an embodiment, the described compounds are inhibitors of ULK kinase activity, including ULK1 and ULK2 activity.

For example, compounds provided herein may be described Formula I

Formula I

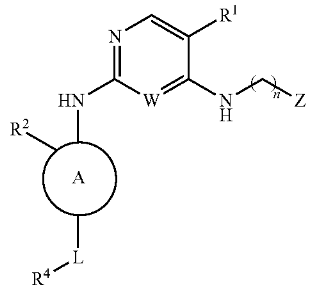

or a pharmaceutically acceptable salt, enantiomer, stereoisomer, or tautomer thereof, wherein: A is 5-membered heteroaryl with at least one ring nitrogen; W is CH or N; $R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine; $R^2$ is selected from the group consisting of H, halogen, cyano, $C_1$-$C_5$ alkyl, $C_3$-$C_6$ cycloalkyl, $C_2$-$C_5$alkenyl, $C_2$-$C_5$ alkynyl, $C_1$-$C_5$ alkoxy, and $C_1$-$C_5$ alkoxy-$C_1$-$C_5$ alkyl, wherein each $C_1$-$C_5$ alkyl, $C_3$-$C_6$ cycloalkyl, $C_2$-$C_5$alkenyl, $C_2$-$C_5$ alkynyl, and $C_1$-$C_5$ alkoxy may be optionally substituted by one, two, or three independent occurrences of fluorine or cyano; $R^4$ is selected from the group consisting of B, D, $NR^6R^9$, $NR^6$—$(C(R^{10})_2)_p$—$NR^6R^9$, C(O)—$NR^6R^9$; C(O)—B; C(O)-D, and CN; B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$; D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$; each occurrence of $R^5$ is independently selected from the group consisting of H, $C_1$-$C_6$ alkyl, $C_3$-$C_6$ cycloalkyl, and heterocyclyl, wherein each $C_1$-$C_6$ alkyl and $C_3$-$C_6$ cycloalkyl may be optionally substituted by one or more independent occurrences of fluorine; each occurrence of $R^7$ is independently selected from the group consisting of H, $C_1$-$C_6$ alkyl, $C_3$-$C_6$ cycloalkyl, cyano, and $(C(R^{10})_2)_h$—$NR^6R^9$, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo; each occurrence of $R^6$ and $R^9$ is independently selected from the group consisting of H, $C_1$-$C_6$ alkyl, $C_3$-$C_6$ cycloalkyl, $C_1$-$C_5$ alkoxy-$C_2$-$C_5$ alkyl, C(=O)$R^5$, $SO_2R^5$, and D, wherein each $C_1$-$C_6$ alkyl and $C_3$-$C_6$ cycloalkyl may be optionally substituted by one or more independent occurrences of fluorine; each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$cycloalkyl may be optionally substituted by one or more independent occurrences of fluorine, or two $R^{10}$ are joined together with the carbon to which they are attached to form a $C_3$-$C_5$ cycloalkyl; Z is selected from the group consisting of a 4-10 membered lactam ring wherein the lactam ring is bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by one or more independent occurrences of $R^{36}$; each occurrence of $R^{36}$ is independently selected from $C_1$-$C_6$ alkyl and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl; L is —$(C(R^{10})_2)_m$—; h is 1, 2, or 3; m is 0, 1, 2, or 3; n is 2, 3, or 4; and p is 2 or 3; provided that: when m is 0, $R^4$ is C-linked to ring A, when m is 1, $R^4$ is C-linked to L, then and when m is 2 or 3, $R^4$ is N-linked or C-linked to L.

DETAILED DESCRIPTION

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The term "alkyl" as used herein refers to a saturated straight or branched hydrocarbon. Exemplary alkyl groups include, but are not limited to, straight or branched hydrocarbons of 1-6, 1-4, 1-3, or 1-2 carbon atoms, referred to herein as $C_1$-$C_6$ alkyl, $C_1$-$C_4$ alkyl, $C_1$-$C_3$ alkyl, and $C_1$-$C_2$ alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_2$-$C_6$alkenyl, and $C_3$-$C_4$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_1$-$C_6$ alkoxy, and $C_2$-$C_6$ alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_1$-$C_6$ alkoxy-$C_1$-$C_6$ alkyl and $C_1$-$C_6$ alkoxy-$C_2$-$C_6$ alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_2$-$C_6$ alkynyl, and $C_3$-$C_6$ alkynyl, respectively. Exemplary alkynyl groups include, but are not limited to, ethynyl, propynyl, butynyl, pentynyl, hexynyl, methylpropynyl, etc.

The term "cyano" as used herein refers to the radical —CN.

The terms "cycloalkyl" or a "carbocyclic group" as used herein refers to a saturated or partially unsaturated hydrocarbon group of, for example, 3-6, or 4-6 carbons, referred to herein as $C_3$-$C_6$ cycloalkyl or $C_4$-$C_6$ cycloalkyl, respectively. Exemplary cycloalkyl groups include, but are not limited to, cyclohexyl, cyclopentyl, cyclopentenyl, cyclobutyl or cyclopropyl.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as C3-6 cycloalkoxy groups. Exemplary cycloalkoxy groups include, but are not limited to, cyclopropoxy, cyclobutoxy, cyclopentoxy, cyclohexyloxy, etc.

The terms "halo" or "halogen" as used herein refer to F, Cl, Br, or I.

The term "heteroaryl" as used herein refers to a monocyclic aromatic 5 or 6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated, 4-10 membered ring structures, including monocyclic, bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

As used herein, the term "lactam" refers to cyclic amides of amino carboxylic acids, having a 1-azacycloalkan-2-one structure, or analogues having unsaturation or heteroatoms replacing one or more carbon atoms of the ring. An "alpha-lactam," refers to a lactam comprised of a 3-membered ring. A "beta-lactam," refers to a lactam comprised of a 4-membered ring. A "gamma-lactam," refers to a lactam comprised of a 5-membered ring. A "delta-lactam," refers to a lactam comprised of a 6-membered ring. An "epsilon-lactam," refers to a lactam comprised of a 7-membered ring.

The term "oxo" as used herein refers to the radical =O.

A "combination therapy" is a treatment that includes the administration of two or more therapeutic agents, e.g., a compound of Formula I and a MAPKAP pathway inhibitor, to a patient in need thereof.

"Disease," "disorder," and "condition" are used interchangeably herein.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

A "MAPKAP pathway inhibitor" is an inhibitor of the MAP kinase signaling pathway. Inhibitors of this pathway include Ras inhibitors (e.g. AMG-510 or MRTX 849), RAF inhibitors (e.g. dabrafenib, vemurafenib, or LY3009120), MEK inhibitors (e.g. trametinib, binimetinib, selumetinib, or cobimetinib), and ERK inhibitors (e.g. ulixertinib SCH772984, or LY3214996). The terms "MAPKAP pathway inhibitor" and "MAPKAP kinase inhibitor are used interchangeably herein.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The presently described compounds encompasses various stereoisomers of these compounds and mixtures thereof. Mixtures of enantiomers or diastereomers may be designated "(±)" in nomenclature, but the skilled artisan will recognize that a structure may denote a chiral center implicitly.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds described herein are administered in therapeutically effective amounts to treat a disorder.

"Treating" includes any effect, e.g., lessening, reducing, modulating, or eliminating, that results in the improvement of the condition, disease, disorder and the like.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atoms replaced with deuterium.

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

COMPOUNDS

Described herein is a compound represented by Formula I:

Formula I

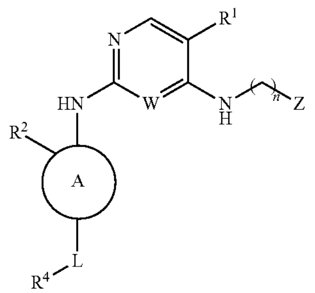

or a pharmaceutically acceptable salt, enantiomer, stereoisomer, or tautomer thereof, wherein: A is 5-membered heteroaryl with at least one ring nitrogen; W is CH or N; $R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine; $R^2$ is selected from the group consisting of H, halogen, cyano, $C_1$-$C_5$ alkyl, $C_3$-$C_6$ cycloalkyl, $C_2$-$C_5$alkenyl, $C_2$-$C_5$ alkynyl, $C_1$-$C_5$ alkoxy, and $C_1$-$C_5$ alkoxy-$C_1$-$C_5$ alkyl, wherein each $C_1$-$C_5$ alkyl, $C_3$-$C_6$ cycloalkyl, $C_2$-$C_5$alkenyl, $C_2$-$C_5$ alkynyl, and $C_1$-$C_5$ alkoxy may be optionally substituted by one, two, or three independent occurrences of fluorine or cyano; $R^4$ is selected from the group consisting of B, D, $NR^6R^9$, $NR^6$—$(C(R^{10})_2)_p$—$NR^6R^9$, C(O)—$NR^6R^9$; C(O)—B; C(O)-D, and CN; B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$; D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$; each occurrence of $R^5$ is independently selected from the group consisting of H, $C_1$-$C_6$ alkyl, $C_3$-$C_6$ cycloalkyl, and heterocyclyl, wherein each $C_1$-$C_6$ alkyl and $C_3$-$C_6$ cycloalkyl may be optionally substituted by one or more independent occurrences of fluorine; each occurrence of $R^7$ is independently selected from the group consisting of H, $C_1$-$C_6$ alkyl, $C_3$-$C_6$ cycloalkyl, cyano, and $(C(R^{10})_2)_h$—$NR^6R^9$, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo; each occurrence of $R^6$ and $R^9$ is independently selected from the group consisting of H, $C_1$-$C_6$ alkyl, $C_3$-$C_6$ cycloalkyl, $C_1$-$C_5$ alkoxy-$C_2$-$C_5$ alkyl, C(═O)$R^5$, $SO_2R^5$, and D, wherein each $C_1$-$C_6$ alkyl and $C_3$-$C_6$ cycloalkyl may be optionally substituted by one or more independent occurrences of fluorine; each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$cycloalkyl may be optionally substituted by one or more independent occurrences of fluorine, or two $R^{10}$ are joined together with the carbon to which they are attached to form a $C_3$-$C_5$ cycloalkyl; Z is selected from the group consisting of a 4-10 membered lactam ring wherein the lactam ring is bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by $R^{36}$; each occurrence of $R^{36}$ is independently selected from $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl; L is —$(C(R^{10})_2)_m$—; m is 0, 1, 2, or 3; n is 2, 3, or 4; p is 2 or 3; and h is 1, 2, or 3; provided that: when m is 0, $R^4$ is C-linked to ring A, when m is 1, $R^4$ is C-linked to L, then and when m is 2 or 3, $R^4$ is N-linked or C-linked to L.

In some embodiments, Z is selected from the group consisting of a 4 membered lactam ring bound through the nitrogen atom or a 6-10 membered lactam ring bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by $R^{36}$.

In some embodiments, Z is selected from the group consisting of a 4-10 membered lactam ring bound through the nitrogen atom, wherein any available carbon atom on a 4-10 membered lactam is optionally substituted by $R^{36}$, and wherein a lactam ring atom may optionally be oxygen or $NR^6$ when the lactam ring is a 6-10 membered ring.

In some embodiments, W is N. In some embodiments, A is selected from the group consisting of pyrazolyl, triazolyl, thiazolyl, and oxazolyl.

In some embodiments,

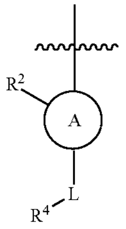

is selected from the group consisting of:

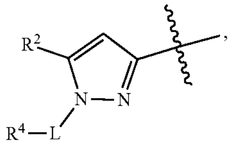

,

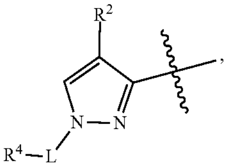

,

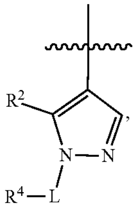

, and

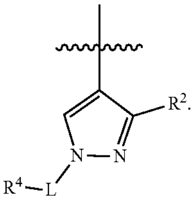

.

In some embodiments,

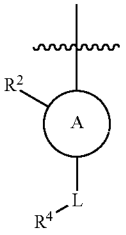

is selected from the group consisting of:

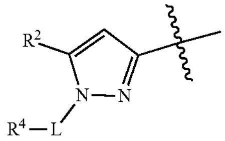

and

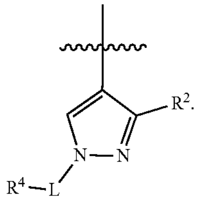

.

In some embodiments,

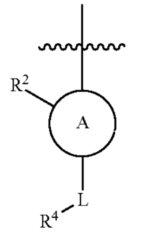

is:

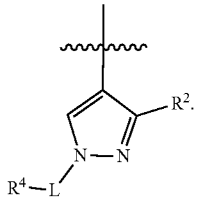

In some embodiments, Z is selected from:

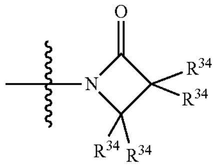

and

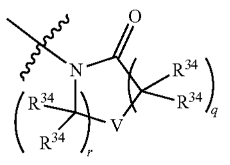

wherein V is selected from the group consisting of oxygen, $C(R^{34})_2$, and $NR^6$, each occurrence of $R^{34}$ is independently selected from H and $R^{36}$, wherein each occurrence of $R^{36}$ is independently selected from $C_1$-$C_6$ alkyl and $C_3$-$C_6$ cycloalkyl and wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl; q is 0, 1, 2, or 3; and r is 2 or 4.

In some embodiments, Z is selected from:

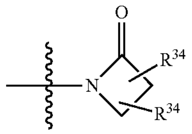

and

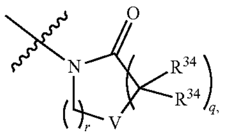

wherein V is selected from the group consisting of oxygen, $C(R^{34})_2$, and $NR^6$; each occurrence of $R^{34}$ is independently selected from H and $R^{36}$, wherein each occurrence of $R^{36}$ is independently selected from $C_1$-$C_6$ alkyl and $C_3$-$C_6$ cycloalkyl and wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl; q is 0, 1, 2, or 3; and r is 2 or 3.

In some embodiments, Z is selected from the group consisting of:

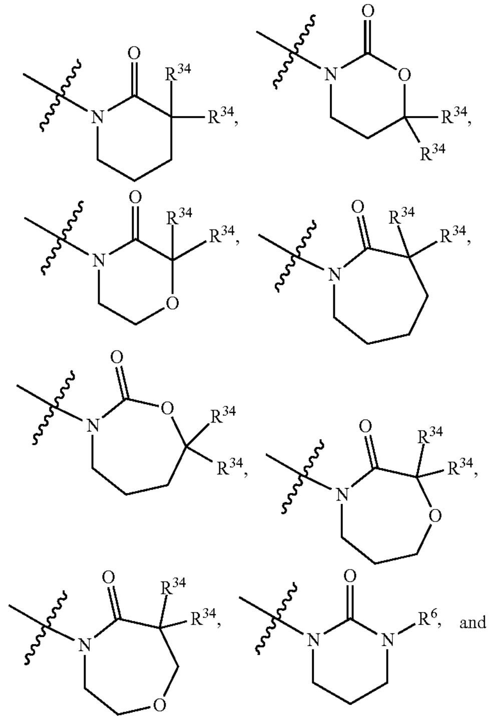

and

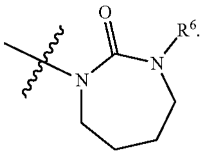

In some embodiments, Z is selected from:

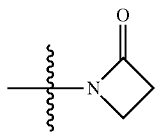

and

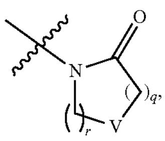

wherein V is selected from the group consisting of oxygen, $CH_2$, and $NR^6$; q is 0, 1, 2, or 3; and r is 2 or 3.

In some embodiments, Z is selected from the group consisting of:

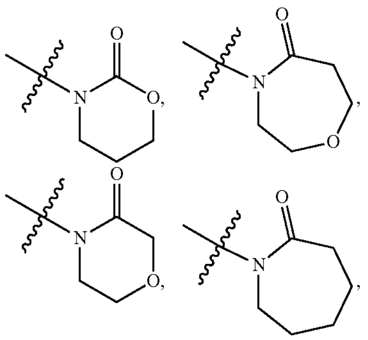

-continued
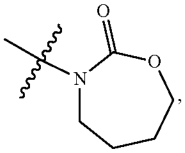,
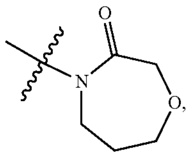,
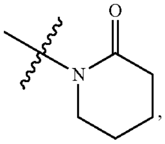,
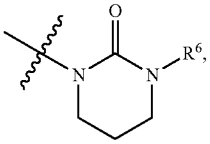, and
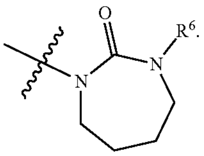.
In some embodiments, $R^4$ is D.
In some embodiments, $R^4$ is selected from the group consisting of:
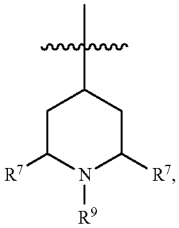,
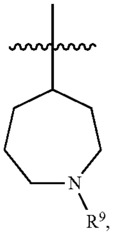,
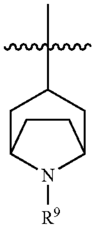,
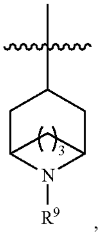,
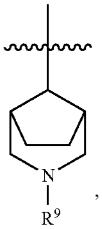,
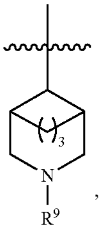,
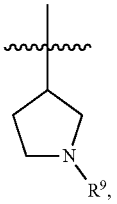,
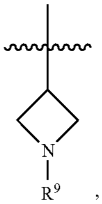,
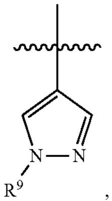,
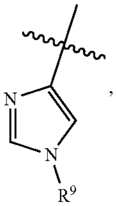,
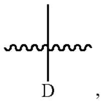,
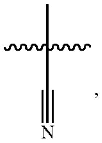, or
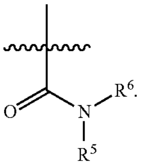.
In some embodiments, $R^4$ is selected from the group consisting of:
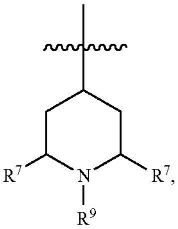,
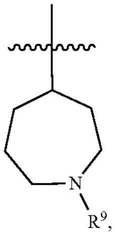,
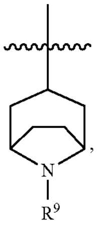,
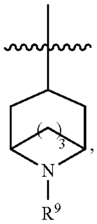,
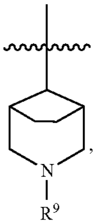,
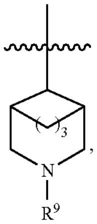,
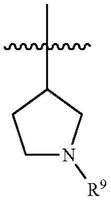 or
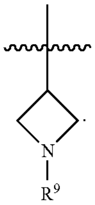.
In some embodiments, $R^4$ is B.
In some embodiments, $R^4$ is selected from the group consisting of:
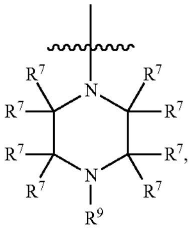,
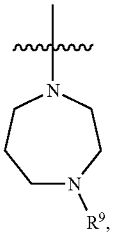,
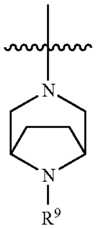,
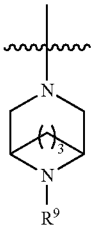,
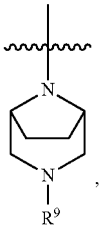,
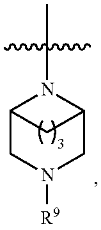,
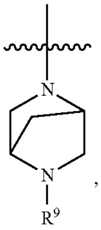,
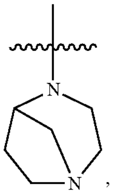, -continued
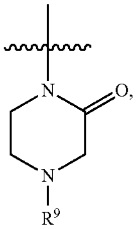, 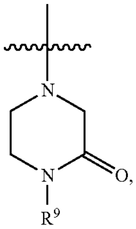, 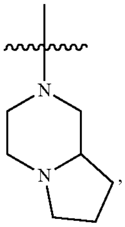, 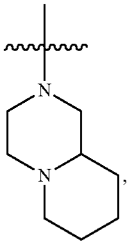,
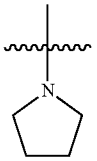, 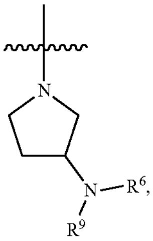, 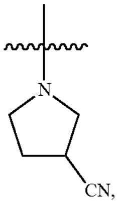, 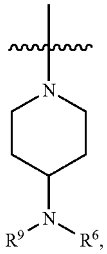,
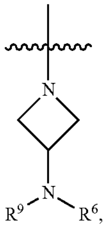, 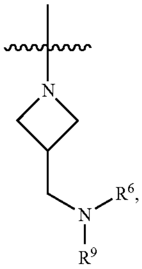, 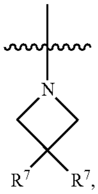, 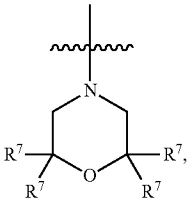,
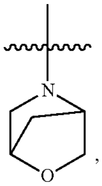, 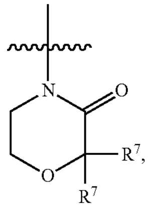, 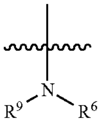 and
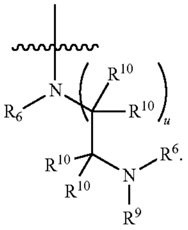.
wherein u is 1 or 2.
In some embodiments, $R^4$ is selected from the group consisting of:
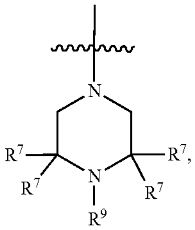, 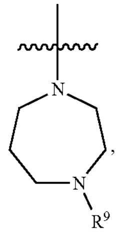, 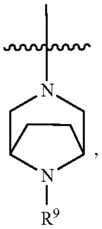,
-continued
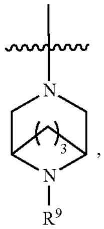, 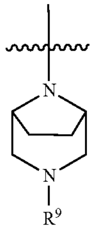, 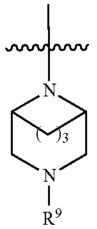, 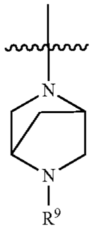,
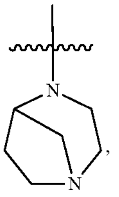, 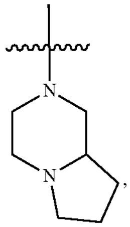, 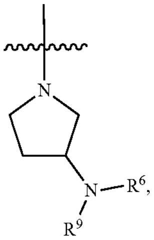,
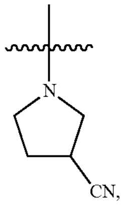, 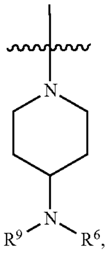,
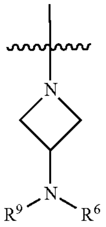 and 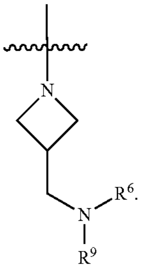.
In some embodiments, $R^4$ is selected from the group consisting of:
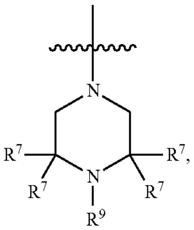, 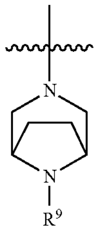, 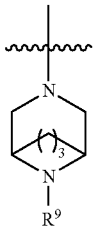, 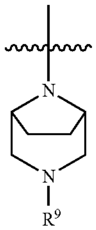,
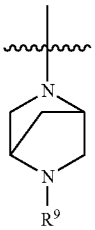 and 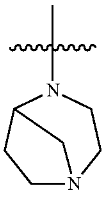.
In some embodiments, m is 0. In some embodiments, m is 1. In some embodiments, m is 2. In some embodiments, m is 3.

In some embodiments, L is a direct bond to the A ring, i.e. where m is 0.

In some embodiments, L is selected from the group consisting of —$CH_2$—, —$CH_2CH_2$—, and —$CH_2CH_2CH_2$—. In some embodiments, L is —$CH_2$—. In some embodiments, L is —$CH_2CH_2$—. In some embodiments, L is —$CH_2CH_2CH_2$—.

In some embodiments, $R^1$ is selected from the group consisting of halogen, $C_1$-$C_5$ alkyl, and $C_3$-$C_5$ cycloalkyl, wherein $C_1$-$C_5$ alkyl or $C_3$-$C_5$ cycloalkyl may be optionally substituted with one, two, or three independent occurrences of fluorine. In some embodiments, $R^1$ is $CF_3$. In some embodiments, $R^1$ is halogen. In some embodiments, $R^1$ is bromo. In some embodiments, $R^1$ is cyclopropyl. In some embodiments, $R^1$ is $CF_2H$.

In some embodiments, $R^2$ is selected from the group consisting of $C_1$-$C_5$ alkyl, H, and $C_3$-$C_4$ cycloalkyl, wherein $C_1$-$C_5$ alkyl or $C_3$-$C_4$ cycloalkyl may be optionally substituted with one, two, or three independent occurrences of fluorine.

In some embodiments, $R^2$ is selected from the group consisting of $C_1$-$C_2$ alkyl and $C_3$-$C_4$ cycloalkyl. In some embodiments, $R^2$ is halogen. In some embodiments, $R^2$ is selected from the group consisting of chloro and bromo. In some embodiments, $R^2$ is bromo. In some embodiments, $R^2$ is chloro.

In some embodiments, n is 3.

In an embodiment, the compound is represented by:

Formula II

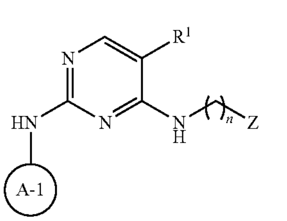

or a pharmaceutically acceptable salt thereof, wherein A-1 is selected from the group consisting of:

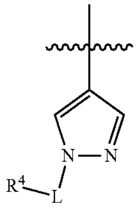
,
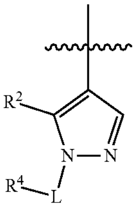
, and
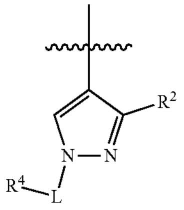

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine; $R^2$ is selected from the group consisting of halogen, $C_1$-$C_2$ alkyl and $C_3$-$C_4$ cycloalkyl, wherein each $C_1$-$C_2$ alkyl and $C_3$-$C_4$ cycloalkyl may be optionally substituted by one, two or three independent occurrences of fluorine; $R^4$ is selected from the group consisting of:

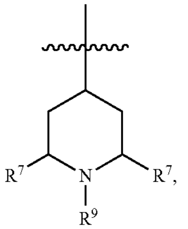
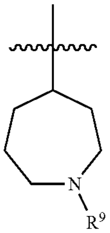
,
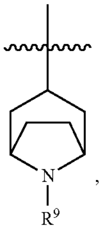
,
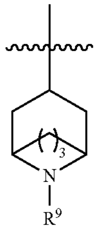
,
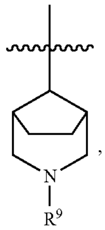
,
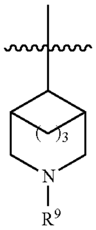
,
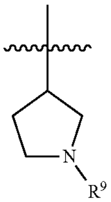
or
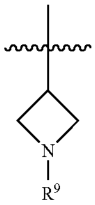
;

each occurrence of $R^7$ is independently selected from the group consisting of H, $C_1$-$C_6$ alkyl, $C_3$-$C_6$ cycloalkyl, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo; each occurrence of $R^6$ and $R^9$ is independently selected from the group consisting of H, $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine; Z is selected from the group consisting of:

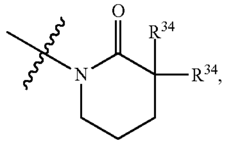
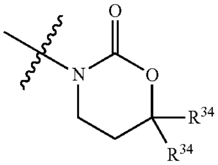
,
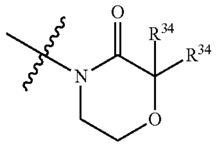
,
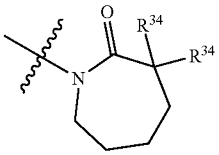
,
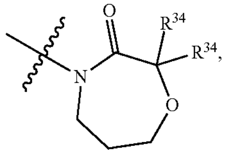
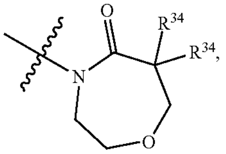
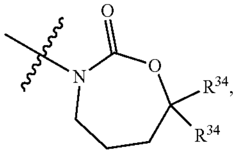
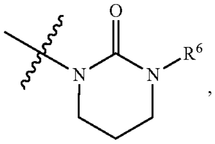
, and
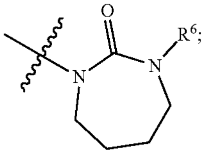

each occurrence of $R^{34}$ is independently selected from H and $R^{36}$, wherein each occurrence of $R^{36}$ is independently selected from $C_1$-$C_6$ alkyl and $C_3$-$C_6$ cycloalkyl and wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl; L is —$(C(R^{10})_2)_m$—; each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl; m is 0, 1, 2, or 3; and n is 2, 3, or 4; provided that: when m is 0, $R^4$ is C-linked to the pyrazole ring, when m is 1, $R^4$ is C-linked to L, then and when m is 2 or 3, $R^4$ is N-linked or C-linked to L.

In some embodiments, A-1 is:

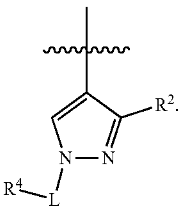

In some embodiments, n is 3.

In some embodiments, m is 0. In some embodiments, m is 1. In some embodiments, m is 2. In some embodiments, m is 3.

In some embodiments, L is a direct bond.

In some embodiments, L is selected from the group consisting of —$CH_2$—, —$CH_2CH_2$—, and —$CH_2CH_2CH_2$—. In some embodiments, L is —$CH_2$—. In some embodiments, L is —$CH_2CH_2$—. In some embodiments, L is —$CH_2CH_2CH_2$—.

In some embodiments, Z is selected from the group consisting of:

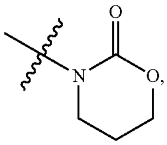, 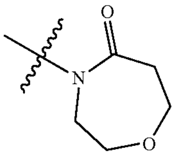, 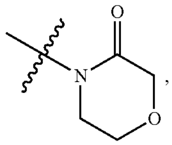, 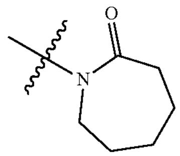, 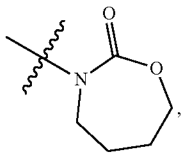, 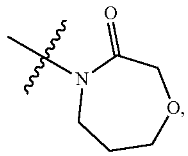, 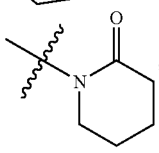, 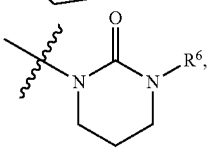, and 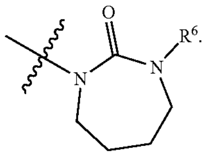

In some embodiments, Z is selected from the group consisting of:

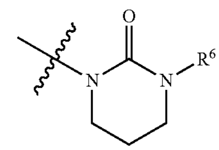 and 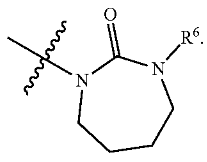

In some embodiments, $R^1$ is selected from the group consisting of halogen, $C_1$-$C_5$ alkyl, and $C_3$-$C_5$ cycloalkyl, wherein $C_1$-$C_5$ alkyl may be optionally substituted with one, two, or three occurrences of fluorine. In some embodiments, $R^1$ is $CF_3$. In some embodiments, $R^1$ is $CF_2H$. In some embodiments, $R^1$ is halogen. In some embodiments, $R^1$ is bromo. In some embodiments, $R^1$ is cyclopropyl.

In some embodiments, $R^2$ is selected from the group consisting of H, $C_3$-$C_5$cycloalkyl, $C_1$-$C_5$ alkyl, halogen, CN, $C_2$-$C_5$alkenyl, and $C_2$-$C_5$ alknyl, wherein $C_1$-$C_5$ alkyl and $C_3$-$C_5$ cycloalkyl may be optionally substituted with one, two, or three independent occurrences of fluorine. In some embodiments, $R^2$ is selected from the group consisting of $C_1$-$C_2$ alkyl and $C_{3-4}$ cycloalkyl. In some embodiments, $R^2$ is selected from the group consisting of chloro and bromo.

In some embodiments, $R^2$ is selected from the group consisting of $C_1$-$C_5$ alkyl, H, and $C_3$-$C_4$ cycloalkyl. In some embodiments, $R^2$ is selected from the group consisting of $C_1$-$C_2$ alkyl and $C_3$-$C_4$ cycloalkyl. In some embodiments, $R^2$ is selected from the group consisting of chloro and bromo.

In some embodiments, $R^4$ is:

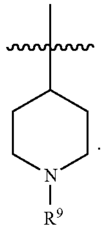

In an embodiment, the compound is represented by a formula selected from the group consisting of:

Formula IIA.1

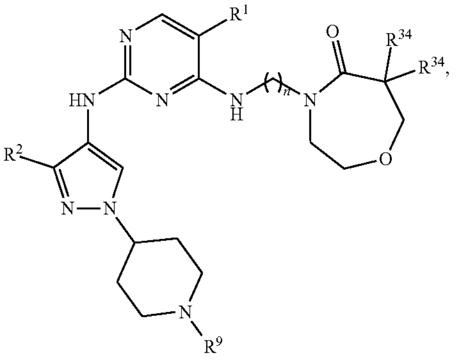

-continued

Formula IIA.2

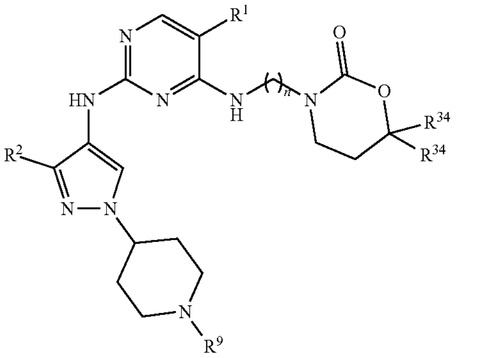

Formula IIA.3

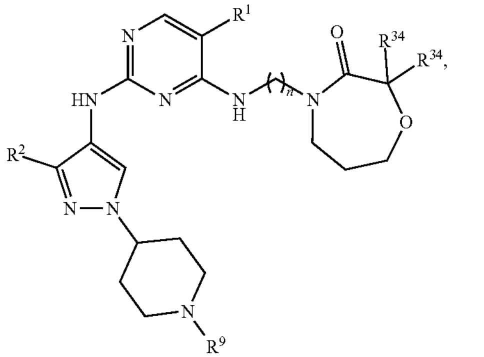

Formula IIIA.4

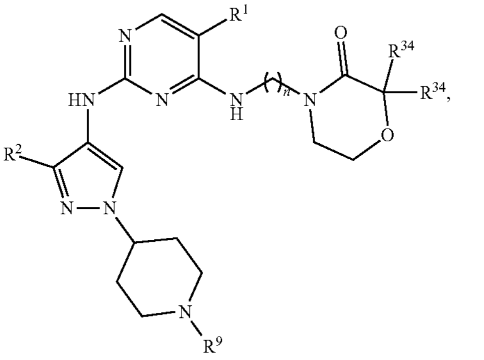

Formula IIA.5

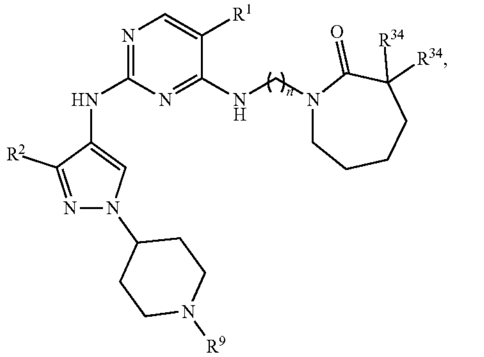

-continued

Formula IIA.6

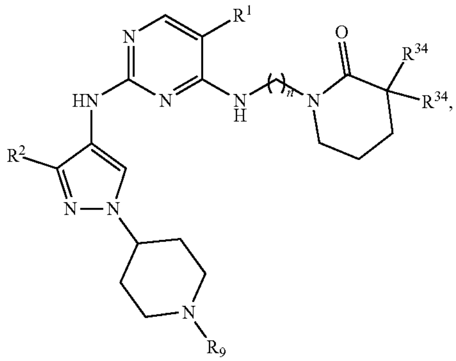

and

Formula IIA.7

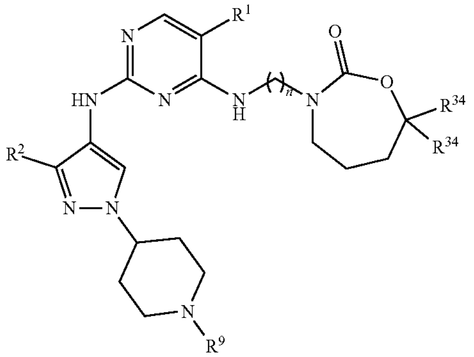

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^9$ is independently selected from the group consisting of H, $C_1$-$C_3$ alkyl, and $C_3$-$C_5$ cycloalkyl; each occurrence of $R^{34}$ is independently selected from the group consisting of H, $C_1$-$C_2$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is bromo; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^9$ is independently selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CF_3$; each occurrence of $R^2$ is independently selected from $C_1$-$C_2$ alkyl and $C_3$-$C_4$ cycloalkyl; each occurrence of $R^9$ is independently selected from H and $C_1$-$C_3$ alkyl; each $R^{34}$ is H; and n is 3.

In some embodiments, each occurrence of $R^1$ is $CHF_2$; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CHF_2$; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, the compound is represented by Formula IIA.1 as defined above. In some embodiments, the compound is represented Formula IIA.3 as defined above. In some embodiments, the compound is represented a formula selected from the group consisting of Formula IIA.3, Formula IIA.4, Formula IIA.5, Formula IIA.6, and Formula IIA.7 as defined above.

In some embodiments, the compound is represented by a formula selected from the group consisting of:

Formula IIA.8

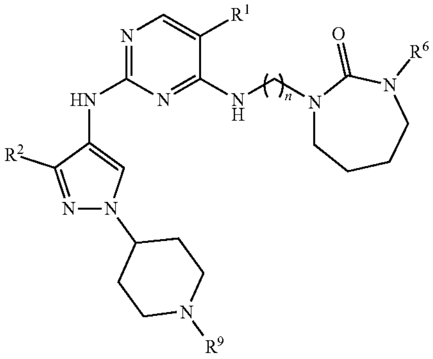

and

Formula IIA.9

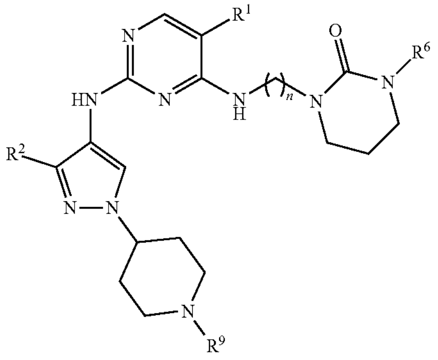

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^6$ is independently selected from $C_1$-$C_3$ alkyl and $C_3$-$C_4$ cycloalkyl; each occurrence of $R^9$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from the group consisting of $C_1$-$C_2$ alkyl, $C_3$-$C_4$ cycloalkyl, bromo, and chloro; each occurrence of $R^6$ is selected from $C_1$-$C_3$ alkyl and $C_3$-$C_4$ cycloalkyl; each occurrence of $R^9$ is selected from H and $C_1$-$C_3$ alkyl; and n is 3. In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3. In some embodiments, each occurrence of $R^1$ is $CF_2H$; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3.

In some embodiments, the compound is represented by a formula selected from the group consisting of:

Formula IIA.10

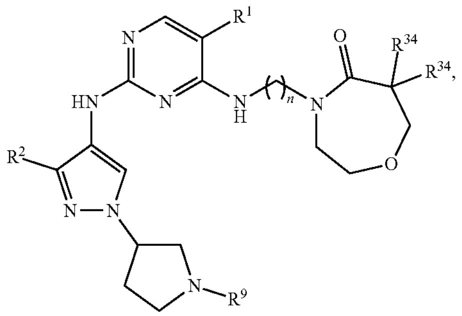

Formula IIA.11

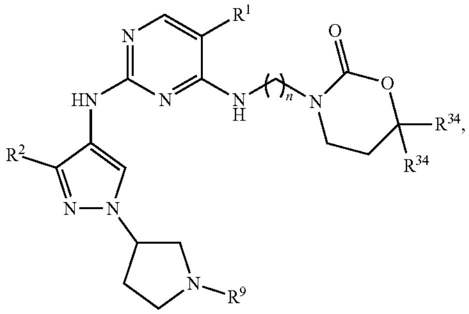

Formula IIA.12

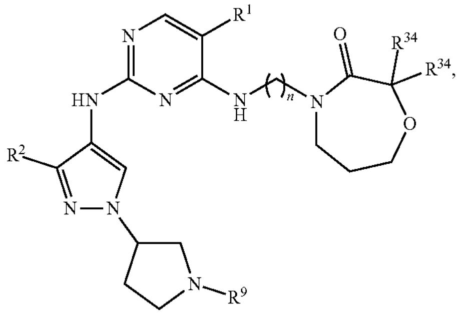

Formula IIA.13

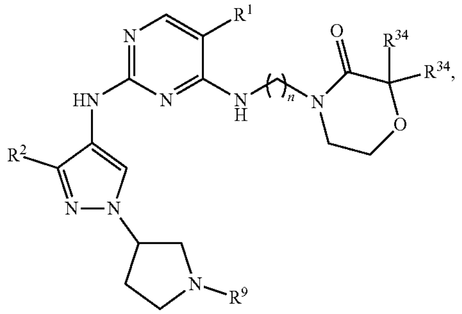

-continued

Formula IIA.14

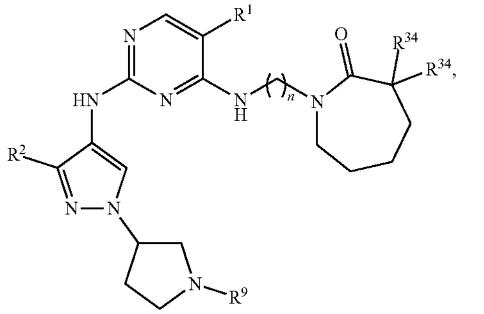

Formula IIA.15

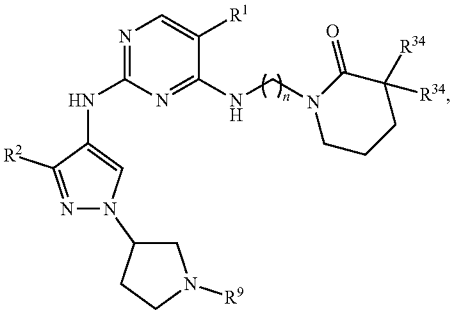

and

Formula IIA.16

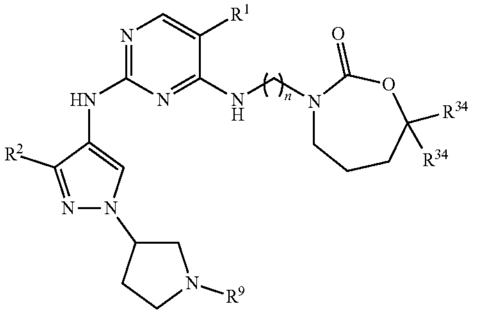

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^9$ is independently selected from the group consisting of H, $C_1$-$C_3$ alkyl, and $C_3$-$C_5$ cycloalkyl; each occurrence of $R^{34}$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is bromo; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^9$ is independently selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CF_3$; each occurrence of $R^2$ is independently selected from $C_1$-$C_2$ alkyl and $C_3$-$C_4$ cycloalkyl; each occurrence of $R^9$ is independently selected from H and $C_1$-$C_3$ alkyl; each $R^{34}$ is H; and n is 3.

In some embodiments, each occurrence of $R^1$ is $CHF_2$; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CHF_2$; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, the compound is represented by a formula selected from the group consisting of:

Formula IIA.17

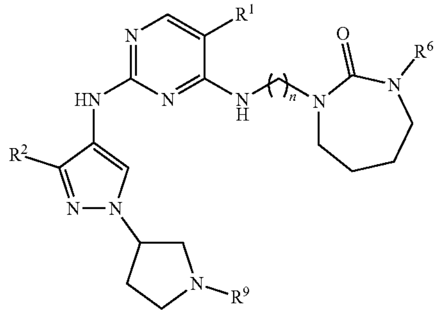

and

Formula IIA.18

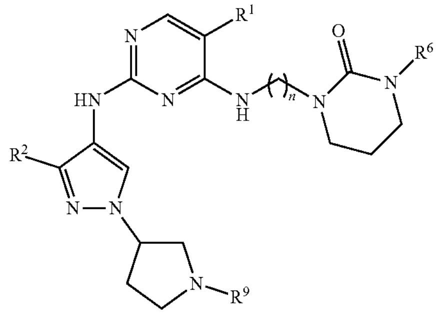

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^6$ is independently selected from $C_1$-$C_3$ alkyl and $C_3$-$C_4$ cycloalkyl; each occurrence of $R^9$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^6$ is selected from $C_1$-$C_3$ alkyl and $C_3$-$C_4$ cycloalkyl; and each occurrence of $R^9$ is selected from H and $C_1$-$C_3$ alkyl. In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^6$ is independently selected from the group consisting of $C_1$-$C_3$ alkyl and $C_3$-$C_4$ cycloalkyl; each occurrence of $R^9$ is independently selected from H and $C_1$-$C_3$ alkyl; and n is 3. In some embodiments, each occurrence of $R^1$ is $CF_2H$; each occurrence of $R^2$ is independently selected from $C_1$-$C_2$ alkyl, $C_3$-$C_4$ cycloalkyl, bromo, and chloro; each occurrence of $R^6$ is independently selected from the group consisting of $C_1$-$C_3$ alkyl and $C_3$-$C_4$ cycloalkyl; each occurrence of $R^9$ is independently selected from H and $C_1$-$C_3$ alkyl; and n is 3.

In some embodiments, the compound is represented by a formula selected from the group consisting of:

Formula IIA.19

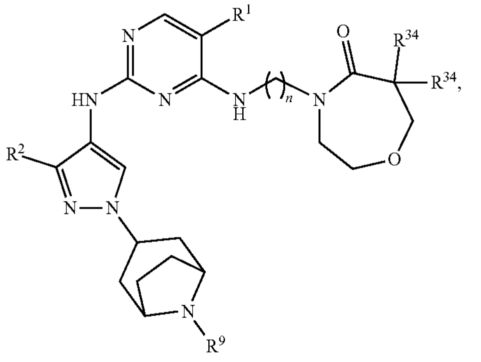

Formula IIA.20

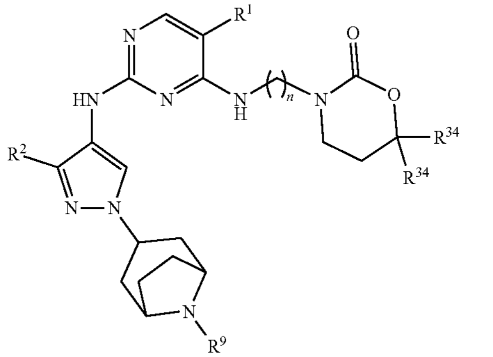

Formula IIA.21

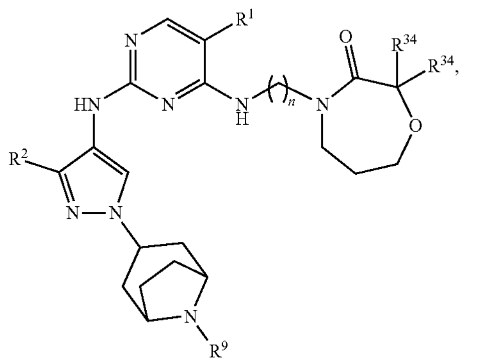

-continued

Formula IIA.22

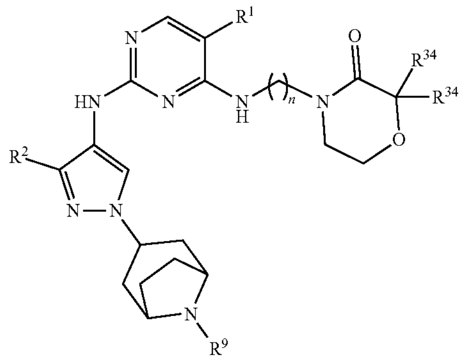

Formula IIA.23

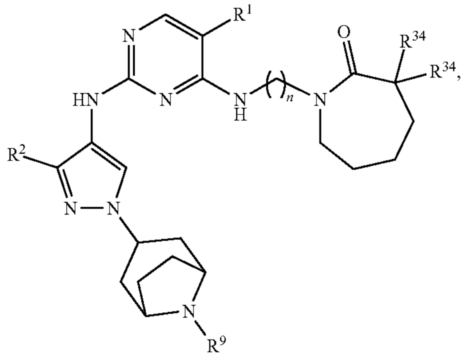

Formula IIA.24

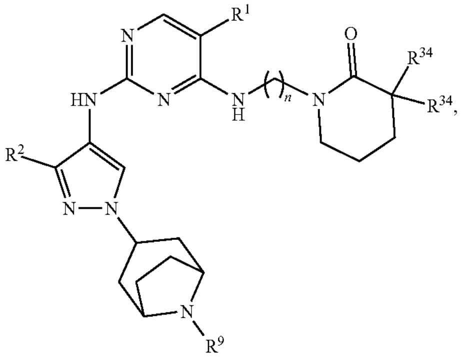

and

Formula IIA.25

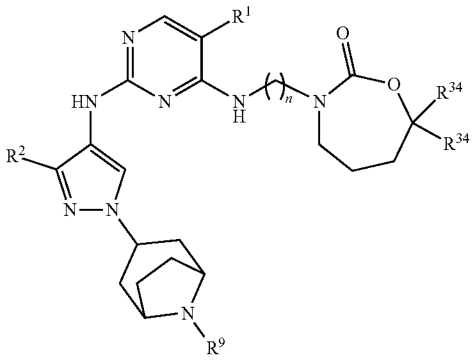

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^9$ is independently selected from the group consisting of H, $C_1$-$C_3$ alkyl, and $C_3$-$C_5$ cycloalkyl; each occurrence of $R^{34}$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is bromo; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^9$ is independently selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CF_3$; each occurrence of $R^2$ is independently selected from $C_1$-$C_2$ alkyl and $C_3$-$C_4$ cycloalkyl; each occurrence of $R^9$ is independently selected from H and $C_1$-$C_3$ alkyl; each $R^{34}$ is H; and n is 3.

In some embodiments, each occurrence of $R^1$ is $CHF_2$; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CHF_2$; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, the compound is represented by Formula IIA.19 as defined above. In some embodiments, the compound is represented by Formula IIA.21 as defined above.

In some embodiments, the compound is represented by a formula selected from:

Formula IIA.26

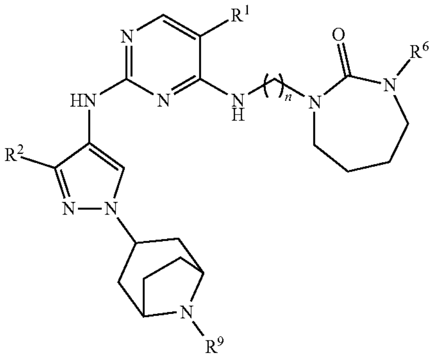

and

-continued

Formula IIA.27

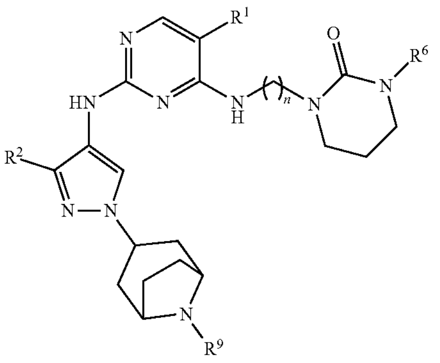

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^6$ is independently selected from $C_1$-$C_3$ alkyl and $C_3$-$C_4$ cycloalkyl; each occurrence of $R^9$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3. In some embodiments, each occurrence of $R^1$ is $CF_3$; each occurrence of $R^2$ is independently selected from $C_1$-$C_2$ alkyl $C_3$-$C_4$ cycloalkyl, bromo, and chloro; each occurrence of $R^6$ is independently selected from $C_1$-$C_3$ alkyl and $C_3$-$C_4$ cycloalkyl; $R^9$ is independently selected from H and $C_1$-$C_3$ alkyl; and n is 3. In some embodiments, each occurrence of $R^1$ is $CF_2H$; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3.

In an embodiment, the compound is represented by:

Formula III

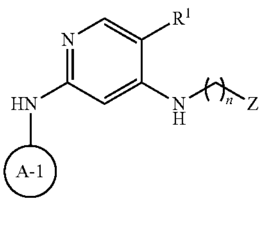

or a pharmaceutically acceptable salt thereof, wherein A-1 is selected from the group consisting of:

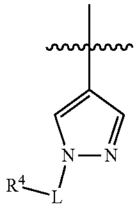, 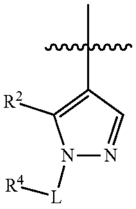, and 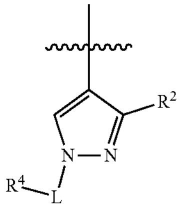

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine; $R^2$ is selected from $C_1$-$C_2$ alkyl, $C_3$-$C_4$ cycloalkyl, and halogen; $R^4$ is selected from the group consisting of:

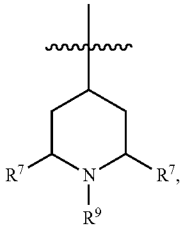 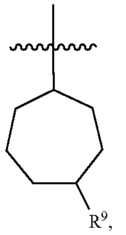 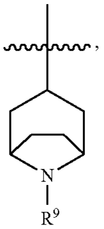 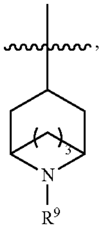

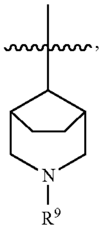 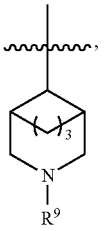 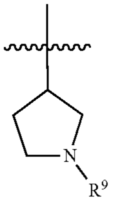 or 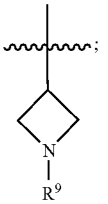

each occurrence of $R^7$ is independently selected from the group consisting of H, $C_1$-$C_6$ alkyl, $C_3$-$C_6$ cycloalkyl, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo; each occurrence of $R^6$ and $R^9$ is independently selected from the group consisting of H, $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine; Z is selected from the group consisting of:

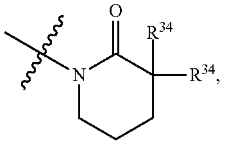 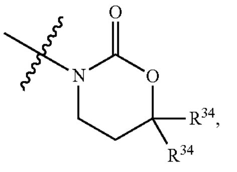

-continued

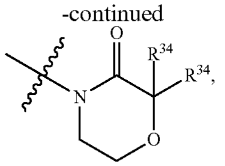

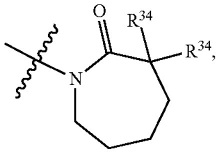 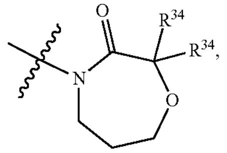

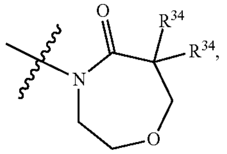 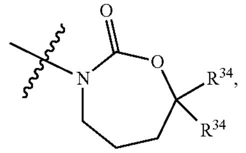

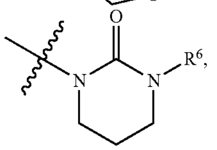 and 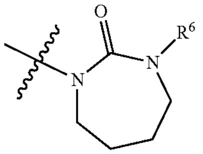

each occurrence of $R^{34}$ is independently selected from H and $R^{36}$, wherein each occurrence of $R^{36}$ is independently selected from $C_1$-$C_6$ alkyl and $C_3$-$C_6$ cycloalkyl and wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl; L is $-(C(R^{10})_2)_m-$; each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl; m is 0, 1, 2, or 3; and n is 2, 3, or 4; provided that: when m is 0, $R^4$ is C-linked to the pyrazole ring, when m is 1, $R^4$ is C-linked to L, then and when m is 2 or 3, $R^4$ is N-linked or C-linked to L.

In some embodiments, A-1 is:

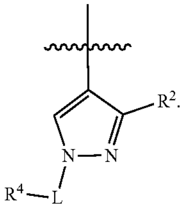

In some embodiments, n is 3.

In some embodiments, m is 0. In some embodiments, m is 1. In some embodiments, m is 2. In some embodiments, m is 3.

In some embodiments, L is a direct bond.

In some embodiments, L is selected from the group consisting of $-CH_2-$, $-CH_2CH_2-$, and $-CH_2CH_2CH_2-$. In some embodiments, L is $-CH_2-$. In some embodiments, L is $-CH_2CH_2-$. In some embodiments, L is $-CH_2CH_2CH_2-$.

In some embodiments, Z is selected from the group consisting of:

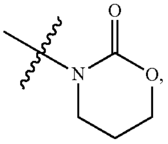 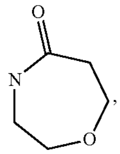, 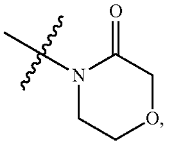

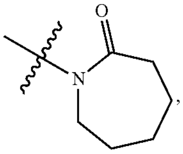, 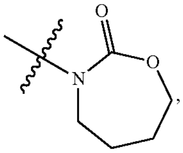, 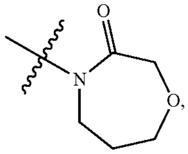

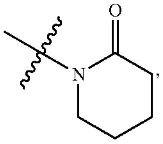, 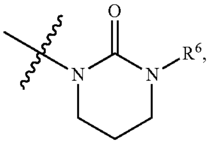 and

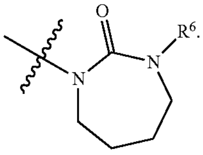

In some embodiments, Z is selected from the group consisting of:

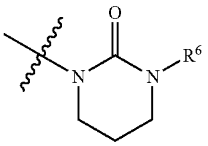 and 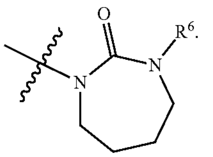

In some embodiments, $R^1$ is selected from the group consisting of halogen, $C_1$-$C_5$ alkyl, and $C_3$-$C_5$ cycloalkyl, wherein $C_1$-$C_5$ alkyl or $C_3$-$C_5$ cycloalkyl may be optionally substituted with one, two, or three occurrences of fluorine. In some embodiments, $R^1$ is $CF_3$. In some embodiments, $R^1$ is $CF_2H$. In some embodiments, $R^1$ is halogen. In some embodiments, $R^1$ is bromo. In some embodiments, $R^1$ is cyclopropyl.

In some embodiments, $R^2$ is selected from the group consisting of H, $C_3$-$C_5$cycloalkyl, $C_1$-$C_5$ alkyl, halogen, CN, $C_2$-$C_5$alkenyl, and $C_2$-$C_5$ alknyl, wherein $C_1$-$C_5$ alkyl or $C_3$-$C_5$ cycloalkyl may be optionally substituted with one, two, or three independent occurrences of fluorine. In some embodiments, $R^2$ is selected from $C_{1-2}$ alkyl and $C_{3-4}$cycloalkyl. In some embodiments, $R^2$ is selected from chloro and bromo.

In some embodiments, $R^2$ is selected from the group consisting of $C_1$-$C_5$ alkyl, H, and $C_3$-$C_4$ cycloalkyl. In some embodiments, $R^2$ is selected from $C_1$-$C_2$ alkyl and $C_3$-$C_4$ cycloalkyl. In some embodiments, $R^2$ is selected from chloro and bromo.

In some embodiments, $R^4$ is:

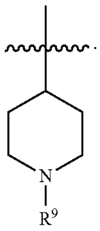

In an embodiment, the compound is represented by a formula selected from the group consisting of:

Formula IIIA.1

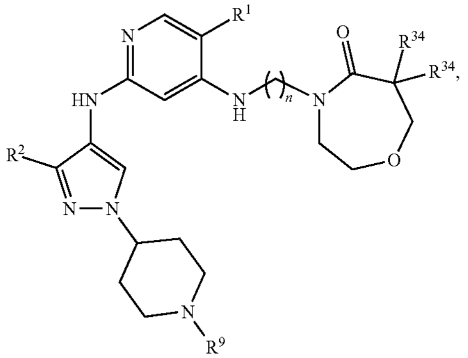

Formula IIIA.2

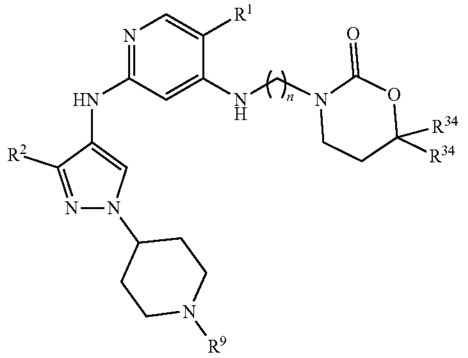

Formula IIIA.3

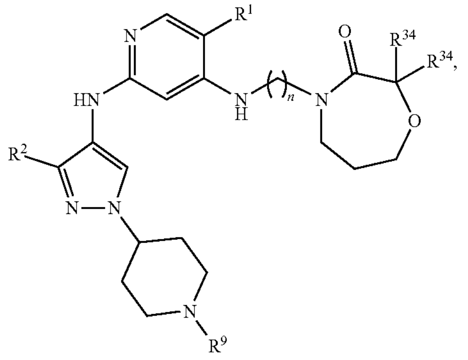

-continued

Formula IIIA.4

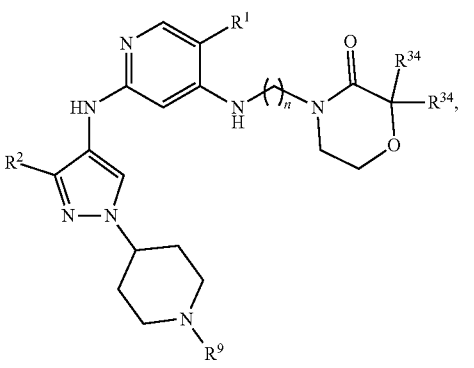

Formula IIIA.5

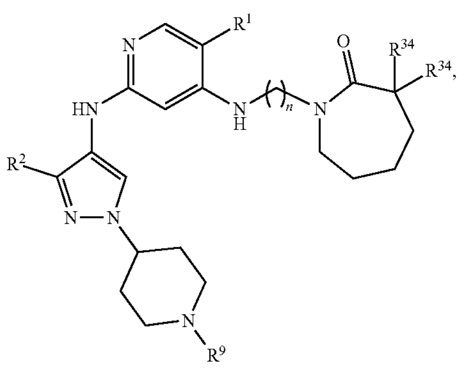

Formula IIIA.6

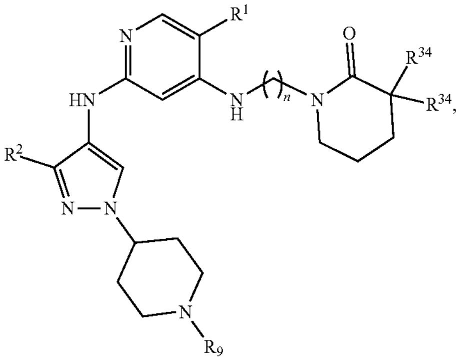

and

Formula IIIA.7

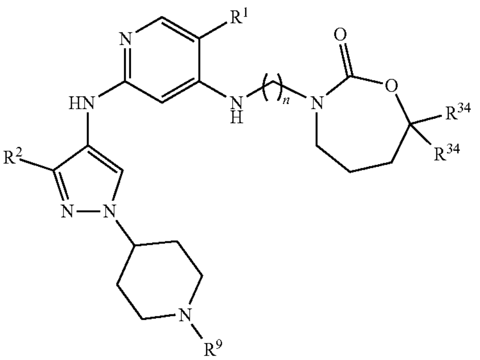

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^9$ is independently selected from the group consisting of H, $C_1$-$C_3$ alkyl, and $C_3$-$C_5$ cycloalkyl; each occurrence of $R^{34}$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is bromo; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^9$ is independently selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CF_3$; each occurrence of $R^2$ is independently selected from $C_1$-$C_2$ alkyl and $C_3$-$C_4$ cycloalkyl; each occurrence of $R^9$ is independently selected from H and $C_1$-$C_3$ alkyl; each $R^{34}$ is H; and n is 3.

In some embodiments, each occurrence of $R^1$ is $CHF_2$; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CHF_2$; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, the compound is represented by a formula selected from the group consisting of:

Formula IIIA.8

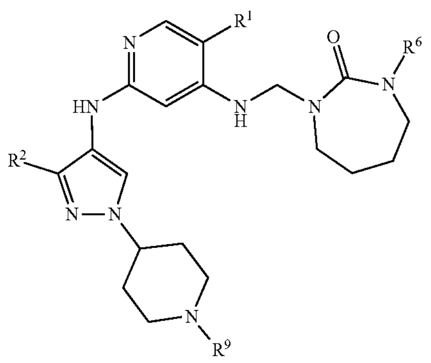

and

-continued

Formula IIIA.9

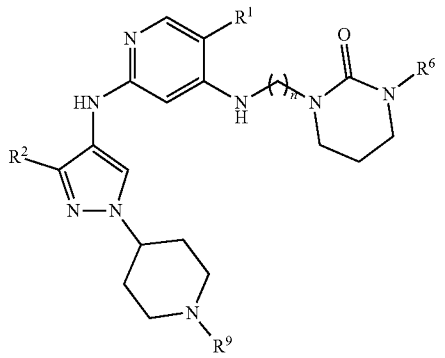

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^6$ is independently selected from $C_1$-$C_3$ alkyl and $C_3$-$C_4$ cycloalkyl; each occurrence of $R^9$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from the group consisting of $C_1$-$C_2$ alkyl, $C_3$-$C_4$ cycloalkyl, bromo, and chloro; each occurrence of $R^6$ is selected from $C_1$-$C_3$ alkyl and $C_3$-$C_4$ cycloalkyl; each occurrence of $R^9$ is selected from H and $C_1$-$C_3$ alkyl; and n is 3. In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3. In some embodiments, each occurrence of $R^1$ is $CF_2H$; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3.

In some embodiments, the compound is represented by a formula selected from the group consisting of:

Formula IIIA.10

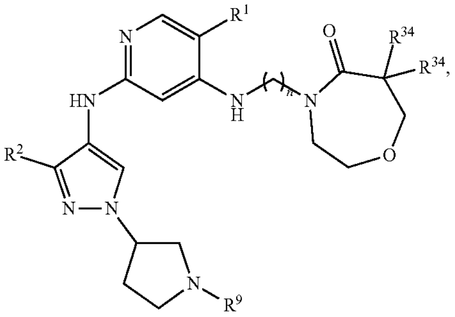

-continued

Formula IIIA.11

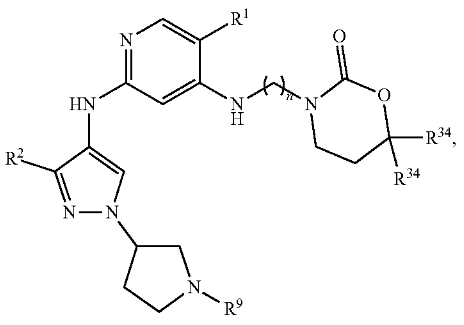

Formula IIIA.12

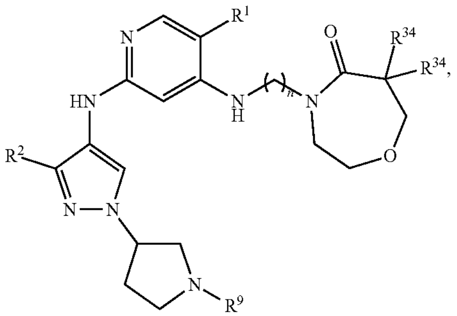

Formula IIIA.13

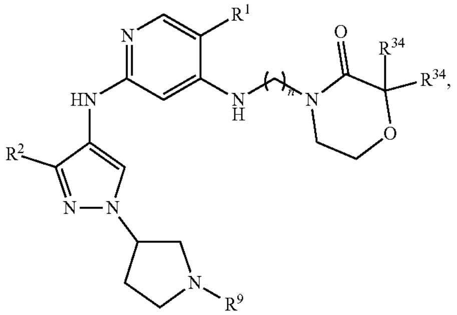

Formula IIIA.14

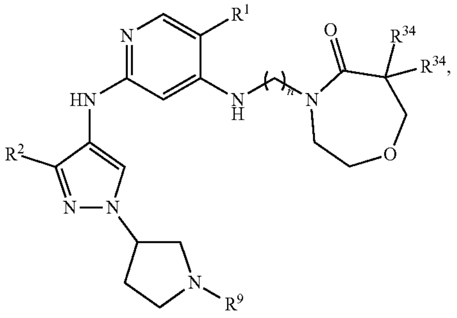

-continued

Formula IIIA.15

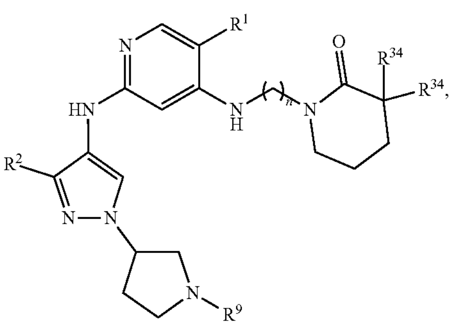

and

Formula IIIA.16

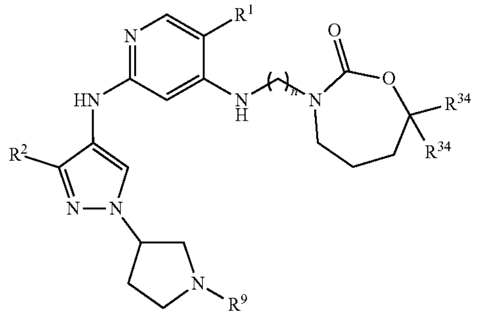

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^9$ is independently selected from the group consisting of H, $C_1$-$C_3$ alkyl, and $C_3$-$C_5$ cycloalkyl; each occurrence of $R^{34}$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is bromo; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^9$ is independently selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CF_3$; each occurrence of $R^2$ is independently selected from $C_1$-$C_2$ alkyl and $C_3$-$C_4$ cycloalkyl; each occurrence of $R^9$ is independently selected from H and $C_1$-$C_3$ alkyl; each $R^{34}$ is H; and n is 3.

In some embodiments, each occurrence of $R^1$ is $CHF_2$; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CHF_2$; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, the compound is represented by a formula selected from the group consisting of:

Formula IIIA.17

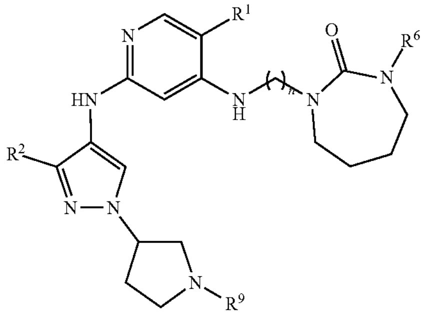

and

Formula IIIA.18

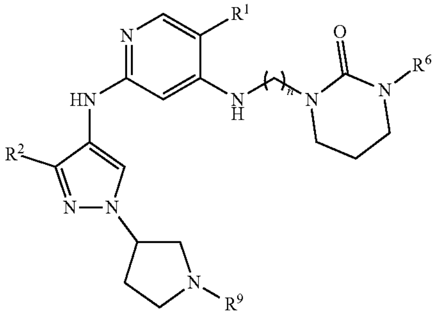

wherein each occurrence of $R^1$ is independently selected from the group consisting of bromo, chloro, $CF_3$, $CF_2H$, and cyclopropyl; each occurrence of $R^2$ is independently selected from the group consisting of C1-C2 alkyl, C3-C4 cycloalkyl, bromo, and chloro, and halogen; each occurrence of R6 is independently selected from C1-C3 alkyl and C3-C4 cycloalkyl; each occurrence of R9 is independently selected from the group consisting of H, C1-C3 alkyl, and C3-C5 cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^6$ is selected from $C_1$-$C_3$ alkyl and $C_3$-$C_4$ cycloalkyl; and each occurrence of $R^9$ is selected from H and $C_1$-$C_3$ alkyl. In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^6$ is independently selected from the group consisting of $C_1$-$C_3$ alkyl and $C_3$-$C_4$ cycloalkyl; each occurrence of $R^9$ is independently selected from H and $C_1$-$C_3$ alkyl; and n is 3. In some embodiments, each occurrence of $R^1$ is $CF_2H$; each occurrence of $R^2$ is independently selected from $C_1$-$C_2$ alkyl, $C_3$-$C_4$ cycloalkyl, bromo, and chloro; each occurrence of $R^6$ is independently selected from the group consisting of $C_1$-$C_3$ alkyl and $C_3$-$C_4$ cycloalkyl; each occurrence of $R^9$ is independently selected from H and $C_1$-$C_3$ alkyl; and n is 3.

In some embodiments, the compound is represented by a formula selected from the group consisting of:

-continued

Formula IIIA.19

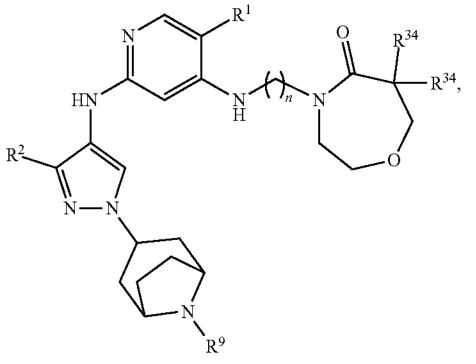

Formula IIIA.20

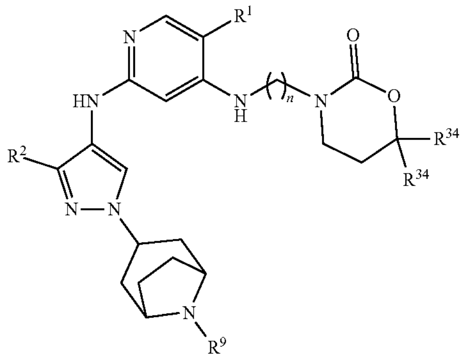

Formula IIIA.21

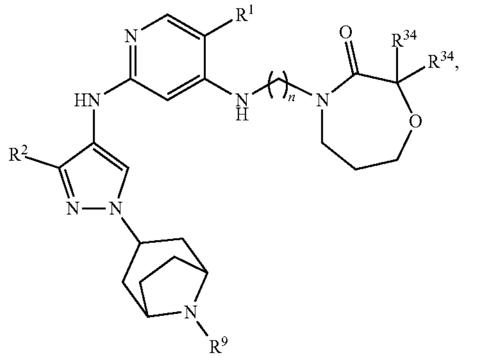

Formula IIIA.22

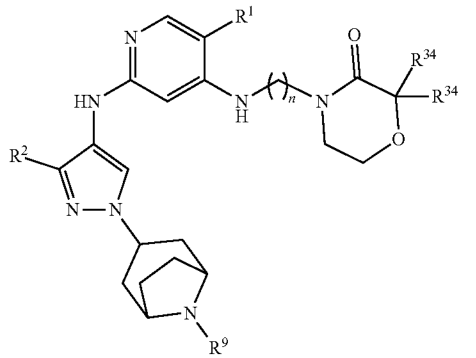

Formula IIIA.23

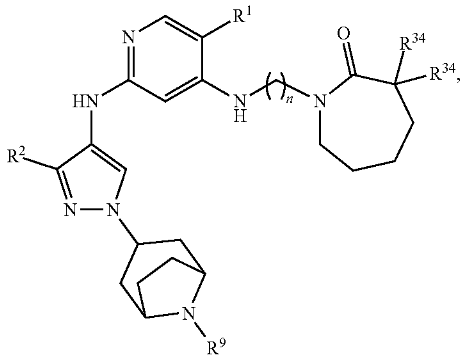

Formula IIIA.24

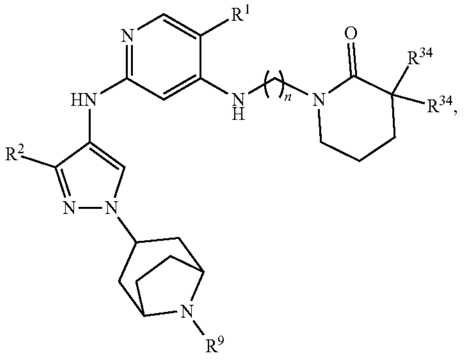

and

Formula IIIA.25

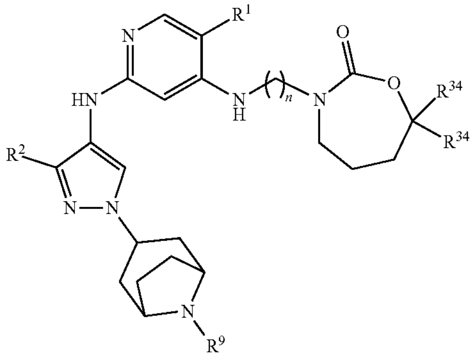

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^9$ is independently selected from the group consisting of H, $C_1$-$C_3$ alkyl, and $C_3$-$C_5$ cycloalkyl; each occurrence of $R^{34}$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is bromo; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^9$ is independently selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CF_3$; each occurrence of $R^2$ is independently selected from $C_1$-$C_2$ alkyl and $C_3$-$C_4$ cycloalkyl; each occurrence of $R^9$ is independently selected from H and $C_1$-$C_3$ alkyl; each $R^{34}$ is H; and n is 3.

In some embodiments, each occurrence of $R^1$ is $CHF_2$; each occurrence of $R^2$ is independently selected from $C_1$-$C_2$ alkyl, $C_3$-$C_4$ cycloalkyl, bromo, and chloro; each occurrence of $R^9$ is selected from H and $C_1$-$C_3$ alkyl; each occurrence of $R^{34}$ is independently selected from the group consisting of H and $C_1$-$C_3$ alkyl; and n is 3. In some embodiments, each occurrence of $R^1$ is $CHF_2$; each occurrence of $R^2$ is independently selected from $C_1$-$C_2$ alkyl and $C_3$-$C_4$ cycloalkyl; each occurrence of $R^9$ is selected from H and $C_1$-$C_3$ alkyl; each $R^{34}$ is H; and n is 3.

In some embodiments, the compound is represented by a formula selected from:

Formula IIIA.26

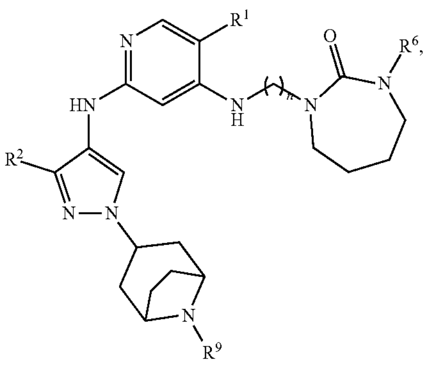

, and

Formula IIIA.27

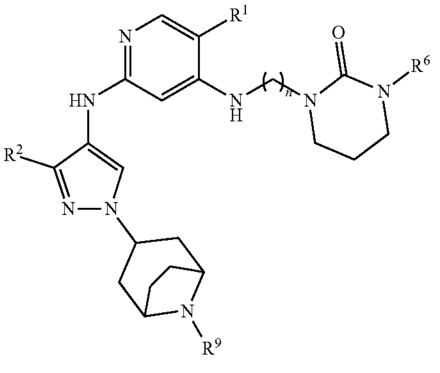

wherein each occurrence of $R^1$ is independently selected from the group consisting of bromo, chloro, $CF_3$, $CF_2H$, and cyclopropyl; each occurrence of $R^2$ is independently selected from the group consisting of $C_1$-$C_2$ alkyl, $C_3$-$C_4$ cycloalkyl, and halogen; each occurrence of $R^6$ is independently selected from $C_1$-$C_3$ alkyl and $C_3$-$C_4$ cycloalkyl; each occurrence of $R^9$ is independently selected from the group consisting of H, $C_1$-$C_3$ alkyl, and $C_3$-$C_5$ cycloalkyl; and n is 3.

In some embodiments, each occurrence of $R^1$ is bromo; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3. In some embodiments, each occurrence of $R^1$ is $CF_3$; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; $R^9$ is independently selected from H and $C_1$-$C_3$ alkyl; and n is 3. In some embodiments, each occurrence of $R^1$ is $CF_2H$; each occurrence of $R^2$ is independently selected from $C_1$-$C_2$ alkyl, $C_3$-$C_4$ cycloalkyl, bromo, and chloro; each occurrence of $R^6$ is independently selected from $C_1$-$C_3$ alkyl and $C_3$-$C_4$ cycloalkyl; each occurrence of $R^9$ is independently selected from H and $C_1$-$C_3$ alkyl; and n is 3.

In some embodiments, the compound is represented by a formula selected from the group consisting of: 1-(3-((5-cyclopropyl-2-((1-(1-methylpiperidin-4-yl)-1H-pyrazol-4-yl)amino)pyrimidin-4-yl)amino)propyl)piperidin-2-one, 1-(3-((5-chloro-2-((1-(1-methylpiperidin-4-yl)-1H-pyrazol-4-yl)amino)pyrimidin-4-yl)amino)propyl)piperidin-2-one, 1-(3-((5-chloro-2-((1-(1-(cyclopropylmethyl)piperidin-4-yl)-1H-pyrazol-4-yl)amino)pyrimidin-4-yl)amino)propyl)piperidin-2-one, 1-(3-((5-chloro-2-((1-(piperidin-4-yl)-1H-pyrazol-4-yl)amino)pyrimidin-4-yl)amino)propyl)piperidin-2-one, 1-(3-((5-chloro-2-((1-(1-isopropylpiperidin-4-yl)-1H-pyrazol-4-yl)amino)pyrimidin-4-yl)amino)propyl)piperidin-2-one, 1-(3-((2-((1-(1-isopropylpiperidin-4-yl)-1H-pyrazol-4-yl)amino)-5-(trifluoromethyl)pyrimidin-4-yl)amino)propyl)piperidin-2-one, 1-(3-((2-((1-(piperidin-4-yl)-1H-pyrazol-4-yl)amino)-5-(trifluoromethyl)pyrimidin-4-yl)amino)propyl)piperidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)piperidin-2-one, 1-(3-((5-bromo-2-((1-(piperidin-4-yl)-1H-pyrazol-4-yl)amino)pyrimidin-4-yl)amino)propyl)piperidin-2-one, 1-(3-((2-((1-(1-methylpiperidin-4-yl)-1H-pyrazol-4-yl)amino)-5-(trifluoromethyl)pyrimidin-4-yl)amino)propyl)piperidin-2-one, 1-(3-((5-chloro-2-((1-(1-isobutylazetidin-3-yl)-1H-pyrazol-4-yl)amino)pyrimidin-4-yl)amino)propyl)piperidin-2-one, 1-(3-((2-((1-(1-isobutylazetidin-3-yl)-1H-pyrazol-4-yl)amino)-5-(trifluoromethyl)pyrimidin-4-yl)amino)propyl)piperidin-2-one, 1-(3-((2-((1-(1-isopropyl-d7-piperidin-4-yl)-1H-pyrazol-4-yl)amino)-5-(trifluoromethyl)pyrimidin-4-yl)amino)propyl)piperidin-2-one, 1-(3-((2-((3-methyl-1-(piperidin-4-yl)-1H-pyrazol-4-yl)amino)-5-(trifluoromethyl)pyrimidin-4-yl)amino)propyl)piperidin-2-one, 1-(3-((2-((1-(1-isopropylpiperidin-4-yl)-3-methyl-1H-pyrazol-4-yl)amino)-5-(trifluoromethyl)pyrimidin-4-yl)amino)propyl)piperidin-2-one, 1-(3-((2-((1-(1-ethylpiperidin-4-yl)-1H-pyrazol-4-yl)amino)-5-(trifluoromethyl)pyridin-4-yl)amino)propyl)piperidin-2-one, 1-(3-((5-bromo-2-((1-(1-isobutylazetidin-3-yl)-1H-pyrazol-4-yl)amino)pyrimidin-4-yl)amino)propyl)piperidin-2-one, rac-(R)-1-(3-((2-((3-methyl-1-(1-methylpyrrolidin-3-yl)-1H-pyrazol-4-yl)amino)-5-(trifluoromethyl)pyrimidin-4-yl)amino)propyl)piperidin-2-one, 1-(3-((2-((1-(1-(cyclopropylmethyl)piperidin-4-yl)-3-methyl-1H-pyrazol-4-yl)amino)-5-(trifluoromethyl)pyrimidin-4-yl)amino)propyl)piperidin-2-one, 1-(3-((2-((3-methyl-1-(3-(pyrrolidin-1-yl)propyl)-1H-pyrazol-4-yl)amino)-5-(trifluoromethyl)pyrimidin-4-yl)amino)propyl)piperidin-2-one, 1-(3-((2-((1-(2-(dimethylamino)ethyl)-3-methyl-1H-pyrazol-4-yl)amino)-5-(trifluoromethyl)pyrimidin-4-yl)amino)propyl)piperidin-2-one, 1-(3-((2-((3-methyl-1-(2-(piperidin-1-yl)ethyl)-1H-pyrazol-4-yl)amino)-

5-(trifluoromethyl)pyrimidin-4-yl)amino)propyl)piperidin-2-one, 1-(3-((2-((1-(1-isobutylazetidin-3-yl)-3-methyl-1H-pyrazol-4-yl)amino)-5-(trifluoromethyl)pyrimidin-4-yl)amino)propyl)piperidin-2-one, rac-(R)-1-(3-((5-chloro-2-((3-methyl-1-(1-methylpyrrolidin-3-yl)-1H-pyrazol-4-yl)amino)pyrimidin-4-yl)amino)propyl)piperidin-2-one, rac-(R)-1-(3-((2-((1-(1-ethylpyrrolidin-3-yl)-3-methyl-1H-pyrazol-4-yl)amino)-5-(trifluoromethyl)pyrimidin-4-yl)amino)propyl)piperidin-2-one, 1-(3-((5-bromo-2-((3-methyl-1-(piperidin-4-yl)-1H-pyrazol-4-yl)amino)pyrimidin-4-yl)amino)propyl)piperidin-2-one, 1-(3-((5-chloro-2-((3-methyl-1-(piperidin-4-yl)-1H-pyrazol-4-yl)amino)pyrimidin-4-yl)amino)propyl)piperidin-2-one, 1-(3-((2-((3-methyl-1-(3-(piperidin-1-yl)propyl)-1H-pyrazol-4-yl)amino)-5-(trifluoromethyl)pyrimidin-4-yl)amino)propyl)piperidin-2-one, 1-(3-((2-((3-methyl-1-(2-morpholinoethyl)-1H-pyrazol-4-yl)amino)-5-(trifluoromethyl)pyrimidin-4-yl)amino)propyl)piperidin-2-one, 1-(3-((2-((3-methyl-1-(3-morpholinopropyl)-1H-pyrazol-4-yl)amino)-5-(trifluoromethyl)pyrimidin-4-yl)amino)propyl)piperidin-2-one, 1-(3-((2-((3-methyl-d3-1-(1-methylpiperidin-4-yl)-1H-pyrazol-4-yl)amino)-5-(trifluoromethyl)pyrimidin-4-yl)amino)propyl)piperidin-2-one, 1-(3-((2-((1-(2-(dimethylamino)ethyl)-1H-pyrazol-4-yl)amino)-5-(trifluoromethyl)pyrimidin-4-yl)amino)propyl)piperidin-2-one, 1-(3-((2-((3-methyl-1-(1-(oxetan-3-yl)piperidin-4-yl)-1H-pyrazol-4-yl)amino)-5-(trifluoromethyl)pyrimidin-4-yl)amino)propyl)piperidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)piperidin-2-one, 1-(3-((2-((1-(3-(dimethylamino)propyl)-3-methyl-1H-pyrazol-4-yl)amino)-5-(trifluoromethyl)pyrimidin-4-yl)amino)propyl)piperidin-2-one, rac-(R)-1-(3-((2-((1-(1-isopropylpyrrolidin-3-yl)-3-methyl-1H-pyrazol-4-yl)amino)-5-(trifluoromethyl)pyrimidin-4-yl)amino)propyl)piperidin-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)piperidin-2-one, 1-(3-((5-chloro-2-((1-(1-isobutylazetidin-3-yl)-3-methyl-1H-pyrazol-4-yl)amino)pyrimidin-4-yl)amino)propyl)piperidin-2-one, 1-(3-((5-chloro-2-((3-ethyl-1-(piperidin-4-yl)-1H-pyrazol-4-yl)amino)pyrimidin-4-yl)amino)propyl)piperidin-2-one, 1-(3-((2-((3-ethyl-1-(piperidin-4-yl)-1H-pyrazol-4-yl)amino)-5-(trifluoromethyl)pyrimidin-4-yl)amino)propyl)piperidin-2-one, 1-(3-((5-bromo-2-((3-ethyl-1-(piperidin-4-yl)-1H-pyrazol-4-yl)amino)pyrimidin-4-yl)amino)propyl)piperidin-2-one, 1-(3-((2-((3-ethyl-1-(1-ethylpiperidin-4-yl)-1H-pyrazol-4-yl)amino)-5-(trifluoromethyl)pyrimidin-4-yl)amino)propyl)piperidin-2-one, 1-(3-((2-((3-ethyl-1-(1-isopropylpiperidin-4-yl)-1H-pyrazol-4-yl)amino)-5-(trifluoromethyl)pyrimidin-4-yl)amino)propyl)piperidin-2-one, rac-(R)-1-(3-((5-bromo-2-((3-methyl-1-(1-methylpyrrolidin-3-yl)-1H-pyrazol-4-yl)amino)pyrimidin-4-yl)amino)propyl)piperidin-2-one, 1-(3-((2-((3-methyl-1-(2-(pyrrolidin-1-yl)ethyl)-1H-pyrazol-4-yl)amino)-5-(trifluoromethyl)pyrimidin-4-yl)amino)propyl)piperidin-2-one, 1-(3-((5-chloro-2-((3-ethyl-1-(1-ethylpiperidin-4-yl)-1H-pyrazol-4-yl)amino)pyrimidin-4-yl)amino)propyl)piperidin-2-one, 1-(3-((2-((3-ethyl-1-(1-methylpiperidin-4-yl)-1H-pyrazol-4-yl)amino)-5-(trifluoromethyl)pyrimidin-4-yl)amino)propyl)piperidin-2-one, 1-(3-((5-iodo-2-((3-methyl-1-(piperidin-4-yl)-1H-pyrazol-4-yl)amino)pyrimidin-4-yl)amino)propyl)piperidin-2-one, 1-(3-((5-bromo-2-((3-methyl-d3-1-(1-methylpiperidin-4-yl)-1H-pyrazol-4-yl)amino)pyrimidin-4-yl)amino)propyl)piperidin-2-one, 1-(3-((5-bromo-2-((1-(1-ethylpiperidin-4-yl)-3-methyl-1H-pyrazol-4-yl)amino)pyrimidin-4-yl)amino)propyl)piperidin-2-one, 1-(3-((5-bromo-2-((3-methyl-1-(1-methylpiperidin-4-yl)-1H-pyrazol-4-yl)amino)pyrimidin-4-yl)amino)propyl)piperidin-2-one, 1-(3-((2-((3-ethyl-1-(1-methyl-d3-piperidin-4-yl)-1H-pyrazol-4-yl)amino)-5-(trifluoromethyl)pyrimidin-4-yl)amino)propyl)piperidin-2-one, 1-(3-((5-bromo-2-((3-ethyl-1-(1-methylpiperidin-4-yl)-1H-pyrazol-4-yl)amino)pyrimidin-4-yl)amino)propyl)piperidin-2-one, 1-(3-((5-bromo-2-((3-ethyl-1-(1-ethylpiperidin-4-yl)-1H-pyrazol-4-yl)amino)pyrimidin-4-yl)amino)propyl)piperidin-2-one, 1-(3-((5-chloro-2-((3-ethyl-1-(1-methylpiperidin-4-yl)-1H-pyrazol-4-yl)amino)pyrimidin-4-yl)amino)propyl)piperidin-2-one, 1-(3-((5-chloro-2-((3-methyl-1-(1-methylpiperidin-4-yl)-1H-pyrazol-4-yl)amino)pyrimidin-4-yl)amino)propyl)piperidin-2-one, 1-(3-((5-chloro-2-((3-methyl-1-(1-(methyl-d3)piperidin-4-yl)-1H-pyrazol-4-yl)amino)pyrimidin-4-yl)amino)propyl)piperidin-2-one, 1-(3-((5-chloro-2-((1-(1-ethylpiperidin-4-yl)-3-methyl-1H-pyrazol-4-yl)amino)pyrimidin-4-yl)amino)propyl)piperidin-2-one, 1-(3-((2-((1-(1-(2-fluoroethyl)piperidin-4-yl)-3-methyl-1H-pyrazol-4-yl)amino)-5-(trifluoromethyl)pyrimidin-4-yl)amino)propyl)piperidin-2-one, rac-(R)-1-(3-((5-bromo-2-((3-methyl-1-(pyrrolidin-3-yl)-1H-pyrazol-4-yl)amino)pyrimidin-4-yl)amino)propyl)piperidin-2-one, rac-(R)-1-(3-((5-bromo-2-((3-methyl-1-(1-methylpyrrolidin-3-yl)-1H-pyrazol-4-yl)amino)pyrimidin-4-yl)amino)propyl)piperidin-2-one, 1-(3-((5-bromo-2-((3-methyl-1-(2-(pyrrolidin-1-yl)ethyl)-1H-pyrazol-4-yl)amino)pyrimidin-4-yl)amino)propyl)piperidin-2-one, 1-(3-((5-bromo-2-((3-methyl-1-(2-morpholinoethyl)-1H-pyrazol-4-yl)amino)pyrimidin-4-yl)amino)propyl)piperidin-2-one, rac-(R)-1-(3-((5-bromo-2-((1-(1-ethylpyrrolidin-3-yl)-3-methyl-1H-pyrazol-4-yl)amino)pyrimidin-4-yl)amino)propyl)piperidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)piperidin-2-one, rac-(R)-1-(3-((2-((1-(1-ethylpyrrolidin-3-yl)-3-methyl-1H-pyrazol-4-yl)amino)-5-(trifluoromethyl)pyrimidin-4-yl)amino)propyl)piperidin-2-one, 2-methyl-2-(3-methyl-4-((4-((3-(2-oxopiperidin-1-yl)propyl)amino)-5-(trifluoromethyl)pyrimidin-2-yl)amino)-1H-pyrazol-1-yl)propanamide, 3-(3-((2-((1-(1-isopropylpiperidin-4-yl)-3-methyl-1H-pyrazol-4-yl)amino)-5-(trifluoromethyl)pyrimidin-4-yl)amino)propyl)-1,3-oxazinan-2-one, 1-(3-((5-cyclopropyl-2-((1-(1-cyclopropylpiperidin-4-yl)-1H-pyrazol-4-yl)amino)pyrimidin-4-yl)amino)propyl)-5,5-dimethylpyrrolidin-2-one, 3-(3-((2-((3-ethyl-1-(1-isopropylpiperidin-4-yl)-1H-pyrazol-4-yl)amino)-5-(trifluoromethyl)pyrimidin-4-yl)amino)propyl)-1,3-oxazinan-2-one, 3-(3-((5-bromo-2-((1-(1-isopropylpiperidin-4-yl)-3-methyl-1H-pyrazol-4-yl)amino)pyrimidin-4-yl)amino)propyl)-1,3-oxazinan-2-one, 3-(3-((5-chloro-2-((1-(1-isopropylpiperidin-4-yl)-3-methyl-1H-pyrazol-4-yl)amino)pyrimidin-4-yl)amino)propyl)-1,3-oxazinan-2-one, 3-(3-((5-chloro-2-((3-ethyl-1-(1-isopropylpiperidin-4-yl)-1H-pyrazol-4-yl)amino)pyrimidin-4-yl)amino)propyl)-1,3-oxazinan-2-one, 4-(3-((2-((1-(1-isopropylpiperidin-4-yl)-1H-pyrazol-4-yl)amino)-5-(trifluoromethyl)pyrimidin-4-yl)amino)propyl)morpholin-3-one, 4-(3-((5-cyclopropyl-2-((1-(1-isopropylpiperidin-4-yl)-3-methyl-1H-pyrazol-4-yl)amino)pyrimidin-4-yl)amino)propyl)morpholin-3-one, 4-(3-((5-cyclopropyl-2-((3-ethyl-1-(1-isopropylpiperidin-4-yl)-1H-pyrazol-4-yl)amino)pyrimidin-4-yl)amino)propyl)morpholin-3-one, 1-(3-((2-((1-(piperidin-4-yl)-1H-pyrazol-4-yl)amino)-5-(trifluoromethyl)pyrimidin-4-yl)amino)propyl)azepan-2-one, 1-(3-((2-((1-(1-methylpiperidin-4-yl)-1H-pyrazol-4-yl)amino)-5-(trifluoromethyl)pyrimidin-4-yl)amino)propyl)

azepan-2-one, 1-(3-((2-((3-methyl-1-(1-methylpiperidin-4-yl)-1H-pyrazol-4-yl)amino)-5-(trifluoromethyl)pyrimidin-4-yl)amino)propyl)azepan-2-one, 1-(3-((5-chloro-2-((3-methyl-1-(1-methylpiperidin-4-yl)-1H-pyrazol-4-yl)amino)pyrimidin-4-yl)amino)propyl)azepan-2-one, 1-(3-((5-chloro-2-((1-(1-methylpiperidin-4-yl)-1H-pyrazol-4-yl)amino)pyrimidin-4-yl)amino)propyl)azepan-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)pyrrolidin-2-one, 1-(3-((2-((3-methyl-1-(piperidin-4-yl)-1H-pyrazol-4-yl)amino)-5-(trifluoromethyl)pyrimidin-4-yl)amino)propyl)azepan-2-one, 1-(3-((5-cyclopropyl-2-((1-(1-methylpiperidin-4-yl)-1H-pyrazol-4-yl)amino)pyrimidin-4-yl)amino)propyl)pyrrolidin-2-one, 1-(3-((2-((1-(1-isopropylpiperidin-4-yl)-3-methyl-1H-pyrazol-4-yl)amino)-5-(trifluoromethyl)pyrimidin-4-yl)amino)propyl)azepan-2-one, 1-(3-((5-chloro-2-((3-methyl-1-(piperidin-4-yl)-1H-pyrazol-4-yl)amino)pyrimidin-4-yl)amino)propyl)azepan-2-one, 1-(3-((5-chloro-2-((1-(1-isopropylpiperidin-4-yl)-3-methyl-1H-pyrazol-4-yl)amino)pyrimidin-4-yl)amino)propyl)azepan-2-one, 1-(3-((2-((1-(1-isopropylpiperidin-4-yl)-1H-pyrazol-4-yl)amino)-5-(trifluoromethyl)pyrimidin-4-yl)amino)propyl)azepan-2-one, 1-(3-((2-((1-(1-isobutylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)azepan-2-one, 1-(3-((2-((3-methyl-1-(1-(oxetan-3-yl)piperidin-4-yl)-1H-pyrazol-4-yl)amino)-5-(trifluoromethyl)pyrimidin-4-yl)amino)propyl)azepan-2-one, 1-(3-((2-((1-(1-cyclobutylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-cyclopentylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-(sec-butyl)piperidin-4-yl)-3-methyl-1H-pyrazol-4-yl)amino)-5-(trifluoromethyl)pyrimidin-4-yl)amino)propyl)azepan-2-one, (S)-1-(3-((2-((1-(1-isopropylpyrrolidin-3-yl)-3-methyl-1H-pyrazol-4-yl)amino)-5-(trifluoromethyl)pyrimidin-4-yl)amino)propyl)azepan-2-one, 1-(3-((2-((1-(2-morpholinoethyl)-1H-pyrazol-4-yl)amino)-5-(trifluoromethyl)pyrimidin-4-yl)amino)propyl)azepan-2-one, 1-(3-((2-((1-(1-isobutylazetidin-3-yl)-1H-pyrazol-4-yl)amino)-5-(trifluoromethyl)pyrimidin-4-yl)amino)propyl)azepan-2-one, 1-(3-((2-((3-methyl-1-(2-morpholinoethyl)-1H-pyrazol-4-yl)amino)-5-(trifluoromethyl)pyrimidin-4-yl)amino)propyl)azepan-2-one, 1-(3-((2-((3-methyl-1-(3-(pyrrolidin-1-yl)propyl)-1H-pyrazol-4-yl)amino)-5-(trifluoromethyl)pyrimidin-4-yl)amino)propyl)azepan-2-one, 1-(3-((2-((3-methyl-1-(3-morpholinopropyl)-1H-pyrazol-4-yl)amino)-5-(trifluoromethyl)pyrimidin-4-yl)amino)propyl)azepan-2-one, 1-(3-((2-((3-methyl-1-(1-methyl-d3-piperidin-4-yl)-1H-pyrazol-4-yl)amino)-5-(trifluoromethyl)pyrimidin-4-yl)amino)propyl)azepan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-3-one, 1-(3-((2-((3-methyl-1-(piperidin-4-yl)-1H-pyrazol-4-yl)amino)-5-(trifluoromethyl)pyrimidin-4-yl)amino)propyl)pyrrolidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)pyrrolidin-2-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-3-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 4-(3-((2-((1-(1-ethylpiperidin-4-yl)-3-methyl-1H-pyrazol-4-yl)amino)-5-(trifluoromethyl)pyrimidin-4-yl)amino)propyl)-1,4-oxazepan-3-one, 4-(3-((2-((1-(1-isopropylpiperidin-4-yl)-3-methyl-1H-pyrazol-4-yl)amino)-5-(trifluoromethyl)pyrimidin-4-yl)amino)propyl)-1,4-oxazepan-3-one, 4-(3-((2-((3-ethyl-1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((5-chloro-2-((1-(1-isopropylpiperidin-4-yl)-3-methyl-1H-pyrazol-4-yl)amino)pyrimidin-4-yl)amino)propyl)-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-3-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-3-one, (R)-4-(3-((5-chloro-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((1-(1-isopropylpiperidin-4-yl)-3-methyl-1H-pyrazol-4-yl)amino)pyrimidin-4-yl)amino)propyl)-1,4-oxazepan-3-one, 4-(3-((5-cyclopropyl-2-((3-methyl-1-(3-morpholinopropyl)-1H-pyrazol-4-yl)amino)pyrimidin-4-yl)amino)propyl)-1,4-oxazepan-3-one, 4-(3-((5-cyclopropyl-2-((1-(2-(dimethylamino)ethyl)-3-methyl-1H-pyrazol-4-yl)amino)pyrimidin-4-yl)amino)propyl)-1,4-oxazepan-3-one, 4-(3-((2-((1-(2-(dimethylamino)ethyl)-3-methyl-1H-pyrazol-4-yl)amino)-5-(trifluoromethyl)pyrimidin-4-yl)amino)propyl)-1,4-oxazepan-3-one, (R)-4-(3-((5-bromo-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((3-ethyl-1-(1-methylpiperidin-4-yl)-1H-pyrazol-4-yl)amino)pyrimidin-4-yl)amino)propyl)-1,4-oxazepan-3-one, 4-(3-((5-chloro-2-((3-methyl-1-(3-morpholinopropyl)-1H-pyrazol-4-yl)amino)pyrimidin-4-yl)amino)propyl)-1,4-oxazepan-3-one, 4-(3-((5-bromo-2-((3-methyl-1-(3-morpholinopropyl)-1H-pyrazol-4-yl)amino)pyrimidin-4-yl)amino)propyl)-1,4-oxazepan-3-one, 4-(3-((5-bromo-2-((1-(2-(dimethylamino)ethyl)-3-methyl-1H-pyrazol-4-yl)amino)pyrimidin-4-yl)amino)propyl)-1,4-oxazepan-3-one, 4-(3-((5-chloro-2-((1-(2-(dimethylamino)ethyl)-3-methyl-1H-pyrazol-4-yl)amino)pyrimidin-4-yl)amino)propyl)-1,4-oxazepan-3-one, 4-(3-((2-((1-(2-(diethylamino)ethyl)-3-methyl-1H-pyrazol-4-yl)amino)-5-(trifluoromethyl)pyrimidin-4-yl)amino)propyl)-1,4-oxazepan-3-one, 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanamide, 3-(3-((2-((4-methyl-1-(1-methylpiperidin-4-yl)-1H-pyrazol-3-yl)amino)-5-(trifluoromethyl)pyrimidin-4-yl)amino)propyl)-1,3-oxazinan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-5-one, 1-(3-((2-((1-(1-isobutylazetidin-3-yl)-3-methyl-1H-pyrazol-4-yl)amino)-5-(trifluoromethyl)pyrimidin-4-yl)amino)propyl)pyrrolidin-2-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-5-one, 4-(3-((2-((1-(1-ethylpiperidin-4-yl)-3-methyl-1H-pyrazol-4-yl)amino)-5-(trifluoromethyl)pyrimidin-4-yl)amino)propyl)-1,4-oxazepan-5-one, 4-(3-((2-((1-(1-isopropylpiperidin-4-yl)-3-methyl-1H-pyrazol-4-yl)amino)-5-(trifluoromethyl)pyrimidin-4-yl)amino)propyl)-1,4-oxazepan-5-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-5-one, (R)-4-(3-((2-((3-methyl-1-(1-methylpyrrolidin-3-yl)-1H-pyrazol- 4-yl)amino)-5-(trifluoromethyl)pyrimidin-4-yl)amino)propyl)-1,4-oxazepan-5-one, (R)-4-(3-((5-chloro-2-((3-methyl-1-(1-methylpyrrolidin-3-yl)-1H-pyrazol-4-yl)amino)pyrimidin-4-yl)amino)propyl)-1,4-oxazepan-5-one, 4-(3-((5-chloro-2-((3-methyl-1-(3-morpholinopropyl)-1H-pyrazol-4-yl)amino)pyrimidin-4-yl)amino)propyl)-1,4-oxazepan-5-one, 4-(3-((2-((3-ethyl-1-(1-methylpiperidin-4-yl)-1H-pyrazol-4-yl)amino)-5-(trifluoromethyl)pyrimidin-4-yl)amino)propyl)-1,4-oxazepan-5-one, 4-(3-((2-((1-(2-(dimethylamino)ethyl)-3-methyl-1H-pyrazol-4-yl)amino)-5-(trifluoromethyl)pyrimidin-4-yl)amino)propyl)-1,4-oxazepan-5-one, (R)-4-(3-((5-bromo-2-((3-methyl-1-(1-methylpyrrolidin-3-yl)-1H-pyrazol-4-yl)amino)pyrimidin-4-yl)amino)propyl)-1,4-oxazepan-5-one, 4-(3-((5-cyclopropyl-2-((3-methyl-1-(3-morpholinopropyl)-1H-pyrazol-4-yl)amino)pyrimidin-4-yl)amino)propyl)-1,4-oxazepan-5-one, 4-(3-((5-cyclopropyl-2-((1-(2-(dimethylamino)ethyl)-3-methyl-1H-pyrazol-4-yl)amino)pyrimidin-4-yl)amino)propyl)-1,4-oxazepan-5-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-5-one, 4-(3-((5-cyclopropyl-2-((1-(1-ethylpiperidin-4-yl)-3-methyl-1H-pyrazol-4-yl)amino)pyrimidin-4-yl)amino)propyl)-1,4-oxazepan-5-one, 4-(3-((5-chloro-2-((1-(1-isopropylpiperidin-4-yl)-3-methyl-1H-pyrazol-4-yl)amino)pyrimidin-4-yl)amino)propyl)-1,4-oxazepan-5-one, 4-(3-((5-bromo-2-((1-(2-(dimethylamino)ethyl)-3-methyl-1H-pyrazol-4-yl)amino)pyrimidin-4-yl)amino)propyl)-1,4-oxazepan-5-one, 2-methyl-2-(3-methyl-4-((4-((3-(5-oxo-1,4-oxazepan-4-yl)propyl)amino)-5-(trifluoromethyl)pyrimidin-2-yl)amino)-1H-pyrazol-1-yl)propanamide, 4-(3-((2-((1-(2-(diethylamino)ethyl)-3-methyl-1H-pyrazol-4-yl)amino)-5-(trifluoromethyl)pyrimidin-4-yl)amino)propyl)-1,4-oxazepan-5-one, 1-(3-((5-cyclopropyl-2-((1-(1-methylpiperidin-4-yl)-1H-pyrazol-4-yl)amino)pyrimidin-4-yl)amino)propyl)-3-methylimidazolidin-2-one, 1-(3-((5-chloro-2-((1-(1-cyclopropylpiperidin-4-yl)-1H-pyrazol-4-yl)amino)pyrimidin-4-yl)amino)propyl)-3-methylimidazolidin-2-one, 1-(3-((5-chloro-2-((1-(1-cyclopropylpiperidin-4-yl)-1H-pyrazol-4-yl)amino)pyrimidin-4-yl)amino)propyl)-5,5-dimethylpyrrolidin-2-one, 1-(3-((5-chloro-2-((1-(1-cyclopropylpiperidin-4-yl)-1H-pyrazol-4-yl)amino)pyrimidin-4-yl)amino)propyl)-5-methylpyrrolidin-2-one, 1-methyl-3-(3-((2-((1-(1-methylpiperidin-4-yl)-1H-pyrazol-4-yl)amino)-5-(trifluoromethyl)pyrimidin-4-yl)amino)propyl)imidazolidin-2-one, 1-methyl-3-(3-((2-((3-methyl-1-(1-methylpiperidin-4-yl)-1H-pyrazol-4-yl)amino)-5-(trifluoromethyl)pyrimidin-4-yl)amino)propyl)imidazolidin-2-one, 1-(3-((5-bromo-2-((1-(1-cyclopropylpiperidin-4-yl)-1H-pyrazol-4-yl)amino)pyrimidin-4-yl)amino)propyl)-3,3-dimethylpyrrolidin-2-one, 1-(3-((5-bromo-2-((1-(1-isobutylazetidin-3-yl)-3-methyl-1H-pyrazol-4-yl)amino)pyrimidin-4-yl)amino)propyl)pyrrolidin-2-one, 1-(3-((5-chloro-2-((1-(1-cyclopropylpiperidin-4-yl)-1H-pyrazol-4-yl)amino)pyrimidin-4-yl)amino)propyl)-3-methylpyrrolidin-2-one, rac-(R)-1-(4-((5-chloro-2-((1-(1-cyclopropylpiperidin-4-yl)-1H-pyrazol-4-yl)amino)pyrimidin-4-yl)amino)butan-2-yl)pyrrolidin-2-one, rac-(R)-1-(4-((5-chloro-2-((1-(1-methylpiperidin-4-yl)-1H-pyrazol-4-yl)amino)pyrimidin-4-yl)amino)butan-2-yl)pyrrolidin-2-one, (R)-1-(3-((5-chloro-2-((3-methyl-1-(pyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-1H-pyrazol-4-yl)amino)pyrimidin-4-yl)amino)propyl)pyrrolidin-2-one, (R)-1-(3-((5-chloro-2-((3-methyl-1-(1-methylpyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-3-methyl-1H-pyrazol-4-yl)amino)pyrimidin-4-yl)amino)propyl)pyrrolidin-2-one, 1-(3-((5-chloro-2-((3-methyl-1-(2-(pyrrolidin-1-yl)ethyl)-1H-pyrazol-4-yl)amino)pyrimidin-4-yl)amino)propyl)pyrrolidin-2-one, 1-(3-((5-chloro-2-((3-methyl-1-(2-morpholinoethyl)-1H-pyrazol-4-yl)amino)pyrimidin-4-yl)amino)propyl)pyrrolidin-2-one, (R)-1-(3-((5-bromo-2-((3-methyl-1-(pyrrolidin-3-yl)-1H-pyrazol-4-yl)amino)pyrimidin-4-yl)amino)propyl)pyrrolidin-2-one, 1-(3-((5-bromo-2-((1-(1-isobutylazetidin-3-yl)-1H-pyrazol-4-yl)amino)pyrimidin-4-yl)amino)propyl)pyrrolidin-2-one, 1-(3-((2-((1-(1-methylpiperidin-4-yl)-1H-pyrazol-4-yl)amino)-5-(trifluoromethyl)pyrimidin-4-yl)amino)propyl)pyrrolidin-2-one, (S)-1-(3-((2-((3-methyl-1-(pyrrolidin-3-yl)-1H-pyrazol-4-yl)amino)-5-(trifluoromethyl)pyrimidin-4-yl)amino)propyl)pyrrolidin-2-one, (S)-1-(3-((2-((1-(1-ethylpyrrolidin-3-yl)-3-methyl-1H-pyrazol-4-yl)amino)-5-(trifluoromethyl)pyrimidin-4-yl)amino)propyl)pyrrolidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)pyrrolidin-2-one, 1-(3-((2-((1-(1-isobutylazetidin-3-yl)-1H-pyrazol-4-yl)amino)-5-(trifluoromethyl)pyrimidin-4-yl)amino)propyl)pyrrolidin-2-one, 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanenitrile, 1-(3-((2-((4-methyl-1-(1-methylpiperidin-4-yl)-1H-pyrazol-3-yl)amino)-5-(trifluoromethyl)pyridin-4-yl)amino)propyl)piperidin-2-one, 1-(3-((2-((1-(1-methylpiperidin-4-yl)-1H-pyrazol-3-yl)amino)-5-(trifluoromethyl)pyridin-4-yl)amino)propyl)piperidin-2-one, 4-(3-((2-((1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((2-((1-(1-methylpiperidin-4-yl)-1H-pyrazol-4-yl)amino)-5-(trifluoromethyl)pyrimidin-4-yl)amino)propyl)-1,4-oxazepan-5-one, 3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazinan-2-one, 4-(3-((2-((2-(1-methylpiperidin-4-yl)-2H-1,2,3-triazol-4-yl)amino)-5-(trifluoromethyl)pyrimidin-4-yl)amino)propyl)-1,4-oxazepan-3-one, 4-(3-((2-((2-(1-methylpiperidin-4-yl)-2H-1,2,3-triazol-4-yl)amino)-5-(trifluoromethyl)pyrimidin-4-yl)amino)propyl)-1,4-oxazepan-5-one, 3-(3-((2-((2-(1-methylpiperidin-4-yl)-2H-1,2,3-triazol-4-yl)amino)-5-(trifluoromethyl)pyrimidin-4-yl)amino)propyl)-1,3-oxazinan-2-one, 4-(3-((2-((1-(1-methylpiperidin-4-yl)-1H-1,2,3-triazol-4-yl)amino)-5-(trifluoromethyl)pyrimidin-4-yl)amino)propyl)-1,4-oxazepan-3-one, 4-(3-((2-((1-(1-methylpiperidin-4-yl)-1H-1,2,3-triazol-4-yl)amino)-5-(trifluoromethyl)pyrimidin-4-yl)amino)propyl)-1,4-oxazepan-5-one, 3-(3-((2-((1-(1-methylpiperidin-4-yl)-1H-1,2,3-triazol-4-yl)amino)-5-(trifluoromethyl)pyrimidin-4-yl)amino)propyl)-1,3-oxazinan-2-one, 4-(3-((2-((2-(1-methylpiperidin-4-yl)thiazol-4-yl)amino)-5-(trifluoromethyl)pyrimidin-4-yl)amino)propyl)-1,4-oxazepan-3-one, 4-(3-((2-((2-(1-methylpiperidin-4-yl)thiazol-4-yl)amino)-5-(trifluoromethyl)pyrimidin-4-yl)amino)propyl)-1,4-oxazepan-5-one, 3-(3-((2-((2-(1-methylpiperidin-4-yl)thiazol-4-yl)amino)-5-(trifluoromethyl)pyrimidin-4-yl)amino)propyl)-1,3-oxazinan-2-one, 4-(3-((2-((2-(1-methylpiperidin-4-yl)oxazol-4-yl)amino)-5-(trifluoromethyl)pyrimidin-4-yl)amino)propyl)-1,4-oxazepan-3-one, 4-(3-((2-((2-(1-methylpiperidin-4-yl)oxazol-4-yl)amino)-5-(trifluoromethyl)pyrimidin-4-yl)

amino)propyl)-1,4-oxazepan-5-one, 3-(3-((2-((2-(1-methylpiperidin-4-yl)oxazol-4-yl)amino)-5-(trifluoromethyl)pyrimidin-4-yl)amino)propyl)-1,3-oxazinan-2-one, 4-(3-((2-((2-(4-methylpiperazin-1-yl)thiazol-4-yl)amino)-5-(trifluoromethyl)pyrimidin-4-yl)amino)propyl)-1,4-oxazepan-3-one, 4-(3-((2-((2-(4-methylpiperazin-1-yl)thiazol-4-yl)amino)-5-(trifluoromethyl)pyrimidin-4-yl)amino)propyl)-1,4-oxazepan-5-one, 3-(3-((2-((2-(4-methylpiperazin-1-yl)thiazol-4-yl)amino)-5-(trifluoromethyl)pyrimidin-4-yl)amino)propyl)-1,3-oxazinan-2-one, 4-(3-((2-((2-(4-methylpiperazin-1-yl)oxazol-4-yl)amino)-5-(trifluoromethyl)pyrimidin-4-yl)amino)propyl)-1,4-oxazepan-3-one, 4-(3-((2-((2-(4-methylpiperazin-1-yl)oxazol-4-yl)amino)-5-(trifluoromethyl)pyrimidin-4-yl)amino)propyl)-1,4-oxazepan-5-one, 3-(3-((2-((2-(4-methylpiperazin-1-yl)oxazol-4-yl)amino)-5-(trifluoromethyl)pyrimidin-4-yl)amino)propyl)-1,3-oxazinan-2-one, 4-(3-((2-((2-(4-methylpiperazin-1-yl)thiazol-5-yl)amino)-5-(trifluoromethyl)pyrimidin-4-yl)amino)propyl)-1,4-oxazepan-3-one, 4-(3-((2-((2-(4-methylpiperazin-1-yl)thiazol-5-yl)amino)-5-(trifluoromethyl)pyrimidin-4-yl)amino)propyl)-1,4-oxazepan-5-one, 3-(3-((2-((2-(4-methylpiperazin-1-yl)thiazol-5-yl)amino)-5-(trifluoromethyl)pyrimidin-4-yl)amino)propyl)-1,3-oxazinan-2-one, 4-(3-((2-((2-(4-methylpiperazin-1-yl)oxazol-5-yl)amino)-5-(trifluoromethyl)pyrimidin-4-yl)amino)propyl)-1,4-oxazepan-3-one, 4-(3-((2-((2-(4-methylpiperazin-1-yl)oxazol-5-yl)amino)-5-(trifluoromethyl)pyrimidin-4-yl)amino)propyl)-1,4-oxazepan-5-one, 3-(3-((2-((2-(4-methylpiperazin-1-yl)oxazol-5-yl)amino)-5-(trifluoromethyl)pyrimidin-4-yl)amino)propyl)-1,3-oxazinan-2-one, 4-(3-((2-((2-(1-methylpiperidin-4-yl)thiazol-5-yl)amino)-5-(trifluoromethyl)pyrimidin-4-yl)amino)propyl)-1,4-oxazepan-3-one, 4-(3-((2-((2-(1-methylpiperidin-4-yl)thiazol-5-yl)amino)-5-(trifluoromethyl)pyrimidin-4-yl)amino)propyl)-1,4-oxazepan-5-one, 3-(3-((2-((2-(1-methylpiperidin-4-yl)thiazol-5-yl)amino)-5-(trifluoromethyl)pyrimidin-4-yl)amino)propyl)-1,3-oxazinan-2-one, 4-(3-((2-((2-(1-methylpiperidin-4-yl)oxazol-5-yl)amino)-5-(trifluoromethyl)pyrimidin-4-yl)amino)propyl)-1,4-oxazepan-3-one, 4-(3-((2-((2-(1-methylpiperidin-4-yl)oxazol-5-yl)amino)-5-(trifluoromethyl)pyrimidin-4-yl)amino)propyl)-1,4-oxazepan-5-one, 3-(3-((2-((2-(1-methylpiperidin-4-yl)oxazol-5-yl)amino)-5-(trifluoromethyl)pyrimidin-4-yl)amino)propyl)-1,3-oxazinan-2-one, 4-(3-((2-((5-methyl-2-(1-methylpiperidin-4-yl)-2H-1,2,3-triazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl)-2H-1,2,3-triazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl)-2H-1,2,3-triazol-4-yl)amino)-5-(trifluoromethyl)pyrimidin-4-yl)amino)propyl)-1,3-oxazinan-2-one, 4-(3-((2-((5-methyl-2-(1-methylpiperidin-4-yl)thiazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl)thiazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl)thiazol-4-yl)amino)-5-(trifluoromethyl)pyrimidin-4-yl)amino)propyl)-1,3-oxazinan-2-one, 4-(3-((2-((5-methyl-2-(1-methylpiperidin-4-yl)oxazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl)oxazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl)oxazol-4-yl)amino)-5-(trifluoromethyl)pyrimidin-4-yl)amino)propyl)-1,3-oxazinan-2-one, 4-(3-((2-((5-methyl-2-(4-methylpiperazin-1-yl)thiazol-4-yl)amino)-5-(trifluoromethyl)pyrimidin-4-yl)amino)propyl)-1,4-oxazepan-3-one, 4-(3-((2-((5-methyl-2-(4-methylpiperazin-1-yl)thiazol-4-yl)amino)-5-(trifluoromethyl)pyrimidin-4-yl)amino)propyl)-1,4-oxazepan-5-one, 3-(3-((2-((5-methyl-2-(4-methylpiperazin-1-yl)thiazol-4-yl)amino)-5-(trifluoromethyl)pyrimidin-4-yl)amino)propyl)-1,3-oxazinan-2-one, 4-(3-((2-((5-methyl-2-(4-methylpiperazin-1-yl)oxazol-4-yl)amino)-5-(trifluoromethyl)pyrimidin-4-yl)amino)propyl)-1,4-oxazepan-3-one, 4-(3-((2-((5-methyl-2-(4-methylpiperazin-1-yl)oxazol-4-yl)amino)-5-(trifluoromethyl)pyrimidin-4-yl)amino)propyl)-1,4-oxazepan-5-one, 3-(3-((2-((5-methyl-2-(4-methylpiperazin-1-yl)oxazol-4-yl)amino)-5-(trifluoromethyl)pyrimidin-4-yl)amino)propyl)-1,3-oxazinan-2-one, 4-(3-((2-((4-methyl-2-(4-methylpiperazin-1-yl)thiazol-5-yl)amino)-5-(trifluoromethyl)pyrimidin-4-yl)amino)propyl)-1,4-oxazepan-3-one, 4-(3-((2-((4-methyl-2-(4-methylpiperazin-1-yl)thiazol-5-yl)amino)-5-(trifluoromethyl)pyrimidin-4-yl)amino)propyl)-1,4-oxazepan-5-one, 3-(3-((2-((4-methyl-2-(4-methylpiperazin-1-yl)thiazol-5-yl)amino)-5-(trifluoromethyl)pyrimidin-4-yl)amino)propyl)-1,3-oxazinan-2-one, 4-(3-((2-((4-methyl-2-(4-methylpiperazin-1-yl)oxazol-5-yl)amino)-5-(trifluoromethyl)pyrimidin-4-yl)amino)propyl)-1,4-oxazepan-3-one, 4-(3-((2-((4-methyl-2-(4-methylpiperazin-1-yl)oxazol-5-yl)amino)-5-(trifluoromethyl)pyrimidin-4-yl)amino)propyl)-1,4-oxazepan-5-one, 3-(3-((2-((4-methyl-2-(4-methylpiperazin-1-yl)oxazol-5-yl)amino)-5-(trifluoromethyl)pyrimidin-4-yl)amino)propyl)-1,3-oxazinan-2-one, 4-(3-((2-((4-methyl-2-(1-methylpiperidin-4-yl)thiazol-5-yl)amino)-5-(trifluoromethyl)pyrimidin-4-yl)amino)propyl)-1,4-oxazepan-3-one, 4-(3-((2-((4-methyl-2-(1-methylpiperidin-4-yl)thiazol-5-yl)amino)-5-(trifluoromethyl)pyrimidin-4-yl)amino)propyl)-1,4-oxazepan-5-one, 3-(3-((2-((4-methyl-2-(1-methylpiperidin-4-yl)thiazol-5-yl)amino)-5-(trifluoromethyl)pyrimidin-4-yl)amino)propyl)-1,3-oxazinan-2-one, 4-(3-((2-((4-methyl-2-(1-methylpiperidin-4-yl)oxazol-5-yl)amino)-5-(trifluoromethyl)pyrimidin-4-yl)amino)propyl)-1,4-oxazepan-3-one, 4-(3-((2-((4-methyl-2-(1-methylpiperidin-4-yl)oxazol-5-yl)amino)-5-(trifluoromethyl)pyrimidin-4-yl)amino)propyl)-1,4-oxazepan-5-one, 3-(3-((2-((4-methyl-2-(1-methylpiperidin-4-yl)oxazol-5-yl)amino)-5-(trifluoromethyl)pyrimidin-4-yl)amino)propyl)-1,3-oxazinan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)morpholin-3-one, 1-methyl-3-(3-((2-((3-methyl-1-(1-methylpiperidin-4-yl)-1H-pyrazol-4-yl)amino)-5-(trifluoromethyl)pyrimidin-4-yl)amino)propyl)tetrahydropyrimidin-2(1H)-one, 3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazepan-2-one, 1-methyl-3-(3-((2-((3-methyl-1-(1-methylpiperidin-4-yl)-1H-pyrazol-4-yl)amino)-5-(trifluoromethyl)pyrimidin-4-yl)amino)propyl)-1,3-diazepan-2-one, 1-methyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-diazepan-5-one, 4-methyl-1-(3-((2-((3-methyl-1-(1-methylpiperidin-4-yl)-1H-pyrazol-4-yl)amino)-5-(trifluoromethyl)pyrimidin-4-yl)amino)propyl)-1,4-diazepan-2-one, 1-(3-((2-((3-methyl-1-(8-methyl-8-azabicyclo[3.2.1]octan-3-yl)-1H-pyrazol-4-yl)amino)-5-

(trifluoromethyl)pyrimidin-4-yl)amino)propyl)piperidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azepan-2-one, 4-methyl-1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-diazepan-2-one, 3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-oxazinan-2-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)morpholin-3-one, 1-methyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)tetrahydropyrimidin-2(1H)-one, 3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-oxazepan-2-one, 1-methyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-diazepan-2-one, 1-methyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-diazepan-5-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-3-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-5-one, 1-(3-((2-((3-methyl-1-(1-methylpyrrolidin-3-yl)-1H-pyrazol-4-yl)amino)-5-(trifluoromethyl)pyrimidin-4-yl)amino)propyl)piperidin-2-one, 1-(3-((2-((3-methyl-1-(1-methylpyrrolidin-3-yl)-1H-pyrazol-4-yl)amino)-5-(trifluoromethyl)pyrimidin-4-yl)amino)propyl)azepan-2-one, 4-methyl-1-(3-((2-((3-methyl-1-(1-methylpyrrolidin-3-yl)-1H-pyrazol-4-yl)amino)-5-(trifluoromethyl)pyrimidin-4-yl)amino)propyl)-1,4-diazepan-2-one, 4-(3-((2-((3-methyl-1-(1-methylpyrrolidin-3-yl)-1H-pyrazol-4-yl)amino)-5-(trifluoromethyl)pyrimidin-4-yl)amino)propyl)morpholin-3-one, 1-methyl-3-(3-((2-((3-methyl-1-(1-methylpyrrolidin-3-yl)-1H-pyrazol-4-yl)amino)-5-(trifluoromethyl)pyrimidin-4-yl)amino)propyl)tetrahydropyrimidin-2(1H)-one, 3-(3-((2-((3-methyl-1-(1-methylpyrrolidin-3-yl)-1H-pyrazol-4-yl)amino)-5-(trifluoromethyl)pyrimidin-4-yl)amino)propyl)-1,3-oxazepan-2-one, 1-methyl-3-(3-((2-((3-methyl-1-(1-methylpyrrolidin-3-yl)-1H-pyrazol-4-yl)amino)-5-(trifluoromethyl)pyrimidin-4-yl)amino)propyl)-1,3-diazepan-2-one, 1-methyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-diazepan-5-one, 4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(1-methylpyrrolidin-3-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-5-one, 1-(3-((2-((3-methyl-1-(1-methylpyrrolidin-3-yl)-1H-pyrazol-4-yl)amino)-5-(trifluoromethyl)pyrimidin-4-yl)amino)propyl)azetidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)azetidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(1-methylpyrrolidin-3-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(1-methylpiperidin-4-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azetidin-2-one, 4-(3-((5-(difluoromethyl)-2-((3-methyl-1-(1-methylpiperidin-4-yl)-1H-pyrazol-4-yl)amino)pyrimidin-4-yl)amino)propyl)-1,4-oxazepan-3-one, 4-(3-((5-(difluoromethyl)-2-((3-methyl-1-(1-methylpiperidin-4-yl)-1H-pyrazol-4-yl)amino)pyrimidin-4-yl)amino)propyl)-1,4-oxazepan-5-one, 3-(3-((5-(difluoromethyl)-2-((3-methyl-1-(1-methylpiperidin-4-yl)-1H-pyrazol-4-yl)amino)pyrimidin-4-yl)amino)propyl)-1,3-oxazinan-2-one, 4-(3-((5-(difluoromethyl)-2-((1-(1-methylpiperidin-4-yl)-1H-pyrazol-4-yl)amino)pyrimidin-4-yl)amino)propyl)-1,4-oxazepan-3-one, 4-(3-((5-(difluoromethyl)-2-((1-(1-methylpiperidin-4-yl)-1H-pyrazol-4-yl)amino)pyrimidin-4-yl)amino)propyl)-1,4-oxazepan-5-one, 3-(3-((5-(difluoromethyl)-2-((1-(1-methylpiperidin-4-yl)-1H-pyrazol-4-yl)amino)pyrimidin-4-yl)amino)propyl)-1,3-oxazinan-2-one, 4-(3-((5-(difluoromethyl)-2-((3-methyl-1-(1-methylpiperidin-4-yl)-1H-pyrazol-4-yl)amino)pyrimidin-4-yl)amino)propyl)morpholin-3-one, 1-(3-((5-(difluoromethyl)-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-(difluoromethyl)-2-((3-methyl-1-(1-methylpiperidin-4-yl)-1H-pyrazol-4-yl)amino)pyrimidin-4-yl)amino)propyl)-1,3-oxazepan-2-one, 1-(3-((5-(difluoromethyl)-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-(difluoromethyl)-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-(difluoromethyl)-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl) piperidin-2-one, 1-(3-((5-(difluoromethyl)-2-((3-methyl-1-(8-methyl-8-azabicyclo[3.2.1]octan-3-yl)-1H-pyrazol-4-yl) amino)pyrimidin-4-yl)amino)propyl)azepan-2-one, 1-(3-((5-(difluoromethyl)-2-((3-methyl-1-(8-methyl-8-azabicyclo[3.2.1]octan-3-yl)-1H-pyrazol-4-yl)amino) pyrimidin-4-yl)amino)propyl)-4-methyl-1,4-diazepan-2-one, 3-(3-((5-(difluoromethyl)-2-((3-methyl-1-(8-methyl-8-azabicyclo[3.2.1]octan-3-yl)-1H-pyrazol-4-yl)amino) pyrimidin-4-yl)amino)propyl)-1,3-oxazinan-2-one, 4-(3-((5-(difluoromethyl)-2-((3-methyl-1-(8-methyl-8-azabicyclo[3.2.1]octan-3-yl)-1H-pyrazol-4-yl)amino) pyrimidin-4-yl)amino)propyl)morpholin-3-one, 1-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-3-methyltetrahydropyrimidin-2(1H)-one, 3-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-3-methyl-1,3-diazepan-2-one, 4-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-1-methyl-1,4-diazepan-5-one, 4-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-1,4-oxazepan-3-one, 4-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-1,4-oxazepan-5-one, 3-(3-((5-(difluoromethyl)-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-(difluoromethyl)-2-((3-methyl-1-(1-methylpyrrolidin-3-yl)-1H-pyrazol-4-yl)amino) pyrimidin-4-yl)amino)propyl)-3-methyl-1,3-diazepan-2-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-(difluoromethyl)-2-((3-methyl-1-(1-methylpyrrolidin-3-yl)-1H-pyrazol-4-yl)amino) pyrimidin-4-yl)amino)propyl)-1,4-oxazepan-5-one, 3-(3-((5-(difluoromethyl)-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-(difluoromethyl)-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(1-methylpyrrolidin-3-yl)-1H-pyrazol-4-yl) amino)pyrimidin-4-yl)amino)propyl)-6,6-dimethyl-1,4-oxazepan-5-one, 3-(3-((5-(difluoromethyl)-2-((3-methyl-1-(1-methylpiperidin-4-yl)-1H-pyrazol-4-yl)amino) pyrimidin-4-yl)amino)propyl)-6,6-dimethyl-1,3-oxazinan-2-one, 4-(3-((5-(difluoromethyl)-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-6,6-dimethyl-1,3-oxazinan-2-one, 4-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-2,2-dimethyl-1,4-oxazepan-3-one, 4-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-6,6-dimethyl-1,4-oxazepan-5-one, 1-(3-((5-(difluoromethyl)-2-((3-methyl-1-(1-methylpyrrolidin-3-yl)-1H-pyrazol-4-yl)amino)pyrimidin-4-yl)amino)propyl) azetidin-2-one, 1-(3-((5-(difluoromethyl)-2-((3-methyl-1-(1-methylpiperidin-4-yl)-1H-pyrazol-4-yl)amino) pyrimidin-4-yl)amino)propyl)azetidin-2-one, 1-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)azetidin-2-one, 1-(3-((5-(difluoromethyl)-2-((3-methyl-1-(1-methylpyrrolidin-3-yl)-1H-pyrazol-4-yl) amino)pyrimidin-4-yl)amino)propyl)-3,3-dimethylazetidin-2-one, 1-(3-((5-(difluoromethyl)-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-(difluoromethyl)-2-((3-methyl-1-(8-methyl-8-azabicyclo [3.2.1]octan-3-yl)-1H-pyrazol-4-yl)amino)pyrimidin-4-yl) amino)propyl)-3,3-dimethylazetidin-2-one, 4-(3-((5-bromo-2-((3-methyl-1-(1-methylpiperidin-4-yl)-1H-pyrazol-4-yl) amino)pyrimidin-4-yl)amino)propyl)-1,4-oxazepan-3-one, 4-(3-((5-bromo-2-((3-methyl-1-(1-methylpiperidin-4-yl)-1H-pyrazol-4-yl)amino)pyrimidin-4-yl)amino)propyl)-1,4-oxazepan-5-one, 3-(3-((5-bromo-2-((3-methyl-1-(1-methylpiperidin-4-yl)-1H-pyrazol-4-yl)amino)pyrimidin-4-yl) amino)propyl)-1,3-oxazinan-2-one, 4-(3-((5-bromo-2-((1-(1-methylpiperidin-4-yl)-1H-pyrazol-4-yl)amino) pyrimidin-4-yl)amino)propyl)-1,4-oxazepan-3-one, 4-(3-((5-bromo-2-((1-(1-methylpiperidin-4-yl)-1H-pyrazol-4-yl) amino)pyrimidin-4-yl)amino)propyl)-1,4-oxazepan-5-one, 3-(3-((5-bromo-2-((1-(1-methylpiperidin-4-yl)-1H-pyrazol-4-yl)amino)pyrimidin-4-yl)amino)propyl)-1,3-oxazinan-2-one, 4-(3-((5-bromo-2-((3-methyl-1-(1-methylpiperidin-4-yl)-1H-pyrazol-4-yl)amino)pyrimidin-4-yl)amino)propyl) morpholin-3-one, 1-(3-((5-bromo-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-bromo-2-((3-methyl-1-(1-methylpiperidin-4-yl)-1H-pyrazol-4-yl)amino)pyrimidin-4-yl)amino)propyl)-1,3-oxazepan-2-one, 1-(3-((5-bromo-2-((3-methyl-1-(1-methylpiperidin-4-yl)-1H-pyrazol-4-yl)amino)pyrimidin-4-yl) amino)propyl)-3-methyl-1,3-diazepan-2-one, 4-(3-((5-bromo-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-bromo-2-((3-methyl-1-(1-methylpiperidin-4-yl)-1H-pyrazol-4-yl)amino) pyrimidin-4-yl)amino)propyl)-4-methyl-1,4-diazepan-2-one, 1-(3-((5-bromo-2-((3-methyl-1-(8-methyl-8-azabicyclo [3.2.1]octan-3-yl)-1H-pyrazol-4-yl)amino)pyrimidin-4-yl) amino)propyl)piperidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-bromo-2-((3-methyl-1-(8-methyl-8-azabicyclo[3.2.1]octan-3-yl)-1H-pyrazol-4-yl)amino) pyrimidin-4-yl)amino)propyl)-4-methyl-1,4-diazepan-2-one, 3-(3-((5-bromo-2-((3-methyl-1-(8-methyl-8-azabicyclo [3.2.1]octan-3-yl)-1H-pyrazol-4-yl)amino)pyrimidin-4-yl) amino)propyl)-1,3-oxazinan-2-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl) morpholin-3-one, 1-(3-((5-bromo-2-((3-methyl-1-(8-methyl-8-azabicyclo[3.2.1]octan-3-yl)-1H-pyrazol-4-yl) amino)pyrimidin-4-yl)amino)propyl)-3-methyltetrahydropyrimidin-2(1H)-one, 3-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-bromo-2-((3-methyl-1-(8-methyl- 8-azabicyclo[3.2.1]octan-3-yl)-1H-pyrazol-4-yl)amino) pyrimidin-4-yl)amino)propyl)-3-methyl-1,3-diazepan-2-one, 4-(3-((5-bromo-2-((3-methyl-1-(8-methyl-8-azabicyclo [3.2.1]octan-3-yl)-1H-pyrazol-4-yl)amino)pyrimidin-4-yl) amino)propyl)-1-methyl-1,4-diazepan-5-one, 4-(3-((5-bromo-2-((3-methyl-1-(8-methyl-8-azabicyclo[3.2.1]octan-3-yl)-1H-pyrazol-4-yl)amino)pyrimidin-4-yl)amino) propyl)-1,4-oxazepan-3-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-bromo-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-bromo-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-bromo-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-bromo-2-((3-methyl-1-(1-methylpyrrolidin-3-yl)-1H-pyrazol-4-yl)amino) pyrimidin-4-yl)amino)propyl)-1,4-oxazepan-3-one, 4-(3-((5-bromo-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-bromo-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(1-methylpyrrolidin-3-yl)-1H-pyrazol-4-yl) amino)pyrimidin-4-yl)amino)propyl)-6,6-dimethyl-1,4-oxazepan-5-one, 3-(3-((5-bromo-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(1-methylpiperidin-4-yl)-1H-pyrazol-4-yl)amino) pyrimidin-4-yl)amino)propyl)-6,6-dimethyl-1,4-oxazepan-5-one, 3-(3-((5-bromo-2-((3-methyl-1-(8-methyl-8-azabicyclo[3.2.1]octan-3-yl)-1H-pyrazol-4-yl)amino) pyrimidin-4-yl)amino)propyl)-6,6-dimethyl-1,3-oxazinan-2-one, 4-(3-((5-bromo-2-((3-methyl-1-(8-methyl-8-azabicyclo[3.2.1]octan-3-yl)-1H-pyrazol-4-yl)amino) pyrimidin-4-yl)amino)propyl)-2,2-dimethyl-1,4-oxazepan-3-one, 4-(3-((5-bromo-2-((3-methyl-1-(8-methyl-8-azabicyclo[3.2.1]octan-3-yl)-1H-pyrazol-4-yl)amino) pyrimidin-4-yl)amino)propyl)-6,6-dimethyl-1,4-oxazepan-5-one, 1-(3-((5-bromo-2-((3-methyl-1-(1-methylpyrrolidin-3-yl)-1H-pyrazol-4-yl)amino)pyrimidin-4-yl)amino)propyl) azetidin-2-one, 1-(3-((5-bromo-2-((3-methyl-1-(1-methylpiperidin-4-yl)-1H-pyrazol-4-yl)amino)pyrimidin-4-yl)amino)propyl)azetidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-bromo-2-((3-methyl-1-(1-methylpyrrolidin-3-yl)-1H-pyrazol-4-yl)amino)pyrimidin-4-yl)amino) propyl)-3,3-dimethylazetidin-2-one, 1-(3-((5-bromo-2-((3-methyl-1-(1-methylpiperidin-4-yl)-1H-pyrazol-4-yl)amino) pyrimidin-4-yl)amino)propyl)-3,3-dimethylazetidin-2-one, 1-(3-((5-bromo-2-((3-methyl-1-(8-methyl-8-azabicyclo [3.2.1]octan-3-yl)-1H-pyrazol-4-yl)amino)pyrimidin-4-yl) amino)propyl)-3,3-dimethylazetidin-2-one, 4-(3-((5-chloro-2-((3-methyl-1-(1-methylpiperidin-4-yl)-1H-pyrazol-4-yl) amino)pyrimidin-4-yl)amino)propyl)-1,4-oxazepan-3-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-5-one, 3-(3-((5-chloro-2-((3-methyl-1-(1-methylpiperidin-4-yl)-1H-pyrazol-4-yl)amino)pyrimidin-4-yl) amino)propyl)-1,3-oxazinan-2-one, 4-(3-((5-chloro-2-((1-(1-methylpiperidin-4-yl)-1H-pyrazol-4-yl)amino) pyrimidin-4-yl)amino)propyl)-1,4-oxazepan-3-one, 4-(3-((5-chloro-2-((1-(1-methylpiperidin-4-yl)-1H-pyrazol-4-yl) amino)pyrimidin-4-yl)amino)propyl)-1,4-oxazepan-5-one, 3-(3-((5-chloro-2-((1-(1-methylpiperidin-4-yl)-1H-pyrazol-4-yl)amino)pyrimidin-4-yl)amino)propyl)-1,3-oxazinan-2-one, 4-(3-((5-chloro-2-((3-methyl-1-(1-methylpiperidin-4-yl)-1H-pyrazol-4-yl)amino)pyrimidin-4-yl)amino)propyl) morpholin-3-one, 1-(3-((5-chloro-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-chloro-2-((3-methyl-1-(1-methylpiperidin-4-yl)-1H-pyrazol-4-yl)amino)pyrimidin-4-yl)amino)propyl)-1,3-oxazepan-2-one, 1-(3-((5-chloro-2-((3-methyl-1-(1-methylpiperidin-4-yl)-1H-pyrazol-4-yl)amino)pyrimidin-4-yl) amino)propyl)-3-methyl-1,3-diazepan-2-one, 4-(3-((5-chloro-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-chloro-2-((3-methyl-1-(1-methylpiperidin-4-yl)-1H-pyrazol-4-yl)amino) pyrimidin-4-yl)amino)propyl)-4-methyl-1,4-diazepan-2-one, 1-(3-((5-chloro-2-((3-methyl-1-(8-methyl-8-azabicyclo [3.2.1]octan-3-yl)-1H-pyrazol-4-yl)amino)pyrimidin-4-yl) amino)propyl)piperidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-4-methyl-1,4-diazepan-2-one, 3-(3-((5-chloro-2-((3-methyl-1-(8-methyl-8-azabicyclo [3.2.1]octan-3-yl)-1H-pyrazol-4-yl)amino)pyrimidin-4-yl) amino)propyl)-1,3-oxazinan-2-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl) morpholin-3-one, 1-(3-((5-chloro-2-((3-methyl-1-(8-methyl-8-azabicyclo[3.2.1]octan-3-yl)-1H-pyrazol-4-yl) amino)pyrimidin-4-yl)amino)propyl)-3-methyltetrahydropyrimidin-2(1H)-one, 3-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-3-methyl-1,3-diazepan-2-one, 4-(3-((5-chloro-2-((3-methyl-1-(8-methyl-8-azabicyclo [3.2.1]octan-3-yl)-1H-pyrazol-4-yl)amino)pyrimidin-4-yl) amino)propyl)-1-methyl-1,4-diazepan-5-one, 4-(3-((5-chloro-2-((3-methyl-1-(8-methyl-8-azabicyclo[3.2.1]octan-3-yl)-1H-pyrazol-4-yl)amino)pyrimidin-4-yl)amino) propyl)-1,4-oxazepan-3-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-chloro-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-chloro-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-chloro-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-chloro-2-((3-methyl-1-(1-methylpyrrolidin-3-yl)-1H-pyrazol-4-yl)amino) pyrimidin-4-yl)amino)propyl)-1,4-oxazepan-3-one, 4-(3-((5-chloro-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-chloro-2-((3-methyl-1-(1-methylpyrrolidin-3-yl)-1H-pyrazol-4-yl)amino)pyrimidin- 4-yl)amino)propyl)-6,6-dimethyl-1,3-oxazinan-2-one, 4-(3-((5-chloro-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-chloro-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-chloro-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-chloro-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-chloro-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-chloro-2-((3-methyl-1-(1-methylpyrrolidin-3-yl)-1H-pyrazol-4-yl)amino)pyrimidin-4-yl)amino)propyl)azetidin-2-one, 1-(3-((5-chloro-2-((3-methyl-1-(1-methylpiperidin-4-yl)-1H-pyrazol-4-yl)amino)pyrimidin-4-yl)amino)propyl)azetidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-chloro-2-((3-methyl-1-(1-methylpyrrolidin-3-yl)-1H-pyrazol-4-yl)amino)pyrimidin-4-yl)amino)propyl)-3,3-dimethylazetidin-2-one, 1-(3-((5-chloro-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-3,3-dimethylazetidin-2-one, 2-((3-methyl-1-(1-methylpiperidin-4-yl)-1H-pyrazol-4-yl)amino)-4-((3-(3-oxo-1,4-oxazepan-4-yl)propyl)amino)pyrimidine-5-carbonitrile, 2-((3-methyl-1-(1-methylpiperidin-4-yl)-1H-pyrazol-4-yl)amino)-4-((3-(5-oxo-1,4-oxazepan-4-yl)propyl)amino)pyrimidine-5-carbonitrile, 2-((3-methyl-1-(1-methylpiperidin-4-yl)-1H-pyrazol-4-yl)amino)-4-((3-(2-oxo-1,3-oxazinan-3-yl)propyl)amino)pyrimidine-5-carbonitrile, 2-((1-(1-methylpiperidin-4-yl)-1H-pyrazol-4-yl)amino)-4-((3-(3-oxo-1,4-oxazepan-4-yl)propyl)amino)pyrimidine-5-carbonitrile, 2-((1-(1-methylpiperidin-4-yl)-1H-pyrazol-4-yl)amino)-4-((3-(5-oxo-1,4-oxazepan-4-yl)propyl)amino)pyrimidine-5-carbonitrile, 2-((1-(1-methylpiperidin-4-yl)-1H-pyrazol-4-yl)amino)-4-((3-(2-oxo-1,3-oxazinan-3-yl)propyl)amino)pyrimidine-5-carbonitrile, 2-((3-methyl-1-(1-methylpiperidin-4-yl)-1H-pyrazol-4-yl)amino)-4-((3-(3-oxomorpholino)propyl)amino)pyrimidine-5-carbonitrile, 2-((3-methyl-1-(1-methylpiperidin-4-yl)-1H-pyrazol-4-yl)amino)-4-((3-(3-methyl-2-oxotetrahydropyrimidin-1(2H)-yl)propyl)amino)pyrimidine-5-carbonitrile, 2-((3-methyl-1-(1-methylpiperidin-4-yl)-1H-pyrazol-4-yl)amino)-4-((3-(2-oxo-1,3-oxazepan-3-yl)propyl)amino)pyrimidine-5-carbonitrile, 2-((3-methyl-1-(1-methylpiperidin-4-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(1-methylpiperidin-4-yl)-1H-pyrazol-4-yl)amino)-4-((3-(4-methyl-7-oxo-1,4-diazepan-1-yl)propyl)amino)pyrimidine-5-carbonitrile, 2-((3-methyl-1-(1-methylpiperidin-4-yl)-1H-pyrazol-4-yl)amino)-4-((3-(4-methyl-2-oxo-1,4-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxopiperidin-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxoazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(4-methyl-2-oxo-1,4-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxo-1,3-oxazinan-3-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-oxomorpholino)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-methyl-2-oxotetrahydropyrimidin-1(2H)-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxo-1,3-oxazepan-3-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(4-methyl-7-oxo-1,4-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-oxo-1,4-oxazepan-4-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(5-oxo-1,4-oxazepan-4-yl)propyl)amino)pyrimidine-5-carbonitrile, 2-((3-methyl-1-(1-methylpyrrolidin-3-yl)-1H-pyrazol-4-yl)amino)-4-((3-(2-oxo-1,3-oxazepan-3-yl)propyl)amino)pyrimidine-5-carbonitrile, 2-((3-methyl-1-(1-methylpyrrolidin-3-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(1-methylpyrrolidin-3-yl)-1H-pyrazol-4-yl)amino)-4-((3-(4-methyl-7-oxo-1,4-diazepan-1-yl)propyl)amino)pyrimidine-5-carbonitrile, 2-((3-methyl-1-(1-methylpyrrolidin-3-yl)-1H-pyrazol-4-yl)amino)-4-((3-(3-oxo-1,4-oxazepan-4-yl)propyl)amino)pyrimidine-5-carbonitrile, 2-((3-methyl-1-(1-methylpyrrolidin-3-yl)-1H-pyrazol-4-yl)amino)-4-((3-(5-oxo-1,4-oxazepan-4-yl)propyl)amino)pyrimidine-5-carbonitrile, 4-((3-(6,6-dimethyl-2-oxo-1,3-oxazinan-3-yl)propyl)amino)-2-((3-methyl-1-(1-methylpyrrolidin-3-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(1-methylpyrrolidin-3-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(1-methylpyrrolidin-3-yl)-1H-pyrazol-4-yl)amino)pyrimidine-5-carbonitrile, 4-((3-(6,6-dimethyl-2-oxo-1,3-oxazinan-3-yl)propyl)amino)-2-((3-methyl-1-(1-methylpiperidin-4-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(1-methylpiperidin-4-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(1-methylpiperidin-4-yl)-1H-pyrazol-4-yl)amino)pyrimidine-5-carbonitrile, 4-((3-(6,6-dimethyl-2-oxo-1,3-oxazinan-3-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(8-methyl-8-azabicyclo[3.2.1]octan-3-yl)-1H-pyrazol-4-yl)amino)pyrimidine-5-carbonitrile, 2-((3-methyl-1-(1-methylpyrrolidin-3-yl)-1H-pyrazol-4-yl)amino)-4-((3-(2-oxoazetidin-1-yl)propyl)amino)pyrimidine-5-carbonitrile, 2-((3-methyl-1-(1-methylpiperidin-4-yl)-1H-pyrazol-4-yl)amino)-4-((3-(2-oxoazetidin-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxoazetidin-1-yl)propyl)amino)pyrimidine-5-carbonitrile, 4-((3-(3,3-dimethyl-2-oxoazetidin-1-yl)propyl)amino)-2-((3-methyl-1-(1-methylpyrrolidin-3-yl)-1H-pyrazol-4-yl)amino)pyrimidine-5-carbonitrile, 4-((3-(3,3-dimethyl-2-oxoazetidin-1-yl)propyl)amino)-2-((3-methyl-1-(1-methylpiperidin-4-yl)-1H-pyrazol-4-yl)amino)pyrimidine-5-carbonitrile, 4-((3-(3,3-dimethyl-2-oxoazetidin-1-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpiperidin-4-yl)-1H-pyrazol-4-yl)amino)pyrimidin-4-yl)amino)propyl)-1,3-oxazinan-2-one, 4-(3-((5-cyclopropyl-2-((1-(1-methylpiperidin-4-yl)-1H-pyrazol-4-yl)amino)pyrimidin-4-yl)amino)propyl)-1,4-oxazepan-3-one, 4-(3-((5-cyclopropyl-2-((1-(1-methylpiperidin-4-yl)-1H-pyrazol-4-yl)amino)pyrimidin-4-yl)amino)propyl)-1,4-oxazepan-5-one, 3-(3-((5-cyclopropyl-2-((1-(1-methylpiperidin-4-yl)-1H-pyrazol-4-yl)amino)pyrimidin-4-yl)amino)propyl)-1,3-oxazinan-2-one, 4-(3-((5-cyclopropyl-2-((3-methyl-1-(1-methylpiperidin-4-yl)-1H-pyrazol-4-yl)amino)pyrimidin-4-yl)amino)propyl)morpholin-3-one, 1-(3-((5-cyclopropyl-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-cyclopropyl-2-((3-methyl-1-(1-methylpiperidin-4-yl)-1H-pyrazol-4-yl)amino)pyrimidin-4-yl)amino)propyl)-1,3-oxazepan-2-one, 1-(3-((5-cyclopropyl-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-cyclopropyl-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-cyclopropyl-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-cyclopropyl-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-cyclopropyl-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-cyclopropyl-2-((3-methyl-1-(1-methylpyrrolidin-3-yl)-1H-pyrazol-4-yl)amino)pyrimidin-4-yl)amino)propyl)azetidin-2-one, 1-(3-((5-cyclopropyl-2-((3-methyl-1-(1-methylpiperidin-4-yl)-1H-pyrazol-4-yl)amino)pyrimidin-4-yl)amino)propyl)azetidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-cyclopropyl-2-((3-methyl-1-(1-methylpyrrolidin-3-yl)-1H-pyrazol-4-yl)amino)pyrimidin-4-yl)amino)propyl)-3,3-dimethylazetidin-2-one, 1-(3-((5-cyclopropyl-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3,3-dimethylazetidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)pyrrolidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)pyrrolidin-2-one, 3,3-dimethyl-1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)pyrrolidin-2-one, 1-(3-((2-((3-methyl-1-(1-methylpyrrolidin-3-yl)-1H-pyrazol-4-yl)amino)-5-(trifluoromethyl)pyrimidin-4-yl)amino)propyl)pyrrolidin-2-one, 1-(3-((5-(difluoromethyl)-2-((3-methyl-1-(1-methylpyrrolidin-3-yl)-1H-pyrazol-4-yl)amino)pyrimidin-4-yl)amino)propyl)pyrrolidin-2-one, 3,3-dimethyl-1-(3-((2-((3-methyl-1-(1-methylpyrrolidin-3-yl)-1H-pyrazol-4-yl)amino)-5-(trifluoromethyl)pyrimidin-4-yl)amino)propyl)pyrrolidin-2-one, 1-(3-((2-((1-(1-isobutylazetidin-3-yl)-3-methyl-1H-pyrazol-4-yl)amino)-5-(trifluoromethyl)pyrimidin-4-yl)amino)propyl)pyrrolidin-2-one, 1-(3-((5-(difluoromethyl)-2-((1-(1-isobutylazetidin-3-yl)-3-methyl-1H-pyrazol-4-yl)amino)pyrimidin-4-yl)amino)propyl)pyrrolidin-2-one, 1-(3-((2-((1-(1-isobutylazetidin-3-yl)-3-methyl-1H-pyrazol-4-yl)amino)-5-(trifluoromethyl)pyrimidin-4-yl)amino)propyl)-3,3-dimethylpyrrolidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)pyrrolidin-2-one, 1-(3-((5-bromo-2-((3-methyl-1-(1-methylpyrrolidin-3-yl)-1H-pyrazol-4-yl)amino)pyrimidin-4-yl)amino)propyl)pyrrolidin-2-one, 1-(3-((5-bromo-2-((1-(1-isobutylazetidin-3-yl)-3-methyl-1H-pyrazol-4-yl)amino)pyrimidin-4-yl)amino)propyl)pyrrolidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-3,3-dimethylpyrrolidin-2-one, 1-(3-((5-bromo-2-((3-methyl-1-(1-methylpyrrolidin-3-yl)-1H-pyrazol-4-yl)amino)pyrimidin-4-yl)amino)propyl)-3,3-dimethylpyrrolidin-2-one, 1-(3-((5-bromo-2-((1-(1-isobutylazetidin-3-yl)-3-methyl-1H-pyrazol-4-yl)amino)pyrimidin-4-yl)amino)propyl)-3,3-dimethylpyrrolidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)pyrrolidin-2-one, 1-(3-((5-chloro-2-((3-methyl-1-(1-methylpyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-3-methyl-1H-pyrazol-4-yl)amino)pyrimidin-4-yl)amino)propyl)pyrrolidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-3,3-dimethylpyrrolidin-2-one, 1-(3-((5-chloro-2-((3-methyl-1-(1-methylpyrrolidin-3-yl)-1H-pyrazol-4-yl)amino)pyrimidin-4-yl)amino)propyl)-3,3-dimethylpyrrolidin-2-one, 1-(3-((5-chloro-2-((1-(1-isobutylazetidin-3-yl)-3-methyl-1H-pyrazol-4-yl)amino)pyrimidin-4-yl)amino)propyl)-3,3-dimethylpyrrolidin-2-one, 4-(3-((2-((2-(3-(dimethylamino)propyl)-2H-1,2,3-triazol-4-yl)amino)-5-(trifluoromethyl)pyrimidin-4-yl)amino)propyl)-1,4-oxazepan-3-one, 4-(3-((2-((2-(2-(dimethylamino)ethyl)-2H-1,2,3-triazol-4-yl)amino)-5-(trifluoromethyl)pyrimidin-4-yl)amino)propyl)-1,4-oxazepan-5-one, 3-(3-((2-((5-ethyl-2-(1-methylpiperidin-4-yl)-2H-1,2,3-triazol-4-yl)amino)-5-(trifluoromethyl)pyrimidin-4-yl)amino)propyl)-1,3-oxazinan-2-one, 4-(3-((2-((2-((4-methylpiperazin-1-yl)methyl)thiazol-4-yl)amino)-5-(trifluoromethyl)pyrimidin-4-yl)amino)propyl)-1,4-oxazepan-3-one, 4-(3-((2-((2-(azetidin-1-ylmethyl)thiazol-4-yl)amino)-5-(trifluoromethyl)pyrimidin-4-yl)amino)propyl)-1,4-oxazepan-5-one, N-(1-methylpiperidin-4-yl)-4-((4-((3-(2-oxo-1,3-oxazinan-3-yl)propyl)amino)-5-(trifluoromethyl)pyrimidin-2-yl)amino)thiazole-2-carboxamide, 4-(3-((2-((2-(3-(dimethylamino)propyl)oxazol-4-yl)amino)-5-(trifluoromethyl)pyrimidin-4-yl)amino)propyl)-1,4-oxazepan-3-one, 4-(3-((2-((2-(2-(dimethylamino)ethyl)oxazol-4-yl)amino)-5-(trifluoromethyl)pyrimidin-4-yl)amino)propyl)-1,4-oxazepan-5-one, 3-(3-((2-((2-(4-methylpiperazine-1-carbonyl)oxazol-4-yl)amino)-5-(trifluoromethyl)pyrimidin-4-yl)amino)propyl)-1,3-oxazinan-2-one, 4-(3-((2-((2-(4-(dimethylglycyl)piperazin-1-yl)thiazol-4-yl)amino)-5-(trifluoromethyl)pyrimidin-4-yl)amino)propyl)-1,4-oxazepan-3-one, 4-(3-((2-((2-(methyl(2-(methylsulfonyl)ethyl)amino)thiazol-4-yl)amino)-5-(trifluoromethyl)pyrimidin-4-yl)amino)propyl)-1,4-oxazepan-5-one, 3-(3-((2-((2-(1,1-dioxidothiomorpholino)thiazol-4-yl)amino)-5-(trifluoromethyl)pyrimidin-4-yl)amino)propyl)-1,3-oxazinan-2-one, 4-(3-((2-((2-morpholinooxazol-4-yl)amino)-5-(trifluoromethyl)pyrimidin-4-yl)amino)propyl)-1,4-oxazepan-5-one, 3-(3-((2-((2-(methyl(2-(pyrrolidin-1-yl)ethyl)amino)oxazol-4-yl)amino)-5-(trifluoromethyl)pyrimidin-4-yl)amino)propyl)-1,3-oxazinan-2-one, 4-(3-((2-((2-((dimethylamino)methyl)oxazol-5-yl)amino)-5-(trifluoromethyl)pyrimidin-4-yl)amino)propyl)-1,4-oxazepan-3-one, 4-(3-((2-((2-((2-(dimethylamino)ethyl)(methyl)amino)oxazol-5-yl)amino)-5-(trifluoromethyl)pyrimidin-4-yl)amino)propyl)-1,4-oxazepan-5-one, 2-(dimethylamino)-N-methyl-N-(5-((4-((3-(2-oxo-1,3-oxazinan-3-yl)propyl)amino)-5-(trifluoromethyl)pyrimidin-2-yl)amino)oxazol-2-yl)acetamide, 1-(3-((2-((1-(1-(dimethylglycyl)pyrrolidin-3-yl)-3-methyl-1H-pyrazol-4-yl)amino)-5-(trifluoromethyl)pyrimidin-4-yl)amino)propyl)-3,3-dimethylazetidin-2-one, 3,3-dimethyl-1-(3-((2-((5-methyl-2-(1-methylpiperidin-4-yl)-2H-1,2,3-triazol-4-yl)amino)-5-(trifluoromethyl)pyrimidin-4-yl)amino)propyl)azetidin-2-one, 4-(3-((2-((1-(3-(dimethylamino)propyl)-1H-pyrazol-4-yl)amino)-5-(trifluoromethyl)pyrimidin-4-yl)amino)propyl)-1,4-oxazepan-3-one, 4-(3-((2-((1-(3-(pyrrolidin-1-yl)propyl)-1H-pyrazol-4-yl)amino)-5-(trifluoromethyl)pyrimidin-4-yl)amino)propyl)-1,4-oxazepan-5-one, 3-(3-((2-((3-methyl-1-(2-morpholinoethyl)-1H-pyrazol-4-yl)amino)-5-(trifluoromethyl)pyrimidin-4-yl)amino)propyl)-1,3-oxazinan-2-one, 4-(3-((2-((3-fluoro-1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((2-((1-(1-methylpiperidin-4-yl)-3-(trifluoromethyl)-1H-pyrazol-4-yl)amino)-5-(trifluoromethyl)pyrimidin-4-yl)amino)propyl)-1,4-oxazepan-5-one, 3-(3-((2-((3-methoxy-1-(1-methylpiperidin-4-yl)-1H-pyrazol-4-yl)amino)-5-(trifluoromethyl)pyrimidin-4-yl)amino)propyl)-1,3-oxazinan-2-one, 1-(1-methylpiperidin-4-yl)-4-((4-((3-(2-oxopiperidin-1-yl)propyl)amino)-5-(trifluoromethyl)pyrimidin-2-yl)amino)-1H-pyrazole-3-carbonitrile, 4-(3-((2-((3-ethynyl-1-(1-methylpiperidin-4-yl)-1H-pyrazol-4-yl)amino)-5-(trifluoromethyl)pyrimidin-4-yl)amino)propyl)-1,4-oxazepan-3-one, 3-(3-((2-((1-(1-methylpiperidin-4-yl)-3-vinyl-1H-pyrazol-4-yl)amino)-5-(trifluoromethyl)pyrimidin-4-yl)amino)propyl)-1,3-oxazinan-2-one, 4-(3-((2-((3-cyclopropyl-1-(1-methylpiperidin-4-yl)-1H-pyrazol-4-yl)amino)-5-(trifluoromethyl)pyrimidin-4-yl)amino)propyl)-1,4-oxazepan-5-one, 8-(3-((2-((3-methyl-1-(1-methylpiperidin-4-yl)-1H-pyrazol-4-yl)amino)-5-(trifluoromethyl)pyrimidin-4-yl)amino)propyl)-4-oxa-8-azaspiro[2.6]nonan-9-one, 8-(3-((2-((3-methyl-1-(1-methylpiperidin-4-yl)-1H-pyrazol-4-yl)amino)-5-(trifluoromethyl)pyrimidin-4-yl)amino)propyl)-5-oxa-8-azaspiro[2.6]nonan-9-one, 9-(3-((2-

((3-methyl-1-(1-methylpiperidin-4-yl)-1H-pyrazol-4-yl)amino)-5-(trifluoromethyl)pyrimidin-4-yl)amino)propyl)-5-oxa-9-azaspiro[3.6]decan-10-one, 9-(3-((2-((3-methyl-1-(1-methylpiperidin-4-yl)-1H-pyrazol-4-yl)amino)-5-(trifluoromethyl)pyrimidin-4-yl)amino)propyl)-6-oxa-9-azaspiro[3.6]decan-10-one, 4-(3-((2-((3-methyl-1-(1-methylpiperidin-4-yl)-1H-pyrazol-4-yl)amino)-5-(trifluoromethyl)pyridin-4-yl)amino)propyl)-1,4-oxazepan-5-one, 4-(3-((2-((3-methyl-1-(1-methylpiperidin-4-yl)-1H-pyrazol-4-yl)amino)-5-(trifluoromethyl)pyridin-4-yl)amino)propyl)-1,4-oxazepan-3-one, 3-(3-((2-((3-methyl-1-(1-methylpiperidin-4-yl)-1H-pyrazol-4-yl)amino)-5-(trifluoromethyl)pyridin-4-yl)amino)propyl)-1,3-oxazepan-2-one, 3-(3-((2-((3-methyl-1-(1-methylpiperidin-4-yl)-1H-pyrazol-4-yl)amino)-5-(trifluoromethyl)pyridin-4-yl)amino)propyl)-1,3-oxazinan-2-one, 2,2-dimethyl-4-(3-((2-((3-methyl-1-(1-methylpiperidin-4-yl)-1H-pyrazol-4-yl)amino)-5-(trifluoromethyl)pyridin-4-yl)amino)propyl)-1,4-oxazepan-3-one, 4-(3-((5-(difluoromethyl)-2-((3-methyl-1-(1-methylpiperidin-4-yl)-1H-pyrazol-4-yl)amino)pyridin-4-yl)amino)propyl)-1,4-oxazepan-5-one, 3-(3-((5-chloro-2-((3-methyl-1-(1-methylpiperidin-4-yl)-1H-pyrazol-4-yl)amino)pyridin-4-yl)amino)propyl)-1,3-oxazinan-2-one, 4-(3-((2-((5-methyl-2-(1-methylpiperidin-4-yl)-2H-1,2,3-triazol-4-yl)amino)-5-(trifluoromethyl)pyridin-4-yl)amino)propyl)-1,4-oxazepan-3-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-5-one, 4-(3-((2-((1-(2-(dimethylamino)ethyl)-3-methyl-1H-pyrazol-4-yl)amino)-5-(trifluoromethyl)pyridin-4-yl)amino)propyl)-1,4-oxazepan-5-one, (S)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 1-methyl-3-(3-((2-((3-methyl-1-(1-methylpiperidin-4-yl)-1H-pyrazol-4-yl)amino)-5-(trifluoromethyl)pyridin-4-yl)amino)propyl)tetrahydropyrimidin-2(1H)-one, 1-methyl-3-(3-((2-((3-methyl-1-(1-methylpiperidin-4-yl)-1H-pyrazol-4-yl)amino)-5-(trifluoromethyl)pyridin-4-yl)amino)propyl)-1,3-diazepan-2-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 4-(3-((2-((1-(1-((dimethylamino)methyl)azetidin-3-yl)-3-methyl-1H-pyrazol-4-yl)amino)-5-(trifluoromethyl)pyrimidin-4-yl)amino)propyl)-1,4-oxazepan-5-one, 4-(3-((2-((5-methyl-2-(1-methylpiperidin-4-yl)thiazol-4-yl)amino)-5-(trifluoromethyl)pyridin-4-yl)amino)propyl)-1,4-oxazepan-3-one, 4-(3-((2-((2-(1-methylpiperidin-4-yl)thiazol-4-yl)amino)-5-(trifluoromethyl)pyridin-4-yl)amino)propyl)-1,4-oxazepan-3-one, 4-(3-((2-((2-(1-methylpiperidin-4-yl)oxazol-4-yl)amino)-5-(trifluoromethyl)pyridin-4-yl)amino)propyl)-1,4-oxazepan-5-one, 4-(3-((2-((5-methyl-2-(4-methylpiperazin-1-yl)thiazol-4-yl)amino)-5-(trifluoromethyl)pyridin-4-yl)amino)propyl)-1,4-oxazepan-3-one, 4-(3-((2-((2-(4-methylpiperazin-1-yl)thiazol-4-yl)amino)-5-(trifluoromethyl)pyridin-4-yl)amino)propyl)-1,4-oxazepan-3-one, 4-(3-((2-((3-ethyl-1-(1-methylpiperidin-4-yl)-1H-pyrazol-4-yl)amino)-5-(trifluoromethyl)pyridin-4-yl)amino)propyl)-1,4-oxazepan-5-one, 4-(3-((5-chloro-2-((3-ethyl-1-(1-methylpiperidin-4-yl)-1H-pyrazol-4-yl)amino)pyridin-4-yl)amino)propyl)-1,4-oxazepan-5-one, 4-(3-((2-((3-methoxy-1-(1-methylpiperidin-4-yl)-1H-pyrazol-4-yl)amino)-5-(trifluoromethyl)pyridin-4-yl)amino)propyl)-1,4-oxazepan-3-one, 4-(3-((2-((1-(1-methylpiperidin-4-yl)-3-vinyl-1H-pyrazol-4-yl)amino)-5-(trifluoromethyl)pyridin-4-yl)amino)propyl)-1,4-oxazepan-5-one, 1-((3-methyl-4-((4-((3-(5-oxo-1,4-oxazepan-4-yl)propyl)amino)-5-(trifluoromethyl)pyridin-2-yl)amino)-1H-pyrazol-1-yl)methyl)cyclopropane-1-carbonitrile, 2-methyl-2-(3-methyl-4-((4-((3-(5-oxo-1,4-oxazepan-4-yl)propyl)amino)-5-(trifluoromethyl)pyridin-2-yl)amino)-1H-pyrazol-1-yl)propanenitrile, 6-((3-methyl-1-(1-methylpiperidin-4-yl)-1H-pyrazol-4-yl)amino)-4-((3-(5-oxo-1,4-oxazepan-4-yl)propyl)amino)nicotinonitrile, 4-(3-((5-cyclopropyl-2-((3-methyl-1-(1-methylpiperidin-4-yl)-1H-pyrazol-4-yl)amino)pyridin-4-yl)amino)propyl)-1,4-oxazepan-5-one, 4-(3-((2-((1-(1-ethylpiperidin-4-yl)-3-methyl-1H-pyrazol-4-yl)amino)-5-(trifluoromethyl)pyridin-4-yl)amino)propyl)-1,4-oxazepan-5-one, 1-(1-methylpiperidin-4-yl)-4-((4-((3-(5-oxo-1,4-oxazepan-4-yl)propyl)amino)-5-(trifluoromethyl)pyridin-2-yl)amino)-1H-pyrazole-3-carbonitrile, 4-(3-((2-((2-(1-methylpiperidin-4-yl)-2H-1,2,3-triazol-4-yl)amino)-5-(trifluoromethyl)pyridin-4-yl)amino)propyl)-1,4-oxazepan-3-one, 4-(3-((5-(difluoromethyl)-2-((2-(1-methylpiperidin-4-yl)-2H-1,2,3-triazol-4-yl)amino)pyridin-4-yl)amino)propyl)-1,4-oxazepan-3-one, 3-(3-((2-((2-(1-methylpiperidin-4-yl)oxazol-4-yl)amino)-5-(trifluoromethyl)pyridin-4-yl)amino)propyl)-1,3-oxazinan-2-one, 1-(3-((2-((3-methyl-1-(1-methylpiperidin-4-yl)-1H-pyrazol-4-yl)amino)-5-(trifluoromethyl)pyridin-4-yl)amino)propyl)pyrrolidin-2-one, 1-(3-((2-((3-methyl-1-(1-methylpiperidin-4-yl)-1H-pyrazol-4-yl)amino)-5-(trifluoromethyl)pyridin-4-yl)amino)propyl)piperidin-2-one, 1-(3-((2-((3-methyl-1-(1-methylpiperidin-4-yl)-1H-pyrazol-4-yl)amino)-5-(trifluoromethyl)pyridin-4-yl)amino)propyl)azetidin-2-one, 2-methyl-2-(3-methyl-4-((4-((3-(5-oxo-1,4-oxazepan-4-yl)propyl)amino)-5-(trifluoromethyl)pyridin-2-yl)amino)-1H-pyrazol-1-yl)propanamide, 4-(3-((2-((2-(4-(dimethylglycyl)piperazin-1-yl)-5-methylthiazol-4-yl)amino)-5-(trifluoromethyl)pyrimidin-4-yl)amino)propyl)-1,4-oxazepan-3-one, 4-(3-((2-((5-methyl-2-(methyl(2-(methylsulfonyl)ethyl)amino)thiazol-4-yl)amino)-5-(trifluoromethyl)pyrimidin-4-yl)amino)propyl)-1,4-oxazepan-5-one, 3-(3-((2-((2-(1,1-dioxidothiomorpholino)-5-methylthiazol-4-yl)amino)-5-(trifluoromethyl)pyrimidin-4-yl)amino)propyl)-1,3-oxazinan-2-one, 1-(1-methylpiperidin-4-yl)-4-((4-((3-(3-oxo-1,4-oxazepan-4-yl)propyl)amino)-5-(trifluoromethyl)pyrimidin-2-yl)amino)-1H-pyrazole-3-carbonitrile, 4-(3-((5-(difluoromethyl)-2-((3-methyl-1-(piperidin-4-yl)-1H-pyrazol-4-yl)amino)pyrimidin-4-yl)amino)propyl)-1,4-oxazepan-5-one, 3-(3-((5-(difluoromethyl)-2-((3-methyl-1-(piperidin-4-yl)-1H-pyrazol-4-yl)amino)pyrimidin-4-yl)amino)propyl)-1,3-oxazinan-2-one, 1-methyl-4-(3-((2-((3-methyl-1-(piperidin-4-yl)-1H-pyrazol-4-yl)amino)-5-(trifluoromethyl)pyrimidin-4-yl)amino)propyl)-1,4-diazepan-5-one, and 4-methyl-1-(3-((2-((3-methyl-1-(piperidin-4-yl)-1H-pyrazol-4-yl)amino)-5-(trifluoromethyl)pyrimidin-4-yl)amino)propyl)-1,4-diazepan-2-one, or pharmaceutically acceptable salts, enantiomers, stereoisomers, or tautomers thereof.

Methods of Treatment

Compounds described herein can act as inhibitors of autophagy useful in the treatment of a disorder in a patient in need thereof. The disorder, for example, can be a tumor, e.g., a solid tumor. The disorder may also be cancer.

Exemplary disorders also include gastrointestinal stromal tumors, esophageal cancer, gastric cancer, melanomas, gliomas, glioblastomas, ovarian cancer, bladder cancer, pancreatic cancer, prostate cancer, lung cancers, breast cancers, renal cancers, hepatic cancers, osteosarcomas, multiple myelomas, cervical carcinomas, cancers that are metastatic to bone, papillary thyroid carcinoma, non-small cell lung cancer, and colorectal cancers, A cancer treated by the methods described herein may be a metastatic cancer.

In some embodiments, the compounds described herein are useful for the treatment of cancers caused by RAS mutation. In some embodiments, the cancer is caused by a KRAS mutation. In some embodiments, the cancer has additional mutations in tumor suppressor proteins, including mutations in TP53, PTEN, CDN2A/INK4A, p16, or STAG2. In some embodiments, these additional mutations occur in one or more of TP53, PTEN, CDN2A/INK4A, p16, or STAG2. In some embodiments, the cancer is pancreatic ductal adenocarcinoma. In some embodiments, the cancer is lung cancer. In some embodiments, the cancer is colorectal.

In some embodiments, determination of cellular inhibition of autophagy by compounds described herein is determined by monitoring of autophagic flux, for instance by monitoring inhibition of autophagy-mediated clearance of mCherry/GFP-LC3 fusion protein. In some embodiments, determination of cellular inhibition of autophagy by compounds described herein is determined by monitoring of accumulation of autophagic proteins such as p62 or LC-3. In some embodiments, determination of cellular inhibition of autophagy by compounds described herein is determined by decreased clearance of luciferase-tagged LC3 protein. In some embodiments, determination of cellular inhibition of autophagy by compounds described herein is determined by monitoring decreases in cellular autophagosomes, for instance by measurement of fluorescent puncta with the autophagosome marker Cyto-ID.

In some embodiments, cellular inhibition of ULK kinase by compounds described herein is determined by inhibition of phosphorylation of cellular ULK substrates including ATG13, ATG14, Beclin 1, or STING either in tumor cells or in non-tumor host tissues. In some embodiments, cellular inhibition of ULK kinase by compounds described herein is determined in host tissues including immune cells.

In some embodiments, in vivo inhibition of autophagy by compounds described herein is determined by inhibition of phosphorylation of cellular ULK substrates including ATG13, ATG14, Beclin 1, or STING either in tumor cells or in non-tumor host tissues. In some embodiments, in vivo inhibition of ULK kinase by compounds described herein is determined in host tissues including immune cells. In some embodiments, the in vivo inhibition of autophagic flux by compounds described herein can be used as a pharmacodynamic model for monitoring the kinetics and extent of such ULK inhibition. In some embodiments, tin vivo inhibition of ULK kinase by compounds described herein is determined in pancreatic cancer-bearing animals. In some embodiments, in vivo inhibition of ULK kinase by compounds described herein is determined in lung cancer-bearing animals. In some embodiments, in vivo inhibition of ULK kinase is determined in colorectal cancer-bearing animals. In some embodiments, in vivo inhibition of autophagy by compounds described herein is determined by inhibition of autophagic flux in tumor cells, or in non-tumor host tissues by monitoring inhibition of autophagosome formation, or by accumulation of autophagic proteins such as p62 or LC-III. In some embodiments, in vivo inhibition of autophagy is determined in host tissues including immune cells. In some embodiments, the in vivo inhibition of autophagic flux can be used as a pharmacodynamic model for monitoring the kinetics and extent of such ULK inhibition.

In some embodiments, inhibition of autophagy and anti-tumor activity by compounds described herein are evaluated in xenograft studies utilizing human RAS mutant cell lines in immunocompromised mice, for instance in SCID or nude mice. In some embodiments, inhibition of autophagy and anti-tumor activity by compounds described herein are evaluated in xenograft studies utilizing human RAS mutant patient-derived tumor xenografts (PDXs) in immunocompromised mice, for instance in SCID or nude mice. In some embodiments, xenograft studies include evaluation of compounds described herein in pancreatic cancer models. In some embodiments, inhibition of autophagy and anti-tumor activity by compounds described herein are evaluated in syngeneic murine genetically engineered models (GEMs) of mutant RAS cancers. In some embodiments, inhibition of autophagy and anti-tumor activity by compounds described herein are evaluated in the murine GEM syngeneic orthotopic pancreatic cancer model known as the KPC model (LSL-Kras$^{G12D/+}$; LSL-Trp53$^{R172H/+}$; Pdx-1-Cre) or variants of the KPC model.

In some embodiments, compounds described herein will be evaluated in xenograft or GEM cancer models in combination with a MEK inhibitor. In some embodiments, compounds described herein will be evaluated in xenograft or GEM cancer models in combination with a RAF inhibitor. In some embodiments, compounds described herein will be evaluated in xenograft or GEM cancer models in combination with an ERK inhibitor. In some embodiments, compounds described herein will be evaluated in xenograft or GEM cancer models in combination with a RAS G12C direct inhibitor.

In some embodiments, inhibition of autophagy and anti-tumor activity by compounds described herein is evaluated in immunocompetent murine cancer models to assess an immunomodulatory component to the mechanism of action of ULK inhibitors. In some embodiments, the immunocompetent murine model is the murine GEM syngeneic orthotopic pancreatic cancer model known as the KPC model (LSL-Kras$^{G12D/+}$; LSL-Trp53$^{R172H/+}$; Pdx-1-Cre) or variants of the KPC model. In some embodiments, immunomodulatory properties of compounds described herein are evaluated in combination with a MEK inhibitor. In some embodiments, immunomodulatory properties of compounds described herein are evaluated in combination with a RAF inhibitor. In some embodiments, immunomodulatory properties of compounds described herein are evaluated in combination with an ERK inhibitor. In some embodiments, immunomodulatory properties of compounds described herein are evaluated in combination with a RAS G12C direct inhibitor.

In some embodiments, the immunomodulatory component of ULK inhibition is an enhanced innate immune response. In some embodiments, the immunomodulatory component of ULK inhibition is an enhanced adaptive immune response. In some embodiments, the immunomodulatory component of ULK inhibition is an enhanced activity of antigen-presenting cells. In some embodiments, the immunomodulatory component of ULK inhibition is an enhanced anti-tumor activity of myeloid cells including macrophages. In some embodiments, the immunomodulatory component of ULK inhibition is an enhanced anti-tumor activity of Natural Killer cells. In some embodiments, the immunomodulatory component of ULK inhibition is an enhanced activity of effector T Cells, including cytotoxic T Cells.

In some embodiments, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a phospho-ATG13 antibody ELISA assay to detect inhibition of ULK kinase activity, e.g., based on the level of phospho-ATG13 in the sample. In some embodiments, a contemplated method comprises optionally contacting a sample obtained from the patient (including but not limited to a tumor, blood, saliva, or tissue) prior to administration of the compound with a phospho-ATG13 antibody ELISA assay, and comparing the level of phospho-ATG13 in the sample obtained prior to administration with the level of phospho-ATG13 in the sample obtained during or after the course of administration. In some embodiments, the phospho-ATG13 is p-S318ATG13.

In some embodiments, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a phospho-ATG14 antibody ELISA assay to detect inhibition of ULK kinase activity, e.g., based on the level of phospho-ATG14 in the sample. In some embodiments, a contemplated method comprises optionally contacting a sample obtained from the patient (including but not limited to a tumor, blood, saliva, or tissue) prior to administration of the compound with a phospho-ATG14 antibody ELISA assay, and comparing the level of phospho-ATG14 in the sample obtained prior to administration with the level of phospho-ATG14 in the sample obtained during or after the course of administration. In some embodiments, the phospho-ATG14 is p-ATG14 Ser29.

In some embodiments, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a p62 antibody ELISA assay to detect inhibition of ULK kinase activity, e.g., based on the level of p62 in the sample. In some embodiments, a contemplated method comprises optionally contacting a sample obtained from the patient (including but not limited to a tumor, blood, saliva, or tissue) prior to administration of the compound with a p62 antibody ELISA assay, and comparing the level of p62 in the sample obtained prior to administration with the level of p62 in the sample obtained during or after the course of administration.

In some embodiments, provided herein is a method of treating a disorder described herein that includes: administering a therapeutically effective amount of compound described herein in a patient in need thereof, and during or after the course of administration (e.g., at discrete time points, such as one week, two weeks, or on month after initial administration of a contemplated compound) detecting the engagement of the compound with an ULK kinase, wherein detecting comprises contacting a sample obtained from the patient (including but not limited to a tumor, blood, saliva, or tissue) with a pBeclin antibody ELISA assay to detect inhibition of ULK kinase activity, e.g., based on the level of pBeclin in the sample. In some embodiments, a contemplated method comprises optionally contacting a sample obtained from the patient (including but not limited to a tumor, blood, saliva, or tissue) prior to administration of the compound with a pBeclin antibody ELISA assay, and comparing the level of pBeclin in the sample obtained prior to administration with the level of pBeclin in the sample obtained during or after the course of administration.

The compounds provided herein may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound provided herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result is achieved.

Combination Therapy

Compounds described herein, e.g., a compound of Formula I as defined herein, can be administered in combination with one or more additional therapeutic agents to treat a disorder described herein, such as cancer. For example, provided in the present disclosure is a pharmaceutical composition comprising a compound described herein, e.g., a compound of Formula I as defined herein, one or more additional therapeutic agents, and a pharmaceutically acceptable excipient. In some embodiments, a compound of Formula I as defined herein and one additional therapeutic agent is administered. In some embodiments, a compound of Formula I as defined herein and two additional therapeutic agents are administered. In some embodiments, a compound of Formula I as defined herein and three additional therapeutic agents are administered. Combination therapy can be achieved by administering two or more therapeutic agents, each of which is formulated and administered separately. For example, a compound of Formula I as defined herein and an additional therapeutic agent can be formulated and administered separately. Combination therapy can also be achieved by administering two or more therapeutic agents in a single formulation, for example a pharmaceutical composition comprising a compound of Formula I as one therapeutic agent and one or more additional therapeutic agents such as a MAPKAP pathway inhibitor or chemotherapeutic agent. For example, a compound of Formula I as defined herein and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X—Y—X, X—X—Y, Y—X—Y, Y—Y—X, X—X—Y—Y, etc.

In some embodiments, the one or more additional therapeutic agents that may be administered in combination with a compound provided herein can be a MAPKAP pathway inhibitor. Such MAPKAP pathway inhibitors include, for example, MEK inhibitors, ERK inhibitors, RAF inhibitors, and Ras inhibitors.

Exemplary MEK inhibitors include, but are not limited to, trametinib, selumetinib, cobimetinib, binimetinib, and pharmaceutically acceptable salts thereof. Exemplary ERK inhibitors include, but are not limited to, include, but are not limited to, ulixertinib, SCH772984, LY3214996, ravoxertinib, VX-11e, and pharmaceutically acceptable salts thereof. Exemplary RAF inhibitors include, but are not limited to, LY3009120, LXH254, RAF709, dabrafenib, vemurafenib, and pharmaceutically acceptable salts thereof. Exemplary Ras inhibitors include, but are not limited to, AMG-510, MRTX849, and pharmaceutically acceptable salts thereof.

The compounds described herein may be administered in combination with other therapeutic agents known to treat cancers. Such other therapeutic agents include radiation therapy, anti-tubulin agents, DNA alkylating agents, DNA synthesis-inhibiting agents, DNA intercalating agents, anti-estrogen agents, anti-androgens, steroids, anti-EGFR agents, kinase inhibitors, mTOR inhibitors, PI3 kinase inhibitors, cyclin-dependent kinase inhibitors, CD4/CD6 kinase inhibitors, topoisomerase inhibitors, Histone Deacetylase (HDAC) inhibitors, DNA methylation inhibitors, anti-HER2 agents, anti-angiogenic agents, proteasome inhibitors, thalidomide, lenalidomide, antibody-drug-conjugates (ADCs), immunotherapeutic agents including immunomodulating agents, targeted therapeutic agents cancer vaccines, and CAR-T cell therapy.

In some embodiments, the additional therapeutic agents can be chemotherapeutic agents including but not limited to an anti-tubulin agents (for example, paclitaxel, paclitaxel protein-bound particles for injectable suspension including nab-paclitaxel, eribulin, docetaxel, ixabepilone, vincristine, auristatins, or maytansinoids), vinorelbine, DNA-alkylating agents (including cisplatin, carboplatin, oxaliplatin, cyclophosphamide, ifosfamide, temozolomide), DNA intercalating agents or DNA topoisomerase inhibitors (including anthracyclines such as doxorubicin, pegylated liposomal doxorubicin, daunorubicin, idarubicin, mitoxantrone, or epirubicin, camptothecins such as topotecan, irinotecan, or exatecan), 5-fluorouracil, capecitabine, cytarabine, decitabine, 5-aza cytadine, gemcitabine and methotrexate.

In some other embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, sunitinib, pazopanib, sorafenib, regorafenib, sunitinib, axitinib, dasatinib, imatinib, nilotinib, idelalisib, ibrutinib, BLU-667, Loxo 292, larotrectinib, and quizartinib, anti-estrogen agents including but not limited to tamoxifen, fulvestrant, anastrozole, letrozole, and exemestane, anti-androgen agents including but not limited to abiraterone acetate, enzalutamide, nilutamide, bicalutamide, flutamide, cyproterone acetate, steroid agents including but not limited to prednisone and dexamethasone, PARP inhibitors including but not limited to neraparib, olaparib, talazoparib, and rucaparib, topoisomerase I inhibitors including but not limited to irinotecan, camptothecin, exatecan, and topotecan, topoisomerase II inhibitors including but not limited to anthracyclines, etoposide, etoposide phosphate, and mitoxantrone, Histone Deacetylase (HDAC) inhibitors including but not limited to vorinostat, romidepsin, panobinostat, valproic acid, and belinostat, DNA methylation inhibitors including but not limited to DZNep and 5-aza-2'-deoxycytidine, proteasome inhibitors including but not limited to bortezomib and carfilzomib, thalidomide, lenalidomide, pomalidomide, biological agents including but not limited to trastuzumab, ado-trastuzumab, pertuzumab, cetuximab, panitumumab, ipilimumab, tremelimumab, anti-PD-1 agents including pembrolizumab, nivolumab, pidilizumab, and cemiplimab, anti-PD-L1 agents including atezolizumab, avelumab, durvalumab and BMS-936559, anti-angiogenic agents including bevacizumab and aflibercept, and antibody-drug-conjugates (ADCs) including DM1, DM4, MMAE, MMAF, or camptothecin payloads, brentuximab vedotin and trastuzumab emtansine, radiotherapy, therapeutic vaccines including but not limited to sipuleucel-T.

In some embodiments, the additional therapeutic agents can be immunomodulatory agents including but not limited to anti-PD-1 or anti-PDL-1 therapeutics including pembrolizumab, nivolumab, atezolizumab, durvalumab, BMS-936559, or avelumab, anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or R07009789, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles, anthracyclines including but not limited to doxorubicin or mitoxanthrone, hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone.

In some embodiments, the additional therapeutic agent is selected from a luteinizing hormone-releasing hormone (LHRH) analog, including goserelin and leuprolide.

In some embodiments, the additional therapeutic agent is selected from the group consisting of selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, of atumtunab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)-ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser (Bu t) 6, Azgly 10] (pyro-Glu-His-Trp-Ser-Tyr-D-Ser(Bu t)-Leu-Arg-Pro-Azgly-$NH_2$ acetate[$C_{54}H_{84}N_{18}O_4$—$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutanide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, spegfilgrastim, erythropoietin, epoetin alfa and darbepoetin alfa, ipilumumab, vemurafenib, and mixtures thereof.

Pharmaceutical Compositions and Kits

Another aspect of this disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which contains one or more of the compound described herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound provided herein, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another aspect, provided are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5.

Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methylacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives described herein.

Advantageously, provided herein are kits for use by a e.g. a consumer in need of treatment of cancer. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

The following abbreviation are used in this disclosure and have the following definitions: "ADP" is adenosine diphosphate, "Boc" is t-butylcarbonate, "CDI" is carbodiimidazole, "conc." is concentrated, "$Cs_2CO_3$" is cesium carbonate, "CuI" is copper (I) iodide, "DBU" is 1,8-diazabicyclo [5.4.0]undec-7-ene, "DCC" is N,N'-Dicyclohexylcarbodiimide, "DCE" is dichloroethane, "DCM" is dichloromethane, "DIEA" is N,N-diisopropylethylamine, "DMA" is N,N-dimethylacetamide, "DMAP" is 4-(dimethylamino)pyridine, "DMF" is N,N-dimethylformamide, "dppf" is 1,1'-bis(diphenylphosphino)ferrocene, "DMEM" is Dulbecco's Modified Eagle Media, "DMSO" is dimethylsulfoxide, "DPPA" is diphenylphosphoryl azide, "EDC" is 1-Ethyl-3-(3-dimethylaminopropyl)carbodiimide, "ESI" is electrospray ionization, "$Et_2O$" is diethylether, "EtOAc" is ethyl acetate, "EtOH" is ethanol, "GST" is glutathione S-transferase, "h" is hour or hours, "HBTU" is (2-(1H-benzotriazol-1-yl)-1,1,3,3-tetramethyluronium hexafluorophosphate, "$H_2$" is hydrogen gas, "HCl" is hydrochloric acid, "Hex" is hexane, "$H_2O$" is water, "HOBt" is Hydroxybenzotriazole "$IC_{50}$" is half maximal inhibitory concentration, "$K_2CO_3$" is potassium carbonate, "$K_3PO_4$" is potassium phosphate, "LiMHDS" is lithium bis(trimethylsilyl)amide, "MeCN" is acetonitrile, "MeOH" is methanol, "$Me_4$tBuXPhos" is di-tert-butyl(2',4',6'-triisopropyl-3,4,5,6-tetramethyl-[1,1'-biphenyl]-2-yl)phosphine, "$MgSO_4$" is magnesium sulfate, "MHz" is megahertz, "min" is minute or minutes, "MS" is mass spectrometry, "MTBE" is methyl tert-butyl ether, "NADH" is nicotinamide adenine dinucleotide, "NaH" is sodium hydride, "$NaHCO_3$" is sodium bicarbonate, "$Na_2SO_4$" is sodium sulfate, "$NH_4Cl$" is ammonium chloride, "NaSMe" is sodium thiomethoxide, "NBS" is N-bromosuccinimide, "NMR" is nuclear magnetic resonance, "PBS" is phosphate buffered saline, "Pd/C" is palladium on carbon, "$Pd_2(dba)_3$" is tris(dibenzylideneacetone)dipalladium(0), "$Pd(OAc)_2$" is palladium (II) acetate, "$Pd(PPh_3)_4$" is tetrakis(triphenylphosphine)palladium (0), "prep-HPLC" is preparative high performance liquid chromatography, "PyBOP" is benzotriazol-1-yl-oxytripyrrolidinophosphonium hexafluorophosphate, "RT" is room temperature which is also known as "ambient temp," which will be understood to consist of a range of normal laboratory temperatures ranging from 15-25° C., "satd." is saturated, "$T_3P$" is n-propanephosphonic acid anhydride, "TEA" is triethylamine, "TFA" is trifluoroacetic acid, "THF" is tetrahydrofuran, "TMS" is trimethylsilyl, "Tris" is tris(hydroxymethyl)aminomethane, "Xantphos" is 4,5-bis(diphenylphosphino)-9,9-dimethylxanthene, "X-Phos" is 2-dicyclohexylphosphino-2',4',6'-triisopropylbiphenyl and "$ZnCl_2$" is zinc chloride.

General Chemistry

Exemplary compounds described herein are available by the general synthetic methods illustrated in the Schemes below, Intermediate preparations, and the accompanying Examples.

Scheme 1

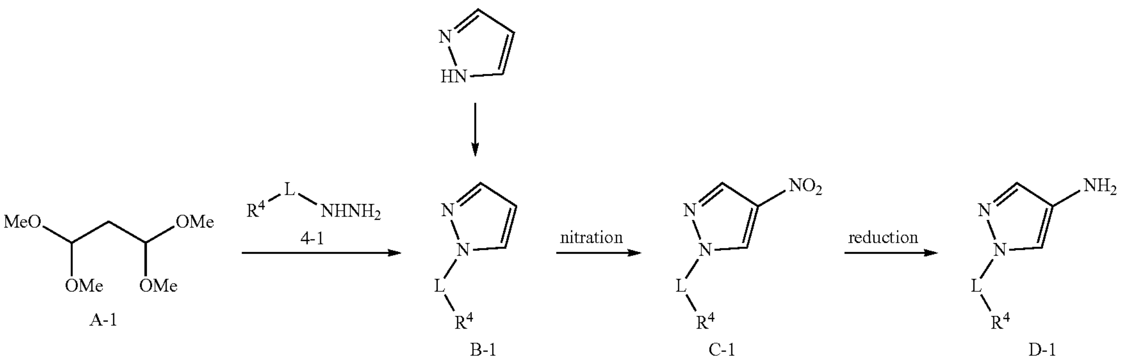

A-1 B-1 C-1 D-1

Exemplary methods for the preparation of pyrazoles have been disclosed in WO 2006/071940 and WO 2008/1311227, the contents of which are hereby incorporated by reference in their entireties. In Scheme 1, $R^4$-L-substituted pyrazole amines D-I are available by the condensation of hydrazines 4-1 (readily available to those skilled in the art) and 1,1,3,3-tetramethoxypropane A-I to provide $R^4$-L-substituted pyrazoles B—I. Conditions for this transformation include heating in ethanolic HCl. Those skilled in the art will further recognize that, in some embodiments, $R^4$-L-substituted pyrazoles B—I are prepared by direct alkylation of pyrazole. In some embodiments, pyrazoles B—I are regioselectively nitrated to provide nitro-pyrazoles C—I by standard conditions familiar to those skilled in the art. Finally, hydrogenation of nitro-pyrazoles C—I employing a hydrogenation catalyst, such as palladium or nickel, provides pyrazole amines D-I.

In Scheme 1, examples of $R^4$ include heterocyclyl with suitable optional substituents as exemplified by the tables of intermediates below and $NR^6R^9$, where each of $R^6$ and $R^9$ can independently be an alkyl group, examples of L include $—(CH_2)_m—$ where m can be 0, 1, 2, or 3 and when m is 0, $R^4$ is C-linked to the pyrazole, when m is 1, $R^4$ is C-linked to L, and when m is 2 or 3, $R^4$ is N-linked or C-linked to L.

Scheme 2

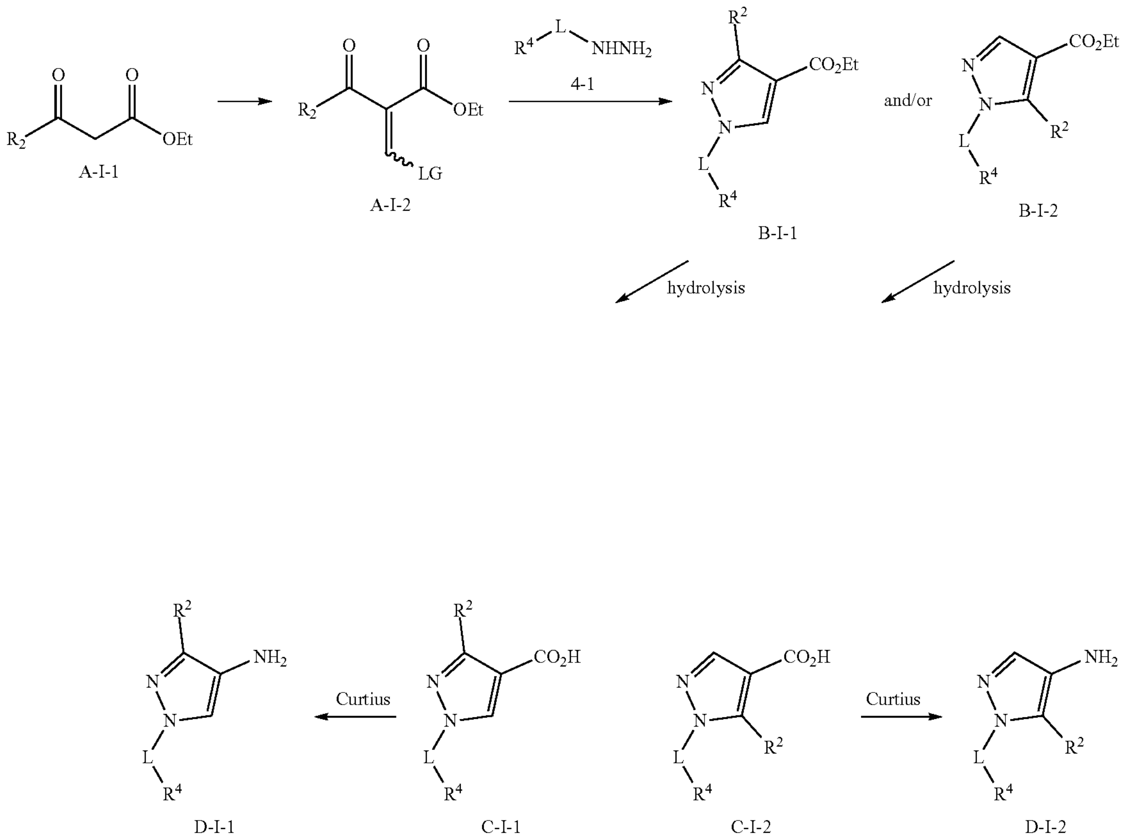

A-I-1 A-I-2 B-I-1 B-I-2 D-I-1 C-I-1 C-I-2 D-I-2

Additional examples of general pyrazole-amines D-I-1 and D-I-2 substituted with a single $R^2$ (i.e. wherein one $R^2$ is not hydrogen) are prepared as described in Scheme 2. Keto-ester A-I-1 is reacted with either N,N-dimethylformamide dimethyl acetal or triethylorthoformate/acetic anhydride to provide A-I-2 (wherein LG is an appropriate leaving group needed in the subsequent cyclization/pyrazole-forming reaction). Reaction of A-I-2 with hydrazine 4-1 (readily available to those skilled in the art) in the presence of acid provides predominately either B—I-1 or its regioisomer B—I-2. The regiochemistry of cyclization is controlled under conditions familiar to one skilled in the art (such as temperature and solvent). Conditions for the synthesis of B—I-1 (where $R^2$ is not hydrogen) include where LG is OEt, in a protic solvent (such as ethanol) at low temperature (−10° C. to RT) in the presence of acid. Conditions for the synthesis of B—I-2 include where LG is $NMe_2$, in a protic solvent (such as ethanol) at reflux in the presence of acid. In turn, either esters B—I-1 or B—I-2 are converted to the corresponding acids C—I-1 or C—I-2, using standard conditions known to those skilled in the art. Either C—I-1 or C—I-2 is converted to the corresponding amines D-I-1 or D-I-2 by Curtius rearrangement.

In Scheme 2, examples of LG include OMe, OEt, and $N(CH_3)_2$, examples of $R^2$ include alkyl and cycloalkyl, where alkyl and cycloalkyl can be optionally fluorinated, examples of $R^4$ include heterocyclyl with suitable optional substituents as exemplified by the tables of intermediates below and $NR^6R^9$, where each of $R^6$ and $R^9$ can independently be an alkyl group, examples of L include $-(CH_2)_m-$ where m can be 0, 1, 2, or 3 and when m is 0, $R^4$ is C-linked to the pyrazole, when m is 1, $R^4$ is C-linked to L, and when m is 2 or 3, $R^4$ is N-linked or C-linked to L.

Scheme 3

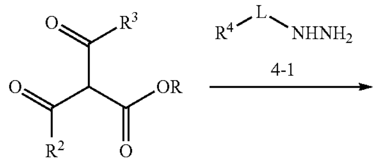

A-I-3

-continued

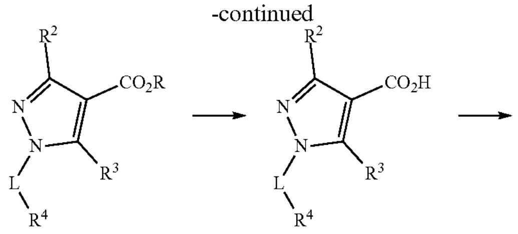

B-I-3 C-I-3

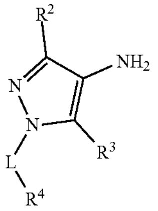

D-I-3

In a similar manner to Scheme 2, Scheme 3 illustrates the general preparation of amines D-I-3. Pyrazole esters B—I-3 are prepared by reaction of hydrazines 4-1 (readily available to those skilled in art) with intermediates A-I-3. In some embodiments, the $R^2$ and $R^3$ moieties are varied independently such that the $R^3$ is the same, or different to $R^2$. Esters B—I-3 are converted to the corresponding acids C—I-3 using standard conditions known to those skilled in the art. Acids C—I-3 are converted to amines D-I-3 under standard Curtius rearrangement conditions known to those skilled in the art.

In Scheme 3, examples of $R^2$ and $R^3$ can independently include alkyl and cycloalkyl, where alkyl and cycloalkyl can be optionally fluorinated, examples of $R^4$ include heterocyclyl with suitable optional substituents as exemplified by the tables of intermediates below and $NR^6R^9$, where each of $R^6$ and $R^9$ can independently be an alkyl group, examples of L include $-(CH_2)_m-$ where m can be 0, 1, 2, or 3 and when m is 0, $R^4$ is C-linked to the pyrazole, when m is 1, $R^4$ is C-linked to L, and when m is 2 or 3, $R^4$ is N-linked or C-linked to L.

Scheme 4

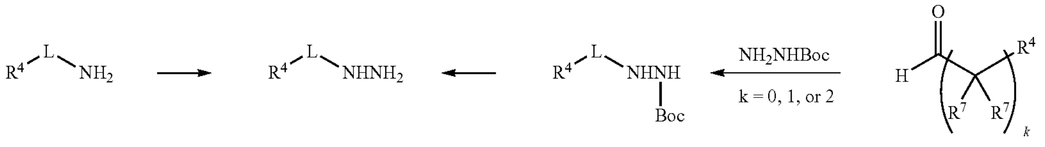

4-2 4-1 4-3 4-4

In some embodiments, hydrazines 4-1 that are not commercially available are readily prepared by the two methods shown in Scheme 4. One method involves the diazotization of amines 4-2 followed by reduction using conditions familiar to those skilled in the art, for example by the treatment with $Sn(II)Cl_2$ in the presence of a proton source. Alternately hydrazines 4-1 are available from the corresponding N-tert-butoxycarbonylhydrazines 4-3 by acid-catalyzed removal of the tert-butoxycarbonyl group. Those skilled in the art will recognize that, in some embodiments, the conversion of carbamates 4-3 to hydrazines 4-1 are also accomplished in situ within a reaction sequence. Thus, carbamates 4-3 are surrogates for hydrazines 4-1 in all schemes in which the hydrazines 4-1 is normally used in the presence of an acid. The N-tert-butoxycarbonylhydrazines 4-3 can be prepared by reductive amination with commercially available aldehydes or ketones 4-4 and tert-butyl hydrazinecarboxylate.

In Scheme 4, examples of $R^4$ include heterocyclyl with suitable optional substituents as exemplified by the tables of intermediates below and $NR^6R^9$, where each of $R^6$ and $R^9$ can independently be an alkyl group, examples of L include $—(C(R^{10})_2)_m—$ where an example of $R^{10}$ is H and where m can be 0, 1, 2, or 3, and when m is 0, $R^4$ is C-linked to a nitrogen, when m is 1, $R^4$ is C-linked to L, and when m is 2 or 3, $R^4$ is N-linked or C-linked to L.

In some embodiments, general pyrazole-amines D-I-4 or D-I-5 are prepared by the two methods shown in Scheme 5. In this scheme, examples of $R^4$-L-linked 5-1 or 5-2 are shown. One method involves alkylation of B—I-4 (readily available to those skilled in art) with commercially available 5-1 to provide nitro-pyrazoles C—I-4 and/or C—I-5 in the presence of base (e.g. potassium carbonate, cesium carbonate or sodium hydride) and a polar aprotic solvent (dimethyl sulfoxide, dimethylformamide, tetrahydrofuran or the like), at temperatures between ambient and 150° C. An alternative preparation of D-I-4 or D-I-5, involves a Mitsunobu reaction of B—I-4 with commercially available 5-2 to provide the nitro-pyrazoles C—I-4 and C—I-5. When produced as a mixture, it is understood by those skilled in the art that C—I-4 and C—I-5, are separated by SFC purification, crystallization or chromatography. Finally, reduction of nitro-pyrazoles C—I-4 and C—I-5 in the presence of a hydrogenation catalyst, such as palladium or nickel or mild reducing conditions such as zinc or iron and ammonium chloride provides pyrazole-amines D-I-4 and D-I-5.

In Scheme 5, examples of LG include Cl and Br, examples of $R^2$ include alkyl, cycloalkyl, alkoxy, halogen, and CN, where alkyl, cycloalkyl, or alkoxy can be optionally fluorinated, examples of $R^4$ include heterocyclyl with suitable optional substituents as exemplified by the tables of intermediates below, $C(O)NR^6R^9$, and $NR^6R^9$, where each of $R^6$ and $R^9$ can independently be H or an alkyl group, examples of L include $—(CH_2)_m—$ where m can be 0, 1, 2, or 3, and when m is 0, $R^4$ is C-linked to the pyrazole, when m is 1, $R^4$ is C-linked to L, and when m is 2 or 3, $R^4$ is N-linked or C-linked to L.

Scheme 5

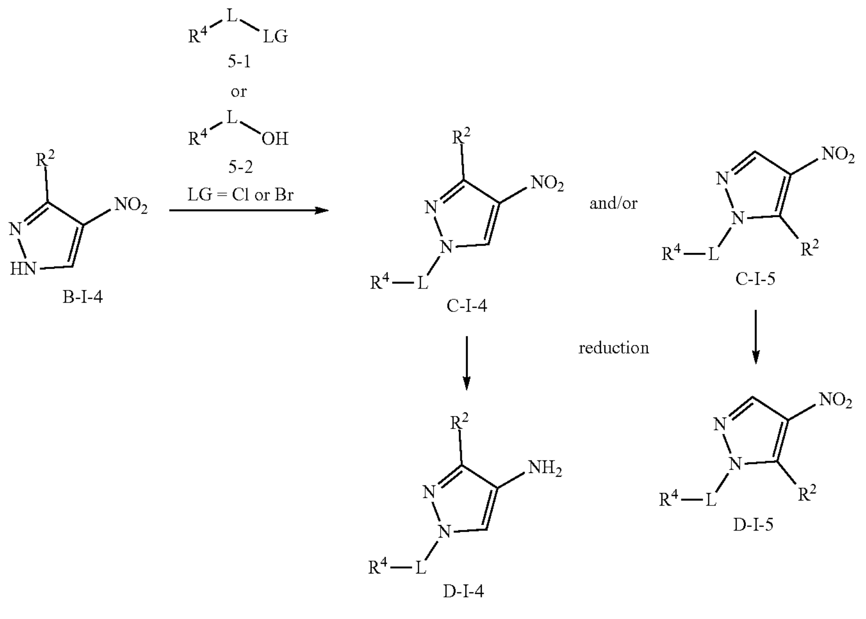

Scheme 6

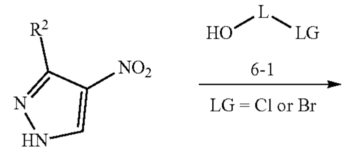

B-I-4

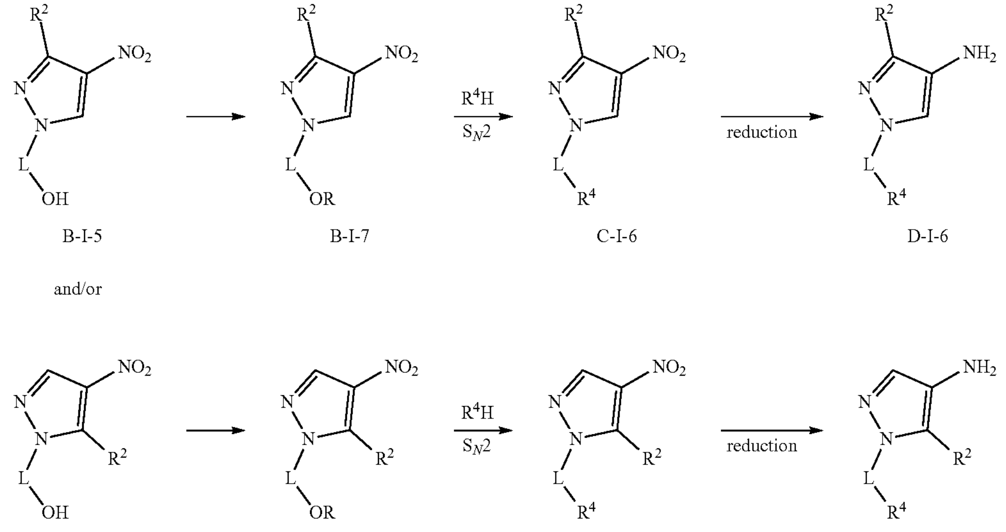

B-I-5 B-I-7 C-I-6 D-I-6 and/or

B-I-6 B-I-8 C-I-7 D-I-7

R = Ms or Ts

In some embodiments, general pyrazole-amines D-I-6 and D-I-7 are prepared as shown in Scheme 6. In this scheme, examples of $R^4$-L-linked 6-1 are shown. Alkylation of B—I-4 (readily available to those skilled in the art) with 6-1 provide a mixture of nitro-pyrazoles B—I-5 and B—I-6. These two isomers B—I-5 and B—I-6 are separated by SFC purification, crystallization or chromatography. Each isomer B—I-5 or B—I-6 are activated using MsCl or TsCl to provide B—I-7 or B—I-8 (R is Ms or Ts), respectively. Displacement of OMs or OTs with amines $R^4$—H furnishes C—I-6 or C—I-7 respectively. Finally, reduction of nitro-pyrazoles C—I-6 or C—I-7 in the presence of a hydrogenation catalyst, such as palladium, nickel or mild reducing conditions such as zinc or iron and ammonium chloride provides pyrazole-amines D-I-6 or D-I-7.

In Scheme 6, examples of LG include Cl and Br, examples of R include mesylate and tosylate, examples of $R^2$ include alkyl, cycloalkyl, alkoxy, halogen, and CN, where alkyl, cycloalkyl, or alkoxy can be optionally fluorinated, examples of $R^4$ include heterocyclyl with suitable optional substituents as exemplified by the tables of intermediates below and $NR^6R^9$, where each of $R^6$ and $R^9$ can independently be an alkyl group, examples of L include $-(CH_2)_m-$ where m is 2 or 3, and $R^4$ is N-linked.

Scheme 7

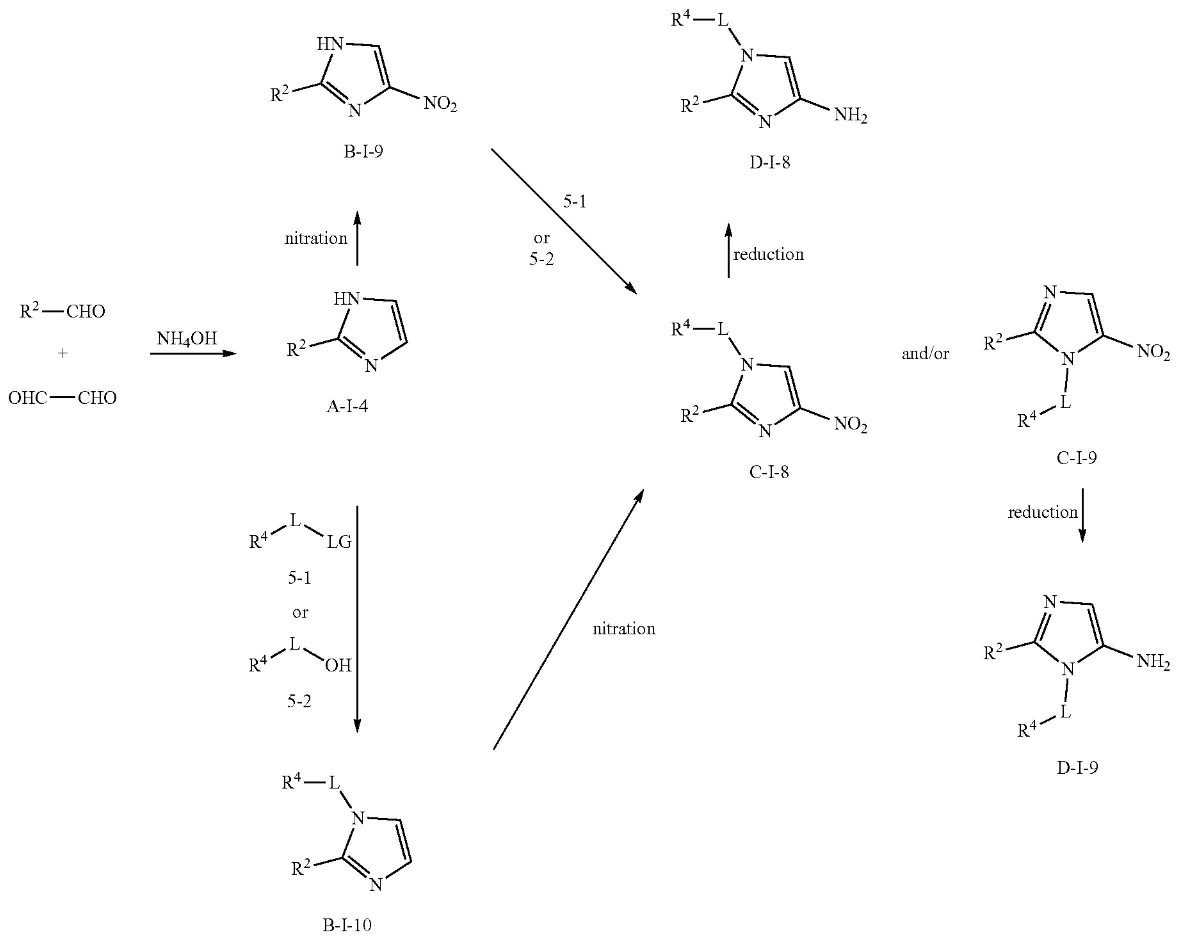

Scheme 7 illustrates the synthesis of general amines D-I-8 and D-I-9. Thus, condensation of commercially available aldehydes with glyoxal in the presence of ammonium hydroxide provides $R^2$-substituted imidazoles A-I-4. In this scheme, examples of $R^4$-L-linked 5-1 or 5-2 are shown. Nitration of imidazoles A-I-4 by conditions known to those skilled in the art (e.g., nitric acid/concentrated sulfuric acid at temperatures ranging from 0° C. to 100° C.) provides nitroimidazoles B—I-9. B—I-9 are converted to a mixture of C—I-8 and C—I-9 by alkylation (5-1) or Mitsunobu reaction (5-2). In some embodiments substituted nitro-imidazoles C—I-8 and C—I-9 are available by either alkylation (5-1) or Mitsunobu reaction (5-2) from A-I-4 to afford B—I-10. Subsequent nitration of B—I-10 then provides C—I-8 and C—I-9. These two regioisomers C—I-8 and C—I-9 can be separated by SFC purification, crystallization or chromatography. Reduction of each nitro-imidazole C—I-6 and C—I-7 in the presence of a hydrogenation catalyst, such as palladium or nickel, or mild reducing conditions such as zinc or iron and ammonium chloride provides the corresponding imidazole-amines D-I-8 and D-I-9, respectively.

In Scheme 7, examples of LG include Cl and Br, examples of $R^2$ include alkyl and cycloalkyl, where alkyl and cycloalkyl can be optionally fluorinated, examples of $R^4$ include heterocyclyl with suitable optional substituents as exemplified by the tables of intermediates below and $NR^6R^9$, where each of $R^6$ and $R^9$ can independently be an alkyl group, examples of L include $-(CH_2)_m-$ where m can be 2 or 3, L is N-linked to the imidazole ring.

Scheme 8

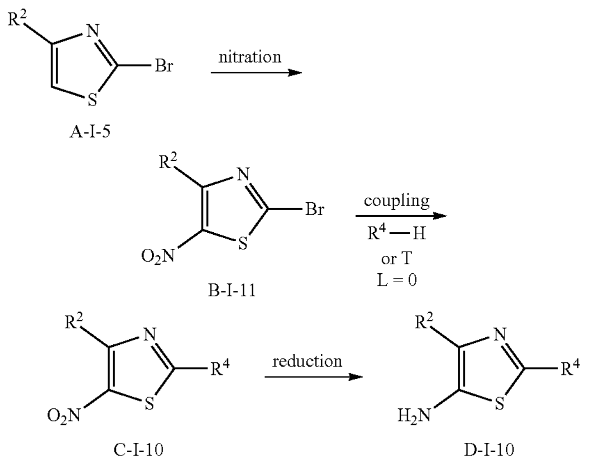

As illustrated in Scheme 8, in some embodiments substituted thiazole amines D-I-10 can be prepared from appropriately substituted thiazoles A-I-5 (readily available to those skilled in the art). This method has been described in WO2006072436, the contents of which are hereby incorporated by reference in their entireties. Nitration of bromothiazoles A-I-5 using fuming nitric acid or nitric acid with sulfuric acid afford bromo-nitrothiazoles B—I-11. The bromo functionality on B—I-11 can be displaced by various amines $R^4$—H using conditions familiar to those skilled in the art such as Buchwald, Ullmann or nucleophilic aromatic substitution reactions in the presence of TEA or $K_2CO_3$ to furnish C—I-10 where $R^4$ is N-linked. A Suzuki reaction of B—I-11 with commercially available or synthetic boronates T including but not limited to other boron salts (see scheme 16) is used to provide C—I-10 where $R^4$ is C-linked. Finally, reduction of C—I-10 in the presence of a hydrogenation catalyst, such as palladium or nickel, or mild reducing conditions such as zinc or iron and ammonium chloride provides the corresponding thiazole-amines D-I-10.

In Scheme 8, examples of $R^2$ include alkyl, cycloalkyl, alkoxy, halogen, and CN, where alkyl, cycloalkyl, or alkoxy can be optionally fluorinated and examples of $R^4$ include heterocyclyl with suitable optional substituents as exemplified by the tables of intermediates below and $NR^6R^9$, where each of $R^6$ and $R^9$ can independently be an alkyl group.

Scheme 9

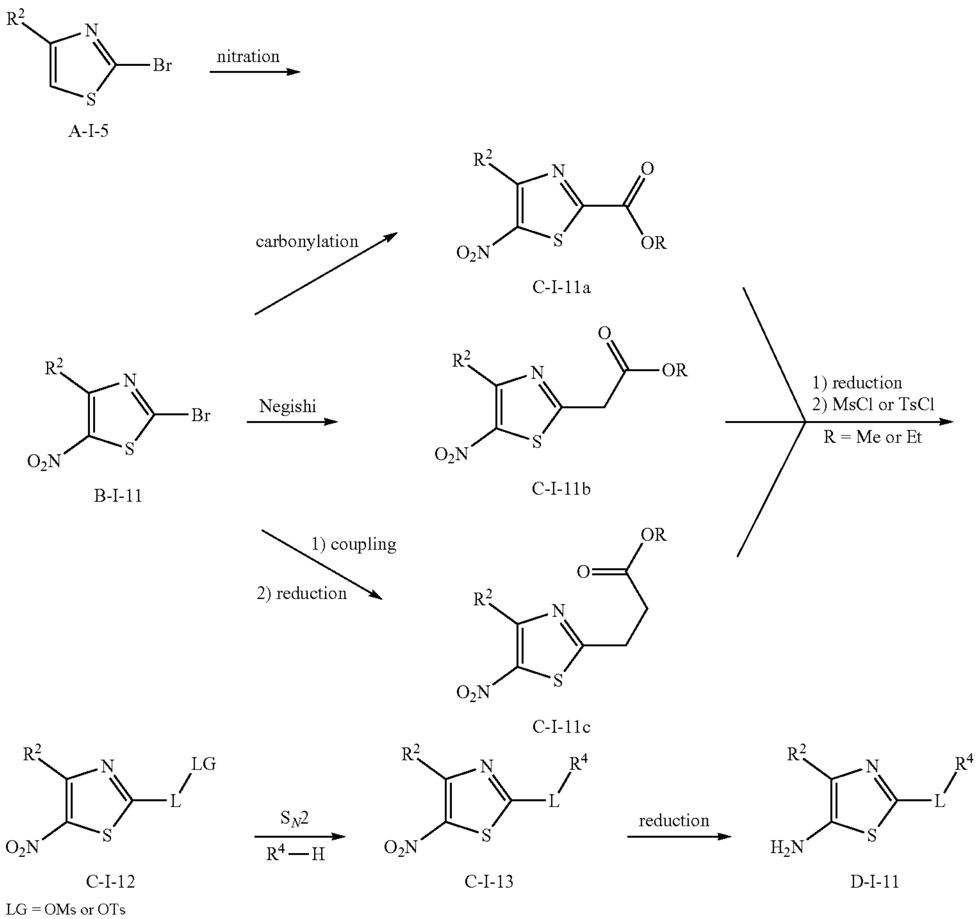

As illustrated in Scheme 9, in some embodiments substituted thiazole amines D-I-11 can be prepared from appropriately substituted thiazoles A-I-5 (readily available to those skilled in the art). This method has been described in WO2009158373, WO2016135163, and WO2011075515, the contents of which are hereby incorporated by reference in their entireties. Nitration of bromothiazoles A-I-5 using fuming nitric acid or nitric acid with sulfuric acid afford bromo-nitrothiazoles B—I-11. The bromo functionality on B—I-11 can be displaced by various linker (L) synthons using conditions familiar to those skilled in the art such as carbonylation (C—I-11a), Negishi (zinc mediated coupling conditions, (C—I-11b)), Sonogashira or Heck coupling reaction following by appropriate reduction to furnish C—C linked C—I-11c. C—I-11a, C—I-11b and C—I-11c can be reduced to primary alcohols, followed by mesylation or tosylation to form C—I-12. Nucleophilic substitution of C—I-12 with different nucleophiles $R^4$—H furnishes C—I-13. Finally, reduction of C—I-13 in presence of hydrogenation catalyst such as palladium or nickel or mild reducing conditions such as zinc or iron and ammonium chloride provides corresponding thiazole-amines D-I-11.

In Scheme 9, examples of LG include OTs and OMs, examples of R include methyl and ethyl, examples of $R^2$ include alkyl, cycloalkyl, alkoxy, halogen, and CN, where alkyl, cycloalkyl, or alkoxy can be optionally fluorinated, examples of $R^4$ include heterocyclyl with suitable optional substituents as exemplified by the tables of intermediates below and $NR^6R^9$, where each of $R^6$ and $R^9$ can independently be an alkyl group, and examples of L include $-(CH_2)_m-$ where m can be 1, 2, or 3.

Scheme 10

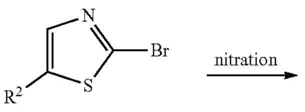

A-I-6

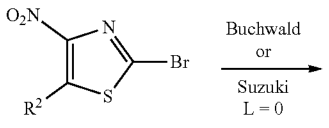

B-I-12

-continued

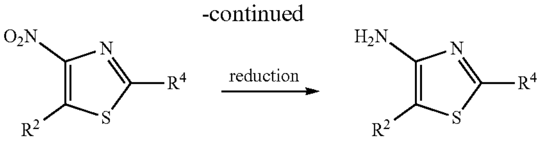

C-I-14 D-I-12

In a similar reaction sequence as shown in Scheme 10, bromothiazoles A-I-6 (readily available to those skilled in the art) afford thiazole-amines D-I-12 as shown in Scheme 10 (Science of Synthesis, 627, 2002).

In Scheme 10, examples of $R^2$ can be alkyl, cycloalkyl, alkoxy, halogen, or CN, where alkyl, cycloalkyl, or alkoxy can be optionally fluorinated, and examples of $R^4$ include heterocyclyl with suitable optional substituents as exemplified by the tables of intermediates below and $NR^6R^9$, where each of $R^6$ and $R^9$ can independently be an alkyl group.

Scheme 11

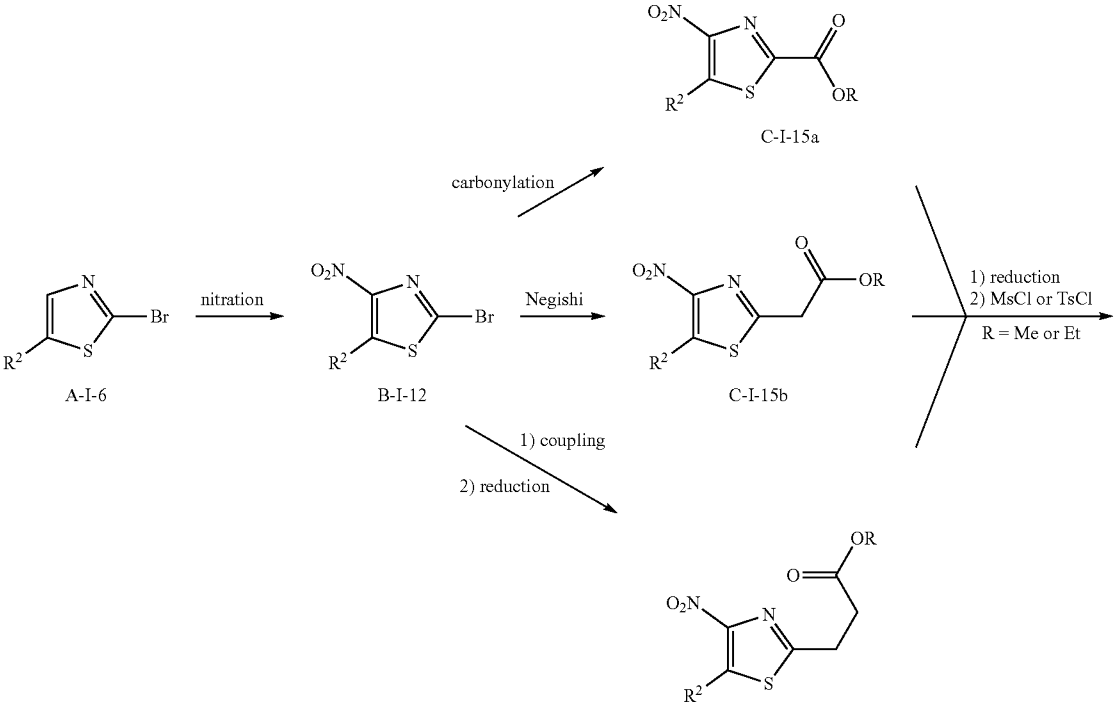

C-I-15a

A-I-6 B-I-12 C-I-15b

C-I-15c

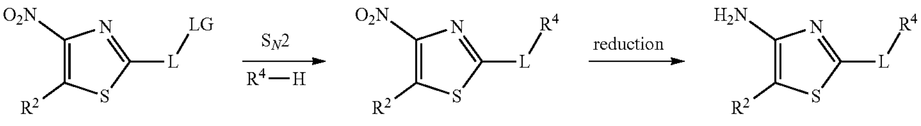

C-I-16
LG = OMs or OTs

C-I-17

D-I-13

As illustrated in Scheme 11, in some embodiments substituted thiazole amines D-I-13 can be prepared from appropriately substituted thiazoles A-I-6 (readily available to those skilled in the art). This method has been described in WO2009158373, WO2016135163, and WO2011075515, the contents of which are hereby incorporated by reference in their entireties. Nitration of bromothiazoles A-I-6 using fuming nitric acid or nitric acid with sulfuric acid afford bromo-nitrothiazoles B—I-12. The bromo functionality on B—I-12 can be displaced by various $R^4$ groups using conditions familiar to those skilled in the art such as carbonylation (C—I-15a), Negishi (zinc mediated coupling conditions (C—I-15b), Sonogashira or Heck coupling reaction followed by reduction to furnish C—C linked C—I-15c. C—I-15a, C—I-15b and C—I-15c can be reduced to primary alcohols, followed by mesylation or tosylation to form C—I-16. Nucleophilic substitution of C—I-16 with different nucleophiles $R^4$—H furnishes C—I-17. Finally, reduction of C—I-17 in presence of hydrogen catalyst such as palladium or nickel or mild reducing conditions such as zinc or iron and ammonium chloride provides corresponding thiazole-amines D-I-13.

In Scheme 11, examples of LG include OTs and OMs, examples of R include methyl and ethyl, examples of $R^2$ include alkyl, cycloalkyl, alkoxy, halogen, and CN, where alkyl, cycloalkyl, or alkoxy can be optionally fluorinated, examples of $R^4$ include heterocyclyl with suitable optional substituents as exemplified by the tables of intermediates below and $NR^6R^9$, where each of $R^6$ and $R^9$ can independently be an alkyl group, and examples of L include $-(CH_2)_m-$ where m can be 1, 2, or 3.

Scheme 12

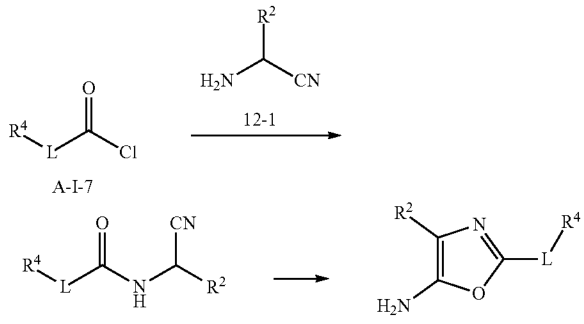

A-I-7

A-I-8

D-I-14

Scheme 12 describes the synthesis of substituted oxazoles D-I-14 as reported in WO2014078378, the content of which are hereby incorporated by reference in its entirety. Various acid chlorides A-I-7 react with $R^2$ substituted aminoalkyl nitriles 12-1 (readily available to those skilled in the art) to furnish A-I-8. A-I-8 are converted oxazole-amines D-I-14 under acidic conditions such as acetic acid, sulfuric acid or hydrochloric acid.

In Scheme 12, examples of $R^2$ include alkyl, and cycloalkyl, where alkyl, cycloalkyl, or alkoxy can be optionally fluorinated, and examples of $R^4$ include heterocyclyl with suitable optional substituents as exemplified by the tables of intermediates below and $NR^6R^9$, where each of $R^6$ and $R^9$ can independently be an alkyl group, and examples of L include $-(CH_2)_m-$ where m can be 0, 1, 2, or 3.

Scheme 13

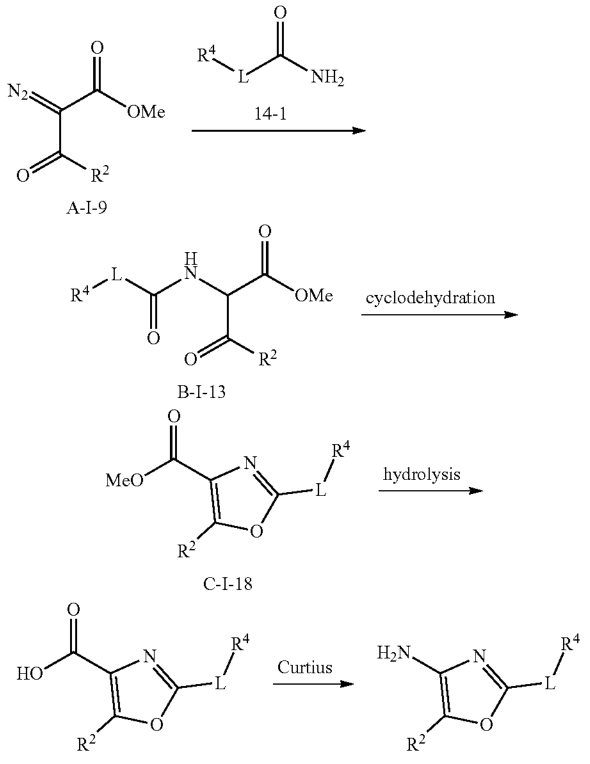

A-I-9

B-I-13

C-I-18

C-I-19

D-I-15

As shown in Scheme 13, some substituted oxazoles can be prepared from 2-diazo-3-oxo substituted carboxylic esters A-I-9 as reported in Synlett, 1996, 1171, the content of which are hereby incorporated by reference in its entirety. Diazo esters A-I-9 upon treatment with primary amides 14-1 (readily available to those skilled in the art) under Rh-catalyzed coupling conditions afford amides B—I-13. Intermediates B—I-13 provide oxazole esters C—I-18 under cyclodehydration conditions using a dehydrating reagent (e.g. $POCl_3$, $T_3P$, or Burgess reagent). Hydrolysis of oxazole-esters C—I-18 furnish carboxylic acids C—I-19, which are converted into oxazole-amines D-I-15 under Curtius rearrangement using sodium azide or DPPA.

In Scheme 13, examples of $R^2$ include alkyl, cycloalkyl, and alkoxy, where alkyl, cycloalkyl, or alkoxy can be optionally fluorinated, and examples of $R^4$ include heterocyclyl with suitable optional substituents as exemplified by the tables of intermediates below and $NR^6R^9$, where each of $R^6$ and $R^9$ can independently be an alkyl group, and examples of L include $-(CH_2)_m-$ where m can be 0, 1, 2, or 3.

Scheme 14

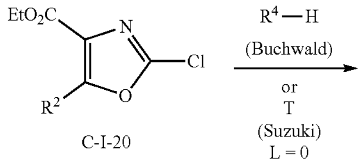

C-I-20

-continued

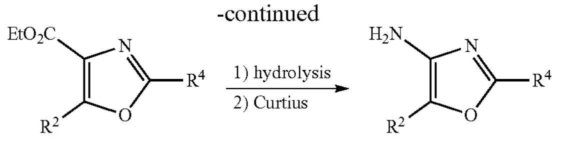

C-I-21 D-I-16

As shown in Scheme 14, in other embodiments, the oxazole-amines D-I-16 can be prepared from 2-halo oxazoles C—I-20 as described in WO2012033195, the contents of which are hereby incorporated by reference in their entireties. Reaction of C—I-20 with various amines $R^4$—H under Buchwald coupling conditions provide 2-aminoalkyl substituted oxazoles C—I-21 where $R^4$ is N-linked. A Suzuki reaction of C—I-20 with commercially available or synthetic boronates T including but not limited to other boron salts (see scheme 16) are used to provide C—I-21 where $R^4$ is C-linked. Hydrolysis of oxazole-esters C—I-21 furnish carboxylic acids which can be converted into oxazole-amines D-I-16 under Curtius rearrangement using sodium azide or DPPA.

In Scheme 15, examples of $R^2$ can be alkyl, cycloalkyl, or alkoxy, where alkyl, cycloalkyl, or alkoxy can be optionally fluorinated, and examples of $R^4$ include heterocyclyl with suitable optional substituents as exemplified by the tables of intermediates below and $NR^6R^9$, where each of $R^6$ and $R^9$ can independently be an alkyl group, where each of $R^6$ and $R^9$ can independently be an alkyl group.

In some embodiments, general triazole-amines D-I-17 and D-I-18 are prepared as shown in Scheme 15. In this scheme, examples of $R^4$-L-linked 5-1 or 5-2 are shown. Triazoles B—I-14 are prepared from dinitro-esters A-I-10 by reaction with aldehydes 15-1 (readily available to those skilled in the art) using the procedure described in Asian J. of Chem, 2014, 26, 4744 and Hanneng Cailliao, 2008, 16, 49, the contents of which are hereby incorporated by reference in their entireties. Alternatively, B—I-14 may be prepared by nitration of A-I-11. B—I-14 are converted to a mixture of C—I-22 and C—I-23 by alkylation (5-1) or Mitsunobu reaction (5-2). These two regioisomers C—I-22 and C—I-23 can be separated by SFC purification, crystallization or chromatography. Reduction of nitro-triazoles C—I-22 or C—I-23 in the presence of a hydrogenation catalyst, such as palladium or nickel, or mild reducing conditions such as zinc or iron and ammonium chloride provides the corresponding triazole-amines D-I-17 and D-I-18, respectively.

In Scheme 15, examples of $R^2$ can be alkyl, cycloalkyl, alkoxy, halogen, or CN, where alkyl, cycloalkyl, or alkoxy can be optionally fluorinated, examples of $R^4$ include heterocyclyl with suitable optional substituents as exemplified by the tables of intermediates below and $NR^6R^9$, where each of $R^6$ and $R^9$ can independently be an alkyl group, examples of L include $-(CH_2)_m-$ where m can be 2 or 3.

Scheme 15

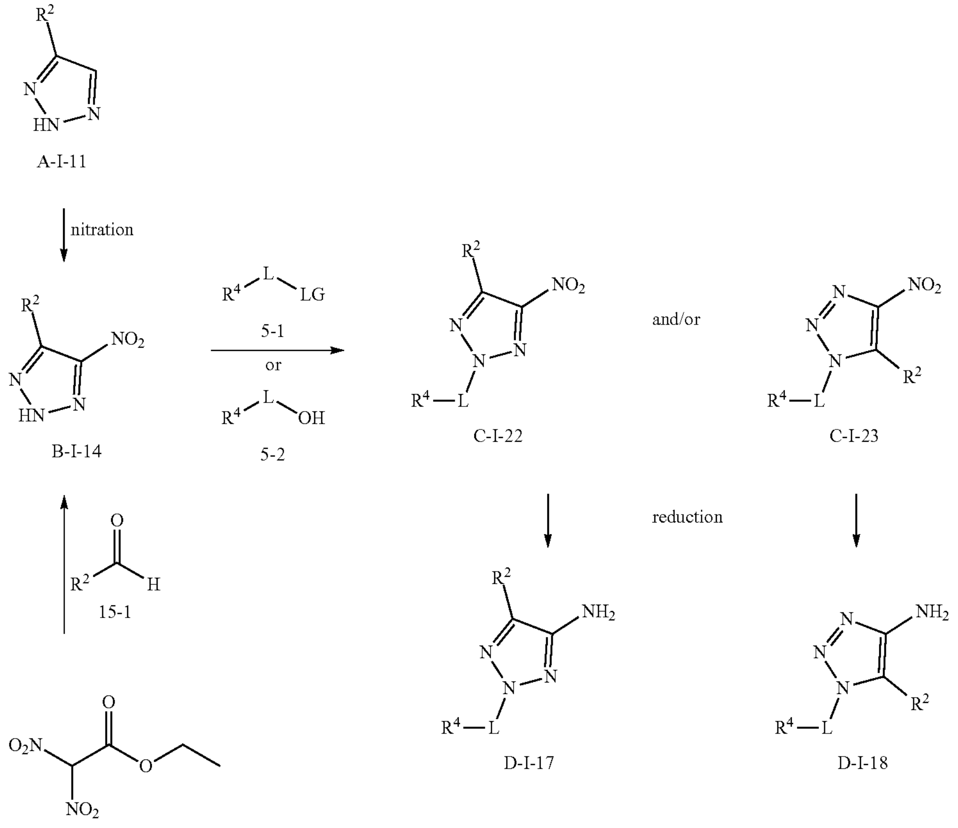

A-I-11, B-I-14, C-I-22, C-I-23, D-I-17, D-I-18, A-I-10

Scheme 16

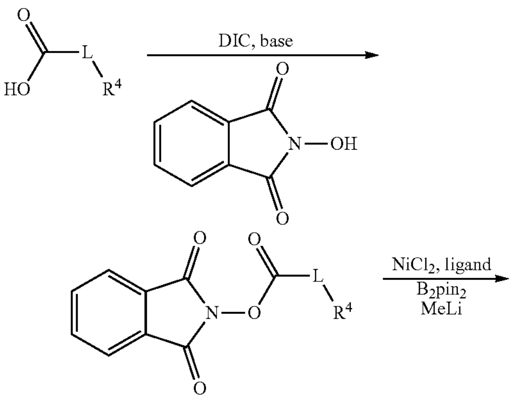

Q

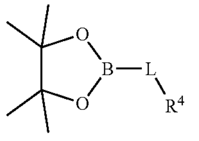

T

Scheme 16 illustrates the general preparation of boronic acid/boronic ester T, which are not commercially available. These compounds can be readily prepared from substituted carboxylic acids. The carboxylic acids can be activated by 2-hydroxyisoindoline-1,3-dione in the presence of coupling reagent (e.g. DCI or $Et_3N$/HATU) to afford Q. Intermediates Q are converted to boronic ester T by nickel-catalyzed decarboxylative borylation with the $[B_2pin_2Me]Li$ complex, which is premixed with methyllithium and $B_2pin_2$ (Science, 2107, 356, 1045 and JACS, 2016, 138, 2174), the contents of which are hereby incorporated by reference in their entireties.

In Scheme 16, examples of $R^4$ include alkyl, cycloalkyl, and heterocyclyl with suitable optional substituents as exemplified by the tables of intermediates below and examples of L include $-(CH_2)_m-$ where m can be 0, 1, 2, or 3, and when m is 0, $R^4$ is C-linked to the boronate ester, when m is 1, then $R^4$ is C-linked to L, and when m is 2 or 3, then $R^4$ is N-linked or C-linked to L.

Scheme 17

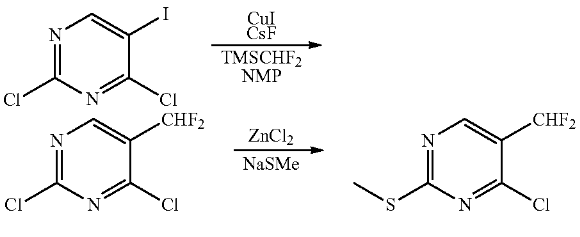

L-II-1 L-I-1

L-II-1 L-I-2

Scheme 17 illustrates the general preparation of L-I-1 and L-I-2. Commercially available 2,4-dichloro-5-iodopyrimidine reacts with $TMSCHF_2$ in a solvent such as NMP or DMF in the presence of CuI and CsF to produce difluoromethylpyrimidine L-II-1 (US20150284341, the contents of which are hereby incorporated by reference in its entirety). Difluoromethylpyrimidine L-II-1 can be converted to methylthiopyrimidine L-I-1 by treatment with sodium thiomethoxide and zinc chloride in diethyl ether at a temperature lower than 10° C. (WO2012110773, the content of which is hereby incorporated by reference in its entirety). In a similar manner to L-I-1, trifluoromethylpyrimidine L-I-2 can be prepared from the commercially available 2,4-dichloro-5-(trifluoromethyl)pyrimidine, L-II-2.

Scheme 18

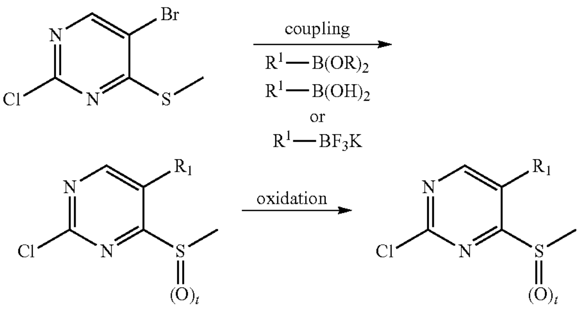

L-III (t = 0) L-III (t = 2)

Scheme 18 illustrates the general preparation of sulfanylpyrimidine L-III (t=2) where $R^1$ can be cycloalkyl. Treatment of commercially available 5-bromo-2-chloro-4-(methylthio)pyrimidine with boronic esters/boronic acids/trifluoroborates in the presence of a palladium catalyst (Suzuki coupling) afford $R^1$-substituted thiopyrimidines L-III (t=0). Examples or $R^1$ in this scheme include cycloalkyl such as cyclopropyl. The intermediate thiopyrimidines L-III (t=0) are converted to sulfanylpyrimidine L-III (t=2) by standard oxidations, for example, by mCPBA.

Scheme 19

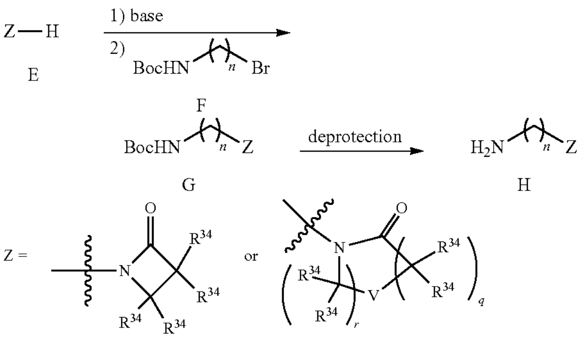

E F G H

Scheme 19 illustrates the general preparation of intermediates H (I-XIII) by a widely known method. The treatment of commercially available lactam/cyclic-carbamate/oxo-lactam/cyclic-urea/diazepanones E (Z—H) with Boc (tert-butoxycarbonyl group)-protected bromo compound F in the presence of base, for example sodium hydride or potassium tert-butoxide, provide G. The Boc group of G is a protecting group that is removed upon exposure to acid, for example HCl or TFA. H—I through H—XIII are prepared by this method.

In Scheme 19, q can be 0, 1, 2, or 3, r can be 2, 3, or 4, V can be $C(R^{34})_2$, O, or $NR^6$, where $R^6$ is alkyl, n can be 2, 3, or 4, each $R^{34}$ can, independently, be H, $C_1$-$C_6$ alkyl, or two $R^{34}$ can be taken together to form a cycloalkyl.

Scheme 20

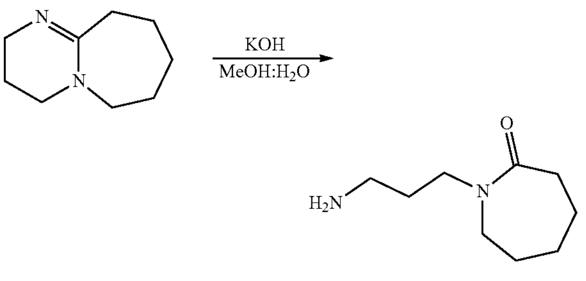

H-XIV

In another embodiment, lactam H—XIV can be prepared from DBU via one step process as illustrated in Scheme 20. DBU is hydrolyzed by potassium hydroxide in a solution of methanol and water at ambient temperature to provide H—XIV.

Scheme 21

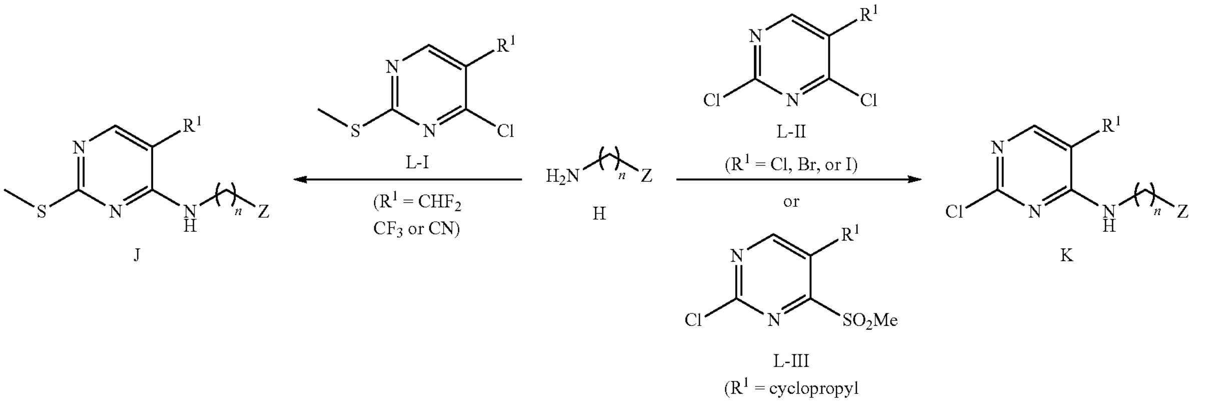

J H K

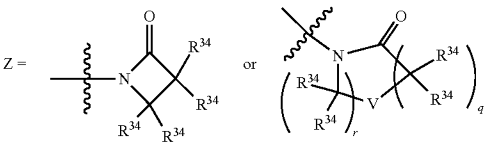

Scheme 21 illustrates the general preparation of key intermediates J and K. Key intermediates J can be prepared from H (either free base or HCl salt) and methylthiopyrimidine L-I in the presence of an organic base (e.g. triethylamine or DIEA) with optional heating to provide key intermediates J. In a similar manner, key intermediates K can be prepared from H with either L-II or L-III In Scheme 21, q can be 0, 1, 2, or 3, r can be 2, 3, or 4, V can be $C(R^{34})_2$, O, or $NR^6$, where $R^6$ is alkyl, n can be 2, 3, or 4, each $R^{34}$ can, independently, be H, $C_1$-$C_6$ alkyl, or two $R^{34}$ can be taken together to form a cycloalkyl group.

Scheme 22

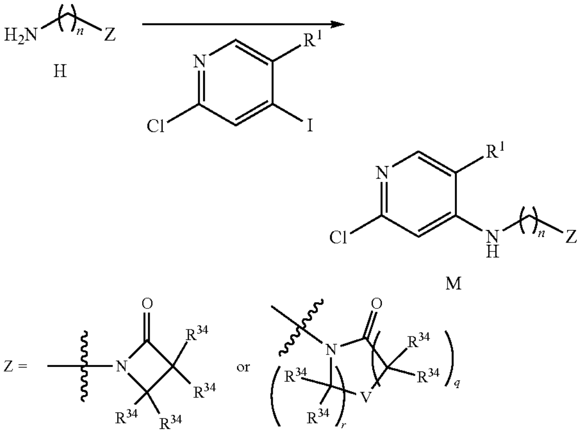

H

M

Scheme 22 illustrates the general preparation of key pyridine intermediates M. Treatment of H with commercially available chloroiodopyridines under Buchwald-Hartwig coupling conditions ($Cs_2CO_3$, Xantphos and $Pd(OAc)_2$), performed in an aprotic solvent (e.g. DME, DMF, DMSO, or NMP) at temperatures ranging from ambient to 140° C., provide key intermediates M.

In Scheme 22, $R^1$ can be Br, Cl, alkyl optionally substituted by one or more fluorine atoms, or cycloalkyl, q can be 0, 1, 2, or 3, r can be 2, 3, or 4, V can be $C(R^{34})_2$, O, or $NR^6$, where $R^6$ is alkyl, n can be 2, 3, or 4, each $R^{34}$ can, independently, be H, $C_1$-$C_6$ alkyl, or two $R^{34}$ can be taken together to form a cycloalkyl.

Scheme 23

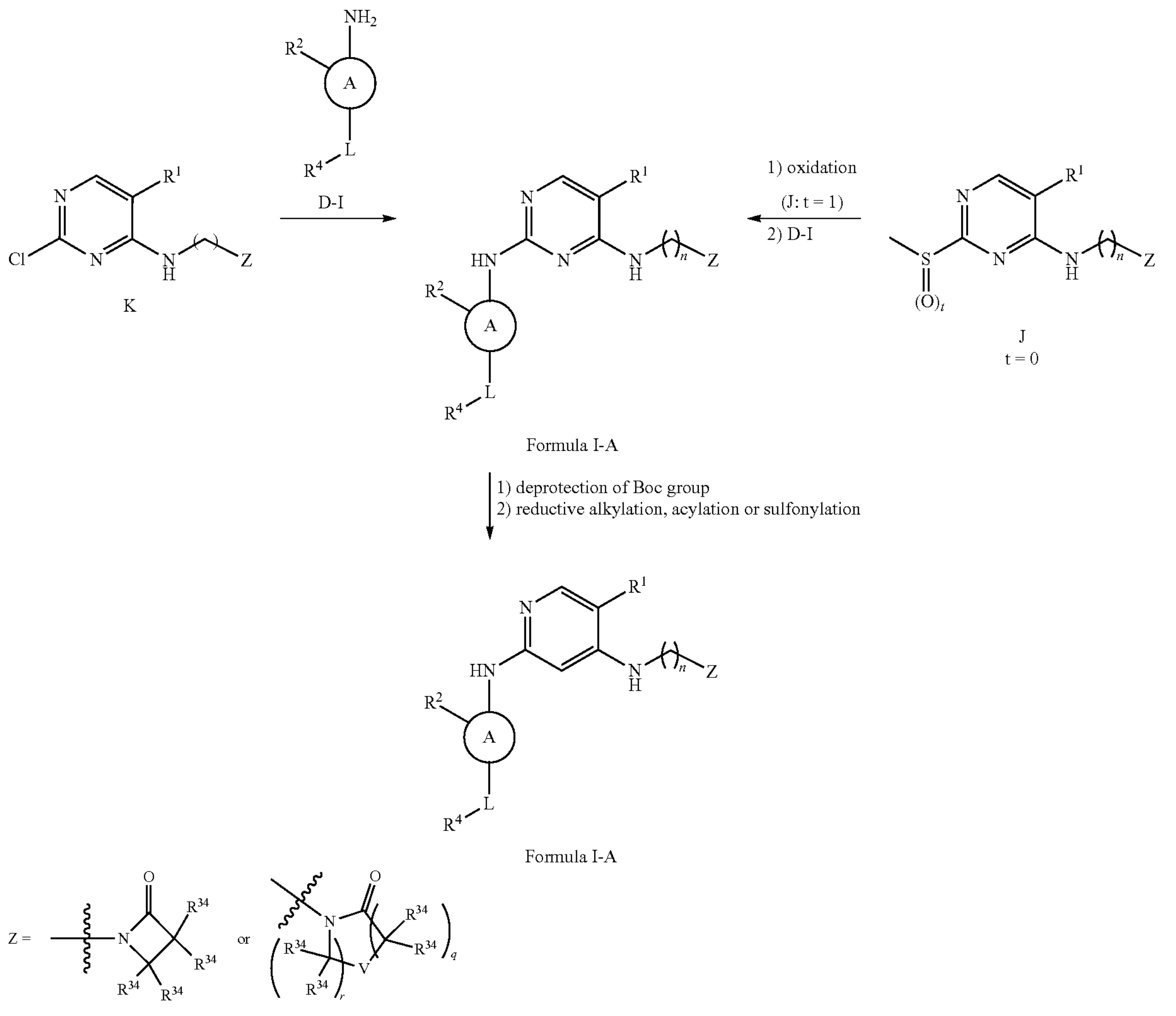

Scheme 23 illustrates general preparations of compounds of Formula I-A from substituted D-I. The preparation of Formula I-A can be accomplished from key intermediates K and J. The nucleophilic substitution reaction of K with amines D-I is typically performed in a polar solvent at temperatures ranging from ambient temp to 150° C., in some embodiments with microwave heating, optionally in the presence of an acid for example 4N HCl in 1,4-dioxane to provide compounds of Formula I-A. Compounds D-I, which are not commercially available, can be readily prepared (see schemes 1-16). An alternative general synthesis of formula II is via a two-step process by first converting J (t=0) to sulfoxide J (t=1) by oxidation using various oxidants, such as mCPBA. The sulfoxides react with amines D-I by a nucleophilic substitution reaction, typically performed in a polar solvent at temperatures ranging from ambient temp to 150° C., in some embodiments with microwave heating, optionally in the presence of an acid for example 4N HCl in 1,4-dioxane or pTSA to afford compounds of Formula I-A. In the event that Formula I-A contains a protecting group such as a Boc group, this protecting group can be deprotected under acidic conditions to provide Formula I-A (free amine or salt). Further treatment of Formula I-A (free base or salt) with sodium cyanoborohydride or sodium triacetoxyborohydride and an aldehyde or ketone in the presence of a catalytic amount of acetic acid in polar solvents such as MeOH (reductive amination conditions) afford N-substituted Formula I-A. For acylation and sulfonylation, the free amine (or salt) can be treated with commercially available acyl chloride or sulfonyl chloride to afford N-substituted Formula I-A.

Scheme 24

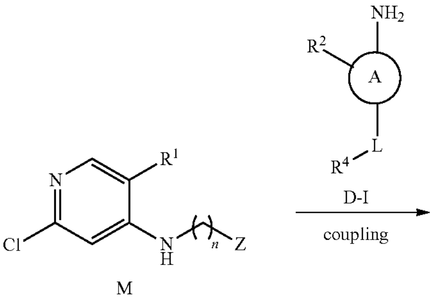

-continued

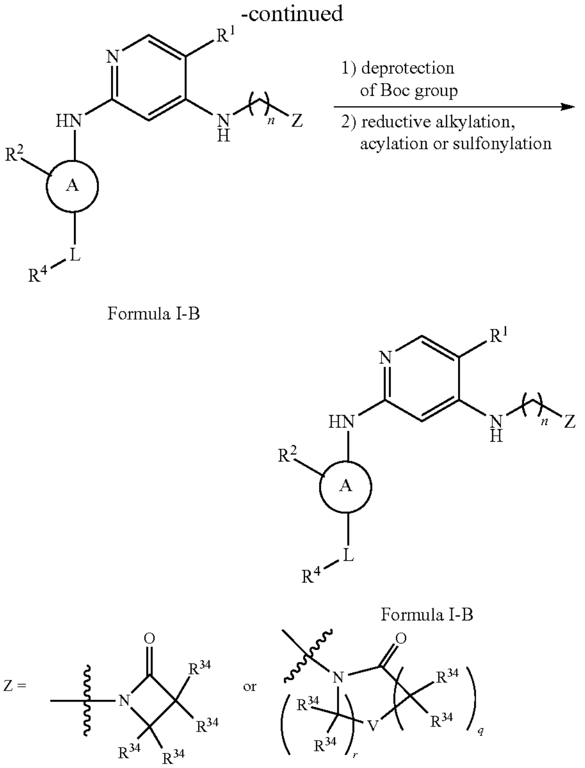

Formula I-B

Formula I-B

Z = or

Scheme 24 illustrates the general preparation of compounds of Formula I-B. The preparation of Formula I-B can be accomplished by a Buchwald-Hartwig coupling reaction with D-I and M. Many amines D-I which are not commercially available can be readily prepared (see schemes 1-16). In a similar manner as shown in scheme 24, reductive alkylation, acylation and sulfonylation can be performed to provide Formula I-B after deprotection of Formula I-B that contains a protecting group such as a Boc group.

General Method A: Mitsunobu Reaction

Intermediate C1

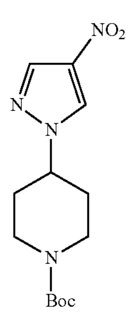 [SMILES: CC(C)(C)OC(=O)N1CCC(n2cc([N+](=O)[O-])cn2)CC1]

A solution of tert-butyl 4-hydroxypiperidine-1-carboxylate (29 g, 146 mmol) and 4-nitro-1H-pyrazole (15 g, 132 mmol) in dry THF (300 mL) was treated with triphenyl phosphine (52 g, 199 mmol). The mixture was cooled to 0° C. and diisopropyl azodicarboxylate (40 mL, 199 mmol) was added drop-wise and stirred at rt for 16 h. The solvent was removed under reduced pressure, and then the residue was quenched with water (200 mL). The resulting solution was extracted with EtOAc (3×100 mL) and the combined organics were dried over anhydrous $Na_2SO_4$, filtered, and concentrated under reduced pressure. The crude was purified by silica gel column chromatography (0 to 5% MeOH/DCM, 10 CV's) to obtain tert-butyl 4-(4-nitro-1H-pyrazol-1-yl)piperidine-1-carboxylate (8.0 g, 20% yield) as white solid. $^1H$ NMR (400 MHz, DMSO-$d_6$): δ 8.94 (s, 1H), 8.27 (s, 1H), 4.42-4.48 (m, 1H), 3.97-4.10 (m, 2H), 2.89 (brs, 2H), 2.02 (d, J=12.5 Hz, 2H), 1.80 (m, 2H), 1.40 (s, 9H); MS (ESI) m/z: 297.4 (M+H$^+$).

General Method B: Boc-Group Deprotection and Reductive Amination

Intermediate C4

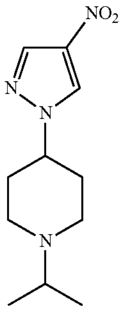 [SMILES: CC(C)N1CCC(n2cc([N+](=O)[O-])cn2)CC1]

(A) A solution tert-butyl 4-(4-nitro-1H-pyrazol-1-yl)piperidine-1-carboxylate (17 g, 57 mmol) in DCM (90 mL) was treated with 4N HCl in 1,4-dioxane (90 mL) at 0° C. and the mixture was stirred at rt for 2 h. The solvent was evaporated under reduced pressure and the residue was triturated with $Et_2O$ (100 mL) followed by pentane (100 mL). The solid was filtered and dried under vacuum to obtain 4-(4-nitro-1H-pyrazol-1-yl)piperidine hydrochloride (12.5 g, 94% n yield) as white solid. $^1H$ NMR (400 MHz, DMSO-$d_6$): δ 8.89 (s, 1H), 8.25 (s, 1H), 4.28 (m, 1H), 3.21 (m, 2H), 2.55 (m, 2H), 1.93 (m, 2H), 1.76 (m, 2H); MS (ESI) m/z: 197.34 (M+H$^+$)

(B) A solution of 4-(4-nitro-1H-pyrazol-1-yl)piperidine hydrochloride (12.5 g, 54 mmol) in MeOH (250 mL) at 0° C. was treated with acetone (24 g, 323 mmol). The reaction mixture was continuously stirred at 0° C. for 15 min. and then sodium cyanoborohydride (22 g, 323 mmol) was added portion wise and stirred at rt for 24 h. The reaction mixture was concentrated and then the residue was treated with sat. solution of $NaHCO_3$ (100 mL). The solution was extracted with DCM (3×100 mL) and the combined organic extracts were washed with brine (100 mL), dried over anhydrous $Na_2SO_4$, filtered and concentrated under reduced pressure to obtain 1-isopropyl-4-(4-nitro-1H-pyrazol-1-yl)piperidine (11.5 g, 90% yield) as a white solid. $^1H$ NMR (400 MHz, DMSO-$d_6$): δ 9.92 (s, 1H), 8.27 (s, 1H), 4.20 (m, 1H), 2.86 (m, 2H), 2.72 (m, 1H), 2.24 (m, 2H), 2.01 (m, 2H), 1.89 (m, 2H), 0.98 (d, J=6.4 Hz, 6H); MS (ESI) m/z: 239.3 (M+H$^+$).

General Method C: Boc-Group Deprotection and Alkylation

Intermediate C7

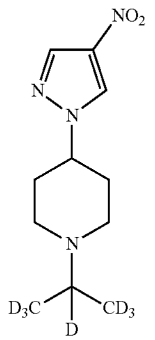 [SMILES: [2H]C([2H])([2H])C([2H])(N1CCC(n2cc([N+](=O)[O-])cn2)CC1)C([2H])([2H])[2H]]

(A) A solution tert-butyl 4-(4-nitro-1H-pyrazol-1-yl)piperidine-1-carboxylate (17 g, 57 mmol) in DCM (90 mL) was treated with 4N HCl in 1,4-dioxane (90 mL) at 0° C. and the mixture was stirred at rt for 2 h. The solvent was evaporated under reduced pressure and the residue was triturated with $Et_2O$ (100 mL) followed by pentane (100 mL). The solid was filtered and dried under vacuum to obtain 4-(4-nitro-1H-pyrazol-1-yl)piperidine hydrochloride (12.5 g, 94% n yield) as white solid. $^1H$ NMR (400 MHz, DMSO-$d_6$): δ 8.89 (s, 1H), 8.25 (s, 1H), 4.28 (m, 1H), 3.21 (m, 2H), 2.55 (m, 2H), 1.93 (m, 2H), 1.76 (m, 2H); MS (ESI) m/z: 197.34 ($M+H^+$).

(B) A mixture of 4-(4-nitro-1H-pyrazol-1-yl)piperidine hydrochloride (0.24 g, 0.96 mmol), 2-iodopropane-1,1,1,2,3,3,3-d7 (0.22 g, 1.2 mmol) and potassium carbonate (0.66 g, 4.8 mmol) in MeCN (5 mL) was heated to 90° C. for 2 h. The mixture was cooled to rt and the mixture was treated with water and brine and extracted with EtOAc (3×15 mL). The combined organics were dried over anhydrous $Na_2SO_4$, filtered and concentrated to dryness. The crude was purified via silica gel column chromatography (2 to 8% MeOH/DCM, 16 CV's) to afford 4-(4-nitro-1H-pyrazol-1-yl)-1-(propan-2-yl-d7)piperidine (0.18 g, 76% yield) as a white solid. $^1H$ NMR (400 MHz, DMSO-$d_6$): δ 8.91 (s, 1H), 8.25 (s, 1H), 4.15-4.21 (m, 1H), 2.86 (d, J=11.5 Hz, 2H), 2.22 (m, 2H), 2.01 (d, J=11.9 Hz, 2H), 1.85-1.93 (m, 2H); MS (ESI) m/z: 246.2 ($M+H^+$).

General Method D: Alkylation and Mesylation

Intermediate C29

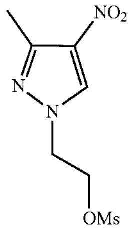 [SMILES: Cc1nn(CCOS(C)(=O)=O)cc1[N+](=O)[O-]]

(A) A solution of 3-methyl-4-nitro-1H-pyrazole (15 g, 118 mmol) in acetonitrile (200 mL) was treated with 2-bromo-ethan-1-ol (16 g, 130 mmol) and potassium carbonate (48.8 g, 354 mmol). The reaction mixture was heated at 90° C. for 16 h. The reaction mixture was diluted with water (100 mL) and extracted with ethyl acetate (3×200 mL). The combined organic extracts were washed with brine (50 mL), dried over anhydrous $Na_2SO_4$, filtered, and concentrated under reduced pressure. The crude was purified by SFC purification to obtain 2-(3-methyl-4-nitro-1H-pyrazol-1-yl)ethan-1-ol. $^1H$ NMR (400 MHz, DMSO-$d_6$): δ 8.72 (s, 1H), 4.96 (t, J=5.2, Hz, 1H), 4.12 (t, J=5.2 Hz, 2H), 3.73 (t, J=5.2 Hz, 2H), 2.42 (s, 3H); MS (ESI) m/z: 172.13 (M+1).

(B) A solution of 2-(3-methyl-4-nitro-1H-pyrazol-1-yl) ethan-1-ol (5.0 g, 29 mmol) in DCM (50 mL) was treated with triethyl amine, (5.8 g, 58 mmol), followed by methane sulfonyl chloride (5.0 g, 44 mmol) under $N_2$ atmosphere at 0° C. The reaction mixture was stirred at rt for 4 h. The reaction mixture was quenched with chilled water (20 mL). The solution was extracted with DCM (2×200 mL) and the combined organic extracts were washed with brine (50 mL), dried over anhydrous $Na_2SO_4$, filtered and concentrated under reduced pressure to obtain 2-(3-methyl-4-nitro-1H-pyrazol-1-yl)ethyl methanesulfonate (6.0 g, 83% yield) as off white solid. $^1H$ NMR (400 MHz, DMSO-$d_6$): δ 8.88 (s, 1H), 4.57 (t, J=5.2, Hz, 2H), 4.46 (t, J=5.2 Hz, 2H), 3.32 (s, 3H), 2.45 (s, 3H); MS (ESI) m/z: 250.19 ($M+H^+$).

General Method E: Nucleophilic Substitution Reaction

Intermediate C30

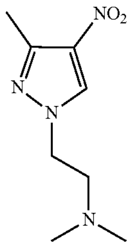

A solution of 2-(3-methyl-4-nitro-1H-pyrazol-1-yl)ethyl methanesulfonate (C29, 5.0 g, 20 mmol) in dry THF (70 mL) was treated with potassium carbonate (3.8 g, 28 mmol) and 2N dimethyl amine in THF (60 mL, 12 mmol) under $N_2$ atmosphere at 10° C. The reaction mixture was quenched with chilled water (20 mL). The solution was extracted with ethyl acetate (3×100 mL) and the combined organic extracts were washed with brine (50 mL), dried over anhydrous $Na_2SO_4$, filtered and concentrated under reduced pressure to obtain N,N-dim ethyl-2-(3-methyl-4-nitro-1H-pyrazol-1-yl) ethan-1-amine (1.9 g, 48% yield). $^1H$ NMR (400 MHz, DMSO-$d_6$): δ 8.77 (s, 1H), 4.17 (t, J=6.4, Hz, 2H), 2.64 (t, J=6.4 Hz, 2H), 2.41 (s, 3H), 2.15 (s, 6H); LC-MS (ESI) m/z: 199.2 ($M+H^+$).

TABLE A
| Example No | Structure | Method | Yield (%) | $^1$H NMR (400 MHz, DMSO-$d_6$): δ | LC-MS m/z: (M + H$^+$). |
|---|---|---|---|---|---|
| Examples of Intermediate C prepared by General Methods A-E above. | | | | | |
| C2 | 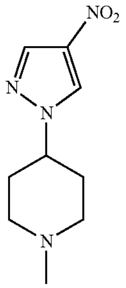 | A | 49 | No NMR data | 211.2 |
| C3 | 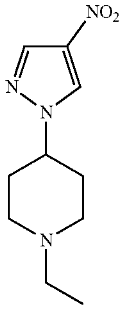 [SMILES: CCN1CCC(n2cc([N+](=O)[O-])cn2)CC1] | A & B | 33 | 8.92 (s, 1H), 8.26 (s, 1H), 4.21 (m, 1H), 2.94 (d, J = 10.2 Hz, 2H), 2.34 (q, J = 7.2 Hz, 2H), 1.91-2.01 (m, 6H), 1.00 (t, J = 7.2 Hz, 3H). | 225.2 |
| C5 | 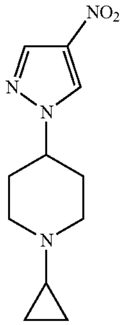 [SMILES: O=[N+]([O-])c1cnn(C2CCN(C3CC3)CC2)c1] | A & B | 60 | 8.91 (s, 1H), 8.26 (s, 1H), 4.25 (m, 1H), 3.02 (m, 2H), 2.28 (m, 2H), 1.97 (m, 2H), 1.92 (m, 2H), 1.65 (m, 1H), 0.42 (m, 2H), 0.32 (m, 2H) | 237.4 |
| C6 | 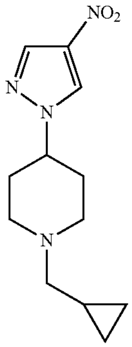 [SMILES: O=[N+]([O-])c1cnn(C2CCN(CC3CC3)CC2)c1] | A & B | 93 | 8.94 (s, 1H), 8.28 (s, 1H), 4.21 (m, 1H), 3.01 (m, 2H), 2.21 (m, 2H), 2.02 (m, 6H), 0.84 (m, 1H), 0.48 (m, 2H), 0.09 (m, 2H) | 251.4 |

TABLE A-continued
Examples of Intermediate C prepared by General Methods A-E above.
| Example No | Structure | Method | Yield (%) | $^1$H NMR (400 MHz, DMSO-$d_6$): δ | LC-MS m/z: (M + H$^+$). |
|---|---|---|---|---|---|
| C8 | 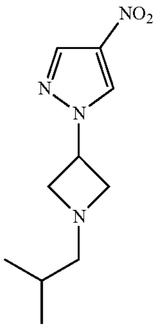 [SMILES: CC(C)CN1CC(n2cc([N+](=O)[O-])cn2)C1] | A & B | 49 | 8.37 (s, 1H), 8.11 (s, 1H), 5.09 (m, 1H), 3.88 (m, 2H), 3.56 (m, 2H), 2.46 (m, 2H), 1.66 (m, 1H), 0.92 (d, J = 6.4, 6H) | 225.4 |
| C9 | 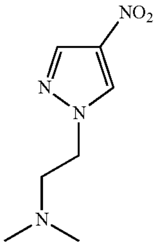 | D & E | 15 | No NMR Data | 185.4 |
| C10 | 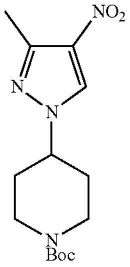 [SMILES: Cc1nn(C2CCN(C(=O)OC(C)(C)C)CC2)cc1[N+](=O)[O-]] | A | 16 | 8.85 (s, 1H), 4.36 (m, 1H), 4.02 (m, 2H), 2.87 (m, 2H), 2.42 (s, 3H), 1.98 (m, 2H), 1.78 (m, 2H), 1.41 (s, 9H) | 255.4 (M-56) |
| C11 | 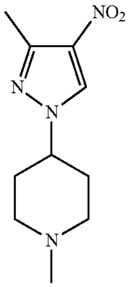 [SMILES: Cc1nn(C2CCN(C)CC2)cc1[N+](=O)[O-]] | A & B | 18 | 8.84 (s, 1H), 4.16 (m, 1H), 2.91 (m, 2H), 2.42 (s, 3H), 2.26 (s, 3H), 2.13 (m, 2H), 1.98 (m, 4H) | 225.4 |
| C12 | 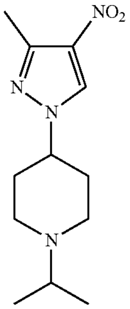 [SMILES: Cc1nn(C2CCN(C(C)C)CC2)cc1[N+](=O)[O-]] | A & B | 97 | 8.83 (s, 1H), 4.14 (m, 1H), 2.85 (m, 4H), 2.18 (s, 3H), 1.97 (m, 6H), 1.19 (t, J = 7.2 Hz, 3H). | 253.5 |

TABLE A-continued
Examples of Intermediate C prepared by General Methods A-E above.
| Example No | Structure | Method | Yield (%) | $^1$H NMR (400 MHz, DMSO-$d_6$): δ | LC-MS m/z: (M + $H^+$). |
|---|---|---|---|---|---|
| C13 | 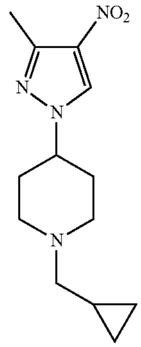 [SMILES: Cc1nn(C2CCN(CC3CC3)CC2)cc1[N+](=O)[O-]] | A & B | 93 | 8.82 (s, 1H), 4.11 (m, 1H), 3.04 (m, 2H), 2.42 (s, 3H), 2.20 (m, 2H), 1.98 (m, 6H), 0.83 (m, 1H), 0.46 (m, 2H), 0.07 (m, 2H) | 265.5 |
| C14 | 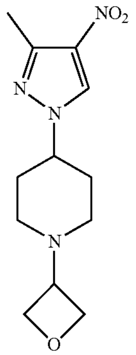 [SMILES: Cc1nn(C2CCN(C3COC3)CC2)cc1[N+](=O)[O-]] | A & B | 97 | 8.83 (s, 1H), 4.53 (m, 2H), 4.42 (m, 2H), 4.17 (m, 1H), 3.42 (t, J = 6.2 Hz, 1H), 2.77 (m, 2H), 2.42 (s, 3H), 2.02 (m, 2H), 1.93 (m, 4H) | 267.2 |
| C15 | 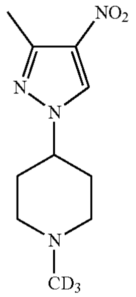 | A & C | 46 | 8.85 (s, 1H), 4.25 (m, 1H), 3.07 (m, 4H), 2.43 (s, 3H), 2.06 (m, 4H). | 228.4 |
| C16 | 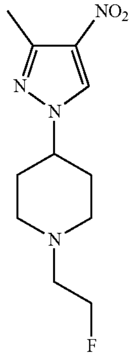 [SMILES: Cc1nn(C2CCN(CCF)CC2)cc1[N+](=O)[O-]] | A & C | 36 | 8.82 (s, 1H), 4.58 (m, 2H), 4.48 (m, 2H), 4.01 (m, 1H), 2.95 (m, 4H), 2.67 (m, 2H), 2.61 (m, 2H), 2.45 (s, 3H), | 257.2 |

TABLE A-continued
Examples of Intermediate C prepared by General Methods A-E above.
| Example No | Structure | Method | Yield (%) | $^1$H NMR (400 MHz, DMSO-$d_6$): δ | LC-MS m/z: (M + H$^+$). |
|---|---|---|---|---|---|
| C17 | 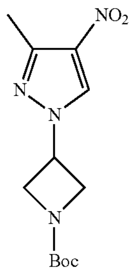 [SMILES: Cc1nn(C2CN(C(=O)OC(C)(C)C)C2)cc1[N+](=O)[O-]] | A | 31 | 8.87 (s, 1H), 4.76 (m, 1H), 4.27 (t, J = 8.4, 2H), 4.14 (m, 2H), 2.45 (s, 3H), 1.40 (s, 9H) | 283.4 |
| C18 | 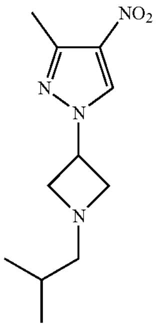 [SMILES: Cc1nn(C2CN(CC(C)C)C2)cc1[N+](=O)[O-]] | A & B | 58 | 8.92 (s, 1H), 4.97 (m, 1H), 3.63 (t, J = 7.2 Hz, 2H), 3.35 (t, J = 6.8 Hz, 2H), 2.44 (s, 3H), 2.28 (d, J = 6.8 Hz, 2H), 1.51 (m, 1H), 0.85 (d, J = 6.4 Hz, 6H). | 239.4 |
| C19 | 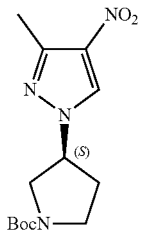 | A | 36 | 8.86 (s, 1H), 4.96 (brs, 1H), 3.71 (m, 1H), 3.57 (m, 1H), 3.46 (m, 1H), 3.40 (m, 1H), 2.42 (s, 3H), 2.29 (m, 2H), 1.39 (s, 9H). | 241.2 (M-56) |
| C20 | 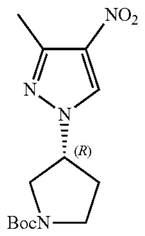 | A | 56 | 8.86 (s, 1H), 4.96 (brs, 1H), 3.70 (m, 1H), 3.57 (m, 1H), 3.47 (m, 1H), 3.45 (m, 1H), 2.42 (s, 3H), 2.32 (m, 2H), 1.39 (s, 9H). | 241.1 (M-56) |
| C21 | 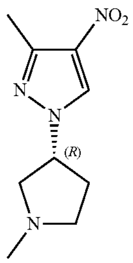 | A & B | 84 | 8.78 (s, 1H), 4.87 (m, 1H), 2.80 (m, 2H), 2.64 (m, 1H), 2.42 (m, 1H), 2.40 (s, 3H), 2.35 (m, 2H), 2.21 (s, 3H) | 211.4 |

TABLE A-continued
Examples of Intermediate C prepared by General Methods A-E above.
| Example No | Structure | Method | Yield (%) | $^1$H NMR (400 MHz, DMSO-$d_6$): δ | LC-MS m/z: (M + H$^+$). |
|---|---|---|---|---|---|
| C22 | 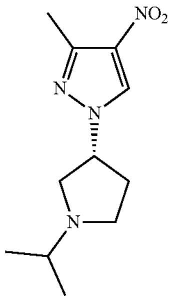 [SMILES: Cc1nn([C@@H]2CCN(C(C)C)C2)cc1[N+](=O)[O-]] | A & B | 85 | 8.79 (s, 1H), 4.85 (m, 1H), 2.90 (brs, 1H), 2.81 (brs, 2H), 2.56 (brs, 1H), 2.42 (s, 3H), 2.32 (brs, 1H), 2.11 (brs, 1H), 1.98 (m, 1H), 1.02 (d, J = 6.4 Hz, 6H) | 239.4 |
| C23 | 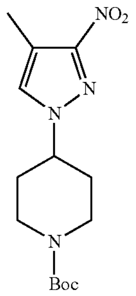 [SMILES: Cc1cn(C2CCN(C(=O)OC(C)(C)C)CC2)nc1[N+](=O)[O-]] | A | 36 | 7.31 (s, 1H), 4.25-4.31 (m, 3H), 2.86 (t, J = 12.8 Hz, 2H), 2.34 (s, 3H), 2.13 (d, J = 12.6 Hz, 2H), 1.92 (m, 2H), 1.47 (s, 9H). | 333.2 (M + Na + H$^+$) |
| C24 | 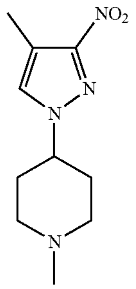 [SMILES: Cc1cn(C2CCN(C)CC2)nc1[N+](=O)[O-]] | D-(A) | 98 | 7.95 (s, 1H), 4.18 (m, 1H), 2.83 (d, J = 11.2 Hz, 2H), 2.24 (s, 3H), 2.18 (s, 3H), 2.00 (m, 4H), 1.90 (m, 2H). | 225.2 |
| C25 | 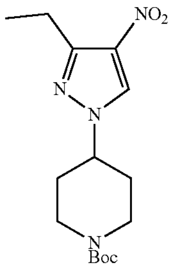 [SMILES: CCc1nn(C2CCN(C(=O)OC(C)(C)C)CC2)cc1[N+](=O)[O-]] | A | 26 | 8.85 (s, 1H), 4.37 (m, 1H), 4.03 (m, 2H), 2.85 (m, 4H), 2.00 (m, 2H), 1.77 (m, 2H), 1.41 (s, 9H), 1.18 (t, J = 7.4 Hz, 3H). | 369.4 (M-56) |
| C26 | 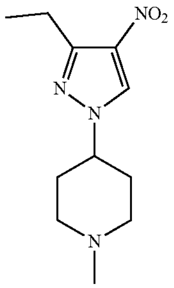 [SMILES: CCc1nn(C2CCN(C)CC2)cc1[N+](=O)[O-]] | A | 95 | 8.83 (s, 1H), 4.14 (m, 1H), 2.85 (m, 4H), 2.18 (s, 3H), 1.97 (m, 6H), 1.19 (t, J = 7.2 Hz, 3H). | 239.3 |

TABLE A-continued
Examples of Intermediate C prepared by General Methods A-E above.
| Example No | Structure | Method | Yield (%) | $^1$H NMR (400 MHz, DMSO-$d_6$): δ | LC-MS m/z: (M + H$^+$). |
|---|---|---|---|---|---|
| C27 | 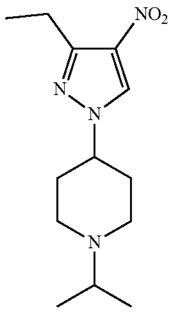 [SMILES: CCc1nn(C2CCN(C(C)C)CC2)cc1[N+](=O)[O-]] | A & B | 87 | 8.81 (s, 1H), 4.11 (m, 1H), 2.84 (m, 4H), 2.73 (m, 1H), 2.22 (m, 2H), 2.01 (m, 2H), 1.89 (m, 2H), 1.19 (m, 3H), 0.97 (d, J = 6.2 Hz, 6H). | 267.2 |
| C28 | 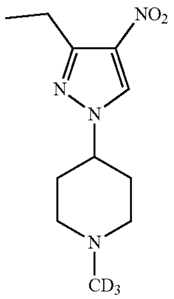 [SMILES: [2H]C([2H])([2H])N1CCC(n2cc([N+](=O)[O-])c(CC)n2)CC1] | A & C | 39 | 8.27 (s, 1H), 4.14 (m, 1H), 2.85 (m, 4H), 1.98 (m, 6H), 1.19 (t, J = 7.6 Hz, 3H). | 242.4 |
| C31 | 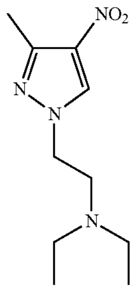 [SMILES: CCN(CC)CCn1cc([N+](=O)[O-])c(C)n1] | D & E | 60 | 8.74 (s, 1H), 4.11 (t, J = 6.4, Hz, 2H), 2.75 (t, J = 6.0 Hz, 2H), 2.50 (m, 4H), 2.41 (s, 3H), 0.86 (t, J = 6.8 Hz, 6H) | 227.2 |
| C32 | 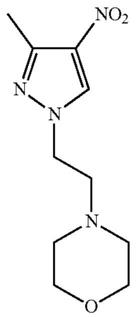 [SMILES: Cc1nn(CCN2CCOCC2)cc1[N+](=O)[O-]] | D & E | 24 | 8.78 (s, 1H), 4.20 (t, J = 6.4 Hz, 2H), 3.52 (t, J = 4.4 Hz, 4H), 2.70 (t, J = 6.2 Hz, 2H), 2.41 (s, 3H), 2.40 (m, 4H). | 241.5 |

TABLE A-continued
| Example No | Structure | Method | Yield (%) | $^1$H NMR (400 MHz, DMSO-$d_6$): δ | LC-MS m/z: (M + H$^+$). |
|---|---|---|---|---|---|
| Examples of Intermediate C prepared by General Methods A-E above. | | | | | |
| C33 | 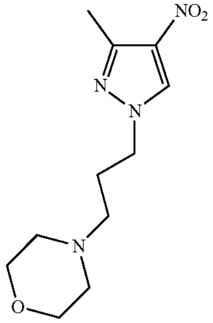 [SMILES: Cc1nn(CCCN2CCOCC2)cc1[N+](=O)[O-]] | D & E | 26 | 8.79 (s, 1H), 4.12 (t, J = 7.0 Hz, 2H), 3.54 (t, J = 4.6 Hz, 4H), 2.41 (s, 3H), 2.29 (m, 4H), 2.24 (m, 2H), 1.93 (t, J = 6.8 Hz, 2H). | 255.4 |
| C34 | 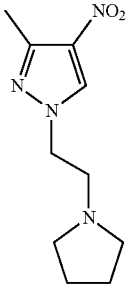 [SMILES: Cc1nn(CCN2CCCC2)cc1[N+](=O)[O-]] | D & E | 73 | 8.79 (s, 1H), 4.19 (t, J = 5.6 Hz, 2H), 2.81 (t, J = 6.8 Hz, 2H), 2.45 (m, 4H), 2.41 (s, 3H), 1.65 (m, 4H). | 225.2 |
| C35 | 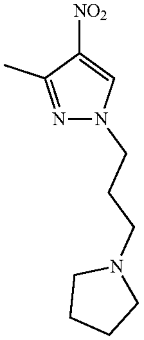 [SMILES: Cc1nn(CCCN2CCCC2)cc1[N+](=O)[O-]] | D & E | 80 | 8.78 (s, 1H), 4.15 (t, J = 6.8 Hz, 2H), 3.82 (m, 4H), 2.52 (m, 2H), 2.42 (m, 2H), 1.95 (s, 3H), 1.65 (m, 4H). | 239.2 |
| C36 | 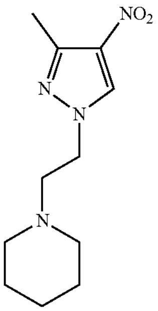 [SMILES: Cc1nn(CCN2CCCCC2)cc1[N+](=O)[O-]] | D & E | 85 | 8.75 (s, 1H), 4.18 (t, J = 6.4 Hz, 2H), 2.65 (t, J = 6.0 Hz, 2H), 2.41 (s, 3H), 2.35 (m, 4H), 1.44 (m, 4H), 1.35 (m, 2H). | 239.4 |

TABLE A-continued

Examples of Intermediate C prepared by General Methods A-E above.

| Example No | Structure | Method | Yield (%) | $^1H$ NMR (400 MHz, DMSO-$d_6$): δ | LC-MS m/z: (M + $H^+$). |
|---|---|---|---|---|---|
| C37 | 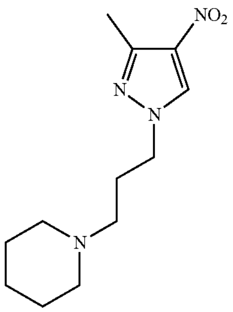 [SMILES: Cc1nn(CCCN2CCCCC2)cc1[N+](=O)[O-]] | D & E | 40 | 8.77 (s, 1H), 4.10 (t, J = 6.8 Hz, 2H), 2.41 (s, 3H), 2.25 (brs, 4H), 2.19 (t, J = 6.8 Hz, 2H), 1.93 (m, 2H), 1.46 (m, 4H), 1.31 (brs, 2H). | 253.4 |

Preparation of Intermediate C38

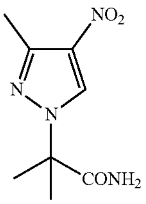

(A) A solution of 5-methyl-4-nitro-1H-pyrazole (2.0 g, 16 mmol) in DMF (15 mL) was treated with sodium hydride (0.94 g, 24 mmol) in portions over a period of 15 min at 0° C. under Ar. The mixture was stirred at rt for 2 h then added methyl 2-bromo-2-methylpropanoate (4.3 g, 24 mmol). The reaction mixture was continued to stir at rt for 16 h. The reaction mixture was quenched with sat'd $NH_4Cl$ solution (100 mL) and the solution was extracted with EtOAc (2×80 mL). The combined organics were washed with water (80 mL), 10% aq. LiCl solution (80 mL), dried over anhydrous $Na_2SO_4$, filtered, concentrated under reduced pressure. The crude was purified by flash chromatography to afford methyl 2-methyl-2-(3-methyl-4-nitro-1H-pyrazol-1-yl)propanoate (2.9 g, 81% yield) as a white solid. $^1H$ NMR (400 MHz, DMSO-$d_6$): δ 8.98 (s, 1H), 3.65 (s, 3H), 2.42 (s, 4H), 1.78 (s, 6H); LC-MS m/z: 228.2 (M+$H^+$).

(B) A solution of methyl 2-methyl-2-(3-methyl-4-nitro-1H-pyrazol-1-yl)propanoate (2.9 g, 13 mmol) in THF (40 mL) was treated with a solution lithium hydroxide hydrate (0.54 g, 13 mmol) in water (10 mL). The mixture was stirred at rt for 16 h. The reaction mixture was concentrated, diluted with water (60 mL) and acidified with 1N aq. HCl to pH around 4. The resultant suspension was filtered, washed with water (2×10 mL) and air dried to afford 2-methyl-2-(3-methyl-4-nitro-1H-pyrazol-1-yl)propanoic acid (2.2 g, 81% yield) as a white solid. LC-MS m/z: 214.2 (M+$H^+$).

(C) A suspension of 2-methyl-2-(3-methyl-4-nitro-1H-pyrazol-1-yl)propanoic acid (2.3 g, 11 mmol) in DCM (30 mL) was treated with a drop of DMF, followed by oxalyl chloride (2.8 mL, 32 mmol). The suspension was stirred at rt for 3 h then the clear solution was concentrated. The residue was dissolved in THF (30 mL) and the solution was added into a solution of $NH_4OH$ (10 mL/water (40 mL)) slowly. The suspension was stirred at rt for 1 h, then concentrated. The suspension (around 10 mL) was diluted with water (50 mL) and the solid was filtered, washed with water and air dried to afford 2-methyl-2-(3-methyl-4-nitro-1H-pyrazol-1-yl)propanamide (2.1 g, 92% yield). LC-MS m/z: 213.2 (M+$H^+$).

General Method F: Reduction to Afford Intermediate D9

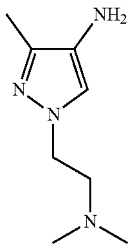

A solution of N,N-dim ethyl-2-(3-methyl-4-nitro-1H-pyrazol-1-yl)ethan amine (C30, 1.9 g, 9.5 mmol) in EtOAc (50 mL) was treated with Pd/C (1.9 g, 10% w/w, 50% moisture). The reaction mixture was stirred under hydrogen balloon pressure (1 atm) at rt for 6 h. The mixture was filtered through a pad of Celite and washed with EtOAc (200 mL). The filtrate was concentrated under reduced pressure to afford 1-(2-(dimethylamino)ethyl)-3-methyl-1H-pyrazol-4-amine. (1.5 g, 94% yield). $^1H$ NMR (400 MHz, DMSO-$d_6$): δ 7.02 (s, 1H), 6.86 (s, 1H), 4.99 (m, 2H), 3.78 (brs, 2H), 2.51 (m, 2H), 2.13 (s, 6H); LC-MS m/z: 155.2 (M+$H^+$).

TABLE B
| Example No | Structure | Yield (%) | $^1H$ NMR (400 MHz, DMSO-$d_6$): δ | MS (ESI) m/z: (M + $H^+$). |
|---|---|---|---|---|
| Examples of Intermediates D prepared by the above General Method F. | | | | |
| D1 | 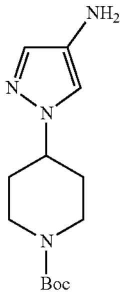 | 100 | 7.05 (s, 1H), 6.89 (s, 1H), 4.11 (m, 1H), 3.98 (brm, 2H), 3.80 (brs, 2H), 2.80-2.93 (brm, 2H), 1.89 (m, 2H), 1.66 (m, 2H), 1.40 (s, 9H). | 289.2 |
| D2 | 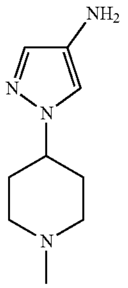 | 90 | 7.03 (s, 1H), 6.88 (s, 1H), 3.86 (m, 1H), 3.76 (brs, 2H), 2.78 (m, 2H), 2.16 (s, 3H), 1.97 (m, 2H), 1.81 (m, 4H) | 181.1 |
| D3 | 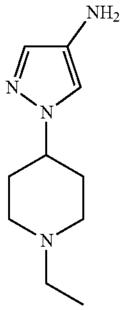 | 93 | 7.04 (s, 1H), 6.88 (s, 1H), 3.85-3.90 (m, 1H), 3.78 (brs, 2H), 2.90 (m, 2H), 2.32 (q, J = 6.4 Hz, 2H), 1.97 (m 2H), 1.88 (m, 2H), 1.77 (m, 2H), 0.99 (t, J = 6.4 Hz, 3H). | 195.4 |
| D4 | 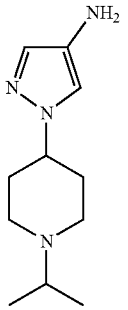 | 95 | 7.04 (s, 1H), 6.08 (s, 1H), 3.84 (m, 1H), 3.52 (brs, 2H), 2.81 (m, 2H), 2.69 (m, 1H), 2.19 (m, 2H), 1.89 (m, 2H), 1.75 (s, 2H), 0.98 (d, J = 6.8 Hz, 6H) | 209.3 |

TABLE B-continued
| Examples of Intermediates D prepared by the above General Method F. | | | | |
|---|---|---|---|---|
| Example No | Structure | Yield (%) | $^1$H NMR (400 MHz, DMSO-$d_6$): δ | MS (ESI) m/z: (M + $H^+$). |
| D5 | 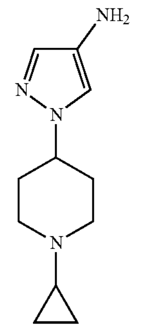 [SMILES: Nc1cnn(C2CCN(C3CC3)CC2)c1] | 91 | 7.03 (s, 1H), 6.87 (s, 1H), 3.91 (m, 1H), 3.74 (brs, 2H), 2.95 (m, 2H), 2.29 (m, 2H), 1.87 (m, 2H), 1.72 (m, 1H), 1.18 (m, 2H), 0.41 (brs, 2H), 0.29 (brs, 2H) | 207.2 |
| D6 | 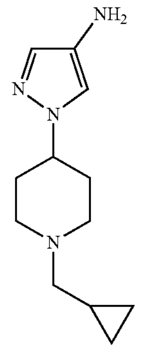 [SMILES: Nc1cnn(C2CCN(CC3CC3)CC2)c1] | 85 | 7.05 (s, 1H), 6.88 (s, 1H), 3.88 (m, 1H), 3.80 (brs, 2H), 3.03 (m, 2H), 2.18 (m, 2H), 2.03 (m, 2H), 1.84 (m, 4H), 0.82 (m, 1H), 0.45 (m, 2H), 0.07 (m, 2H) | 221.1 |
| D7 | 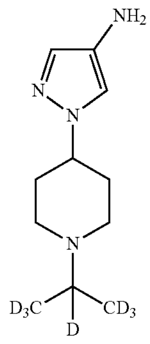 | 96 | 7.03 (s, H), 6.87 (s, 1H), 3.85 (m, 1H), 3.64-3.79 (brs, 2H), 2.82 (d, J = 11.2 Hz, 2H), 2.20 (t, J = 11.6 Hz, 2H), 1.89 (d, J = 11.8 Hz, 2H), 1.76 (m, 2H). | 216.2 |
| D8 | 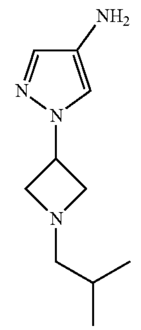 | 80 | 7.14 (s, 1H), 6.95 (s, 1H), 4.73 (m, 1H), 3.82 (brs, 2H), 3.60 (t, J = 7.2 Hz, 2H), 3.20 (t, J = 6.8 Hz, 2H), 2.25 (m, 2H), 1.51 (m, 1H), 0.85 (d, J = 6.8 Hz, 6H) | 195.4 |

TABLE B-continued
| Examples of Intermediates D prepared by the above General Method F. | | | | |
|---|---|---|---|---|
| Example No | Structure | Yield (%) | $^1$H NMR (400 MHz, DMSO-$d_6$): δ | MS (ESI) m/z: (M + H$^+$). |
| D10 | 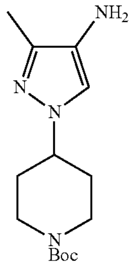 | 94 | 7.01 (s, 1H), 4.03 (m, 1H), 3.97 (brs, 2H), 3.85 (m, 2H), 2.83 (brs, 2H), 1.99 (s, 3H), 1.97 (m, 2H), 1.64 (m, 2H), 1.40 (s, 9H). | 281.5 |
| D11 | 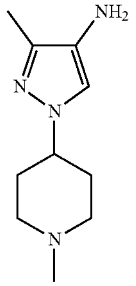 | 75 | 6.97 (s, 1H), 4.02 (brs, 2H), 3.85 (m, 1H), 3.86 (m, 2H), 2.88 (m, 2H), 2.25 (s, 3H), 2.12 (m, 2H), 1.99 (s, 3H), 1.85 (m, 2H). | 195.1 |
| D12 | 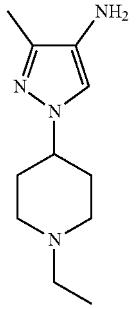 | 94 | 6.96 (s, 1H), 3.77 (m, 1H), 3.55 (brs, 2H), 2.89 (m, 2H), 2.32 (m, 2H), 1.95 (m, 5H), 1.86 (m, 2H), 1.75 (m, 2H), 0.98 (t, J = 7.2 Hz, 3H). | 209.2 |
| D13 | 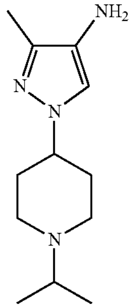 [SMILES: Cc1nn(C2CCN(C(C)C)CC2)cc1N] | 85 | 7.01 (s, 1H), 3.79 (m, 1H), 3.53 (brs, 2H), 2.80 (m, 2H), 2.71 (m, 1H), 2.18 (m, 2H), 1.97 (s, 3H), 1.88 (m, 2H), 1.74 (m, 2H), 0.96 (d, J = 6.4 Hz, 6H). | 223.1 |

TABLE B-continued
| Example No | Structure | Yield (%) | $^1$H NMR (400 MHz, DMSO-$d_6$): δ | MS (ESI) m/z: (M + $H^+$). |
|---|---|---|---|---|
| Examples of Intermediates D prepared by the above General Method F. | | | | |
| D14 | 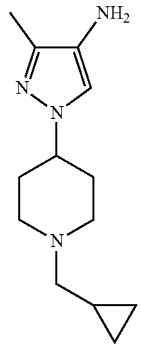 | 98 | 6.97 (s, 1H), 4.02 (brs, 2H), 3.77 (m, 1H), 3.01 (m, 2H), 2.19 (m, 2H), 1.97 (s, 3H), 1.80 (m, 2H), 1.31 (m, 4H), 0.83 (m, 1H), 0.46 (m, 2H), 0.06 (m, 2H) | 235.5 |
| D15 | 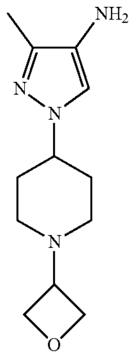 [SMILES: Cc1nn(C2CCN(C3COC3)CC2)cc1N] | 95 | 6.98 (s, 1H), 4.53 (t, J = 6.4 Hz, 2H), 4.42 (t, J = 6.0 Hz, 2H), 3.85 (m, 1H), 3.74 (brs, 2H), 3.40 (m, 1H), 2.73 (m, 2H), 1.98 (s, 3H), 1.85 (m, 6H) | 237.2 |
| D16 | 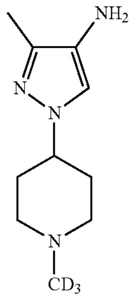 | 84 | 6.95 (s, 1H), 3.81 (m, 1H), 3.75 (brs, 2H), 2.78 (m, 2H), 2.39 (m, 2H), 1.96 (s, 3H), 1.75 (m, 4H). | 198.4 |
| D17 | 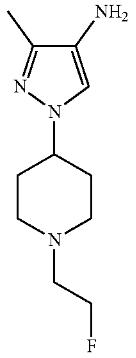 [SMILES: Cc1nn(C2CCN(CCF)CC2)cc1N] | 72 | 6.97 (s, 1H), 4.58 (m, 2H), 4.48 (m, 2H), 3.81 (m, 1H), 3.55 (brs, 2H), 2.96 (m, 4H), 2.67 (m, 2H), 2.60 (m, 2H), 1.97 (s, 3H). | 227.2 |

TABLE B-continued
| Examples of Intermediates D prepared by the above General Method F. | | | | |
|---|---|---|---|---|
| Example No | Structure | Yield (%) | $^1$H NMR (400 MHz, DMSO-$d_6$): δ | MS (ESI) m/z: (M + H$^+$). |
| D18 | 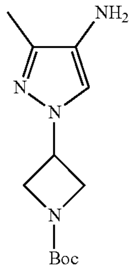 [SMILES: Cc1nn(C2CN(C(=O)OC(C)(C)C)C2)cc1N] | 92 | 7.04 (s, 1H), 4.88 (m, 1H), 4.16 (t, J = 8.0 Hz, 2H), 4.00 (brs, 2H), 3.71 (brs, 2H), 2.02 (s, 3H), 1.39 (s, 9H) | 253.23 |
| D19 | 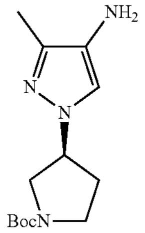 [SMILES: Cc1nn([C@H]2CCN(C(=O)OC(C)(C)C)C2)cc1N] | 93 | 6.97 (s, 1H), 4.65 (m, 1H), 4.05 (brs, 2H), 3.42 (m, 2H), 2.16 (m, 2H), 1.98 (s, 3H), 1.39 (s, 9H), 1.35 (m, 2H). | 267.4 |
| D20 | 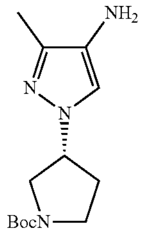 [SMILES: Cc1nn([C@@H]2CCN(C(=O)OC(C)(C)C)C2)cc1N] | 89 | 6.97 (s, 1H), 4.64 (m, 1H), 3.63 (brs, 2H), 3.59 (m, 2H), 3.39 (m, 2H), 2.16 (m, 2H), 1.98 (s, 3H), 1.39 (s, 9H) | 267.2 |
| D21 | 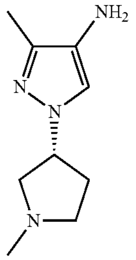 | 88 | 6.99 (s, 1H), 4.58 (m, 1H), 3.62 (brs, 2H), 2.67 (m, 2H), 2.56 (m, 1H), 2.41 (m, 1H), 2.24 (s, 3H), 1.97 (s, 3H), 1.91 (m, 1H), 1.20 (m, 1H). | 181.1 |
| D22 | 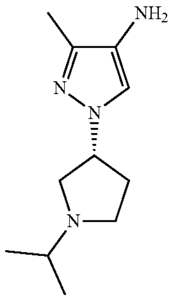 | 85 | 7.01 (s, 1H), 4.54 (t, J = 7.6 Hz, 1H), 3.74 (brs, 2H), 2.84 (m, 1H), 2.74 (m, 1H), 2.69 (m, 1H), 2.58 (m, 1H), 2.37 (m, 1H), 2.19 (m, 1H), 1.98 (s, 3H), 1.94 (m, 1H), 1.01 (t, J = 5.6 Hz, 6H). | 209.5 |

TABLE B-continued
| Examples of Intermediates D prepared by the above General Method F. | | | | |
|---|---|---|---|---|
| Example No | Structure | Yield (%) | $^1$H NMR (400 MHz, DMSO-$d_6$): δ | MS (ESI) m/z: (M + $H^+$). |
| D23 | 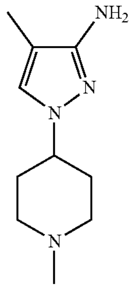 | 99 | No NMR Data | 195.2 |
| D24 | 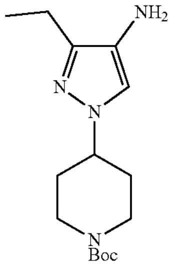 [SMILES: CCc1nn(C2CCN(C(=O)OC(C)(C)C)CC2)cc1N] | 92 | 7.35 (s, 1H), 4.14 (m, 1H), 4.01 (brs, 2H), 2.75 (brs, 2H), 2.45 (m, 2H), 2.12 (m, 2H), 1.99 (m, 2H), 1.75 (m, 2H), 1.40 (s, 9H), 1.17 (t, J = 7.4 Hz, 3H). | 295.3 |
| D25 | 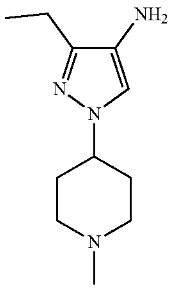 | 88 | 6.95 (s, 1H), 4.25 (m, 1H), 4.09 (brs, 2H), 3.50 (m, 2H), 3.38 (m, 2H), 2.79 (m, 2H), , 2.16 (s, 3H), 1.80 (m, 4H), 1.06 (t, J = 7.8 Hz, 3H | 209.2 |
| D26 | 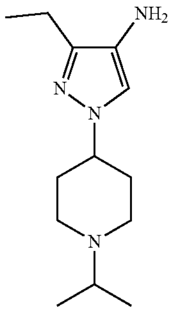 | 94 | 6.96 (s, 1H), 3.78 (m, 1H), 3.52 (brs, 2H), 2.82 (m, 2H), 2.71 (m, 1H), 2.20 (m, 2H), 1.96 (s, 3H), 1.92 (m, 2H), 1.87 (m, 2H), 1.72 (m, 2H), 0.96 (d, J = 6.8 Hz, 6H) | 237.2 |
| D27 | 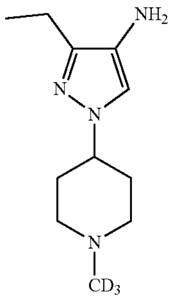 [SMILES: [2H]C([2H])([2H])N1CCC(n2cc(N)c(CC)n2)CC1] | 63 | 6.96 (s, 1H), 3.78 (m, 1H), 3.67 (brs, 2H), 2.78 (m, 2H), 2.39 (m, 2H), 1.93 (m, 2H), 1.84 (m, 4H), 1.06 (t, J = 7.8 Hz, 3H) | 212.4 |

TABLE B-continued
| Examples of Intermediates D prepared by the above General Method F. | | | | |
|---|---|---|---|---|
| Example No | Structure | Yield (%) | $^1H$ NMR (400 MHz, DMSO-$d_6$): δ | MS (ESI) m/z: (M + $H^+$). |
| D28 | 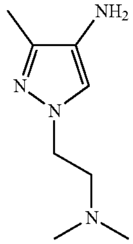 | 94 | 6.95 (s, 1H), 4.01 (brs, 2H), 3.89 (t, J = 6.4 Hz, 2H), 4.01 (brs, 2H), 3.56 (m, 2H), 2.13 (s, 6H), 1.96 (s, 3H). | 169.2 |
| D29 | 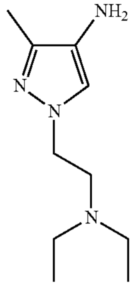 | 88 | 6.95 (s, 1H), 4.11 (m, 2H), 3.87 (t, J = 6.8 Hz, 2H), 3.51 (brs, 2H), 2.44 (m, 4H), 1.95 (s, 3H), 0.91 (t, J = 6.8 Hz, 6H). | 197.3 |
| D30 | 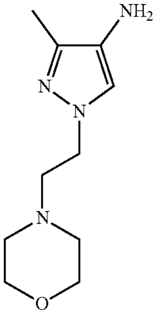 | 91 | 6.96 (s, 1H), 3.93 (t, J = 6.8 Hz, 2H), 3.54 (m, 6H), 2.57 (t, J = 6.8 Hz, 2H), 2.36 (brs, 4H), 1.96 (s, 3H) | 211.1 |
| D31 | 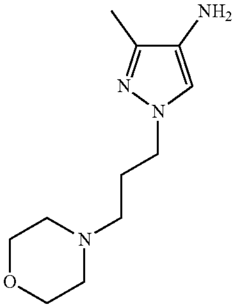 [SMILES: Cc1nn(CCCN2CCOCC2)cc1N] | 83 | 6.92 (s, 1H), 3.84 (t, J = 7.6 Hz, 2H), 3.55 (m, 6H), 2.49 (brs, 1H), 2.29 (m, 4H), 2.17 (t, J = 6.8 Hz, 2H), 1.77 (m, 2H), 1.35 (s, 2H) | 225.2 |
| D32 | 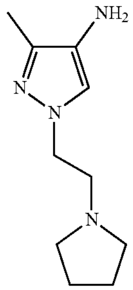 | 99 | 6.95 (s, 1H), 4.03 (brs, 2H), 3.92 (t, J = 7.2, Hz, 2H), 2.68 (t, J = 6.8 Hz, 2H), 2.41 (m, 4H), 1.96 (s, 3H), 1.64 (m, 4H). | 195.1 |

TABLE B-continued
Examples of Intermediates D prepared by the above General Method F.
| Example No | Structure | Yield (%) | $^1$H NMR (400 MHz, DMSO-$d_6$): δ | MS (ESI) m/z: (M + $H^+$). |
|---|---|---|---|---|
| D33 | 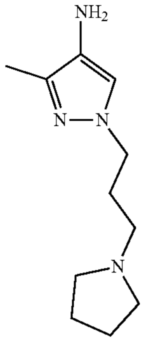 | 88 | 6.93 (s, 1H), 4.01 (t, J = 6.8 Hz, 2H), 3.82 (t, J = 6.8 Hz, 2H), 2.37 (m, 4H), 2.22 (m, 2H), 1.97 (s, 3H), 1.75 (m, 4H). | 209.2 |
| D34 | 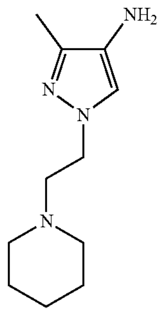 | 79 | 6.95 (s, 1H), 3.91 (t, J = 6.8 Hz, 2H), 3.64 (brs, 2H), 2.52 (t, J = 6.4 Hz, 2H), 2.33 (m, 4H), 1.96 (s, 3H), 1.44 (m, 4H), 1.35 (m, 2H). | 209.5 |
| D35 | 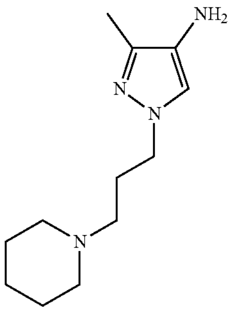 [SMILES: Cc1nn(CCCN2CCCCC2)cc1N] | 90 | 6.91 (s, 1H), 3.82 (t, J = 6.8 Hz, 2H), 3.55 (brs, 2H), 2.32 (m, 4H), 2.13 (m, 2H), 1.97 (s, 3H), 1.77 (m, 2H), 1.46 (m, 4H), 1.35 (brm, 2H). | 223.5 |
| D36 | 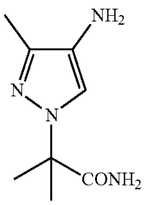 | 99 | No NMR Data | 183.2 |

General Method G: Alkylation and Deprotection of Boc Protecting Group

Intermediate H—VIII-1

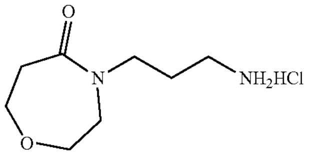

A solution of 1,4-oxazepan-5-one (10 g, 87 mmol) in dry THF (400 mL) at 0° C. was treated with sodium hydride (3.0 g, 130 mmol) portion wise under nitrogen atmosphere. The reaction mixture was stirred for 15 min at 0° C. then tert-butyl (3-bromopropyl) carbamate (21 g, 87 mmol) was added. The solution was continued stirred from 0° C. rt for 16 h. The reaction mixture was quenched with saturated solution of $NH_4Cl$ (200 mL) and then the solution was extracted with EtOAc (2×150 mL). The combined organic extract was washed with brine (150 mL), dried over anhydrous $Na_2SO_4$, and filtered under reduced pressure. The crude was purified by silica gel column chromatography (40 to 50% EtOAc/hexane, 15 CV's) to obtain tert-butyl (3-(5-oxo-1,4-oxazepan-4-yl)propyl carbamate (12 g, 50% yield) as yellow liquid. The product was dissolved in DCM (50 mL) and treated with 4N HCl in 1,4-dioxane (4 eq). The mixture was stirred at rt for 3 h and concentrated, dried under high vacuum to obtain 4-(3-aminopropyl)-1,4-oxazepan-5-one HCl salt (100% yield). $^1H$ NMR (400 MHz, DMSO-$d_6$): δ 8.09 (brs, 3H), 3.62 (m, 4H), 3.49 (m, 2H), 3.35 (t, J=6.8 Hz, 2H), 2.73 (m, 2H), 2.62 (t, J=4.8 Hz, 2H), 1.78 (m, 2H). LC-MS (ESI) m/z: 173.2 (M+$H^+$).

TABLE C

Examples of Intermediate H that can be prepared by General Method G.

| Example | Intermediate | Yield (%) | $^1H$ NMR (400 MHz, DMSO-$d_6$): δ | LC-MS (m/z: M + $H^+$) |
|---|---|---|---|---|
| H-II-1 | 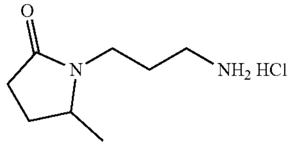 | 98 | No NMR Data | 157.2 |
| H-II-2 | 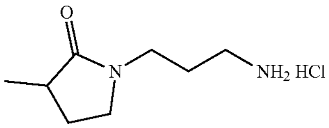 | 43 | Boc: 6.73 (brm, 1H), 3.24 (m, 2H), 3.16 (m, 2H), 2.78 (m, 2H), 2.31 (m, 1H), 1.90 (m, 1H), 1.53 (m, 3H), 1.36 (s, 9H), 1.04 (d, J = 6.8 Hz, 3H). | 157.2 |
| H-II-3 | 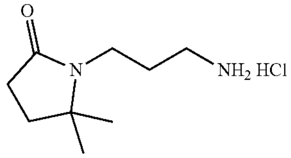 | 52 | Boc: 4.17 (m, 2H), 3.26 (m, 2H), 2.52 (m, 2H), 2.23 (m, 2H), 1.80 (m, 2H), 1.71 (m, 2H), 1.39 (s, 6H), 1.17 (s, 9H). | 171.2 |
| H-II-4 | 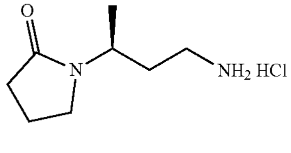 | 60 | No NMR Data | 157.2 |
| H-IX-1 | 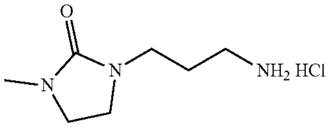 | 50 | No NMR Data | 158.2 |
| H-III-1 | 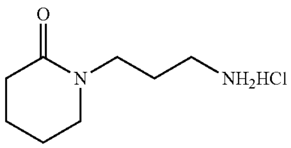 | 36 | Boc: 6.76 (t, J = 5.6 Hz, 1H), 3.20 (m, 4H), 2.86 (m, 2H), 2.17 (m, 2H), 1.67 (m, 4H), 1.53 (m, 2H), 1.35 (s, 9H). | 157.2 |

TABLE C-continued

Examples of Intermediate H that can be prepared by General Method G.

| Example | Intermediate | Yield (%) | $^1$H NMR (400 MHz, DMSO-$d_6$): δ | LC-MS (m/z: M + H$^+$) |
|---|---|---|---|---|
| H-IV-1 | 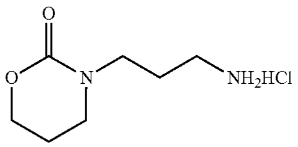 | 64 | Boc: 4.14 (m, 2H), 3.25 (m, 2H), 3.18 (m, 2H), 2.92 (m, 2H), 1.92 (m, 2H), 1.62 (m, 2H), 1.36 (s, 9H). | 159.2 |
| H-V-1 | 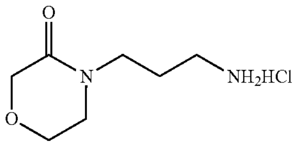 | 84 | Boc: 3.99 (m, 2H), 3.48 (m, 2H), 3.30 (m, 4H), 2.91 (m, 2H), 1.58 (m, 2H), 1.36 (s, 9H). | 159.2 |
| H-VII-1 | 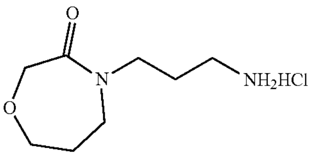 | 57 | Boc: 6.73 (s, 1H), 4.08 (s, 2H), 3.73 (t, J = 5.6 Hz, 2H), 3.46 (m, 2H), 3.25 (m, 2H), 2.88 (q, J = 6.6 Hz, 2H), 1.98 (s, 1H), 1.78 (m, 2H), 1.53 (m, 2H), 1.36 (s, 9H). | 173.2 |

Preparation of Intermediate H—XIV: 1-(3-aminopropyl)azepan-2-one

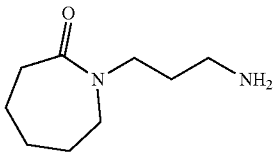 [SMILES: NCCCN1CCCCCC1=O]

A suspension of DBU (22 g, 145 mmol) in MeOH:$H_2O$ (1:1) (130 mL) was treated with KOH (12 g, 217 mmol) at 0° C. under $N_2$ atmosphere and the reaction mixture was stirred at rt for 16 h. The reaction mixture was evaporated under reduced pressure and the residue was diluted with water (200 mL). The solution was extracted with 10% MeOH in DCM (3×250 mL) and the combined organic extracts were dried over anhydrous sodium sulphate, filtered and concentrated under reduced pressure to obtain 1-(3-aminopropyl) azepan-2-one (21 g, 85% yield) as a liquid oil. $^1$H NMR (400 MHz, $CDCl_3$): δ 3.45 (t, J=3.5 Hz, 2H), 3.31 (t, J=4.4 Hz, 2H), 2.68 (t, J=6.5 Hz, 2H), 2.51 (t, J=5.8 Hz, 2H), 1.70 (m, 2H), 1.65 (m, 8H); LC-MS (ESI) m/z: 171.4 (M+H$^+$).

Preparation of Intermediate L-III-1: 2-chloro-5-cyclopropyl-4-(methylsulfonyl)pyrimidine

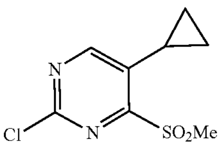

A suspension of 5-bromo-2-chloro-4-(methylthio)pyrimidine (25.0 g, 105 mmol) and cyclopropylboronic acid (13.7 g, 158 mmol) in toluene:$H_2O$ (9:1) (650 mL) was treated with $K_3PO_4$ (66.7 g, 315 mmol) was added. The reaction mixture was purged with nitrogen for 20 min and then added tricyclohexyl phosphine (5.9 g, 21 mmol) and $Pd(OAc)_2$ (2.35 g, 10.50 mmol). The reaction mixture was stirred at 90° C. for 16 h. The reaction mixture was diluted with water (200 mL) and extracted with EtOAc (3×300 mL). The combined organic extracts were washed with brine (200 mL), dried over anhydrous $Na_2SO_4$, filtered and concentrated under reduced pressure. The crude was purified by silica gel column chromatography (0 to 10% EtOAc/hexane) to obtain 2-chloro-5-cyclopropyl-4-(methylthio)pyrimidine (14.0 g, 66% yield) as a yellow oil. $^1$H NMR (400 MHz, DMSO-$d_6$): δ 7.92 (s, 1H), 2.58 (s, 3H), 1.67 (m, 1H), 1.03 (m, 2H), 0.67 (m, 2H); LC-MS (ESI) m/z: 201.0 (M+H$^+$). A solution of 2-chloro-5-cyclopropyl-4-(methylthio)pyrimidine (4.0 g, 20 mmol) in DCM (60 mL) at 0° C. was treated with m-CPBA (4.8 g, 28 mmol). The reaction mixture was warmed to rt and stirred for 3 h. The reaction mixture was washed with saturated aq. $NaHCO_3$ (2×40 mL). The organic layer was dried over anhydrous $Na_2SO_4$, filtered and concentrated under reduced pressure to obtain 2-chloro-5-cyclopropyl-4-(methylsulfonyl)pyrimidine (3.6 g, 86% yield) as a yellow solid. $^1$H NMR (400 MHz, DMSO-$d_6$): δ 8.57 (s, 1H), 2.89 (s, 3H), 2.16 (m, 1H), 1.16 (m, 2H), 0.93 (m, 2H); LC-MS (ESI) m/z: 217.0 (M+H$^+$).

Preparation of Intermediate L-I-2: 4-chloro-2-(methylthio)-5-(trifluoromethyl)pyrimidine

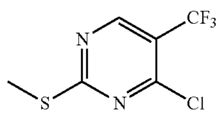

A solution of 2,4-dichloro-5-(trifluoromethyl)pyrimidine (100 g, 0.46 mol) in diethyl ether (2 L) was treated with $ZnCl_2$ (1.0N in ether) (555 mL, 0.56 mol) dropwise at 0° C. and the reaction mixture was stirred for 2 h. Sodium thiomethoxide (49 g, 0.94 mol) was added at 0° C. and the reaction mixture was warmed to rt and stirred for 48 h. The reaction mixture was quenched with 2N HCl under an ice-water bath and then the solution was extracted with $Et_2O$ (3×500 mL). The combined organic extracts were washed with water (500 mL), dried over anhydrous $Na_2SO_4$, filtered, and concentrated under reduced pressure at 35° C. to obtain 4-chloro-2-(methylthio)-5-(trifluoromethyl)pyrimidine (100 g, 95% yield) as a colorless liquid. $^1H$ NMR (400 MHz, DMSO-$d_6$): δ 9.01 (s 1H), 2.62 (s 3H).

These three intermediates are commercially available.

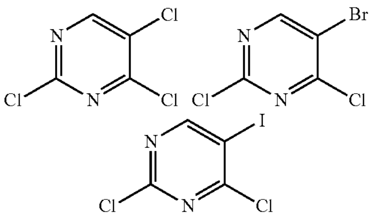

General Method H: Substitution Reaction

Intermediate J-7

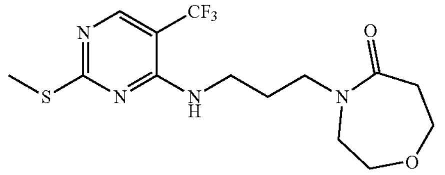 [SMILES: CSc1ncc(C(F)(F)F)c(NCCCN2CCOCCC2=O)n1]

A solution of 4-(3-aminopropyl) 1,4-oxazepan-5-one hydrochloride (H-VIII-I, 3.0 g, 17.4 mmol) in DMF (60 mL) was treated with DIEA (15.5 ml, 87.2 mmol) at 0° C. and stirred for 15 min. Then 4-chloro-2-(methylthio)-5-(trifluoromethyl)pyrimidine (L-I-2, 0.0 g, 26.2 mmol) was added and stirring continued from 0° C. to rt for 16 h. The reaction mixture was quenched with ice water (120 mL) and extracted with ethyl acetate (3×50 mL). The combined organic extracts were washed with brine (50 mL), dried over anhydrous $Na_2SO_4$, and filtered, concentrated under reduced pressure. The crude was purified by silica gel column chromatography (40 to 50% EtOAc/hexane, 15 CV's) to obtain 4-(3-((2-(methylthio)-5-(trifluoromethyl)pyrimidin-4-yl)amino)propyl)-1,4-oxazepan-5-one (3.0 g, 47% yield) as yellow liquid. $^1H$ NMR (400 MHz, DMSO-$d_6$): δ 8.25 (s, 1H), 7.52 (brs, 1H), 3.64 (m, 4H), 3.47 (m, 2H), 3.42 (m, 2H), 3.32 (m, 2H), 2.63 (t, J=4.8 Hz, 2H), 2.47 (s, 3H), 1.68 (m, 2H); LC-MS (ESI) m/z: 365.3 (M+$H^+$).

TABLE D

Examples of Intermediate K that can be prepared by General Method H.

| Example No | Intermediate | Yield (%) | $^1H$ NMR (400 MHz, DMSO-$d_6$): δ | LC-MS (m/z: M + $H^+$) |
|---|---|---|---|---|
| K-1 | 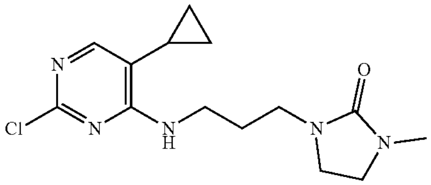 [SMILES: CN1CCN(CCCNc2nc(Cl)ncc2C2CC2)C1=O] | 100 | No NMR Data | 310.2 |
| K-2 | 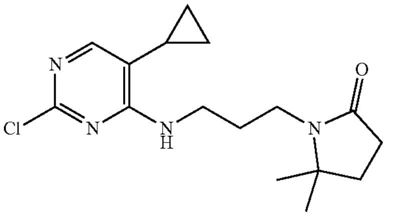 [SMILES: CC1(C)CCC(=O)N1CCCNc1nc(Cl)ncc1C1CC1] | 31 | No NMR Data | 323.2 |
| K-3 | 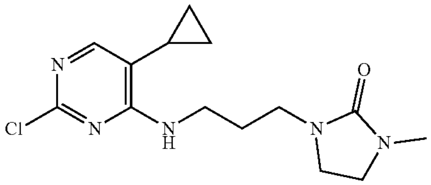 [SMILES: CN1CCN(CCCNc2nc(Cl)ncc2C2CC2)C1=O] | 60 | No NMR Data | 310.2 |

TABLE D-continued

Examples of Intermediate K that can be prepared by General Method H.

| Example No | Intermediate | Yield (%) | $^1$H NMR (400 MHz, DMSO-$d_6$): δ | LC-MS (m/z: M + H$^+$) |
|---|---|---|---|---|
| K-4 | 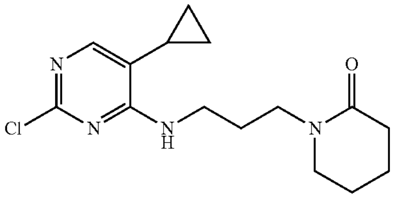 [SMILES: O=C1CCCCN1CCCNc1nc(Cl)ncc1C1CC1] | 82 | 7.69 (s, 1H), 7.51 (t, J = 6.0 Hz, 1H), 3.34 (t, J = 6.4 Hz, 3H), 3.23-3.26 (m, 2H), 2.22 (t, J = 6.4 Hz, 2H), 1.69 (m, 6H), 1.46-1.56 (m, 2H), 0.88 (m, 2H), 0.54 (m, 2H). | 309.2 |
| K-5 | 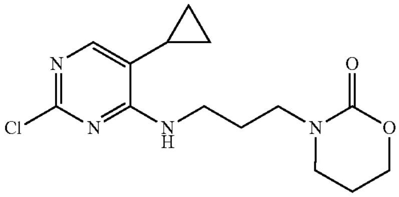 [SMILES: O=C1OCCCN1CCCNc1nc(Cl)ncc1C1CC1] | 47 | 7.69 (s, 1H), 7.43 (s, 1H), 4.17 (m, 2H), 3.39 (m, 2H), 3.29 (m, 4H), 1.94 (m, 2H), 1.77 (m, 2H), 1.48 (m, 1H), 0.89 (m, 2H), 0.56 (m, 2H). | 311.3 |
| K-6 | 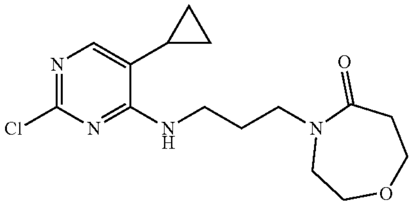 [SMILES: O=C1CCOCCN1CCCNc1nc(Cl)ncc1C1CC1] | 42 | 7.69 (s, 1H), 7.45 (s, 1H), 3.66 (m, 4H), 3.56 (brs, 2H), 3.35 (m, 4H), 2.64 (m, 2H), 1.69 (m, 2H), 1.50 (m, 1H), 0.88 (m, 2H), 0.56 (m, 2H). | 325.3 |
| K-7 | 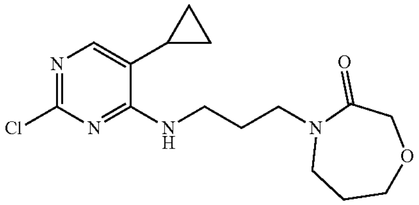 [SMILES: O=C1COCCCN1CCCNc1nc(Cl)ncc1C1CC1] | 51 | 7.70 (s, 1H), 7.45 (brs, 1H), 4.12 (s, 2H), 3.76 (t, J = 5.2 Hz, 2H), 3.50 (m, 2H), 3.37 (m, 4H), 1.85 (m, 2H), 1.72 (m, 2H), 1.51 (m, 1H), 0.89 (m, 2H), 0.55 (m, 2H). | 325.1 |
| K-8 | 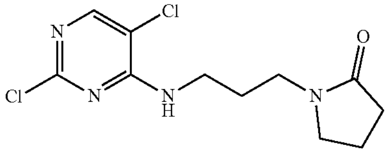 | 40 | 8.15 (s, 1H), 7.90 (t, 1H), 3.35 (m, 4H), 3.21 (t, J = 6.8 Hz, 2H), 2.23 (t, J = 8.0 Hz, 2H), 1.93 (m, 2H), 1.72 (m, 2H). | 289.3 |
| K-9 | 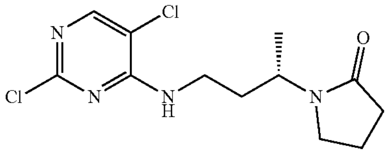 [SMILES: C[C@@H](CCNc1nc(Cl)ncc1Cl)N1CCCC1=O] | 55 | No NMR Data | 304.2 |
| K-10 | 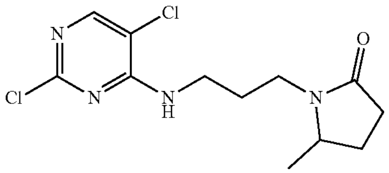 [SMILES: CC1CCC(=O)N1CCCNc1nc(Cl)ncc1Cl] | 23 | No NMR Data | 304.2 |
| K-11 | 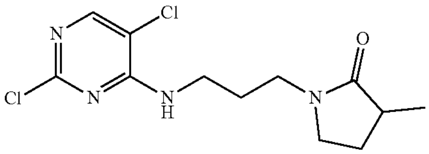 [SMILES: CC1CCN(CCCNc2nc(Cl)ncc2Cl)C1=O] | 97 | 8.15 (s, 1H), 7.9 (brm, 1H), 3.32 (m, 4H), 3.25 (m, 2H), 2.37 (m, 1H), 2.20 (m, 1H), 1.71 (m, 2H), 1.49 (m, 1H), 1.03 (d, J = 6.8 Hz, 3H). | 304.2 |

TABLE D-continued
| Examples of Intermediate K that can be prepared by General Method H. | | | | |
|---|---|---|---|---|
| Example No | Intermediate | Yield (%) | $^1H$ NMR (400 MHz, DMSO-$d_6$): δ | LC-MS (m/z: M + H$^+$) |
| K-12 | 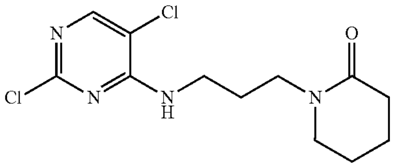 | 37 | 8.15 (s, 1H), 7.94 (m, 1H), 3.35 (m, 2H), 3.30 (m, 2H), 3.25 (m, 2H), 2.21 (m, 2H), 1.72 (m, 6H). | 303.20 |
| K-13 | 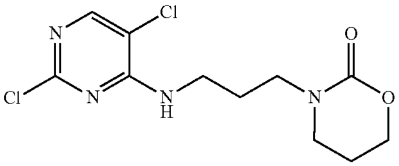 [SMILES: O=C1OCCCN1CCCNc1nc(Cl)ncc1Cl] | 64 | 8.15 (s, 1H), 7.90 (brs, 1H), 4.16 (m, 2H), 3.37 (m, 2H), 3.27 (m, 4H), 1.94 (m, 2H), 1.77 (m, 2H). | 305.2 |
| K-14 | 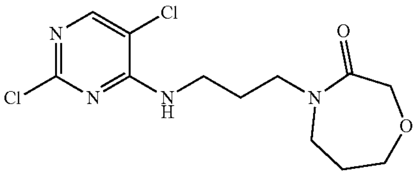 | 47 | 8.20 (s, 1H), 7.88 (m, 1H), 4.11 (s, 2H), 3.76 (m, 2H), 3.50 (m, 2H), 3.36 (m, 4H), 1.84 (m, 2H), 1.72 (m, 2H). | 319.1 |
| K-15 | 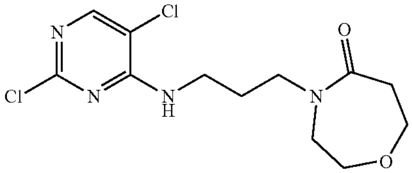 | 51 | 8.15 (s, 1H), 7.91 (brs, 1H), 3.65 (m, 4H), 3.48 (m, 2H), 3.35 (m, 4H), 2.63 (m, 2H), 1.66 (m, 2H). | 319.0 |
| K-16 | 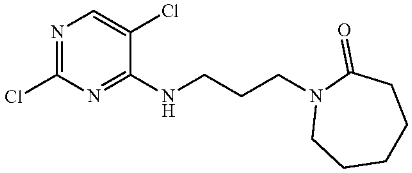 [SMILES: O=C1CCCCCN1CCCNc1nc(Cl)ncc1Cl] | 39 | No NMR Data | 317.2 |
| K-17 | 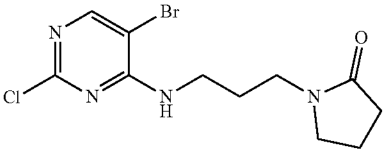 [SMILES: O=C1CCCN1CCCNc1nc(Cl)ncc1Br] | 68 | 8.23 (s, 1H), 7.73 (t, 1H), 3.34 (m, 4H), 3.26 (t, J = 6.6 Hz, 2H), 2.22 (t, J = 8.0 Hz, 2H), 1.93 (m, 2H), 1.71 (m, 2H). | 333.3 |
| K-18 | 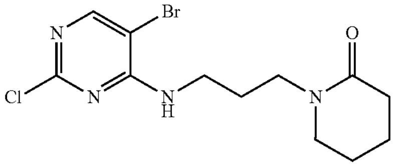 [SMILES: O=C1CCCCN1CCCNc1nc(Cl)ncc1Br] | 39 | 8.23 (s, 1H), 7.58 (brs, 1H), 3.33 (m, 2H), 3.31 (m, 2H), 3.25 (m, 2H), 2.22 (m, 2H), 1.71 (m, 6H) | 347.1 |
| K-19 | 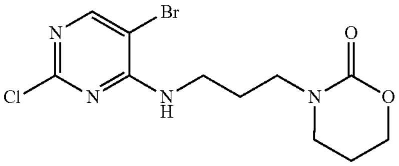 [SMILES: O=C1OCCCN1CCCNc1nc(Cl)ncc1Br] | 56 | 8.23 (s, 1H), 7.72 (brs, 1H), 4.16 (m, 2H), 3.36 (m, 2H), 3.28 (m, 4H), 1.95 (m, 2H), 1.76 (m, 2H). | 349.0 |

TABLE D-continued

| Examples of Intermediate K that can be prepared by General Method H. | | | | |
|---|---|---|---|---|
| Example No | Intermediate | Yield (%) | $^1$H NMR (400 MHz, DMSO-$d_6$): δ | LC-MS (m/z: M + H$^+$) |
| K-20 | 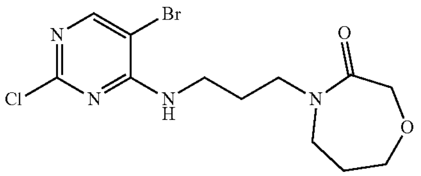 [SMILES: O=C1COCCCN1CCCNc1nc(Cl)ncc1Br] | 48 | 8.23 (s, 1H), 7.72 (m, 1H), 4.11 (s, 2H), 3.76 (m, 2H), 3.49 (m, 2H), 3.33 (m, 4H), 1.83 (m, 2H), 1.71 (m, 2H). | 363.0 |
| K-21 | 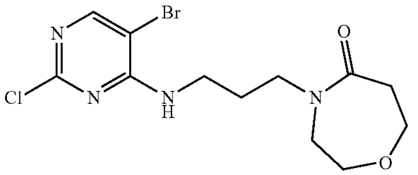 [SMILES: O=C1CCOCCN1CCCNc1nc(Cl)ncc1Br] | 50 | 8.23 (s, 1H), 7.74 (brs, 1H), 3.66 (brs, 4H), 3.48 (m, 2H), 3.34 (m, 4H), 2.63 (m, 2H), 1.67 (m, 2H). | 363.2 |
| J-1 | 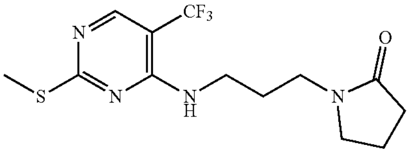 [SMILES: CSc1ncc(C(F)(F)F)c(NCCCN2CCCC2=O)n1] | 100 | 7.53 (t, J = 5.8 Hz, 1H), 3.40 (q, J = 6.6 Hz, 2H), 3.34 (t, J = 7.0 Hz, 2H), 3.19 (t, J = 6.8 Hz, 2H), 2.46 (s, 3H), 2.21 (t, J = 8.0 Hz, 2H), 1.91 (p, J = 7.4 Hz, 2H), 1.71 (m, 2H). | 335.2 |
| J-2 | 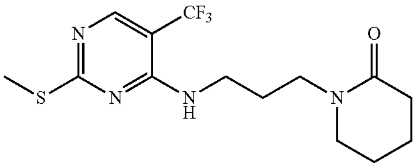 [SMILES: CSc1ncc(C(F)(F)F)c(NCCCN2CCCCC2=O)n1] | 91 | 8.24 (s, 1H), 7.58 (t, J = 5.8 Hz, 1H), 3.40 (q, J = 6.6 Hz, 2H), 3.21-3.28 (m, 4 H), 2.46 (s, 3H), 2.21 (t, J = 6.2 Hz, 2H), 1.65-1.75 (m, 6H). | 349.2 |
| J-3 | 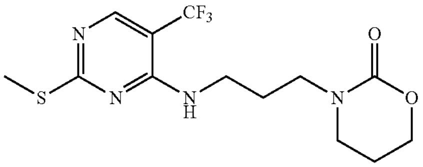 [SMILES: CSc1ncc(C(F)(F)F)c(NCCCN2CCCOC2=O)n1] | 65 | 8.25 (d, J = 1.1 Hz, 1H), 7.51 (t, J = 5.8 Hz, 1H), 4.15 (t, J = 5.4 Hz, 2H), 3.44 (q, J = 6.6 Hz, 2H), 3.22-3.27 (m, 4H), 2.46 (s, 3H), 1.92 (m, 2H), 1.77 (m, 2H). | 351.2 |
| J-4 | 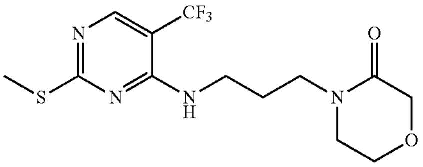 [SMILES: CSc1ncc(C(F)(F)F)c(NCCCN2CCOCC2=O)n1] | 77 | 8.25 (s, 1H), 1.54 (t, J = 5.2 Hz, 1H), 4.02 (s, 2H), 3.82 (t, J = 5.2 Hz, 2H), 3.44 (q, 2H), 3.34 (m, 4H), 2.47 (s, 3H), 1.77 (m, 2H). | 351.1 |
| J-5 | 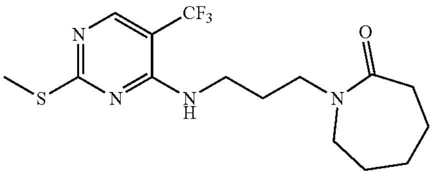 [SMILES: CSc1ncc(C(F)(F)F)c(NCCCN2CCCCCC2=O)n1] | 65 | 8.26 (s, 1H), 7.53 (m, 1H), 3.45 (m, 2H), 3.34 (m, 4H), 2.48 (s, 3H), 2.43 (m, 2H), 1.66 (m, 4H), 1.52 (m, 4H). | 363.2 |
| J-6 | 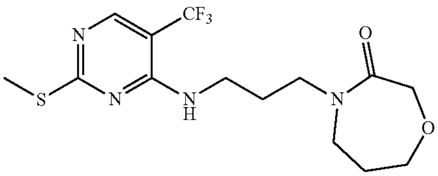 [SMILES: CSc1ncc(C(F)(F)F)c(NCCCN2CCCOCC2=O)n1] | 64 | 8.25 (s, 1H), 7.52 (brs, 1H), 4.11 (s, 2H), 3.75 (t, J = 5.6 Hz, 2H), 3.48 (m, 2H), 3.45 (m, 2H), 3.34 (m, 2H), 2.47 (s, 3H), 1.82 (m, 2H), 1.72 (m, 2H). | 365.3 |

General Method I: Pd Coupling Reaction

Intermediate M-1

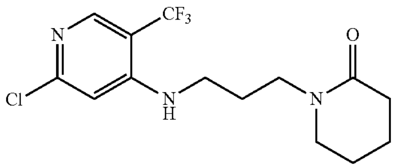 [SMILES: O=C1CCCCN1CCCNc1cc(Cl)ncc1C(F)(F)F]

A mixture of 1-(3-aminopropyl)piperidin-2-one hydrochloride (9.0 g, 29 mmol) and 2-chloro-4-iodo-5-(trifluoromethyl)pyridine (6.2 g, 32 mmol) in toluene (180 mL) was treated with cesium carbonate (23.9 g, 73 mmol). The mixture was purged with nitrogen gas for 15 min. $PdCl_2$ (dppf) DCM (2.4 g, 2.9 mmol) was added and the mixture was purged with nitrogen gas for further 5 min. The seal tube was closed and conventionally heated in a pre-heated oil bath at 90° C. for 16 h. The reaction mixture was cooled to rt, poured into water (100 mL) and extracted with EtOAc (3×100 mL). The combined organic extracts were washed with brine, dried over anhydrous $Na_2SO_4$, and filtered, concentrated under reduced pressure. The crude was purified by silica gel column chromatography (40 to 45% EtOAc/hexane, 10 CV's) to obtain 1-(3-((2-chloro-5-(trifluoromethyl)pyridin-4-yl)amino)propyl)piperidin-2-one (2.6 g, 26% yield) as brown solid. $^1$H NMR (400 MHz, DMSO-$d_6$): δ 8.18 (s, 1H), 6.99 (brs, 1H), 6.88 (s, 1H), 3.29 (m, 2H), 3.24 (m, 4H), 2.22 (m, 2H), 1.70 (m, 6H); LC-MS (ESI) m/z: 336.1 (M+H$^+$).

TABLE E

Examples of Intermediate J that can be prepared by General Method I.

| Example No | Intermediate | Yield (%) | $^1$H NMR (400 MHz, DMSO-$d_6$): δ | LC-MS (m/z: M + H$^+$) |
|---|---|---|---|---|
| M-1 | 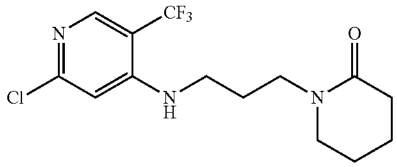 [SMILES: O=C1CCCCN1CCCNc1cc(Cl)ncc1C(F)(F)F] | 26 | 8.18 (s, 1H), 6.99 (brs, 1H), 6.88 (s, 1H), 3.29 (m, 2H), 3.24 (m, 4H), 2.22 (m, 2H), 1.70 (m, 6H). | 336.1 |
| M-2 | 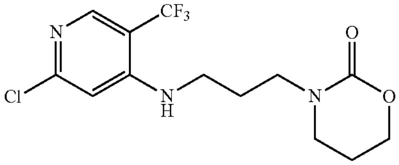 [SMILES: O=C1OCCCN1CCCNc1cc(Cl)ncc1C(F)(F)F] | 26 | 8.18 (s, 1H), 6.90 (s, 1H), 6.87 (brs, 1H), 4.16 (m, 2H), 3.25 (m, 6H), 1.92 (m, 2H), 1.72 (m, 2H). | 338.2 |
| M-3 | 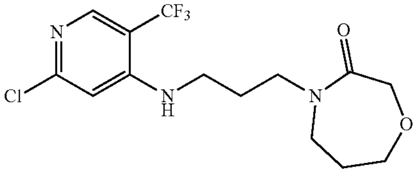 [SMILES: O=C1COCCCN1CCCNc1cc(Cl)ncc1C(F)(F)F] | 27 | 8.18 (s, 1H), 6.90 (brs, 2H), 3.64 (brs, 4H), 3.48 (m, 2H), 3.26 (m, 4H), 2.63 (m, 2H), 1.63 (m, 2H). | 351.1 |
| M-4 | 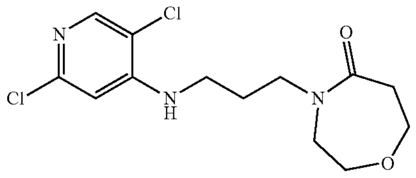 [SMILES: O=C1CCOCCN1CCCNc1cc(Cl)ncc1Cl] | 19 | 7.99 (s, 1H), 6.75 (s, 2H), 3.62 (m, 4H), 3.49 (m, 2H), 3.35 (m, 2H), 3.20 (m, 2H), 2.94 (brs, 2H), 1.65 (m, 2H). | 318.2 |

General Method J: Oxidation

Intermediate J-14

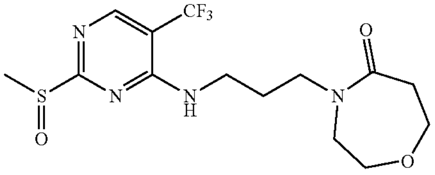 [SMILES: CS(=O)c1ncc(C(F)(F)F)c(NCCCN2CCOCCC2=O)n1]

A solution of 4-(3-((2-(methylthio)-5-(trifluoromethyl)pyrimidin-4-yl)amino)propyl)-1,4-oxazepan-5-one (J-7, 3.0 g, 8.2 mmol) in DCM (60 mL) at 0° C., m-CPBA (2.0 g, 11.5 mmol) was added and stirred from 0° C. to room temperature for 3 h. The reaction mixture was washed with saturated aq. sodium bicarbonate (2×90 mL). Organic layer was dried over anhydrous $Na_2SO_4$ and filtered. The filtrate was concentrated under reduced pressure to obtain mixture of 4-(3-((2-(methylsulfinyl)-5-(trifluoromethyl)pyrimidin-4-yl)amino)propyl)-1,4-oxazepan-5-one and 4-(3-((2-(methylsulfonyl)-5-(trifluoromethyl)pyrimidin-4-yl)amino)propyl)-1,4-oxazepan-5-one (3.0 g, 95%, 9:1) as light yellow semi-solid. $^1H$ NMR (400 MHz, DMSO-$d_6$): δ 8.59 (s, 1H), 7.94 (brs, 1H), 3.60 (m, 4H), 3.45 (m, 4H), 3.36 (m, 2H), 2.88 (s, 3H), 2.63 (m, 2H), 1.70 (m, 2H); LC-MS (ESI) m/z: 381.3 (M+$H^+$).

TABLE F

Additional Examples of Intermediate J that can be prepared by General Method J.

| Example No | Intermediate | Yield (%) | $^1H$ NMR (400 MHz, DMSO-$d_6$): δ | LC-MS (m/z: M + $H^+$) |
|---|---|---|---|---|
| J-8 | 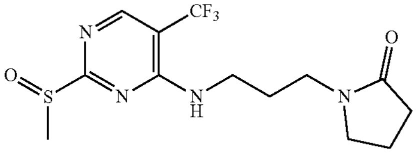 [SMILES: CS(=O)c1ncc(C(F)(F)F)c(NCCCN2CCCC2=O)n1] | 90 | 8.58 (s, 1H), 8.01 (s, 1H), 3.46 (m, 2H), 3.35 (m, 2H), 3.20 (m, 2H), 2.83 (s, 3H), 2.22 (m, 2H), 1.96 (m, 2H), 1.71 (m, 2H). | 351.2 |
| J-9 | 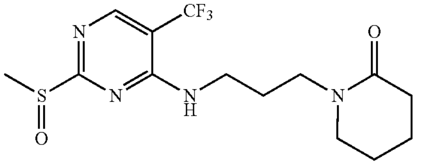 [SMILES: CS(=O)c1ncc(C(F)(F)F)c(NCCCN2CCCCC2=O)n1] | 96 | 8.58 (s, 1H), 8.06 (s, 1H), 3.46 (m, 2H), 3.35 (m, 2H), 3.24 (m, 2H), 2.72 (s, 3H), 2.23 (m, 2H), 1.73 (m, 6H). | 365.3 |
| J-10 | 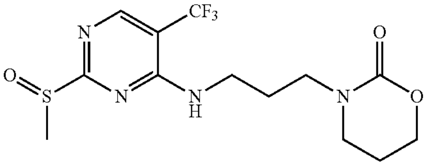 [SMILES: CS(=O)c1ncc(C(F)(F)F)c(NCCCN2CCCOC2=O)n1] | 92 | 8.58 (s, 1H), 7.99 (brs, 1H), 4.16 (m, 2H), 3.48 (m, 2H), 3.26 (m, 4H), 2.83 (s, 3H), 1.92 (m, 2H), 1.78 (m, 2H). | 367.2 |
| J-11 | 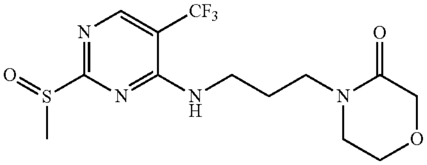 [SMILES: CS(=O)c1ncc(C(F)(F)F)c(NCCCN2CCOCC2=O)n1] | 96 | 8.59 (s, 1H), 8.00 (brs, 1H), 4.03 (s, 2H), 3.84 (m, 2H), 3.48 (m, 2H), 3.35 (m, 4H), 2.84 (s, 3H), 1.79 (m, 2H). | 367.1 |
| J-12 | 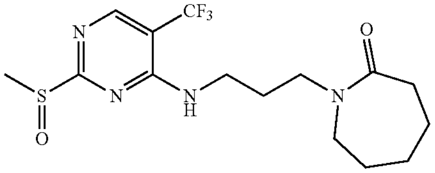 [SMILES: CS(=O)c1ncc(C(F)(F)F)c(NCCCN2CCCCCC2=O)n1] | 83 | 8.58 (s, 1H), 8.02 (brs, 1H), 3.45 (m, 2H), 3.34 (m, 4H), 2.83 (s, 3H), 2.43 (m, 2H), 1.69 (m, 4H), 1.56 (m, 4H). | 379.4 |
| J-13 | 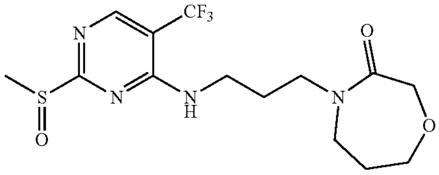 [SMILES: CS(=O)c1ncc(C(F)(F)F)c(NCCCN2CCCOCC2=O)n1] | 96 | 8.58 (s, 1H), 7.98 (s, 1H), 4.12 (s, 2H), 3.74 (m, 2H), 3.48 (m, 4H), 3.34 (m, 2H), 2.83 (s, 3H), 1.77 (m, 2H), 1.73 (m, 2H). | 381.3 |

General Method K: Substitution Reaction A

Example 80

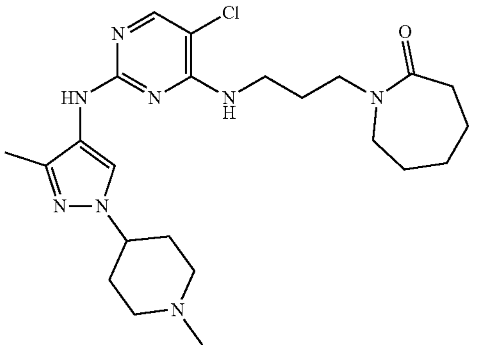 [SMILES: Cc1nn(C2CCN(C)CC2)cc1Nc1ncc(Cl)c(NCCCN2CCCCCC2=O)n1]

A mixture of 1-(3-((2,5-dichloropyrimidin-4-yl)amino)propyl)azepan-2-one (K-16, 0.06 g, 0.19 mmol) and methyl-1-(1-methylpiperidin-4-yl)-1H-pyrazol-4-amine hydrochloride (D11, 0.044 g, 0.19 mmol)) in EtOH (3 mL) was treated with 4.0N HCl in 1,4-dioxane (0.047 mL) and then the reaction mixture was heated at 90° C. for 15 h. The solution was concentrated under reduced pressure. The residue was treated with EtOAc and sonicated. The solid was filtered and the solid was treated with $CH_3CN$ and stirred at rt for 3 h. The solid was filtered and washed with $CH_3CN$ to obtain the desired product which was treated with MP carbonate resin (150 mg, 3.14 mmol/g loading, 0.47 mmol, 2.5 eq) in MeOH (5 mL). The solution was stirred at rt for 2 h. The resin was filtered off and washed with MeOH. The filtrate was concentrated and the residue was treated with $CH_3CN:H_2O$ (1:1, 3 mL) and lyophilized to obtain 1-(3-((5-chloro-2-((3-methyl-1-(1-methylpiperidin-4-yl)-1H-pyrazol-4-yl)amino)pyrimidin-4-yl)amino)propyl)azepan-2-one (42 mg, 46% yield). $^1$H NMR (400 MHz, DMSO-$d_6$): δ 8.28 (brs, H), 7.81 (s, 1H), 7.79 (s, 1H), 7.04 (s, 1H), 3.95 (m, 1H), 3.31-3.30 (m, 4H), 2.80 (m, 2H), 2.42 (m, 2H), 2.17 (s, 3H), 2.08 (s, 3H), 1.75-2.00 (m, 8H), 1.63-1.68 (m, 4H), 1.53 (m, 4H); LC-MS (ESI) m/z: 476.4 (M+H$^+$).

General Method L: Substitution Reaction B and Deprotection of Boc Nitrogen Protecting Group Example 83

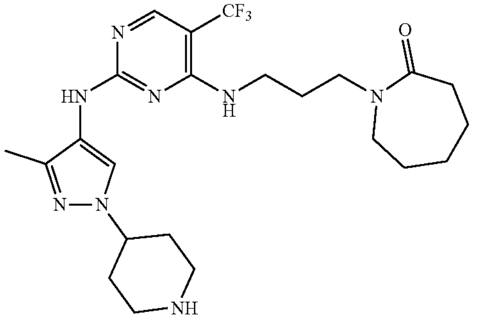 [SMILES: Cc1nn(C2CCNCC2)cc1Nc1ncc(C(F)(F)F)c(NCCCN2CCCCCC2=O)n1]

A solution of 1-(3-((2-(methylsulfinyl)-5-(trifluoromethyl)pyrimidin-4-yl)amino)propyl)azepan-2-one (J-12, 0.53 g, 1.4 mmol)) and tert-butyl 4-(4-amino-3-methyl-1H-pyrazol-1-yl)piperidine-1-carboxylate (D-10, 0.43 g, 1.5 mmol) in dry DMF (7 mL, in molecular sieves 3 Å) was treated with 4.0N HCl in 1,4-dioxane (0.11 mL) was added and then the reaction mixture was heated at 80° C. for 15 h. The mixture was concentrated under high vacuum and the residue was dissolved in 1,4-dioxane (5 mL). 4.0N HCl in 1,4-dioxane (0.35 mL) was added and the mixture was stirred at rt for 2 h. The mixture was concentrated under reduced pressure and the crude was purified by reverse-phase column chromatography (0 to 40% $CH_3CN/H_2O$ (0.1% FA), 15 CV's) to obtain 1-(3-((2-((3-methyl-1-(piperidin-4-yl)-1H-pyrazol-4-yl)amino)-5-(trifluoromethyl)pyrimidin-4-yl)amino)propyl)azepan-2-one (0.57 g, 82% yield). $^1$H NMR (400 MHz, DMSO-$d_6$): δ 8.94 (brs, 1H), 8.30 (s, 1H), 8.08 (s, 1H), 7.84 (brs, 1H), 7.07 (brs, 1H), 4.18 (brm, 1H), 3.31 (brm, 4H), 3.17 (m, 2H), 2.77 (m, 2H), 2.42 (s, 3H), 2.26 (m, 2H), 2.11 (m, 4H), 1.97 (m, 2H), 1.84 (m, 2H), 1.67 (m, 4H), 1.54 (m, 4H); LC-MS (ESI) m/z: 495.4 (M+H$^+$).

General Method M: Reductive Alkylation

Example 90

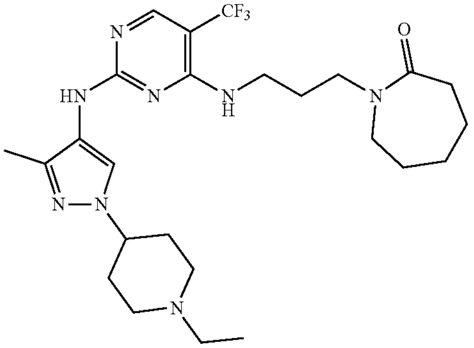 [SMILES: CCN1CCC(n2cc(Nc3ncc(C(F)(F)F)c(NCCCN4CCCCCC4=O)n3)c(C)n2)CC1]

A mixture of (1-(3-((2-((3-methyl-1-(piperidin-4-yl)-1H-pyrazol-4-yl)amino)-5-(trifluoromethyl)pyrimidin-4-yl)amino)propyl)azepan-2-one (83, 0.10 g, 0.20 mmol)), acetaldehyde (0.1 mL, 1.8 mmol), and acetic acid (2 drops) in methanol (0.5 mL) was treated with sodium cyanoborohydride (0.025 g, 0.40 mmol). The mixture was stirred at rt for 16 h. The solution was quenched with brine and then extracted with EtOAc (2×25 mL). The combined organics were dried over anhydrous $Na_2SO_4$, filtered and concentrated. The crude was purified by reverse-phase column chromatography (0 to 40% $CH_3CN/H_2O$ (0.1% FA), 15 CV's) to obtain 1-(3-((2-((1-(1-ethylpiperidin-4-yl)-3-methyl-1H-pyrazol-4-yl)amino)-5-(trifluoromethyl)pyrimidin-4-yl)amino)propyl)azepan-2-one (46 mg, 43% yield). $^1$H NMR (400 MHz, DMSO-$d_6$): δ 8.91 (brs, 1H), 8.08 (s, 1H), 7.85 (brs, 1H), 7.06 (brs, 1H), 4.02 (brm, 1H), 3.32 (m, 7H), 2.99 (m, 2H), 2.43 (m, 4H), 2.10 (m, 4H), 1.92 (m, 2H), 1.88 (m, 2H), 1.65 (m, 4H), 1.49 (m, 4H), 1.04 (t, J=7.4 Hz, 3H); LC-MS (ESI) m/z: 523.4 (M+H$^+$).

General Method N: Pd Coupling Reaction

Example 171

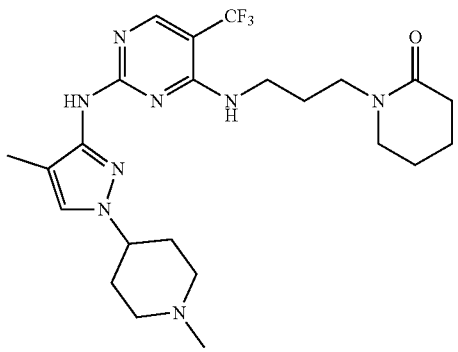 [SMILES: Cc1cn(C2CCN(C)CC2)nc1Nc1ncc(C(F)(F)F)c(NCCCN2CCCCC2=O)n1]

A mixture of 4-methyl-1-(1-methylpiperidin-4-yl)-1H-pyrazol-3-amine (D23, 0.076 g, 0.39 mmol), 1-(3-((2-chloro-5-(trifluoromethyl)pyridin-4-yl)amino)propyl)piperidin-2-one (M-1, 0.12 g, 0.36 mmol) and cesium carbonate (0.23 g, 0.71 mmol) in 1,4-dioxane (2.0 mL) was sparged with Ar, treated with $Pd_2(dba)_3$ (0.033 g, 0.039 mmol) and Xantphos (0.041 g, 0.071 mmol), sparged again with Ar, capped tightly and heated at 85° C. for 16 h. The mixture was cooled to rt and diluted with brine and extracted with DCM (3×15 mL). The combined organics were dried over anhydrous $Na_2SO_4$, filtered and concentrated under reduced pressure. The crude material was purified via reverse-phase column chromatography (5 to 10% MeCN/$H_2O$ (0.1% FA)) to obtain 1-(3-((2-((4-methyl-1-(1-methylpiperidin-4-yl)-1H-pyrazol-3-yl)amino)-5-(trifluoromethyl)pyridin-4-yl)amino)propyl)piperidin-2-one (0.043 g, 24% yield) as a white solid. $^1H$ NMR (400 MHz, DMSO-$d_6$): δ 9.12 (brs, 1H), 8.13 (s, 2H), 7.13 (brs, 1H), 4.10 (s, 2H), 3.72 (m, 2H), 3.29-3.44 (m, 6H), 2.17 (s, 3H), 1.92 (s, 6H), 1.77 (m, 2H), 1.68 (m, 2H); LC-MS (ESI) m/z: 481.2 (M+$H^+$).

Synthesis of Example 172

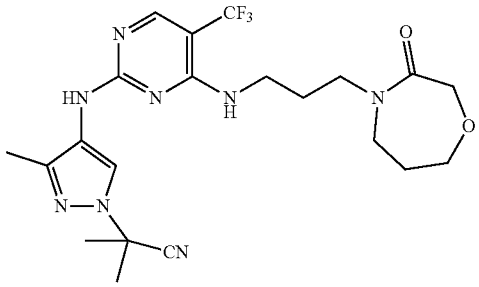 [SMILES: Cc1nn(C(C)(C)C#N)cc1Nc1ncc(C(F)(F)F)c(NCCCN2CCCOCC2=O)n1]

A mixture of 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanamide (125, 0.11 g, 0.22 mmol) and 2,4,6-tripropyl-1,3,5,2,4,6-trioxatriphosphinane 2,4,6-trioxide (0.562 g, 0.88 mmol) in EtOAc (5 mL) was treated with triethylamine (0.12 mL, 0.88 mmol). The reaction mixture was stirred at rt for 16 h. The reaction mixture was quenched with sat'd $NaHCO_3$ solution (40 mL) and stirred for few minutes. Layers were separated and the aqueous layer was extracted with EtOAc (2×30 mL) and combined organics were washed with brine, dried over anhydrous $Na_2SO_4$, filtered, concentrated under reduced pressure. The crude was purified by flash column chromatography (0 to 100% EtOAc/DCM, 10 CV's) to afford 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanenitrile (0.069 g, 65% yield). $^1H$ NMR (400 MHz, DMSO-$d_6$): δ 8.48 (s, 1H), 7.93 (s, 1H), 7.45 (s, 1H), 6.67 (s, 1H), 6.15 (t, J=6.0 Hz, 1H), 3.89-3.95 (m, 1H), 3.28 (m, 2H), 3.19-3.23 (m, 2H), 3.08 (q, J=6.2 Hz, 2H), 2.81 (d, J=11.0 Hz, 2H), 2.20 (t, J=6.2 Hz, 2H), 2.17 (s, 3H), 1.99 (m, 2H), 1.92 (m, 4H), 1.89 (s, 3H), 1.68 (m, 6H); LC-MS (ESI) m/z: 494.2 (M+$H^+$).

TABLE G

Exemplary Compounds that can be prepared by General Methods K through N.

| Example No. | Product | General Method | Yield (%) | $^1H$ NMR (400 MHz, DMSO-$d_6$): δ | LC-MS (m/z: M + $H^+$) |
|---|---|---|---|---|---|
| 1 | 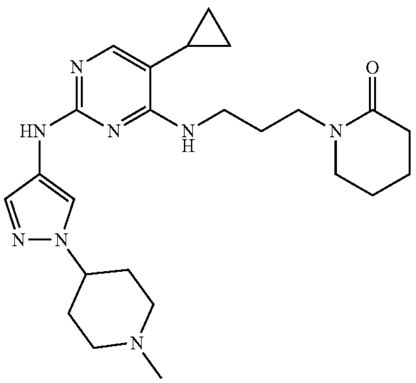 [SMILES: CN1CCC(n2cc(Nc3ncc(C4CC4)c(NCCCN4CCCCC4=O)n3)cn2)CC1] | K | 49 | 7.88 (s, 1H), 7.53 (s, 2H), 4.41 (m, 1H), 3.46 (m, H), 3.40 (m, 2H), 3.37 (t, J = 6.8 Hz, 3H), 3.25 (t, J = 5.8 Hz, 2H), 3.00-3.20 (m, 2H), 2.76 (s, 3H), 2.18-2.22 (m, 6H), 1.77 (m, 2H), 1.69 (m, 4H), 1.44 (m, 1H), 0.80 (m, 2H), 0.46 (m, 2H). | 453.4 |

TABLE G-continued

| Example No. | Product | General Method | Yield (%) | $^1$H NMR (400 MHz, DMSO-$d_6$): δ | LC-MS (m/z: M + H$^+$) |
|---|---|---|---|---|---|
| Exemplary Compounds that can be prepared by General Methods K through N. | | | | | |
| 2 | 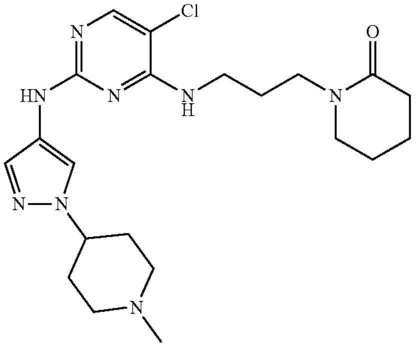 | K | 42 | 10.5 (brs, 1H), 8.04 (brs, 1H), 7.90 (s, 1H), 7.58 (s, 1H), 4.45 (brs, 1H), 3.51 (d, J = 14.4 Hz, 4H), 3.40-3.44 (m, 2H), 3.34 (t, J = 6.8 Hz, 2H), 3.24 (t, J = 5.6 Hz, 2H), 3.07-3.14 (m, 2H), 2.77 (d, J = 4.8 Hz, 3H), 2.21 (t, J = 6.2 Hz, 4H), 1.75-1.85 (m, 2H), 1.63-1.74 (m, 4H). | 447.4 |
| 3 | 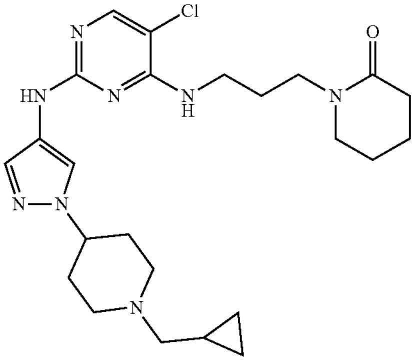 [SMILES: O=C1CCCCN1CCCNc1nc(Nc2cnn(C3CCN(CC4CC4)CC3)c2)ncc1Cl] | K & M | 94 | 11.1 (brs, 1H), 10.8 (brs, 1H), 8.84 (brs, 1H), 8.22 (brs, 1H), 7.95 (s, 1H), 7.64 (s, 1H), 4.51 (m, 1H), 3.63 (m, 2H), 3.46 (m, 2H), 3.33 (m, 2H), 3.23 (m, 2H), 3.06-3.13 (m, 2H), 2.96 (m, 2H), 2.40 (m, 2H), 2.22-2.27 (m, 4H), 1.78-1.86 (m, 2H), 1.62-1.73 (m, 4H), 1.14 (m, 1H), 0.61 (m, 2H), 0.40 (m, 2H). | 487.4 |
| 4 | 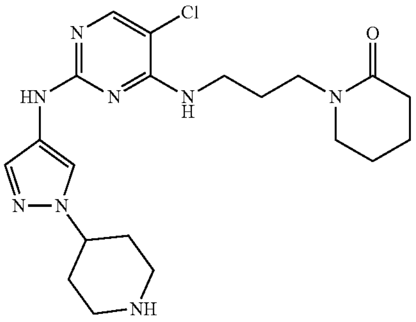 | K | 67 | 9.11 (brs, 1H), 9.00 (brs, 1H), 8.11 (brd, J = 8.8 Hz, 1H), 7.91 (s, 1H), 7.59-7.63 (m, 1H), 4.51 (brs, 1H), 3.56 (s, 1H), 3.43-3.44 (m, 2H), 3.32-3.38 (m, 4H), 3.23 (t, J = 5.8 Hz, 2H), 3.03 (d, J = 12.2 Hz, 2H), 2.21 (t, J = 6.4 Hz, 2H), 2.13-2.17 (m, 4H), 1.65-1.78 (m, 6H). | 433.2 |
| 5 | 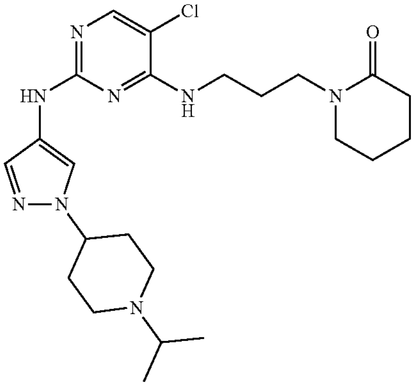 [SMILES: CC(C)N1CCC(n2cc(Nc3ncc(Cl)c(NCCCN4CCCCC4=O)n3)cn2)CC1] | K & M | 77 | 7.96 (s, 1H), 7.91 (s, 1H), 7.62 (s, 1H), 3.44-3.51 (m, 4H), 3.36 (t, J = 7.0 Hz, 2H), 3.24-3.26 (m, 2H), 3.12-3.16 (m, 2H), 2.20-2.35 (m, 8H), 1.65-1.85 (m, 6H), 1.29 (t, J = 6.6 Hz, 6H). | 475.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 6 | 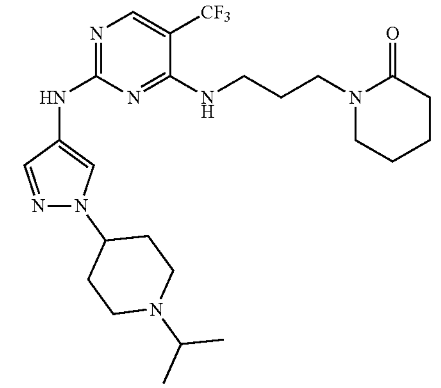 [SMILES: CC(C)N1CCC(n2cc(Nc3ncc(C(F)(F)F)c(NCCCN4CCCCC4=O)n3)cn2)CC1] | L & M | 22 | 8.21 (s, 1H), 7.89 (s, 1H), 7.61 (s, 1H), 4.46-4.58 (brs, 1H), 3.47 (d, J = 14.8 Hz, 4H), 3.30-3.34 (m, 2H), 3.24 (t, J = 5.6 Hz, 2H), 3.14 (m, 2H), 2.34 (brm, 2H), 2.23 (t, J = 7.2 Hz, 4H), 1.81 (brm, 2H), 1.70 (brm, 4H), 1.27 (brm, 6H), 1.20 (m, 1H). | 509.4 |
| 7 | 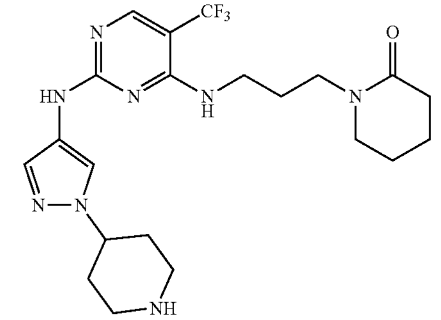 [SMILES: O=C1CCCCN1CCCNc1nc(Nc2cnn(C3CCNCC3)c2)ncc1C(F)(F)F] | L | 73 | 10.2 (brs, 1H), 8.98 (brs, 1H), 8.85 (brs, 1H), 8.24 (s, 1H), 7.90 (s, 1H), 7.62 (s, 1H), 3.30-3.47 (m, 6H), 3.24 (t, 2H), 3.01-3.06 (m, 2H), 2.20-2.23 (m, 2H), 2.13 (m, 4H), 1.70-1.80 (brm, 6H). | 467.4 |
| 8 | 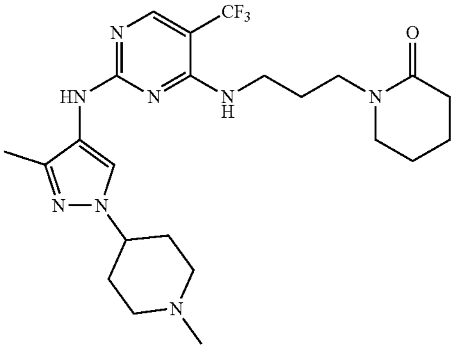 [SMILES: Cc1nn(C2CCN(C)CC2)cc1Nc1ncc(C(F)(F)F)c(NCCCN2CCCCC2=O)n1] | L | 13 | 8.89 (s, 1H), 8.19 (s, 1H, FA), 8.07 (s, 1H), 7.84 (s, 1H), 7.09 (s, 1H), 3.97 (brs, 1H), 3.15-3.30 (m, 6H), 2.83 (d, J = 11.2 Hz, 2H), 2.20-2.40 (m, 2H), 2.19 (s, 3H), 2.07-2.12 (m, 2H), 2.03 (t, J = 12.4 Hz, 3H), 1.80-1.93 (m, 4H), 1.69 (s, 6H). | 495.4 |
| 9 | 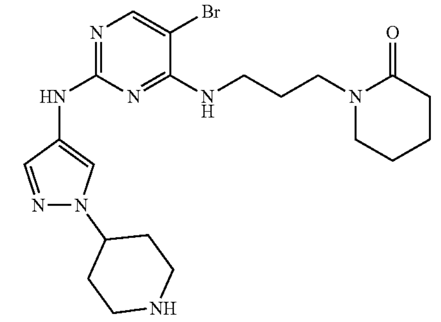 [SMILES: O=C1CCCCN1CCCNc1nc(Nc2cnn(C3CCNCC3)c2)ncc1Br] | K | 42 | 10.8 (brs, 1H), 9.36-9.14 (brm, 1H), 8.62 (s, 1H), 8.25 (s, 1H), 7.93 (s, 1H), 7.63 (s, 1H), 4.53 (brs, 1H), 3.44 (q, J = 6.4 Hz, 2H), 3.03 (brs, 3H), 2.17-2.21 (m, 8 H), 1.81 (t, J = 7.4 Hz, 2H), 1.69 (d, J = 11.4 Hz, 6H). | 477.2<br>479.2 |

TABLE G-continued

| Example No. | Product | General Method | Yield (%) | $^1$H NMR (400 MHz, DMSO-$d_6$): δ | LC-MS (m/z: M + H$^+$) |
|---|---|---|---|---|---|
| Exemplary Compounds that can be prepared by General Methods K through N. | | | | | |
| 10 | 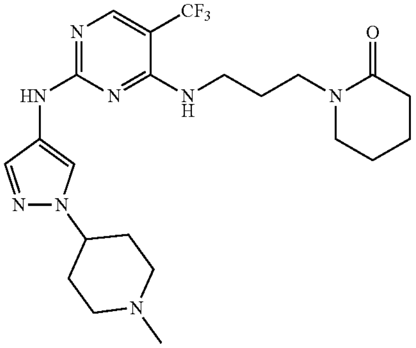 [SMILES: CN1CCC(n2cc(Nc3ncc(C(F)(F)F)c(NCCCN4CCCCC4=O)n3)cn2)CC1] | L | 46 | 9.52 (s, 1H), 8.08 (s, 1H), 7.82 (s, 1H), 7.52 (s, 1H), 7.14 (s, 1H), 4.06 (brs, 1H), 3.41 (brs, 2H), 3.28 (s, 2H), 3.22 (d, J = 6.4 Hz, 2H), 2.82 (d, J = 11.0 Hz, 2H), 2.22 (t, J = 6.2 Hz, 2H), 2.18 (s, 3H), 1.85-2.05 (m, 6H), 1.73 (m, 6H). | 481.4 |
| 11 | 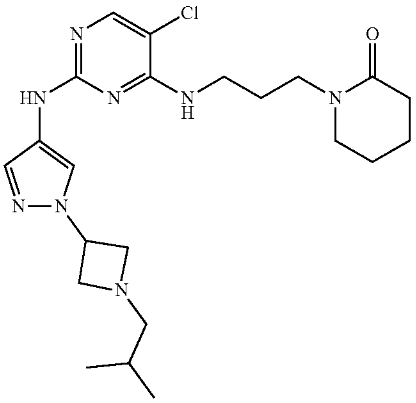 | K & M | 26 | 9.06 (brs, 1H), 7.94 (s, 1H), 7.86 (s, 1H), 7.51 (s, 1H), 7.09 (t, 1H), 4.92 (brs, 1H), 3.66 (brs, 2H), 3.40 (m, 2H), 3.33 (m, 2H), 3.25 (m, 2H), 3.18 (m, 2H), 2.28 (m, 2H), 2.22 (t, J = 6.4 Hz, 2H), 1.77 (t, J = 6.2 Hz, 2H), 1.70 (m, 4H), 1.55 (m, 1H), 0.86 (d, J = 6.6 Hz, 6H). | 461.3 |
| 12 | 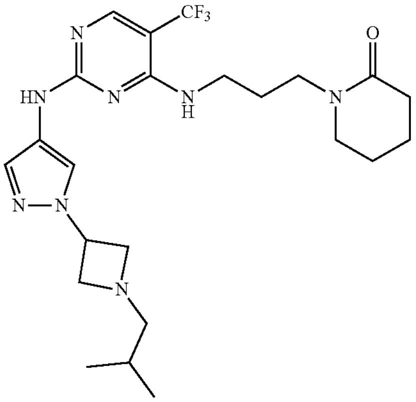 [SMILES: CC(C)CN1CC(n2cc(Nc3ncc(C(F)(F)F)c(NCCCN4CCCCC4=O)n3)cn2)C1] | L & M | 46 | 9.22 (brs, 1H), 8.11 (s, 1H), 7.96 (s, 1H), 7.55 (s, 1H), 6.84 (t, 1H), 4.93 (m, 1H), 3.70 (brs, 2H), 3.46 (q, 2H), 3.35 (t, J = 6.6 Hz, 4H), 3.24 (m, 2H), 2.31 (d, J = 6.6 Hz, 2H), 2.24 (t, J = 6.0 Hz, 2H), 1.81 (t, J = 6.6 Hz, 2H), 1.72 (m, 4H), 1.59 (m, 1H), 0.88 (d, J = 6.6 Hz, 6H). | 495.3 |

TABLE G-continued
Exemplary Compounds that can be prepared by General Methods K through N.
| Example No. | Product | General Method | Yield (%) | $^1H$ NMR (400 MHz, DMSO-$d_6$): δ | LC-MS (m/z: M + $H^+$) |
|---|---|---|---|---|---|
| 13 | 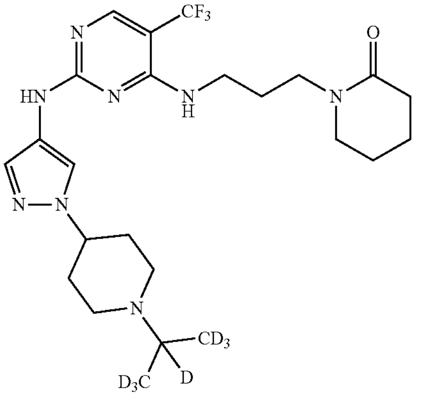 [SMILES: [2H]C([2H])([2H])C([2H])(N1CCC(n2cc(Nc3ncc(C(F)(F)F)c(NCCCN4CCCCC4=O)n3)cn2)CC1)C([2H])([2H])[2H]] | L | 63 | 9.53 (s, 1H), 8.08 (s, 1H), 7.82 (s, 1H), 7.50 (s, 1H), 7.14 (s, 1H), 4.03 (brs, 1H), 3.20-3.28 (m, 4H), 2.83 (d, J = 11.0 Hz, 3H), 2.15-2.26 (m, 4H), 1.97 (s, 3H), 1.70-1.83 (m, 8 H). | 516.4 |
| 14 | 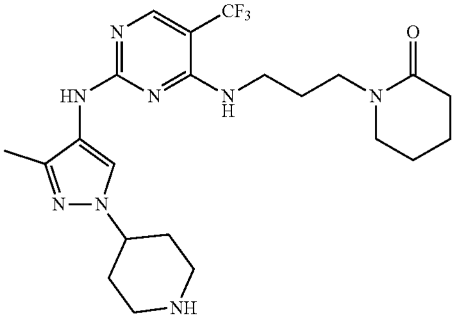 [SMILES: Cc1nn(C2CCNCC2)cc1Nc1ncc(C(F)(F)F)c(NCCCN2CCCCC2=O)n1] | L | 95 | 8.98 (s, 1H), 8.09 (s, 1H), 7.86 (s, 1H), 7.08 (brs, 1H), 4.29 (brs, 1H), 3.19-3.28 (m, 6H), 2.91 (t, J = 12.2 Hz, 2H), 2.22 (t, J = 6.0 Hz, 2H), 1.91-2.17 (m, 8 H), 1.62-1.75 (m, 7 H). | 481.4 |
| 15 | 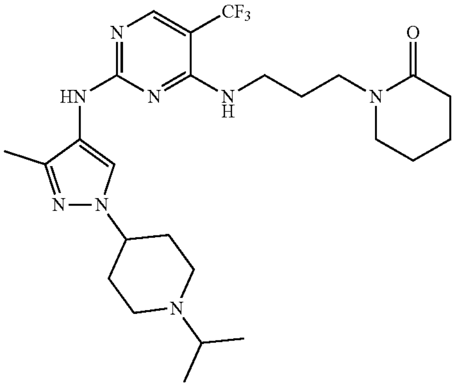 [SMILES: Cc1nn(C2CCN(C(C)C)CC2)cc1Nc1ncc(C(F)(F)F)c(NCCCN2CCCCC2=O)n1] | L | 73 | 8.90 (s, 1H), 8.07 (s, 1H), 7.84 (s, 1H), 7.09 (s, 1H), 3.95 (brs, 1H), 3.17-3.30 (m, 4H), 2.85 (brs, 2H), 2.72 (brs, 1H), 1.93-2.29 (m, 10H), 1.64-1.87 (m, 9H), 0.97 (d, J = 6.4 Hz, 6H) | 523.4 |
| 16 | 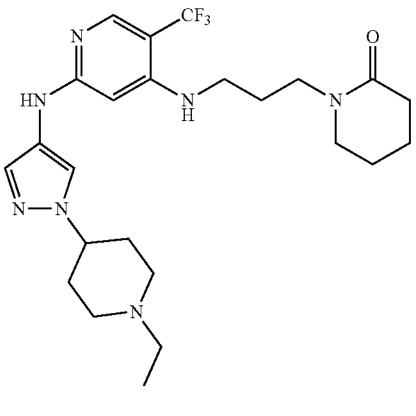 [SMILES: CCN1CCC(n2cc(Nc3cc(NCCCN4CCCCC4=O)c(C(F)(F)F)cn3)cn2)CC1] | N | 55 | 8.74 (s, 1H), 7.97 (s, 1H), 7.89 (s, 1H), 7.40 (s, 1H), 6.01 (t, J = 6.0 Hz, 1H), 5.83 (s, 1H), 4.06 (brs, 1H), 3.28-3.30 (m, 2H), 3.22 (m, 2H), 3.05-3.09 (m, 2H), 2.94 (brs, 2H), 2.29-2.42 (m, 2H), 2.19-2.24 (m, 2H), 1.80-2.09 (m, 6H), 1.64-1.75 (m, 6H), 1.01 (brm, 3H). | 494.4 |

TABLE G-continued
| Example No. | Product | General Method | Yield (%) | $^1H$ NMR (400 MHz, DMSO-$d_6$): δ | LC-MS (m/z: M + H$^+$) |
|---|---|---|---|---|---|
| Exemplary Compounds that can be prepared by General Methods K through N. | | | | | |
| 17 | 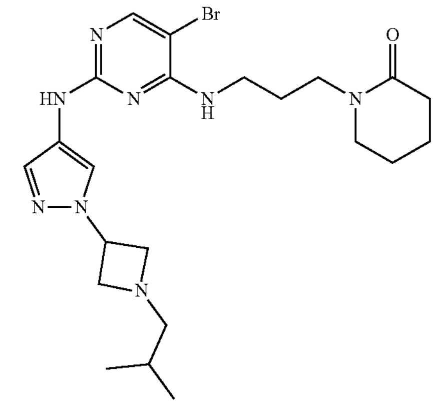 [SMILES: CC(C)CN1CC(n2cc(Nc3ncc(Br)c(NCCCN4CCCCC4=O)n3)cn2)C1] | K | 19 | 9.09 (brs, 1H), 7.93 (s, 2H), 7.51 (s, 1H), 6.95 (s, 1H), 4.93 (brs, 1H), 3.66 (brs, 2H), 3.36 (m, 2H), 3.33 (m, 2H), 3.31 (m, 2H), 3.22 (m, 2H), 2.26 (m, 2H), 2.24 (m, 2H), 1.74 (m, 6H), 1.54 (m, 1H), 0.85 (d, J = 6.6 Hz, 6H). | 505.3 |
| 18 | 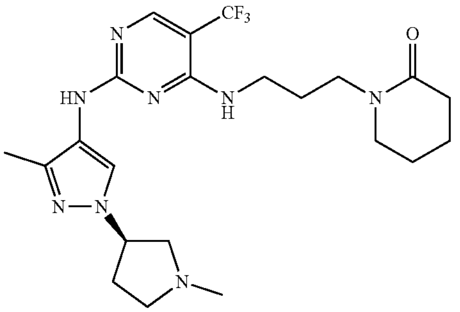 [SMILES: Cc1nn([C@@H]2CCN(C)C2)cc1Nc1ncc(C(F)(F)F)c(NCCCN2CCCCC2=O)n1] | L | 35 | 8.47 (brs, 1H), 8.08 (s, 1H), 7.86 (m, 1H), 6.78 (brs, 1H), 4.76 (brs, 1H), 3.40 (m, 2H), 3.31 (t, J = 6.6 Hz, 2H), 3.21 (m, 2H), 2.82 (m, 1H), 2.76 (m, 2H), 2.31 (s, 3H), 2.23 (m, 2H), 2.12 (s, 3H), 2.05 (m, 2H), 1.73 (m, 7H). | 481.4 |
| 19 | 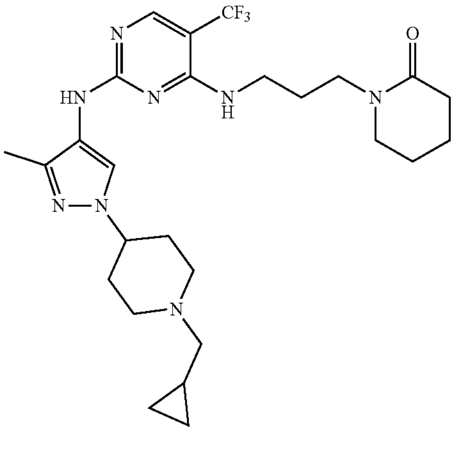 [SMILES: Cc1nn(C2CCN(CC3CC3)CC2)cc1Nc1ncc(C(F)(F)F)c(NCCCN2CCCCC2=O)n1] | L | 19 | 8.89 (brs, 1H), 8.08 (s, 1H), 7.84 (brs, 1H), 7.07 (brs, 1H), 4.01 (brs, 1H), 3.33 (m, 2H), 3.30 (m, 2H), 3.21 (brs, 2H), 3.02 (brs, 2H), 2.21 (brs, 4H), 2.10 (brs, 5H), 1.95 (m, 2H), 1.89 (brs, 2H), 1.69 (brs, 6H), 0.83 (m, 1H), 0.47 (m, 2H), 0.08 (m, 2H). | 535.5 |

TABLE G-continued
Exemplary Compounds that can be prepared by General Methods K through N.
| Example No. | Product | General Method | Yield (%) | $^1$H NMR (400 MHz, DMSO-$d_6$): δ | LC-MS (m/z: M + H$^+$) |
|---|---|---|---|---|---|
| 20 | 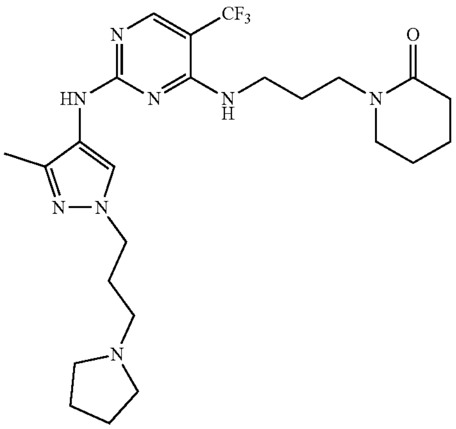 [SMILES: Cc1nn(CCCN2CCCC2)cc1Nc1ncc(C(F)(F)F)c(NCCCN2CCCCC2=O)n1] | L | 17 | 8.44 (brs, 1H), 8.07 (s, 1H), 7.73 (s, 1H), 6.76 (brs, 1H), 4.02 (m, 2H), 3.38 (m, 2H), 3.31 (m, 2H), 3.22 (m, 2H), 2.41 (m, 6H), 2.22 (m, 2H), 2.11 (s, 3H), 1.90 (t, 2H), 1.70 (m, 10H). | 509.4 |
| 21 | 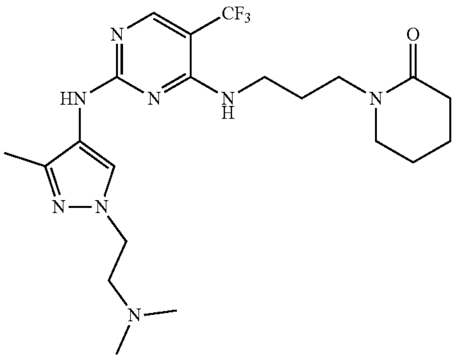 [SMILES: Cc1nn(CCN(C)C)cc1Nc1ncc(C(F)(F)F)c(NCCCN2CCCCC2=O)n1] | L | 35 | 8.43 (brs, 1H), 8.07 (s, 1H), 7.77 (s, 1H), 6.76 (brs, 1H), 4.07 (t, J = 6.4 Hz, 2H), 3.39 (m, 2H), 3.32 (t, J = 6.6 Hz, 2H), 3.22 (m, 2H), 2.64 (t, J = 6.6 Hz, 2H), 2.23 (m, 2H), 2.19 (s, 6H), 2.11 (s, 3H), 1.73 (m, 6H). | 469.3 |
| 22 | 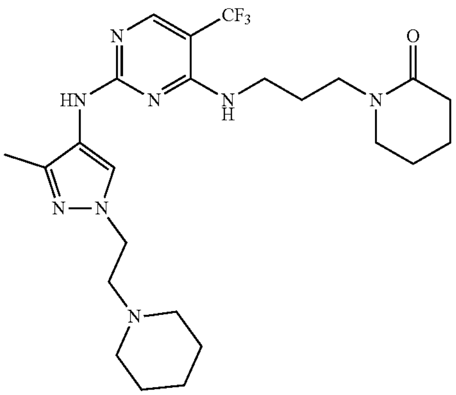 [SMILES: Cc1nn(CCN2CCCCC2)cc1Nc1ncc(C(F)(F)F)c(NCCCN2CCCCC2=O)n1] | L | 34 | 8.43 (brs, 1H), 8.07 (s, 1H), 7.76 (s, 1H), 6.76 (brs, 1H), 4.07 (t, J = 6.6 Hz, 2H), 3.39 (m, 2H), 3.31 (t, J = 6.6 Hz, 2H), 3.22 (m, 2H), 2.65 (t, J = 6.6 Hz, 2H), 2.39 (t, J = 4.8 Hz, 4H), 2.22 (t, J = 6.2 Hz, 2H), 2.11 (s, 3H), 1.73 (m, 6H), 1.48 (m, 4H), 1.35 (m, 2H). | 509.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + $H^+$) |
|---|---|---|---|---|---|
| 23 | 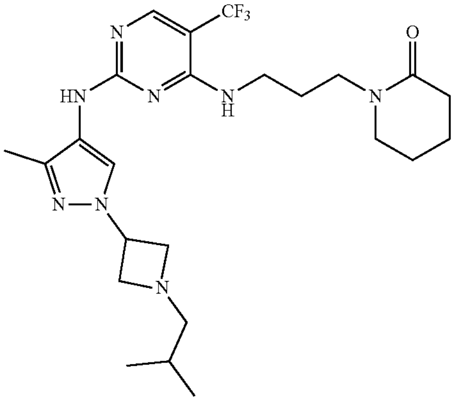 [SMILES: Cc1nn(C2CN(CC(C)C)C2)cc1Nc1ncc(C(F)(F)F)c(NCCCN2CCCCC2=O)n1] | L | 35 | 8.57 (brs, 1H), 8.09 (s, 1H), 7.94 (s, 1H), 6.80 (brs, 1H), 5.13 (brs, 1H), 4.03 (m, 4H), 3.40 (m, 2H), 3.32 (t, J = 6.6 Hz, 2H), 3.23 (t, J = 5.0 Hz, 2H), 2.23 (t, J = 6.2 Hz, 2H), 2.19 (s, 3H), 2.07 (m, 1H), 1.84 (m, 8H), 0.93 (d, J = 6.6 Hz, 6H). | 509.5 |
| 24 | 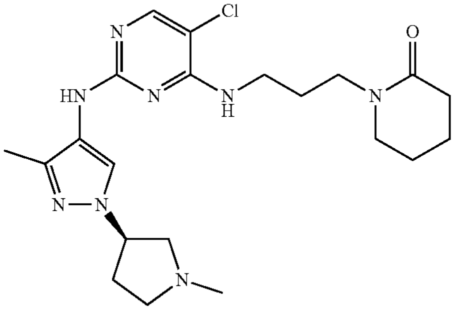 [SMILES: Cc1nn([C@@H]2CCN(C)C2)cc1Nc1ncc(Cl)c(NCCCN2CCCCC2=O)n1] | K | 21 | 7.98 (brs, 1H), 7.85 (s, 1H), 7.82 (s, 1H), 6.79 (t, J = 6.0 Hz, 1H), 4.85 (brs, 1H), 3.36 (m, 4H), 3.23 (m, 2H), 2.98 (m, 2H), 2.72 (m, 1H), 2.46 (t, 3H), 2.36 (m, 2H), 2.22 (t, J = 6.2 Hz, 2H), 2.11 (s, 4H), 1.75 (m, 6H). | 447.4 |
| 25 | 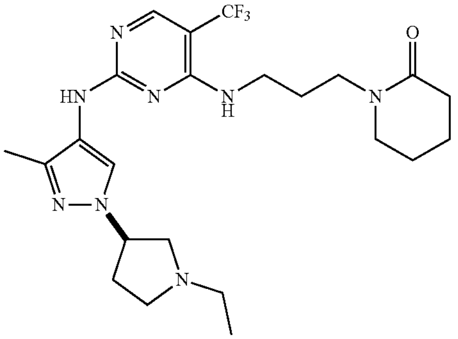 | L & M | 73 | 8.94 (brs, 1H), 8.14 (s, 1H), 8.09 (s, 1H), 7.93 (brs, 1H), 7.08 (brs, 1H), 4.77 (brm, 1H), 3.37 (brm, 4H), 3.20 (brm, 4H), 2.85 (m, 1H), 2.73 (m, 2H), 2.31 (m, 1H), 2.22 (m, 2H), 2.11 (m, 2H), 2.08 (m, 1H), 1.71 (m, 6H), 1.04 (t, J = 6.8 Hz, 3H). | 495.4 |
| 26 | 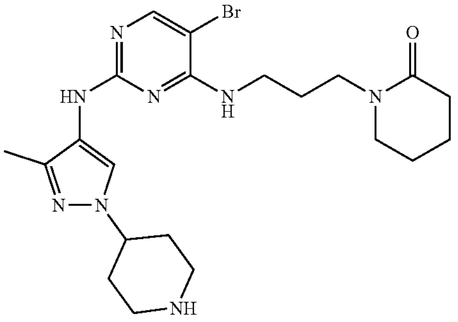 [SMILES: Cc1nn(C2CCNCC2)cc1Nc1ncc(Br)c(NCCCN2CCCCC2=O)n1] | K | 39 | 10.3 (brs, 1H), 9.15 (brm, 2H), 8.60 (s, 1H), 8.35 (s, 1H), 7.89 (s, 1H), 4.45 (brs, 1H), 3.47-3.18 (brm, 7H), 3.04-2.92 (brm, 3H), 2.25-2.06 (brm, 8H), 1.81-1.63 (brm, 6H). | 491.2<br>493.2 |

TABLE G-continued
| Exemplary Compounds that can be prepared by General Methods K through N. | | | | | |
|---|---|---|---|---|---|
| Example No. | Product | General Method | Yield (%) | $^1$H NMR (400 MHz, DMSO-d$_6$): δ | LC-MS (m/z: M + H$^+$) |
| 27 | 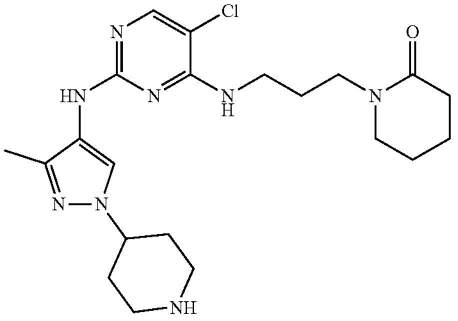 | K | 34 | 10.3 (brs, 1H), 9.25-9.10 (brm, 2H), 8.58 (s, 1H), 8.33 (s, 1H), 7.89 (s, 1H), 4.44 (brs, 1H), 3.50-3.15 (brm, 7H), 3.02 (s, 3H), 2.13-2.21 (m, 8H), 1.81-1.58 (brm, 6H). | 447.4 |
| 28 | 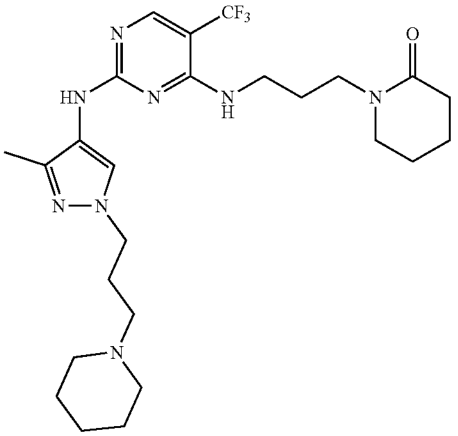 [SMILES: Cc1nn(CCCN2CCCCC2)cc1Nc1ncc(C(F)(F)F)c(NCCCN2CCCCC2=O)n1] | L | 21 | 8.88 (brs, 1H), 8.08 (s, 1H), 7.78 (brs, 1H), 7.05 (brs, 1H), 3.99 (brs, 2H), 3.39 (m, 2H), 3.31 (m, 2H), 3.23 (m, 2H), 2.49 (m, 2H), 2.25 (m, 6H), 2.10 (s, 3H), 1.82 (s, 2H), 1.69 (s, 6H), 1.47 (m, 4H), 1.36 (m, 2H). | 523.5 |
| 29 | 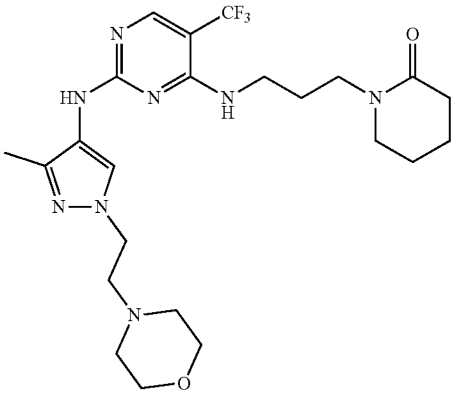 [SMILES: Cc1nn(CCN2CCOCC2)cc1Nc1ncc(C(F)(F)F)c(NCCCN2CCCCC2=O)n1] | L | 36 | 8.89 (brs, 1H), 8.08 (s, 1H), 7.81 (brs, 1H), 7.05 (brs, 1H), 4.11 (brs, 2H), 3.53 (m, 4H), 3.31 (m, 2H), 3.25 (m, 2H), 3.21 (m, 2H), 2.65 (t, J = 6.4 Hz, 2H), 2.39 (s, 4H), 2.21 (brs, 2H), 2.21 (s, 3H), 1.69 (brs, 6H). | 511.5 |

TABLE G-continued
| Exemplary Compounds that can be prepared by General Methods K through N. | | | | | |
|---|---|---|---|---|---|
| Example No. | Product | General Method | Yield (%) | $^1$H NMR (400 MHz, DMSO-$d_6$): δ | LC-MS (m/z: M + $H^+$) |
| 30 | 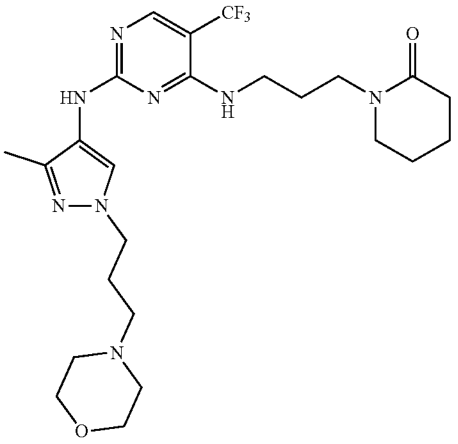 [SMILES: Cc1nn(CCCN2CCOCC2)cc1Nc1ncc(C(F)(F)F)c(NCCCN2CCCCC2=O)n1] | L | 45 | 8.89 (brs, 1H), 8.08 (s, 1H), 7.79 (brs, 1H), 7.06 (brs, 1H), 4.01 (brs, 2H), 3.55 (m, 4H), 3.36 (m, 2H), 3.31 (m, 2H), 3.21 (m, 2H), 2.30 (brs, 4H), 2.22 (brs, 4H), 2.10 (s, 3H), 1.88 (m, 2H), 1.69 (brs, 6H). | 525.7 |
| 31 | 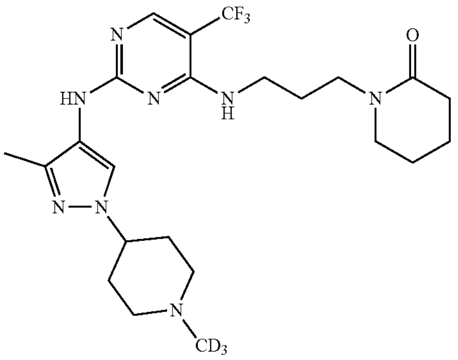 | L | 20 | 8.90 (brs, 1H), 8.08 (s, 1H), 7.87 (brs, 1H), 7.09 (brs, 1H), 4.00 (brs, 1H), 3.31 (m, 2H), 3.26 (m, 2H), 3.21 (m, 2H), 2.88 (brs, 2H), 2.21 (brs, 2H), 2.11 (brs, 5H), 1.90 (m, 4H), 1.69 (brs, 6H). | 498.5 |
| 32 | 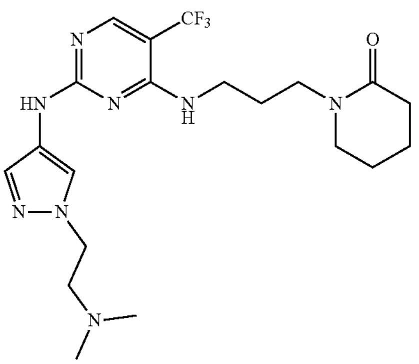 [SMILES: CN(C)CCn1cc(Nc2ncc(C(F)(F)F)c(NCCCN3CCCCC3=O)n2)cn1] | L | 26 | 9.53 (brs, 1H), 8.09 (s, 1H), 7.83 (s, 1H), 7.49 (s, 1H), 7.13 (brs, 1H), 4.16 (brs, 2H), 3.42 (brs, 2H), 3.31 (m, 2H), 3.23 (m, 2H), 2.62 (brs, 2H), 2.22 (m, 8H), 1.70 (brs, 6H). | 455.4 |

TABLE G-continued

Exemplary Compounds that can be prepared by General Methods K through N.

| Example No. | Product | General Method | Yield (%) | $^1H$ NMR (400 MHz, DMSO-$d_6$): δ | LC-MS (m/z: M + H$^+$) |
|---|---|---|---|---|---|
| 33 | 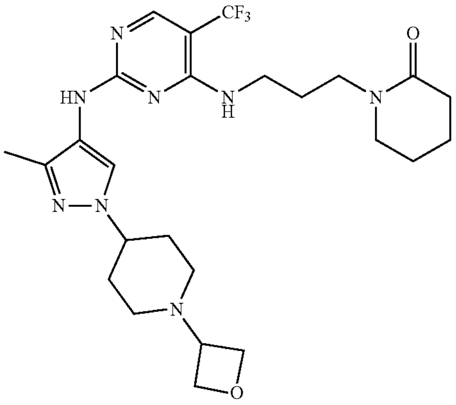 [SMILES: Cc1nn(C2CCN(C3COC3)CC2)cc1Nc1ncc(C(F)(F)F)c(NCCCN2CCCCC2=O)n1] | L | 44 | 8.90 (brs, 1H), 8.14 (s, 1H), 8.07 (s, 1H), 7.85 (brs, 1H), 7.07 (brs, 1H), 4.54 (m, 2H), 4.35 (m, 2H), 4.01 (brm, 1H), 3.41 (m, 1H), 3.31 (m, 2H), 3.21 (brm, 2H), 2.76 (brm, 2H), 2.21 (m, 2H), 2.07 (m, 3H), 1.7-2.0 (m, 6H), 1.69 (m, 6H). | 537.4 |
| 34 | 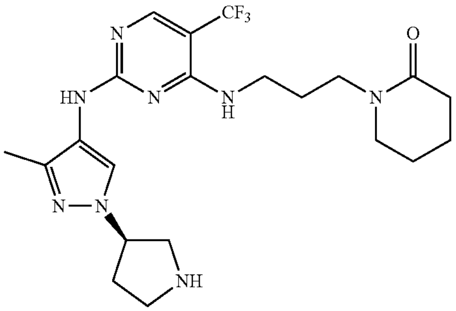 [SMILES: Cc1nn([C@@H]2CCNC2)cc1Nc1ncc(C(F)(F)F)c(NCCCN2CCCCC2=O)n1] | L | 92 | 9.56 (brs, 2H), 9.30 (brs, 1H), 8.23 (s, 1H), 7.98 (s, 1H), 7.68 (brs, 1H), 3.62 (brs, 2H), 3.53 (brs, 2H), 3.44 (d, J = 6.1 Hz, 2H), 3.32 (m, 3H), 3.24 (t, J = 5.0 Hz, 1H), 2.42 (m, 2H), 2.30 (m, 1H), 2.23 (t, J = 6.4 Hz, 2H), 2.18 (s, 3H), 1.75 (m, 6H). | 467.4 |
| 35 | 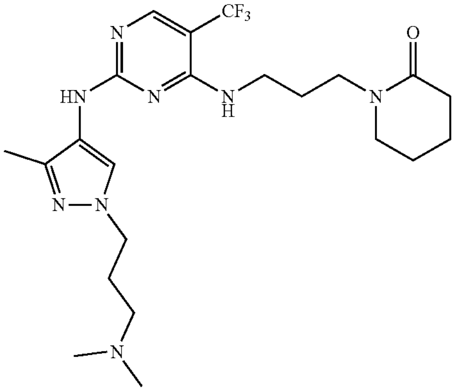 [SMILES: Cc1nn(CCCN(C)C)cc1Nc1ncc(C(F)(F)F)c(NCCCN2CCCCC2=O)n1] | L | 21 | 8.42 (brs, 1H), 8.07 (s, 1H), 7.73 (s, 1H), 6.75 (brs, 1H), 4.00 (t, J = 7.0 Hz, 2H), 3.39 (q, 2H), 3.32 (t, J = 6.8 Hz, 2H), 3.22 (m, 2H), 2.49 (m, 3H), 2.22 (m, 4H), 2.12 (m, 6H), 1.87 (m, 2H), 1.73 (m, 6H). | 483.6 |
| 36 | 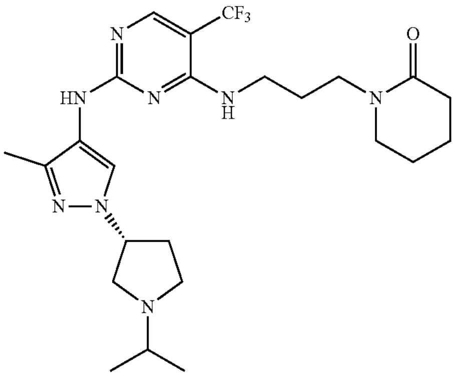 [SMILES: Cc1nn([C@@H]2CCN(C(C)C)C2)cc1Nc1ncc(C(F)(F)F)c(NCCCN2CCCCC2=O)n1] | L & M | 15 | 8.94 (brs, 1H), 7.09 (s, 1H), 7.92 (brs, 1H), 7.08 (brs, 1H), 4.75 (brs, 1H), 3.37 (m, 2H), 3.31 (m, 2H), 3.20 (brs, 2H), 2.76 (m, 3H), 2.50 (m, 2H), 2.21 (s, 3H), 2.12 (brs, 4H), 1.69 (brs, 6H), 0.95 (d, J = 6.8 Hz, 6H). | 509.5 |

TABLE G-continued
| Example No. | Product | General Method | Yield (%) | $^1H$ NMR (400 MHz, DMSO-$d_6$): δ | LC-MS (m/z: M + $H^+$) |
|---|---|---|---|---|---|
| 37 | 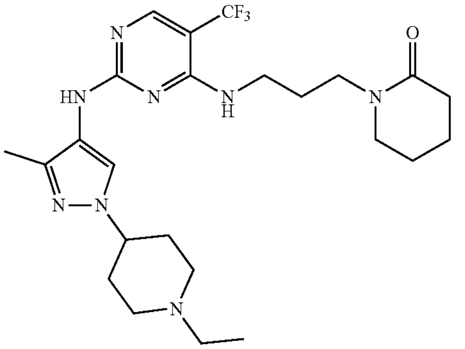 [SMILES: CCN1CCC(n2cc(Nc3ncc(C(F)(F)F)c(NCCCN4CCCCC4=O)n3)c(C)n2)CC1] | L | 55 | 8.90 (brs, 1H), 8.19 (s, 1H), 8.07 (s, 1H), 7.85 (brs, 1H), 7.08 (brs, 1H), 4.01 (brs, 1H), 3.1-3.4 (brm, 6H), 2.98 (m, 2H), 2.42 (m, 2H), 2.21 (m, 2H), 2.07 (m, 3H), 1.7-2.0 (m, 6H), 1.69 (m, 6H), 1.03 (t, J = 7.4 Hz, 3H). | 509.4 |
| 38 | 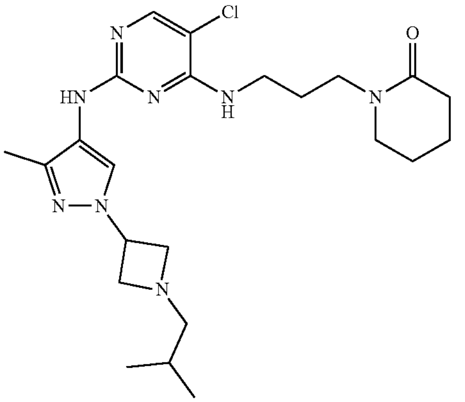 [SMILES: Cc1nn(C2CN(CC(C)C)C2)cc1Nc1ncc(Cl)c(NCCCN2CCCCC2=O)n1] | K | 12 | 8.36 (brs, 1H), 7.92 (s, 1H), 7.83 (s, 1H), 7.06 (t, J = 5.4 Hz, 1H), 4.85 (brs, 1H), 3.65 (brs, 2H), 3.34 (m, 2H), 3.31 (m, 2H), 3.20 (m, 2H), 2.27 (m, 2H), 2.21 (t, J = 6.2 Hz, 2H), 2.12 (s, 3H), 1.64 (m, 9H), 0.85 (d, J = 6.6 Hz, 6H). | 475.4 |
| 39 | 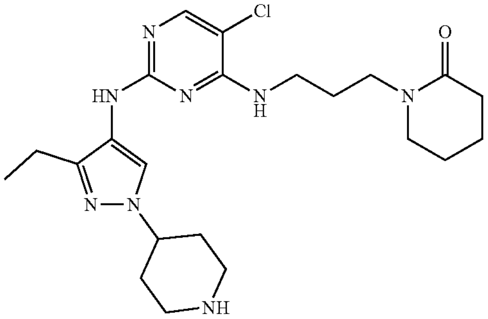 [SMILES: CCc1nn(C2CCNCC2)cc1Nc1ncc(Cl)c(NCCCN2CCCCC2=O)n1] | K | 86 | 9.86 (brs, 1H), 9.07 (brs, 2H), 8.43 (brs, 1H), 8.12 (s, 1H), 7.87 (s, 1H), 4.46 (brs, 1H), 3.39 (m, 6H), 3.25 (t, J = 5.0 Hz, 2H), 3.05 (brs, 2H), 2.61 (m, 2H), 2.21 (m, 6H), 1.78 (m, 6H), 1.17 (t, J = 7.8 Hz, 3H). | 461.4 |
| 40 | 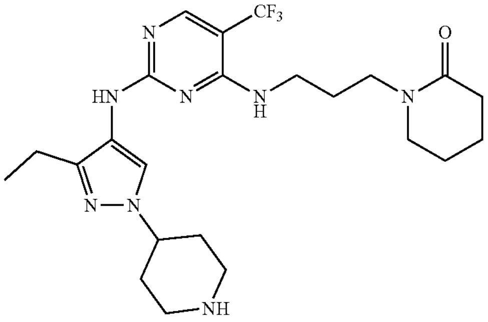 | L | 96 | 9.66 (brs, 1H), 9.04 (brs, 1H), 8.89 (brs, 1H), 8.27 (s, 1H), 7.86 (s, 1H), 7.81 (s, 1H), 4.45 (brs, 1H), 3.32 (m, 6H), 3.23 (t, J = 6.0 Hz, 2H), 3.05 (brs, 2H), 2.61 (m, 2H), 2.21 (m, 6H), 1.76 (m, 6H), 1.17 (t, J = 7.8 Hz, 3H). | 495.5 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 41 | 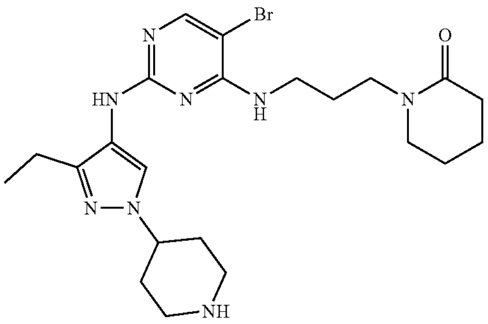 | K | 86 | 9.67 (brs, 1H), 9.06 (brs, 1H), 8.91 (brs, 1H), 8.15 (brs, 2H), 7.86 (s, 1H), 4.45 (brs, 1H), 3.42 (m, 4H), 3.35 (m, 2H), 3.24 (m, 2H), 3.07 (brs, 2H), 2.58 (m, 2H), 2.21 (m, 6H), 1.87 (t, J = 6.8 Hz, 2H), 1.72 (brs, 4H), 1.17 (t, J = 7.4 Hz, 3H). | 505.4 |
| 42 | 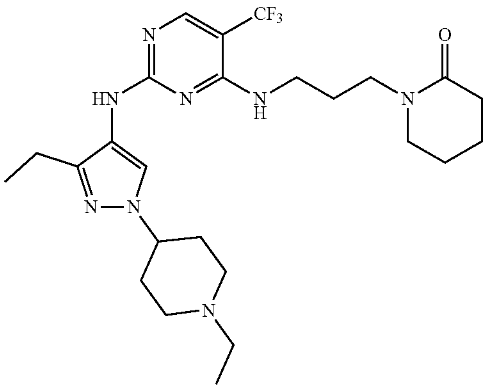 [SMILES: CCc1nn(C2CCN(CC)CC2)cc1Nc1ncc(C(F)(F)F)c(NCCCN2CCCCC2=O)n1] | L & M | 30 | 8.65 (brs, 1H), 8.07 (s, 1H), 7.83 (brs, 1H), 7.06 (brs, 1H), 3.99 (brs, 1H), 3.31 (m, 2H), 3.28 (m, 2H), 3.20 (m, 2H), 2.93 (d, J = 11.0 Hz, 2H), 2.49 (m, 2H), 2.34 (d, J = 7.2 Hz, 2H), 2.21 (brs, 2H), 1.97 (m, 4H), 1.83 (m, 2H), 1.69 (brs, 6H), 1.09 (t, J = 7.4 Hz, 3H), 1.00 (t, J = 7.2 Hz, 3H). | 523.5 |
| 43 | 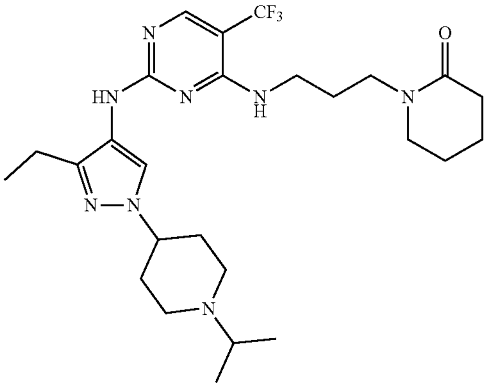 [SMILES: CCc1nn(C2CCN(C(C)C)CC2)cc1Nc1ncc(C(F)(F)F)c(NCCCN2CCCCC2=O)n1] | L & M | 20 | 8.36 (brs, 1H), 8.06 (s, 1H), 7.76 (s, 1H), 6.75 (brs, 1H), 3.96 (m, 1H), 3.37 (q, 2H), 3.30 (t, J = 6.8 Hz, 2H), 3.21 (m, 2H), 2.87 (d, J = 11.4 Hz, 2H), 2.73 (m, 1H), 2.56 (m, 2H), 2.26 (m, 4H), 2.00 (m, 2H), 1.84 (m, 2H), 1.72 (brs, 6H), 1.13 (t, J = 7.4 Hz, 3H), 0.99 (d, J = 6.4 Hz, 6H). | 537.5 |
| 44 | 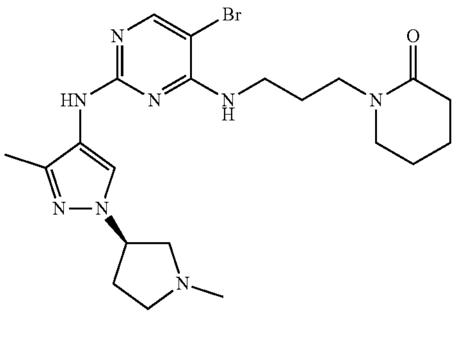 | K | 43 | 8.36 (brs, 1H), 7.90 (s, 1H), 7.87 (brs, 1H), 6.90 (t, 1H), 4.74 (brs, 1H), 3.35 (m, 2H), 3.31 (m, 2H), 3.21 (m, 2H), 2.72 (m, 3H), 2.43 (m, 1H), 2.26 (brs, 4H), 2.22 (m, 2H), 2.09 (s, 3H), 1.96 (m, 1H), 1.71 (brs, 6H). | 491.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 45 | 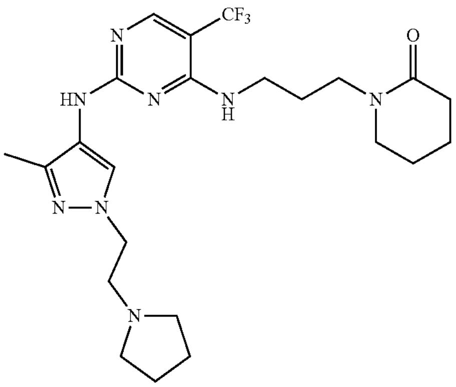 [SMILES: Cc1nn(CCN2CCCC2)cc1Nc1ncc(C(F)(F)F)c(NCCCN2CCCCC2=O)n1] | L | 15 | 9.24 (brs, 1H), 8.15 (brs, 1H), 7.95 (s, 1H), 7.32 (brs, 1H), 4.42 (brs, 2H), 3.62 (brs, 2H), 3.50 (brs, 2H), 3.38 (m, 2H), 3.31 (t, J = 6.6 Hz, 2H), 2.23 (m, 2H), 2.99 (brs, 2H), 2.23 (t, J = 6.0 Hz, 2H), 2.17 (s, 3H), 1.99 (brs, 2H), 1.83 (brs, 2H), 1.72 (m, 6H). | 495.4 |
| 46 | 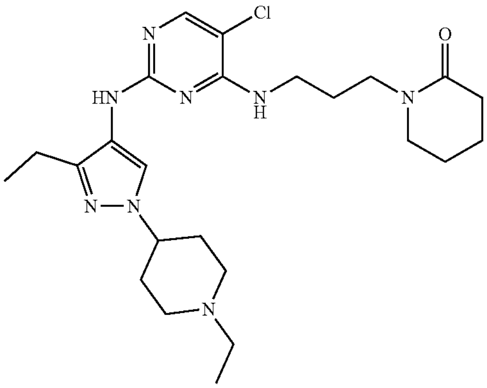 [SMILES: CCc1nn(C2CCN(CC)CC2)cc1Nc1ncc(Cl)c(NCCCN2CCCCC2=O)n1] | K & M | 41 | 8.23 (brs, 1H), 7.81 (s, 1H), 7.79 (s, 1H), 7.04 (brs, 1H), 3.98 (m, 1H), 3.33 (m, 2H), 3.28 (m, 2H), 3.21 (m, 2H), 2.93 (d, J = 11.2 Hz, 2H), 2.53 (m, 2H), 2.34 (q, 2H), 2.21 (t, J = 6.2 Hz, 2H), 1.99 (m, 4H), 1.83 (m, 2H), 1.71 (brs, 6H), 1.09 (t, J = 7.5 Hz, 3H), 1.00 (t, J = 6.8 Hz, 3H). | 489.5 |
| 47 | 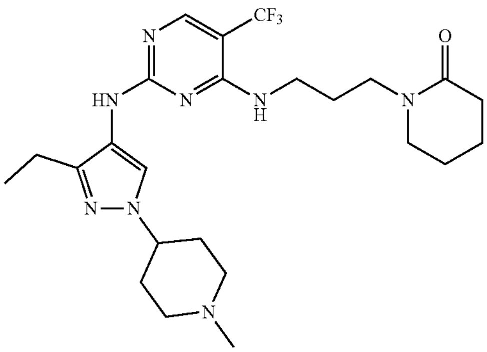 [SMILES: CCc1nn(C2CCN(C)CC2)cc1Nc1ncc(C(F)(F)F)c(NCCCN2CCCCC2=O)n1] | L | 37 | 8.85 (brs, 1H), 8.07 (s, 1H), 7.84 (s, 1H), 7.09 (brs, 1H), 3.97 (brs, 1H), 3.38 (m, 2H), 3.25 (m, 2H), 3.20 (m, 2H), 2.82 (d, J = 11.0 Hz, 2H), 2.49 (m, 2H), 2.21 (m, 2H), 2.18 (s, 3H), 1.93 (m, 6H), 1.61 (brs, 6H), 1.09 (t, J = 7.4 Hz, 3H). | 509.5 |
| 48 | 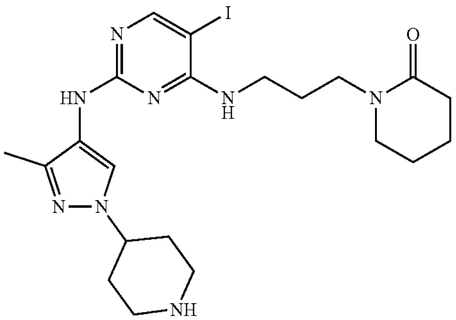 | K | 98 | 10.2 (brs, 1H), 9.18 (brs, 1H), 9.08 (brs, 1H), 8.31 (brs, 1H), 8.27 (brs, 1H), 7.88 (s, 1H), 4.43 (brm, 1H), 3.2-3.4 (m, 8H), 3.02 (m, 2H), 2.0-2.3 (m, 9H), 1.6-1.8 (m, 6H). | 539.2 540.2 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 49 | 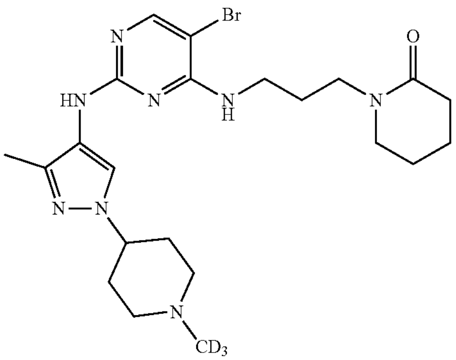 | K | 46 | 8.03 (brs, 1H) 7.89 (s, 1H), 7.78 (s, 1H), 6.89 (s, 1H), 3.91-3.96 (m, 1H), 3.30 (m, 4H), 3.21 (m, 2H), 2.81 (d, J = 11.2 Hz, 2H), 2.21 (t, J = 6.1 Hz, 2H), 2.08 (s, 3H), 1.99 (t, J = 11.6 Hz, 2H), 1.82-1.92 (m, 4H), 1.69 (m, 6H). | 508.3 510.3 |
| 50 | 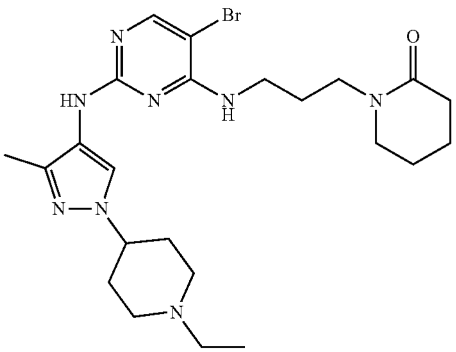 [SMILES: CCN1CCC(n2cc(Nc3ncc(Br)c(NCCCN4CCCCC4=O)n3)c(C)n2)CC1] | K & M | 68 | 8.30 (brs, 1H), 7.89 (s, 1H), 7.78 (s, 1H), 6.89 (s, 1H), 3.95 (m, 1H), 3.31 (m, 4H), 3.21 (m, 2H), 2.90 (d, J = 11.2 Hz, 2H), 2.33 (q, J = 6.0 Hz, 2H), 2.21 (t, J = 6.0 Hz, 2H), 2.08 (s, 3H), 1.82-1.92 (m, 6H), 1.69 (m, 6H), 0.98 (t, J = 6.0 Hz, 3H). | 519.3 521.3 |
| 51 | 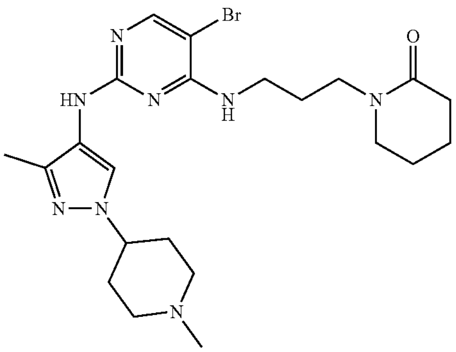 [SMILES: Cc1nn(C2CCN(C)CC2)cc1Nc1ncc(Br)c(NCCCN2CCCCC2=O)n1] | K | 58 | 8.30 (brs, 1H), 7.89 (s, 1H), 7.78 (s, 1H), 6.89 (s, 1H), 3.93 (m, 1H), 3.31 (m, 4H), 3.21 (m, 2H), 2.81 (d, J = 11.2 Hz, 2H), 2.21 (t, J = 6.2 Hz, 2H), 2.17 (s, 3H), 2.08 (s, 3H), 1.99 (t, J = 11.6 Hz, 2H), 1.82-1.92 (m, 4H), 1.69 (m, 6H). | 505.4 507.4 |
| 52 | 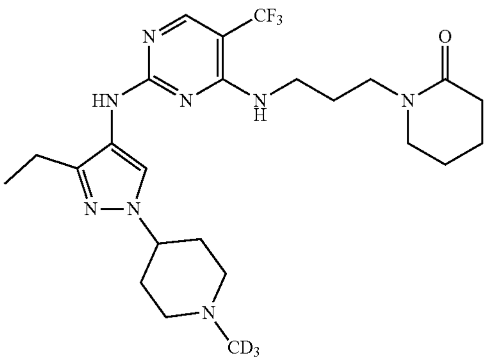 [SMILES: [2H]C([2H])([2H])N1CCC(n2cc(Nc3ncc(C(F)(F)F)c(NCCCN4CCCCC4=O)n3)c(CC)n2)CC1] | L | 21 | 8.42 (brs, 1H), 8.07 (s, 1H), 7.80 (s, 1H), 6.77 (brs, 1H), 4.19 (brs, 1H), 3.38 (m, 2H), 3.31 (t, J = 6.8 Hz, 2H), 3.23 (m, 2H), 3.15 (brs, 2H), 3.11 (m, 2H), 2.57 (m, 2H), 2.23 (m, 2H), 2.08 (m, 4H), 1.74 (m, 6H), 1.13 (t, J = 7.4 Hz, 3H). | 512.5 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 53 | 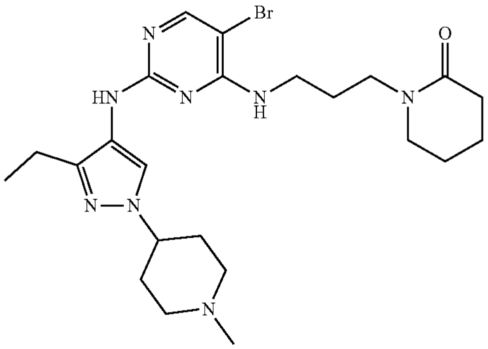 [SMILES: CCc1nn(C2CCN(C)CC2)cc1Nc1ncc(Br)c(NCCCN2CCCCC2=O)n1] | K | 60 | 8.26 (brs, 1H), 7.88 (s, 1H), 7.78 (s, 1H), 6.90 (brs, 1H), 3.96 (m, 1H), 3.33 (m, 2H), 3.28 (m, 2H), 3.23 (m, 2H), 2.82 (d, J = 11.0 Hz, 2H), 2.54 (m, 2H), 2.21 (m, 2H), 2.18 (s, 3H), 1.98 (m, 2H), 1.89 (m, 2H), 1.85 (m, 2H), 1.69 (brs, 6H), 1.09 (t, J = 7.4 Hz, 3H). | 519.4 |
| 54 | 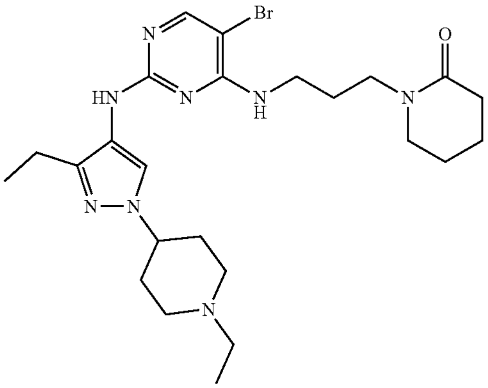 [SMILES: CCc1nn(C2CCN(CC)CC2)cc1Nc1ncc(Br)c(NCCCN2CCCCC2=O)n1] | K & M | 70 | 8.25 (brs, 1H), 7.88 (s, 1H), 7.78 (s, 1H), 6.89 (m, 1H), 3.97 (brs, 1H), 3.34 (m, 2H), 3.27 (m, 2H), 3.21 (m, 2H), 2.93 (m, 2H), 2.54 (m, 2H), 2.32 (m, 2H), 2.22 (m, 2H), 1.97 (m, 4H), 1.83 (m, 2H), 1.69 (brs, 6H), 1.09 (t, J = 7.4 Hz, 3H), 1.00 (t, J = 7.4 Hz, 3H). | 533.4 |
| 55 | 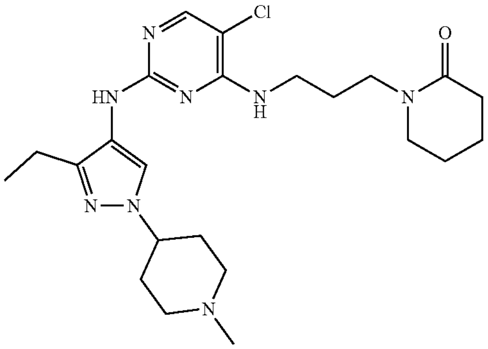 [SMILES: CCc1nn(C2CCN(C)CC2)cc1Nc1ncc(Cl)c(NCCCN2CCCCC2=O)n1] | K | 30 | 8.25 (brs, 1H), 7.81 (s, 1H), 7.79 (s, 1H), 7.04 (t, 1H), 4.00 (m, 1H), 3.33 (m, 2H), 3.27 (m, 2H), 3.21 (m, 2H), 2.88 (brs, 2H), 2.54 (m, 2H), 2.22 (m, 5H), 2.12 (brs, 2H), 1.95 (m, 2H), 1.88 (m, 2H), 1.70 (m, 6H), 1.09 (t, J = 7.4 Hz, 3H). | 475.4 |
| 56 | 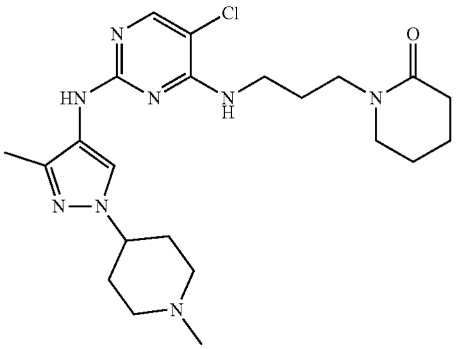 | K | 8 | 8.23 (brs, 1H), 8.21 (s, 1H), 7.81 (m, 2H), 7.04 (m, 1H), 3.94 (brs, 1H), 3.36-3.10 (brm, 7H), 2.83 (brs, 2H), 2.20-1.82 (m, 7H), 2.14-1.99 (m, 6H), 1.69 (brm, 6H). | 461.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 57 | 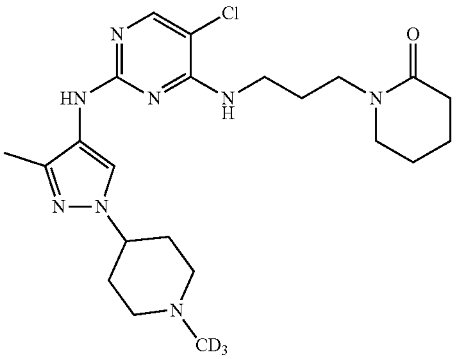 [SMILES: [2H]C([2H])([2H])N1CCC(n2cc(Nc3ncc(Cl)c(NCCCN4CCCCC4=O)n3)c(C)n2)CC1] | K | 33 | 8.31 (brs, 1H), 8.17 (s, 1H), 7.80 (m, 2H), 7.05 (m, 1H), 3.95 (m, 1H), 3.43-3.29 (m, 4H), 3.23-3.19 (m, 2H), 2.87 (d, J = 11.2 Hz, 2H), 2.21 (t, J = 6.2 Hz, 2H), 2.11-2.08 (m, 5H), 1.84-1.96 (m, 4H), 1.68-1.72 (m, 6H). | 464.4 |
| 58 | 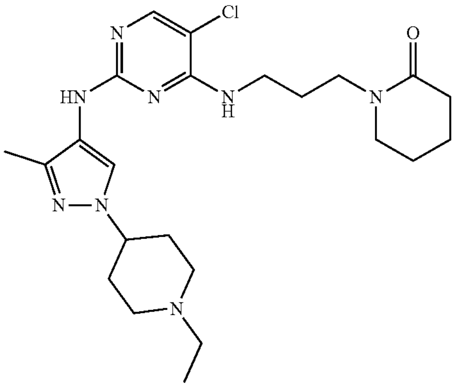 [SMILES: CCN1CCC(n2cc(Nc3ncc(Cl)c(NCCCN4CCCCC4=O)n3)c(C)n2)CC1] | K & M | 33 | 8.29 (brs, 1H), 8.18 (s, 1H), 7.83 (s, 1H), 7.81 (brs, 1H), 7.04 (s, 1H), 4.01 (m, 1H), 3.34-3.27 (m, 4H), 3.22-3.19 (m, 2H), 2.99 (d, J = 11.2 Hz, 2H), 2.42 (q, J = 7.2 Hz, 2H), 2.22 (t, J = 6.2 Hz, 2H), 2.10 (m, 5H), 1.98 (d, J = 12.2 Hz, 2H), 1.88 (m, 2H), 1.70 (m, 6H), 1.03 (t, J = 7.2 Hz, 3H). | 475.4 |
| 59 | 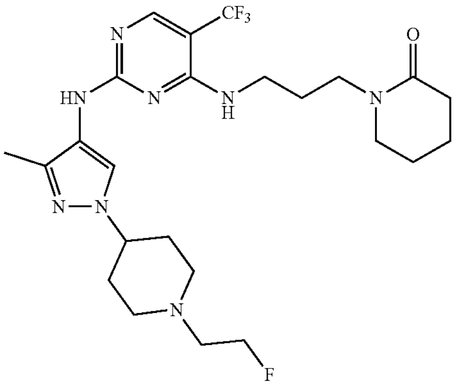 [SMILES: Cc1nn(C2CCN(CCF)CC2)cc1Nc1ncc(C(F)(F)F)c(NCCCN2CCCCC2=O)n1] | K | 51 | 8.88 (brs, 1H), 8.07 (s, 1H), 7.84 (brs, 1H), 7.08 (brs, 1H), 4.57 (t, J = 5.0 Hz, 1H), 4.47 (t, J = 5.0 Hz, 1H), 3.99 (m, 1H), 3.25-3.40 (m, 6H), 3.14-3.23 (m, 2H), 2.95 (brm, 2H), 2.97 (t, J = 5.0 Hz, 1H), 2.60 (t, J = 5.0 Hz, 1H), 2.0-2.3 (m, 7H), 1.80-2.0 (m, 4H), 1.62-1.75 (m, 4H). | 527.4 |
| 60 | 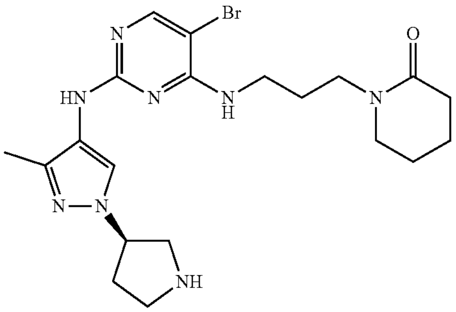 [SMILES: Cc1nn([C@@H]2CCNC2)cc1Nc1ncc(Br)c(NCCCN2CCCCC2=O)n1] | K | 47 | 9.72 (brs, 1H), 9.26 (brs, 2H), 8.15 (brs, 1H), 7.98 (s, 1H), 5.11 (brs, 1H), 3.59 (m, 2H), 3.40 (m, 2H), 3.31 (m, 2H), 3.23 (m, 2H), 2.36 (m, 2H), 2.22 (m, 5H), 2.14 (s, 3H), 1.72 (m, 6H). | 477.2 479.2 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 61 | 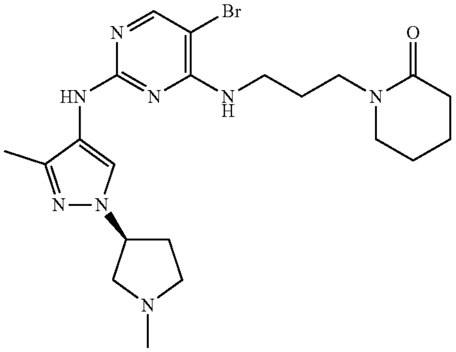 [SMILES: Cc1nn([C@H]2CCN(C)C2)cc1Nc1ncc(Br)c(NCCCN2CCCCC2=O)n1] | K | 34 | 8.37 (brs, 1H), 7.90 (s, 1H), 7.88 (brs, 1H), 6.91 (t, 1H), 4.81 (brs, 1H), 3.35 (m, 2H), 3.22 (m, 2H), 2.84 (m, 2H), 2.58 (m, 2H), 2.35 (m, 5H), 2.22 (m, 2H), 2.10 (s, 3H), 2.03 (m, 2H), 1.71 (m, 6H). | 491.14 |
| 62 | 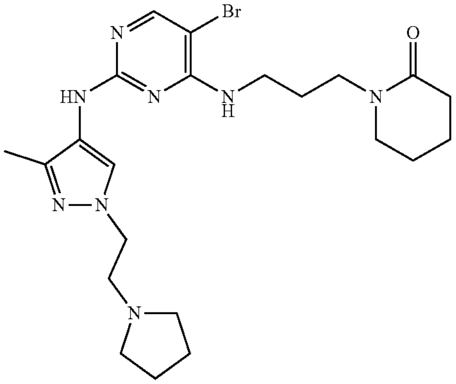 [SMILES: Cc1nn(CCN2CCCC2)cc1Nc1ncc(Br)c(NCCCN2CCCCC2=O)n1] | K | 22 | 8.35 (brs, 1H), 7.90 (s, 1H), 7.81 (s, 1H), 6.90 (t, J = 5.4 Hz, 1H), 4.16 (brs, 2H), 3.32 (m, 2H), 3.21 (m, 2H), 2.94 (m, 2H), 2.58 (m, 2H), 2.40 (m, 2H), 2.22 (m, 2H), 2.10 (s, 3H), 1.70 (m, 12H). | 505.44 |
| 63 | 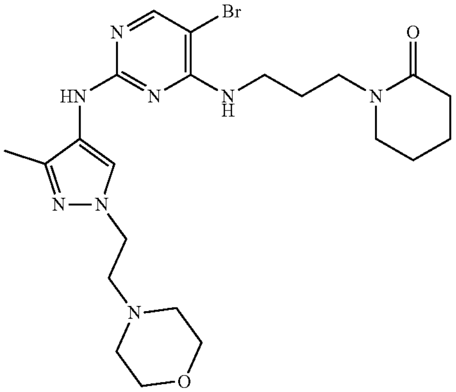 [SMILES: Cc1nn(CCN2CCOCC2)cc1Nc1ncc(Br)c(NCCCN2CCCCC2=O)n1] | K | 16 | 8.30 (brs, 1H), 7.89 (s, 1H), 7.77 (s, 1H), 6.88 (m, 1H), 4.09 (t, J = 6.6 Hz, 2H), 3.53 (m, 4H), 3.34 (m, 2H), 3.29 (m, 2H), 3.22 (m, 2H), 2.64 (t, J = 6.8 Hz, 2H), 2.39 (m, 4H), 2.22 (m, 2H), 2.08 (s, 3H), 1.69 (m, 6H). | 521.43 |
| 64 | 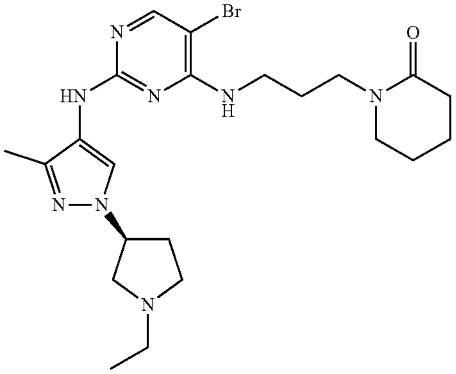 [SMILES: CCN1CC[C@H](n2cc(Nc3ncc(Br)c(NCCCN4CCCCC4=O)n3)c(C)n2)C1] | K & M | 31 | 8.37 (brs, 1H), 7.90 (s, 1H), 7.86 (brs, 1H), 6.90 (m, 1H), 4.73 (brs, 1H), 3.35 (m, 2H), 3.31 (m, 2H), 3.21 (m, 2H), 2.80 (m, 1H), 2.70 (m, 2H), 2.45 (m, 1H), 2.41 (m, 2H), 2.29 (m, 1H), 2.26 (m, 2H), 2.09 (s, 3H), 1.97 (m, 1H), 1.70 (m, 6H), 1.02 (t, J = 7.2 Hz, 3H). | 505.36 |

TABLE G-continued

| Exemplary Compounds that can be prepared by General Methods K through N. | | | | | |
|---|---|---|---|---|---|
| Example No. | Product | General Method | Yield (%) | $^1$H NMR (400 MHz, DMSO-$d_6$): δ | LC-MS (m/z: M + H$^+$) |
| 65 | 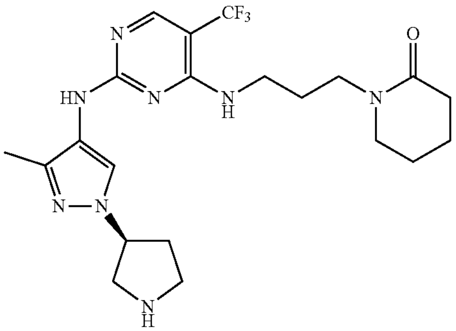 [SMILES: Cc1nn([C@H]2CCNC2)cc1Nc1ncc(C(F)(F)F)c(NCCCN2CCCCC2=O)n1] | L | 85 | 9.47 (brs, 1H), 9.29 (brs, 2H), 8.20 (s, 1H), 7.96 (s, 1H), 7.48 (brs , 1H), 5.11 (brs, 1H), 3.62 (m, 2H), 3.53 (m, 1H), 3.43 (m, 2H), 3.32 (t, J = 6.6 Hz, 3H), 3.24 (t, J = 5.0 Hz, 2H), 2.41 (m, 1H), 2.30 (m, 1H), 2.23 (m, 2H), 2.17 (s, 3H), 1.76 (m, 6H). | 467.38 |
| 66 | 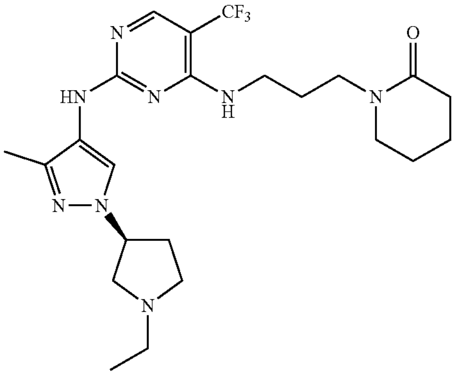 [SMILES: CCN1CC[C@H](n2cc(Nc3ncc(C(F)(F)F)c(NCCCN4CCCCC4=O)n3)c(C)n2)C1] | L & M | 15 | 8.97 (brs, 1H), 8.09 (s, 1H), 7.89 (brs, 1H), 7.09 (brs, 1H), 4.88 (brs, 1H), 3.38 (m, 2H), 3.28 (m, 2H), 3.22 (m, 2H), 2.89 (m, 4H), 2.32 (m, 2H), 2.22 (brs, 2H), 2.09 (brs, 5H), 1.69 (brs, 6H), 1.07 (t, J = 7.4 Hz, 3H). | 495.50 |
| 67 | 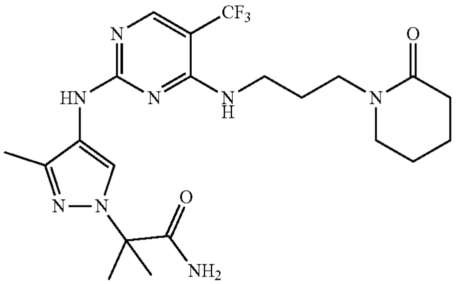 [SMILES: Cc1nn(C(C)(C)C(N)=O)cc1Nc1ncc(C(F)(F)F)c(NCCCN2CCCCC2=O)n1] | L | 53 | 9.03 (s, 1H); 8.11 (s, 1H); 7.99 (s, 1H), 7.16 (s, 2H), 6.64 (s, 1H), 3.21-3.35 (m, 6H), 2.21 (t, J = 6.0 Hz, 2H), 2.15 (s, 3H), 1.69 (s, 6H), 1.64 (s, 6H). | 483.2 |
| 68 | 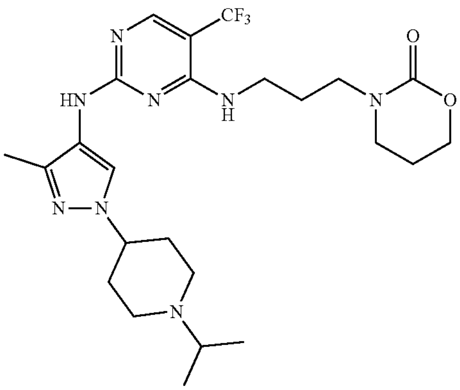 | L | 7 | 8.71 (brs, 1H), 8.08 (s, 1H), 7.83 (brs, 1H), 6.95 (brs, 1H), 4.14 (t, J = 6.3 Hz, 2H), 3.94 (m, 1H), 3.39 (m, 2H), 3.23 (m, 4H), 2.85 (d, J = 10.6 Hz, 2H), 2.73 (m, 1H), 2.23 (t, J = 10.8 Hz, 2H), 2.10 (s, 3H), 1.98 (m, 4H), 1.81 (m, 2H), 1.76 (m, 2H), 0.97 (d, J = 6.6 Hz, 6H). | 525.5 |

TABLE G-continued
Exemplary Compounds that can be prepared by General Methods K through N.
| Example No. | Product | General Method | Yield (%) | $^1$H NMR (400 MHz, DMSO-$d_6$): δ | LC-MS (m/z: M + H$^+$) |
|---|---|---|---|---|---|
| 69 | 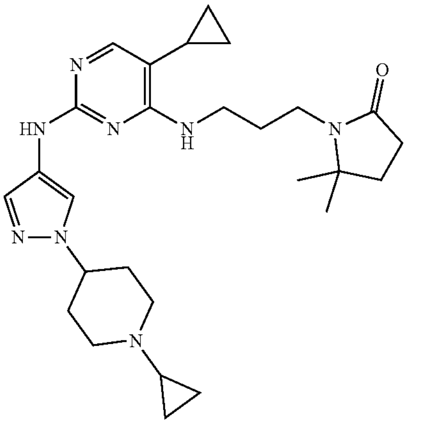 [SMILES: CC1(C)CCC(=O)N1CCCNc1nc(Nc2cnn(C3CCN(C4CC4)CC3)c2)ncc1C1CC1] | K | 34 | 10.7 (brs, 1H), 8.62 (brs, 1H), 7.92 (s, 1H), 7.64 (s, 1H), 7.58 (brs, 1H), 4.94 (m, 1H), 3.59 (m, 2H), 3.40 (m, 2H), 3.2-3.15 (m, 4H), 3.18 9m, 2H), 2.79 (brm, 1H), 2.2-2.4 (m, 4H), 1.81 (m, 4H), 1.53 (m, 1H), 1.18 (s, 6H), 1.16 (m, 2H), 0.91 (m, 2H), 0.76 (m, 2H), 0.54 (m, 2H). | 493.4 |
| 70 | 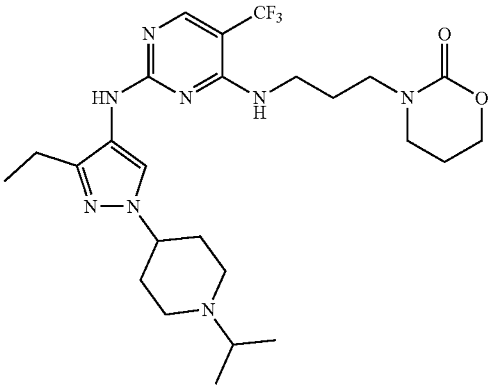 [SMILES: CCc1nn(C2CCN(C(C)C)CC2)cc1Nc1ncc(C(F)(F)F)c(NCCCN2CCCOC2=O)n1] | L & M | 41 | 8.75 (m, 1H), 8.01 (s, 1H), 7.77 (s, 1H), 7.01 (s, 1H), 4.08 (s, 2H), 3.85-3.95 (brm, 1H), 3.27 (brm, 6H), 3.16 (s, 4H), 2.82 (brs, 1H), 2.42-2.44 (m, 2H), 1.67-1.92 (brm, 8 H), 1.03 (t, J = 7.4 Hz, 3H), 0.94 (d, J = 6.8 Hz, 6H). | 539.4 |
| 71 | 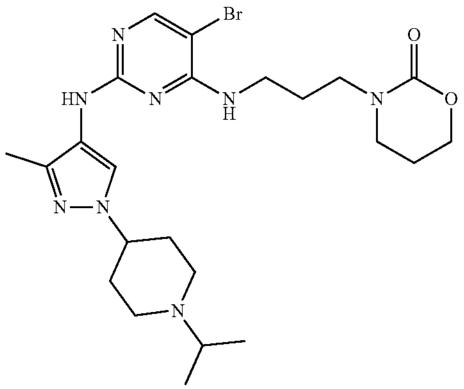 [SMILES: Cc1nn(C2CCN(C(C)C)CC2)cc1Nc1ncc(Br)c(NCCCN2CCCOC2=O)n1] | K | 60 | 9.97 (brs, 1H), 8.84 (brs, 1H), 8.03 (s, 1H), 7.83 (s, 1H), 7.44 (brs, 1H), 4.41 (brs, 1H), 4.17 (m, 2H), 3.46 (m, 4H), 3.29 (m, 4H), 3.15 (m, 2H), 2.50 (m, 1H), 2.38 (m, 2H), 2.25 (m, 2H), 2.15 (s, 3H), 1.95 (t, J = 5.6 Hz, 2H), 1.84 (t, J = 6.8 Hz, 2H), 1.31 (d, J = 6.4 Hz, 6H). | 535.2<br>537.2 |

TABLE G-continued
Exemplary Compounds that can be prepared by General Methods K through N.
| Example No. | Product | General Method | Yield (%) | $^1$H NMR (400 MHz, DMSO-$d_6$): δ | LC-MS (m/z: M + H$^+$) |
|---|---|---|---|---|---|
| 72 | 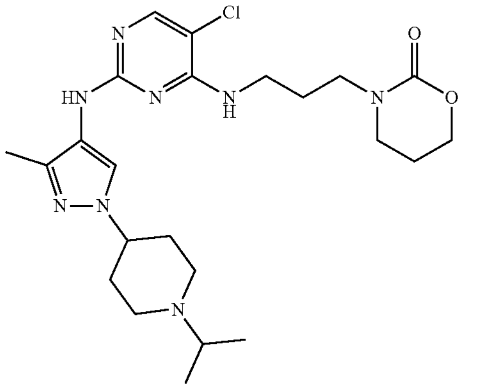 | K | 24 | 7.93 (brs, 1H), 7.81 (s, 1H), 7.76 (s, 1H), 6.74 (brs, 1H), 4.15 (t, J = 5.0 Hz, 2H), 3.93 (m, 1H), 3.39 (m, 2H), 3.27 (m, 4H), 2.87 (m, 2H), 2.73 (m, 1H), 2.26 (t, J = 11.6 Hz, 2H), 2.10 (s, 3H), 1.96 (m, 4H), 1.83 (m, 4H), 0.99 (d, J = 6.4 Hz, 6H). | 491.2 |
| 73 | 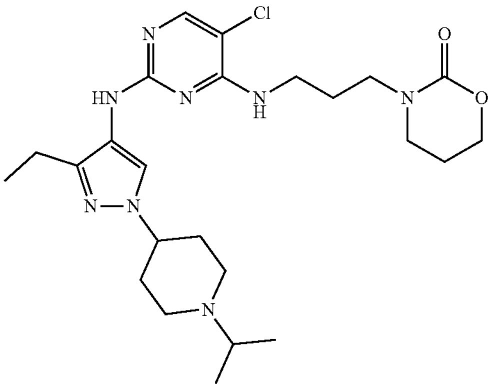 [SMILES: CCc1nn(C2CCN(C(C)C)CC2)cc1Nc1ncc(Cl)c(NCCCN2CCCOC2=O)n1] | K & M | 20 | 10.44 (brs, 1H), 9.49 (brs, 1H), 8.06 (s, 2H), 7.85 (s, 1H), 4.44 (brs, 1H), 4.16 (t, J = 5.4 Hz, 2H), 3.47 (m, 5H), 3.29 (m, 4H), 3.14 (m, 2H), 2.59 (m, 2H), 2.43 (m, 2H), 2.28 (m, 2H), 1.90 (m, 4H), 1.32 (d, J = 6.6 Hz, 6H), 1.17 (t, J = 7.2 Hz, 3H). | 505.24 |
| 74 | 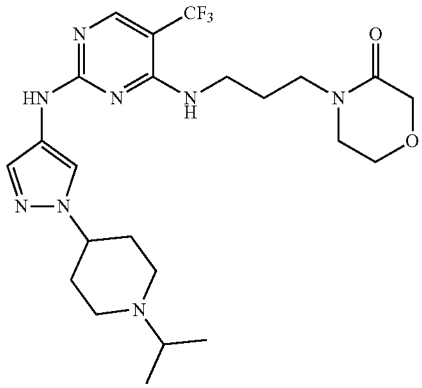 [SMILES: CC(C)N1CCC(n2cc(Nc3ncc(C(F)(F)F)c(NCCCN4CCOCC4=O)n3)cn2)CC1] | L | 76 | 9.53 (brs, 1H), 8.16 (s, 1H), 8.08 (brs, 1H), 7.82 (brs, 1H), 7.52 (brs, 1H), 7.08 (brs, 1H), 4.06 (m, 1H), 4.03 (s, 2H), 3.81 (m, 2H), 3.2-3.5 (m, 6H), 2.87 (m, 2H), 2.75 (m, 1H), 2.27 (t, J = 11.6 Hz, 2H), 1.99 (m, 2H), 1.75-1.86 (m, 4H). 0.98 (d, J = 6.6 Hz, 6H). | 511.4 |

TABLE G-continued

| Example No. | Product | General Method | Yield (%) | $^1H$ NMR (400 MHz, DMSO-$d_6$): δ | LC-MS (m/z: M + $H^+$) |
|---|---|---|---|---|---|
| Exemplary Compounds that can be prepared by General Methods K through N. | | | | | |
| 75 | 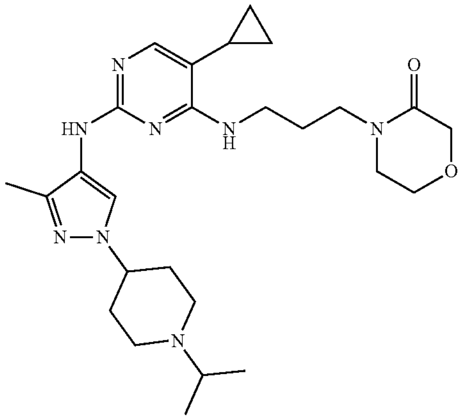 [SMILES: Cc1nn(C2CCN(C(C)C)CC2)cc1Nc1ncc(C2CC2)c(NCCCN2CCOCC2=O)n1] | K | 90 | 12.2 (brs, 1H), 10.6 (brs, 1H), 9.87 (brs, 1H), 8.45 (s, 1H), 7.89 (s, 1H), 7.41 (brs, 1H), 4.43 (brs, 1H), 4.02 (s, 2H), 3.82 (brs, 2H), 3.48 (m, 8H), 3.13 (m, 2H), 2.38 (m, 3H), 2.23 (m, 2H), 2.14 (s, 3H), 1.86 (m, 2H), 1.52 (brs, 1H), 1.29 (d, J = 6.4 Hz, 6H), 0.89 (m, 2H), 0.56 (m, 2H). | 497.4 |
| 76 | 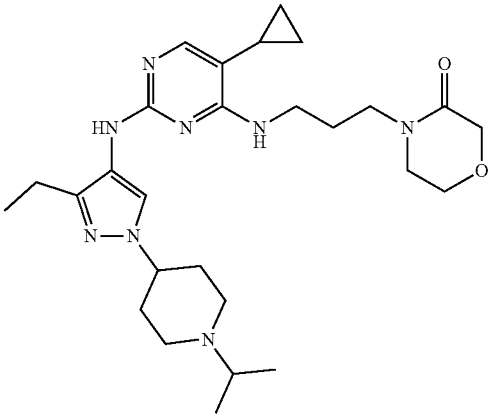 [SMILES: CCc1nn(C2CCN(C(C)C)CC2)cc1Nc1ncc(C2CC2)c(NCCCN2CCOCC2=O)n1] | K & M | 91 | 11.8 (brs, 1H), 10.5 (brs, 1H), 9.61 (brs, 1H), 8.22 (s, 1H), 7.86 (s, 1H), 7.57 (s, 1H), 4.52 (brs, 1H), 4.02 (s, 2H), 3.83 (m, 2H), 3.43 (m, 10H), 3.09 (m, 2H), 2.58 (m, 2H), 2.43 (m, 1H), 2.29 (m, 2H), 1.89 (m, 2H), 1.56 (brs, 1H), 1.32 (d, J = 6.4 Hz, 6H), 1.17 (t, J = 7.4 Hz, 3H), 0.92 (m, 2H), 0.56 (m, 2H). | 511.3 |
| 77 | 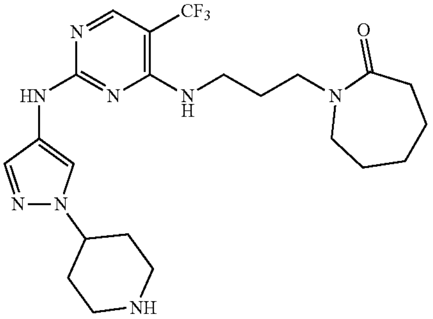 [SMILES: O=C1CCCCCN1CCCNc1nc(Nc2cnn(C3CCNCC3)c2)ncc1C(F)(F)F] | L | 20 | 9.56 (s, 1H), 8.31 (s, 1H), 8.15 (s, 1H), 7.83 (s, 1H), 7.53 (brs, 1H), 7.12 (brm, 1H), 4.31 (brm, 1H), 3.42 (brm, 2H), 3.31 (m, 4H), 3.21 (m, 2H), 2.85 (s, 2H), 2.42 (m, 2H), 2.04 (m, 2H), 1.90 (m, 2H), 1.74 (m, 2H), 1.69 (m, 2H), 1.54 (m, 4H). | 481.4 |
| 78 | 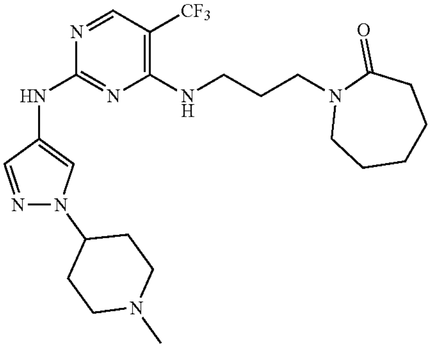 [SMILES: CN1CCC(n2cc(Nc3ncc(C(F)(F)F)c(NCCCN4CCCCCC4=O)n3)cn2)CC1] | L | 49 | 9.53 (brs, 1H), 8.16 (s, 1H), 8.09 (s, 1H), 7.82 (brs, 1H), 7.52 (brs, 1H), 7.12 (brm, 1H), 4.08 (brm, 1H), 3.42 (brm, 2H), 3.24 (m, 6H), 2.87 (m, 2H), 2.43 (m, 2H), 2.21 (s, 3H), 2.04 (m, 2H), 1.97 (m, 2H), 1.71 (m, 2H), 1.69 (m, 2H), 1.54 (m, 4H). | 495.4 |

TABLE G-continued

| Exemplary Compounds that can be prepared by General Methods K through N. | | | | | |
|---|---|---|---|---|---|
| Example No. | Product | General Method | Yield (%) | $^1$H NMR (400 MHz, DMSO-$d_6$): δ | LC-MS (m/z: M + $H^+$) |
| 79 | 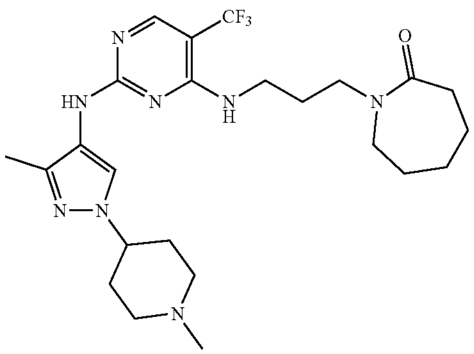 [SMILES: Cc1nn(C2CCN(C)CC2)cc1Nc1ncc(C(F)(F)F)c(NCCCN2CCCCCC2=O)n1] | L | 29 | 8.90 (brs, 1H), 8.18 (s, 1H), 8.09 (s, 1H), 7.84 (brs, 1H), 7.05 (brs, 1H), 4.00 (brm, 1H), 3.31 (brm, 4H), 2.89 (m, 2H), 2.52 (s, 3H), 2.42 (m, 2H), 2.23 (s, 3H), 2.05 (m, 6H), 1.90 (m, 4H), 1.71 (m, 2H), 1.64 (m, 2H), 1.54 (m, 2H). | 509.4 |
| 81 | 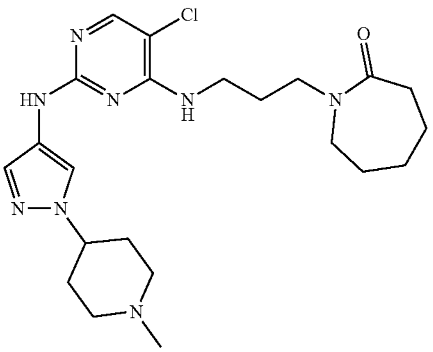 [SMILES: CN1CCC(n2cc(Nc3ncc(Cl)c(NCCCN4CCCCCC4=O)n3)cn2)CC1] | K | 55 | 9.00 (brs, 1H), 7.84 (s, 1H), 7.80 (s, 1H), 7.48 (brm, 1H), 7.08 (m, 1H), 4.04 (t, J = 10.2 Hz, 1H), 3.38 (m, 6H), 2.83 (m, 2H), 2.43 (m, 2H), 2.18 (s, 3H), 2.01 (m, 2H), 1.94 (m, 4H), 1.74 (m, 2H), 1.64 (m, 2H), 1.54 (m, 4H). | 462.4 |
| 82 | 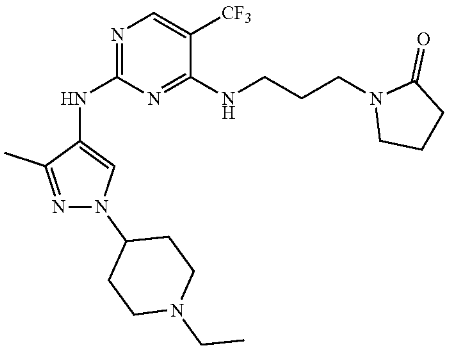 [SMILES: CCN1CCC(n2cc(Nc3ncc(C(F)(F)F)c(NCCCN4CCCC4=O)n3)c(C)n2)CC1] | L & M | 41 | 8.96 (s, 1H), 8.17 (s, 1H), 8.08 (s, 1H), 7.85 (s, 1H), 7.06 (s, 1H), 4.03 (brs, 1H), 3.32 (brs, 3H), 3.16 (brs, H), 3.01 (d, J = 11.4 Hz, 3H), 2.42-2.47 (m, 2H), 1.86-2.22 (m, 12H), 1.67 (brs, 2H), 1.02 (t, J = 7.2 Hz, 3H). | 495.4 |
| 84 | 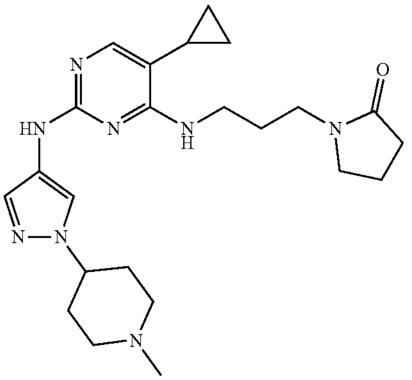 [SMILES: CN1CCC(n2cc(Nc3ncc(C4CC4)c(NCCCN4CCCC4=O)n3)cn2)CC1] | K | 67 | 8.62 (brs, 1H), 7.82 (s, 1H), 7.55 (s, 1H), 7.44 (s, 1H), 6.68 (t, J = 5.2 Hz, 1H), 4.01 (m, 1H), 3.39 (m, 2H), 3.34 (m, 2H), 3.26 (t, J = 6.8 Hz, 2H), 2.82 (m, 2H), 2.24 (t, J = 8.0 Hz, 2H), 2.18 (s, 3H), 2.01 (m, 2H), 1.90 (m, 6H), 1.75 (t, J = 6.6 Hz, 2H), 1.43 (m, 1H), 0.79 (m, 2H), 042 (m, 2H). | 439.2 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 85 | 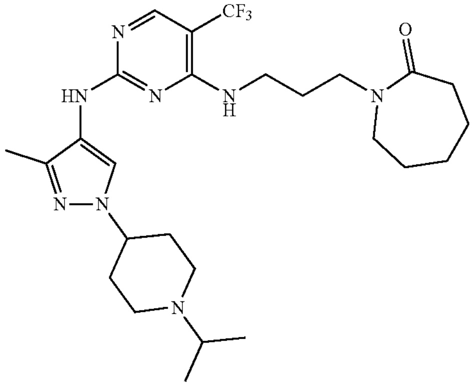 [SMILES: Cc1nn(C2CCN(C(C)C)CC2)cc1Nc1ncc(C(F)(F)F)c(NCCCN2CCCCCC2=O)n1] | L & M | 40 | 8.71 (brs, 1H), 8.08 (s, 1H), 7.90 (brs, 1H), 7.09 (brs, 1H), 3.95 (brs, 1H), 3.31 (m, 2H), 3.25 (m, 4H), 2.83 (m, 2H), 2.69 (m, 1H), 2.42 (d, J = 8.6 Hz, 2H), 2.22 (m, 2H), 2.10 (s, 3H), 1.95 (m, 2H), 1.81 (m, 2H), 1.63 (d, J = 5.2 Hz, 4H), 1.53 (brs, 4H), 0.97 (d, J = 6.8 Hz, 6H). | 537.6 |
| 86 | 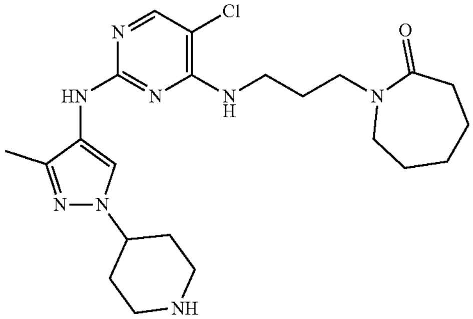 | K | 12 | 8.28 (s, 2H), 7.82 (s, 1H), 7.80 (s, 1H), 7.06 (s, 1H), 4.18 (brm, 1H), 3.32 (m, 6H), 3.15 (m, 2H), 2.76 (m, 2H), 2.42 (m, 2H), 2.10 (s, 3H), 1.99 (m, 2H), 1.88 (m, 2H), 1.68 (m, 4H), 1.54 (s, 4H). | 462.4 |
| 87 | 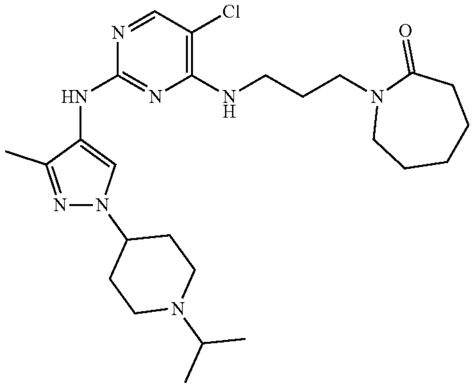 [SMILES: Cc1nn(C2CCN(C(C)C)CC2)cc1Nc1ncc(Cl)c(NCCCN2CCCCCC2=O)n1] | K & M | 60 | 8.31 (brs, 1H), 8.17 (s, 1H), 7.81 (s, 1H), 7.79 (s, 1H), 7.05 (s, 1H), 4.01 (m, 1H), 3.33 (m, 6H), 2.92 (m, 2H), 2.72 (m, 1H), 2.43 (m, 2H), 2.33 (m, 2H), 2.08 (s, 3H), 1.90 (m, 2H), 1.88 (m, 2H), 1.69 (m, 4H), 1.54 (m, 4H). 1.00 (d, J = 7.4 Hz, 6H). | 503.4 |
| 88 | 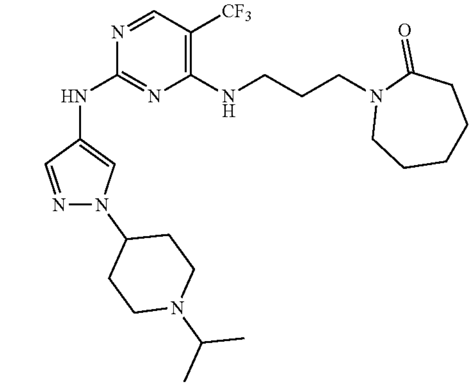 [SMILES: CC(C)N1CCC(n2cc(Nc3ncc(C(F)(F)F)c(NCCCN4CCCCCC4=O)n3)cn2)CC1] | L | 47 | 9.54 (brs, 1H), 8.16 (s, 1H), 8.09 (s, 1H), 7.82 (brs, 1H), 7.52 (brs, 1H), 7.12 (brs, 1H), 4.08 (brm, 1H), 3.42 (brm, 2H), 3.24 (m, 2H), 2.90 (m, 2H), 2.81 (m, 1H), 2.43 (m, 2H), 2.21 (s, 2H), 1.99 (m, 2H), 1.85 (m, 2H), 1.79 (m, 2H), 1.72 (m, 2H), 1.69 (m, 2H), 1.54 (m, 4H), 1.00 (d, J = 7.0 Hz, 6H). | 523.4 |

TABLE G-continued
| Exemplary Compounds that can be prepared by General Methods K through N. | | | | | |
|---|---|---|---|---|---|
| Example No. | Product | General Method | Yield (%) | $^1$H NMR (400 MHz, DMSO-$d_6$): δ | LC-MS (m/z: M + H$^+$) |
| 89 | 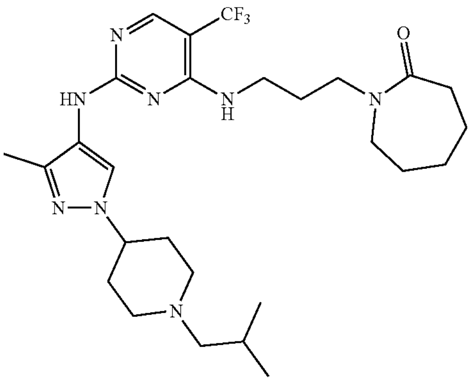 [SMILES: Cc1nn(C2CCN(CC(C)C)CC2)cc1Nc1ncc(C(F)(F)F)c(NCCCN2CCCCCC2=O)n1] | L & M | 42 | 8.91 (brs, 1H), 8.08 (s, 1H), 7.85 (brs, 1H), 7.06 (brs, 1H), 3.98 (brm, 1H), 3.32 (s, 3H), 3.31 (s, 2H), 2.88 (m, 2H), 2.42 (m, 2H), 1.8-2.2 (m, 12H), 1.76 (m, 1H), 1.66 (m, 4H), 1.53 (m, 4H), 0.85 (d, J = 7.0 Hz, 6H). | 551.4 |
| 91 | 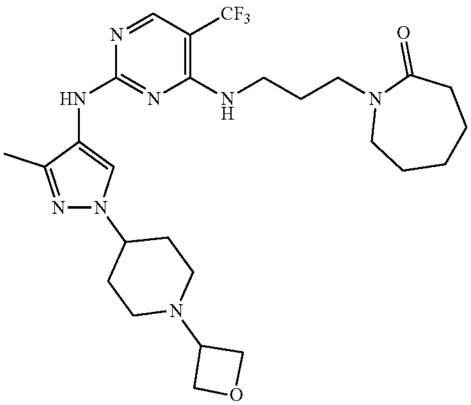 [SMILES: Cc1nn(C2CCN(C3COC3)CC2)cc1Nc1ncc(C(F)(F)F)c(NCCCN2CCCCCC2=O)n1] | L & M | 35 | 8.90 (brs, 1H), 8.19 (s, 1H), 8.07 (s, 1H), 7.86 (brs, 1H), 7.05 (brs, 1H), 3.54 (brm, 2H), 4.45 (m, 2H), 4.06 (brm, 1H), 3.43 (m, 2H), 3.2-3.3 (brm, 6H), 2.76 (m, 2H), 2.43 (m, 2H), 2.10 (m, 3H), 1.6-2.0 (m, 6H), 1.65 (m, 4H), 1.50 (m, 4H). | 551.4 |
| 92 | 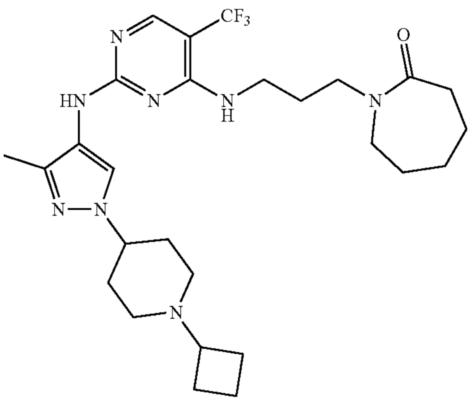 [SMILES: Cc1nn(C2CCN(C3CCC3)CC2)cc1Nc1ncc(C(F)(F)F)c(NCCCN2CCCCCC2=O)n1] | L & M | 43 | 8.89 (brs, 1H), 8.19 (s, 1H), 8.07 (s, 1H), 7.84 (brs, 1H), 7.04 (brs, 1H), 3.97 (brm, 1H), 3.31 (5H, s), 2.84 (m, 2H), 2.68 (m, 1H), 2.43 (m, 2H), 2.10 (m, 4H), 1.94 (m, 4H), 1.65-1.85 (m, 6H), 1.3-1.6 (m, 10H). | 549.4 |

TABLE G-continued
Exemplary Compounds that can be prepared by General Methods K through N.
| Example No. | Product | General Method | Yield (%) | $^1$H NMR (400 MHz, DMSO-$d_6$): δ | LC-MS (m/z: M + H$^+$) |
|---|---|---|---|---|---|
| 93 | 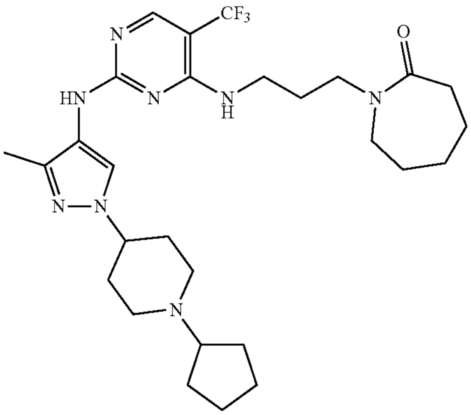 [SMILES: Cc1nn(C2CCN(C3CCCC3)CC2)cc1Nc1ncc(C(F)(F)F)c(NCCCN2CCCCCC2=O)n1] | L & M | 48 | 8.89 (brs, 1H), 8.17 (s, 1H), 8.07 (s, 1H), 7.84 (brs, 1H), 7.04 (brs, 1H), 3.99 (brm, 1H), 3.31 (5H, s), 3.01 (m, 2H), 2.56 (m, 1H), 2.41 (m, 2H), 2.10 (m, 6H), 1.95 (m, 2H), 1.82 (m, 2H), 1.79 (m, 2H), 1.4-1.7 (m, 2H), 1.33 (m, 2H). | 563.4 |
| 94 | 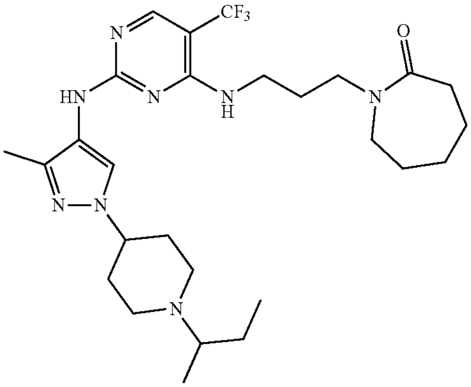 [SMILES: CCC(C)N1CCC(n2cc(Nc3ncc(C(F)(F)F)c(NCCCN4CCCCCC4=O)n3)c(C)n2)CC1] | L & M | 44 | 8.91 (brs, 1H), 8.24 (s, 1H), 8.08 (s, 1H), 7.85 (brs, 1H), 7.06 (brs, 1H), 3.94 (brm, 1H), 3.31 (s, 4H), 2.76 (m, 2H), 2.40 (m, 3H), 2.18 (m, 1H), 2.10 (m, 3H), 1.94 (m, 2H), 1.78 (m, 2H), 1.65 (m, 4H), 1.54 (m, 4H), 1.48 (m, 1H), 1.25 (m, 1H), 0.90 (d, J = 7.0 Hz, 3H), 0.85 (t, J = 7.4 Hz, 3H). | 551.4 |
| 95 | 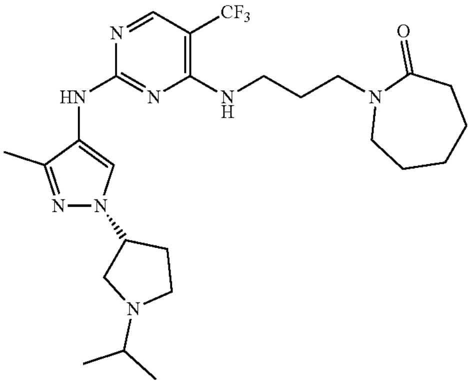 | L & M | 18 | 8.95 (brs, 1H), 8.09 (s, 1H), 7.92 (brs, 1H), 7.06 (brs, 1H), 4.78 (brs, 1H), 3.40 (m, 2H), 3.25 (m, 4H), 2.86 (m, 2H), 2.43 (m, 4H), 2.28 (m, 1H), 2.12 (s, 5H), 1.64 (d, J = 5.8 Hz, 4H), 1.54 (brs, 4H), 1.08 (d, J = 7.0 Hz, 6H). | 523.5 |

TABLE G-continued
Exemplary Compounds that can be prepared by General Methods K through N.
| Example No. | Product | General Method | Yield (%) | $^1$H NMR (400 MHz, DMSO-$d_6$): δ | LC-MS (m/z: M + H$^+$) |
|---|---|---|---|---|---|
| 96 | 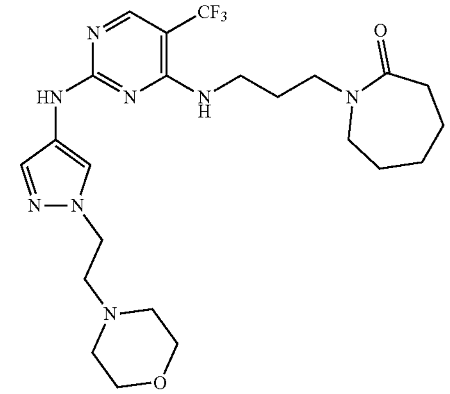 [SMILES: O=C1CCCCCN1CCCNc1nc(Nc2cnn(CCN3CCOCC3)c2)ncc1C(F)(F)F] | L | 28 | 9.42 (brs, 1H), 8.09 (brs, 1H), 7.82 (brs, 1H), 7.51 (s, 1H), 7.06 (brs, 1H), 4.19 (brs, 2H), 3.53 (brs, 4H), 3.42 (m, 2H), 3.31 (m, 4H), 2.67 (m, 2H), 2.44 (m, 2H), 2.38 (brs, 4H), 1.65 (m, 4H), 1.55 (brs, 4H). | 511.5 |
| 97 | 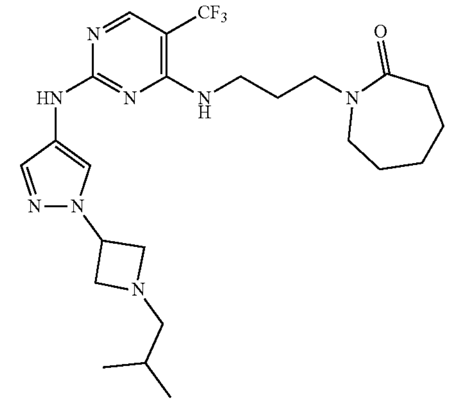 [SMILES: CC(C)CN1CC(n2cc(Nc3ncc(C(F)(F)F)c(NCCCN4CCCCCC4=O)n3)cn2)C1] | L | 16 | 9.23 (brs, 1H), 8.11 (s, 1H), 7.96 (s, 1H), 7.61 (s, 1H), 6.83 (t, J = 4.0 Hz, 1H), 5.00 (brs, 1H), 3.82 (brs, 2H), 3.47 (m, 4H), 3.36 (m, 4H), 2.45 (m, 4H), 1.76 (m, 2H), 1.67 (d, J = 5.0 Hz, 3H), 1.57 (m, 4H), 0.89 (d, J = 6.6 Hz, 6H). | 509.6 |
| 98 | 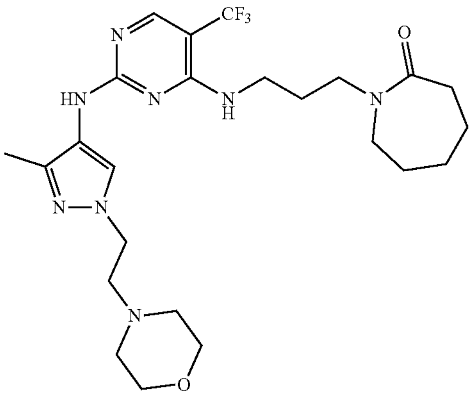 [SMILES: Cc1nn(CCN2CCOCC2)cc1Nc1ncc(C(F)(F)F)c(NCCCN2CCCCCC2=O)n1] | L | 25 | 8.89 (brs, 1H), 8.08 (s, 1H), 7.81 (brs, 1H), 7.04 (brs, 1H), 4.11 (brs, 2H), 3.53 (brs, 4H), 3.37 (m, 2H), 3.31 (m, 2H), 2.65 (t, J = 6.0 Hz ,2H), 2.40 (m, 8H), 2.10 (s, 3H), 1.65 (brs, 4H), 1.54 (brs, 4H). | 525.5 |

TABLE G-continued
| Example No. | Product | General Method | Yield (%) | $^1H$ NMR (400 MHz, DMSO-$d_6$): δ | LC-MS (m/z: M + H$^+$) |
|---|---|---|---|---|---|
| Exemplary Compounds that can be prepared by General Methods K through N. | | | | | |
| 99 | 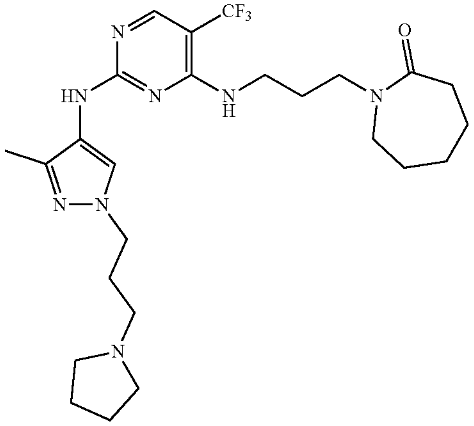 [SMILES: Cc1nn(CCCN2CCCC2)cc1Nc1ncc(C(F)(F)F)c(NCCCN2CCCCCC2=O)n1] | L | 15 | 8.72 (brs, 1H), 8.08 (s, 1H), 7.79 (brs, 1H), 7.05 (brs, 1H), 4.01 (brs, 2H), 3.28 (m, 4H), 2.37 (m, 10H), 2.10 (s, 3H), 1.88 (t, J = 6.8 Hz, 2H), 1.66 (m, 8H), 1.54 (brs, 4H). | 523.5 |
| 100 | 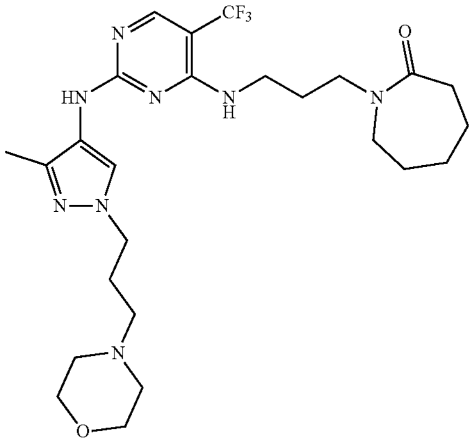 [SMILES: Cc1nn(CCCN2CCOCC2)cc1Nc1ncc(C(F)(F)F)c(NCCCN2CCCCCC2=O)n1] | L | 26 | 8.43 (brs, 1H), 8.07 (s, 1H), 7.74 (s, 1H), 6.75 (t, J = 7.0 Hz, 1H), 4.02 (t, J = 7.0 Hz, 2H), 3.57 (m, 4H), 3.39 (m, 2H), 3.32 (m, 4H), 2.44 (m, 2H), 2.32 (m, 6H), 2.11 (s, 3H), 1.89 (m, 2H), 1.70 (m, 4H), 1.57 (m, 4H). | 539.5 |
| 101 | 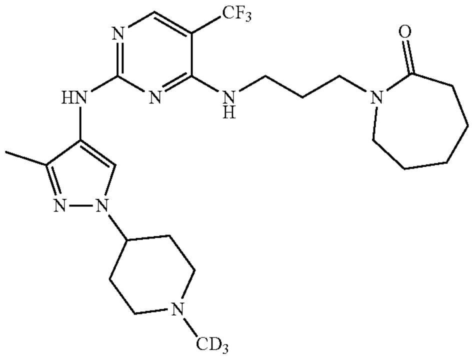 [SMILES: [2H]C([2H])([2H])N1CCC(n2cc(Nc3ncc(C(F)(F)F)c(NCCCN4CCCCCC4=O)n3)c(C)n2)CC1] | L | 10 | 8.71 (brs, 1H), 8.08 (s, 1H), 7.90 (brs, 1H), 7.06 (brs, 1H), 3.97 (brs, 1H), 3.32 (m, 2H), 3.17 (m, 2H), 2.82 (d, J = 11.0 Hz, 4H), 2.41 (m, 2H), 2.10 (s, 3H), 2.01 (m, 2H), 1.87 (m, 4H), 1.65 (m, 4H), 1.55 (m, 4H). | 512.5 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 102 | 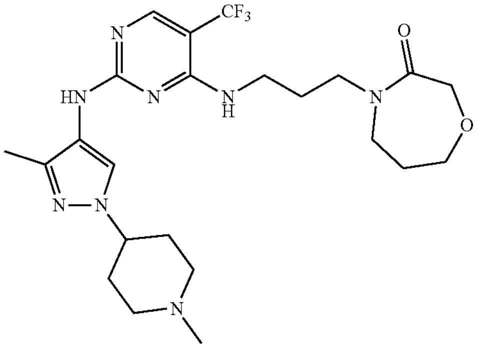 [SMILES: Cc1nn(C2CCN(C)CC2)cc1Nc1ncc(C(F)(F)F)c(NCCCN2CCCOCC2=O)n1] | L | 52 | 8.90 (brs, 1H), 8.08 (s, 1H), 7.84 (brs, 1H), 7.01 (brs, 1H), 4.11 (s, 2H), 3.74 (m, 2H), 3.30-3.50 (m, 9H), 2.87-2.93 (m, 2H), 2.25 (s, 3H), 2.06-2.17 (m, 4H), 1.86-1.94 (m, 4H), 1.76 (m, 2H), 1.68 (m, 2H). | 511.4 |
| 103 | 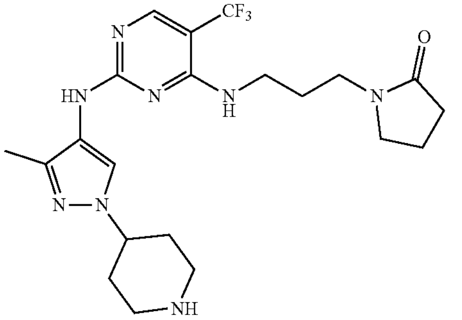 [SMILES: Cc1nn(C2CCNCC2)cc1Nc1ncc(C(F)(F)F)c(NCCCN2CCCC2=O)n1] | L | 13 | 8.44 (brs, 1H), 8.07 (s, 1H), 7.76 (s, 1H), 6.69 (t, 1H), 4.06 (m, 1H), 3.39 (m, 2H), 3.32 (t, J = 6.8 Hz, 2H), 3.20 (t, J = 6.8 Hz, 2H), 2.60 (m, 2H), 2.22 (t, J = 7.8 Hz, 2H), 2.11 (s, 3H), 1.93 (m, 5H), 1.73 (m, 5H). | 467.4 |
| 104 | 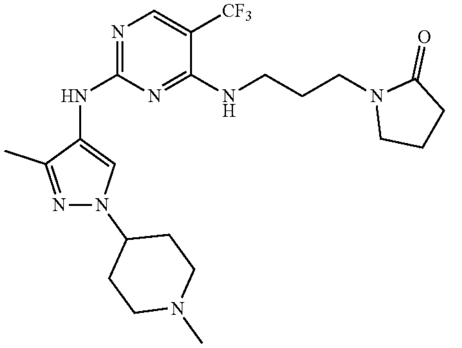 [SMILES: Cc1nn(C2CCN(C)CC2)cc1Nc1ncc(C(F)(F)F)c(NCCCN2CCCC2=O)n1] | L | 11 | 8.89 (brs, 1H), 8.08 (s, 1H), 7.83 (brs, 1H), 7.01 (brs, 1H), 3.97 (brs, 1H), 3.36 (m, 2H), 3.17 (brs, 3H), 2.83 (d, J = 11.2 Hz, 2H), 2.21 (m, 5H), 2.10 (brs, 2H), 2.02 (m, 2H), 1.87 (m, 8H), 1.68 (brs, 2H). | 481.4 |
| 105 | 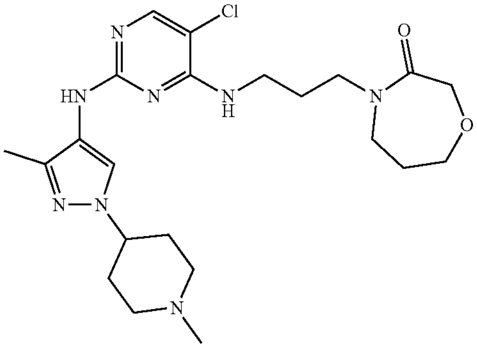 | K | 67 | 8.29 (brs, 1H), 8.14 (s, 1H), 7.82 (s, 1H), 7.80 (s, 1H), 7.01 (s, 1H), 4.11 (s, 2H), 3.99 (m, 1H), 3.74 (t, J = 5.6 Hz, 2H), 3.45-3.47 (m, 2H), 3.31-3.35 (m, 4H), 2.91 (d, J = 11.4 Hz, 2H), 2.53 (s, 3H), 2.27 (s, 3H), 2.17 (t, J = 11.8 Hz, 2H), 1.89-1.97 (m, 4H), 1.79 (brs, 2H), 1.70 (m, 2H). | 477.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 106 | 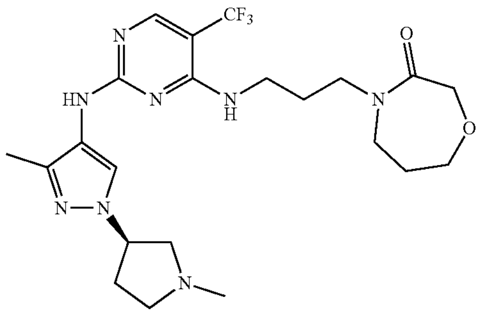 | L | 21 | 8.47 (brs, 1H), 8.08 (s, 1H), 7.85 (s, 1H), 6.72 (t, J = 5.2 Hz, 1H), 4.76 (brs, 1H), 4.12 (s, 2H), 3.75 (t, J = 5.6 Hz, 2H), 3.42 (m, 5H), 3.34 (t, J = 6.6 Hz, 2H), 2.78 (m, 3H), 2.30 (m, 4H), 2.12 (s, 3H), 2.05 (m, 1H), 1.84 (m, 2H), 1.74 (m, 2H). | 497.4 |
| 107 | 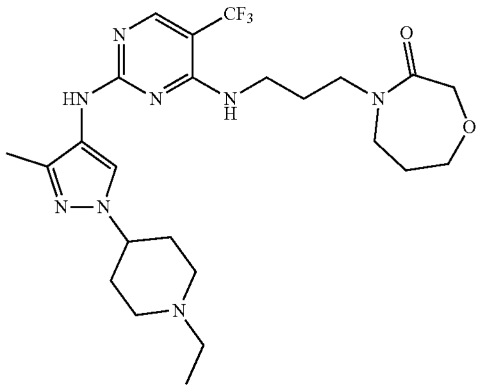 [SMILES: CCN1CCC(n2cc(Nc3ncc(C(F)(F)F)c(NCCCN4CCCOCC4=O)n3)c(C)n2)CC1] | L & M | 43 | 8.59 (s, 1H), 8.08 (s, 1H), 7.80 (s, 1H), 6.82 (s, 1H), 4.11 (s, 2H), 3.75 (t, J = 5.4 Hz, 2H), 3.4-3.5 (m, 8H), 3.33 (s, 2H), 3.06-3.15 (m, 1H), 2.55 (t, J = 7.0 Hz, 2H), 2.11 (s, 3H), 2.00 (m, 4H), 1.81 (m, 2H), 1.76 (m, 2H), 1.08 (t, J = 7.0 Hz, 3H). | 525.4 |
| 108 | 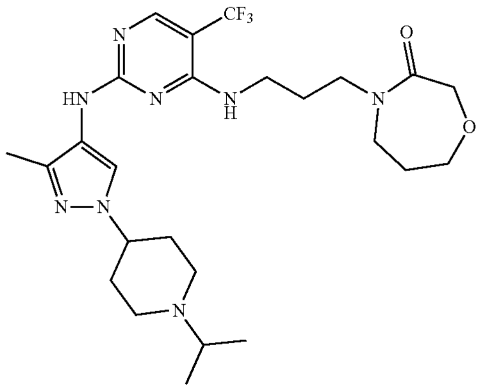 [SMILES: Cc1nn(C2CCN(C(C)C)CC2)cc1Nc1ncc(C(F)(F)F)c(NCCCN2CCCOCC2=O)n1] | L | 29 | 8.59 (brs, 1H), 8.07 (s, 1H), 7.80 (s, 1H), 6.82 (brm, 1H), 4.11 (s, 2H), 3.76 (t, J = 5.4 Hz, 2H), 3.4-3.5 (m, 6H), 3.2 (brm, 9H), 2.11 (s, 3H), 2.00 (m, 1H), 1.81 (m, 2H), 1.75 (m, 2H), 1.05 (brd, J = 7.0 Hz, 6H). | 539.4 |
| 109 | 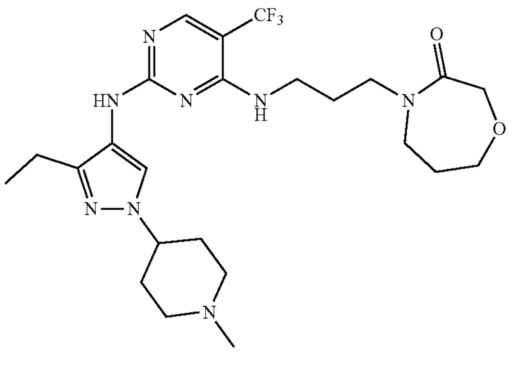 [SMILES: CCc1nn(C2CCN(C)CC2)cc1Nc1ncc(C(F)(F)F)c(NCCCN2CCCOCC2=O)n1] | L | 34 | 8.87 (brs, 1H), 8.19 (s, 1H), 8.08 (s, 1H), 7.83 (brs, 1H), 7.02 (brs, 1H), 4.10 (s, 2H), 4.00 (brm, 1H), 3.75 (t, J = 5.4 Hz, 2H), 3.3-3.5 (m, 6H), 2.87 (m, 2H), 2.54 (m, 1H), 2.21 (s, 3H), 2.06 (m, 2H), 1.5-2.0 (m, 8H), 1.10 (t, J = 6.8 Hz, 3H). | 525.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 110 | 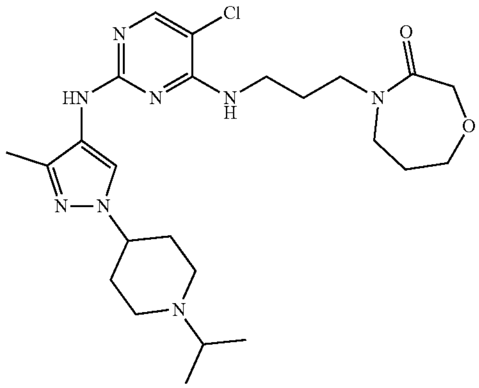 [SMILES: Cc1nn(C2CCN(C(C)C)CC2)cc1Nc1ncc(Cl)c(NCCCN2CCCOCC2=O)n1] | K | 75 | 10.4 (brs, 1H), 7.87 (s, 1H), 4.42 (brs, 1H), 4.10 (s, 2H), 3.75 (t, J = 5.4 Hz, 2H), 3.42-3.46 (m, 8H), 3.33 (s, 2H), 3.06-3.15 (m, 1H), 2.31-2.40 (m, 2H), 2.14-2.24 (m, 5H), 1.75-1.79 (m, 4H), 1.27 (d, J = 6.8 Hz, 6H). | 505.4 |
| 111 | 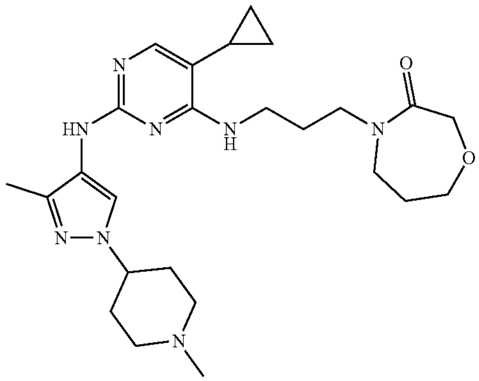 [SMILES: Cc1nn(C2CCN(C)CC2)cc1Nc1ncc(C2CC2)c(NCCCN2CCCOCC2=O)n1] | K | 19 | 10.4 (brs, 1H), 8.13 (s, 1H), 7.88 (s, 1H), 7.50 (brs, 1H), 4.31 (brm, 1H), 4.12 (s, 2H), 3.77 (t, J = 5.4 Hz, 2H), 3.3-3.5 (m, 8H), 3.06 (brm, 2H), 2.74 (brm, 4H), 2.17 (brm, 3H), 2.10 (s, 3H), 1.8 (m, 4H), 1.46 (m, 1H), 0.85 (m, 2H), 0.47 (m, 2H). | 483.4 |
| 112 | 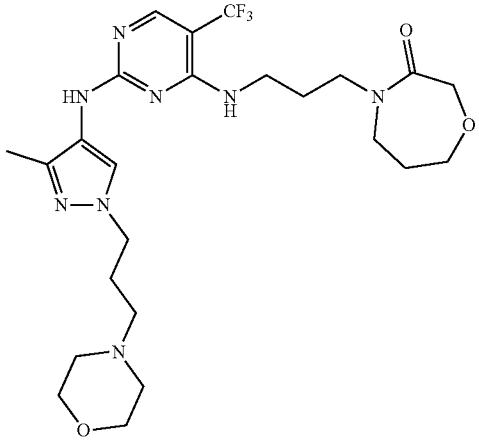 [SMILES: Cc1nn(CCCN2CCOCC2)cc1Nc1ncc(C(F)(F)F)c(NCCCN2CCCOCC2=O)n1] | L | 18 | 8.44 (brs, 1H), 8.07 (s, 1H), 7.74 (s, 1H), 6.71 (brs, 1H), 4.12 (s, 2H), 4.03 (t, J = 6.6 Hz, 2H), 3.76 (t, J = 5.6 Hz, 2H), 3.59 (brs, 4H), 3.42 (m, 4H), 3.35 (t, J = 6.8 Hz, 2H), 2.34 (m, 6H), 2.11 (s, 3H), 1.92 (m, 2H), 1.85 (m, 2H), 1.73 (m, 2H). | 541.5 |
| 113 | 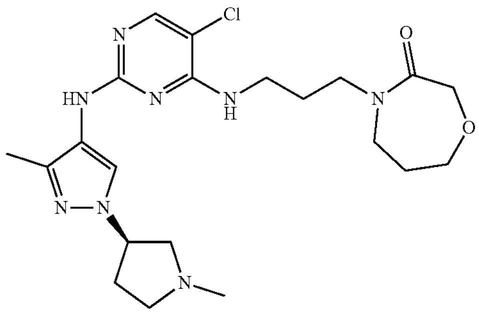 | K | 16 | 11.18 (brs, 1H), 9.22 (brs, 1H), 8.00 (s, 1H), 7.97 (s, 1H), 7.85 (brs, 1H), 5.19 (brs, 1H), 4.12 (s, 2H), 3.94 (m, 4H), 3.76 (t, J = 5.6 Hz, 2H), 3.48 (m, 2H), 3.43 (m, 2H), 3.35 (m, 2H), 2.91 (s, 3H), 2.36 (m, 2H), 2.17 (s, 3H), 1.85 (m, 2H), 1.79 (m, 2H). | 463.36 |

TABLE G-continued

| Exemplary Compounds that can be prepared by General Methods K through N. | | | | | |
|---|---|---|---|---|---|
| Example No. | Product | General Method | Yield (%) | $^1H$ NMR (400 MHz, DMSO-$d_6$): δ | LC-MS (m/z: M + $H^+$) |
| 114 | 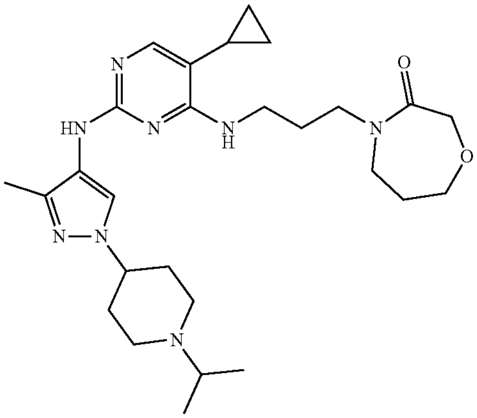 [SMILES: Cc1nn(C2CCN(C(C)C)CC2)cc1Nc1ncc(C2CC2)c(NCCCN2CCCOCC2=O)n1] | K | 76 | 10.2 (brs, 1H), 9.49 (s, 1H), 8.18 (s, 1H), 7.85 (s, 1H), 7.49 (s, 1H), 4.42 (brs, 1H), 4.13 (s, 2H), 3.77 (t, J = 5.6 Hz, 2H), 3.49 (m, 6H), 3.39 (t, J = 6.8 Hz, 2H), 3.32 (m, 1H), 3.08 (m, 2H), 2.39 (m, 2H), 2.28 (m, 2H), 2.14 (s, 3H), 1.84 (m, 4H), 1.56 (m, 1H), 1.32 (d, J = 6.6 Hz, 6H), 0.92 (m, 2H), 0.56 (m, 2H). | 511.5 |
| 115 | 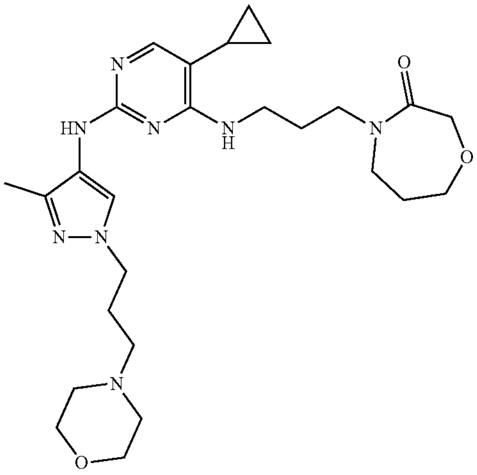 [SMILES: Cc1nn(CCCN2CCOCC2)cc1Nc1ncc(C2CC2)c(NCCCN2CCCOCC2=O)n1] | K | 63 | 11.6 (brs, 1H), 9.66 (s, 1H), 8.24 (s, 1H), 7.88 (s, 1H), 7.50 (s, 1H), 4.18 (t, J = 6.6 Hz, 2H), 4.13 (s, 2H), 3.88 (brs, 4H), 3.77 (t, J = 5.6 Hz, 2H), 3.50 (d, J = 7.0 Hz, 4H), 3.40 (t, J = 7.0 Hz, 2H), 3.19 (m, 2H), 3.05 (m, 4H), 2.25 (t, J = 7.4 Hz, 2H), 2.14 (s, 3H), 1.83 (m, 4H), 1.55 (m, 1H), 0.91 (m, 2H), 0.56 (m, 2H). | 513.5 |
| 116 | 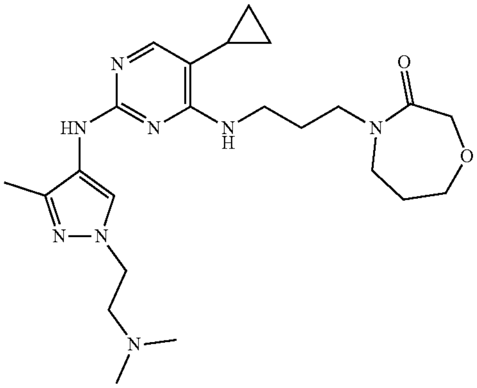 [SMILES: Cc1nn(CCN(C)C)cc1Nc1ncc(C2CC2)c(NCCCN2CCCOCC2=O)n1] | K | 43 | 9.71 (s, 1H), 8.22 (s, 1H), 7.95 (s, 1H), 7.44 (s, 1H), 4.51 (t, J = 6.0 Hz, 2H), 4.14 (s, 2H), 3.77 (t, J = 5.5 Hz, 2H), 3.53 (m, 6H), 3.41 (t, J = 6.8 Hz, 2H), 2.78 (s, 6H), 2.13 (s, 3H), 1.85 (m, 4H), 1.56 (m, 1H), 0.92 (m, 2H), 0.54 (m, 2H). | 457.4 |

TABLE G-continued

| Example No. | Product | General Method | Yield (%) | $^1$H NMR (400 MHz, DMSO-$d_6$): δ | LC-MS (m/z: M + H$^+$) |
|---|---|---|---|---|---|
| Exemplary Compounds that can be prepared by General Methods K through N. | | | | | |
| 117 | 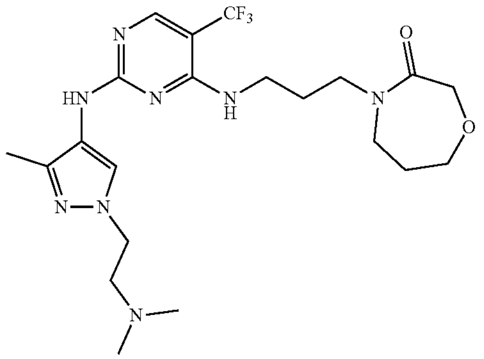 [SMILES: Cc1nn(CCN(C)C)cc1Nc1ncc(C(F)(F)F)c(NCCCN2CCCOCC2=O)n1] | L | 20 | 8.92 (brs, 1H), 8.08 (s, 1H), 7.83 (brs, 1H), 7.00 (brs, 1H), 4.11 (s, 4H), 3.75 (t, J = 5.2 Hz, 2H), 3.45 (m, 4H), 3.00 (m, 4H), 2.15 (m, 6H), 2.21 (s, 3H), 1.79 (m, 2H), 1.70 (m, 2H). | 485.4 |
| 118 | 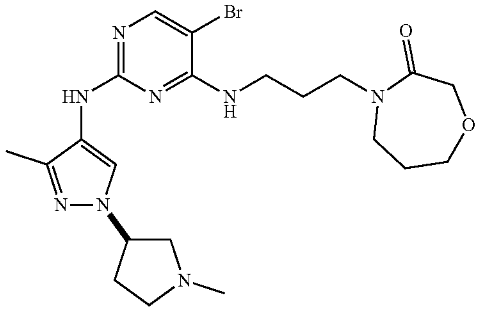 | K | 14 | 8.02 (brs, 1H), 7.90 (s, 1H), 7.83 (s, 1H), 6.63 (brs, 1H), 4.74 (brs, 1H), 4.12 (s, 2H), 3.75 (t, J = 5.4 Hz, 2H), 3.46 (m, 2H), 3.35 (m, 4H), 2.79 (m, 1H), 2.71 (m, 2H), 2.49 (m, 1H), 2.29 (s, 4H), 2.10 (s, 3H), 2.04 (m, 1H), 1.83 (m, 2H), 1.75 (m, 2H). | 507.2 |
| 119 | 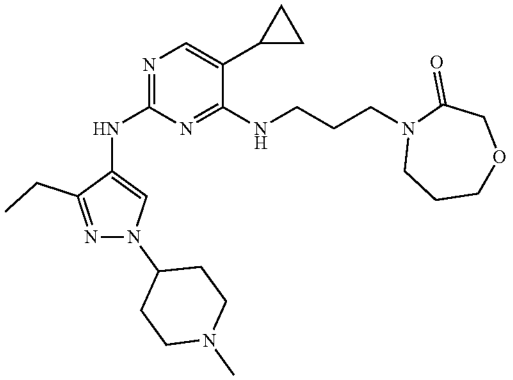 [SMILES: CCc1nn(C2CCN(C)CC2)cc1Nc1ncc(C2CC2)c(NCCCN2CCCOCC2=O)n1] | K | 46 | 12.2 (brs, 1H), 10.78 (brs, 1H), 9.68 (s, 1H), 8.28 (brs, 1H), 7.88 (s, 1H), 7.52 (s, 1H), 4.41 (brs, 1H), 4.12 (s, 2H), 3.76 (t, J = 5.4 Hz, 2H), 3.49 (m, 6H), 3.39 (t, J = 6.6 Hz, 2H), 3.16 (m, 2H), 2.77 (s, 3H), 2.56 (m, 2H), 2.30 (m, 4H), 1.84 (m, 4H), 1.55 (m, 1H), 1.16 (t, J = 7.4 Hz, 3H), 0.91 (m, 2H), 0.56 (m, 2H). | 497.3 |
| 120 | 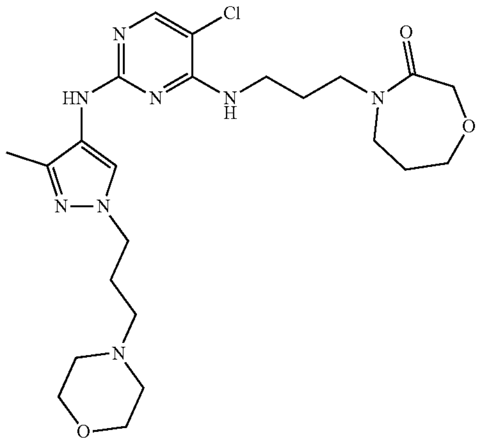 [SMILES: Cc1nn(CCCN2CCOCC2)cc1Nc1ncc(Cl)c(NCCCN2CCCOCC2=O)n1] | K | 11 | 9.80 (brs, 1H), 9.16 (brs, 1H), 7.98 (brs, 1H), 7.86 (s, 1H), 4.12 (s, 4H), 3.96 (m, 2H), 3.76 (t, J = 5.4 Hz, 2H), 3.62 (m, 2H), 3.41 (m, 8H), 3.10 (m, 4H), 2.16 (m, 2H), 2.12 (s, 3H), 1.79 (m, 2H), 1.74 (m, 2H). | 507.2 |

TABLE G-continued
| Exemplary Compounds that can be prepared by General Methods K through N. | | | | | |
|---|---|---|---|---|---|
| Example No. | Product | General Method | Yield (%) | $^1$H NMR (400 MHz, DMSO-$d_6$): δ | LC-MS (m/z: M + H$^+$) |
| 121 | 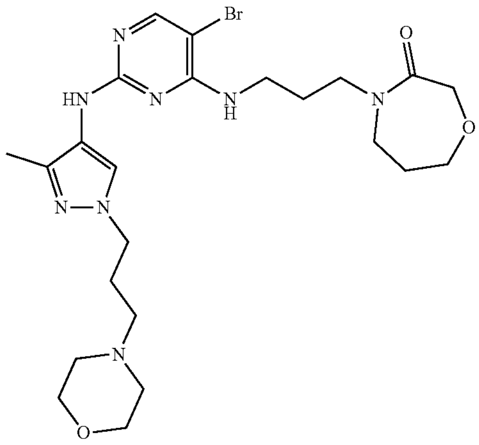 [SMILES: Cc1nn(CCCN2CCOCC2)cc1Nc1ncc(Br)c(NCCCN2CCCOCC2=O)n1] | K | 8 | 7.93 (brs, 1H), 7.88 (s, 1H), 7.71 (s, 1H), 6.58 (t, 1H), 4.12 (s, 2H), 4.00 (t, J = 6.8 Hz, 2H), 3.76 (t, J = 5.6 Hz, 2H), 3.57 (m, 4H), 3.46 (m, 2H), 3.37 (m, 4H), 2.34 (m, 4H), 2.28 (t, J = 7.0 Hz, 2H), 2.10 (s, 3H), 1.88 (m, 4H), 1.75 (t, J = 6.8 Hz, 2H). | 551.2 |
| 122 | 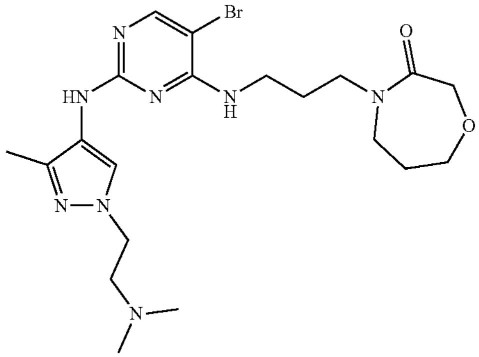 [SMILES: Cc1nn(CCN(C)C)cc1Nc1ncc(Br)c(NCCCN2CCCOCC2=O)n1] | K | 8 | 7.93 (s, 1H), 7.89 (s, 1H), 7.74 (s, 1H), 6.58 (brs, 1H), 4.12 (s, 2H), 4.05 (t, J = 6.6 Hz, 2H), 3.76 (t, J = 5.6 Hz, 2H), 3.46 (m, 2H), 3.37 (m, 4H), 2.63 (t, J = 6.6 Hz, 2H), 2.18 (s, 6H), 2.09 (s, 3H), 1.85 (m, 2H), 1.74 (m, 2H). | 495.2 |
| 123 | 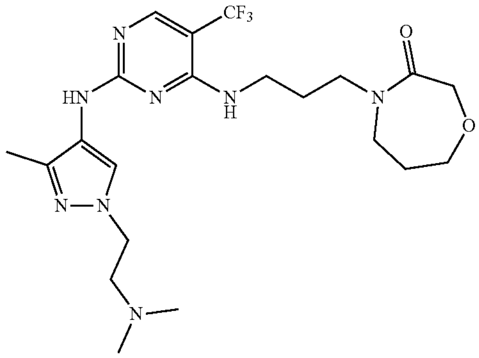 [SMILES: Cc1nn(CCN(C)C)cc1Nc1ncc(C(F)(F)F)c(NCCCN2CCCOCC2=O)n1] | K | 12 | 7.90 (s, 1H), 7.81 (s, 1H), 7.74 (s, 1H), 6.74 (brs, 1H), 4.12 (s, 2H), 4.05 (t, J = 6.6 Hz, 2H), 3.76 (t, J = 5.6 Hz, 2H), 3.45 (m, 2H), 3.37 (m, 4H), 2.63 (t, J = 6.6 Hz, 2H), 2.19 (s, 6H), 2.09 (s, 3H), 1.85 (m, 2H), 1.75 (m, 2H). | 451.4 |

TABLE G-continued

Exemplary Compounds that can be prepared by General Methods K through N.

| Example No. | Product | General Method | Yield (%) | $^1$H NMR (400 MHz, DMSO-d$_6$): δ | LC-MS (m/z: M + H$^+$) |
|---|---|---|---|---|---|
| 124 | 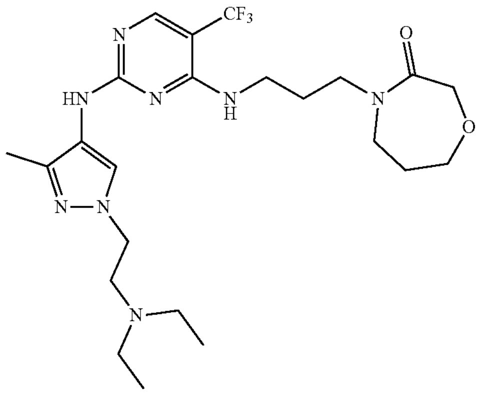 [SMILES: CCN(CC)CCn1cc(Nc2ncc(C(F)(F)F)c(NCCCN3CCCOCC3=O)n2)c(C)n1] | L | 39 | 10.5 (brs, 1H), 8.81 (brs, 1H), 8.12 (s, 1H), 7.93 (s, 1H), 6.95 (brs, 1H), 4.52 (t, J = 6.6 Hz, 2H), 4.19 (s, 2H), 3.76 (t, J = 5.6 Hz, 2H), 3.50 (m, 4H), 3.42 (m, 2H), 3.36 (m, 2H), 3.14 (m, 2H), 2.54 (m, 2H), 2.16 (s, 3H), 1.85 (m, 2H), 1.76 (t, J = 6.8 Hz, 2H), 1.23 (t, J = 7.2 Hz, 6H). | 513.46 |
| 125 | 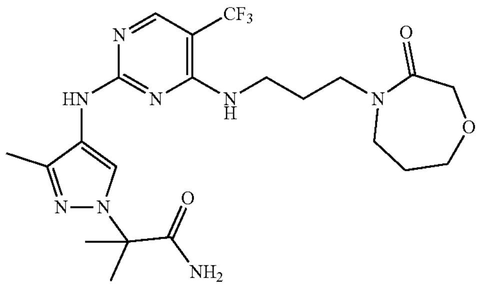 [SMILES: Cc1nn(C(C)(C)C(N)=O)cc1Nc1ncc(C(F)(F)F)c(NCCCN2CCCOCC2=O)n1] | L | 58 | 9.02 (s, 1H), 8.11 (s, 1H), 7.99 (s, 1H), 7.16 (s, 1H), 7.08 (brs, 1H), 6.64 (s, 1H), 4.11 (s, 2H), 3.74 (t, J = 5.4 Hz, 2H), 3.45 (brs, 2H), 3.29-3.38 (m, 4H), 2.15 (s, 3H), 1.79 (m, 2H), 1.60-1.69 (m, 8 H). | 499.2 |
| 126 | 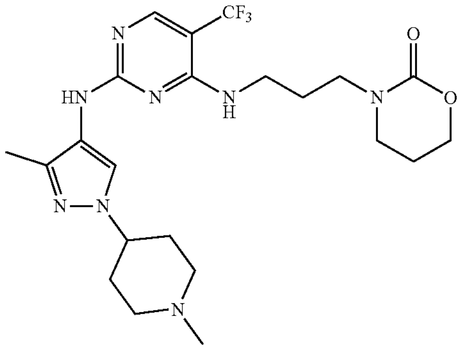 [SMILES: Cc1nn(C2CCN(C)CC2)cc1Nc1ncc(C(F)(F)F)c(NCCCN2CCCOC2=O)n1] | L | 64 | 8.86 (s, 1H), 8.04 (s, 1H), 7.47 (s, 1H), 6.89 (t, J = 5.8 Hz, 1H), 4.13 (t, J = 5.4 Hz, 2H), 3.91 (m, 1H), 3.11-3.28 (brm, 6H), 2.82 (d, J = 11.2 Hz, 2H), 2.18 (s, 3H), 2.00 (t, J = 11.4 Hz, 2H), 1.87 (m, 6H), 1.81 (s, 3H), 1.65 (brs, 2H). | 497.2 |
| 127 | 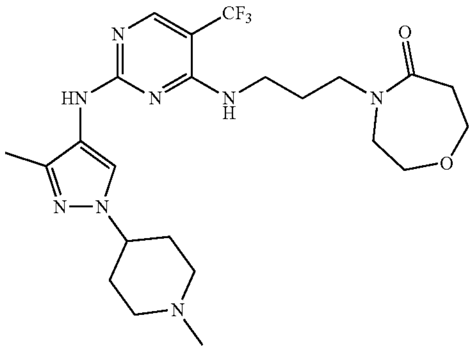 [SMILES: Cc1nn(C2CCN(C)CC2)cc1Nc1ncc(C(F)(F)F)c(NCCCN2CCOCCC2=O)n1] | L | 18 | 8.92 (brs, 1H), 8.15 (s, 1H), 8.08 (s, 1H), 7.84 (brs, 1H), 7.03 (brs, 1H), 3.98 (brm, 1H), 3.62 (brm, 3H), 3.2-3.5 (m, 8H), 2.86 (m, 2H), 2.60 (brm, 2H), 2.21 (s, 3H), 2.0-2.2 (m, 4H), 1.8-2.0 (m, 4H), 1.64 (m, 2H). | 511.4 |

TABLE G-continued

| Exemplary Compounds that can be prepared by General Methods K through N. | | | | | |
|---|---|---|---|---|---|
| Example No. | Product | General Method | Yield (%) | $^1$H NMR (400 MHz, DMSO-$d_6$): δ | LC-MS (m/z: M + H$^+$) |
| 128 | 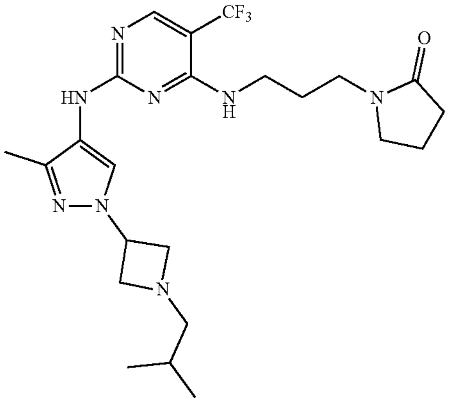 [SMILES: Cc1nn(C2CN(CC(C)C)C2)cc1Nc1ncc(C(F)(F)F)c(NCCCN2CCCC2=O)n1] | L | 19 | 8.81 (brs, 1H), 8.09 (s, 1H), 7.97 (brs, 1H), 7.01 (brs, 1H), 4.85 (brs, 1H), 3.64 (t, J = 6.8 Hz, 2H), 3.32 (m, 2H), 3.25 (m, 4H), 3.18 (m, 2H), 2.26 (d, J = 6.8 Hz, 2H), 2.21 (t, J = 7.6 Hz, 2H), 2.13 (s, 3H), 1.90 (m, 2H), 1.70 (t, J = 6.6 Hz, 2H), 1.54 (m, 1H), 0.85 (d, J = 6.6 Hz, 6H). | 495.4 |
| 129 | 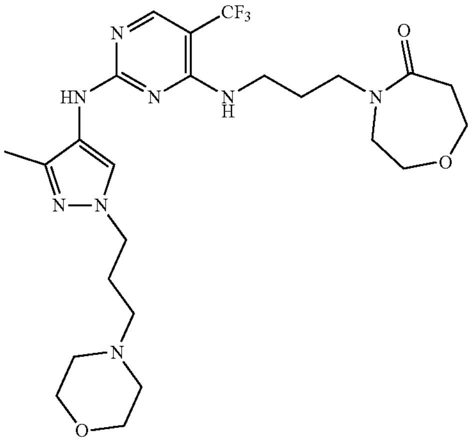 [SMILES: Cc1nn(CCCN2CCOCC2)cc1Nc1ncc(C(F)(F)F)c(NCCCN2CCOCCC2=O)n1] | L | 18 | 8.71 (brs, 1H), 8.08 (s, 1H), 7.77 (s, 1H), 6.99 (brs, 1H), 4.01 (brs, 2H), 3.63 (brs, 4H), 3.55 (brs, 4H), 3.43 (brs, 2H), 3.35 (m, 4H), 2.63 (t, J = 4.2 Hz, 2H), 2.30 (brs, 4H), 2.22 (t, J = 6.7 Hz, 2H), 2.10 (s, 3H), 1.87 (t, J = 6.6 Hz, 2H), 1.65 (t, J = 5.8 Hz, 2H). | 541.5 |
| 130 | 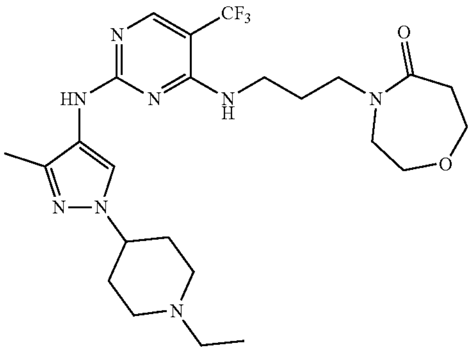 [SMILES: CCN1CCC(n2cc(Nc3ncc(C(F)(F)F)c(NCCCN4CCOCCC4=O)n3)c(C)n2)CC1] | L & M | 59 | 8.38-8.93 (brm, 1H), 8.08 (s, 1H), 7.83 (s, 1H), 7.01 (brs, 1H), 3.99 (brs, 1H), 3.62 (s, 4H), 3.32-3.48 (brm, 6H), 2.94 (brs, 2H), 2.58-2.65 (m, 2H), 2.29-2.43 (m, 2H), 2.09 (s, 3H), 1.77-2.05 (m, 6H), 1.59-1.70 (m, 2H), 1.00 (t, J = 7.0 Hz, 3H). | 525.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 131 | 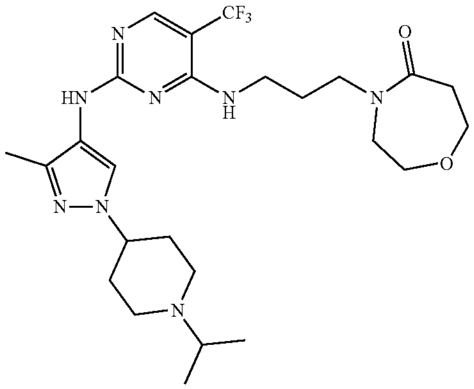 [SMILES: Cc1nn(C2CCN(C(C)C)CC2)cc1Nc1ncc(C(F)(F)F)c(NCCCN2CCOCCC2=O)n1] | L | 58 | 8.95 (s, 1H), 8.11 (s, 1H), 7.86 (s, 1H), 7.04 (s, 1H), 3.65 (brs, 4H), 3.35-3.51 (m, 5H), 2.65 (m, 3H), 2.01-2.34 (brm, 8H), 1.68 (m, 2H), 0.75-1.32 (brm, 7H) [spectrum extremely poor - not correct # of protons] | 539.4 |
| 132 | 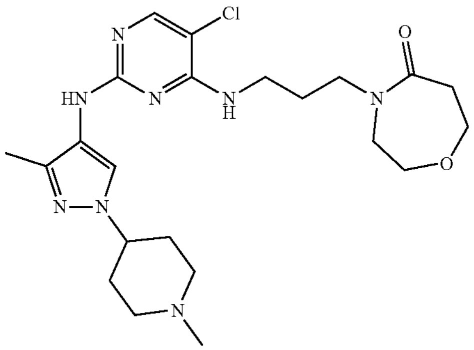 [SMILES: Cc1nn(C2CCN(C)CC2)cc1Nc1ncc(Cl)c(NCCCN2CCOCCC2=O)n1] | K | 13 | 8.16 (s, 1H), 7.82 (s, 1H), 7.79 (brs, 1H), 7.02 (m, 1H), 3.91-4.00 (m, 1H), 3.58-3.65 (m, 4H), 3.30-3.45 (m, 4H), 2.81-2.87 (m, 2H), 2.59-2.64 (m, 2H), 2.19 (s, 3H), 2.08 (s, 3H), 1.98-2.11 (m, 2H), 1.82-1.95 (m, 4H), 1.62-1.73 (m, 2H). | 477.4 |
| 133 | 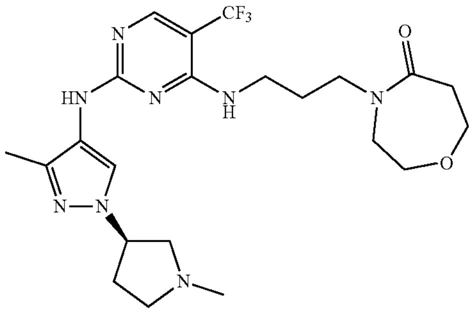 [SMILES: Cc1nn([C@@H]2CCN(C)C2)cc1Nc1ncc(C(F)(F)F)c(NCCCN2CCOCCC2=O)n1] | L | 10 | 8.47 (brs, 1H), 8.08 (s, 1H), 7.85 (s, 1H), 6.73 (brs, 1H), 4.77 (brs, 1H), 3.64 (d, J = 3.6 Hz, 4H), 3.42 (m, 4H), 3.34 (t, J = 6.5 Hz, 2H), 2.81 (m, 3H), 2.63 (t, J = 4.6 Hz, 2H), 2.32 (s, 5H), 2.12 (s, 3H), 2.06 (m, 1H), 1.70 (t, J = 6.4 Hz, 2H). | 497.4 |
| 134 | 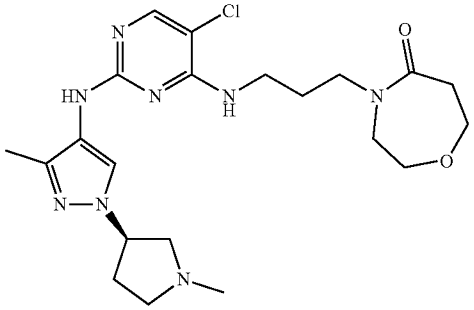 | K | 44 | 11.0 (brs, 1H), 10.4 (brs, 1H), 9.77 (brs, 1H), 8.39 (brs, 1H), 8.04 (s, 1H), 8.00 (s, 1H), 5.19 (brs, 1H), 3.63 (m, 4H), 3.47 (m, 6H), 3.34 (m, 2H), 2.93 (m, 2H), 2.86 (m, 2H), 2.64 (m, 3H), 2.32 (m, 2H), 2.15 (s, 3H), 1.73 (m, 2H). | 463.3 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 135 | 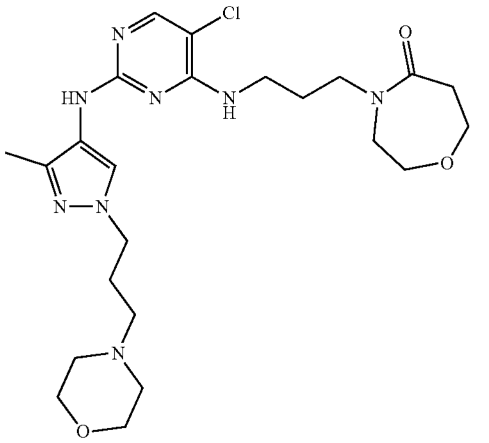 [SMILES: Cc1nn(CCCN2CCOCC2)cc1Nc1ncc(Cl)c(NCCCN2CCOCCC2=O)n1] | K | 58 | 10.81 (brs, 1H), 9.73 (brs, 1H), 8.23 (brs, 1H), 7.89 (s, 1H), 4.15 (m, 2H), 3.93 (m, 2H), 3.76 (m, 2H), 3.63 (brs, 4H), 3.40 (m, 2H), 3.35 (m, 4H) 3.12 (m, 4H) 2.64 (m, 2H), 2.54 (m, 2H), 2.21 (t, J = 7.4 Hz, 2H), 2.15 (s, 3H), 1.73 (t, J = 6.8 Hz, 2H). | 507.4 |
| 136 | 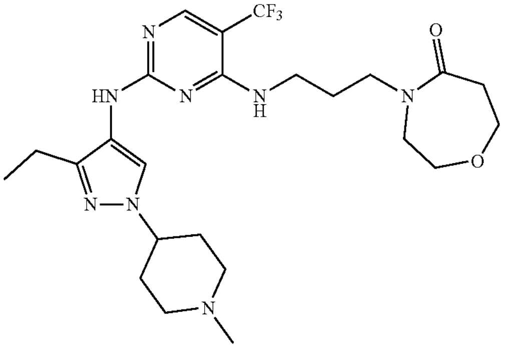 [SMILES: CCc1nn(C2CCN(C)CC2)cc1Nc1ncc(C(F)(F)F)c(NCCCN2CCOCCC2=O)n1] | L | 27 | 8.36-8.91 (brm, 1H), 8.15 (s, 1H), 8.07 (s, 1H), 7.68-7.88 (m, 1H), 6.84-7.06 (m, 1H), 3.99 (brs, 1H), 3.62 (s, 4H), 3.23-3.51 (brm, 6H), 2.86 (d, J = 11.2 Hz, 2H), 2.62 (s, 2H), 2.54 (m, 2H), 2.22 (s, 3H), 2.09 (t, J = 11.6 Hz, 2H), 1.96 (m, 2H), 1.87 (q, J = 12.0 Hz, 2H), 1.63 (brs, 2H), 1.09 (t, J = 7.6 Hz, 3H). | 525.4 |
| 137 | 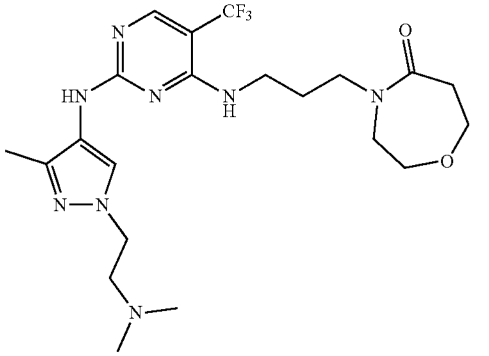 [SMILES: Cc1nn(CCN(C)C)cc1Nc1ncc(C(F)(F)F)c(NCCCN2CCOCCC2=O)n1] | L | 23 | 8.46 (brs, 1H), 8.08 (s, 1H), 7.78 (s, 1H), 6.72 (t, 1H), 4.12 (t, J = 6.6 Hz, 2H), 3.64 (m, 4H), 3.42 (m, 4H), 3.34 (t, J = 6.6 Hz, 2H), 2.77 (m, 2H), 2.64 (t, J = 4.9 Hz, 2H), 2.28 (m, 6H), 2.12 (s, 3H), 1.71 (m, 2H). | 485.4 |
| 138 | 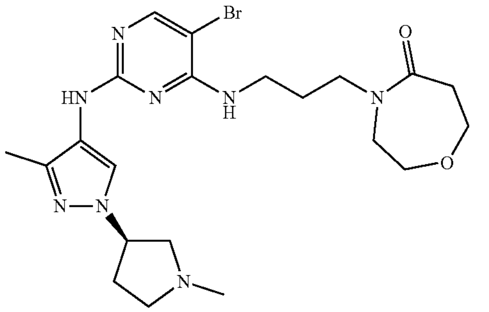 [SMILES: Cc1nn([C@@H]2CCN(C)C2)cc1Nc1ncc(Br)c(NCCCN2CCOCCC2=O)n1] | K | 9 | 7.98 (brs, 1H), 7.90 (s, 1H), 7.83 (s, 1H), 6.61 (m, 1H), 4.79 (brs, 1H), 3.65 (m, 4H), 3.45 (m, 2H), 3.38 (m, 4H), 2.92 (m, 1H), 2.85 (m, 2H), 2.64 (m, 3H), 2.38 (s, 3H), 2.33 (m, 1H), 2.11 (s, 3H), 2.07 (m, 1H), 1.72 (m, 2H). | 507.4 509.4 |

TABLE G-continued

| Example No. | Product | General Method | Yield (%) | $^1H$ NMR (400 MHz, DMSO-$d_6$): δ | LC-MS (m/z: M + $H^+$) |
|---|---|---|---|---|---|
| | Exemplary Compounds that can be prepared by General Methods K through N. | | | | |
| 139 | 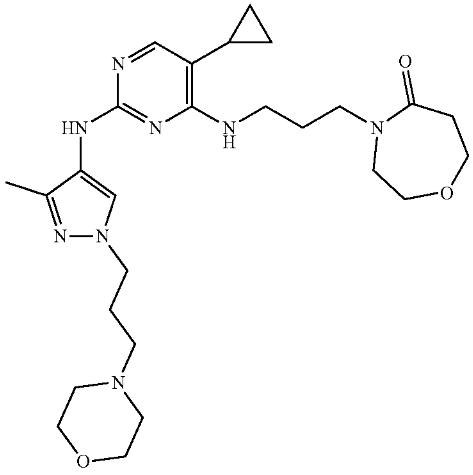 [SMILES: Cc1nn(CCCN2CCOCC2)cc1Nc1ncc(C2CC2)c(NCCCN2CCOCCC2=O)n1] | K | 68 | 11.9 (brs, 1H), 10.94 (brs, 1H), 9.77 (brs, 1H), 8.44 (brs, 1H), 7.90 (s, 1H), 7.37 (brs, 1H), 4.16 (brs, 2H), 3.93 (m, 2H), 3.78 (m, 2H), 3.64 (brs, 4H), 3.48 (brs, 4H), 3.38 (m, 4H), 3.08 (brs, 4H), 2.64 (m, 2H), 2.22 (m ,2H), 2.12 (s, 3H), 1.75 (t, J = 6.6 Hz, 2H), 1.52 (m, 1H), 0.89 (m, 2H), 0.54 (m, 2H). | 513.3 |
| 140 | 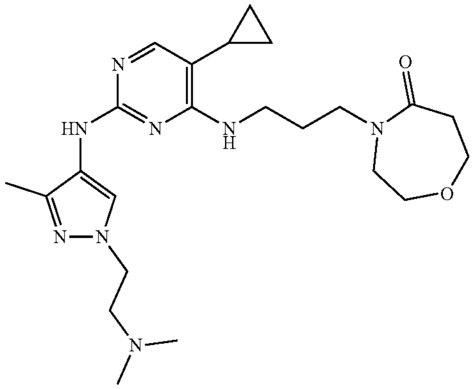 [SMILES: Cc1nn(CCN(C)C)cc1Nc1ncc(C2CC2)c(NCCCN2CCOCCC2=O)n1] | K | 22 | 7.93 (brs, 1H), 7.81 (s, 1H), 7.52 (s, 1H), 6.68 (t, J = 5.6 Hz, 1H), 4.05 (t, J = 6.6 Hz 2H), 3.63 (m, 4H), 3.47 (m, 2H), 3.38 (m, 4H), 2.61 (m, 4H), 2.16 (s, 6H), 2.08 (s, 3H), 1.68 (t, J = 6.4 Hz, 2H), 1.42 (m, 1H), 0.80 (m, 2H), 0.42 (m, 2H). | 457.3 |
| 141 | 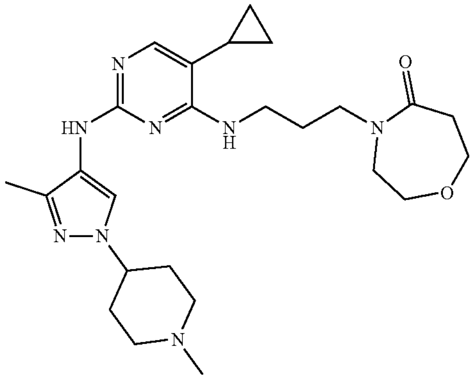 [SMILES: Cc1nn(C2CCN(C)CC2)cc1Nc1ncc(C2CC2)c(NCCCN2CCOCCC2=O)n1] | K | 77 | 10.7 (brs, 1H), 9.80 (brs, 1H), 8.44 (brs, 1H), 8.01 (s, 1H), 7.89 (s, 1H), 4.37 (brs, 1H), 3.63 (s, 4H), 3.47 (brm, 4H), (3.30 brs, 3H): 3.10 (brs, 2H), 2.75 (s, 3H), 2.63 (s, 3H), 2.22-2.26 (m, 5H), 2.12 (brs, 2H), 1.76 (t, J = 7.6 Hz, 2H), 1.51 (s, 1H), 0.89 (d, J = 7.8 Hz, 2H), 0.54 (d, J = 5.2 Hz, 2H). | 483.4 |

TABLE G-continued

| Exemplary Compounds that can be prepared by General Methods K through N. | | | | | |
|---|---|---|---|---|---|
| Example No. | Product | General Method | Yield (%) | $^1$H NMR (400 MHz, DMSO-$d_6$): δ | LC-MS (m/z: M + H$^+$) |
| 142 | 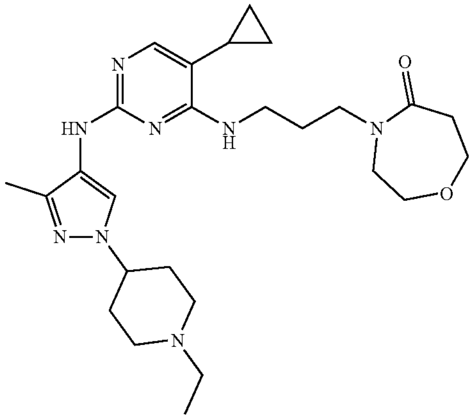 [SMILES: CCN1CCC(n2cc(Nc3ncc(C4CC4)c(NCCCN4CCOCCC4=O)n3)c(C)n2)CC1] | K & M | 59 | 10.7 (brs, 1H), 9.91 (brs, 1H), 8.46 (s, 1H), 8.02 (s, 1H), 7.92 (s, 1H), 4.42 (brs, 1H), 3.65 (s, 4H), 3.58 (m, 2H), 3.49 (s, 4H), 3.38 (brm, 5H), 3.11-3.05 (brm, 4H), 2.65 (s, 3H), 2.30-2.37 (m, 2H), 2.25 (brm, 2H), 2.05 (brm, 2H), 1.79 (m, 2H), 1.54 (s, 1H), 1.25 (t, J = 7.2 Hz, 2H), 0.89 (m, 2H), 0.57 (m, 2H). | 497.4 |
| 143 | 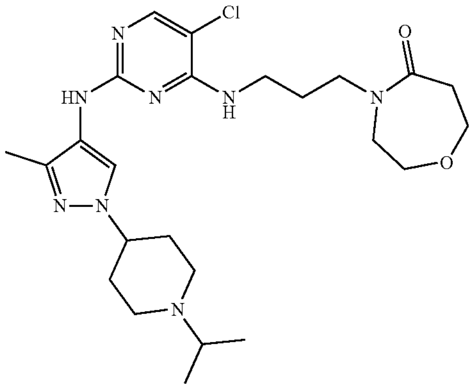 [SMILES: Cc1nn(C2CCN(C(C)C)CC2)cc1Nc1ncc(Cl)c(NCCCN2CCOCCC2=O)n1] | K | 38 | 8.28 (brs, 1H), 8.16 (s, 1H), 7.81 (s, 1H), 7.79 (brs, 1H), 7.01 (brm, 1H), 4.01 (m, 1H), 3.62 (m, 4H), 3.44 (m, 2H), 3.33 (m, 4H), 2.94 (m, 2H), 2.85 (m, 1H), 2.62 (m, 2H), 2.37 (m, 2H), 2.08 (s, 3H), 1.99 (m, 2H), 1.85 (m, 2H), 1.66 (m, 2H), 1.01 (d, J = 6.6 Hz, 6H). | 505.2 |
| 144 | 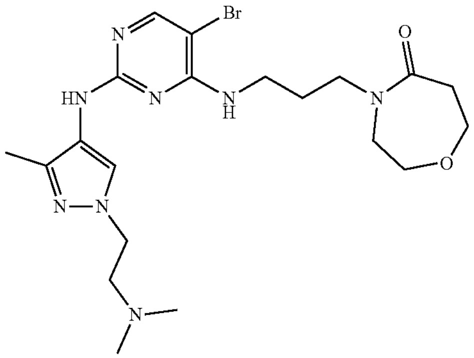 [SMILES: Cc1nn(CCN(C)C)cc1Nc1ncc(Br)c(NCCCN2CCOCCC2=O)n1] | K | 22 | 7.92 (s, 1H), 7.89 (s, 1H), 7.73 (s, 1H), 6.58 (t, J = 8.2 Hz, 1H), 4.05 (t, J = 6.6 Hz, 2H), 3.64 (m, 4H), 3.45 (m, 2H), 3.37 (m, 4H), 2.63 (m, 4H), 2.18 (s, 6H), 2.09 (s, 3H), 1.72 (m, 2H). | 495.2 |
| 145 | 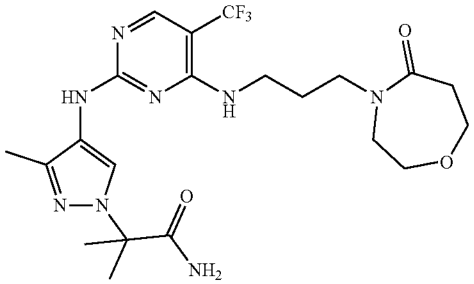 [SMILES: Cc1nn(C(C)(C)C(N)=O)cc1Nc1ncc(C(F)(F)F)c(NCCCN2CCOCCC2=O)n1] | L | 58 | 9.00 (s, 1H), 8.10 (s, 1H), 7.98 (s, 1H), 7.15 (s, 1H), 7.05 (s, 1H), 6.63 (s, 1H), 3.62 (s, 4H), 3.44 (brs, 2H), 3.37 (brs, 2H), 3.30 (s, 2H), 2.62 (brs, 2H), 2.15 (s, 3H), 1.62-1.65 (m, 8H). | 499.2 |

TABLE G-continued
Exemplary Compounds that can be prepared by General Methods K through N.
| Example No. | Product | General Method | Yield (%) | $^1H$ NMR (400 MHz, DMSO-$d_6$): δ | LC-MS (m/z: M + H$^+$) |
|---|---|---|---|---|---|
| 146 | 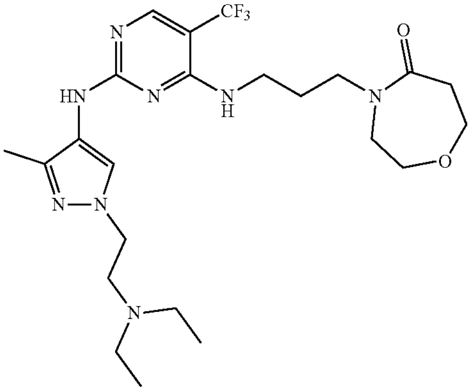 [SMILES: CCN(CC)CCn1cc(Nc2ncc(C(F)(F)F)c(NCCCN3CCOCCC3=O)n2)c(C)n1] | L | 24 | 8.91 (brs, 1H), 8.08 (s, 1H), 7.82 (s, 1H), 7.01 (brs, 1H), 4.03 (brs, 2H), 3.62 (brs, 4H), 3.40 (m, 4H), 2.74 (m, 2H), 2.64 (m, 2H), 2.50 (m, 6H), 2.10 (s, 3H), 1.65 (m, 2H), 0.92 (t, J = 7.0 Hz, 6H). | 513.49 |
| 147 | 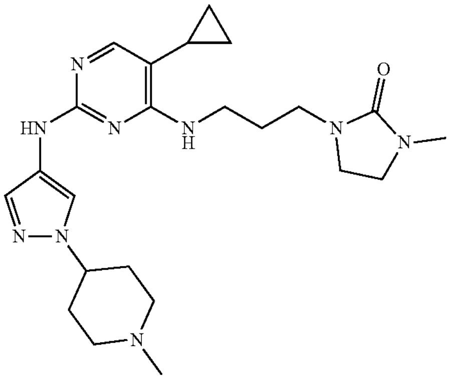 [SMILES: CN1CCC(n2cc(Nc3ncc(C4CC4)c(NCCCN4CCN(C)C4=O)n3)cn2)CC1] | K | | 10.8 (brs, 1H), 8.53 (s, 1H), 7.93 (s, 1H), 7.63 (s, 1H), 7.54 (brs, 1H,), 4.46 (t, J = 10.8 Hz, 1H), 3.51 (d, J = 9.6 Hz, 5H), 3.09-3.27 (m, 8H), 2.76 (dd, J = 10.8 and 4.5 Hz, 3H), 2.61 (s, 3H), 2.25 (m, 4H), 1.81 (m, 2H), 1.52 (t, J = 7.0 Hz, 1H), 0.87 (m, 2H), 0.53 (m, 2H). | 454.4 |
| 148 | 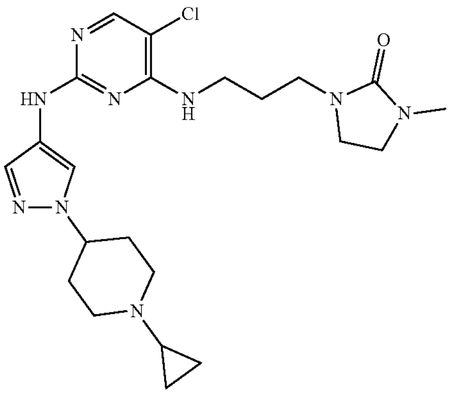 [SMILES: CN1CCN(CCCNc2nc(Nc3cnn(C4CCN(C5CC5)CC4)c3)ncc2Cl)C1=O] | K | 61 | 10.8 (brs, 1H), 10.3 (brs, 1H), 8.57 (brs, 1H), 8.12 (brs, 1H), 7.92 (s, 1H), 7.61 (brm, 1H), 4.49 (m, 1H), 3.61 (brm, 2H), 3.55 (s, 3H), 3.47 (m, 2H), 3.15-3.4 (m, 4H), 3.11 (m, 2H), 2.79 (m, 1H), 2.36 (s, 2H), 2.23 (m, 2H), 2.21 (m, 2H), 1.88 (m, 2H), 1.15 (m, 2H), 0.81 (brm, 2H). | 474.4 |

TABLE G-continued
Exemplary Compounds that can be prepared by General Methods K through N.
| Example No. | Product | General Method | Yield (%) | $^1$H NMR (400 MHz, DMSO-d$_6$): δ | LC-MS (m/z: M + H$^+$) |
|---|---|---|---|---|---|
| 149 | 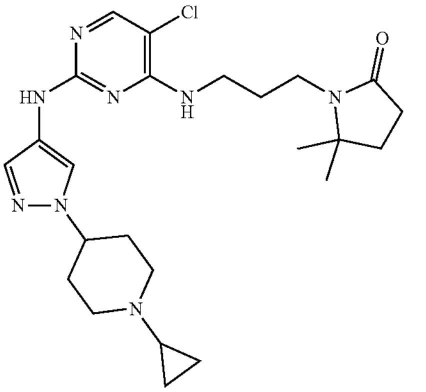 [SMILES: CC1(C)CCC(=O)N1CCCNc1nc(Nc2cnn(C3CCN(C4CC4)CC3)c2)ncc1Cl] | K | 10 | 9.00 (brs, 1H), 8.21 (s, 1H), 7.84 (s, 1H), 7.80 (s, 1H), 7.45 (s, 1H), 7.16 (brm, 1H), 4.08 (m, 1H), 3.41 (m, 2H), 3.15 (m, 2H), 2.98 (m, 2H), 2.28 (m, 4H), 1.95 (m, 2H), 1.76 (m, 4H), 1.62 (m, 1H), 1.16 (s, 6H), 1.15 (m, 2H), 0.42 (m, 2H), 0.28 (m, 2H). | 488.4 |
| 150 | 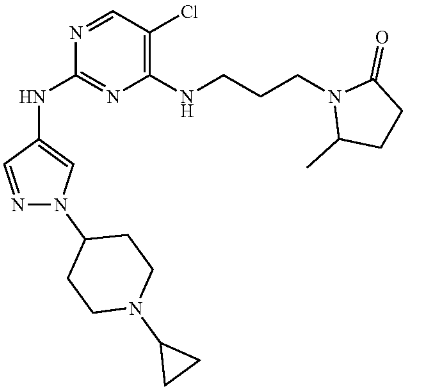 [SMILES: CC1CCC(=O)N1CCCNc1nc(Nc2cnn(C3CCN(C4CC4)CC3)c2)ncc1Cl] | K | 41 | 9.00 (brs, 1H), 8.25 (s, 1H), 7.84 s, (s, 1H), 7.83 (s, 1H), 7.44 (s, 1H), 7.06 (brm, 1H), 4.10 (s, 1H), 3.02 (m, 4H), 2.0-2.5 (m, 9H), 1.95 (m, 3H), 1.76 (m, 2H), 1.62 (m, 1H), 1.45 (m, 1H), 1.13 (s, 3H), 1.43 (m, 2H), 0.27 (m, 2H). | 473.4 |
| 151 | 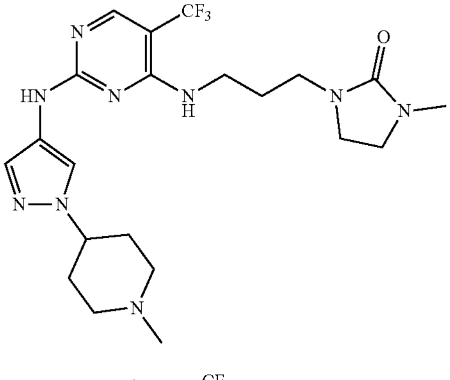 | L | 41 | 9.52 (s, 1H), 8.14 (s, 1H, ), 8.13 (s, 1H), 7.82 (s, 1H), 7.52 (brs, 1H), 7.07 (brm, 1H), 4.08 (m, 1H), 3.44 (brm, 2H), 3.22 (s, 4H), 3.12 (m, 2H), 2.88 (m, 2H), 2.62 (s, 3H), 2.23 (s, 3H), 2.15 (m, 2H), 1.98 (m, 2H), 1.88 (m, 2H), 1.74 (brm, 2H). | 482.4 |
| 152 | 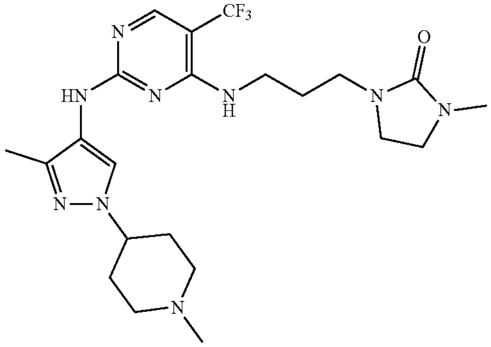 | L | 32 | 8.88 (brs, 1H), 8.07 (s, 1H), 7.83 (s, 1H), 7.00 (brm, 1H), 3.95 (m, 1H), 3.20 (brm, 7H), 3.05 (brm, 2H), 2.83 (m, 2H), 2.62 (s, 3H), 2.18 (s, 3H), 1.5-2.1 (m, 10H). | 496.4 |

TABLE G-continued
Exemplary Compounds that can be prepared by General Methods K through N.
| Example No. | Product | General Method | Yield (%) | $^1$H NMR (400 MHz, DMSO-$d_6$): δ | LC-MS (m/z: M + H$^+$) |
|---|---|---|---|---|---|
| 153 | 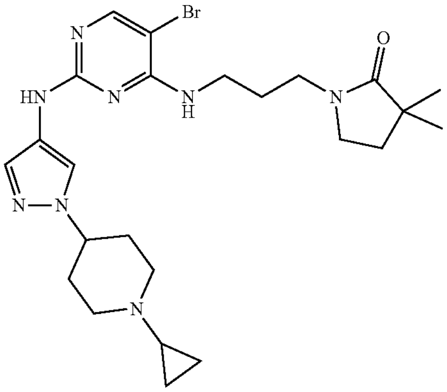 [SMILES: CC1(C)CCN(CCCNc2nc(Nc3cnn(C4CCN(C5CC5)CC4)c3)ncc2Br)C1=O] | K | 23 | 11.1 (brs, 1H), 8.54 (brs, 1H), 8.24 (brs, 1H), 7.91 (s, 1H), 7.62 (s, 1H), 4.45-4.55 (brm, 1H), 3.58 (d, J = 12.0 Hz, 2H), 3.36-3.49 (brm, 2H), 3.19-3.33 (brm, 6H), 2.77 (brm, 1H), 2.34-2.42 (m, 2H), 2.22 (d, J = 13.0 Hz, 2H), 1.74-1.81 (m, 4H), 1.16 (m, 2H), 1.00 (s, 6H), 0.78 (t, J = 7.2 Hz, 2H). | 531.4 533.4 |
| 154 | 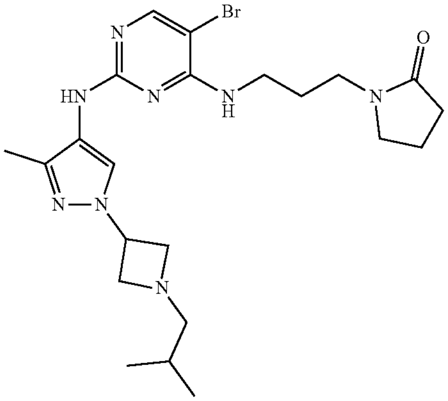 [SMILES: Cc1nn(C2CN(CC(C)C)C2)cc1Nc1ncc(Br)c(NCCCN2CCCC2=O)n1] | K | 9 | 8.38 (brs, 1H), 7.91 (s, 2H), 6.85 (t, J = 6.28 Hz, 1H), 4.83 (m, 1H), 3.29 (m, 5H), 3.20 (m, 5H), 2.23 (m, 2H), 2.21 (m, 2H), 2.11 (s, 3H), 1.90 (t, J = 7.4 Hz, 2H), 1.71 (m, 2H), 1.54 (m, 1H), 0.85 (d, J = 6.6 Hz, 6H). | 505.4 |
| 155 | 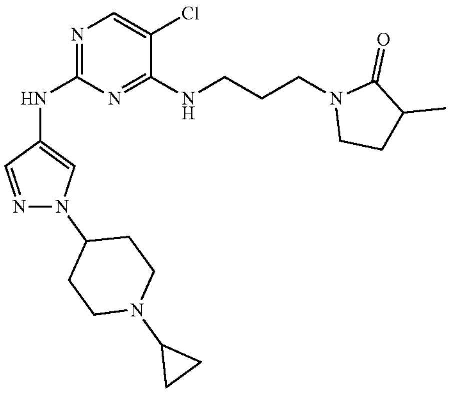 [SMILES: CC1CCN(CCCNc2nc(Nc3cnn(C4CCN(C5CC5)CC4)c3)ncc2Cl)C1=O] | K | 63 | 11.0 (brs, 1H), 10.6 (brs, 1H), 8.73 (brs, 1H), 8.18 (brs, 1H), 7.92 (s, 1H), 7.62 (s, 1H), 4.50 (m, 1H), 3.59 (d, J = 12.2 Hz, 2H), 3.43 (m, 2H), 3.20-3.37 (m, 6H), 2.77 (m, 1H), 2.35 (m, 3H), 2.10-2.23 (m, 3H), 1.76-1.86 (m, 2H), 1.44-1.52 (m, 1H), 1.14 (m, 2H), 1.01 (d, J = 7.0 Hz, 3H), 0.79 (m, 2H). | 473.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 156 | 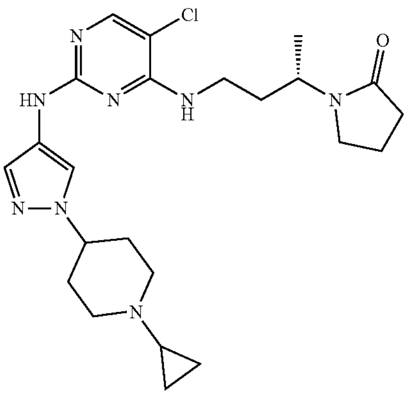 [SMILES: C[C@@H](CCNc1nc(Nc2cnn(C3CCN(C4CC4)CC3)c2)ncc1Cl)N1CCCC1=O] | K | 41 | 8.99 (brs, 1H), 8.13 (s, 1H), 7.84 (s, 1H), 7.79 (s, 1H), 7.44 (s, 1H), 6.96 (brs, 1H), 4.09 (m, 2H), 3.1-3.5 (m, 4H), 3.01 (m, 2H), 2.34 (m, 2H), 2.25 (m, 2H), 1.87-1.95 (m, 4H), 1.69 (m, 5H), 1.08 (d, J = 6.8 Hz, 3H), 0.42 (m, 2H), 0.29 (m, 2H). | 473.4 |
| 157 | 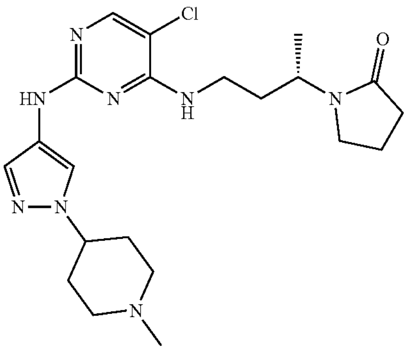 [SMILES: C[C@@H](CCNc1nc(Nc2cnn(C3CCN(C)CC3)c2)ncc1Cl)N1CCCC1=O] | K | 44 | 9.00 (brs, 1H), 8.16 (s, 1H), 7.84 (s, 1H), 7.80 (s, 1H), 7.46 (s, 1H), 6.95 (brs, 1H), 4.10 (m, 2H), 3.37 (m, 1H), 3.26 (m 3H), 2.94 (d, J = 11.4 Hz, 2H), 2.28 (s, 3H), 2.18 (m, 4H), 1.87-2.00 (m, 6H), 1.72 (m, 2H), 1.08 (d, J = 6.8 Hz, 3H). | 447.4 |
| 158 | 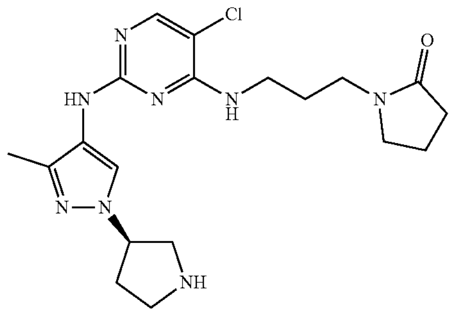 | K | 50 | 9.55 (brs, 2H), 9.32 (brs, 1H), 8.14 (brs, 1H), 8.04 (s, 1H), 7.97 (s, 1H), 5.11 (m, 1H), 3.55 (m, 2H), 3.44 (d, J = 5.8 Hz, 2H), 3.34 (t, J = 7.0 Hz, 2H), 3.23 (t, J = 6.8 Hz, 2H), 2.41 (m, 4H), 2.22 (t, J = 7.9 Hz, 2H), 2.16 (s, 3H), 1.93 (m, 2H), 1.81 (m, 2H). | 419.5 |
| 159 | 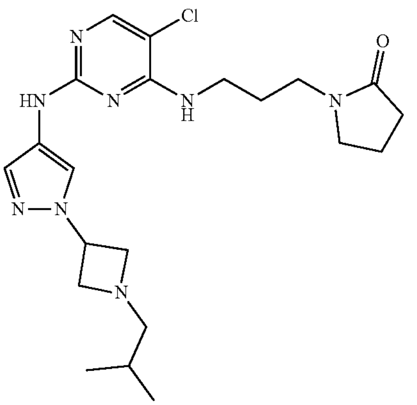 | K | 21 | 9.08 (brs, 1H), 7.92 (s, 1H), 7.86 (s, 1H), 7.52 (s, 1H), 7.04 (s, 1H), 4.95 (brs, 1H), 3.65 (m, 2H), 3.38 (m, 2H), 3.34 (m, 2H), 3.24 (t, J = 6.8 Hz, 2H), 2.30 (m, 1H), 2.22 (t, J = 7.8 Hz, 3H), 1.92 (m, 2H), 1.76 (m, 3H), 1.57 (m, 1H), 1.21 (m, 1H), 0.86 (d, J = 6.6 Hz, 6H). | 447.3 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 160 | 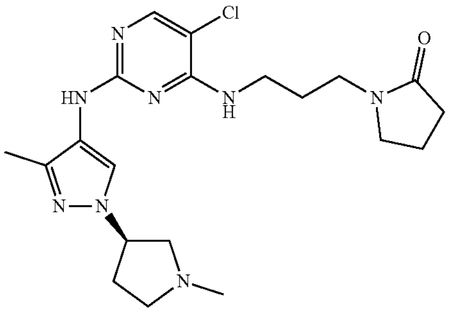 [SMILES: Cc1nn([C@@H]2CCN(C)C2)cc1Nc1ncc(Cl)c(NCCCN2CCCC2=O)n1] | K | 11 | 7.94 (s, 1H), 7.82 (s, 2H), 6.73 (t, J = 5.6 Hz, 1H), 4.73 (m, 1H), 3.37 (m, 2H), 3.32 (m, 2H), 3.21 (t, J = 6.8 Hz, 2H), 2.71 (m, 1H), 2.46 (m, 1H), 2.28 (m, 1H), 2.29 (s, 3H), 2.21 (t, J = 7.8 Hz, 2H), 2.10 (s, 3H), 2.06 (m, 1H), 1.92 (m, 4H), 1.74 (m, 2H). | 433.4 |
| 161 | 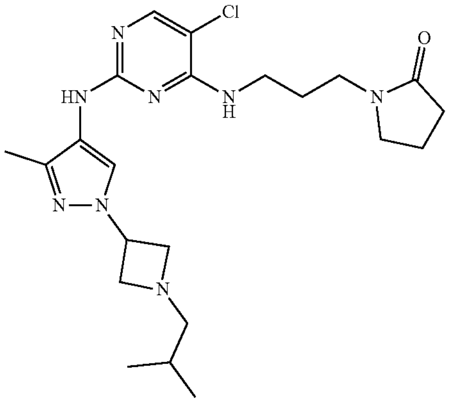 | K | 40 | 8.32 (brs, 1H), 7.90 (s, 1H), 7.83 (s, 1H), 7.00 (t, 1H), 4.84 (t, J = 7.0 Hz, 1H), 3.64 (t, J = 7.0 Hz, 2H), 3.34 (m, 2H), 3.31 (m, 2H), 3.23 (m, 4H), 2.26 (d, J = 6.9 Hz, 2H), 2.21 (t, J = 8.0 Hz, 2H), 2.12 (s, 3H), 1.90 (m, 2H), 1.72 (t, J = 6.8 Hz, 2H), 1.54 (m, 1H), 0.85 (d, J = 6.6 Hz, 6H). | 461.4 |
| 162 | 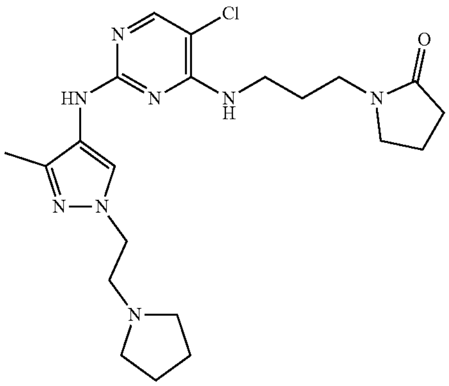 [SMILES: Cc1nn(CCN2CCCC2)cc1Nc1ncc(Cl)c(NCCCN2CCCC2=O)n1] | K | 18 | 8.35 (brs, 1H), 7.83 (s, 2H), 7.01 (brs, 1H), 4.18 (brs, 2H), 3.32 (m, 2H), 3.23 (m, 2H), 3.22 (t, J = 6.6 Hz, 2H), 2.66 (m, 2H), 2.50 (m, 4H), 2.22 (t, J = 8.0 Hz, 2H), 2.11 (s, 3H), 1.90 (t, J = 8.4 Hz, 2H), 1.72 (d, J = 6.4 Hz, 6H). | 447.3 |
| 163 | 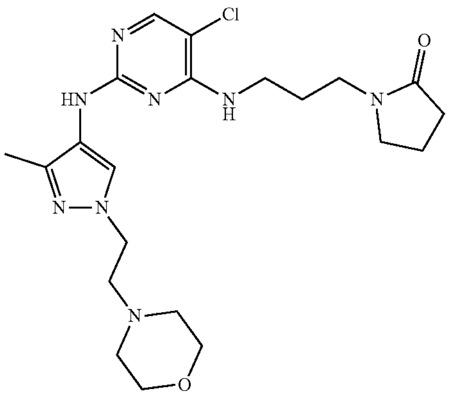 [SMILES: Cc1nn(CCN2CCOCC2)cc1Nc1ncc(Cl)c(NCCCN2CCCC2=O)n1] | K | 62 | 9.44 (brs, 1H), 8.06 (brs, 1H), 7.99 (s, 1H), 7.93 (s, 1H), 4.56 (t, J = 6.4 Hz, 2H), 3.90 (m, 4H), 3.56 (t, J = 6.4 Hz, 2H), 3.45 (q, 2H), 3.35 (t, J = 7.0 Hz, 2H), 3.27 (m, 6H), 2.23 (t, J = 7.8 Hz, 2H), 2.15 (s, 3H), 1.94 (m, 2H), 1.81 (m, 2H). | 463.4 |

TABLE G-continued

Exemplary Compounds that can be prepared by General Methods K through N.

| Example No. | Product | General Method | Yield (%) | $^1$H NMR (400 MHz, DMSO-$d_6$): δ | LC-MS (m/z: M + H$^+$) |
|---|---|---|---|---|---|
| 164 | 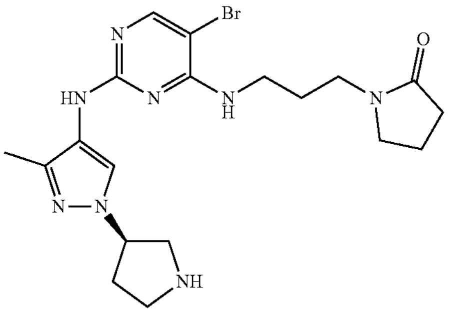 [SMILES: Cc1nn([C@@H]2CCNC2)cc1Nc1ncc(Br)c(NCCCN2CCCC2=O)n1] | K | 97 | 10.1 (brs, 1H), 9.52 (brs, 1H), 9.36 (brs, 1H), 8.42 (brs, 1H), 8.01 (s, 1H), 5.14 (brs, 1H), 3.38 (m, 10H), 2.35 (m, 2H), 2.16 (m, 5H), 1.91 (brs, 2H), 1.67 (brs, 2H). | 463.3 |
| 165 | 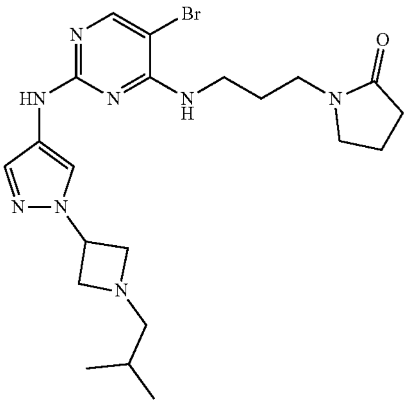 [SMILES: CC(C)CN1CC(n2cc(Nc3ncc(Br)c(NCCCN4CCCC4=O)n3)cn2)C1] | K | 23 | 9.09 (brs, 1H), 7.94 (s, 1H), 7.92 (s, 1H), 7.51 (s, 1H), 6.90 (brs, 1H), 4.94 (brs, 1H), 3.69 (brs, 2H), 3.37 (m, 2H), 3.34 (m, 2H), 3.33 (m, 2H), 3.24 (t, J = 6.8 Hz, 2H), 2.28 (m, 2H), 2.22 (t, J = 7.8 Hz, 2H), 1.91 (m, 2H), 1.75 (t, J = 6.2 Hz, 2H), 1.55 (m, 1H), 0.85 (d, J = 6.6 Hz, 6H). | 491.4 |
| 166 | 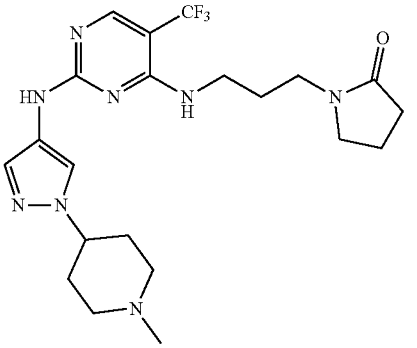 [SMILES: CN1CCC(n2cc(Nc3ncc(C(F)(F)F)c(NCCCN4CCCC4=O)n3)cn2)CC1] | L | 91 | 11.1 (brs, 1H), 10.9 (s, 1H), 8.40 (brm, 2H), 7.94 (s, 1H), 7.66 (s, 1H), 4.48 (m, 1H), 3.50 (m, 4H), 3.32 (m, 2H), 3.20 (m, 2H), 3.11 (m, 2H), 2.76 (m, 1H), 2.75 (d, J = 4.6 Hz, 3H), 2.27-2.35 (m, 2H), 2.19 (t, J = 13.0 Hz, 3H), 1.77-1.89 (m, 4H). | 467.2 |
| 167 | 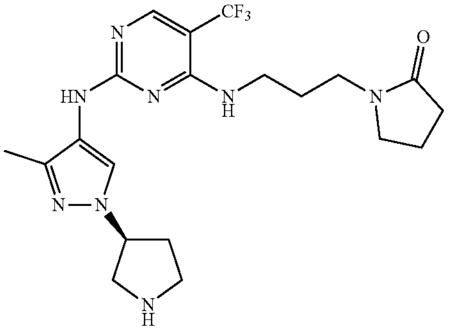 [SMILES: Cc1nn([C@H]2CCNC2)cc1Nc1ncc(C(F)(F)F)c(NCCCN2CCCC2=O)n1] | L | 95 | 9.40 (brs, 1H), 9.16 (brs, 2H), 8.17 (s, 1H), 7.94 (s, 1H), 7.26 (brs, 1H), 5.10 (m, 1H), 3.62 (m, 2H), 3.38 (m, 6H), 3.21 (t, J = 6.8 Hz, 2H), 2.42 (m, 2H), 2.23 (t, 2H), 2.17 (s, 3H), 1.93 (m, 2H), 1.75 (m, 2H). | 453.22 |

TABLE G-continued

| Example No. | Product | General Method | Yield (%) | $^1$H NMR (400 MHz, DMSO-$d_6$): δ | LC-MS (m/z: M + H$^+$) |
|---|---|---|---|---|---|
| Exemplary Compounds that can be prepared by General Methods K through N. | | | | | |
| 168 | 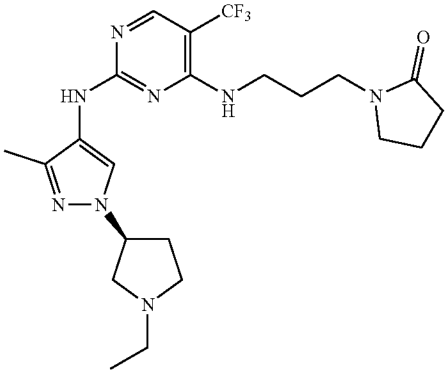 [SMILES: CCN1CC[C@H](n2cc(Nc3ncc(C(F)(F)F)c(NCCCN4CCCC4=O)n3)c(C)n2)C1] | L | 23 | 8.95 (brs, 1H), 8.09 (s, 1H), 7.92 (brs, 1H), 7.01 (brs, 1H), 4.84 (brs, 1H), 3.31 (m, 4H), 3.18 (m, 2H), 2.92 (m, 4H), 2.32 (m, 4H), 2.21 (t, J = 7.6 Hz, 2H), 2.12 (s, 3H), 1.90 (m, 2H), 1.69 (m, 2H), 1.08 (t, J = 6.8 Hz, 3H). | 481.47 |
| 169 | 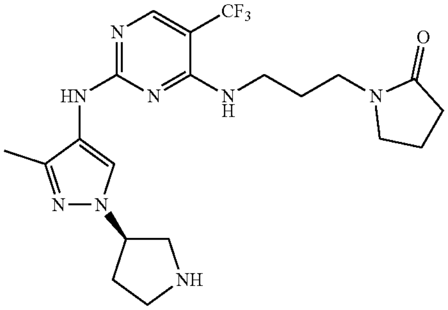 [SMILES: Cc1nn([C@@H]2CCNC2)cc1Nc1ncc(C(F)(F)F)c(NCCCN2CCCC2=O)n1] | L | 98 | 9.55 (brs, 1H), 9.29 (brs, 1H), 8.23 (s, 1H), 7.96 (s, 1H), 7.59 (brs, 1H), 5.10 (brs, 1H), 3.62 (brs, 2H), 3.42 (m, 6H), 3.21 (t, J = 6.8 Hz, 2H), 2.41 (m, 2H), 2.26 (m, 2H), 2.17 (s, 3H), 1.93 (m, 2H), 1.76 (m, 2H). | 453.2 |
| 170 | 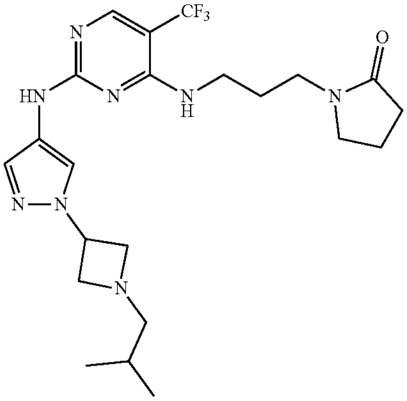 [SMILES: CC(C)CN1CC(n2cc(Nc3ncc(C(F)(F)F)c(NCCCN4CCCC4=O)n3)cn2)C1] | L | 19 | 9.21 (brs, 1H), 8.11 (s, 1H), 7.95 (s, 1H), 7.58 (s, 1H), 6.76 (brs, 1H), 4.92 (t, J = 6.8 Hz, 1H), 3.68 (t, J = 7.2 Hz, 2H), 3.47 (q, 2H), 3.34 (t, J = 6.8 Hz, 4H), 3.25 (t, J = 6.8 Hz, 2H), 2.30 (d, J = 6.8 Hz, 2H), 2.23 (t, J = 8.0 Hz, 2H), 1.93 (m, 2H), 1.79 (m, 2H), 1.58 (m, 1H), 0.88 (d, J = 6.6 Hz, 6H). | 481.4 |
| 173 | 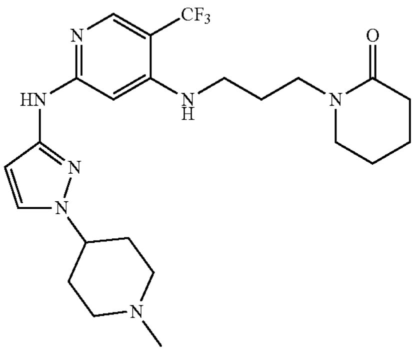 [SMILES: CN1CCC(n2ccc(Nc3cc(NCCCN4CCCCC4=O)c(C(F)(F)F)cn3)n2)CC1] | N | 42 | 9.23 (s, 1H), 7.96 (s, 1H), 7.58 (d, J = 2.4 Hz, 1H), 6.85 (s, 1H), 6.17 (t, J = 6.0 Hz, 1H), 6.12 (s, 1H), 3.97 (m, 1H), 3.31 (m, 2H), 3.23 (t, J = 5.6 Hz, 2H), 3.13 (q, J = 6.2 Hz, 2H), 2.84 (m, 2H), 2.20 (m, 5H), 1.99-2.08 (m, 2H), 1.94 (m, 4H), 1.68-1.76 (m, 6H). | 480.4 |

Example 174. Biochemical Assay for ULK1.2

Activity of ULK1 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 uL final volume) using 19 nM ULK1 (Eurofins CAT #14-959), 0.25 mg/mL myelin basic protein, 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of ULK1 was measured by adding serial diluted test compound (final assay concentration of 1% DMSO). A decrease in absorption at 340 nm was monitored continuously for 6 hours at 30° C. on a multimode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated by fitting a four-parameter sigmoidal curve to the data using Prism (GraphPad software).

ULK1 Protein Sequence (Residues 1-314 with N-Terminal His Tag; SEQ. ID NO: 1)

```
MSYYHHHHHHDYDIPTTENLYFQGAMDPFFMEPGRGGTETVGKFEFSRKD
LIGHGAFAVVFKGRHREKHDLEVAVKCINKKNLAKSQTLLGKEIKILKEL
KHENIVALYDFQEMANSVYLVMEYCNGGDLADYLHAMRTLSEDTIRLFLQ
QIAGAMRLLHSKGIIHRDLKPQNILLSNPAGRRANPNSIRVKIADFGFAR
YLQSNMMAATLCGSPMYMAPEVIMSQHYDGKADLWSIGTIVYQCLTGKAP
FQASSPQDLRLFYEKNKTLVPTIPRETSAPLRQLLLALLQRNHKDRMDFD
EFFHHPFLDASPSVRKSPPVPVPSYPSSGSGSSSSSSSTSHLAS
```

Example 175. Biochemical Assay for ULK1.3

Activity of ULK1 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 uL final volume) using 0.1 nM ULK1 (from Beryllium), 0.075 mM peptide substrate (YANWLAASIYLDGKKK (SEQ ID NO: 5)), 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.004% (w/v) BSA, and 0.004% Triton X-100). Inhibition of ULK1 was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated using software routines in Prism (GraphPad software).

ULK1 Protein Sequence (Residues 1-283; SEQ. ID NO: 2)

```
MEPGRGGTETVGKFEFSRKDLIGHGAFAVVFKGRHRAAHDLEVAVKCINK
KNLAKSQTLLGKEIKILKELKHENIVALYDFQEMANSVYLVMEYCNGGDL
ADYLHAMRTLSEDTIRLFLQQIAGAMRLLHSKGIIHRDLKPQNILLSNPA
GRRANPNSIRVKIADFGFARYLQSNMMAATLCGSPMYMAPEVIMSQHYDG
KADLWSIGTIVYQCLTGKAPFQASSPQDLRLFYEKNKTLVPTIPRETSAP
LRQLLLALLQRNHKDRMDFDEFFHHPFLDASPS
```

Example 176. Biochemical Assay for ULK2

Activity of ULK2 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 uL final volume) using 9.7 nM ULK2 (Eurofins CAT #14-772), 0.25 mg/mL myelin basic protein, 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.1% octyl-glucoside, 0.002% (w/v) BSA, and 0.002% Triton X-100). Inhibition of ULK2 was measured by adding serial diluted test compound (final assay concentration of 1% DMSO). A decrease in absorption at 340 nm was monitored continuously for 6 hours at 30° C. on a multimode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated by fitting a four-parameter sigmoidal curve to the data using Prism (GraphPad software).

ULK2 Protein Sequence (Residues 1-306 with N-Terminal GST and His Tag; SEQ. ID NO: 3)

```
MSPILGYWKIKGLVQPTRLLLEYLEEKYEEHLYERDEGDKWRNKKFELGL
EFPNLPYYIDGDVKLTQSMAIIRYIADKHNMLGGCPKERAEISMLEGAVL
DIRYGVSRIAYSKDFETLKVDFLSKLPEMLKMFEDRLCHKTYLNGDHVTH
PDFMLYDALDVVLYMDPMCLDAFPKLVCFKKRIEAIPQIDKYLKSSKYIA
WPLQGWQATFGGGDHPPKSDLEVLFQGPEFMEVVGDFEYSKRDLVGHGAF
AVVFRGRHRQKTDWEVAIKSINKKNLSKSQILLGKEIKILKELQHENIVA
LYDVQELPNSVFLVMEYCNGGDLADYLQAKGTLSEDTIRVFLHQIAAAMR
ILHSKGIIHRDLKPQNILLSYANRRKSSVSGIRIKIADFGFARYLHSNM
MAATLCGSPMYMAPEVIMSQHYDAKADLWSIGTVIYQCLVGKPPFQANS
PQDLRMFYEKNRSLMPSIPRETSPYLANLLLGLLQRNQKDRMDFEAFFS
HPFLEQGPVKKSCPVPVPMYSGSVSGSSCGSSPSCRFASHHHHHH
```

TABLE 1

Inhibition of biochemical activity of ULK1 and ULK2 kinases by exemplary compounds in Table G.

| Example (Compound) No. | ULK1.2 | ULK1.3 | ULK2.2 |
|---|---|---|---|
| 1 | + + | | + + + + |
| 2 | + | | + + |
| 3 | + | | |
| 4 | + | | + + |
| 5 | + + | | |
| 6 | + | | + + |
| 7 | + | | + |
| 8 | + | | + + |
| 9 | + | | |
| 10 | + | | |
| 11 | + + + | | |
| 12 | + + | | |
| 13 | + | | |
| 14 | + | | + |
| 15 | + + | | + + + |
| 16 | + + | | + + + |
| 17 | + + | | |
| 18 | + | | + + |
| 19 | + | | |
| 20 | + + | | |
| 21 | + + | | + + + |
| 22 | + + + | | |
| 23 | + + | | |
| 24 | + + + | | |
| 25 | + | | + + |
| 26 | + | | + + |
| 27 | + + | | + + + |
| 28 | + + | | |
| 29 | + + + + | | |
| 30 | + + + | | |
| 31 | + | | |
| 32 | + + | | + + + |
| 33 | + + + | | |
| 34 | + | | |
| 35 | + + | | |
| 36 | + + | | |
| 37 | + | | |
| 38 | + + + + | | |
| 39 | + + + | | |
| 40 | + | | |
| 41 | + + | | + + + |
| 42 | + + | | |
| 43 | + + | | |
| 44 | + + | | + + + |
| 45 | + + + | | |
| 46 | + + + | | |
| 47 | + | | |
| 48 | + | | |
| 49 | + | | |
| 50 | + + | | |
| 51 | + | | + + |
| 52 | + | | |
| 53 | + + | | + + + |
| 54 | + + | | |
| 55 | + + + | | |
| 56 | + + + | | |
| 57 | + + + | | |
| 58 | + + + | | |
| 59 | + + | | |
| 60 | + + | | + + + |
| 61 | + + | + + | + + + |
| 62 | + + + | | |
| 63 | + + + + | | |
| 64 | + + | | + + + + |
| 65 | + | | |
| 66 | + + | | + + + |
| 67 | | + + + + | |
| 68 | + + | + + | + + + |
| 69 | + + + + | | |
| 70 | + + | | |
| 71 | | + + | |
| 72 | | + + | |
| 73 | | + + + | |
| 74 | + + | | |
| 75 | | + + + + | |
| 76 | | + + + + | |
| 77 | + | | + |
| 78 | + | | + |
| 79 | + | | + |
| 80 | + | | + + + |
| 81 | + | | + |
| 82 | + + + | | |
| 83 | + | | + |
| 84 | + + + | | |
| 85 | + | | |
| 86 | + + | | + + + |
| 87 | + + | | |
| 88 | + | | |
| 89 | + | | |
| 90 | + | | |
| 91 | + | | + + + |
| 92 | + | | |
| 93 | + | | |
| 94 | + | | |
| 95 | + | | |
| 96 | + + | | |
| 97 | + | | |
| 98 | + + + | | |
| 99 | + | | + + + |
| 100 | + + | | + + + |
| 101 | + | | |
| 102 | + | + | + + |
| 103 | + + | | + + |
| 104 | + + | | + + |
| 105 | + + | | + + + + |
| 106 | + + | | + + + |
| 107 | + + | | + + + |
| 108 | + + | | + + + + |
| 109 | + + | | |
| 110 | + + + + | | |
| 111 | + + + + | | |
| 112 | + + + | | |
| 113 | | + + + | |
| 114 | | + + + + | |
| 115 | | + + + + | |
| 116 | | + + + + | |
| 117 | | + + | |
| 118 | | + + | |
| 119 | | + + + + | |
| 120 | | + + + + | |
| 121 | | + + + | |
| 122 | | + + + | |
| 123 | | + + + + | |
| 125 | | + + + + | |
| 126 | | + + + + | |
| 127 | + | + | + + + |
| 128 | + | | |
| 129 | + + + | | + + + + |
| 130 | + + | | + + + |
| 131 | + + | | + + + + |
| 132 | + + + | | |
| 133 | + | | |
| 134 | + + + | | |
| 135 | + + + + | | |
| 136 | | + | |
| 137 | | + + + | |
| 138 | | + + | |
| 139 | | + + + + | |
| 140 | | + + + + | |
| 141 | | + + + | |
| 142 | | + + + + | |
| 143 | | + + + | |
| 144 | | + + + | |
| 145 | | + + + | |
| 146 | | + + + | |
| 147 | + + + | | + + + + |

TABLE 1-continued

Inhibition of biochemical activity of ULK1 and ULK2 kinases by exemplary compounds in Table G.

| Example (Compound) No. | ULK1.2 | ULK1.3 | ULK2.2 |
|---|---|---|---|
| 148 | + + + | | |
| 149 | + + + | | |
| 150 | + + + | | |
| 151 | + | | |
| 152 | + + | | |
| 153 | + + + | | |
| 154 | + + + + | | |
| 155 | + + + | | |
| 156 | + + + + | | |
| 157 | + + + + | | |
| 158 | + + + + | | |
| 159 | + + + + | | |
| 160 | + + + + | | |
| 161 | + + + + | | |
| 162 | + + + + | | |
| 163 | + + + + | | |
| 164 | + + + | | |
| 165 | + + + | | |
| 166 | + | | + + |
| 167 | + + + | | |
| 168 | + + + | | |
| 169 | + + + | | |
| 170 | + + + | | |
| 171 | | + + + | |
| 172 | | + + + | |
| 173 | | + | |

For Table 1, "+" refers to an $IC_{50}$ greater than 1 nM and less than or equal to 25 nM; "++" refers to an $IC_{50}$ greater than 25 nM and less than or equal to 100 nM; "+++" refers to an $IC_{50}$ greater than 100 nM and less than or equal to 500 nM; and "++++" refers to an $IC_{50}$ greater than 500 nM.

Example 177. Cellular Inhibition of ULK Kinase Substrate ATG13 Protein pATG13 Levels of Mutant KRas A549 Cells after Treatment with ULK Inhibitors in Combination with Trametinib A549 (KRAS mutant) human lung cancer cells (6,000 cells/well) were added to a 384-well tissue-culture treated plate in 50 μL of pre-warmed DMEM medium supplemented with 10% characterized fetal bovine serum (Invitrogen, Carlsbad, CA), 100 units/mL penicillin G, and 100 μg/mL streptomycin and allowed to grow overnight at 37° C., 5% CO2, and 95% humidity. The following day, 10 μL of media containing trametinib or DMSO as a control was added to wells. The final concentration of trametinib in wells was 250 nM. A dose response of a test compound (0.6 μL per well) was added. DMSO (0.6 μL) was added to control wells. The plate was briefly shaken to mix wells and then incubated at 37 t overnight. The next day, the media was aspirated and cells were washed with Dulbecco's Phosphate Buffered Saline (Gibco). Cells were lysed using MPER lysis buffer (Pierce, Rockford, IL) containing Halt Phosphatase and Protease Inhibitors (Pierce, Rockford, IL) and Phosphatase inhibitor cocktail 2 (Sigma, St. Louis, MO) at 4 t for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4 t overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate $IC_{50}$ values.

Example 178. pATG13 Levels of Mutant KRas MiaPaCa-2 Cells after Treatment with ULK Inhibitors in Combination with Trametinib MiaPaCa-2 human pancreatic cancer cells (10000 cells/well) were added to a 384-well tissue-culture treated plate in 50 μL of pre-warmed DMEM medium supplemented with 10% characterized fetal bovine serum (Invitrogen, Carlsbad, CA), 100 units/mL penicillin G, 100 μg/mL streptomycin, and 2.5% Horse Serum and allowed to grow overnight at 37° C., 5% CO2, and 95% humidity. The following day, 10 μL of media containing trametinib or DMSO as a control was added to wells. The final concentration of trametinib in wells was 250 nM. A dose response of a test compound (0.6 μL per well) was added. DMSO (0.6 μL) was added to control wells. The plate was briefly shaken to mix wells and then incubated at 37 t overnight. The next day, the media was aspirated and cells were washed with Dulbecco's Phosphate Buffered Saline (Gibco). Cells were lysed using 1VIPER lysis buffer (Pierce, Rockford, IL) containing Halt Phosphatase and Protease Inhibitors (Pierce, Rockford, IL) and Phosphatase inhibitor cocktail 2 (Sigma, St. Louis, MO) at 4 t for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4 t overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate $IC_{50}$ values.

Example 179. pATG13 Levels of Mutant KRas HCT-116 Cells after Treatment with ULK Inhibitors in Combination with Trametinib HCT-116 human colon cancer cells (10000 cells/well) were added to a 384-well tissue-culture treated plate in 50 μL of pre-warmed DMEM medium supplemented with 10% characterized fetal bovine serum (Invitrogen, Carlsbad, CA), 100 units/mL penicillin G, and 100 μg/mL streptomycin and allowed to grow overnight at 37° C., 5% CO2, and 95% humidity. The following day, 10 μL of media containing trametinib or DMSO as a control was added to wells. The final concentration of trametinib in wells was 250 nM. A dose response of a test compound (0.6 μL per well) was added. DMSO (0.6 μL) was added to control wells. The plate was briefly shaken to mix wells and then incubated at 37 t overnight. The next day, the media was aspirated and cells were washed with Dulbecco's Phosphate Buffered Saline (Gibco). Cells were lysed using 1VIPER lysis buffer (Pierce, Rockford, IL) containing Halt Phosphatase and Protease Inhibitors (Pierce, Rockford, IL) and Phosphatase inhibitor cocktail 2 (Sigma, St. Louis, MO) at 4° C. for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4 t overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate $IC_{50}$ values.

Example 180. pATG13 Levels of Mutant BRAF A375 Cells after Treatment with ULK Inhibitors in Combination with Trametinib A375 human malignant melanoma cancer cells (20000 cells/well) were added to a 96-well tissue-culture treated plate in 100 μL of pre-warmed DMEM medium supplemented with 10% characterized fetal bovine serum (Invitrogen, Carlsbad, CA), 100 units/mL penicillin G, and 100 μg/mL streptomycin and allowed to grow overnight at 37° C., 5% CO2, and 95% humidity. The following day, 100 μL of media containing trametinib or DMSO as a control was added to wells. The final concentration of trametinib in wells was 250 nM. A dose response of a test compound (0.5 μL per well) was added. DMSO (0.5 μL) was added to control wells. The plate was briefly shaken to mix wells and then incubated at 37 t overnight. The next day, the media was aspirated and cells were washed with Dulbecco's Phosphate Buffered Saline (Gibco). Cells were lysed using MPER lysis buffer (Pierce, Rockford, IL) containing Halt Phosphatase and Protease Inhibitors (Pierce, Rockford, IL) and Phosphatase inhibitor cocktail 2 (Sigma, St. Louis, MO) at 4 t for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4° C. overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate $IC_{50}$ values.

Example 181. pATG13 Levels of Mutant HRas T24 Cells after Treatment with ULK Inhibitors in Combination with Trametinib T24 human urinary bladder cancer cells (25000 cells/well) were added to a 96-well tissue-culture treated plate in 100 μL of pre-warmed DMEM medium supplemented with 10% characterized fetal bovine serum (Invitrogen, Carlsbad, CA), 100 units/mL penicillin G, and 100 μg/mL streptomycin and allowed to grow overnight at 37° C., 5% CO2, and 95% humidity. The following day, 100 μL of media containing trametinib or DMSO as a control was added to wells. The final concentration of trametinib in wells was 250 nM. A dose response of a test compound (0.5 μL per well) was added. DMSO (0.5 μL) was added to control wells. The plate was briefly shaken to mix wells and then incubated at 37 t overnight. The next day, the media was aspirated and cells were washed with Dulbecco's Phosphate Buffered Saline (Gibco). Cells were lysed using 1VIPER lysis buffer (Pierce, Rockford, IL) containing Halt Phosphatase and Protease Inhibitors (Pierce, Rockford, IL) and Phosphatase inhibitor cocktail 2 (Sigma, St. Louis, MO) at 4° C. for 10 minutes with shaking.

Cellular levels of phospho-Serine 318 ATG13 (pATG13) were measured via an ELISA method. Total ATG13 Antibody (Cell Signaling Cat #13273) was used to coat the wells. The plate was incubated at 4 t overnight and washed with ELISA wash buffer (Biolegend Cat #421601). The wells were then blocked with assay diluent (Biolegend Cat #421203) for 1 hour at room temperature. Plate wells were washed with ELISA wash buffer. Cell lysate was added to wells and incubated at room temperature for 2 hours. Plate wells were washed with ELISA wash buffer. Biotinylated pS318-ATG13 antibody (Rockland Immunochemicals Cat #600-401-C49) was diluted in assay diluent and added to each well and incubated at room temperature for 1 hour. Plate wells were washed with ELISA wash buffer. Streptavidin linked to horseradish peroxidase (Thermo Fisher Cat #21140) was diluted in assay diluent and added to each well and incubated at room temperature for 1 hour. Plate wells were washed with ELISA wash buffer. High sensitivity TMB substrate (Biolegend Cat #421101) was added to each well and incubated at room temperature for 20 minutes. The reaction was stopped with 2N Sulfuric Acid. The plate was analyzed at on a plate reader measuring absorbance at 450 nm and 540 nm (background). Signal was calculated by first subtracting the background absorbance at 540 nm from the absorbance at 450 nm for each well. Next, the background corrected absorbance at 450 nm from blank wells was subtracted from test wells. Data was compared to control wells to determine % ATG13 phosphorylation. GraphPad Prism was used to calculate $IC_{50}$ values.

TABLE 2

Inhibition of ULK kinase in mutant Ras or mutant BRAF cell lines by exemplary compounds from Table G.

| Example (Compound) No. | A549 pATG13 ELISA | MiaPaca-2 pATG13 ELISA | HCT-116 pATG13 ELISA | T24 pATG13 ELISA | A375 pATG13 ELISA |
|---|---|---|---|---|---|
| 3 | + | | | | |
| 4 | + + + + | | | | |
| 6 | + | + | + + | | |
| 7 | + | | + + | | |
| 8 | + | | | + | + |
| 9 | + + + + | | | | |
| 12 | + + + | | | | |
| 13 | + + | | | | |
| 14 | + + + | | + | | |
| 15 | + | + | + | + | + |
| 16 | + + | + | | | |
| 17 | + + | | | | |
| 18 | + + | | | + + | + |
| 20 | + + | | | | |
| 21 | + + + | + + | + + | | |
| 25 | + | | | | |
| 26 | + + + + | | | | |
| 27 | + + + + | | | | |
| 31 | + + | | | | |
| 32 | + + | + | + | + | |
| 40 | + + + | + | + | | |
| 44 | + + | + + | | | |
| 48 | + + + + | | | | |
| 51 | + + + + | | | | |
| 53 | + + | + + | + | | + + |
| 54 | + + | + + | | | |
| 58 | + + + | | | | |
| 60 | + + + + | + | | | |
| 61 | + + | + | + | | + |
| 64 | + + | + | | | |
| 66 | + + | + + | | | |
| 68 | + + + | + | + | + + | + + |

TABLE 2-continued

Inhibition of ULK kinase in mutant Ras or mutant BRAF cell lines by exemplary compounds from Table G.

| Example (Compound) No. | A549 pATG13 ELISA | MiaPaca-2 pATG13 ELISA | HCT-116 pATG13 ELISA | T24 pATG13 ELISA | A375 pATG13 ELISA |
|---|---|---|---|---|---|
| 71 | + + + + | + + | | | |
| 72 | + + + + | + + | | | |
| 74 | + + + + | | | | |
| 77 | + + | | | | |
| 78 | + | | | | |
| 79 | + | + | + | | |
| 80 | + | | | | |
| 81 | + | | | | |
| 83 | + + | | | | |
| 86 | + + + + | | | | |
| 90 | + | | | | |
| 91 | + + + | | | | |
| 94 | + | | | | |
| 96 | + + + | + + | | | |
| 99 | + + | + | | | |
| 100 | + + | + + | + + | + + | |
| 102 | + + | + | + | | |
| 103 | + + + + | | | | |
| 104 | + + + + | | | | |
| 105 | + + + + | + + | + + | + + | |
| 106 | + + | + | + | | |
| 107 | + + | + + | + | | |
| 108 | + + + | + + | + + | | |
| 109 | + + | + + | + | | |
| 118 | + + + | + + | | | |
| 127 | + + | + | + + | + | + |
| 129 | + + + + | + + + + | | | |
| 130 | + + | + | + | | |
| 131 | + + + | + + | + + | | |
| 133 | + | + | | | |
| 138 | + + + | + + | | | |
| 152 | + + | | | | |
| 166 | + + | | | | |
| 173 | + | + | | | |

For Table 2, "+" refers to an $IC_{50}$ greater than 10 nM and less than or equal to 100 nM; "++" refers to an $IC_{50}$ greater than 100 nM and less than or equal to 300 nM; "+++" refers to an $IC_{50}$ greater than 300 nM and less than or equal to 600 nM; and "++++" refers to an $IC_{50}$ greater than 600 nM.

Example 182. Biochemical Assay for LRRK2 (SEQ. ID NO. 4)

Activity of LRRK2 kinase was determined spectroscopically using a coupled pyruvate kinase/lactate dehydrogenase assay that continuously monitors the ATP hydrolysis-dependent oxidation of NADH (e.g., Schindler et al. Science (2000) 289: 1938-1942). Assays were conducted in 384-well plates (100 uL final volume) using 26.4 nM LRRK2 (Thermo Fisher), 0.1 mM peptide substrate (RLGRDKYKTLRQIRQ (SEQ ID NO: 6)), 1.5 units pyruvate kinase, 2.1 units lactate dehydrogenase, 1 mM phosphoenol pyruvate, 0.28 mM NADH and 1 mM ATP in assay buffer (100 mM Tris, pH 7.5, 15 mM $MgCl_2$, 0.5 mM DTT, 0.004% (w/v) BSA, and 0.004% Triton X-100). Inhibition of LRRK2 was measured by adding serial diluted test compound (final assay concentration of 1% DMSO). A decrease in absorption at 340 nm was monitored continuously for 6 hours at 30° C. on a multi-mode microplate reader (BioTek). The reaction rate was calculated using the 2-3 h time frame. The reaction rate at each concentration of compound was converted to percent inhibition using controls (i.e. reaction with no test compound and reaction with a known inhibitor) and $IC_{50}$ values were calculated using software routines in Prism (GraphPad software).

LRRK2 Protein Sequence (Residues 970-2528; SEQ. ID NO. 4)

```
MAPILGYWKIKGLVQPTRLLLEYLEEKYEEHLYERDEGDKWRNKKFELGL
EFPNLPYYIDGDVKLTQSMAIIRYIADKHNMLGGCPKERAEISMLEGAVL
DIRYGVSRIAYSKDFETLKVDFLSKLPEMLKMFEDRLCHKTYLNGDHVTH
PDFMLYDALDVVLYMDPMCLDAFPKLVCFKKRIEAIPQIDKYLKSSKYIA
WPLQGWQATFGGGDHPPKSDLVPRHNQTSLYKKAGTMHSDSISSLASERE
YITSLDLSANELRDIDALSQKCCISVHLEHLEKLELHQNALTSFPQQLCE
TLKSLTHLDLHSNKFTSFPSYLLKMSCIANLDVSRNDIGPSVVLDPTVKC
PTLKQFNLSYNQLSFVPENLTDVVEKLEQLILEGNKISGICSPLRLKELK
ILNLSKNHISSLSENFLEACPKVESFSARMNFLAAMPFLPPSMTILKLSQ
NKFSCIPEAILNLPHLRSLDMSSNDIQYLPGPAHWKSLNLRELLFSHNQI
SILDLSEKAYLWSRVEKLHLSHNKLKEIPPEIGCLENLTSLDVSYNLELR
SFPNEMGKLSKIWDLPLDELHLNFDFKHIGCKAKDIIRFLQQRLKKAVPY
NRMKLMIVGNTGSGKTTLLQQLMKTKKSDLGMQSATVGIDVKDWPIQIRD
KRKRDLVLNVWDFAGREEFYSTHPHFMTQRALYLAVYDLSKGQAEVDAMK
PWLFNIKARASSSPVILVGTHLDVSDEKQRKACMSKITKELLNKRGFPAI
RDYHFVNATEESDALAKLRKTIINESLNFKIRDQLVVGQLIPDCYVELEK
IILSERKNVPIEFPVIDRKRLLQLVRENQLQLDENELPHAVHFLNESGVL
LHFQDPALQLSDLYFVEPKWLCKIMAQILTVKVEGCPKHPKGIISRRDVE
KFLSKKRKFPKNYMSQYFKLLEKFQIALPIGEEYLLVPSSLSDHRPVIEL
PHCENSEIIIRLYEMPYFPMGFWSRLINRLLEISPYMLSGRERALRPNRM
YWRQGIYLNWSPEAYCLVGSEVLDNHPESFLKITVPSCRKGCILLGQVVD
HIDSLMEEWFPGLLEIDICGEGETLLKKWALYSFNDGEEHQKILLDDLMK
KAEEGDLLVNPDQPRLTIPISQIAPDLILADLPRNIMLNNDELEFEQAPE
FLLGDGSFGSVYRAAYEGEEVAVKIFNKHTSLRLLRQELVVLCHLHHPSL
ISLLAAGIRPRMLVMELASKGSLDRLLQQDKASLTRTLQHRIALHVADGL
RYLHSAMIIYRDLKPHNVLLFTLYPNAAIIAKIADYGIAQYCCRMGIKTS
EGTPGFRAPEVARGNVIYNQQADVYSFGLLLYDILTTGGRIVEGLKFPNE
FDELEIQGKLPDPVKEYGCAPWPMVEKLIKQCLKENPQERPTSAQVFDIL
NSAELVCLTRRILLPKNVIVECMVATHHNSRNASIWLGCGHTDRGQLSFL
DLNTEGYTSEEVADSRILCLALVHLPVEKESWIVSGTQSGTLLVINTEDG
KKRHTLEKMTDSVTCLYCNSFSKQSKQKNFLLVGTADGKLAIFEDKTVKL
KGAAPLKILNIGNVSTPLMCLSESTNSTERNVMWGGCGTKIFSFSNDFTI
QKLIETRTSQLFSYAAFSDSNIITVVVDTALYIAKQNSPVVEVWDKKTEK
LCGLIDCVHFLREVMVKENKESKHKMSYSGRVKTLCLQKNTALWIGTGGG
HILLLDLSTRRLIRVIYNFCNSVRVMMTAQLGSLKNVMLVLGYNRKNTEG
TQKQKEIQSCLTVWDINLPHEVQNLEKHIEVRKELAEKMRRTSVE
```

TABLE 3

| LRRK2 IC50 data. | |
|---|---|
| Example (compound) No. | LRRK2 |
| 1 | + + + + |
| 8 | + + |
| 23 | + + + + |
| 26 | + + + |
| 29 | + + + + |
| 33 | + + + |
| 38 | + + + + |
| 39 | + + + + |
| 45 | + + + + |
| 56 | + + + + |
| 62 | + + + + |
| 64 | + + + |
| 67 | + |
| 69 | + + + + |
| 73 | + + + |
| 76 | + + + + |
| 80 | + + |
| 84 | + + + + |
| 98 | + + |
| 104 | + + + |
| 110 | + + |
| 111 | + + + + |
| 113 | + + |
| 114 | + + + + |
| 115 | + + + + |
| 116 | + + + + |
| 118 | + |
| 122 | + + |
| 123 | + + + + |
| 125 | + |
| 126 | + + + + |
| 132 | + + + + |
| 135 | + + + + |
| 139 | + + + + |
| 140 | + + + + |
| 141 | + + + + |
| 145 | + |
| 147 | + + + + |
| 150 | + + |
| 153 | + + + |
| 156 | + + + |
| 157 | + + + + |
| 159 | + + + + |
| 164 | + + + |
| 165 | + + + |
| 168 | + + + + |
| 170 | + + + |
| 171 | + + + |
| 172 | + |

For Table 3, "+" refers to an $IC_{50}$ greater than 1 nM and less than or equal to 100 nM; "++" refers to an $IC_{50}$ greater than 100 nM and less than or equal to 300 nM; "+++" refers to an $IC_{50}$ greater than 300 nM and less than or equal to 600 nM; and "++++" refers to an $IC_{50}$ greater than 600 nM.

Example 183. Evaluation of ULK Inhibitors in Pancreatic Ductal Adenocarcinoma (PDAC) In Vitro and In Vivo ULK inhibitors will be evaluated in PDAC flux assays, and the $IC_{50}$ of the compounds in a panel of multiple PDAC cell lines, including cells derived from primary tumors of a $Trp53^{lox/+}$, LSL-$Kras^{G12D}$, Rosa-$rtTA^{LSL}$, $p48Cre^{+}$) will be determined using a clonogenicity 2D assay and a 3D organoid assay, in the absence or the presence of trametinib.

The inhibition of autophagic flux using flux reporters in PDAC tumors in vivo using syngeneic orthotopic models after single and multiple doses will be evaluated.

The therapeutic efficacy of ULK inhibitors in PDAC models will be evaluated by (i) assessing the tumor kinetics of PDAC subcutaneously; (ii) assessing the tumor kinetics of PDAC (KPC implanted C57 black mice) orthotopically in the pancreas in syngeneic models; (iii) assessing tumor growth kinetics in syngeneic models with ULK inhibitors and MEK inhibitors; (iv) assessing the compounds in the PDAC autochthonous model; (v) assessing histological changes in the tumor microenvironment; (vi) assessing the changes in the immune cell infiltrates in the tumors upon inhibition by ULK inhibitors; (vii) assessing the efficacy of ULK inhibitors in combination with immune checkpoint blockade.

EQUIVALENTS

While specific embodiments have been discussed, the above specification is illustrative and not restrictive. Many variations of the embodiments will become apparent to those skilled in the art upon review of this specification. The full scope of what is disclosed should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A method of treating a cancer in a patient in need thereof, comprising administering to the patient:

a) a therapeutically effective amount of a compound of Formula I:

Formula I

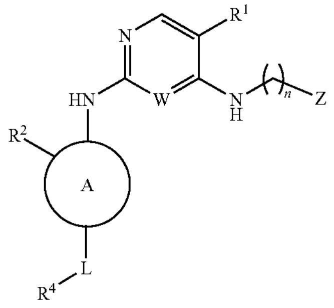

or a pharmaceutically acceptable salt, enantiomer, stereoisomer, or tautomer thereof, wherein:

A is 5-membered heteroaryl with at least one ring nitrogen;

W is CH or N;

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine;

$R^2$ is selected from the group consisting of H, halogen, cyano, $C_1$-$C_5$ alkyl, $C_3$-$C_6$ cycloalkyl, $C_2$-$C_5$ alkenyl, $C_2$-$C_5$ alkynyl, $C_1$-$C_5$ alkoxy, and $C_1$-$C_5$ alkoxy-$C_1$-$C_5$ alkyl, wherein each $C_1$-$C_5$ alkyl, $C_3$-$C_6$ cycloalkyl, $C_2$-$C_5$ alkenyl, $C_2$-$C_5$ alkynyl, and $C_1$-$C_5$ alkoxy may be optionally substituted by one, two, or three independent occurrences of fluorine or cyano;

$R^4$ is selected from the group consisting of B, D, $NR^6R^9$, $NR^6$—$(C(R^{10})_2)_p$—$NR^6R^9$, C(O)—$NR^6R^9$, C(O)—B, C(O)-D, and CN;

B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$;

D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$;

each occurrence of $R^5$ is independently selected from the group consisting of H, $C_1$-$C_6$ alkyl, $C_3$-$C_6$ cycloalkyl, and heterocyclyl, wherein each $C_1$-$C_6$ alkyl and $C_3$-$C_6$ cycloalkyl may be optionally substituted by one or more independent occurrences of fluorine;

each occurrence of $R^7$ is independently selected from the group consisting of H, $C_1$-$C_6$ alkyl, $C_3$-$C_6$ cycloalkyl, cyano, and $(C(R^{10})_2)_h$—$NR^6R^9$, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$ alkyl, $C_3$-$C_6$ cycloalkyl, $C_1$-$C_5$ alkoxy-$C_2$-$C_5$ alkyl, C(=O)$R^5$, $SO_2R^5$, C-linked heterocyclyl having at least one nitrogen and optionally having an additional ring nitrogen or oxygen, and heteroaryl, wherein each $C_1$-$C_6$ alkyl and $C_3$-$C_6$ cycloalkyl may be optionally substituted by one or more independent occurrences of fluorine;

each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl;

Z is selected from the group consisting of a 4-10 membered lactam ring wherein the lactam ring is bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by one or more independent occurrences of $R^{36}$;

each occurrence of $R^{36}$ is independently selected from $C_1$-$C_6$ alkyl and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl;

L is $-(C(R^{10})_2)_m-$;

h is 1, 2, or 3;

m is 0, 1, 2, or 3;

n is 2, 3, or 4; and p is 2 or 3;

provided that: when m is 0, $R^4$ is C-linked to ring A, when m is 1, $R^4$ is C-linked to L, and when m is 2 or 3, $R^4$ is N-linked or C-linked to L; and b) a therapeutically effective amount of a MEK inhibitor, wherein the cancer is selected from the group consisting of pancreatic cancer, lung cancer, colorectal cancer, melanoma, renal cancer, urinary bladder cancer, and gastrointestinal stromal tumors.

2. The method of claim 1, wherein the MEK inhibitor is selumetinib, cobimetinib, or pharmaceutically acceptable salts thereof.

3. A method of treating a cancer in a patient in need thereof, comprising administering to the patient:

a) a therapeutically effective amount of a compound of Formula I:

Formula I

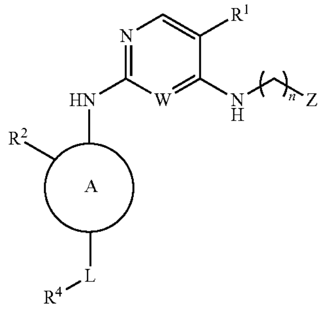

or a pharmaceutically acceptable salt, enantiomer, stereoisomer, or tautomer thereof, wherein:

A is 5-membered heteroaryl with at least one ring nitrogen;

W is CH or N;

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine;

$R^2$ is selected from the group consisting of H, halogen, cyano, $C_1$-$C_5$ alkyl, $C_3$-$C_6$ cycloalkyl, $C_2$-$C_5$ alkenyl, $C_2$-$C_5$ alkynyl, $C_1$-$C_5$ alkoxy, and $C_1$-$C_5$ alkoxy-$C_1$-$C_5$ alkyl, wherein each $C_1$-$C_5$ alkyl, $C_3$-$C_6$ cycloalkyl, $C_2$-$C_5$ alkenyl, $C_2$-$C_5$ alkynyl, and $C_1$-$C_5$ alkoxy may be optionally substituted by one, two, or three independent occurrences of fluorine or cyano;

$R^4$ is selected from the group consisting of B, D, $NR^6R^9$, $NR^6-(C(R^{10})_2)_p-NR^6R^9$, C(O)$-NR^6R^9$, C(O)$-$B, C(O)-D, and CN;

B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$;

D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$;

each occurrence of $R^5$ is independently selected from the group consisting of H, $C_1$-$C_6$ alkyl, $C_3$-$C_6$ cycloalkyl, and heterocyclyl, wherein each $C_1$-$C_6$ alkyl and $C_3$-$C_6$ cycloalkyl may be optionally substituted by one or more independent occurrences of fluorine;

each occurrence of $R^7$ is independently selected from the group consisting of H, $C_1$-$C_6$ alkyl, $C_3$-$C_6$ cycloalkyl, cyano, and $(C(R^{10})$ 2) n-$NR^6R^9$, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$ alkyl, $C_3$-$C_6$ cycloalkyl, $C_1$-$C_5$ alkoxy-$C_2$-$C_5$ alkyl, C(=O)$R^5$, $SO_2R^5$, C-linked heterocyclyl having at least one nitrogen and optionally having an additional ring nitrogen or oxygen, and heteroaryl, wherein each $C_1$-$C_6$ alkyl and $C_3$-$C_6$ cycloalkyl may be optionally substituted by one or more independent occurrences of fluorine;

each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl;

Z is selected from the group consisting of a 4-10 membered lactam ring wherein the lactam ring is bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by one or more independent occurrences of $R^{36}$;

each occurrence of $R^{36}$ is independently selected from $C_1$-$C_6$ alkyl and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl;

L is $-(C(R^{10})_2)_m-$;

h is 1, 2, or 3;

m is 0, 1, 2, or 3;

n is 2, 3, or 4; and p is 2 or 3;

provided that: when m is 0, $R^4$ is C-linked to ring A, when m is 1, $R^4$ is C-linked to L, and when m is 2 or 3, $R^4$ is N-linked or C-linked to L; and b) a therapeutically effective amount of trametinib, or a pharmaceutically acceptable salt thereof, wherein the cancer is selected from the group consisting of pancreatic cancer, lung cancer, colorectal cancer, melanoma, renal cancer, urinary bladder cancer, and gastrointestinal stromal tumors.

4. The method of claim 3, wherein

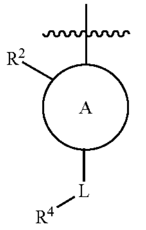

is selected from the group consisting of:

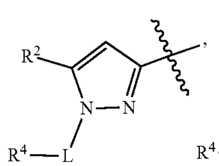

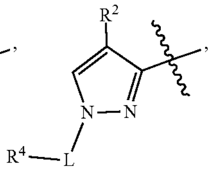

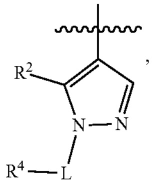

, and

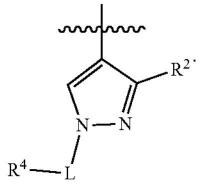

5. The method of claim 3, wherein Z is selected from the group consisting of:

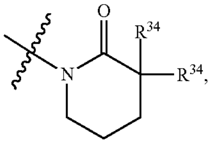

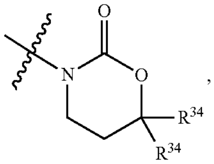

-continued

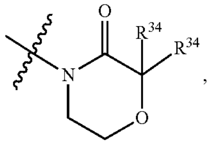

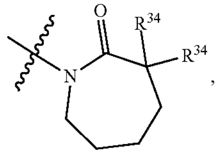

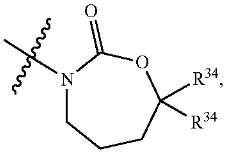

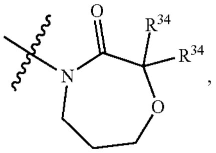

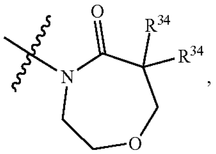

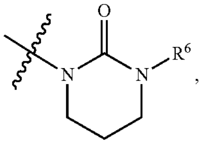

, and

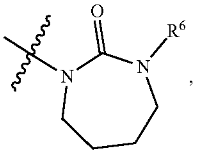

wherein each occurrence of $R^{34}$ is independently selected from H and $R^{36}$, wherein each occurrence of $R^{36}$ is independently selected from $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl.

6. The method of claim 3, wherein $R^4$ is selected from the group consisting of:

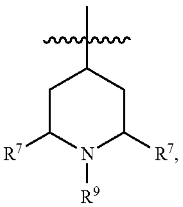

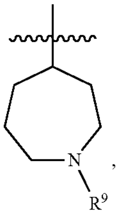

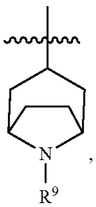

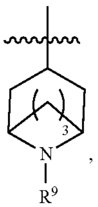

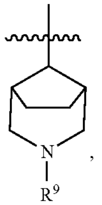

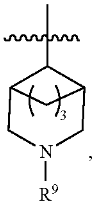

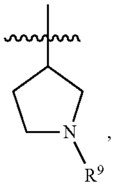

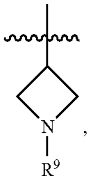

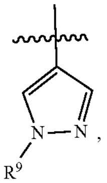

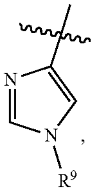

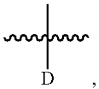

, and

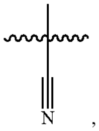

-continued

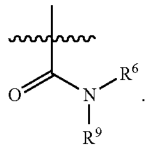

7. The method of claim 3, wherein $R^4$ is selected from the group consisting of:

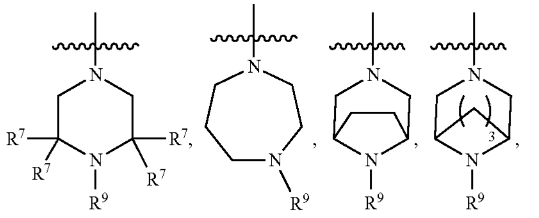

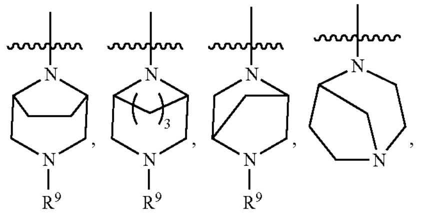

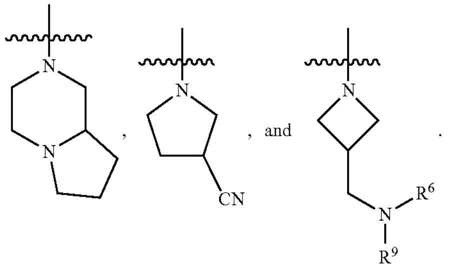

8. The method of claim 3, wherein $R^1$ is selected from the group consisting of halogen, $C_1$-$C_5$ alkyl, and $C_3$-$C_5$ cycloalkyl, wherein $C_1$-$C_5$ alkyl and $C_3$-$C_5$ cycloalkyl may be optionally substituted with one, two, or three independent occurrences of fluorine.

9. The method of claim 3, wherein $R^2$ is selected from the group consisting of $C_1$-$C_5$ alkyl, H, and $C_3$-$C_4$ cycloalkyl.

10. The method of claim 3, wherein the compound of Formula I is a compound represented by:

Formula II

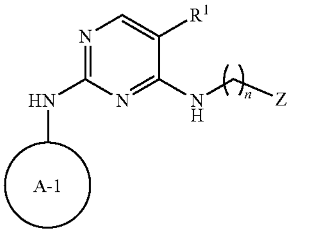

or a pharmaceutically acceptable salt thereof, wherein

A-1 is selected from the group consisting of:

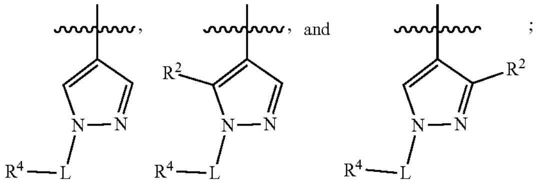

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine;

$R^2$ is selected from the group consisting of halogen, $C_1$-$C_2$ alkyl, and $C_3$-$C_4$ cycloalkyl;

$R^4$ is selected from the group consisting of:

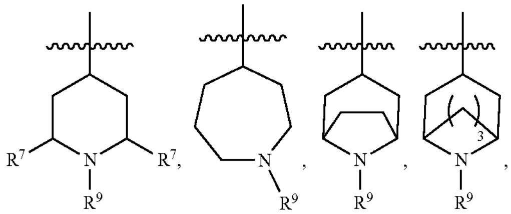

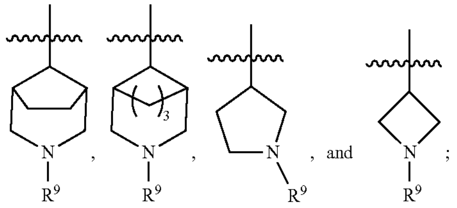

each occurrence of $R^7$ is independently selected from the group consisting of H, $C_1$-$C_6$ alkyl, $C_3$-$C_6$ cycloalkyl, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine;

Z is selected from the group consisting of:

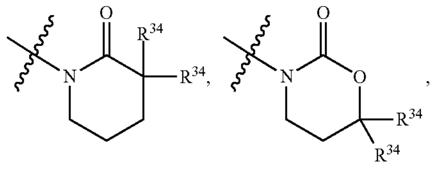

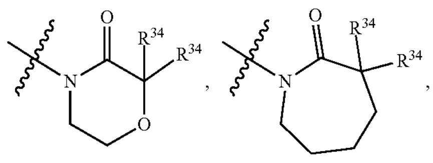

-continued

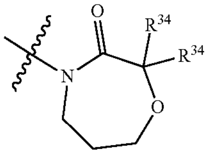,
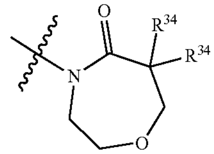,
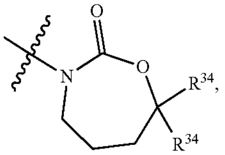
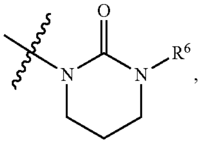, and
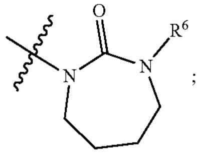;

each occurrence of $R^{34}$ is independently selected from H and $R^{36}$, wherein each occurrence of $R^{36}$ is independently selected from $C_1$-$C_6$ alkyl and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl;

L is $—(C(R^{10})_2)_m—$;

each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl;

m is 0, 1, 2, or 3; and n is 2, 3, or 4;

provided that: when m is 0, $R^4$ is C-linked to the pyrazole ring, when m is 1, $R^4$ is C-linked to L, and when m is 2 or 3, $R^4$ is C-linked to L.

11. The method of claim 10, wherein A-1 is:

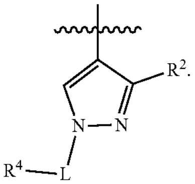

12. The method of claim 3, wherein the compound of Formula I is a compound represented by:

Formula III

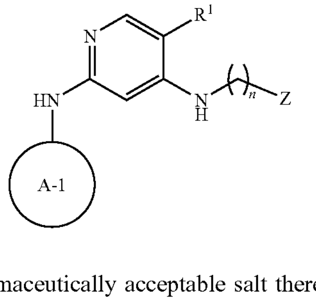

or a pharmaceutically acceptable salt thereof, wherein

A-1 is selected from the group consisting of:

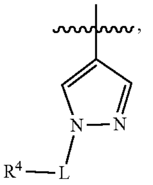,
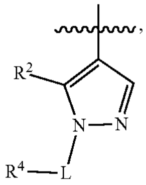, and
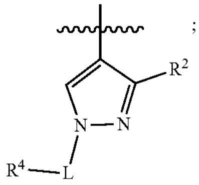;

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine;

$R^2$ is selected from $C_1$-$C_2$ alkyl, $C_3$-$C_4$ cycloalkyl, and halogen;

$R^4$ is selected from the group consisting of:

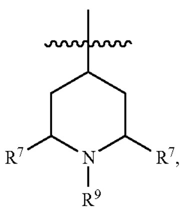
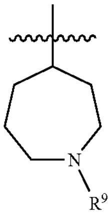,
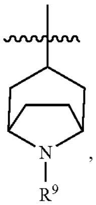,
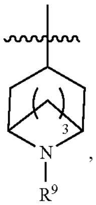,
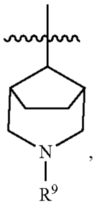,
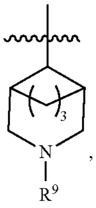,
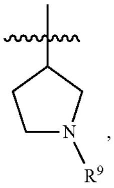, and
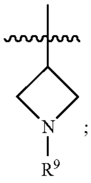;

each occurrence of $R^7$ is independently selected from the group consisting of H, $C_1$-$C_6$ alkyl, $C_3$-$C_6$ cycloalkyl, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine;

Z is selected from the group consisting of:

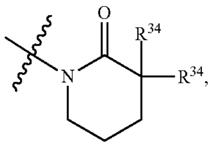
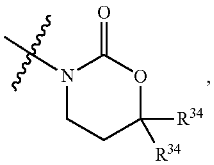,
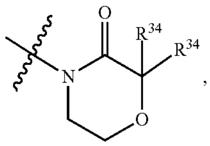,
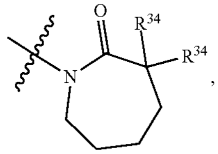,

-continued

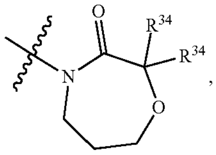,
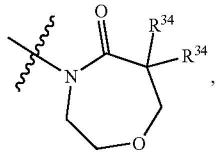,
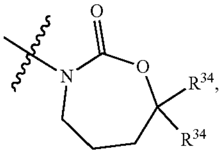
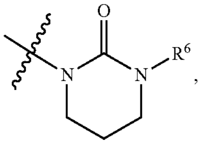, and
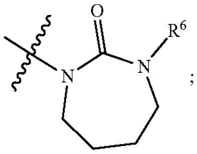;

each occurrence of $R^{34}$ is independently selected from H and $R^{36}$, wherein each occurrence of $R^{36}$ is independently selected from $C_1$-$C_6$ alkyl and $C_3$-$C_6$ cycloalkyl and wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl;

L is $—(C(R^{10})_2)_m—$;

each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl;

m is 0, 1, 2, or 3; and n is 2, 3, or 4;

provided that: when m is 0, $R^4$ is C-linked to the pyrazole ring, when m is 1, $R^4$ is C-linked to L, and when m is 2 or 3, $R^4$ is C-linked to L.

13. The method of claim 3, wherein the compound of Formula I is represented by a formula selected from the group consisting of:

Formula IIA.1

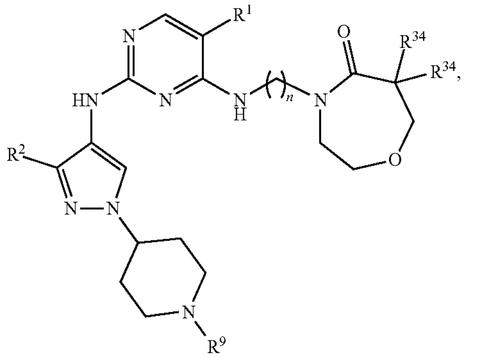

-continued

Formula IIA.2

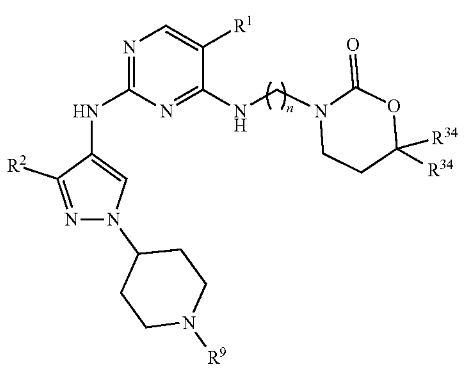

Formula IIA.3

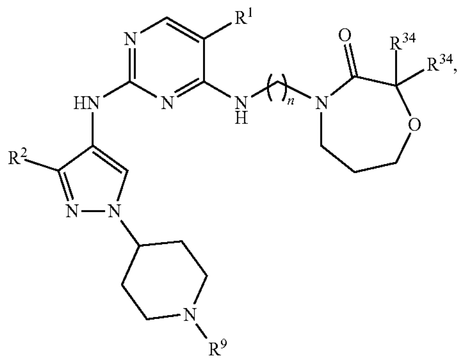

Formula IIA.4

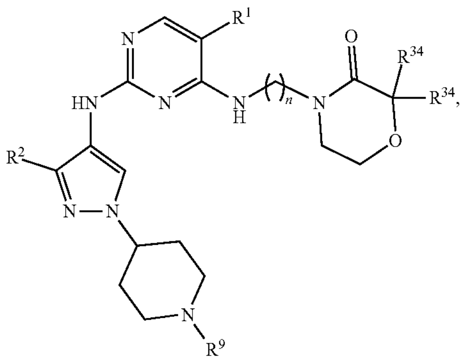

Formula IIA.5

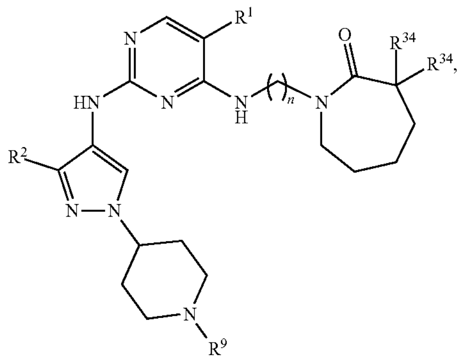

-continued
Formula IIA.6
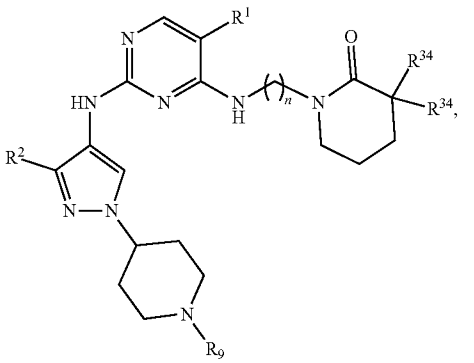
Formula IIA.7
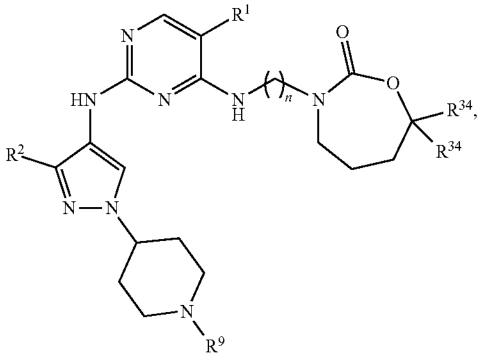
Formula IIA.19
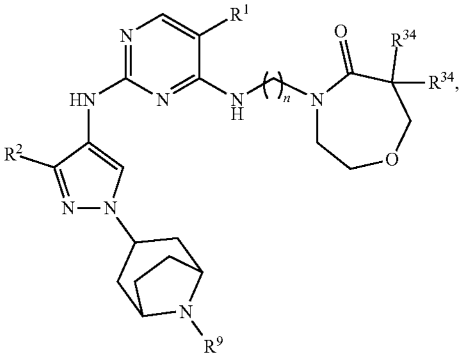
Formula IIA.20
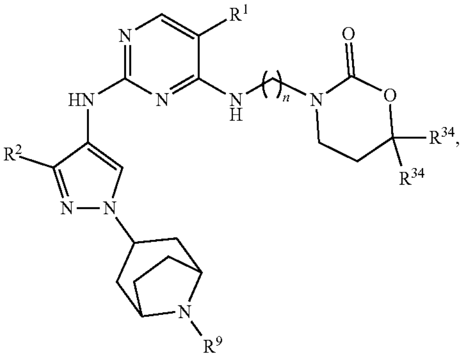
-continued
Formula IIA.21
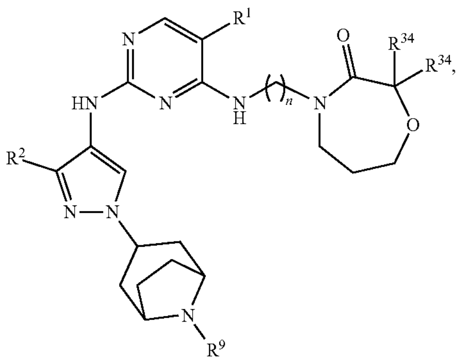
Formula IIA.22
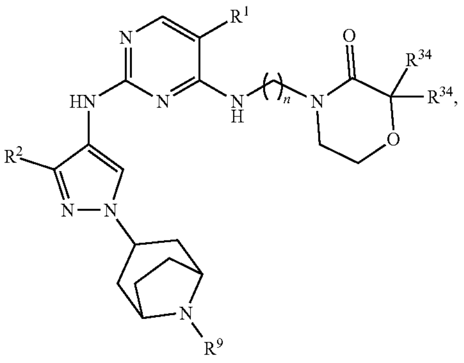
Formula IIA.23
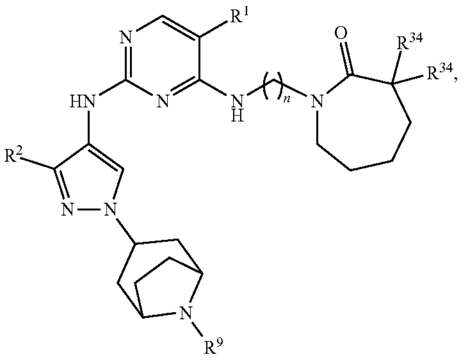
Formula IIA.24
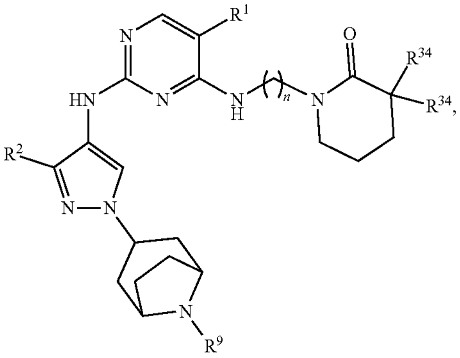
and -continued Formula IIA.25

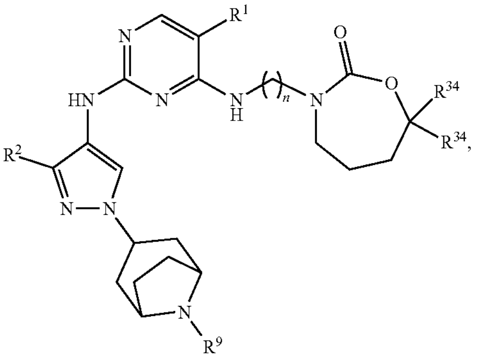

wherein each occurrence of $R^1$ is independently selected from the group consisting of bromo, chloro, $CF_3$, $CF_2H$, and cyclopropyl;

each occurrence of $R^2$ is independently selected from the group consisting of $C_1$-$C_2$ alkyl, $C_3$-$C_4$ cycloalkyl, and halogen;

each occurrence of $R^9$ is independently selected from the group consisting of H, $C_1$-$C_3$ alkyl, and $C_3$-$C_5$ cycloalkyl;

each occurrence of $R^{34}$ is independently selected from the group consisting of H, $C_1$-$C_2$ alkyl, and $C_3$-$C_5$ cycloalkyl; and n is 3.

14. The method of claim 3, wherein the compound of Formula I is selected from the group consisting of: 1-(3-((5-cyclopropyl-2-((1-(1-methylpiperidin-4-yl)-1H-pyrazol-4-yl)amino)pyrimidin-4-yl)amino)propyl)piperidin-2-one, 1-(3-((5-chloro-2-((1-(1-methylpiperidin-4-yl)-1H-pyrazol-4-yl)amino)pyrimidin-4-yl)amino)propyl)piperidin-2-one, 1-(3-((5-chloro-2-((1-(piperidin-4-yl)-1H-pyrazol-4-yl)amino)pyrimidin-4-yl)amino)propyl)piperidin-2-one, 1-(3-((5-chloro-2-((1-(1-isopropylpiperidin-4-yl)-1H-pyrazol-4-yl)amino)pyrimidin-4-yl)amino)propyl)piperidin-2-one, 1-(3-((2-((1-(1-isopropylpiperidin-4-yl)-1H-pyrazol-4-yl)amino)-5-(trifluoromethyl)pyrimidin-4-yl)amino)propyl)piperidin-2-one, 1-(3-((2-((1-(piperidin-4-yl)-1H-pyrazol-4-yl)amino)-5-(trifluoromethyl)pyrimidin-4-yl)amino)propyl)piperidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)piperidin-2-one, 1-(3-((5-bromo-2-((1-(piperidin-4-yl)-1H-pyrazol-4-yl)amino)pyrimidin-4-yl)amino)propyl)piperidin-2-one, 1-(3-((2-((1-(1-methylpiperidin-4-yl)-1H-pyrazol-4-yl)amino)-5-(trifluoromethyl)pyrimidin-4-yl)amino)propyl)piperidin-2-one, 1-(3-((5-chloro-2-((1-(1-isobutylazetidin-3-yl)-1H-pyrazol-4-yl)amino)pyrimidin-4-yl)amino)propyl)piperidin-2-one, 1-(3-((2-((1-(1-isobutylazetidin-3-yl)-1H-pyrazol-4-yl)amino)-5-(trifluoromethyl)pyrimidin-4-yl)amino)propyl)piperidin-2-one, 1-(3-((2-((1-(1-isopropyl-d7-piperidin-4-yl)-1H-pyrazol-4-yl)amino)-5-(trifluoromethyl)pyrimidin-4-yl)amino)propyl)piperidin-2-one, 1-(3-((2-((3-methyl-1-(piperidin-4-yl)-1H-pyrazol-4-yl)amino)-5-(trifluoromethyl)pyrimidin-4-yl)amino)propyl)piperidin-2-one, 1-(3-((2-((1-(1-isopropylpiperidin-4-yl)-3-methyl-1H-pyrazol-4-yl)amino)-5-(trifluoromethyl)pyrimidin-4-yl)amino)propyl)piperidin-2-one, 1-(3-((2-((1-(1-ethylpiperidin-4-yl)-1H-pyrazol-4-yl)amino)-5-(trifluoromethyl)pyridin-4-yl)amino)propyl)piperidin-2-one, 1-(3-((5-bromo-2-((1-(1-isobutylazetidin-3-yl)-1H-pyrazol-4-yl)amino)pyrimidin-4-yl)amino)propyl)piperidin-2-one, rac-(R)-1-(3-((2-((3-methyl-1-(1-methylpyrrolidin-3-yl)-1H-pyrazol-4-yl)amino)-5-(trifluoromethyl)pyrimidin-4-yl)amino)propyl)piperidin-2-one, 1-(3-((2-((3-methyl-1-(3-(pyrrolidin-1-yl)propyl)-1H-pyrazol-4-yl)amino)-5-(trifluoromethyl)pyrimidin-4-yl)amino)propyl)piperidin-2-one, 1-(3-((2-((1-(2-(dimethylamino)ethyl)-3-methyl-1H-pyrazol-4-yl)amino)-5-(trifluoromethyl)pyrimidin-4-yl)amino)propyl)piperidin-2-one, 1-(3-((2-((3-methyl-1-(2-(piperidin-1-yl)ethyl)-1H-pyrazol-4-yl)amino)-5-(trifluoromethyl)pyrimidin-4-yl)amino)propyl)piperidin-2-one, 1-(3-((2-((1-(1-isobutylazetidin-3-yl)-3-methyl-1H-pyrazol-4-yl)amino)-5-(trifluoromethyl)pyrimidin-4-yl)amino)propyl)piperidin-2-one, rac-(R)-1-(3-((5-chloro-2-((3-methyl-1-(1-methylpyrrolidin-3-yl)-1H-pyrazol-4-yl)amino)pyrimidin-4-yl)amino)propyl)piperidin-2-one, rac-(R)-1-(3-((2-((1-(1-ethylpyrrolidin-3-yl)-3-methyl-1H-pyrazol-4-yl)amino)-5-(trifluoromethyl)pyrimidin-4-yl)amino)propyl)piperidin-2-one, 1-(3-((5-bromo-2-((3-methyl-1-(piperidin-4-yl)-1H-pyrazol-4-yl)amino)pyrimidin-4-yl)amino)propyl)piperidin-2-one, 1-(3-((5-chloro-2-((3-methyl-1-(piperidin-4-yl)-1H-pyrazol-4-yl)amino)pyrimidin-4-yl)amino)propyl)piperidin-2-one, 1-(3-((2-((3-methyl-1-(3-(piperidin-1-yl)propyl)-1H-pyrazol-4-yl)amino)-5-(trifluoromethyl)pyrimidin-4-yl)amino)propyl)piperidin-2-one, 1-(3-((2-((3-methyl-1-(2-morpholinoethyl)-1H-pyrazol-4-yl)amino)-5-(trifluoromethyl)pyrimidin-4-yl)amino)propyl)piperidin-2-one, 1-(3-((2-((3-methyl-1-(3-morpholinopropyl)-1H-pyrazol-4-yl)amino)-5-(trifluoromethyl)pyrimidin-4-yl)amino)propyl)piperidin-2-one, 1-(3-((2-((3-methyl-d3-1-(1-methylpiperidin-4-yl)-1H-pyrazol-4-yl)amino)-5-(trifluoromethyl)pyrimidin-4-yl)amino)propyl)piperidin-2-one, 1-(3-((2-((1-(2-(dimethylamino)ethyl)-1H-pyrazol-4-yl)amino)-5-(trifluoromethyl)pyrimidin-4-yl)amino)propyl)piperidin-2-one, 1-(3-((2-((3-methyl-1-(1-(oxetan-3-yl)piperidin-4-yl)-1H-pyrazol-4-yl)amino)-5-(trifluoromethyl)pyrimidin-4-yl)amino)propyl)piperidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)piperidin-2-one, 1-(3-((2-((1-(3-(dimethylamino)propyl)-3-methyl-1H-pyrazol-4-yl)amino)-5-(trifluoromethyl)pyrimidin-4-yl)amino)propyl)piperidin-2-one, rac-(R)-1-(3-((2-((1-(1-isopropylpyrrolidin-3-yl)-3-methyl-1H-pyrazol-4-yl)amino)-5-(trifluoromethyl)pyrimidin-4-yl)amino)propyl)piperidin-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)piperidin-2-one, 1-(3-((5-chloro-2-((1-(1-isobutylazetidin-3-yl)-3-methyl-1H-pyrazol-4-yl)amino)pyrimidin-4-yl)amino)propyl)piperidin-2-one, 1-(3-((5-chloro-2-((3-ethyl-1-(piperidin-4-yl)-1H-pyrazol-4-yl)amino)pyrimidin-4-yl)amino)propyl)piperidin-2-one, 1-(3-((2-((3-ethyl-1-(piperidin-4-yl)-1H-pyrazol-4-yl)amino)-5-(trifluoromethyl)pyrimidin-4-yl)amino)propyl)piperidin-2-one, 1-(3-((5-bromo-2-((3-ethyl-1-(piperidin-4-yl)-1H-pyrazol-4-yl)amino)pyrimidin-4-yl)amino)propyl)piperidin-2-one, 1-(3-((2-((3-ethyl-1-(1-ethylpiperidin-4-yl)-1H-pyrazol-4-yl)amino)-5-(trifluoromethyl)pyrimidin-4-yl)amino)propyl)piperidin-2-one, 1-(3-((2-((3-ethyl-1-(1-isopropylpiperidin-4-yl)-1H-pyrazol-4-yl)amino)-5-(trifluoromethyl)pyrimidin-4-yl)amino)propyl)piperidin-2-one, rac-(R)-1-(3-((5-bromo-2-((3-methyl-1-(1-methylpyrrolidin-3-yl)-1H-pyrazol-4-yl)amino)pyrimidin-4-yl)amino)propyl)piperidin-2-one, 1-(3-((2-((3-methyl-1-(2-(pyrrolidin-1-yl)ethyl)-1H-pyrazol-4-yl)amino)-5-(trifluoromethyl)pyrimidin-4-yl)amino)propyl)

piperidin-2-one, 1-(3-((5-chloro-2-((3-ethyl-1-(1-ethylpiperidin-4-yl)-1H-pyrazol-4-yl)amino)pyrimidin-4-yl)amino)propyl)piperidin-2-one, 1-(3-((2-((3-ethyl-1-(1-methylpiperidin-4-yl)-1H-pyrazol-4-yl)amino)-5-(trifluoromethyl)pyrimidin-4-yl)amino)propyl)piperidin-2-one, 1-(3-((5-iodo-2-((3-methyl-1-(piperidin-4-yl)-1H-pyrazol-4-yl)amino)pyrimidin-4-yl)amino)propyl)piperidin-2-one, 1-(3-((5-bromo-2-((3-methyl-d3-1-(1-methylpiperidin-4-yl)-1H-pyrazol-4-yl)amino)pyrimidin-4-yl)amino)propyl)piperidin-2-one, 1-(3-((5-bromo-2-((1-(1-ethylpiperidin-4-yl)-3-methyl-1H-pyrazol-4-yl)amino)pyrimidin-4-yl)amino)propyl)piperidin-2-one, 1-(3-((5-bromo-2-((3-methyl-1-(1-methylpiperidin-4-yl)-1H-pyrazol-4-yl)amino)pyrimidin-4-yl)amino)propyl)piperidin-2-one, 1-(3-((2-((3-ethyl-1-(1-methyl-d3-piperidin-4-yl)-1H-pyrazol-4-yl)amino)-5-(trifluoromethyl)pyrimidin-4-yl)amino)propyl)piperidin-2-one, 1-(3-((5-bromo-2-((3-ethyl-1-(1-methylpiperidin-4-yl)-1H-pyrazol-4-yl)amino)pyrimidin-4-yl)amino)propyl)piperidin-2-one, 1-(3-((5-bromo-2-((3-ethyl-1-(1-ethylpiperidin-4-yl)-1H-pyrazol-4-yl)amino)pyrimidin-4-yl)amino)propyl)piperidin-2-one, 1-(3-((5-chloro-2-((3-ethyl-1-(1-methylpiperidin-4-yl)-1H-pyrazol-4-yl)amino)pyrimidin-4-yl)amino)propyl)piperidin-2-one, 1-(3-((5-chloro-2-((3-methyl-1-(1-methylpiperidin-4-yl)-1H-pyrazol-4-yl)amino)pyrimidin-4-yl)amino)propyl)piperidin-2-one, 1-(3-((5-chloro-2-((3-methyl-1-(1-(methyl-d3)piperidin-4-yl)-1H-pyrazol-4-yl)amino)pyrimidin-4-yl)amino)propyl)piperidin-2-one, 1-(3-((5-chloro-2-((1-(1-ethylpiperidin-4-yl)-3-methyl-1H-pyrazol-4-yl)amino)pyrimidin-4-yl)amino)propyl)piperidin-2-one, 1-(3-((2-((1-(1-(2-fluoroethyl)piperidin-4-yl)-3-methyl-1H-pyrazol-4-yl)amino)-5-(trifluoromethyl)pyrimidin-4-yl)amino)propyl)piperidin-2-one, rac-(R)-1-(3-((5-bromo-2-((3-methyl-1-(pyrrolidin-3-yl)-1H-pyrazol-4-yl)amino)pyrimidin-4-yl)amino)propyl)piperidin-2-one, rac-(R)-1-(3-((5-bromo-2-((3-methyl-1-(1-methylpyrrolidin-3-yl)-1H-pyrazol-4-yl)amino)pyrimidin-4-yl)amino)propyl)piperidin-2-one, 1-(3-((5-bromo-2-((3-methyl-1-(2-(pyrrolidin-1-yl)ethyl)-1H-pyrazol-4-yl)amino)pyrimidin-4-yl)amino)propyl)piperidin-2-one, 1-(3-((5-bromo-2-((3-methyl-1-(2-morpholinoethyl)-1H-pyrazol-4-yl)amino)pyrimidin-4-yl)amino)propyl)piperidin-2-one, rac-(R)-1-(3-((5-bromo-2-((1-(1-ethylpyrrolidin-3-yl)-3-methyl-1H-pyrazol-4-yl)amino)pyrimidin-4-yl)amino)propyl)piperidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)piperidin-2-one, rac-(R)-1-(3-((2-((1-(1-ethylpyrrolidin-3-yl)-3-methyl-1H-pyrazol-4-yl)amino)-5-(trifluoromethyl)pyrimidin-4-yl)amino)propyl)piperidin-2-one, 2-methyl-2-(3-methyl-4-((4-((3-(2-oxopiperidin-1-yl)propyl)amino)-5-(trifluoromethyl)pyrimidin-2-yl)amino)-1H-pyrazol-1-yl)propanamide, 3-(3-((2-((1-(1-isopropylpiperidin-4-yl)-3-methyl-1H-pyrazol-4-yl)amino)-5-(trifluoromethyl)pyrimidin-4-yl)amino)propyl)-1,3-oxazinan-2-one, 3-(3-((2-((3-ethyl-1-(1-isopropylpiperidin-4-yl)-1H-pyrazol-4-yl)amino)-5-(trifluoromethyl)pyrimidin-4-yl)amino)propyl)-1,3-oxazinan-2-one, 3-(3-((5-bromo-2-((1-(1-isopropylpiperidin-4-yl)-3-methyl-1H-pyrazol-4-yl)amino)pyrimidin-4-yl)amino)propyl)-1,3-oxazinan-2-one, 3-(3-((5-chloro-2-((1-(1-isopropylpiperidin-4-yl)-3-methyl-1H-pyrazol-4-yl)amino)pyrimidin-4-yl)amino)propyl)-1,3-oxazinan-2-one, 3-(3-((5-chloro-2-((3-ethyl-1-(1-isopropylpiperidin-4-yl)-1H-pyrazol-4-yl)amino)pyrimidin-4-yl)amino)propyl)-1,3-oxazinan-2-one, 4-(3-((2-((1-(1-isopropylpiperidin-4-yl)-1H-pyrazol-4-yl)amino)-5-(trifluoromethyl)pyrimidin-4-yl)amino)propyl)morpholin-3-one, 4-(3-((5-cyclopropyl-2-((1-(1-isopropylpiperidin-4-yl)-3-methyl-1H-pyrazol-4-yl)amino)pyrimidin-4-yl)amino)propyl)morpholin-3-one, 4-(3-((5-cyclopropyl-2-((3-ethyl-1-(1-isopropylpiperidin-4-yl)-1H-pyrazol-4-yl)amino)pyrimidin-4-yl)amino)propyl)morpholin-3-one, 1-(3-((2-((1-(piperidin-4-yl)-1H-pyrazol-4-yl)amino)-5-(trifluoromethyl)pyrimidin-4-yl)amino)propyl)azepan-2-one, 1-(3-((2-((1-(1-methylpiperidin-4-yl)-1H-pyrazol-4-yl)amino)-5-(trifluoromethyl)pyrimidin-4-yl)amino)propyl)azepan-2-one, 1-(3-((2-((3-methyl-1-(1-methylpiperidin-4-yl)-1H-pyrazol-4-yl)amino)-5-(trifluoromethyl)pyrimidin-4-yl)amino)propyl)azepan-2-one, 1-(3-((5-chloro-2-((3-methyl-1-(1-methylpiperidin-4-yl)-1H-pyrazol-4-yl)amino)pyrimidin-4-yl)amino)propyl)azepan-2-one, 1-(3-((5-chloro-2-((1-(1-methylpiperidin-4-yl)-1H-pyrazol-4-yl)amino)pyrimidin-4-yl)amino)propyl)azepan-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)pyrrolidin-2-one, 1-(3-((2-((3-methyl-1-(piperidin-4-yl)-1H-pyrazol-4-yl)amino)-5-(trifluoromethyl)pyrimidin-4-yl)amino)propyl)azepan-2-one, 1-(3-((5-cyclopropyl-2-((1-(1-methylpiperidin-4-yl)-1H-pyrazol-4-yl)amino)pyrimidin-4-yl)amino)propyl)pyrrolidin-2-one, 1-(3-((2-((1-(1-isopropylpiperidin-4-yl)-3-methyl-1H-pyrazol-4-yl)amino)-5-(trifluoromethyl)pyrimidin-4-yl)amino)propyl)azepan-2-one, 1-(3-((5-chloro-2-((3-methyl-1-(piperidin-4-yl)-1H-pyrazol-4-yl)amino)pyrimidin-4-yl)amino)propyl)azepan-2-one, 1-(3-((5-chloro-2-((1-(1-isopropylpiperidin-4-yl)-3-methyl-1H-pyrazol-4-yl)amino)pyrimidin-4-yl)amino)propyl)azepan-2-one, 1-(3-((2-((1-(1-isopropylpiperidin-4-yl)-1H-pyrazol-4-yl)amino)-5-(trifluoromethyl)pyrimidin-4-yl)amino)propyl)azepan-2-one, 1-(3-((2-((1-(1-isobutylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)azepan-2-one, 1-(3-((2-((3-methyl-1-(1-(oxetan-3-yl)piperidin-4-yl)-1H-pyrazol-4-yl)amino)-5-(trifluoromethyl)pyrimidin-4-yl)amino)propyl)azepan-2-one, 1-(3-((2-((1-(1-cyclobutylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-cyclopentylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-(sec-butyl)piperidin-4-yl)-3-methyl-1H-pyrazol-4-yl)amino)-5-(trifluoromethyl)pyrimidin-4-yl)amino)propyl)azepan-2-one, (S)-1-(3-((2-((1-(1-isopropylpyrrolidin-3-yl)-3-methyl-1H-pyrazol-4-yl)amino)-5-(trifluoromethyl)pyrimidin-4-yl)amino)propyl)azepan-2-one, 1-(3-((2-((1-(2-morpholinoethyl)-1H-pyrazol-4-yl)amino)-5-(trifluoromethyl)pyrimidin-4-yl)amino)propyl)azepan-2-one, 1-(3-((2-((1-(1-isobutylazetidin-3-yl)-1H-pyrazol-4-yl)amino)-5-(trifluoromethyl)pyrimidin-4-yl)amino)propyl)azepan-2-one, 1-(3-((2-((3-methyl-1-(2-morpholinoethyl)-1H-pyrazol-4-yl)amino)-5-(trifluoromethyl)pyrimidin-4-yl)amino)propyl)azepan-2-one, 1-(3-((2-((3-methyl-1-(3-(pyrrolidin-1-yl)propyl)-1H-pyrazol-4-yl)amino)-5-(trifluoromethyl)pyrimidin-4-yl)amino)propyl)azepan-2-one, 1-(3-((2-((3-methyl-1-(3-morpholinopropyl)-1H-pyrazol-4-yl)amino)-5-(trifluoromethyl)pyrimidin-4-yl)amino)propyl)azepan-2-one, 1-(3-((2-((3-methyl-1-(1-methyl-d3-piperidin-4-yl)-1H-pyrazol-4-yl)amino)-5-(trifluoromethyl)pyrimidin-4-yl)amino)propyl)azepan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-3-one, 1-(3-((2-((3-methyl-1-

(piperidin-4-yl)-1H-pyrazol-4-yl)amino)-5-(trifluoromethyl)pyrimidin-4-yl)amino)propyl)pyrrolidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)pyrrolidin-2-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-3-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 4-(3-((2-((1-(1-ethylpiperidin-4-yl)-3-methyl-1H-pyrazol-4-yl)amino)-5-(trifluoromethyl)pyrimidin-4-yl)amino)propyl)-1,4-oxazepan-3-one, 4-(3-((2-((1-(1-isopropylpiperidin-4-yl)-3-methyl-1H-pyrazol-4-yl)amino)-5-(trifluoromethyl)pyrimidin-4-yl)amino)propyl)-1,4-oxazepan-3-one, 4-(3-((2-((3-ethyl-1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((5-chloro-2-((1-(1-isopropylpiperidin-4-yl)-3-methyl-1H-pyrazol-4-yl)amino)pyrimidin-4-yl)amino)propyl)-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-3-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-3-one, (R)-4-(3-((5-chloro-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((1-(1-isopropylpiperidin-4-yl)-3-methyl-1H-pyrazol-4-yl)amino)pyrimidin-4-yl)amino)propyl)-1,4-oxazepan-3-one, 4-(3-((5-cyclopropyl-2-((3-methyl-1-(3-morpholinopropyl)-1H-pyrazol-4-yl)amino)pyrimidin-4-yl)amino)propyl)-1,4-oxazepan-3-one, 4-(3-((5-cyclopropyl-2-((1-(2-(dimethylamino)ethyl)-3-methyl-1H-pyrazol-4-yl)amino)pyrimidin-4-yl)amino)propyl)-1,4-oxazepan-3-one, 4-(3-((2-((1-(2-(dimethylamino)ethyl)-3-methyl-1H-pyrazol-4-yl)amino)-5-(trifluoromethyl)pyrimidin-4-yl)amino)propyl)-1,4-oxazepan-3-one, (R)-4-(3-((5-bromo-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((3-ethyl-1-(1-methylpiperidin-4-yl)-1H-pyrazol-4-yl)amino)pyrimidin-4-yl)amino)propyl)-1,4-oxazepan-3-one, 4-(3-((5-chloro-2-((3-methyl-1-(3-morpholinopropyl)-1H-pyrazol-4-yl)amino)pyrimidin-4-yl)amino)propyl)-1,4-oxazepan-3-one, 4-(3-((5-bromo-2-((3-methyl-1-(3-morpholinopropyl)-1H-pyrazol-4-yl)amino)pyrimidin-4-yl)amino)propyl)-1,4-oxazepan-3-one, 4-(3-((5-bromo-2-((1-(2-(dimethylamino)ethyl)-3-methyl-1H-pyrazol-4-yl)amino)pyrimidin-4-yl)amino)propyl)-1,4-oxazepan-3-one, 4-(3-((5-chloro-2-((1-(2-(dimethylamino)ethyl)-3-methyl-1H-pyrazol-4-yl)amino)pyrimidin-4-yl)amino)propyl)-1,4-oxazepan-3-one, 4-(3-((2-((1-(2-(diethylamino)ethyl)-3-methyl-1H-pyrazol-4-yl)amino)-5-(trifluoromethyl)pyrimidin-4-yl)amino)propyl)-1,4-oxazepan-3-one, 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanamide, 3-(3-((2-((4-methyl-1-(1-methylpiperidin-4-yl)-1H-pyrazol-3-yl)amino)-5-(trifluoromethyl)pyrimidin-4-yl)amino)propyl)-1,3-oxazinan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-5-one, 1-(3-((2-((1-(1-isobutylazetidin-3-yl)-3-methyl-1H-pyrazol-4-yl)amino)-5-(trifluoromethyl)pyrimidin-4-yl)amino)propyl)pyrrolidin-2-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-5-one, 4-(3-((2-((1-(1-ethylpiperidin-4-yl)-3-methyl-1H-pyrazol-4-yl)amino)-5-(trifluoromethyl)pyrimidin-4-yl)amino)propyl)-1,4-oxazepan-5-one, 4-(3-((2-((1-(1-isopropylpiperidin-4-yl)-3-methyl-1H-pyrazol-4-yl)amino)-5-(trifluoromethyl)pyrimidin-4-yl)amino)propyl)-1,4-oxazepan-5-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-5-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, (R)-4-(3-((5-chloro-2-((3-methyl-1-(1-methylpyrrolidin-3-yl)-1H-pyrazol-4-yl)amino)pyrimidin-4-yl)amino)propyl)-1,4-oxazepan-5-one, 4-(3-((5-chloro-2-((3-methyl-1-(3-morpholinopropyl)-1H-pyrazol-4-yl)amino)pyrimidin-4-yl)amino)propyl)-1,4-oxazepan-5-one, 4-(3-((2-((3-ethyl-1-(1-methylpiperidin-4-yl)-1H-pyrazol-4-yl)amino)-5-(trifluoromethyl)pyrimidin-4-yl)amino)propyl)-1,4-oxazepan-5-one, 4-(3-((2-((1-(2-(dimethylamino)ethyl)-3-methyl-1H-pyrazol-4-yl)amino)-5-(trifluoromethyl)pyrimidin-4-yl)amino)propyl)-1,4-oxazepan-5-one, (R)-4-(3-((5-bromo-2-((3-methyl-1-(1-methylpyrrolidin-3-yl)-1H-pyrazol-4-yl)amino)pyrimidin-4-yl)amino)propyl)-1,4-oxazepan-5-one, 4-(3-((5-cyclopropyl-2-((3-methyl-1-(3-morpholinopropyl)-1H-pyrazol-4-yl)amino)pyrimidin-4-yl)amino)propyl)-1,4-oxazepan-5-one, 4-(3-((5-cyclopropyl-2-((1-(2-(dimethylamino)ethyl)-3-methyl-1H-pyrazol-4-yl)amino)pyrimidin-4-yl)amino)propyl)-1,4-oxazepan-5-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-5-one, 4-(3-((5-cyclopropyl-2-((1-(1-ethylpiperidin-4-yl)-3-methyl-1H-pyrazol-4-yl)amino)pyrimidin-4-yl)amino)propyl)-1,4-oxazepan-5-one, 4-(3-((5-chloro-2-((1-(1-isopropylpiperidin-4-yl)-3-methyl-1H-pyrazol-4-yl)amino)pyrimidin-4-yl)amino)propyl)-1,4-oxazepan-5-one, 4-(3-((5-bromo-2-((1-(2-(dimethylamino)ethyl)-3-methyl-1H-pyrazol-4-yl)amino)pyrimidin-4-yl)amino)propyl)-1,4-oxazepan-5-one, 2-methyl-2-(3-methyl-4-((4-((3-(5-oxo-1,4-oxazepan-4-yl)propyl)amino)-5-(trifluoromethyl)pyrimidin-2-yl)amino)-1H-pyrazol-1-yl)propanamide, 4-(3-((2-((1-(2-(diethylamino)ethyl)-3-methyl-1H-pyrazol-4-yl)amino)-5-(trifluoromethyl)pyrimidin-4-yl)amino)propyl)-1,4-oxazepan-5-one, 1-(3-((5-bromo-2-((1-(1-isobutylazetidin-3-yl)-3-methyl-1H-pyrazol-4-yl)amino)pyrimidin-4-yl)amino)propyl)pyrrolidin-2-one, (R)-1-(3-((5-chloro-2-((3-methyl-1-(pyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-1H-pyrazol-4-yl)amino)pyrimidin-4-yl)amino)propyl)pyrrolidin-2-one, (R)-1-(3-((5-chloro-2-((3-methyl-1-(1-methylpyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-3-methyl-1H-pyrazol-4-yl)amino)pyrimidin-4-yl)amino)propyl)pyrrolidin-2-one, 1-(3-((5-chloro-2-((3-methyl-1-(2-(pyrrolidin-1-yl)ethyl)-1H-pyrazol-4-yl)amino)pyrimidin-4-yl)amino)propyl)pyrrolidin-2-one, 1-(3-((5-chloro-2-((3-methyl-1-(2-morpholinoethyl)-1H-pyrazol-4-yl)amino)pyrimidin-4-yl)amino)propyl)pyrrolidin-2-one, (R)-1-(3-((5-bromo-2-((3-methyl-1-(pyrrolidin-3-yl)-1H-pyrazol-4-yl)amino)pyrimidin-4-yl)amino)propyl)pyrrolidin-2-one, 1-(3-((5-bromo-2-((1-(1-isobutylazetidin-3-yl)-1H-pyrazol-4-yl)amino)pyrimidin-4-yl)amino)propyl)pyrrolidin-2-one, 1-(3-((2-((1-(1-methylpiperidin-4-yl)-1H-pyrazol-4-yl)amino)-5-(trifluoromethyl)pyrimidin-4-yl)amino)propyl)pyrrolidin-2-one, (S)-1-(3-((2-((3-methyl-1-(pyrrolidin-3-yl)-1H-pyrazol-4-yl)amino)-5-(trifluoromethyl)pyrimidin- 4-yl)amino)propyl)pyrrolidin-2-one, (S)-1-(3-((2-((1-(1-ethylpyrrolidin-3-yl)-3-methyl-1H-pyrazol-4-yl)amino)-5-(trifluoromethyl)pyrimidin-4-yl)amino)propyl)pyrrolidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)pyrrolidin-2-one, 1-(3-((2-((1-(1-isobutylazetidin-3-yl)-1H-pyrazol-4-yl)amino)-5-(trifluoromethyl)pyrimidin-4-yl)amino)propyl)pyrrolidin-2-one, 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanenitrile, 1-(3-((2-((4-methyl-1-(1-methylpiperidin-4-yl)-1H-pyrazol-3-yl)amino)-5-(trifluoromethyl)pyridin-4-yl)amino)propyl)piperidin-2-one, 1-(3-((2-((1-(1-methylpiperidin-4-yl)-1H-pyrazol-3-yl)amino)-5-(trifluoromethyl)pyridin-4-yl)amino)propyl)piperidin-2-one, 4-(3-((2-((1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((2-((1-(1-methylpiperidin-4-yl)-1H-pyrazol-4-yl)amino)-5-(trifluoromethyl)pyrimidin-4-yl)amino)propyl)-1,4-oxazepan-5-one, 3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazinan-2-one, 4-(3-((2-((2-(1-methylpiperidin-4-yl)-2H-1,2,3-triazol-4-yl)amino)-5-(trifluoromethyl)pyrimidin-4-yl)amino)propyl)-1,4-oxazepan-3-one, 4-(3-((2-((2-(1-methylpiperidin-4-yl)-2H-1,2,3-triazol-4-yl)amino)-5-(trifluoromethyl)pyrimidin-4-yl)amino)propyl)-1,4-oxazepan-5-one, 3-(3-((2-((2-(1-methylpiperidin-4-yl)-2H-1,2,3-triazol-4-yl)amino)-5-(trifluoromethyl)pyrimidin-4-yl)amino)propyl)-1,3-oxazinan-2-one, 4-(3-((2-((1-(1-methylpiperidin-4-yl)-1H-1,2,3-triazol-4-yl)amino)-5-(trifluoromethyl)pyrimidin-4-yl)amino)propyl)-1,4-oxazepan-3-one, 4-(3-((2-((1-(1-methylpiperidin-4-yl)-1H-1,2,3-triazol-4-yl)amino)-5-(trifluoromethyl)pyrimidin-4-yl)amino)propyl)-1,4-oxazepan-5-one, 3-(3-((2-((1-(1-methylpiperidin-4-yl)-1H-1,2,3-triazol-4-yl)amino)-5-(trifluoromethyl)pyrimidin-4-yl)amino)propyl)-1,3-oxazinan-2-one, 4-(3-((2-((2-(1-methylpiperidin-4-yl) thiazol-4-yl)amino)-5-(trifluoromethyl)pyrimidin-4-yl)amino)propyl)-1,4-oxazepan-3-one, 4-(3-((2-((2-(1-methylpiperidin-4-yl) thiazol-4-yl)amino)-5-(trifluoromethyl)pyrimidin-4-yl)amino)propyl)-1,4-oxazepan-5-one, 3-(3-((2-((2-(1-methylpiperidin-4-yl) thiazol-4-yl)amino)-5-(trifluoromethyl)pyrimidin-4-yl)amino)propyl)-1,3-oxazinan-2-one, 4-(3-((2-((2-(1-methylpiperidin-4-yl) oxazol-4-yl)amino)-5-(trifluoromethyl)pyrimidin-4-yl)amino)propyl)-1,4-oxazepan-3-one, 4-(3-((2-((2-(1-methylpiperidin-4-yl) oxazol-4-yl)amino)-5-(trifluoromethyl)pyrimidin-4-yl)amino)propyl)-1,4-oxazepan-5-one, 3-(3-((2-((2-(1-methylpiperidin-4-yl) oxazol-4-yl)amino)-5-(trifluoromethyl)pyrimidin-4-yl)amino)propyl)-1,3-oxazinan-2-one, 4-(3-((2-((2-(1-methylpiperidin-4-yl) thiazol-5-yl)amino)-5-(trifluoromethyl)pyrimidin-4-yl)amino)propyl)-1,4-oxazepan-3-one, 4-(3-((2-((2-(1-methylpiperidin-4-yl) thiazol-5-yl)amino)-5-(trifluoromethyl)pyrimidin-4-yl)amino)propyl)-1,4-oxazepan-5-one, 3-(3-((2-((2-(1-methylpiperidin-4-yl) thiazol-5-yl)amino)-5-(trifluoromethyl)pyrimidin-4-yl)amino)propyl)-1,3-oxazinan-2-one, 4-(3-((2-((2-(1-methylpiperidin-4-yl) oxazol-5-yl)amino)-5-(trifluoromethyl)pyrimidin-4-yl)amino)propyl)-1,4-oxazepan-3-one, 4-(3-((2-((2-(1-methylpiperidin-4-yl) oxazol-5-yl)amino)-5-(trifluoromethyl)pyrimidin-4-yl)amino)propyl)-1,4-oxazepan-5-one, 3-(3-((2-((2-(1-methylpiperidin-4-yl) oxazol-5-yl)amino)-5-(trifluoromethyl)pyrimidin-4-yl)amino)propyl)-1,3-oxazinan-2-one, 4-(3-((2-((5-methyl-2-(1-methylpiperidin-4-yl)-2H-1,2,3-triazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl)-2H-1,2,3-triazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl)-2H-1,2,3-triazol-4-yl)amino)-5-(trifluoromethyl)pyrimidin-4-yl)amino)propyl)-1,3-oxazinan-2-one, 4-(3-((2-((5-methyl-2-(1-methylpiperidin-4-yl) thiazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl) thiazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl) thiazol-4-yl)amino)-5-(trifluoromethyl)pyrimidin-4-yl)amino)propyl)-1,3-oxazinan-2-one, 4-(3-((2-((5-methyl-2-(1-methylpiperidin-4-yl) oxazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl) oxazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl) oxazol-4-yl)amino)-5-(trifluoromethyl)pyrimidin-4-yl)amino)propyl)-1,3-oxazinan-2-one, 4-(3-((2-((4-methyl-2-(1-methylpiperidin-4-yl) thiazol-5-yl)amino)-5-(trifluoromethyl)pyrimidin-4-yl)amino)propyl)-1,4-oxazepan-3-one, 4-(3-((2-((4-methyl-2-(1-methylpiperidin-4-yl) thiazol-5-yl)amino)-5-(trifluoromethyl)pyrimidin-4-yl)amino)propyl)-1,4-oxazepan-5-one, 3-(3-((2-((4-methyl-2-(1-methylpiperidin-4-yl) thiazol-5-yl)amino)-5-(trifluoromethyl)pyrimidin-4-yl)amino)propyl)-1,3-oxazinan-2-one, 4-(3-((2-((4-methyl-2-(1-methylpiperidin-4-yl) oxazol-5-yl)amino)-5-(trifluoromethyl)pyrimidin-4-yl)amino)propyl)-1,4-oxazepan-3-one, 4-(3-((2-((4-methyl-2-(1-methylpiperidin-4-yl) oxazol-5-yl)amino)-5-(trifluoromethyl)pyrimidin-4-yl)amino)propyl)-1,4-oxazepan-5-one, 3-(3-((2-((4-methyl-2-(1-methylpiperidin-4-yl) oxazol-5-yl)amino)-5-(trifluoromethyl)pyrimidin-4-yl)amino)propyl)-1,3-oxazinan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)morpholin-3-one, 1-methyl-3-(3-((2-((3-methyl-1-(1-methylpiperidin-4-yl)-1H-pyrazol-4-yl)amino)-5-(trifluoromethyl)pyrimidin-4-yl)amino)propyl)tetrahydropyrimidin-2(1H)-one, 3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazepan-2-one, 1-methyl-3-(3-((2-((3-methyl-1-(1-methylpiperidin-4-yl)-1H-pyrazol-4-yl)amino)-5-(trifluoromethyl)pyrimidin-4-yl)amino)propyl)-1,3-diazepan-2-one, 1-methyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-diazepan-5-one, 4-methyl-1-(3-((2-((3-methyl-1-(1-methylpiperidin-4-yl)-1H-pyrazol-4-yl)amino)-5-(trifluoromethyl)pyrimidin-4-yl)amino)propyl)-1,4-diazepan-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)piperidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azepan-2-one, 4-methyl-1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-diazepan-2-one, 3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-oxazinan-2-one, 4-(3-((2-((3-methyl-1-(8-methyl-8-azabicyclo[3.2.1]octan-3-yl)-1H-pyrazol-4-yl)amino)-5-

(trifluoromethyl)pyrimidin-4-yl)amino)propyl)morpholin-3-one, 1-methyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)tetrahydropyrimidin-2(1H)-one, 3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-oxazepan-2-one, 1-methyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-diazepan-2-one, 1-methyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-diazepan-5-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-3-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-5-one, 1-(3-((2-((3-methyl-1-(1-methylpyrrolidin-3-yl)-1H-pyrazol-4-yl)amino)-5-(trifluoromethyl)pyrimidin-4-yl)amino)propyl)piperidin-2-one, 1-(3-((2-((3-methyl-1-(1-methylpyrrolidin-3-yl)-1H-pyrazol-4-yl)amino)-5-(trifluoromethyl)pyrimidin-4-yl)amino)propyl)azepan-2-one, 4-methyl-1-(3-((2-((3-methyl-1-(1-methylpyrrolidin-3-yl)-1H-pyrazol-4-yl)amino)-5-(trifluoromethyl)pyrimidin-4-yl)amino)propyl)-1,4-diazepan-2-one, 4-(3-((2-((3-methyl-1-(1-methylpyrrolidin-3-yl)-1H-pyrazol-4-yl)amino)-5-(trifluoromethyl)pyrimidin-4-yl)amino)propyl)morpholin-3-one, 1-methyl-3-(3-((2-((3-methyl-1-(1-methylpyrrolidin-3-yl)-1H-pyrazol-4-yl)amino)-5-(trifluoromethyl)pyrimidin-4-yl)amino)propyl)tetrahydropyrimidin-2(1H)-one, 3-(3-((2-((3-methyl-1-(1-methylpyrrolidin-3-yl)-1H-pyrazol-4-yl)amino)-5-(trifluoromethyl)pyrimidin-4-yl)amino)propyl)-1,3-oxazepan-2-one, 1-methyl-3-(3-((2-((3-methyl-1-(1-methylpyrrolidin-3-yl)-1H-pyrazol-4-yl)amino)-5-(trifluoromethyl)pyrimidin-4-yl)amino)propyl)-1,3-diazepan-2-one, 1-methyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-diazepan-5-one, 4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(1-methylpyrrolidin-3-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-5-one, 1-(3-((2-((3-methyl-1-(1-methylpyrrolidin-3-yl)-1H-pyrazol-4-yl)amino)-5-(trifluoromethyl)pyrimidin-4-yl)amino)propyl)azetidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)azetidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(1-methylpyrrolidin-3-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(1-methylpiperidin-4-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azetidin-2-one, 4-(3-((5-(difluoromethyl)-2-((3-methyl-1-(1-methylpiperidin-4-yl)-1H-pyrazol-4-yl)amino)pyrimidin-4-yl)amino)propyl)-1,4-oxazepan-3-one, 4-(3-((5-(difluoromethyl)-2-((3-methyl-1-(1-methylpiperidin-4-yl)-1H-pyrazol-4-yl)amino)pyrimidin-4-yl)amino)propyl)-1,4-oxazepan-5-one, 3-(3-((5-(difluoromethyl)-2-((3-methyl-1-(1-methylpiperidin-4-yl)-1H-pyrazol-4-yl)amino)pyrimidin-4-yl)amino)propyl)-1,3-oxazinan-2-one, 4-(3-((5-(difluoromethyl)-2-((1-(1-methylpiperidin-4-yl)-1H-pyrazol-4-yl)amino)pyrimidin-4-yl)amino)propyl)-1,4-oxazepan-3-one, 4-(3-((5-(difluoromethyl)-2-((1-(1-methylpiperidin-4-yl)-1H-pyrazol-4-yl)amino)pyrimidin-4-yl)amino)propyl)-1,4-oxazepan-5-one, 3-(3-((5-(difluoromethyl)-2-((1-(1-methylpiperidin-4-yl)-1H-pyrazol-4-yl)amino)pyrimidin-4-yl)amino)propyl)-1,3-oxazinan-2-one, 4-(3-((5-(difluoromethyl)-2-((3-methyl-1-(1-methylpiperidin-4-yl)-1H-pyrazol-4-yl)amino)pyrimidin-4-yl)amino)propyl)morpholin-3-one, 1-(3-((5-(difluoromethyl)-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-(difluoromethyl)-2-((3-methyl-1-(1-methylpiperidin-4-yl)-1H-pyrazol-4-yl)amino)pyrimidin-4-yl)amino)propyl)-1,3-oxazepan-2-one, 1-(3-((5-(difluoromethyl)-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-(difluoromethyl)-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-(difluoromethyl)-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-(difluoromethyl)-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-(difluoromethyl)-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-(difluoromethyl)-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-(difluoromethyl)-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-(difluoromethyl)-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-(difluoromethyl)-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-(difluoromethyl)-2-((3-methyl-1-(1-methylpyrrolidin-3-yl)-1H-pyrazol-4-yl)amino)pyrimidin-4-yl)amino)propyl)azetidin-2-one, 1-(3-((5-(difluoromethyl)-2-((3-methyl-1-(1-methylpiperidin-4-yl)-1H-pyrazol-4-yl)amino)pyrimidin-4-yl)amino)propyl)azetidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-(difluoromethyl)-2-((3-methyl-1-(1-methylpyrrolidin-3-yl)-1H-pyrazol-4-yl)amino)pyrimidin-4-yl)amino)propyl)-3,3-dimethylazetidin-2-one, 1-(3-((5-(difluoromethyl)-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-3,3-dimethylazetidin-2-one, 4-(3-((5-bromo-2-((3-methyl-1-(1-methylpiperidin-4-yl)-1H-pyrazol-4-yl)amino)pyrimidin-4-yl)amino)propyl)-1,4-oxazepan-3-one, 4-(3-((5-bromo-2-((3-methyl-1-(1-methylpiperidin-4-yl)-1H-pyrazol-4-yl)amino)pyrimidin-4-yl)amino)propyl)-1,4-oxazepan-5-one, 3-(3-((5-bromo-2-((3-methyl-1-(1-methylpiperidin-4-yl)-1H-pyrazol-4-yl)amino)pyrimidin-4-yl)amino)propyl)-1,3-oxazinan-2-one, 4-(3-((5-bromo-2-((1-(1-methylpiperidin-4-yl)-1H-pyrazol-4-yl)amino)pyrimidin-4-yl)amino)propyl)-1,4-oxazepan-3-one, 4-(3-((5-bromo-2-((1-(1-methylpiperidin-4-yl)-1H-pyrazol-4-yl)amino)pyrimidin-4-yl)amino)propyl)-1,4-oxazepan-5-one, 3-(3-((5-bromo-2-((1-(1-methylpiperidin-4-yl)-1H-pyrazol-4-yl)amino)pyrimidin-4-yl)amino)propyl)-1,3-oxazinan-2-one, 4-(3-((5-bromo-2-((3-methyl-1-(1-methylpiperidin-4-yl)-1H-pyrazol-4-yl)amino)pyrimidin-4-yl)amino)propyl)morpholin-3-one, 1-(3-((5-bromo-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-bromo-2-((3-methyl-1-(1-methylpiperidin-4-yl)-1H-pyrazol-4-yl)amino)pyrimidin-4-yl)amino)propyl)-1,3-oxazepan-2-one, 1-(3-((5-bromo-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-bromo-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-bromo-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-bromo-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-bromo-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-bromo-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-bromo-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-bromo-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-bromo-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-bromo-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-bromo-2-((3-methyl-1-(1-methylpyrrolidin-3-yl)-1H-pyrazol-4-yl)amino)pyrimidin-4-yl)amino)propyl)azetidin-2-one, 1-(3-((5-bromo-2-((3-methyl-1-(1-methylpiperidin-4-yl)-1H-pyrazol-4-yl)amino)pyrimidin-4-yl)amino)propyl)azetidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-bromo-2-((3-methyl-1-(1-methylpyrrolidin-3-yl)-1H-pyrazol-4-yl)amino)pyrimidin-4-yl)amino)propyl)-3,3-dimethylazetidin-2-one, 1-(3-((5-bromo-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-3,3-dimethylazetidin-2-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-3-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-5-one, 3-(3-((5-chloro-2-((3-methyl-1-(1-methylpiperidin-4-yl)-1H-pyrazol-4-yl)amino)pyrimidin-4-yl)amino)propyl)-1,3-oxazinan-2-one, 4-(3-((5-chloro-2-((1-(1-methylpiperidin-4-yl)-1H-pyrazol-4-yl)amino)pyrimidin-4-yl)amino)propyl)-1,4-oxazepan-3-one, 4-(3-((5-chloro-2-((1-(1-methylpiperidin-4-yl)-1H-pyrazol-4-yl)amino)pyrimidin-4-yl)amino)propyl)-1,4-oxazepan-5-one, 3-(3-((5-chloro-2-((1-(1-methylpiperidin-4-yl)-1H-pyrazol-4-yl)amino)pyrimidin-4-yl)amino)propyl)-1,3-oxazinan-2-one, 4-(3-((5-chloro-2-((3-methyl-1-(1-methylpiperidin-4-yl)-1H-pyrazol-4-yl)amino)pyrimidin-4-yl)amino)propyl)morpholin-3-one, 1-(3-((5-chloro-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-chloro-2-((3-methyl-1-(1-methylpiperidin-4-yl)-1H-pyrazol-4-yl)amino)pyrimidin-4-yl)amino)propyl)-1,3-oxazepan-2-one, 1-(3-((5-chloro-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-chloro-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-chloro-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-chloro-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-chloro-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-chloro-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-chloro-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-chloro-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-chloro-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-chloro-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-chloro-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-chloro-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-chloro-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-chloro-2-((3-methyl-1-(1-methylpiperidin-4-yl)-1H-pyrazol-4-yl)amino) pyrimidin-4-yl)amino)propyl)-6,6-dimethyl-1,4-oxazepan-5-one, 3-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-6,6-dimethyl-1,3-oxazinan-2-one, 4-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-2,2-dimethyl-1,4-oxazepan-3-one, 4-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-6,6-dimethyl-1,4-oxazepan-5-one, 1-(3-((5-chloro-2-((3-methyl-1-(1-methylpyrrolidin-3-yl)-1H-pyrazol-4-yl)amino)pyrimidin-4-yl)amino)propyl) azetidin-2-one, 1-(3-((5-chloro-2-((3-methyl-1-(1-methylpiperidin-4-yl)-1H-pyrazol-4-yl)amino)pyrimidin-4-yl)amino)propyl)azetidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-chloro-2-((3-methyl-1-(1-methylpyrrolidin-3-yl)-1H-pyrazol-4-yl)amino)pyrimidin-4-yl)amino) propyl)-3,3-dimethylazetidin-2-one, 1-(3-((5-chloro-2-((3-methyl-1-(1-methylpiperidin-4-yl)-1H-pyrazol-4-yl)amino) pyrimidin-4-yl)amino)propyl)-3,3-dimethylazetidin-2-one, 1-(3-((5-chloro-2-((3-methyl-1-(8-methyl-8-azabicyclo [3.2.1]octan-3-yl)-1H-pyrazol-4-yl)amino)pyrimidin-4-yl) amino)propyl)-3,3-dimethylazetidin-2-one, 2-((3-methyl-1-(1-methylpiperidin-4-yl)-1H-pyrazol-4-yl)amino)-4-((3-(3-oxo-1,4-oxazepan-4-yl)propyl)amino)pyrimidine-5-carbonitrile, 2-((3-methyl-1-(1-methylpiperidin-4-yl)-1H-pyrazol-4-yl)amino)-4-((3-(5-oxo-1,4-oxazepan-4-yl) propyl)amino)pyrimidine-5-carbonitrile, 2-((3-methyl-1-(1-methylpiperidin-4-yl)-1H-pyrazol-4-yl)amino)-4-((3-(2-oxo-1,3-oxazinan-3-yl)propyl)amino)pyrimidine-5-carbonitrile, 2-((1-(1-methylpiperidin-4-yl)-1H-pyrazol-4-yl)amino)-4-((3-(3-oxo-1,4-oxazepan-4-yl)propyl)amino) pyrimidine-5-carbonitrile, 2-((1-(1-methylpiperidin-4-yl)-1H-pyrazol-4-yl)amino)-4-((3-(5-oxo-1,4-oxazepan-4-yl) propyl)amino)pyrimidine-5-carbonitrile, 2-((1-(1-methylpiperidin-4-yl)-1H-pyrazol-4-yl)amino)-4-((3-(2-oxo-1,3-oxazinan-3-yl)propyl)amino)pyrimidine-5-carbonitrile, 2-((3-methyl-1-(1-methylpiperidin-4-yl)-1H-pyrazol-4-yl)amino)-4-((3-(3-oxomorpholino)propyl) amino)pyrimidine-5-carbonitrile, 2-((3-methyl-1-(1-methylpiperidin-4-yl)-1H-pyrazol-4-yl)amino)-4-((3-(3-methyl-2-oxotetrahydropyrimidin-1 (2H)-yl)propyl)amino) pyrimidine-5-carbonitrile, 2-((3-methyl-1-(1-methylpiperidin-4-yl)-1H-pyrazol-4-yl)amino)-4-((3-(2-oxo-1,3-oxazepan-3-yl)propyl)amino)pyrimidine-5-carbonitrile, 2-((3-methyl-1-(1-methylpiperidin-4-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(1-methylpiperidin-4-yl)-1H-pyrazol-4-yl)amino)-4-((3-(4-methyl-7-oxo-1,4-diazepan-1-yl)propyl)amino) pyrimidine-5-carbonitrile, 2-((3-methyl-1-(1-methylpiperidin-4-yl)-1H-pyrazol-4-yl)amino)-4-((3-(4-methyl-2-oxo-1,4-diazepan-1-yl)propyl)amino)pyrimidine-5-carbonitrile, 2-((3-methyl-1-(8-methyl-8-azabicyclo [3.2.1]octan-3-yl)-1H-pyrazol-4-yl)amino)-4-((3-(2-oxopiperidin-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxoazepan-1-yl)propyl) amino)pyrimidine-5-carbonitrile, 2-((3-methyl-1-(8-methyl-8-azabicyclo[3.2.1]octan-3-yl)-1H-pyrazol-4-yl)amino)-4-((3-(4-methyl-2-oxo-1,4-diazepan-1-yl)propyl)amino) pyrimidine-5-carbonitrile, 2-((3-methyl-1-(8-methyl-8-azabicyclo[3.2.1]octan-3-yl)-1H-pyrazol-4-yl)amino)-4-((3-(2-oxo-1,3-oxazinan-3-yl)propyl)amino)pyrimidine-5-carbonitrile, 2-((3-methyl-1-(8-methyl-8-azabicyclo[3.2.1] octan-3-yl)-1H-pyrazol-4-yl)amino)-4-((3-(3-oxomorpholino)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-methyl-2-oxotetrahydro-pyrimidin-1 (2H)-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxo-1,3-oxazepan-3-yl)propyl)amino)pyrimidine-5-carbonitrile, 2-((3-methyl-1-(8-methyl-8-azabicyclo[3.2.1]octan-3-yl)-1H-pyrazol-4-yl) amino)-4-((3-(3-methyl-2-oxo-1,3-diazepan-1-yl)propyl) amino)pyrimidine-5-carbonitrile, 2-((3-methyl-1-(8-methyl-8-azabicyclo[3.2.1]octan-3-yl)-1H-pyrazol-4-yl)amino)-4-((3-(4-methyl-7-oxo-1,4-diazepan-1-yl)propyl)amino) pyrimidine-5-carbonitrile, 2-((3-methyl-1-(8-methyl-8-azabicyclo[3.2.1]octan-3-yl)-1H-pyrazol-4-yl)amino)-4-((3-(3-oxo-1,4-oxazepan-4-yl)propyl)amino)pyrimidine-5-carbonitrile, 2-((3-methyl-1-(8-methyl-8-azabicyclo[3.2.1] octan-3-yl)-1H-pyrazol-4-yl)amino)-4-((3-(5-oxo-1,4-oxazepan-4-yl)propyl)amino)pyrimidine-5-carbonitrile, 2-((3-methyl-1-(1-methylpyrrolidin-3-yl)-1H-pyrazol-4-yl) amino)-4-((3-(2-oxo-1,3-oxazepan-3-yl)propyl)amino)pyrimidine-5-carbonitrile, 2-((3-methyl-1-(1-methylpyrrolidin-3-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(1-methylpyrrolidin-3-yl)-1H-pyrazol-4-yl) amino)-4-((3-(4-methyl-7-oxo-1,4-diazepan-1-yl)propyl) amino)pyrimidine-5-carbonitrile, 2-((3-methyl-1-(1-methylpyrrolidin-3-yl)-1H-pyrazol-4-yl)amino)-4-((3-(3-oxo-1,4-oxazepan-4-yl)propyl)amino)pyrimidine-5-carbonitrile, 2-((3-methyl-1-(1-methylpyrrolidin-3-yl)-1H-pyrazol-4-yl) amino)-4-((3-(5-oxo-1,4-oxazepan-4-yl)propyl)amino)pyrimidine-5-carbonitrile, 4-((3-(6,6-dimethyl-2-oxo-1,3-oxazinan-3-yl)propyl)amino)-2-((3-methyl-1-(1-methylpyrrolidin-3-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(1-methylpyrrolidin-3-yl)-1H-pyrazol-4-yl)amino)pyrimidine-5-carbonitrile, 4-((3-(6,6-dimethyl-5-oxo-1,4-oxazepan-4-yl)propyl) amino)-2-((3-methyl-1-(1-methylpyrrolidin-3-yl)-1H-pyrazol-4-yl)amino)pyrimidine-5-carbonitrile, 4-((3-(6,6-dimethyl-2-oxo-1,3-oxazinan-3-yl)propyl)amino)-2-((3-methyl-1-(1-methylpiperidin-4-yl)-1H-pyrazol-4-yl)amino) pyrimidine-5-carbonitrile, 4-((3-(2,2-dimethyl-3-oxo-1,4-oxazepan-4-yl)propyl)amino)-2-((3-methyl-1-(1-methylpiperidin-4-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(1-methylpiperidin-4-yl)-1H-pyrazol-4-yl)amino)pyrimidine-5-carbonitrile, 4-((3-(6,6-dimethyl-2-oxo-1,3-oxazinan-3-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(8-methyl-8-azabicyclo[3.2.1]octan-3-yl)-1H-pyrazol-4-yl)amino)pyrimidine-5-carbonitrile, 2-((3-methyl-1-(1-methylpyrrolidin-3-yl)-1H-pyrazol-4-yl) amino)-4-((3-(2-oxoazetidin-1-yl)propyl)amino) pyrimidine-5-carbonitrile, 2-((3-methyl-1-(1-methylpiperidin-4-yl)-1H-pyrazol-4-yl)amino)-4-((3-(2-oxoazetidin-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxoazetidin-1-yl)propyl) amino)pyrimidine-5-carbonitrile, 4-((3-(3,3-dimethyl-2-oxoazetidin-1-yl)propyl)amino)-2-((3-methyl-1-(1-methylpyrrolidin-3-yl)-1H-pyrazol-4-yl)amino)pyrimidine-5-carbonitrile, 4-((3-(3,3-dimethyl-2-oxoazetidin-1-yl)propyl)amino)-2-((3-methyl-1-(1-methylpiperidin-4-yl)-1H-pyrazol-4-yl)amino)pyrimidine-5-carbonitrile, 4-((3-(3,3-dimethyl-2-oxoazetidin-1-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpiperidin-4-yl)-1H-pyrazol-4-yl)amino)pyrimidin-4-yl)amino)propyl)-1,3-oxazinan-2-one, 4-(3-((5-cyclopropyl-2-((1-(1-methylpiperidin-4-yl)-1H-pyrazol-4-yl)amino)pyrimidin-4-yl)amino)propyl)-1,4-oxazepan-3-one, 4-(3-((5-cyclopropyl-2-((1-(1-methylpiperidin-4-yl)-1H-pyrazol-4-yl)amino)pyrimidin-4-yl)amino)propyl)-1,4-oxazepan-5-one, 3-(3-((5-cyclopropyl-2-((1-(1-methylpiperidin-4-yl)-1H-pyrazol-4-yl)amino)pyrimidin-4-yl)amino)propyl)-1,3-oxazinan-2-one, 4-(3-((5-cyclopropyl-2-((3-methyl-1-(1-methylpiperidin-4-yl)-1H-pyrazol-4-yl)amino)pyrimidin-4-yl)amino)propyl)morpholin-3-one, 1-(3-((5-cyclopropyl-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-cyclopropyl-2-((3-methyl-1-(1-methylpiperidin-4-yl)-1H-pyrazol-4-yl)amino)pyrimidin-4-yl)amino)propyl)-1,3-oxazepan-2-one, 1-(3-((5-cyclopropyl-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-cyclopropyl-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-cyclopropyl-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-cyclopropyl-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-cyclopropyl-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-cyclopropyl-2-((3-methyl-1-(1-methylpyrrolidin-3-yl)-1H-pyrazol-4-yl)amino)pyrimidin-4-yl)amino)propyl)azetidin-2-one, 1-(3-((5-cyclopropyl-2-((3-methyl-1-(1-methylpiperidin-4-yl)-1H-pyrazol-4-yl)amino)pyrimidin-4-yl)amino)propyl)azetidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-cyclopropyl-2-((3-methyl-1-(1-methylpyrrolidin-3-yl)-1H-pyrazol-4-yl)amino)pyrimidin-4-yl)amino)propyl)-3,3-dimethylazetidin-2-one, 1-(3-((5-cyclopropyl-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3,3-dimethylazetidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)pyrrolidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)pyrrolidin-2-one, 1-(3-((2-((3-methyl-1-(1-methylpyrrolidin-3-yl)-1H-pyrazol-4-yl)amino)-5-(trifluoromethyl)pyrimidin-4-yl)amino)propyl)pyrrolidin-2-one, 1-(3-((5-(difluoromethyl)-2-((3-methyl-1-(1-methylpyrrolidin-3-yl)-1H-pyrazol-4-yl)amino)pyrimidin-4-yl)amino)propyl)pyrrolidin-2-one, 1-(3-((2-((1-(1-isobutylazetidin-3-yl)-3-methyl-1H-pyrazol-4-yl)

amino)-5-(trifluoromethyl)pyrimidin-4-yl)amino)propyl) pyrrolidin-2-one, 1-(3-((5-(difluoromethyl)-2-((1-(1-isobutylazetidin-3-yl)-3-methyl-1H-pyrazol-4-yl)amino) pyrimidin-4-yl)amino)propyl)pyrrolidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl) pyrrolidin-2-one, 1-(3-((5-bromo-2-((3-methyl-1-(1-methylpyrrolidin-3-yl)-1H-pyrazol-4-yl)amino)pyrimidin-4-yl)amino)propyl)pyrrolidin-2-one, 1-(3-((5-bromo-2-((1-(1-isobutylazetidin-3-yl)-3-methyl-1H-pyrazol-4-yl)amino) pyrimidin-4-yl)amino)propyl)pyrrolidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl) pyrrolidin-2-one, 1-(3-((5-chloro-2-((3-methyl-1-(1-methylpyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-3-methyl-1H-pyrazol-4-yl)amino) pyrimidin-4-yl)amino)propyl)pyrrolidin-2-one, 4-(3-((2-((2-(3-(dimethylamino)propyl)-2H-1,2,3-triazol-4-yl) amino)-5-(trifluoromethyl)pyrimidin-4-yl)amino)propyl)-1, 4-oxazepan-3-one, 4-(3-((2-((2-(2-(dimethylamino)ethyl)-2H-1,2,3-triazol-4-yl)amino)-5-(trifluoromethyl)pyrimidin-4-yl)amino)propyl)-1,4-oxazepan-5-one, 3-(3-((2-((5-ethyl-2-(1-methylpiperidin-4-yl)-2H-1,2,3-triazol-4-yl)amino)-5-(trifluoromethyl)pyrimidin-4-yl)amino)propyl)-1,3-oxazinan-2-one, N-(1-methylpiperidin-4-yl)-4-((4-((3-(2-oxo-1,3-oxazinan-3-yl)propyl)amino)-5-(trifluoromethyl) pyrimidin-2-yl)amino) thiazole-2-carboxamide, 4-(3-((2-((2-(3-(dimethylamino)propyl) oxazol-4-yl)amino)-5-(trifluoromethyl)pyrimidin-4-yl)amino)propyl)-1,4-oxazepan-3-one, 4-(3-((2-((2-(2-(dimethylamino)ethyl) oxazol-4-yl)amino)-5-(trifluoromethyl)pyrimidin-4-yl) amino)propyl)-1,4-oxazepan-5-one, 3-(3-((2-((2-(4-methylpiperazine-1-carbonyl) oxazol-4-yl)amino)-5-(trifluoromethyl)pyrimidin-4-yl)amino)propyl)-1,3-oxazinan-2-one, 3,3-dimethyl-1-(3-((2-((5-methyl-2-(1-methylpiperidin-4-yl)-2H-1,2,3-triazol-4-yl)amino)-5-(trifluoromethyl)pyrimidin-4-yl)amino)propyl)azetidin-2-one, 4-(3-((2-((1-(3-(dimethylamino)propyl)-1H-pyrazol-4-yl)amino)-5-(trifluoromethyl)pyrimidin-4-yl)amino)propyl)-1,4-oxazepan-3-one, 4-(3-((2-((1-(3-(pyrrolidin-1-yl)propyl)-1H-pyrazol-4-yl)amino)-5-(trifluoromethyl)pyrimidin-4-yl) amino)propyl)-1,4-oxazepan-5-one, 3-(3-((2-((3-methyl-1-(2-morpholinoethyl)-1H-pyrazol-4-yl)amino)-5-(trifluoromethyl)pyrimidin-4-yl)amino)propyl)-1,3-oxazinan-2-one, 4-(3-((2-((3-fluoro-1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((2-((1-(1-methylpiperidin-4-yl)-3-(trifluoromethyl)-1H-pyrazol-4-yl) amino)-5-(trifluoromethyl)pyrimidin-4-yl)amino)propyl)-1, 4-oxazepan-5-one, 3-(3-((2-((3-methoxy-1-(1-methylpiperidin-4-yl)-1H-pyrazol-4-yl)amino)-5-(trifluoromethyl)pyrimidin-4-yl)amino)propyl)-1,3-oxazinan-2-one, 1-(1-methylpiperidin-4-yl)-4-((4-((3-(2-oxopiperidin-1-yl)propyl)amino)-5-(trifluoromethyl) pyrimidin-2-yl)amino)-1H-pyrazole-3-carbonitrile, 4-(3-((2-((3-ethynyl-1-(1-methylpiperidin-4-yl)-1H-pyrazol-4-yl)amino)-5-(trifluoromethyl)pyrimidin-4-yl)amino) propyl)-1,4-oxazepan-3-one, 3-(3-((2-((1-(1-methylpiperidin-4-yl)-3-vinyl-1H-pyrazol-4-yl)amino)-5-(trifluoromethyl)pyrimidin-4-yl)amino)propyl)-1,3-oxazinan-2-one, 4-(3-((2-((3-cyclopropyl-1-(1-methylpiperidin-4-yl)-1H-pyrazol-4-yl)amino)-5-(trifluoromethyl)pyrimidin-4-yl)amino)propyl)-1,4-oxazepan-5-one, 8-(3-((2-((3-methyl-1-(1-methylpiperidin-4-yl)-1H-pyrazol-4-yl)amino)-5-(trifluoromethyl) pyrimidin-4-yl)amino)propyl)-4-oxa-8-azaspiro[2.6]nonan-9-one, 8-(3-((2-((3-methyl-1-(1-methylpiperidin-4-yl)-1H-pyrazol-4-yl)amino)-5-(trifluoromethyl)pyrimidin-4-yl) amino)propyl)-5-oxa-8-azaspiro[2.6]nonan-9-one, 9-(3-((2-((3-methyl-1-(1-methylpiperidin-4-yl)-1H-pyrazol-4-yl) amino)-5-(trifluoromethyl)pyrimidin-4-yl)amino)propyl)-5-oxa-9-azaspiro[3.6]decan-10-one, 9-(3-((2-((3-methyl-1-(1-methylpiperidin-4-yl)-1H-pyrazol-4-yl)amino)-5-(trifluoromethyl)pyrimidin-4-yl)amino)propyl)-6-oxa-9-azaspiro[3.6]decan-10-one, 4-(3-((2-((3-methyl-1-(1-methylpiperidin-4-yl)-1H-pyrazol-4-yl)amino)-5-(trifluoromethyl)pyridin-4-yl)amino)propyl)-1,4-oxazepan-5-one, 4-(3-((2-((3-methyl-1-(1-methylpiperidin-4-yl)-1H-pyrazol-4-yl)amino)-5-(trifluoromethyl)pyridin-4-yl) amino)propyl)-1,4-oxazepan-3-one, 3-(3-((2-((3-methyl-1-(1-methylpiperidin-4-yl)-1H-pyrazol-4-yl)amino)-5-(trifluoromethyl)pyridin-4-yl)amino)propyl)-1,3-oxazepan-2-one, 3-(3-((2-((3-methyl-1-(1-methylpiperidin-4-yl)-1H-pyrazol-4-yl)amino)-5-(trifluoromethyl)pyridin-4-yl) amino)propyl)-1,3-oxazinan-2-one, 2,2-dimethyl-4-(3-((2-((3-methyl-1-(1-methylpiperidin-4-yl)-1H-pyrazol-4-yl) amino)-5-(trifluoromethyl)pyridin-4-yl)amino)propyl)-1,4-oxazepan-3-one, 4-(3-((5-(difluoromethyl)-2-((3-methyl-1-(1-methylpiperidin-4-yl)-1H-pyrazol-4-yl)amino)pyridin-4-yl)amino)propyl)-1,4-oxazepan-5-one, 3-(3-((5-chloro-2-((3-methyl-1-(1-methylpiperidin-4-yl)-1H-pyrazol-4-yl) amino)pyridin-4-yl)amino)propyl)-1,3-oxazinan-2-one, 4-(3-((2-((5-methyl-2-(1-methylpiperidin-4-yl)-2H-1,2,3-triazol-4-yl)amino)-5-(trifluoromethyl)pyridin-4-yl)amino) propyl)-1,4-oxazepan-3-one, 4-(3-((2-((3-methyl-1-(3-morpholinopropyl)-1H-pyrazol-4-yl)amino)-5-(trifluoromethyl) pyrimidin-4-yl)amino)propyl)-1,4-oxazepan-5-one, 4-(3-((2-((1-(2-(dimethylamino)ethyl)-3-methyl-1H-pyrazol-4-yl)amino)-5-(trifluoromethyl)pyridin-4-yl)amino)propyl)-1, 4-oxazepan-5-one, (S)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 1-methyl-3-(3-((2-((3-methyl-1-(1-methylpiperidin-4-yl)-1H-pyrazol-4-yl)amino)-5-(trifluoromethyl)pyridin-4-yl)amino)propyl) tetrahydropyrimidin-2(1H)-one, 1-methyl-3-(3-((2-((3-methyl-1-(1-methylpiperidin-4-yl)-1H-pyrazol-4-yl) amino)-5-(trifluoromethyl)pyridin-4-yl)amino)propyl)-1,3-diazepan-2-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 4-(3-((2-((5-methyl-2-(1-methylpiperidin-4-yl) thiazol-4-yl)amino)-5-(trifluoromethyl)pyridin-4-yl) amino)propyl)-1,4-oxazepan-3-one, 4-(3-((2-((2-(1-methylpiperidin-4-yl) thiazol-4-yl)amino)-5-(trifluoromethyl)pyridin-4-yl)amino)propyl)-1,4-oxazepan-3-one, 4-(3-((2-((2-(1-methylpiperidin-4-yl) oxazol-4-yl) amino)-5-(trifluoromethyl)pyridin-4-yl)amino)propyl)-1,4-oxazepan-5-one, 4-(3-((2-((3-ethyl-1-(1-methylpiperidin-4-yl)-1H-pyrazol-4-yl)amino)-5-(trifluoromethyl)pyridin-4-yl)amino)propyl)-1,4-oxazepan-5-one, 4-(3-((5-chloro-2-((3-ethyl-1-(1-methylpiperidin-4-yl)-1H-pyrazol-4-yl) amino)pyridin-4-yl)amino)propyl)-1,4-oxazepan-5-one, 4-(3-((2-((3-methoxy-1-(1-methylpiperidin-4-yl)-1H-pyrazol-4-yl)amino)-5-(trifluoromethyl)pyridin-4-yl)amino)propyl)-1,4-oxazepan-3-one, 4-(3-((2-((1-(1-methylpiperidin-4-yl)-3-vinyl-1H-pyrazol-4-yl)amino)-5-(trifluoromethyl) pyridin-4-yl)amino)propyl)-1,4-oxazepan-5-one, 1-((3-methyl-4-((4-((3-(5-oxo-1,4-oxazepan-4-yl)propyl)amino)-5-(trifluoromethyl)pyridin-2-yl)amino)-1H-pyrazol-1-yl) methyl) cyclopropane-1-carbonitrile, 2-methyl-2-(3-methyl-4-((4-((3-(5-oxo-1,4-oxazepan-4-yl)propyl)amino)-5-(trifluoromethyl)pyridin-2-yl)amino)-1H-pyrazol-1-yl)

propanenitrile, 6-((3-methyl-1-(1-methylpiperidin-4-yl)-1H-pyrazol-4-yl)amino)-4-((3-(5-oxo-1,4-oxazepan-4-yl)propyl)amino) nicotinonitrile, 4-(3-((5-cyclopropyl-2-((3-methyl-1-(1-methylpiperidin-4-yl)-1H-pyrazol-4-yl)amino)pyridin-4-yl)amino)propyl)-1,4-oxazepan-5-one, 4-(3-((2-((1-(1-ethylpiperidin-4-yl)-3-methyl-1H-pyrazol-4-yl)amino)-5-(trifluoromethyl)pyridin-4-yl)amino)propyl)-1,4-oxazepan-5-one, 1-(1-methylpiperidin-4-yl)-4-((4-((3-(5-oxo-1,4-oxazepan-4-yl)propyl)amino)-5-(trifluoromethyl)pyridin-2-yl)amino)-1H-pyrazole-3-carbonitrile, 4-(3-((2-((2-(1-methylpiperidin-4-yl)-2H-1,2,3-triazol-4-yl)amino)-5-(trifluoromethyl)pyridin-4-yl)amino)propyl)-1,4-oxazepan-3-one, 4-(3-((5-(difluoromethyl)-2-((2-(1-methylpiperidin-4-yl)-2H-1,2,3-triazol-4-yl)amino)pyridin-4-yl)amino)propyl)-1,4-oxazepan-3-one, 3-(3-((2-((2-(1-methylpiperidin-4-yl) oxazol-4-yl)amino)-5-(trifluoromethyl)pyridin-4-yl)amino)propyl)-1,3-oxazinan-2-one, 1-(3-((2-((3-methyl-1-(1-methylpiperidin-4-yl)-1H-pyrazol-4-yl)amino)-5-(trifluoromethyl)pyridin-4-yl)amino)propyl)pyrrolidin-2-one, 1-(3-((2-((3-methyl-1-(1-methylpiperidin-4-yl)-1H-pyrazol-4-yl)amino)-5-(trifluoromethyl)pyridin-4-yl)amino)propyl)piperidin-2-one, 1-(3-((2-((3-methyl-1-(1-methylpiperidin-4-yl)-1H-pyrazol-4-yl)amino)-5-(trifluoromethyl)pyridin-4-yl)amino)propyl)azetidin-2-one, 2-methyl-2-(3-methyl-4-((4-((3-(5-oxo-1,4-oxazepan-4-yl)propyl)amino)-5-(trifluoromethyl)pyridin-2-yl)amino)-1H-pyrazol-1-yl)propanamide, 1-(1-methylpiperidin-4-yl)-4-((4-((3-(3-oxo-1,4-oxazepan-4-yl)propyl)amino)-5-(trifluoromethyl)pyrimidin-2-yl)amino)-1H-pyrazole-3-carbonitrile, 4-(3-((5-(difluoromethyl)-2-((3-methyl-1-(piperidin-4-yl)-1H-pyrazol-4-yl)amino)pyrimidin-4-yl)amino)propyl)-1,4-oxazepan-5-one, 3-(3-((5-(difluoromethyl)-2-((3-methyl-1-(piperidin-4-yl)-1H-pyrazol-4-yl)amino)pyrimidin-4-yl)amino)propyl)-1,3-oxazinan-2-one, 1-methyl-4-(3-((2-((3-methyl-1-(piperidin-4-yl)-1H-pyrazol-4-yl)amino)-5-(trifluoromethyl)pyrimidin-4-yl)amino)propyl)-1,4-diazepan-5-one, and 4-methyl-1-(3-((2-((3-methyl-1-(piperidin-4-yl)-1H-pyrazol-4-yl)amino)-5-(trifluoromethyl)pyrimidin-4-yl)amino)propyl)-1,4-diazepan-2-one, or pharmaceutically acceptable salts, enantiomers, stereoisomers, or tautomers thereof.

15. A method of treating a cancer in a patient in need thereof, comprising administering to the patient:

a) a therapeutically effective amount of a compound of Formula I:

Formula I

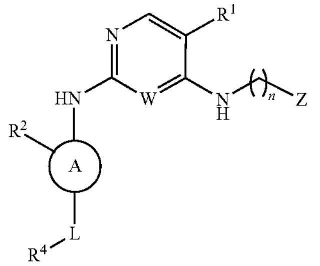

or a pharmaceutically acceptable salt, enantiomer, stereoisomer, or tautomer thereof, wherein:

A is 5-membered heteroaryl with at least one ring nitrogen;

W is CH or N;

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine;

$R^2$ is selected from the group consisting of H, halogen, cyano, $C_1$-$C_5$ alkyl, $C_3$-$C_6$ cycloalkyl, $C_2$-$C_5$ alkenyl, $C_2$-$C_5$ alkynyl, $C_1$-$C_5$ alkoxy, and $C_1$-$C_5$ alkoxy-$C_1$-$C_5$ alkyl, wherein each $C_1$-$C_5$ alkyl, $C_3$-$C_6$ cycloalkyl, $C_2$-$C_5$ alkenyl, $C_2$-$C_5$ alkynyl, and $C_1$-$C_5$ alkoxy may be optionally substituted by one, two, or three independent occurrences of fluorine or cyano;

$R^4$ is selected from the group consisting of B, D, $NR^6R^9$, $NR^6$—$(C(R^{10})_2)_p$—$NR^6R^9$, C(O)—$NR^6R^9$, C(O)—B, C(O)-D, and CN;

B is selected from an N-linked heterocyclyl having at least one nitrogen and optionally having an additional ring nitrogen or oxygen and heteroaryl, wherein B may be optionally substituted on one or more available carbons by $R^7$ and may be optionally substituted on an available nitrogen by $R^9$;

D is selected from a C-linked heterocyclyl having at least one nitrogen and optionally having an additional ring nitrogen or oxygen and heteroaryl, wherein D may be optionally substituted on one or more available carbons by $R^7$ and may be optionally substituted on an available nitrogen by $R^9$;

each occurrence of $R^5$ is independently selected from the group consisting of H, $C_1$-$C_6$ alkyl, $C_3$-$C_6$ cycloalkyl, and heterocyclyl, wherein each $C_1$-$C_6$ alkyl and $C_3$-$C_6$ cycloalkyl may be optionally substituted by one or more independent occurrences of fluorine;

each occurrence of $R^7$ is independently selected from the group consisting of H, $C_1$-$C_6$ alkyl, $C_3$-$C_6$ cycloalkyl, cyano, and $(C(R^{10})_2)_h$—$NR^6R^9$, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$ alkyl, $C_3$-$C_6$ cycloalkyl, $C_1$-$C_5$ alkoxy-$C_2$-$C_5$ alkyl, C(=O)$R^5$, $SO_2R^5$, C-linked heterocyclyl having at least one nitrogen and optionally having an additional ring nitrogen or oxygen, and heteroaryl, wherein each $C_1$-$C_6$ alkyl and $C_3$-$C_6$ cycloalkyl may be optionally substituted by one or more independent occurrences of fluorine;

each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl;

Z is selected from the group consisting of a 4-10 membered lactam ring wherein the lactam ring is bound through the nitrogen atom, wherein a lactam ring atom may optionally be oxygen or $NR^6$ when the lactam ring is a 6-10 membered ring and an available carbon atom on 4 membered lactam ring or a 6-10 membered lactam is optionally substituted by one or more independent occurrences of $R^{36}$;

each occurrence of $R^{36}$ is independently selected from $C_1$-$C_6$ alkyl and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl;

L is $—(C(R^{10})_2)_m—$;

his 1, 2, or 3;

m is 0, 1, 2, or 3;

n is 2, 3, or 4; and p is 2 or 3;

provided that: when m is 0, $R^4$ is C-linked to ring A, when m is 1, $R^4$ is C-linked to L, and when m is 2 or 3, $R^4$ is N-linked or C-linked to L; and b) a therapeutically effective amount of binimetinib, or a pharmaceutically acceptable salt thereof, wherein the cancer is selected from the group consisting of pancreatic cancer, lung cancer, colorectal cancer, melanoma, renal cancer, urinary bladder cancer, and gastrointestinal stromal tumors.

16. The method of claim 15, wherein

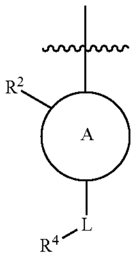

is selected from the group consisting of:

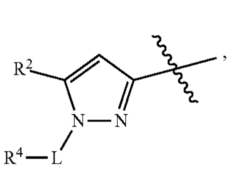

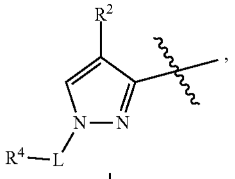

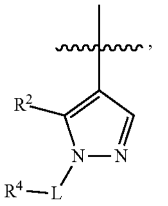

and

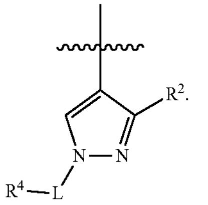

17. The method of claim 15, wherein Z is selected from the group consisting of:

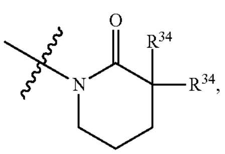

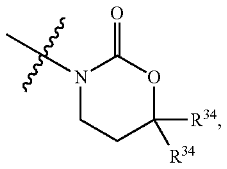

-continued

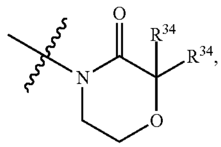

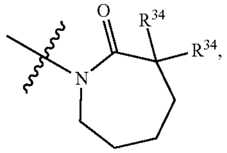

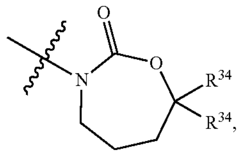

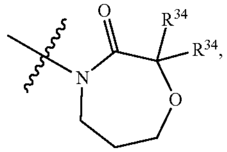

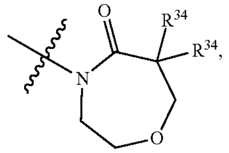

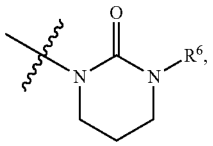

and

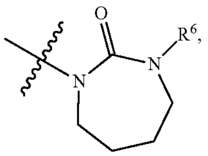

wherein each occurrence of $R^{34}$ is independently selected from H and $R^{36}$, wherein each occurrence of $R^{36}$ is independently selected from $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl.

18. The method of claim 15, wherein $R^4$ is selected from the group consisting of:

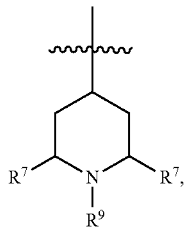

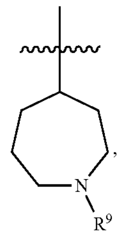

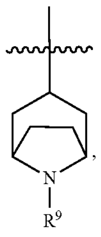

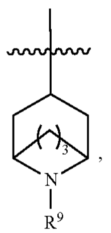

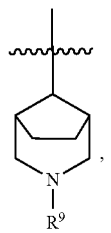

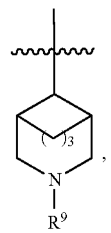

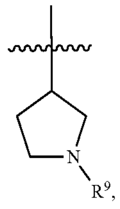

-continued

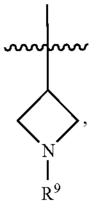,
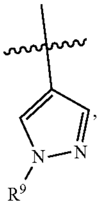,
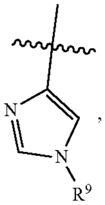,
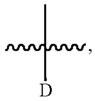,
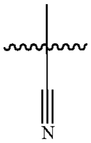, and
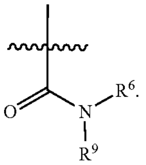.

19. The method of claim 15, wherein $R^4$ is selected from the group consisting of:

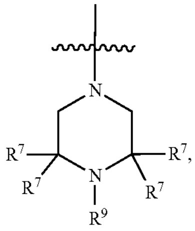
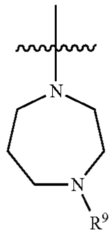,
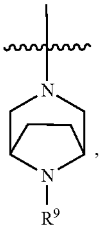,
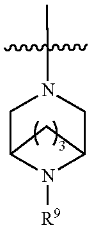,
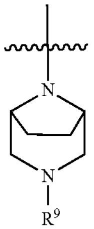,
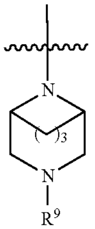,
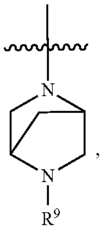,
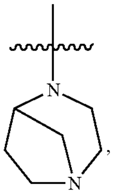,
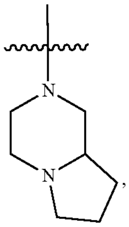,
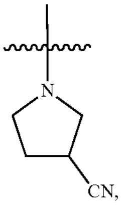 and
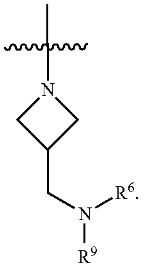.

20. The method of claim 15, wherein $R^1$ is selected from the group consisting of halogen, $C_1$-$C_5$ alkyl, and $C_3$-$C_5$ cycloalkyl, wherein $C_1$-$C_5$ alkyl and $C_3$-$C_5$ cycloalkyl may be optionally substituted with one, two, or three independent occurrences of fluorine.

21. The method of claim 15, wherein $R^2$ is selected from the group consisting of $C_1$-$C_5$ alkyl, H, and $C_3$-$C_4$ cycloalkyl.

22. The method of claim 15, wherein the compound of Formula I is a compound represented by:

Formula II

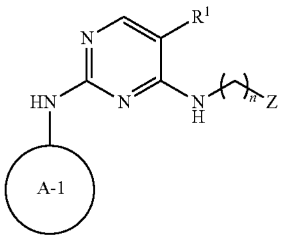

or a pharmaceutically acceptable salt thereof, wherein

A-1 is selected from the group consisting of:

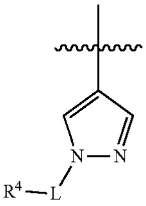,
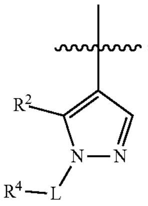, and
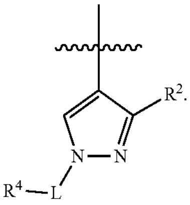.

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine;

$R^2$ is selected from the group consisting of halogen, $C_1$-$C_2$ alkyl, and $C_3$-$C_4$ cycloalkyl;

$R^4$ is selected from the group consisting of:

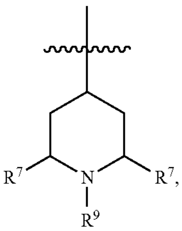,
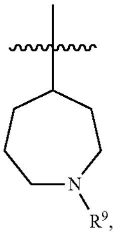,
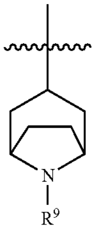,

-continued

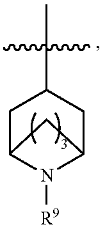,
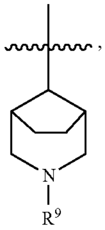,
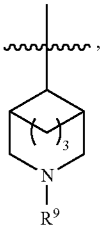,

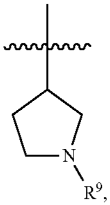, and 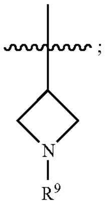;

each occurrence of $R^7$ is independently selected from the group consisting of H, $C_1$-$C_6$ alkyl, $C_3$-$C_6$ cycloalkyl, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine;

Z is selected from the group consisting of:

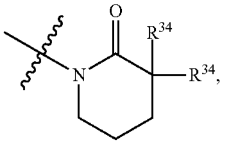,
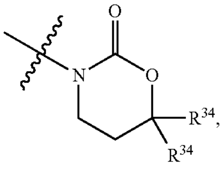,
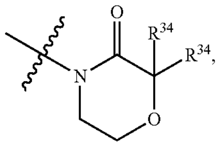,
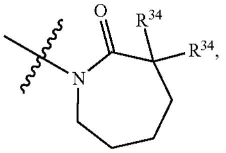,
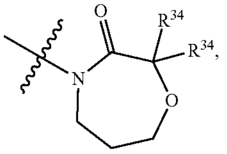,
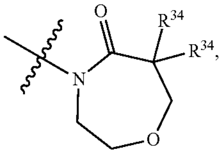,
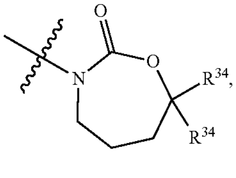,
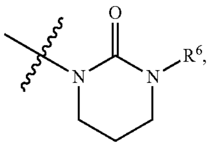, and -continued

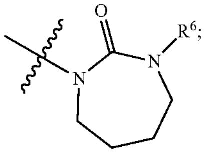;

each occurrence of $R^{34}$ is independently selected from H and $R^{36}$, wherein each occurrence of $R^{36}$ is independently selected from $C_1$-$C_6$ alkyl and $C_3$-$C_6$ cycloalkyl, wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl;

L is $-(C(R^{10})_2)_m-$;

each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl;

m is 0, 1, 2, or 3; and n is 2, 3, or 4;

provided that: when m is 0, $R^4$ is C-linked to the pyrazole ring, when m is 1, $R^4$ is C-linked to L, and when m is 2 or 3, $R^4$ is C-linked to L.

23. The method of claim 22, wherein A-1 is:

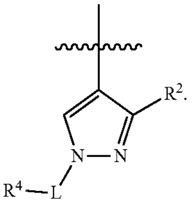

24. The method of claim 15, wherein the compound of Formula I is a compound represented by:

Formula III

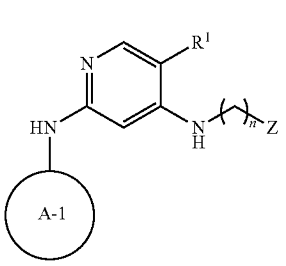

or a pharmaceutically acceptable salt thereof, wherein

A-1 is selected from the group consisting of:

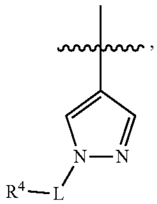,
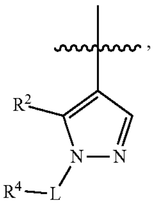, and
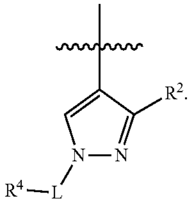.

$R^1$ is selected from the group consisting of halogen, cyano, $C_1$-$C_5$ alkyl, and $C_3$-$C_5$ cycloalkyl, wherein each $C_1$-$C_5$ alkyl and $C_3$-$C_5$ cycloalkyl may be optionally substituted by one, two or three independent occurrences of fluorine;

$R^2$ is selected from $C_1$-$C_2$ alkyl, $C_3$-$C_4$ cycloalkyl, and halogen;

$R^4$ is selected from the group consisting of:

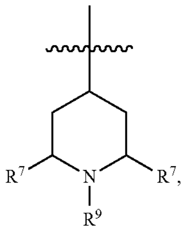,
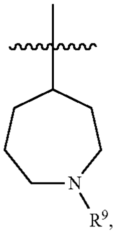,
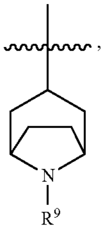,
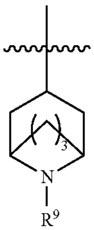,
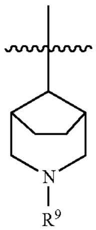,
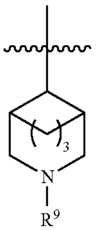,

-continued

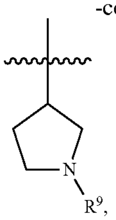, and
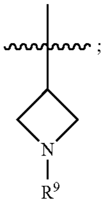;

each occurrence of $R^7$ is independently selected from the group consisting of H, $C_1$-$C_6$ alkyl, $C_3$-$C_6$ cycloalkyl, wherein each $C_1$-$C_6$ alkyl and $C_3$-$C_6$ cycloalkyl may be optionally substituted by one or more independent occurrences of fluorine, or two $R^7$ are joined together with the atom to which they are attached to form oxo;

each occurrence of $R^6$ and $R^9$ is independently selected from the group consisting of H, $C_1$-$C_6$ alkyl, and $C_3$-$C_6$ cycloalkyl, wherein each $C_1$-$C_6$ alkyl and $C_3$-$C_6$ cycloalkyl may be optionally substituted by one or more independent occurrences of fluorine;

Z is selected from the group consisting of:

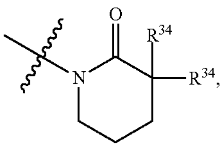,
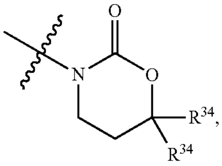,
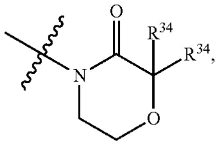,
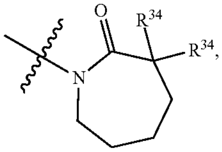,
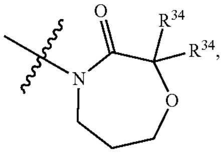,
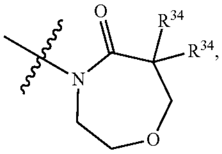,
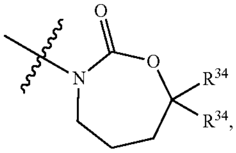,
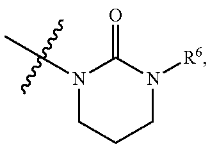, and
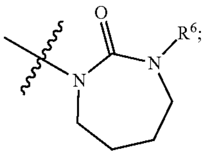;

each occurrence of $R^{34}$ is independently selected from H and $R^{36}$, wherein each occurrence of $R^{36}$ is independently selected from $C_1$-$C_6$ alkyl and $C_3$-$C_6$ cycloalkyl and wherein each $C_1$-$C_6$ alkyl and $C_3$-$C_6$ cycloalkyl may be optionally substituted by one or more independent occurrences of fluorine, or two $R^{36}$ are joined together with the carbon to which they are attached to form a $C_3$-$C_6$ cycloalkyl;

L is $-(C(R^{10})_2)_m-$;

each occurrence of $R^{10}$ is independently selected from the group consisting of H, $C_1$-$C_3$ alkyl, and $C_3$-$C_5$ cycloalkyl, wherein each $C_1$-$C_3$ alkyl and $C_3$-$C_5$ cycloalkyl may be optionally substituted by one or more independent occurrences of fluorine, or two $R^{10}$ are joined together with the carbon to which they are attached to form a $C_3$-$C_5$ cycloalkyl;

m is 0, 1, 2, or 3; and n is 2, 3, or 4;

provided that: when m is 0, $R^4$ is C-linked to the pyrazole ring, when m is 1, $R^4$ is C-linked to L, and when m is 2 or 3, $R^4$ is C-linked to L.

25. The method of claim 15, wherein the compound of Formula I is represented by a formula selected from the group consisting of:

Formula IIA.1

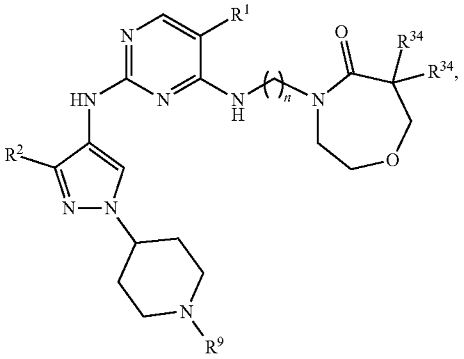

Formula IIA.2

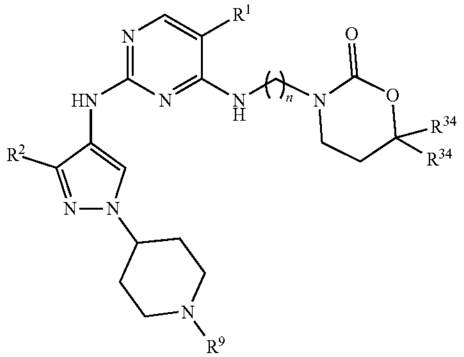

Formula IIA.3

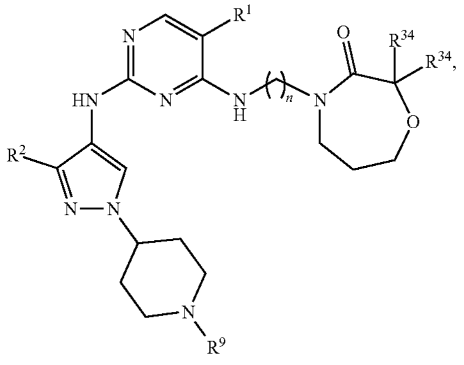

-continued

Formula IIA.4

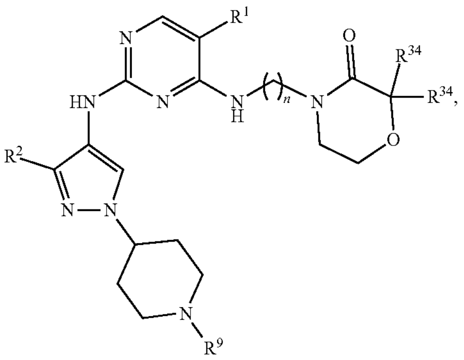

Formula IIA.5

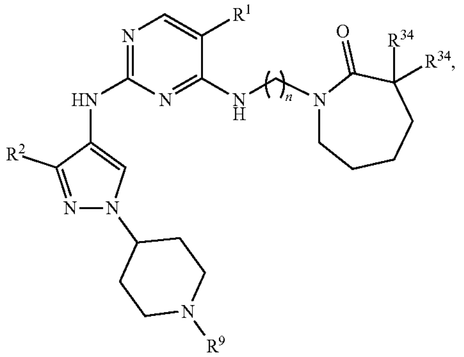

Formula IIA.6

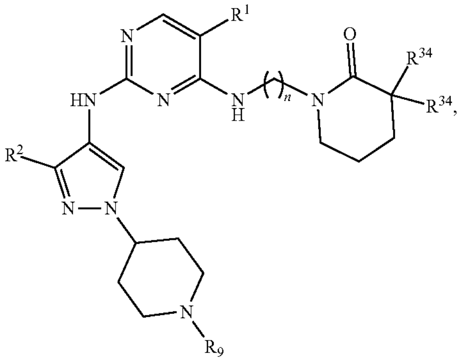

Formula IIA.7

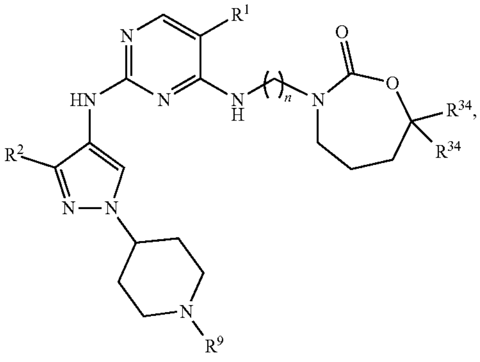

-continued

Formula IIA.19

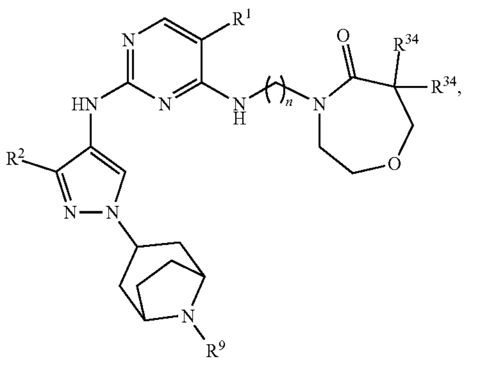

Formula IIA.20

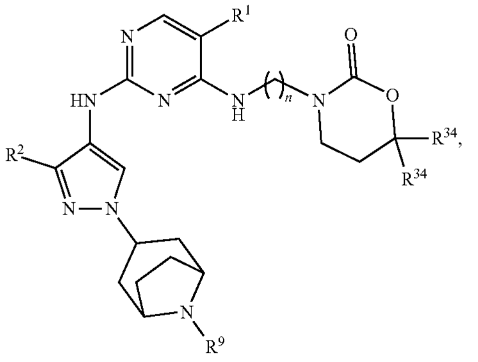

Formula IIA.21

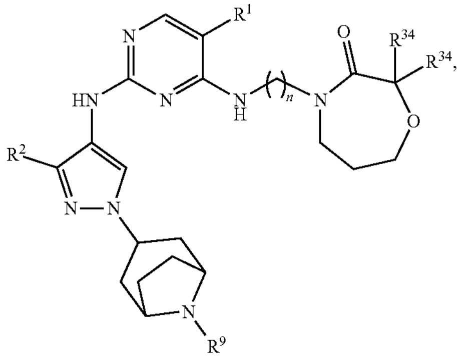

Formula IIA.22

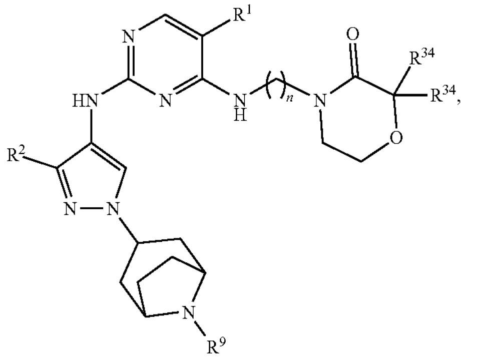

-continued

Formula IIA.23

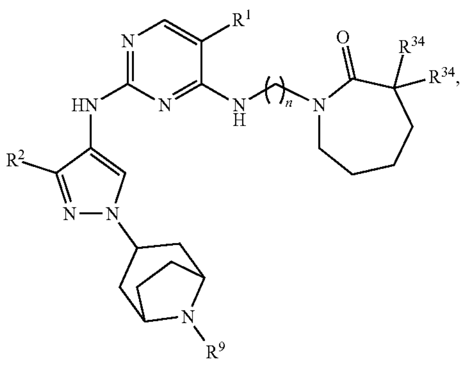

Formula IIA.24

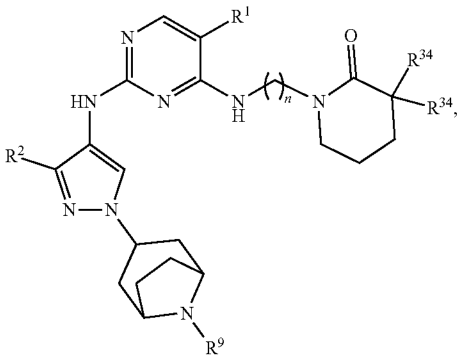

and

Formula IIA.25

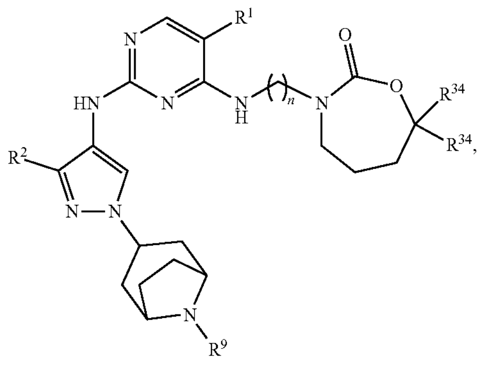

wherein each occurrence of $R^1$ is independently selected from the group consisting of bromo, chloro, $CF_3$, $CF_2H$, and cyclopropyl;

each occurrence of $R^2$ is independently selected from the group consisting of $C_1$-$C_2$ alkyl, $C_3$-$C_4$ cycloalkyl, and halogen;

each occurrence of $R^9$ is independently selected from the group consisting of H, $C_1$-$C_3$ alkyl, and $C_3$-$C_5$ cycloalkyl;

each occurrence of $R^{34}$ is independently selected from the group consisting of H, $C_1$-$C_2$ alkyl, and $C_3$-$C_5$ cycloalkyl; and n is 3.

26. The method of claim 15, wherein the compound of Formula I is selected from the group consisting of: 1-(3-((5-cyclopropyl-2-((1-(1-methylpiperidin-4-yl)-1H-pyrazol-4-yl)amino)pyrimidin-4-yl)amino)propyl)piperidin-2-one, 1-(3-((5-chloro-2-((1-(1-methylpiperidin-4-yl)-1H-pyrazol- 4-yl)amino)pyrimidin-4-yl)amino)propyl)piperidin-2-one, 1-(3-((5-chloro-2-((1-(piperidin-4-yl)-1H-pyrazol-4-yl)amino)pyrimidin-4-yl)amino)propyl)piperidin-2-one, 1-(3-((5-chloro-2-((1-(1-isopropylpiperidin-4-yl)-1H-pyrazol-4-yl)amino)pyrimidin-4-yl)amino)propyl)piperidin-2-one, 1-(3-((2-((1-(1-isopropylpiperidin-4-yl)-1H-pyrazol-4-yl)amino)-5-(trifluoromethyl)pyrimidin-4-yl)amino)propyl)piperidin-2-one, 1-(3-((2-((1-(piperidin-4-yl)-1H-pyrazol-4-yl)amino)-5-(trifluoromethyl)pyrimidin-4-yl)amino)propyl)piperidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)piperidin-2-one, 1-(3-((5-bromo-2-((1-(piperidin-4-yl)-1H-pyrazol-4-yl)amino)pyrimidin-4-yl)amino)propyl)piperidin-2-one, 1-(3-((2-((1-(1-methylpiperidin-4-yl)-1H-pyrazol-4-yl)amino)-5-(trifluoromethyl)pyrimidin-4-yl)amino)propyl)piperidin-2-one, 1-(3-((5-chloro-2-((1-(1-isobutylazetidin-3-yl)-1H-pyrazol-4-yl)amino)pyrimidin-4-yl)amino)propyl)piperidin-2-one, 1-(3-((2-((1-(1-isobutylazetidin-3-yl)-1H-pyrazol-4-yl)amino)-5-(trifluoromethyl)pyrimidin-4-yl)amino)propyl)piperidin-2-one, 1-(3-((2-((1-(1-isopropyl-d7-piperidin-4-yl)-1H-pyrazol-4-yl)amino)-5-(trifluoromethyl)pyrimidin-4-yl)amino)propyl)piperidin-2-one, 1-(3-((2-((3-methyl-1-(piperidin-4-yl)-1H-pyrazol-4-yl)amino)-5-(trifluoromethyl)pyrimidin-4-yl)amino)propyl)piperidin-2-one, 1-(3-((2-((1-(1-isopropylpiperidin-4-yl)-3-methyl-1H-pyrazol-4-yl)amino)-5-(trifluoromethyl)pyrimidin-4-yl)amino)propyl)piperidin-2-one, 1-(3-((2-((1-(1-ethylpiperidin-4-yl)-1H-pyrazol-4-yl)amino)-5-(trifluoromethyl)pyridin-4-yl)amino)propyl)piperidin-2-one, 1-(3-((5-bromo-2-((1-(1-isobutylazetidin-3-yl)-1H-pyrazol-4-yl)amino)pyrimidin-4-yl)amino)propyl)piperidin-2-one, rac-(R)-1-(3-((2-((3-methyl-1-(1-methylpyrrolidin-3-yl)-1H-pyrazol-4-yl)amino)-5-(trifluoromethyl)pyrimidin-4-yl)amino)propyl)piperidin-2-one, 1-(3-((2-((3-methyl-1-(3-(pyrrolidin-1-yl)propyl)-1H-pyrazol-4-yl)amino)-5-(trifluoromethyl)pyrimidin-4-yl)amino)propyl)piperidin-2-one, 1-(3-((2-((1-(2-(dimethylamino)ethyl)-3-methyl-1H-pyrazol-4-yl)amino)-5-(trifluoromethyl)pyrimidin-4-yl)amino)propyl)piperidin-2-one, 1-(3-((2-((3-methyl-1-(2-(piperidin-1-yl)ethyl)-1H-pyrazol-4-yl)amino)-5-(trifluoromethyl)pyrimidin-4-yl)amino)propyl)piperidin-2-one, 1-(3-((2-((1-(1-isobutylazetidin-3-yl)-3-methyl-1H-pyrazol-4-yl)amino)-5-(trifluoromethyl)pyrimidin-4-yl)amino)propyl)piperidin-2-one, rac-(R)-1-(3-((5-chloro-2-((3-methyl-1-(1-methylpyrrolidin-3-yl)-1H-pyrazol-4-yl)amino)pyrimidin-4-yl)amino)propyl)piperidin-2-one, rac-(R)-1-(3-((2-((1-(1-ethylpyrrolidin-3-yl)-3-methyl-1H-pyrazol-4-yl)amino)-5-(trifluoromethyl)pyrimidin-4-yl)amino)propyl)piperidin-2-one, 1-(3-((5-bromo-2-((3-methyl-1-(piperidin-4-yl)-1H-pyrazol-4-yl)amino)pyrimidin-4-yl)amino)propyl)piperidin-2-one, 1-(3-((5-chloro-2-((3-methyl-1-(piperidin-4-yl)-1H-pyrazol-4-yl)amino)pyrimidin-4-yl)amino)propyl)piperidin-2-one, 1-(3-((2-((3-methyl-1-(3-(piperidin-1-yl)propyl)-1H-pyrazol-4-yl)amino)-5-(trifluoromethyl)pyrimidin-4-yl)amino)propyl)piperidin-2-one, 1-(3-((2-((3-methyl-1-(2-morpholinoethyl)-1H-pyrazol-4-yl)amino)-5-(trifluoromethyl)pyrimidin-4-yl)amino)propyl)piperidin-2-one, 1-(3-((2-((3-methyl-1-(3-morpholinopropyl)-1H-pyrazol-4-yl)amino)-5-(trifluoromethyl)pyrimidin-4-yl)amino)propyl)piperidin-2-one, 1-(3-((2-((3-methyl-d3-1-(1-methylpiperidin-4-yl)-1H-pyrazol-4-yl)amino)-5-(trifluoromethyl)pyrimidin-4-yl)amino)propyl)piperidin-2-one, 1-(3-((2-((1-(2-(dimethylamino)ethyl)-1H-pyrazol-4-yl)amino)-5-(trifluoromethyl)pyrimidin-4-yl)amino)propyl)piperidin-2-one, 1-(3-((2-((3-methyl-1-(1-(oxetan-3-yl)piperidin-4-yl)-1H-pyrazol-4-yl)amino)-5-(trifluoromethyl)pyrimidin-4-yl)amino)propyl)piperidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)piperidin-2-one, 1-(3-((2-((1-(3-(dimethylamino)propyl)-3-methyl-1H-pyrazol-4-yl)amino)-5-(trifluoromethyl)pyrimidin-4-yl)amino)propyl)piperidin-2-one, rac-(R)-1-(3-((2-((1-(1-isopropylpyrrolidin-3-yl)-3-methyl-1H-pyrazol-4-yl)amino)-5-(trifluoromethyl)pyrimidin-4-yl)amino)propyl)piperidin-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)piperidin-2-one, 1-(3-((5-chloro-2-((1-(1-isobutylazetidin-3-yl)-3-methyl-1H-pyrazol-4-yl)amino)pyrimidin-4-yl)amino)propyl)piperidin-2-one, 1-(3-((5-chloro-2-((3-ethyl-1-(piperidin-4-yl)-1H-pyrazol-4-yl)amino)pyrimidin-4-yl)amino)propyl)piperidin-2-one, 1-(3-((2-((3-ethyl-1-(piperidin-4-yl)-1H-pyrazol-4-yl)amino)-5-(trifluoromethyl)pyrimidin-4-yl)amino)propyl)piperidin-2-one, 1-(3-((5-bromo-2-((3-ethyl-1-(piperidin-4-yl)-1H-pyrazol-4-yl)amino)pyrimidin-4-yl)amino)propyl)piperidin-2-one, 1-(3-((2-((3-ethyl-1-(1-ethylpiperidin-4-yl)-1H-pyrazol-4-yl)amino)-5-(trifluoromethyl)pyrimidin-4-yl)amino)propyl)piperidin-2-one, 1-(3-((2-((3-ethyl-1-(1-isopropylpiperidin-4-yl)-1H-pyrazol-4-yl)amino)-5-(trifluoromethyl)pyrimidin-4-yl)amino)propyl)piperidin-2-one, rac-(R)-1-(3-((5-bromo-2-((3-methyl-1-(1-methylpyrrolidin-3-yl)-1H-pyrazol-4-yl)amino)pyrimidin-4-yl)amino)propyl)piperidin-2-one, 1-(3-((2-((3-methyl-1-(2-(pyrrolidin-1-yl)ethyl)-1H-pyrazol-4-yl)amino)-5-(trifluoromethyl)pyrimidin-4-yl)amino)propyl)piperidin-2-one, 1-(3-((5-chloro-2-((3-ethyl-1-(1-ethylpiperidin-4-yl)-1H-pyrazol-4-yl)amino)pyrimidin-4-yl)amino)propyl)piperidin-2-one, 1-(3-((2-((3-ethyl-1-(1-methylpiperidin-4-yl)-1H-pyrazol-4-yl)amino)-5-(trifluoromethyl)pyrimidin-4-yl)amino)propyl)piperidin-2-one, 1-(3-((5-iodo-2-((3-methyl-1-(piperidin-4-yl)-1H-pyrazol-4-yl)amino)pyrimidin-4-yl)amino)propyl)piperidin-2-one, 1-(3-((5-bromo-2-((3-methyl-d3-1-(1-methylpiperidin-4-yl)-1H-pyrazol-4-yl)amino)pyrimidin-4-yl)amino)propyl)piperidin-2-one, 1-(3-((5-bromo-2-((1-(1-ethylpiperidin-4-yl)-3-methyl-1H-pyrazol-4-yl)amino)pyrimidin-4-yl)amino)propyl)piperidin-2-one, 1-(3-((5-bromo-2-((3-methyl-1-(1-methylpiperidin-4-yl)-1H-pyrazol-4-yl)amino)pyrimidin-4-yl)amino)propyl)piperidin-2-one, 1-(3-((2-((3-ethyl-1-(1-methyl-d3-piperidin-4-yl)-1H-pyrazol-4-yl)amino)-5-(trifluoromethyl)pyrimidin-4-yl)amino)propyl)piperidin-2-one, 1-(3-((5-bromo-2-((3-ethyl-1-(1-methylpiperidin-4-yl)-1H-pyrazol-4-yl)amino)pyrimidin-4-yl)amino)propyl)piperidin-2-one, 1-(3-((5-bromo-2-((3-ethyl-1-(1-ethylpiperidin-4-yl)-1H-pyrazol-4-yl)amino)pyrimidin-4-yl)amino)propyl)piperidin-2-one, 1-(3-((5-chloro-2-((3-ethyl-1-(1-methylpiperidin-4-yl)-1H-pyrazol-4-yl)amino)pyrimidin-4-yl)amino)propyl)piperidin-2-one, 1-(3-((5-chloro-2-((3-methyl-1-(1-methylpiperidin-4-yl)-1H-pyrazol-4-yl)amino)pyrimidin-4-yl)amino)propyl)piperidin-2-one, 1-(3-((5-chloro-2-((3-methyl-1-(1-(methyl-d3)piperidin-4-yl)-1H-pyrazol-4-yl)amino)pyrimidin-4-yl)amino)propyl)piperidin-2-one, 1-(3-((5-chloro-2-((1-(1-ethylpiperidin-4-yl)-3-methyl-1H-pyrazol-4-yl)amino)pyrimidin-4-yl)amino)propyl)piperidin-2-one, 1-(3-((2-((1-(1-(2-fluoroethyl)piperidin-4-yl)-3-methyl-1H-pyrazol-4-yl)amino)-5-(trifluoromethyl)pyrimidin-4-yl)amino)propyl)piperidin-2-one, rac-(R)-1-(3-((5-bromo-2-((3-methyl-1-(pyrrolidin-3-yl)-1H-pyrazol-4-yl)amino)pyrimidin-4-yl)amino)propyl)piperidin-2-one, rac-(R)-1-(3-((5-bromo-2-((3-methyl-1-(1-methylpyrrolidin-3-yl)-1H-pyrazol-4-yl)amino)pyrimidin-4-yl)amino)

propyl)piperidin-2-one, 1-(3-((5-bromo-2-((3-methyl-1-(2-(pyrrolidin-1-yl)ethyl)-1H-pyrazol-4-yl)amino)pyrimidin-4-yl)amino)propyl)piperidin-2-one, 1-(3-((5-bromo-2-((3-methyl-1-(2-morpholinoethyl)-1H-pyrazol-4-yl)amino)pyrimidin-4-yl)amino)propyl)piperidin-2-one, rac-(R)-1-(3-((5-bromo-2-((1-(1-ethylpyrrolidin-3-yl)-3-methyl-1H-pyrazol-4-yl)amino)pyrimidin-4-yl)amino)propyl)piperidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)piperidin-2-one, rac-(R)-1-(3-((2-((1-(1-ethylpyrrolidin-3-yl)-3-methyl-1H-pyrazol-4-yl)amino)-5-(trifluoromethyl)pyrimidin-4-yl)amino)propyl)piperidin-2-one, 2-methyl-2-(3-methyl-4-((4-((3-(2-oxopiperidin-1-yl)propyl)amino)-5-(trifluoromethyl)pyrimidin-2-yl)amino)-1H-pyrazol-1-yl)propanamide, 3-(3-((2-((1-(1-isopropylpiperidin-4-yl)-3-methyl-1H-pyrazol-4-yl)amino)-5-(trifluoromethyl)pyrimidin-4-yl)amino)propyl)-1,3-oxazinan-2-one, 3-(3-((2-((3-ethyl-1-(1-isopropylpiperidin-4-yl)-1H-pyrazol-4-yl)amino)-5-(trifluoromethyl)pyrimidin-4-yl)amino)propyl)-1,3-oxazinan-2-one, 3-(3-((5-bromo-2-((1-(1-isopropylpiperidin-4-yl)-3-methyl-1H-pyrazol-4-yl)amino)pyrimidin-4-yl)amino)propyl)-1,3-oxazinan-2-one, 3-(3-((5-chloro-2-((1-(1-isopropylpiperidin-4-yl)-3-methyl-1H-pyrazol-4-yl)amino)pyrimidin-4-yl)amino)propyl)-1,3-oxazinan-2-one, 3-(3-((5-chloro-2-((3-ethyl-1-(1-isopropylpiperidin-4-yl)-1H-pyrazol-4-yl)amino)pyrimidin-4-yl)amino)propyl)-1,3-oxazinan-2-one, 4-(3-((2-((1-(1-isopropylpiperidin-4-yl)-1H-pyrazol-4-yl)amino)-5-(trifluoromethyl)pyrimidin-4-yl)amino)propyl)morpholin-3-one, 4-(3-((5-cyclopropyl-2-((1-(1-isopropylpiperidin-4-yl)-3-methyl-1H-pyrazol-4-yl)amino)pyrimidin-4-yl)amino)propyl)morpholin-3-one, 4-(3-((5-cyclopropyl-2-((3-ethyl-1-(1-isopropylpiperidin-4-yl)-1H-pyrazol-4-yl)amino)pyrimidin-4-yl)amino)propyl)morpholin-3-one, 1-(3-((2-((1-(piperidin-4-yl)-1H-pyrazol-4-yl)amino)-5-(trifluoromethyl)pyrimidin-4-yl)amino)propyl)azepan-2-one, 1-(3-((2-((1-(1-methylpiperidin-4-yl)-1H-pyrazol-4-yl)amino)-5-(trifluoromethyl)pyrimidin-4-yl)amino)propyl)azepan-2-one, 1-(3-((2-((3-methyl-1-(1-methylpiperidin-4-yl)-1H-pyrazol-4-yl)amino)-5-(trifluoromethyl)pyrimidin-4-yl)amino)propyl)azepan-2-one, 1-(3-((5-chloro-2-((3-methyl-1-(1-methylpiperidin-4-yl)-1H-pyrazol-4-yl)amino)pyrimidin-4-yl)amino)propyl)azepan-2-one, 1-(3-((5-chloro-2-((1-(1-methylpiperidin-4-yl)-1H-pyrazol-4-yl)amino)pyrimidin-4-yl)amino)propyl)azepan-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)pyrrolidin-2-one, 1-(3-((2-((3-methyl-1-(piperidin-4-yl)-1H-pyrazol-4-yl)amino)-5-(trifluoromethyl)pyrimidin-4-yl)amino)propyl)azepan-2-one, 1-(3-((5-cyclopropyl-2-((1-(1-methylpiperidin-4-yl)-1H-pyrazol-4-yl)amino)pyrimidin-4-yl)amino)propyl)pyrrolidin-2-one, 1-(3-((2-((1-(1-isopropylpiperidin-4-yl)-3-methyl-1H-pyrazol-4-yl)amino)-5-(trifluoromethyl)pyrimidin-4-yl)amino)propyl)azepan-2-one, 1-(3-((5-chloro-2-((3-methyl-1-(piperidin-4-yl)-1H-pyrazol-4-yl)amino)pyrimidin-4-yl)amino)propyl)azepan-2-one, 1-(3-((5-chloro-2-((1-(1-isopropylpiperidin-4-yl)-3-methyl-1H-pyrazol-4-yl)amino)pyrimidin-4-yl)amino)propyl)azepan-2-one, 1-(3-((2-((1-(1-isopropylpiperidin-4-yl)-1H-pyrazol-4-yl)amino)-5-(trifluoromethyl)pyrimidin-4-yl)amino)propyl)azepan-2-one, 1-(3-((2-((1-(1-isobutylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-ethylpiperidin-4-yl)-3-methyl-1H-pyrazol-4-yl)amino)-5-(trifluoromethyl)pyrimidin-4-yl)amino)propyl)azepan-2-one, 1-(3-((2-((3-methyl-1-(1-(oxetan-3-yl)piperidin-4-yl)-1H-pyrazol-4-yl)amino)-5-(trifluoromethyl)pyrimidin-4-yl)amino)propyl)azepan-2-one, 1-(3-((2-((1-(1-cyclobutylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-cyclopentylpiperidin-4-yl)-3-methyl-1H-pyrazol-4-yl)amino)-5-(trifluoromethyl)pyrimidin-4-yl)amino)propyl)azepan-2-one, 1-(3-((2-((1-(1-(sec-butyl)piperidin-4-yl)-3-methyl-1H-pyrazol-4-yl)amino)-5-(trifluoromethyl)pyrimidin-4-yl)amino)propyl)azepan-2-one, (S)-1-(3-((2-((1-(1-isopropylpyrrolidin-3-yl)-3-methyl-1H-pyrazol-4-yl)amino)-5-(trifluoromethyl)pyrimidin-4-yl)amino)propyl)azepan-2-one, 1-(3-((2-((1-(2-morpholinoethyl)-1H-pyrazol-4-yl)amino)-5-(trifluoromethyl)pyrimidin-4-yl)amino)propyl)azepan-2-one, 1-(3-((2-((1-(1-isobutylazetidin-3-yl)-1H-pyrazol-4-yl)amino)-5-(trifluoromethyl)pyrimidin-4-yl)amino)propyl)azepan-2-one, 1-(3-((2-((3-methyl-1-(2-morpholinoethyl)-1H-pyrazol-4-yl)amino)-5-(trifluoromethyl)pyrimidin-4-yl)amino)propyl)azepan-2-one, 1-(3-((2-((3-methyl-1-(3-(pyrrolidin-1-yl)propyl)-1H-pyrazol-4-yl)amino)-5-(trifluoromethyl)pyrimidin-4-yl)amino)propyl)azepan-2-one, 1-(3-((2-((3-methyl-1-(3-morpholinopropyl)-1H-pyrazol-4-yl)amino)-5-(trifluoromethyl)pyrimidin-4-yl)amino)propyl)azepan-2-one, 1-(3-((2-((3-methyl-1-(1-methyl-d3-piperidin-4-yl)-1H-pyrazol-4-yl)amino)-5-(trifluoromethyl)pyrimidin-4-yl)amino)propyl)azepan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-3-one, 1-(3-((2-((3-methyl-1-(piperidin-4-yl)-1H-pyrazol-4-yl)amino)-5-(trifluoromethyl)pyrimidin-4-yl)amino)propyl)pyrrolidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)pyrrolidin-2-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-3-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 4-(3-((2-((1-(1-ethylpiperidin-4-yl)-3-methyl-1H-pyrazol-4-yl)amino)-5-(trifluoromethyl)pyrimidin-4-yl)amino)propyl)-1,4-oxazepan-3-one, 4-(3-((2-((1-(1-isopropylpiperidin-4-yl)-3-methyl-1H-pyrazol-4-yl)amino)-5-(trifluoromethyl)pyrimidin-4-yl)amino)propyl)-1,4-oxazepan-3-one, 4-(3-((2-((3-ethyl-1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((5-chloro-2-((1-(1-isopropylpiperidin-4-yl)-3-methyl-1H-pyrazol-4-yl)amino)pyrimidin-4-yl)amino)propyl)-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-3-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-3-one, (R)-4-(3-((5-chloro-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((1-(1-isopropylpiperidin-4-yl)-3-methyl-1H-pyrazol-4-yl)amino)pyrimidin-4-yl)amino)propyl)-1,4-oxazepan-3-one, 4-(3-((5-cyclopropyl-2-((3-methyl-1-(3-morpholinopropyl)-1H-pyrazol-4-yl)amino)pyrimidin-4-yl)amino)propyl)-1,4-oxazepan-3-one, 4-(3-((5-cyclopropyl-2-((1-(2-(dimethylamino)ethyl)-3-methyl-1H-pyrazol-4-yl)amino)pyrimidin-4-yl)amino)propyl)-1,4-oxazepan-3-one, 4-(3-((2-((1-(2-(dimethylamino)ethyl)-3-methyl-1H-pyrazol-4-yl)amino)-5-(trifluoromethyl)pyrimidin-4-yl)amino)

propyl)-1,4-oxazepan-3-one, (R)-4-(3-((5-bromo-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((3-ethyl-1-(1-methylpiperidin-4-yl)-1H-pyrazol-4-yl)amino)pyrimidin-4-yl)amino)propyl)-1,4-oxazepan-3-one, 4-(3-((5-chloro-2-((3-methyl-1-(3-morpholinopropyl)-1H-pyrazol-4-yl)amino)pyrimidin-4-yl)amino)propyl)-1,4-oxazepan-3-one, 4-(3-((5-bromo-2-((3-methyl-1-(3-morpholinopropyl)-1H-pyrazol-4-yl)amino)pyrimidin-4-yl)amino)propyl)-1,4-oxazepan-3-one, 4-(3-((5-bromo-2-((1-(2-(dimethylamino)ethyl)-3-methyl-1H-pyrazol-4-yl)amino)pyrimidin-4-yl)amino)propyl)-1,4-oxazepan-3-one, 4-(3-((5-chloro-2-((1-(2-(dimethylamino)ethyl)-3-methyl-1H-pyrazol-4-yl)amino)pyrimidin-4-yl)amino)propyl)-1,4-oxazepan-3-one, 4-(3-((2-((1-(2-(diethylamino)ethyl)-3-methyl-1H-pyrazol-4-yl)amino)-5-(trifluoromethyl)pyrimidin-4-yl)amino)propyl)-1,4-oxazepan-3-one, 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanamide, 3-(3-((2-((4-methyl-1-(1-methylpiperidin-4-yl)-1H-pyrazol-3-yl)amino)-5-(trifluoromethyl)pyrimidin-4-yl)amino)propyl)-1,3-oxazinan-2-one, 4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-5-one, 1-(3-((2-((1-(1-isobutylazetidin-3-yl)-3-methyl-1H-pyrazol-4-yl)amino)-5-(trifluoromethyl)pyrimidin-4-yl)amino)propyl)pyrrolidin-2-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-5-one, 4-(3-((2-((1-(1-ethylpiperidin-4-yl)-3-methyl-1H-pyrazol-4-yl)amino)-5-(trifluoromethyl)pyrimidin-4-yl)amino)propyl)-1,4-oxazepan-5-one, 4-(3-((2-((1-(1-isopropylpiperidin-4-yl)-3-methyl-1H-pyrazol-4-yl)amino)-5-(trifluoromethyl)pyrimidin-4-yl)amino)propyl)-1,4-oxazepan-5-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-5-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, (R)-4-(3-((5-chloro-2-((3-methyl-1-(1-methylpyrrolidin-3-yl)-1H-pyrazol-4-yl)amino)pyrimidin-4-yl)amino)propyl)-1,4-oxazepan-5-one, 4-(3-((5-chloro-2-((3-methyl-1-(3-morpholinopropyl)-1H-pyrazol-4-yl)amino)pyrimidin-4-yl)amino)propyl)-1,4-oxazepan-5-one, 4-(3-((2-((3-ethyl-1-(1-methylpiperidin-4-yl)-1H-pyrazol-4-yl)amino)-5-(trifluoromethyl)pyrimidin-4-yl)amino)propyl)-1,4-oxazepan-5-one, 4-(3-((2-((1-(2-(dimethylamino)ethyl)-3-methyl-1H-pyrazol-4-yl)amino)-5-(trifluoromethyl)pyrimidin-4-yl)amino)propyl)-1,4-oxazepan-5-one, (R)-4-(3-((5-bromo-2-((3-methyl-1-(1-methylpyrrolidin-3-yl)-1H-pyrazol-4-yl)amino)pyrimidin-4-yl)amino)propyl)-1,4-oxazepan-5-one, 4-(3-((5-cyclopropyl-2-((3-methyl-1-(3-morpholinopropyl)-1H-pyrazol-4-yl)amino)pyrimidin-4-yl)amino)propyl)-1,4-oxazepan-5-one, 4-(3-((5-cyclopropyl-2-((1-(2-(dimethylamino)ethyl)-3-methyl-1H-pyrazol-4-yl)amino)pyrimidin-4-yl)amino)propyl)-1,4-oxazepan-5-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-5-one, 4-(3-((5-cyclopropyl-2-((1-(1-ethylpiperidin-4-yl)-3-methyl-1H-pyrazol-4-yl)amino)pyrimidin-4-yl)amino)propyl)-1,4-oxazepan-5-one, 4-(3-((5-chloro-2-((1-(1-isopropylpiperidin-4-yl)-3-methyl-1H-pyrazol-4-yl)amino)pyrimidin-4-yl)amino)propyl)-1,4-oxazepan-5-one, 4-(3-((5-bromo-2-((1-(2-(dimethylamino)ethyl)-3-methyl-1H-pyrazol-4-yl)amino)pyrimidin-4-yl)amino)propyl)-1,4-oxazepan-5-one, 2-methyl-2-(3-methyl-4-((4-((3-(5-oxo-1,4-oxazepan-4-yl)propyl)amino)-5-(trifluoromethyl)pyrimidin-2-yl)amino)-1H-pyrazol-1-yl)propanamide, 4-(3-((2-((1-(2-(diethylamino)ethyl)-3-methyl-1H-pyrazol-4-yl)amino)-5-(trifluoromethyl)pyrimidin-4-yl)amino)propyl)-1,4-oxazepan-5-one, 1-(3-((5-bromo-2-((1-(1-isobutylazetidin-3-yl)-3-methyl-1H-pyrazol-4-yl)amino)pyrimidin-4-yl)amino)propyl)pyrrolidin-2-one, (R)-1-(3-((5-chloro-2-((3-methyl-1-(pyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-1H-pyrazol-4-yl)amino)pyrimidin-4-yl)amino)propyl)pyrrolidin-2-one, (R)-1-(3-((5-chloro-2-((3-methyl-1-(1-methylpyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-3-methyl-1H-pyrazol-4-yl)amino)pyrimidin-4-yl)amino)propyl)pyrrolidin-2-one, 1-(3-((5-chloro-2-((3-methyl-1-(2-(pyrrolidin-1-yl)ethyl)-1H-pyrazol-4-yl)amino)pyrimidin-4-yl)amino)propyl)pyrrolidin-2-one, 1-(3-((5-chloro-2-((3-methyl-1-(2-morpholinoethyl)-1H-pyrazol-4-yl)amino)pyrimidin-4-yl)amino)propyl)pyrrolidin-2-one, (R)-1-(3-((5-bromo-2-((3-methyl-1-(pyrrolidin-3-yl)-1H-pyrazol-4-yl)amino)pyrimidin-4-yl)amino)propyl)pyrrolidin-2-one, 1-(3-((5-bromo-2-((1-(1-isobutylazetidin-3-yl)-1H-pyrazol-4-yl)amino)pyrimidin-4-yl)amino)propyl)pyrrolidin-2-one, 1-(3-((2-((1-(1-methylpiperidin-4-yl)-1H-pyrazol-4-yl)amino)-5-(trifluoromethyl)pyrimidin-4-yl)amino)propyl)pyrrolidin-2-one, (S)-1-(3-((2-((3-methyl-1-(pyrrolidin-3-yl)-1H-pyrazol-4-yl)amino)-5-(trifluoromethyl)pyrimidin-4-yl)amino)propyl)pyrrolidin-2-one, (S)-1-(3-((2-((1-(1-ethylpyrrolidin-3-yl)-3-methyl-1H-pyrazol-4-yl)amino)-5-(trifluoromethyl)pyrimidin-4-yl)amino)propyl)pyrrolidin-2-one, rac-(R)-1-(3-((2-((3-methyl-1-(pyrrolidin-3-yl)-1H-pyrazol-4-yl)amino)-5-(trifluoromethyl)pyrimidin-4-yl)amino)propyl)pyrrolidin-2-one, 1-(3-((2-((1-(1-isobutylazetidin-3-yl)-1H-pyrazol-4-yl)amino)-5-(trifluoromethyl)pyrimidin-4-yl)amino)propyl)pyrrolidin-2-one, 2-methyl-2-(3-methyl-4-((4-((3-(3-oxo-1,4-oxazepan-4-yl)propyl)amino)-5-(trifluoromethyl)pyrimidin-2-yl)amino)-1H-pyrazol-1-yl)propanenitrile, 1-(3-((2-((4-methyl-1-(1-methylpiperidin-4-yl)-1H-pyrazol-3-yl)amino)-5-(trifluoromethyl)pyridin-4-yl)amino)propyl)piperidin-2-one, 1-(3-((2-((1-(1-methylpiperidin-4-yl)-1H-pyrazol-3-yl)amino)-5-(trifluoromethyl)pyridin-4-yl)amino)propyl)piperidin-2-one, 4-(3-((2-((1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((2-((1-(1-methylpiperidin-4-yl)-1H-pyrazol-4-yl)amino)-5-(trifluoromethyl)pyrimidin-4-yl)amino)propyl)-1,4-oxazepan-5-one, 3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazinan-2-one, 4-(3-((2-((2-(1-methylpiperidin-4-yl)-2H-1,2,3-triazol-4-yl)amino)-5-(trifluoromethyl)pyrimidin-4-yl)amino)propyl)-1,4-oxazepan-3-one, 4-(3-((2-((2-(1-methylpiperidin-4-yl)-2H-1,2,3-triazol-4-yl)amino)-5-(trifluoromethyl)pyrimidin-4-yl)amino)propyl)-1,4-oxazepan-5-one, 3-(3-((2-((2-(1-methylpiperidin-4-yl)-2H-1,2,3-triazol-4-yl)amino)-5-(trifluoromethyl)pyrimidin-4-yl)amino)propyl)-1,3-oxazinan-2-one, 4-(3-((2-((1-(1-methylpiperidin-4-yl)-1H-1,2,3-triazol-4-yl)amino)-5-(trifluoromethyl)pyrimidin-4-yl)amino)propyl)-1,4-oxazepan-3-one, 4-(3-((2-((1-(1-methylpiperidin-4-yl)-1H-1,2,3-triazol-4-yl)amino)-5-(trifluoromethyl)pyrimidin-4-yl)amino)propyl)-1,4-oxazepan-5-one, 3-(3-((2-((1-(1-methylpiperidin-4-yl)-1H-1,2,3-triazol-4-yl)amino)-5-

(trifluoromethyl)pyrimidin-4-yl)amino)propyl)-1,3-oxazinan-2-one, 4-(3-((2-((2-(1-methylpiperidin-4-yl) thiazol-4-yl)amino)-5-(trifluoromethyl)pyrimidin-4-yl) amino)propyl)-1,4-oxazepan-3-one, 4-(3-((2-((2-(1-methylpiperidin-4-yl) thiazol-4-yl)amino)-5-(trifluoromethyl)pyrimidin-4-yl)amino)propyl)-1,4-oxazepan-5-one, 3-(3-((2-((2-(1-methylpiperidin-4-yl) thiazol-4-yl)amino)-5-(trifluoromethyl)pyrimidin-4-yl)amino)propyl)-1,3-oxazinan-2-one, 4-(3-((2-((2-(1-methylpiperidin-4-yl) oxazol-4-yl)amino)-5-(trifluoromethyl)pyrimidin-4-yl) amino)propyl)-1,4-oxazepan-3-one, 4-(3-((2-((2-(1-methylpiperidin-4-yl) oxazol-4-yl)amino)-5-(trifluoromethyl)pyrimidin-4-yl)amino)propyl)-1,4-oxazepan-5-one, 3-(3-((2-((2-(1-methylpiperidin-4-yl) oxazol-4-yl)amino)-5-(trifluoromethyl)pyrimidin-4-yl)amino)propyl)-1,3-oxazinan-2-one, 4-(3-((2-((2-(1-methylpiperidin-4-yl) thiazol-5-yl)amino)-5-(trifluoromethyl)pyrimidin-4-yl) amino)propyl)-1,4-oxazepan-3-one, 4-(3-((2-((2-(1-methylpiperidin-4-yl) thiazol-5-yl)amino)-5-(trifluoromethyl)pyrimidin-4-yl)amino)propyl)-1,4-oxazepan-5-one, 3-(3-((2-((2-(1-methylpiperidin-4-yl) thiazol-5-yl)amino)-5-(trifluoromethyl)pyrimidin-4-yl)amino)propyl)-1,3-oxazinan-2-one, 4-(3-((2-((2-(1-methylpiperidin-4-yl) oxazol-5-yl)amino)-5-(trifluoromethyl)pyrimidin-4-yl) amino)propyl)-1,4-oxazepan-3-one, 4-(3-((2-((2-(1-methylpiperidin-4-yl) oxazol-5-yl)amino)-5-(trifluoromethyl)pyrimidin-4-yl)amino)propyl)-1,4-oxazepan-5-one, 3-(3-((2-((2-(1-methylpiperidin-4-yl) oxazol-5-yl)amino)-5-(trifluoromethyl)pyrimidin-4-yl)amino)propyl)-1,3-oxazinan-2-one, 4-(3-((2-((5-methyl-2-(1-methylpiperidin-4-yl)-2H-1,2,3-triazol-4-yl)amino)-5-(trifluoromethyl) pyrimidin-4-yl)amino)propyl)-1,4-oxazepan-3-one, 4-(3-((2-((5-methyl-2-(1-methylpiperidin-4-yl)-2H-1,2,3-triazol-4-yl)amino)-5-(trifluoromethyl)pyrimidin-4-yl)amino) propyl)-1,4-oxazepan-5-one, 3-(3-((2-((5-methyl-2-(1-methylpiperidin-4-yl)-2H-1,2,3-triazol-4-yl)amino)-5-(trifluoromethyl)pyrimidin-4-yl)amino)propyl)-1,3-oxazinan-2-one, 4-(3-((2-((5-methyl-2-(1-methylpiperidin-4-yl) thiazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl) thiazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl) thiazol-4-yl)amino)-5-(trifluoromethyl)pyrimidin-4-yl)amino)propyl)-1,3-oxazinan-2-one, 4-(3-((2-((5-methyl-2-(1-methylpiperidin-4-yl) oxazol-4-yl)amino)-5-(trifluoromethyl)pyrimidin-4-yl)amino)propyl)-1,4-oxazepan-3-one, 4-(3-((2-((5-methyl-2-(1-methylpiperidin-4-yl) oxazol-4-yl)amino)-5-(trifluoromethyl)pyrimidin-4-yl)amino)propyl)-1,4-oxazepan-5-one, 3-(3-((2-((5-methyl-2-(1-methylpiperidin-4-yl) oxazol-4-yl)amino)-5-(trifluoromethyl)pyrimidin-4-yl)amino)propyl)-1,3-oxazinan-2-one, 4-(3-((2-((4-methyl-2-(1-methylpiperidin-4-yl) thiazol-5-yl)amino)-5-(trifluoromethyl)pyrimidin-4-yl)amino)propyl)-1,4-oxazepan-3-one, 4-(3-((2-((4-methyl-2-(1-methylpiperidin-4-yl) thiazol-5-yl)amino)-5-(trifluoromethyl)pyrimidin-4-yl)amino)propyl)-1,4-oxazepan-5-one, 3-(3-((2-((4-methyl-2-(1-methylpiperidin-4-yl) thiazol-5-yl)amino)-5-(trifluoromethyl)pyrimidin-4-yl)amino)propyl)-1,3-oxazinan-2-one, 4-(3-((2-((4-methyl-2-(1-methylpiperidin-4-yl) oxazol-5-yl)amino)-5-(trifluoromethyl)pyrimidin-4-yl)amino)propyl)-1,4-oxazepan-3-one, 4-(3-((2-((4-methyl-2-(1-methylpiperidin-4-yl) oxazol-5-yl)amino)-5-(trifluoromethyl)pyrimidin-4-yl)amino)propyl)-1,4-oxazepan-5-one, 3-(3-((2-((4-methyl-2-(1-methylpiperidin-4-yl) oxazol-5-yl)amino)-5-(trifluoromethyl)pyrimidin-4-yl)amino)propyl)-1,3-oxazinan-2-one, 4-(3-((2-((3-methyl-1-(1-methylpiperidin-4-yl)-1H-pyrazol-4-yl)amino)-5-(trifluoromethyl) pyrimidin-4-yl)amino)propyl)morpholin-3-one, 1-methyl-3-(3-((2-((3-methyl-1-(1-methylpiperidin-4-yl)-1H-pyrazol-4-yl)amino)-5-(trifluoromethyl)pyrimidin-4-yl)amino)propyl) tetrahydropyrimidin-2(1H)-one, 3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazepan-2-one, 1-methyl-3-(3-((2-((3-methyl-1-(1-methylpiperidin-4-yl)-1H-pyrazol-4-yl)amino)-5-(trifluoromethyl)pyrimidin-4-yl)amino)propyl)-1,3-diazepan-2-one, 1-methyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-diazepan-5-one, 4-methyl-1-(3-((2-((3-methyl-1-(1-methylpiperidin-4-yl)-1H-pyrazol-4-yl)amino)-5-(trifluoromethyl)pyrimidin-4-yl)amino)propyl)-1,4-diazepan-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)piperidin-2-one, 1-(3-((2-((3-methyl-1-(8-methyl-8-azabicyclo[3.2.1] octan-3-yl)-1H-pyrazol-4-yl)amino)-5-(trifluoromethyl) pyrimidin-4-yl)amino)propyl)azepan-2-one, 4-methyl-1-(3-((2-((3-methyl-1-(8-methyl-8-azabicyclo[3.2.1]octan-3-yl)-1H-pyrazol-4-yl)amino)-5-(trifluoromethyl)pyrimidin-4-yl) amino)propyl)-1,4-diazepan-2-one, 3-(3-((2-((3-methyl-1-(8-methyl-8-azabicyclo[3.2.1]octan-3-yl)-1H-pyrazol-4-yl) amino)-5-(trifluoromethyl)pyrimidin-4-yl)amino)propyl)-1,3-oxazinan-2-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)morpholin-3-one, 1-methyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl) tetrahydropyrimidin-2(1H)-one, 3-(3-((2-((3-methyl-1-(8-methyl-8-azabicyclo[3.2.1]octan-3-yl)-1H-pyrazol-4-yl) amino)-5-(trifluoromethyl)pyrimidin-4-yl)amino)propyl)-1,3-oxazepan-2-one, 1-methyl-3-(3-((2-((3-methyl-1-(8-methyl-8-azabicyclo[3.2.1]octan-3-yl)-1H-pyrazol-4-yl) amino)-5-(trifluoromethyl)pyrimidin-4-yl)amino)propyl)-1,3-diazepan-2-one, 1-methyl-4-(3-((2-((3-methyl-1-(8-methyl-8-azabicyclo[3.2.1]octan-3-yl)-1H-pyrazol-4-yl) amino)-5-(trifluoromethyl)pyrimidin-4-yl)amino)propyl)-1,4-diazepan-5-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-3-one, 4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-5-one, 1-(3-((2-((3-methyl-1-(1-methylpyrrolidin-3-yl)-1H-pyrazol-4-yl)amino)-5-(trifluoromethyl)pyrimidin-4-yl)amino)propyl)piperidin-2-one, 1-(3-((2-((3-methyl-1-(1-methylpyrrolidin-3-yl)-1H-pyrazol-4-yl)amino)-5-(trifluoromethyl)pyrimidin-4-yl) amino)propyl)azepan-2-one, 4-methyl-1-(3-((2-((3-methyl-1-(1-methylpyrrolidin-3-yl)-1H-pyrazol-4-yl)amino)-5-(trifluoromethyl)pyrimidin-4-yl)amino)propyl)-1,4-diazepan-2-one, 4-(3-((2-((3-methyl-1-(1-methylpyrrolidin-3-yl)-1H-pyrazol-4-yl)amino)-5-(trifluoromethyl) pyrimidin-4-yl)amino)propyl)morpholin-3-one, 1-methyl-3-(3-((2-((3-methyl-1-(1-methylpyrrolidin-3-yl)-1H-pyrazol-4-yl)amino)-5-(trifluoromethyl)pyrimidin-4-yl)amino) propyl)tetrahydropyrimidin-2(1H)-one, 3-(3-((2-((3-methyl-1-(1-methylpyrrolidin-3-yl)-1H-pyrazol-4-yl) amino)-5-(trifluoromethyl)pyrimidin-4-yl)amino)propyl)-1,3-oxazepan-2-one, 1-methyl-3-(3-((2-((3-methyl-1-(1-methylpyrrolidin-3-yl)-1H-pyrazol-4-yl)amino)-5-

(trifluoromethyl)pyrimidin-4-yl)amino)propyl)-1,3-diazepan-2-one, 1-methyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-diazepan-5-one, 4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(1-methylpyrrolidin-3-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(1-methylpiperidin-4-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(1-methylpiperidin-4-yl)-1H-pyrazol-4-yl)amino)-5-(trifluoromethyl)pyrimidin-4-yl)amino)propyl)-1,4-oxazepan-5-one, 6,6-dimethyl-3-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,3-oxazinan-2-one, 2,2-dimethyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-3-one, 6,6-dimethyl-4-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)-1,4-oxazepan-5-one, 1-(3-((2-((3-methyl-1-(1-methylpyrrolidin-3-yl)-1H-pyrazol-4-yl)amino)-5-(trifluoromethyl)pyrimidin-4-yl)amino)propyl)azetidin-2-one, 1-(3-((2-((3-methyl-1-(1-methylpiperidin-4-yl)-1H-pyrazol-4-yl)amino)-5-(trifluoromethyl)pyrimidin-4-yl)amino)propyl)azetidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(1-methylpyrrolidin-3-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(1-methylpiperidin-4-yl)-1H-pyrazol-4-yl)amino)-5-(trifluoromethyl)pyrimidin-4-yl)amino)propyl)azetidin-2-one, 3,3-dimethyl-1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)azetidin-2-one, 4-(3-((5-(difluoromethyl)-2-((3-methyl-1-(1-methylpiperidin-4-yl)-1H-pyrazol-4-yl)amino)pyrimidin-4-yl)amino)propyl)-1,4-oxazepan-3-one, 4-(3-((5-(difluoromethyl)-2-((3-methyl-1-(1-methylpiperidin-4-yl)-1H-pyrazol-4-yl)amino)pyrimidin-4-yl)amino)propyl)-1,4-oxazepan-5-one, 3-(3-((5-(difluoromethyl)-2-((3-methyl-1-(1-methylpiperidin-4-yl)-1H-pyrazol-4-yl)amino)pyrimidin-4-yl)amino)propyl)-1,3-oxazinan-2-one, 4-(3-((5-(difluoromethyl)-2-((1-(1-methylpiperidin-4-yl)-1H-pyrazol-4-yl)amino)pyrimidin-4-yl)amino)propyl)-1,4-oxazepan-3-one, 4-(3-((5-(difluoromethyl)-2-((1-(1-methylpiperidin-4-yl)-1H-pyrazol-4-yl)amino)pyrimidin-4-yl)amino)propyl)-1,4-oxazepan-5-one, 3-(3-((5-(difluoromethyl)-2-((1-(1-methylpiperidin-4-yl)-1H-pyrazol-4-yl)amino)pyrimidin-4-yl)amino)propyl)-1,3-oxazinan-2-one, 4-(3-((5-(difluoromethyl)-2-((3-methyl-1-(1-methylpiperidin-4-yl)-1H-pyrazol-4-yl)amino)pyrimidin-4-yl)amino)propyl)morpholin-3-one, 1-(3-((5-(difluoromethyl)-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-(difluoromethyl)-2-((3-methyl-1-(1-methylpiperidin-4-yl)-1H-pyrazol-4-yl)amino)pyrimidin-4-yl)amino)propyl)-1,3-oxazepan-2-one, 1-(3-((5-(difluoromethyl)-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-(difluoromethyl)-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-(difluoromethyl)-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-(difluoromethyl)-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-(difluoromethyl)-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-(difluoromethyl)-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-(difluoromethyl)-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-(difluoromethyl)-2-((3-methyl-1-(1-methylpyrrolidin-3-yl)-

1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-(difluoromethyl)-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-(difluoromethyl)-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-(difluoromethyl)-2-((3-methyl-1-(1-methylpyrrolidin-3-yl)-1H-pyrazol-4-yl)amino)pyrimidin-4-yl)amino)propyl)azetidin-2-one, 1-(3-((5-(difluoromethyl)-2-((3-methyl-1-(1-methylpiperidin-4-yl)-1H-pyrazol-4-yl)amino)pyrimidin-4-yl)amino)propyl)azetidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-(difluoromethyl)-2-((3-methyl-1-(1-methylpyrrolidin-3-yl)-1H-pyrazol-4-yl)amino)pyrimidin-4-yl)amino)propyl)-3,3-dimethylazetidin-2-one, 1-(3-((5-(difluoromethyl)-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)-3,3-dimethylazetidin-2-one, 4-(3-((5-bromo-2-((3-methyl-1-(1-methylpiperidin-4-yl)-1H-pyrazol-4-yl)amino)pyrimidin-4-yl)amino)propyl)-1,4-oxazepan-3-one, 4-(3-((5-bromo-2-((3-methyl-1-(1-methylpiperidin-4-yl)-1H-pyrazol-4-yl)amino)pyrimidin-4-yl)amino)propyl)-1,4-oxazepan-5-one, 3-(3-((5-bromo-2-((3-methyl-1-(1-methylpiperidin-4-yl)-1H-pyrazol-4-yl)amino)pyrimidin-4-yl)amino)propyl)-1,3-oxazinan-2-one, 4-(3-((5-bromo-2-((1-(1-methylpiperidin-4-yl)-1H-pyrazol-4-yl)amino)pyrimidin-4-yl)amino)propyl)-1,4-oxazepan-3-one, 4-(3-((5-bromo-2-((1-(1-methylpiperidin-4-yl)-1H-pyrazol-4-yl)amino)pyrimidin-4-yl)amino)propyl)-1,4-oxazepan-5-one, 3-(3-((5-bromo-2-((1-(1-methylpiperidin-4-yl)-1H-pyrazol-4-yl)amino)pyrimidin-4-yl)amino)propyl)-1,3-oxazinan-2-one, 4-(3-((5-bromo-2-((3-methyl-1-(1-methylpiperidin-4-yl)-1H-pyrazol-4-yl)amino)pyrimidin-4-yl)amino)propyl)morpholin-3-one, 1-(3-((5-bromo-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-bromo-2-((3-methyl-1-(1-methylpiperidin-4-yl)-1H-pyrazol-4-yl)amino)pyrimidin-4-yl)amino)propyl)-1,3-oxazepan-2-one, 1-(3-((5-bromo-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-bromo-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-bromo-2-((3-methyl-1-(1-methylpiperidin-4-yl)-1H-pyrazol-4-yl)amino)pyrimidin-4-yl)amino)propyl)-4-methyl-1,4-diazepan-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-bromo-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-bromo-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-bromo-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-bromo-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-bromo-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-bromo-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-bromo-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-bromo-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-bromo-2-((3-methyl-1-(1-methylpyrrolidin- 3-yl)-1H-pyrazol-4-yl)amino)pyrimidin-4-yl)amino)propyl) azetidin-2-one, 1-(3-((5-bromo-2-((3-methyl-1-(1-methylpiperidin-4-yl)-1H-pyrazol-4-yl)amino)pyrimidin-4-yl)amino)propyl)azetidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-bromo-2-((3-methyl-1-(1-methylpyrrolidin-3-yl)-1H-pyrazol-4-yl)amino)pyrimidin-4-yl)amino) propyl)-3,3-dimethylazetidin-2-one, 1-(3-((5-bromo-2-((3-methyl-1-(1-methylpiperidin-4-yl)-1H-pyrazol-4-yl)amino) pyrimidin-4-yl)amino)propyl)-3,3-dimethylazetidin-2-one, 1-(3-((5-bromo-2-((3-methyl-1-(8-methyl-8-azabicyclo [3.2.1]octan-3-yl)-1H-pyrazol-4-yl)amino)pyrimidin-4-yl) amino)propyl)-3,3-dimethylazetidin-2-one, 4-(3-((5-chloro-2-((3-methyl-1-(1-methylpiperidin-4-yl)-1H-pyrazol-4-yl) amino)pyrimidin-4-yl)amino)propyl)-1,4-oxazepan-3-one, 4-(3-((5-chloro-2-((3-methyl-1-(1-methylpiperidin-4-yl)-1H-pyrazol-4-yl)amino)pyrimidin-4-yl)amino)propyl)-1,4-oxazepan-5-one, 3-(3-((5-chloro-2-((3-methyl-1-(1-methylpiperidin-4-yl)-1H-pyrazol-4-yl)amino)pyrimidin-4-yl) amino)propyl)-1,3-oxazinan-2-one, 4-(3-((5-chloro-2-((1-(1-methylpiperidin-4-yl)-1H-pyrazol-4-yl)amino) pyrimidin-4-yl)amino)propyl)-1,4-oxazepan-3-one, 4-(3-((5-chloro-2-((1-(1-methylpiperidin-4-yl)-1H-pyrazol-4-yl) amino)pyrimidin-4-yl)amino)propyl)-1,4-oxazepan-5-one, 3-(3-((5-chloro-2-((1-(1-methylpiperidin-4-yl)-1H-pyrazol-4-yl)amino)pyrimidin-4-yl)amino)propyl)-1,3-oxazinan-2-one, 4-(3-((5-chloro-2-((3-methyl-1-(1-methylpiperidin-4-yl)-1H-pyrazol-4-yl)amino)pyrimidin-4-yl)amino)propyl) morpholin-3-one, 1-(3-((5-chloro-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-chloro-2-((3-methyl-1-(1-methylpiperidin-4-yl)-1H-pyrazol-4-yl)amino)pyrimidin-4-yl)amino)propyl)-1,3-oxazepan-2-one, 1-(3-((5-chloro-2-((3-methyl-1-(1-methylpiperidin-4-yl)-1H-pyrazol-4-yl)amino)pyrimidin-4-yl) amino)propyl)-3-methyl-1,3-diazepan-2-one, 4-(3-((5-chloro-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-chloro-2-((3-methyl-1-(1-methylpiperidin-4-yl)-1H-pyrazol-4-yl)amino) pyrimidin-4-yl)amino)propyl)-4-methyl-1,4-diazepan-2-one, 1-(3-((5-chloro-2-((3-methyl-1-(8-methyl-8-azabicyclo [3.2.1]octan-3-yl)-1H-pyrazol-4-yl)amino)pyrimidin-4-yl) amino)propyl)piperidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-4-methyl-1,4-diazepan-2-one, 3-(3-((5-chloro-2-((3-methyl-1-(8-methyl-8-azabicyclo [3.2.1]octan-3-yl)-1H-pyrazol-4-yl)amino)pyrimidin-4-yl) amino)propyl)-1,3-oxazinan-2-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl) morpholin-3-one, 1-(3-((5-chloro-2-((3-methyl-1-(8-methyl-8-azabicyclo[3.2.1]octan-3-yl)-1H-pyrazol-4-yl) amino)pyrimidin-4-yl)amino)propyl)-3-methyltetrahydropyrimidin-2(1H)-one, 3-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-3-methyl-1,3-diazepan-2-one, 4-(3-((5-chloro-2-((3-methyl-1-(8-methyl-8-azabicyclo [3.2.1]octan-3-yl)-1H-pyrazol-4-yl)amino)pyrimidin-4-yl) amino)propyl)-1-methyl-1,4-diazepan-5-one, 4-(3-((5-chloro-2-((3-methyl-1-(8-methyl-8-azabicyclo[3.2.1]octan-3-yl)-1H-pyrazol-4-yl)amino)pyrimidin-4-yl)amino) propyl)-1,4-oxazepan-3-one, 4-(3-((5-chloro-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-chloro-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-chloro-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-chloro-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-chloro-2-((3-methyl-1-(1-methylpyrrolidin-3-yl)-1H-pyrazol-4-yl)amino) pyrimidin-4-yl)amino)propyl)-1,4-oxazepan-3-one, 4-(3-((5-chloro-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-chloro-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-chloro-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-chloro-2-((3-methyl-1-(1-methylpyrrolidin-3-yl)-1H-pyrazol-4-yl) amino)pyrimidin-4-yl)amino)propyl)-6,6-dimethyl-1,4-oxazepan-5-one, 3-(3-((5-chloro-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-chloro-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-chloro-2-((3-methyl-1-(1-methylpiperidin-4-yl)-1H-pyrazol-4-yl)amino) pyrimidin-4-yl)amino)propyl)-6,6-dimethyl-1,4-oxazepan-5-one, 3-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-6,6-dimethyl-1,3-oxazinan-2-one, 4-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-2,2-dimethyl-1,4-oxazepan-3-one, 4-(3-((5-chloro-2-((3-methyl-1-(8-methyl-8-azabicyclo[3.2.1]octan-3-yl)-1H-pyrazol-4-yl)amino) pyrimidin-4-yl)amino)propyl)-6,6-dimethyl-1,4-oxazepan-5-one, 1-(3-((5-chloro-2-((3-methyl-1-(1-methylpyrrolidin-3-yl)-1H-pyrazol-4-yl)amino)pyrimidin-4-yl)amino)propyl) azetidin-2-one, 1-(3-((5-chloro-2-((3-methyl-1-(1-methylpiperidin-4-yl)-1H-pyrazol-4-yl)amino)pyrimidin-4-yl)amino)propyl)azetidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-chloro-2-((3-methyl-1-(1-methylpyrrolidin-3-yl)-1H-pyrazol-4-yl)amino)pyrimidin-4-yl)amino) propyl)-3,3-dimethylazetidin-2-one, 1-(3-((5-chloro-2-((3-methyl-1-(1-methylpiperidin-4-yl)-1H-pyrazol-4-yl)amino) pyrimidin-4-yl)amino)propyl)-3,3-dimethylazetidin-2-one, 1-(3-((5-chloro-2-((3-methyl-1-(8-methyl-8-azabicyclo [3.2.1]octan-3-yl)-1H-pyrazol-4-yl)amino)pyrimidin-4-yl) amino)propyl)-3,3-dimethylazetidin-2-one, 2-((3-methyl-1-(1-methylpiperidin-4-yl)-1H-pyrazol-4-yl)amino)-4-((3-(3-oxo-1,4-oxazepan-4-yl)propyl)amino)pyrimidine-5-carbonitrile, 2-((3-methyl-1-(1-methylpiperidin-4-yl)-1H-pyrazol-4-yl)amino)-4-((3-(5-oxo-1,4-oxazepan-4-yl) propyl)amino)pyrimidine-5-carbonitrile, 2-((3-methyl-1-(1-methylpiperidin-4-yl)-1H-pyrazol-4-yl)amino)-4-((3-(2-oxo-1,3-oxazinan-3-yl)propyl)amino)pyrimidine-5-carbonitrile, 2-((1-(1-methylpiperidin-4-yl)-1H-pyrazol-4-yl)amino)-4-((3-(3-oxo-1,4-oxazepan-4-yl)propyl)amino) pyrimidine-5-carbonitrile, 2-((1-(1-methylpiperidin-4-yl)-

1H-pyrazol-4-yl)amino)-4-((3-(5-oxo-1,4-oxazepan-4-yl)propyl)amino)pyrimidine-5-carbonitrile, 2-((1-(1-methylpiperidin-4-yl)-1H-pyrazol-4-yl)amino)-4-((3-(2-oxo-1,3-oxazinan-3-yl)propyl)amino)pyrimidine-5-carbonitrile, 2-((3-methyl-1-(1-methylpiperidin-4-yl)-1H-pyrazol-4-yl)amino)-4-((3-(3-oxomorpholino)propyl)amino)pyrimidine-5-carbonitrile, 2-((3-methyl-1-(1-methylpiperidin-4-yl)-1H-pyrazol-4-yl)amino)-4-((3-(3-methyl-2-oxotetrahydropyrimidin-1 (2H)-yl)propyl)amino)pyrimidine-5-carbonitrile, 2-((3-methyl-1-(1-methylpiperidin-4-yl)-1H-pyrazol-4-yl)amino)-4-((3-(2-oxo-1,3-oxazepan-3-yl)propyl)amino)pyrimidine-5-carbonitrile, 2-((3-methyl-1-(1-methylpiperidin-4-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(1-methylpiperidin-4-yl)-1H-pyrazol-4-yl)amino)-4-((3-(4-methyl-7-oxo-1,4-diazepan-1-yl)propyl)amino)pyrimidine-5-carbonitrile, 2-((3-methyl-1-(1-methylpiperidin-4-yl)-1H-pyrazol-4-yl)amino)-4-((3-(4-methyl-2-oxo-1,4-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxopiperidin-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxoazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(4-methyl-2-oxo-1,4-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxo-1,3-oxazinan-3-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-oxomorpholino)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-methyl-2-oxotetrahydro-pyrimidin-1 (2H)-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxo-1,3-oxazepan-3-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(4-methyl-7-oxo-1,4-diazepan-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(3-oxo-1,4-oxazepan-4-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(5-oxo-1,4-oxazepan-4-yl)propyl)amino)pyrimidine-5-carbonitrile, 2-((3-methyl-1-(1-methylpyrrolidin-3-yl)-1H-pyrazol-4-yl)amino)-4-((3-(2-oxo-1,3-oxazepan-3-yl)propyl)amino)pyrimidine-5-carbonitrile, 2-((3-methyl-1-(1-methylpyrrolidin-3-yl)-1H-pyrazol-4-yl)amino)-4-((3-(3-methyl-2-oxo-1,3-diazepan-1-yl)propyl)amino)pyrimidine-5-carbonitrile, 2-((3-methyl-1-(1-methylpyrrolidin-3-yl)-1H-pyrazol-4-yl)amino)-4-((3-(4-methyl-7-oxo-1,4-diazepan-1-yl)propyl)amino)pyrimidine-5-carbonitrile, 2-((3-methyl-1-(1-methylpyrrolidin-3-yl)-1H-pyrazol-4-yl)amino)-4-((3-(3-oxo-1,4-oxazepan-4-yl)propyl)amino)pyrimidine-5-carbonitrile, 2-((3-methyl-1-(1-methylpyrrolidin-3-yl)-1H-pyrazol-4-yl)amino)-4-((3-(5-oxo-1,4-oxazepan-4-yl)propyl)amino)pyrimidine-5-carbonitrile, 4-((3-(6,6-dimethyl-2-oxo-1,3-oxazinan-3-yl)propyl)amino)-2-((3-methyl-1-(1-methylpyrrolidin-3-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(1-methylpyrrolidin-3-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(1-methylpyrrolidin-3-yl)-1H-pyrazol-4-yl)amino)pyrimidine-5-carbonitrile, 4-((3-(6,6-dimethyl-2-oxo-1,3-oxazinan-3-yl)propyl)amino)-2-((3-methyl-1-(1-methylpiperidin-4-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(1-methylpiperidin-4-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(1-methylpiperidin-4-yl)-1H-pyrazol-4-yl)amino)pyrimidine-5-carbonitrile, 4-((3-(6,6-dimethyl-2-oxo-1,3-oxazinan-3-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-((3-(2,2-dimethyl-3-oxo-1,4-oxazepan-4-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-((3-(6,6-dimethyl-5-oxo-1,4-oxazepan-4-yl)propyl)amino)-2-((3-methyl-1-(8-methyl-8-azabicyclo[3.2.1]octan-3-yl)-1H-pyrazol-4-yl)amino)pyrimidine-5-carbonitrile, 2-((3-methyl-1-(1-methylpyrrolidin-3-yl)-1H-pyrazol-4-yl)amino)-4-((3-(2-oxoazetidin-1-yl)propyl)amino)pyrimidine-5-carbonitrile, 2-((3-methyl-1-(1-methylpiperidin-4-yl)-1H-pyrazol-4-yl)amino)-4-((3-(2-oxoazetidin-1-yl)propyl)amino)pyrimidine-5-carbonitrile, 2-((3-methyl-1-(8-methyl-8-azabicyclo[3.2.1]octan-3-yl)-1H-pyrazol-4-yl)amino)-4-((3-(2-oxoazetidin-1-yl)propyl)amino)pyrimidine-5-carbonitrile, 4-((3-(3,3-dimethyl-2-oxoazetidin-1-yl)propyl)amino)-2-((3-methyl-1-(1-methylpyrrolidin-3-yl)-1H-pyrazol-4-yl)amino)pyrimidine-5-carbonitrile, 4-((3-(3,3-dimethyl-2-oxoazetidin-1-yl)propyl)amino)-2-((3-methyl-1-(1-methylpiperidin-4-yl)-1H-pyrazol-4-yl)amino)pyrimidine-5-carbonitrile, 4-((3-(3,3-dimethyl-2-oxoazetidin-1-yl)propyl)amino)-2-((3-methyl-1-(8-methyl-8-azabicyclo[3.2.1]octan-3-yl)-1H-pyrazol-4-yl)amino)pyrimidine-5-carbonitrile, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpiperidin-4-yl)-1H-pyrazol-4-yl)amino)pyrimidin-4-yl)amino)propyl)-1,3-oxazinan-2-one, 4-(3-((5-cyclopropyl-2-((1-(1-methylpiperidin-4-yl)-1H-pyrazol-4-yl)amino)pyrimidin-4-yl)amino)propyl)-1,4-oxazepan-3-one, 4-(3-((5-cyclopropyl-2-((1-(1-methylpiperidin-4-yl)-1H-pyrazol-4-yl)amino)pyrimidin-4-yl)amino)propyl)-1,4-oxazepan-5-one, 3-(3-((5-cyclopropyl-2-((1-(1-methylpiperidin-4-yl)-1H-pyrazol-4-yl)amino)pyrimidin-4-yl)amino)propyl)-1,3-oxazinan-2-one, 4-(3-((5-cyclopropyl-2-((3-methyl-1-(1-methylpiperidin-4-yl)-1H-pyrazol-4-yl)amino)pyrimidin-4-yl)amino)propyl)morpholin-3-one, 1-(3-((5-cyclopropyl-2-((3-methyl-1-(1-methylpiperidin-4-yl)-1H-pyrazol-4-yl)amino)pyrimidin-4-yl)amino)propyl)-3-methyltetrahydropyrimidin-2(1H)-one, 3-(3-((5-cyclopropyl-2-((3-methyl-1-(1-methylpiperidin-4-yl)-1H-pyrazol-4-yl)amino)pyrimidin-4-yl)amino)propyl)-1,3-oxazepan-2-one, 1-(3-((5-cyclopropyl-2-((3-methyl-1-(1-methylpiperidin-4-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(1-methylpiperidin-4-yl)-1H-pyrazol-4-yl)amino)pyrimidin-4-yl)amino)propyl)-1-methyl-1,4-diazepan-5-one, 1-(3-((5-cyclopropyl-2-((3-methyl-1-(1-methylpiperidin-4-yl)-1H-pyrazol-4-yl)amino)

pyrimidin-4-yl)amino)propyl)-4-methyl-1,4-diazepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)piperidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)azepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-4-methyl-1,4-diazepan-2-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,3-oxazinan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)morpholin-3-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3-methyltetrahydropyrimidin-2(1H)-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,3-oxazepan-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1-methyl-1,4-diazepan-5-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-3-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpyrrolidin-3-yl)-1H-pyrazol-4-yl)amino)pyrimidin-4-yl)amino)propyl)-1,3-oxazepan-2-one, 1-(3-((5-cyclopropyl-2-((3-methyl-1-(1-methylpyrrolidin-3-yl)-1H-pyrazol-4-yl)amino)pyrimidin-4-yl)amino)propyl)-3-methyl-1,3-diazepan-2-one, 4-(3-((5-cyclopropyl-2-((3-methyl-1-(1-methylpyrrolidin-3-yl)-1H-pyrazol-4-yl)amino)pyrimidin-4-yl)amino)propyl)-1-methyl-1,4-diazepan-5-one, 4-(3-((5-cyclopropyl-2-((3-methyl-1-(1-methylpyrrolidin-3-yl)-1H-pyrazol-4-yl)amino)pyrimidin-4-yl)amino)propyl)-1,4-oxazepan-3-one, 4-(3-((5-cyclopropyl-2-((3-methyl-1-(1-methylpyrrolidin-3-yl)-1H-pyrazol-4-yl)amino)pyrimidin-4-yl)amino)propyl)-1,4-oxazepan-5-one, 3-(3-((5-cyclopropyl-2-((3-methyl-1-(1-methylpyrrolidin-3-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(1-methylpyrrolidin-3-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(1-methylpyrrolidin-3-yl)-1H-pyrazol-4-yl)amino)pyrimidin-4-yl)amino)propyl)-6,6-dimethyl-1,4-oxazepan-5-one, 3-(3-((5-cyclopropyl-2-((3-methyl-1-(1-methylpiperidin-4-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(1-methylpiperidin-4-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(1-methylpiperidin-4-yl)-1H-pyrazol-4-yl)amino)pyrimidin-4-yl)amino)propyl)-6,6-dimethyl-1,4-oxazepan-5-one, 3-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,3-oxazinan-2-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-2,2-dimethyl-1,4-oxazepan-3-one, 4-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-6,6-dimethyl-1,4-oxazepan-5-one, 1-(3-((5-cyclopropyl-2-((3-methyl-1-(1-methylpyrrolidin-3-yl)-1H-pyrazol-4-yl)amino)pyrimidin-4-yl)amino)propyl)azetidin-2-one, 1-(3-((5-cyclopropyl-2-((3-methyl-1-(1-methylpiperidin-4-yl)-1H-pyrazol-4-yl)amino)pyrimidin-4-yl)amino)propyl)azetidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)azetidin-2-one, 1-(3-((5-cyclopropyl-2-((3-methyl-1-(1-methylpyrrolidin-3-yl)-1H-pyrazol-4-yl)amino)pyrimidin-4-yl)amino)propyl)-3,3-dimethylazetidin-2-one, 1-(3-((5-cyclopropyl-2-((3-methyl-1-(1-methylpiperidin-4-yl)-1H-pyrazol-4-yl)amino)pyrimidin-4-yl)amino)propyl)-3,3-dimethylazetidin-2-one, 1-(3-((5-cyclopropyl-2-((3-methyl-1-(8-methyl-8-azabicyclo[3.2.1]octan-3-yl)-1H-pyrazol-4-yl)amino)pyrimidin-4-yl)amino)propyl)-3,3-dimethylazetidin-2-one, 1-(3-((2-((3-methyl-1-(8-methyl-8-azabicyclo[3.2.1]octan-3-yl)-1H-pyrazol-4-yl)amino)-5-(trifluoromethyl)pyrimidin-4-yl)amino)propyl)pyrrolidin-2-one, 1-(3-((5-(difluoromethyl)-2-((3-methyl-1-(8-methyl-8-azabicyclo[3.2.1]octan-3-yl)-1H-pyrazol-4-yl)amino)pyrimidin-4-yl)amino)propyl)pyrrolidin-2-one, 1-(3-((2-((3-methyl-1-(1-methylpyrrolidin-3-yl)-1H-pyrazol-4-yl)amino)-5-(trifluoromethyl)pyrimidin-4-yl)amino)propyl)pyrrolidin-2-one, 1-(3-((5-(difluoromethyl)-2-((3-methyl-1-(1-methylpyrrolidin-3-yl)-1H-pyrazol-4-yl)amino)pyrimidin-4-yl)amino)propyl)pyrrolidin-2-one, 1-(3-((2-((1-(1-isobutylazetidin-3-yl)-3-methyl-1H-pyrazol-4-yl)amino)-5-(trifluoromethyl)pyrimidin-4-yl)amino)propyl)pyrrolidin-2-one, 1-(3-((5-(difluoromethyl)-2-((1-(1-isobutylazetidin-3-yl)-3-methyl-1H-pyrazol-4-yl)amino)pyrimidin-4-yl)amino)propyl)pyrrolidin-2-one, 1-(3-((5-bromo-2-((3-methyl-1-(8-methyl-8-azabicyclo[3.2.1]octan-3-yl)-1H-pyrazol-4-yl)amino)pyrimidin-4-yl)amino)propyl)pyrrolidin-2-one, 1-(3-((5-bromo-2-((3-methyl-1-(1-methylpyrrolidin-3-yl)-1H-pyrazol-4-yl)amino)pyrimidin-4-yl)amino)propyl)pyrrolidin-2-one, 1-(3-((5-bromo-2-((1-(1-isobutylazetidin-3-yl)-3-methyl-1H-pyrazol-4-yl)amino)pyrimidin-4-yl)amino)propyl)pyrrolidin-2-one, 1-(3-((5-chloro-2-((3-methyl-1-(8-methyl-8-azabicyclo[3.2.1]octan-3-yl)-1H-pyrazol-4-yl)amino)pyrimidin-4-yl)amino)propyl)pyrrolidin-2-one, 1-(3-((5-chloro-2-((3-methyl-1-(1-methylpyrrolidin-3-yl)-1H-pyrazol-4-yl)amino)pyrimidin-4-yl)amino)propyl)pyrrolidin-2-one, 1-(3-((5-chloro-2-((1-(1-isobutylazetidin-3-yl)-3-methyl-1H-pyrazol-4-yl)amino)pyrimidin-4-yl)amino)propyl)pyrrolidin-2-one, 4-(3-((2-((2-(3-(dimethylamino)propyl)-2H-1,2,3-triazol-4-yl)amino)-5-(trifluoromethyl)pyrimidin-4-yl)amino)propyl)-1,4-oxazepan-3-one, 4-(3-((2-((2-(2-(dimethylamino)ethyl)-2H-1,2,3-triazol-4-yl)amino)-5-(trifluoromethyl)pyrimidin-4-yl)amino)propyl)-1,4-oxazepan-5-one, 3-(3-((2-((5-ethyl-2-(1-methylpiperidin-4-yl)-2H-1,2,3-triazol-4-yl)amino)-5-(trifluoromethyl)pyrimidin-4-yl)amino)propyl)-1,3-oxazinan-2-one, N-(1-methylpiperidin-4-yl)-4-((4-((3-(2-oxo-1,3-oxazinan-3-yl)propyl)amino)-5-(trifluoromethyl)pyrimidin-2-yl)amino) thiazole-2-carboxamide, 4-(3-((2-((2-(3-(dimethylamino)propyl) oxazol-4-yl)amino)-5-(trifluoromethyl)pyrimidin-4-yl)amino)propyl)-1,4-oxazepan-3-one, 4-(3-((2-((2-(2-(dimethylamino)ethyl) oxazol-4-yl)amino)-5-(trifluoromethyl)pyrimidin-4-yl)amino)propyl)-1,4-oxazepan-5-one, 3-(3-((2-((2-(4-methylpiperazine-1-carbonyl) oxazol-4-yl)amino)-5-(trifluoromethyl)pyrimidin-4-yl)amino)propyl)-1,3-oxazinan-2-one, 3,3-dimethyl-1-(3-((2-((5-methyl-2-(1-methylpiperidin-4-yl)-2H-1,2,3-triazol-4-yl)amino)-5-(trifluoromethyl)pyrimidin-4-yl)amino)propyl)azetidin-2-one, 4-(3-((2-((1-(3-(dimethylamino)propyl)-1H-pyrazol-4-yl)amino)-5-(trifluoromethyl)pyrimidin-4-yl)amino)propyl)-1,4-oxazepan-3-one, 4-(3-((2-((1-(3-(pyrrolidin-1-yl)propyl)-1H-pyrazol-4-yl)amino)-5-(trifluoromethyl)pyrimidin-4-yl)amino)propyl)-1,4-oxazepan-5-one, 3-(3-((2-((3-methyl-1-(2-morpholinoethyl)-1H-pyrazol-4-yl)amino)-5-(trifluoromethyl)pyrimidin-4-yl)amino)propyl)-1,3-oxazinan-2-one, 4-(3-((2-((3-fluoro-1-(1-methylpiperidin-4-yl)-1H-pyrazol-4-yl)amino)-5-(trifluoromethyl)pyrimidin-4-yl)amino)propyl)-1,4-oxazepan-3-one, 4-(3-((2-((1-(1-methylpiperidin-4-yl)-3-(trifluoromethyl)-1H-pyrazol-4-yl)amino)-5-(trifluoromethyl)pyrimidin-4-yl)amino)propyl)-1,4-oxazepan-5-one, 3-(3-((2-((3-methoxy-1-(1-methylpiperidin-4-yl)-1H-pyrazol-4-yl)amino)-5-(trifluoromethyl)pyrimidin-4-yl)amino)propyl)-1,3-oxazinan-2-one, 1-(1-methylpiperidin-4-yl)-4-((4-((3-(2-oxopiperidin-1-yl)propyl)amino)-5-(trifluoromethyl)pyrimidin-2-yl)amino)-1H-pyrazole-3-carbonitrile, 4-(3-((2-((3-ethynyl-1-(1-methylpiperidin-4-yl)-1H-pyrazol-4-yl)amino)-5-(trifluoromethyl)pyrimidin-4-yl)amino)propyl)-1,4-oxazepan-3-one, 3-(3-((2-((1-(1-methylpiperidin-4-yl)-3-vinyl-1H-pyrazol-4-yl)amino)-5-(trifluoromethyl)pyrimidin-4-yl)amino)propyl)-1,3-oxazinan-2-one, 4-(3-((2-((3-cyclopropyl-1-(1-methylpiperidin-4-yl)-1H-pyrazol-4-yl)amino)-5-(trifluoromethyl)pyrimidin-4-yl)amino)propyl)-1,4-oxazepan-5-one, 8-(3-((2-((3-methyl-1-(1-methylpiperidin-4-yl)-1H-pyrazol-4-yl)amino)-5-(trifluoromethyl)pyrimidin-4-yl)amino)propyl)-4-oxa-8-azaspiro[2.6]nonan-9-one, 8-(3-((2-((3-methyl-1-(1-methylpiperidin-4-yl)-1H-pyrazol-4-yl)amino)-5-(trifluoromethyl)pyrimidin-4-yl)amino)propyl)-5-oxa-8-azaspiro[2.6]nonan-9-one, 9-(3-((2-((3-methyl-1-(1-methylpiperidin-4-yl)-1H-pyrazol-4-yl)amino)-5-(trifluoromethyl)pyrimidin-4-yl)amino)propyl)-5-oxa-9-azaspiro[3.6]decan-10-one, 9-(3-((2-((3-methyl-1-(1-methylpiperidin-4-yl)-1H-pyrazol-4-yl)amino)-5-(trifluoromethyl)pyrimidin-4-yl)amino)propyl)-6-oxa-9-azaspiro[3.6]decan-10-one, 4-(3-((2-((3-methyl-1-(1-methylpiperidin-4-yl)-1H-pyrazol-4-yl)amino)-5-(trifluoromethyl)pyridin-4-yl)amino)propyl)-1,4-oxazepan-5-one, 4-(3-((2-((3-methyl-1-(1-methylpiperidin-4-yl)-1H-pyrazol-4-yl)amino)-5-(trifluoromethyl)pyridin-4-yl)amino)propyl)-1,4-oxazepan-3-one, 3-(3-((2-((3-methyl-1-(1-methylpiperidin-4-yl)-1H-pyrazol-4-yl)amino)-5-(trifluoromethyl)pyridin-4-yl)amino)propyl)-1,3-oxazepan-2-one, 3-(3-((2-((3-methyl-1-(1-methylpiperidin-4-yl)-1H-pyrazol-4-yl)amino)-5-(trifluoromethyl)pyridin-4-yl)amino)propyl)-1,3-oxazinan-2-one, 2,2-dimethyl-4-(3-((2-((3-methyl-1-(1-methylpiperidin-4-yl)-1H-pyrazol-4-yl)amino)-5-(trifluoromethyl)pyridin-4-yl)amino)propyl)-1,4-oxazepan-3-one, 4-(3-((5-(difluoromethyl)-2-((3-methyl-1-(1-methylpiperidin-4-yl)-1H-pyrazol-4-yl)amino)pyridin-4-yl)amino)propyl)-1,4-oxazepan-5-one, 3-(3-((5-chloro-2-((3-methyl-1-(1-methylpiperidin-4-yl)-1H-pyrazol-4-yl)amino)pyridin-4-yl)amino)propyl)-1,3-oxazinan-2-one, 4-(3-((2-((5-methyl-2-(1-methylpiperidin-4-yl)-2H-1,2,3-triazol-4-yl)amino)-5-(trifluoromethyl)pyridin-4-yl)amino)propyl)-1,4-oxazepan-3-one, 4-(3-((2-((3-methyl-1-(3-morpholinopropyl)-1H-pyrazol-4-yl)amino)-5-(trifluoromethyl)pyrimidin-4-yl)amino)propyl)-1,4-oxazepan-5-one, 4-(3-((2-((1-(2-(dimethylamino)ethyl)-3-methyl-1H-pyrazol-4-yl)amino)-5-(trifluoromethyl)pyridin-4-yl)amino)propyl)-1,4-oxazepan-5-one, (S)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 1-methyl-3-(3-((2-((3-methyl-1-(1-methylpiperidin-4-yl)-1H-pyrazol-4-yl)amino)-5-(trifluoromethyl)pyridin-4-yl)amino)propyl)tetrahydropyrimidin-2(1H)-one, 1-methyl-3-(3-((2-((3-methyl-1-(1-methylpiperidin-4-yl)-1H-pyrazol-4-yl)amino)-5-(trifluoromethyl)pyridin-4-yl)amino)propyl)-1,3-diazepan-2-one, (R)-4-(3-((2-((3-methyl-1-(1-methylpyrrolidin-3-yl)-1H-pyrazol-4-yl)amino)-5-(trifluoromethyl)pyrimidin-4-yl)amino)propyl)-1,4-oxazepan-5-one, 4-(3-((2-((5-methyl-2-(1-methylpiperidin-4-yl) thiazol-4-yl)amino)-5-(trifluoromethyl)pyridin-4-yl)amino)propyl)-1,4-oxazepan-3-one, 4-(3-((2-((2-(1-methylpiperidin-4-yl) thiazol-4-yl)amino)-5-(trifluoromethyl)pyridin-4-yl)amino)propyl)-1,4-oxazepan-3-one, 4-(3-((2-((2-(1-methylpiperidin-4-yl) oxazol-4-yl)amino)-5-(trifluoromethyl)pyridin-4-yl)amino)propyl)-1,4-oxazepan-5-one, 4-(3-((2-((3-ethyl-1-(1-methylpiperidin-4-yl)-1H-pyrazol-4-yl)amino)-5-(trifluoromethyl)pyridin-4-yl)amino)propyl)-1,4-oxazepan-5-one, 4-(3-((5-chloro-2-((3-ethyl-1-(1-methylpiperidin-4-yl)-1H-pyrazol-4-yl)amino)pyridin-4-yl)amino)propyl)-1,4-oxazepan-5-one, 4-(3-((2-((3-methoxy-1-(1-methylpiperidin-4-yl)-1H-pyrazol-4-yl)amino)-5-(trifluoromethyl)pyridin-4-yl)amino)propyl)-1,4-oxazepan-3-one, 4-(3-((2-((1-(1-methylpiperidin-4-yl)-3-vinyl-1H-pyrazol-4-yl)amino)-5-(trifluoromethyl)pyridin-4-yl)amino)propyl)-1,4-oxazepan-5-one, 1-((3-methyl-4-((4-((3-(5-oxo-1,4-oxazepan-4-yl)propyl)amino)-5-(trifluoromethyl)pyridin-2-yl)amino)-1H-pyrazol-1-yl)methyl) cyclopropane-1-carbonitrile, 2-methyl-2-(3-methyl-4-((4-((3-(5-oxo-1,4-oxazepan-4-yl)propyl)amino)-5-(trifluoromethyl)pyridin-2-yl)amino)-1H-pyrazol-1-yl)propanenitrile, 6-((3-methyl-1-(1-methylpiperidin-4-yl)-1H-pyrazol-4-yl)amino)-4-((3-(5-oxo-1,4-oxazepan-4-yl)propyl)amino) nicotinonitrile, 4-(3-((5-cyclopropyl-2-((3-methyl-1-(1-methylpiperidin-4-yl)-1H-pyrazol-4-yl)amino)pyridin-4-yl)amino)propyl)-1,4-oxazepan-5-one, 4-(3-((2-((1-(1-ethylpiperidin-4-yl)-3-methyl-1H-pyrazol-4-yl)amino)-5-(trifluoromethyl)pyridin-4-yl)amino)propyl)-1,4-oxazepan-5-one, 1-(1-methylpiperidin-4-yl)-4-((4-((3-(5-oxo-1,4-oxazepan-4-yl)propyl)amino)-5-(trifluoromethyl)pyridin-2-yl)amino)-1H-pyrazole-3-carbonitrile, 4-(3-((2-((2-(1-methylpiperidin-4-yl)-2H-1,2,3-triazol-4-yl)amino)-5-(trifluoromethyl)pyridin-4-yl)amino)propyl)-1,4-oxazepan-3-one, 4-(3-((5-(difluoromethyl)-2-((2-(1-methylpiperidin-4-yl)-2H-1,2,3-triazol-4-yl)amino)pyridin-4-yl)amino)propyl)-1,4-oxazepan-3-one, 3-(3-((2-((2-(1-methylpiperidin-4-yl) oxazol-4-yl)amino)-5-(trifluoromethyl)pyridin-4-yl)amino)propyl)-1,3-oxazinan-2-one, 1-(3-((2-((3-methyl-1-(1-methylpiperidin-4-yl)-1H-pyrazol-4-yl)amino)-5-(trifluoromethyl)pyridin-4-yl)amino)propyl)pyrrolidin-2-one, 1-(3-((2-((3-methyl-1-(1-methylpiperidin-4-yl)-1H-pyrazol-4-yl)amino)-5-(trifluoromethyl)pyridin-4-yl)amino)propyl)piperidin-2-one, 1-(3-((2-((3-methyl-1-(1-methylpiperidin-4-yl)-1H-pyrazol-4-yl)amino)-5-(trifluoromethyl)pyridin-4-yl)amino)propyl)azetidin-2-one, 2-methyl-2-(3-methyl-4-((4-((3-(5-oxo-1,4-oxazepan-4-yl)propyl)amino)-5-(trifluoromethyl)pyridin-2-yl)amino)-1H-pyrazol-1-yl)propanamide, 1-(1-methylpiperidin-4-yl)-4-((4-((3-(3-oxo-1,4-oxazepan-4-yl)propyl)amino)-5-(trifluoromethyl)pyrimidin-2-yl)amino)-1H-pyrazole-3-carbonitrile, 4-(3-((5-(difluoromethyl)-2-((3-methyl-1-(piperidin-4-yl)-1H-pyrazol-4-yl)amino)pyrimidin-4-yl)amino)propyl)-1,4-oxazepan-5-one, 3-(3-((5-(difluoromethyl)-2-((3-methyl-1-(piperidin-4-yl)-1H-pyrazol-4-yl)amino)pyrimidin-4-yl)amino)propyl)-1,3-oxazinan-2-one, 1-methyl-4-(3-((2-((3-methyl-1-(piperidin-4-yl)-1H-pyrazol-4-yl)amino)-5-(trifluoromethyl)pyrimidin-4-yl)amino)propyl)-1,4-diazepan-5-one, and 4-methyl-1-(3-((2-((3-methyl-1-(piperidin-4-yl)-1H-pyrazol-4-yl)amino)-5-(trifluoromethyl)pyrimidin-4-yl)amino)propyl)-1,4-diazepan-2-one, or pharmaceutically acceptable salts, enantiomers, stereoisomers, or tautomers thereof.

27. The method of claim 1, wherein the cancer is pancreatic cancer, and wherein the pancreatic cancer is pancreatic ductal adenocarcinoma.

28. The method of claim 1, wherein the cancer is lung cancer, and wherein the lung cancer is non-small cell lung cancer.

29. The method of claim 3, wherein the cancer is pancreatic cancer, and wherein the pancreatic cancer is pancreatic ductal adenocarcinoma.

30. The method of claim 3, wherein the cancer is lung cancer, and wherein the lung cancer is non-small cell lung cancer.

* * * * *

SEQUENCE LISTING

```
<160> NUMBER OF SEQ ID NOS: 6

<210> SEQ ID NO 1
<211> LENGTH: 344
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Ser Tyr Tyr His His His His His His Asp Tyr Asp Ile Pro Thr
1               5                   10                  15

Thr Glu Asn Leu Tyr Phe Gln Gly Ala Met Asp Pro Phe Phe Met Glu
            20                  25                  30

Pro Gly Arg Gly Gly Thr Glu Thr Val Gly Lys Phe Glu Phe Ser Arg
        35                  40                  45

Lys Asp Leu Ile Gly His Gly Ala Phe Ala Val Val Phe Lys Gly Arg
    50                  55                  60

His Arg Glu Lys His Asp Leu Glu Val Ala Val Lys Cys Ile Asn Lys
65                  70                  75                  80

Lys Asn Leu Ala Lys Ser Gln Thr Leu Leu Gly Lys Glu Ile Lys Ile
                85                  90                  95

Leu Lys Glu Leu Lys His Glu Asn Ile Val Ala Leu Tyr Asp Phe Gln
            100                 105                 110

Glu Met Ala Asn Ser Val Tyr Leu Val Met Glu Tyr Cys Asn Gly Gly
        115                 120                 125

Asp Leu Ala Asp Tyr Leu His Ala Met Arg Thr Leu Ser Glu Asp Thr
    130                 135                 140

Ile Arg Leu Phe Leu Gln Gln Ile Ala Gly Ala Met Arg Leu Leu His
145                 150                 155                 160

Ser Lys Gly Ile Ile His Arg Asp Leu Lys Pro Gln Asn Ile Leu Leu
                165                 170                 175

Ser Asn Pro Ala Gly Arg Arg Ala Asn Pro Asn Ser Ile Arg Val Lys
            180                 185                 190

Ile Ala Asp Phe Gly Phe Ala Arg Tyr Leu Gln Ser Asn Met Met Ala
        195                 200                 205

Ala Thr Leu Cys Gly Ser Pro Met Tyr Met Ala Pro Glu Val Ile Met
    210                 215                 220

Ser Gln His Tyr Asp Gly Lys Ala Asp Leu Trp Ser Ile Gly Thr Ile
```

```
225                 230                 235                 240

Val Tyr Gln Cys Leu Thr Gly Lys Ala Pro Phe Gln Ala Ser Ser Pro
                245                 250                 255

Gln Asp Leu Arg Leu Phe Tyr Glu Lys Asn Lys Thr Leu Val Pro Thr
            260                 265                 270

Ile Pro Arg Glu Thr Ser Ala Pro Leu Arg Gln Leu Leu Leu Ala Leu
        275                 280                 285

Leu Gln Arg Asn His Lys Asp Arg Met Asp Phe Asp Glu Phe Phe His
    290                 295                 300

His Pro Phe Leu Asp Ala Ser Pro Ser Val Arg Lys Ser Pro Pro Val
305                 310                 315                 320

Pro Val Pro Ser Tyr Pro Ser Ser Gly Ser Gly Ser Ser Ser Ser Ser
                325                 330                 335

Ser Ser Thr Ser His Leu Ala Ser
            340


<210> SEQ ID NO 2
<211> LENGTH: 283
<212> TYPE: PRT
<213> ORGANISM: Unknown
<220> FEATURE:
<221> NAME/KEY: source
<223> OTHER INFORMATION: /note="Description of Unknown:
      ULK1 sequence"

<400> SEQUENCE: 2

Met Glu Pro Gly Arg Gly Gly Thr Glu Thr Val Gly Lys Phe Glu Phe
1               5                   10                  15

Ser Arg Lys Asp Leu Ile Gly His Gly Ala Phe Ala Val Val Phe Lys
            20                  25                  30

Gly Arg His Arg Ala Ala His Asp Leu Glu Val Ala Val Lys Cys Ile
        35                  40                  45

Asn Lys Lys Asn Leu Ala Lys Ser Gln Thr Leu Leu Gly Lys Glu Ile
    50                  55                  60

Lys Ile Leu Lys Glu Leu Lys His Glu Asn Ile Val Ala Leu Tyr Asp
65                  70                  75                  80

Phe Gln Glu Met Ala Asn Ser Val Tyr Leu Val Met Glu Tyr Cys Asn
                85                  90                  95

Gly Gly Asp Leu Ala Asp Tyr Leu His Ala Met Arg Thr Leu Ser Glu
            100                 105                 110

Asp Thr Ile Arg Leu Phe Leu Gln Gln Ile Ala Gly Ala Met Arg Leu
        115                 120                 125

Leu His Ser Lys Gly Ile Ile His Arg Asp Leu Lys Pro Gln Asn Ile
    130                 135                 140

Leu Leu Ser Asn Pro Ala Gly Arg Arg Ala Asn Pro Asn Ser Ile Arg
145                 150                 155                 160

Val Lys Ile Ala Asp Phe Gly Phe Ala Arg Tyr Leu Gln Ser Asn Met
                165                 170                 175

Met Ala Ala Thr Leu Cys Gly Ser Pro Met Tyr Met Ala Pro Glu Val
            180                 185                 190

Ile Met Ser Gln His Tyr Asp Gly Lys Ala Asp Leu Trp Ser Ile Gly
        195                 200                 205

Thr Ile Val Tyr Gln Cys Leu Thr Gly Lys Ala Pro Phe Gln Ala Ser
    210                 215                 220

Ser Pro Gln Asp Leu Arg Leu Phe Tyr Glu Lys Asn Lys Thr Leu Val
225                 230                 235                 240
```

```
Pro Thr Ile Pro Arg Glu Thr Ser Ala Pro Leu Arg Gln Leu Leu Leu
                245                 250                 255

Ala Leu Leu Gln Arg Asn His Lys Asp Arg Met Asp Phe Asp Glu Phe
            260                 265                 270

Phe His His Pro Phe Leu Asp Ala Ser Pro Ser
        275                 280


<210> SEQ ID NO 3
<211> LENGTH: 542
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Glu Phe Met Glu Val Val Gly Asp Phe Glu Tyr Ser
225                 230                 235                 240

Lys Arg Asp Leu Val Gly His Gly Ala Phe Ala Val Val Phe Arg Gly
                245                 250                 255

Arg His Arg Gln Lys Thr Asp Trp Glu Val Ala Ile Lys Ser Ile Asn
            260                 265                 270

Lys Lys Asn Leu Ser Lys Ser Gln Ile Leu Leu Gly Lys Glu Ile Lys
        275                 280                 285

Ile Leu Lys Glu Leu Gln His Glu Asn Ile Val Ala Leu Tyr Asp Val
    290                 295                 300
```

```
Gln Glu Leu Pro Asn Ser Val Phe Leu Val Met Glu Tyr Cys Asn Gly
305                 310                 315                 320

Gly Asp Leu Ala Asp Tyr Leu Gln Ala Lys Gly Thr Leu Ser Glu Asp
                325                 330                 335

Thr Ile Arg Val Phe Leu His Gln Ile Ala Ala Ala Met Arg Ile Leu
            340                 345                 350

His Ser Lys Gly Ile Ile His Arg Asp Leu Lys Pro Gln Asn Ile Leu
        355                 360                 365

Leu Ser Tyr Ala Asn Arg Arg Lys Ser Ser Val Ser Gly Ile Arg Ile
    370                 375                 380

Lys Ile Ala Asp Phe Gly Phe Ala Arg Tyr Leu His Ser Asn Met Met
385                 390                 395                 400

Ala Ala Thr Leu Cys Gly Ser Pro Met Tyr Met Ala Pro Glu Val Ile
                405                 410                 415

Met Ser Gln His Tyr Asp Ala Lys Ala Asp Leu Trp Ser Ile Gly Thr
            420                 425                 430

Val Ile Tyr Gln Cys Leu Val Gly Lys Pro Pro Phe Gln Ala Asn Ser
        435                 440                 445

Pro Gln Asp Leu Arg Met Phe Tyr Glu Lys Asn Arg Ser Leu Met Pro
    450                 455                 460

Ser Ile Pro Arg Glu Thr Ser Pro Tyr Leu Ala Asn Leu Leu Leu Gly
465                 470                 475                 480

Leu Leu Gln Arg Asn Gln Lys Asp Arg Met Asp Phe Glu Ala Phe Phe
                485                 490                 495

Ser His Pro Phe Leu Glu Gln Gly Pro Val Lys Lys Ser Cys Pro Val
            500                 505                 510

Pro Val Pro Met Tyr Ser Gly Ser Val Ser Gly Ser Ser Cys Gly Ser
        515                 520                 525

Ser Pro Ser Cys Arg Phe Ala Ser His His His His His His
    530                 535                 540
```

<210> SEQ ID NO 4
<211> LENGTH: 1795
<212> TYPE: PRT
<213> ORGANISM: Unknown
<220> FEATURE:
<221> NAME/KEY: source
<223> OTHER INFORMATION: /note="Description of Unknown: LRRK2 sequence"

<400> SEQUENCE: 4

```
Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
```

```
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

His Asn Gln Thr Ser Leu Tyr Lys Lys Ala Gly Thr Met His Ser Asp
225                 230                 235                 240

Ser Ile Ser Ser Leu Ala Ser Glu Arg Glu Tyr Ile Thr Ser Leu Asp
                245                 250                 255

Leu Ser Ala Asn Glu Leu Arg Asp Ile Asp Ala Leu Ser Gln Lys Cys
            260                 265                 270

Cys Ile Ser Val His Leu Glu His Leu Glu Lys Leu Glu Leu His Gln
        275                 280                 285

Asn Ala Leu Thr Ser Phe Pro Gln Gln Leu Cys Glu Thr Leu Lys Ser
    290                 295                 300

Leu Thr His Leu Asp Leu His Ser Asn Lys Phe Thr Ser Phe Pro Ser
305                 310                 315                 320

Tyr Leu Leu Lys Met Ser Cys Ile Ala Asn Leu Asp Val Ser Arg Asn
                325                 330                 335

Asp Ile Gly Pro Ser Val Val Leu Asp Pro Thr Val Lys Cys Pro Thr
            340                 345                 350

Leu Lys Gln Phe Asn Leu Ser Tyr Asn Gln Leu Ser Phe Val Pro Glu
        355                 360                 365

Asn Leu Thr Asp Val Val Glu Lys Leu Glu Gln Leu Ile Leu Glu Gly
    370                 375                 380

Asn Lys Ile Ser Gly Ile Cys Ser Pro Leu Arg Leu Lys Glu Leu Lys
385                 390                 395                 400

Ile Leu Asn Leu Ser Lys Asn His Ile Ser Ser Leu Ser Glu Asn Phe
                405                 410                 415

Leu Glu Ala Cys Pro Lys Val Glu Ser Phe Ser Ala Arg Met Asn Phe
            420                 425                 430

Leu Ala Ala Met Pro Phe Leu Pro Pro Ser Met Thr Ile Leu Lys Leu
        435                 440                 445

Ser Gln Asn Lys Phe Ser Cys Ile Pro Glu Ala Ile Leu Asn Leu Pro
    450                 455                 460

His Leu Arg Ser Leu Asp Met Ser Ser Asn Asp Ile Gln Tyr Leu Pro
465                 470                 475                 480

Gly Pro Ala His Trp Lys Ser Leu Asn Leu Arg Glu Leu Leu Phe Ser
                485                 490                 495

His Asn Gln Ile Ser Ile Leu Asp Leu Ser Glu Lys Ala Tyr Leu Trp
            500                 505                 510

Ser Arg Val Glu Lys Leu His Leu Ser His Asn Lys Leu Lys Glu Ile
        515                 520                 525

Pro Pro Glu Ile Gly Cys Leu Glu Asn Leu Thr Ser Leu Asp Val Ser
    530                 535                 540
```

-continued

Tyr Asn Leu Glu Leu Arg Ser Phe Pro Asn Glu Met Gly Lys Leu Ser
545 550 555 560

Lys Ile Trp Asp Leu Pro Leu Asp Glu Leu His Leu Asn Phe Asp Phe
565 570 575

Lys His Ile Gly Cys Lys Ala Lys Asp Ile Ile Arg Phe Leu Gln Gln
580 585 590

Arg Leu Lys Lys Ala Val Pro Tyr Asn Arg Met Lys Leu Met Ile Val
595 600 605

Gly Asn Thr Gly Ser Gly Lys Thr Thr Leu Leu Gln Gln Leu Met Lys
610 615 620

Thr Lys Lys Ser Asp Leu Gly Met Gln Ser Ala Thr Val Gly Ile Asp
625 630 635 640

Val Lys Asp Trp Pro Ile Gln Ile Arg Asp Lys Arg Lys Arg Asp Leu
645 650 655

Val Leu Asn Val Trp Asp Phe Ala Gly Arg Glu Glu Phe Tyr Ser Thr
660 665 670

His Pro His Phe Met Thr Gln Arg Ala Leu Tyr Leu Ala Val Tyr Asp
675 680 685

Leu Ser Lys Gly Gln Ala Glu Val Asp Ala Met Lys Pro Trp Leu Phe
690 695 700

Asn Ile Lys Ala Arg Ala Ser Ser Ser Pro Val Ile Leu Val Gly Thr
705 710 715 720

His Leu Asp Val Ser Asp Glu Lys Gln Arg Lys Ala Cys Met Ser Lys
725 730 735

Ile Thr Lys Glu Leu Leu Asn Lys Arg Gly Phe Pro Ala Ile Arg Asp
740 745 750

Tyr His Phe Val Asn Ala Thr Glu Glu Ser Asp Ala Leu Ala Lys Leu
755 760 765

Arg Lys Thr Ile Ile Asn Glu Ser Leu Asn Phe Lys Ile Arg Asp Gln
770 775 780

Leu Val Val Gly Gln Leu Ile Pro Asp Cys Tyr Val Glu Leu Glu Lys
785 790 795 800

Ile Ile Leu Ser Glu Arg Lys Asn Val Pro Ile Glu Phe Pro Val Ile
805 810 815

Asp Arg Lys Arg Leu Leu Gln Leu Val Arg Glu Asn Gln Leu Gln Leu
820 825 830

Asp Glu Asn Glu Leu Pro His Ala Val His Phe Leu Asn Glu Ser Gly
835 840 845

Val Leu Leu His Phe Gln Asp Pro Ala Leu Gln Leu Ser Asp Leu Tyr
850 855 860

Phe Val Glu Pro Lys Trp Leu Cys Lys Ile Met Ala Gln Ile Leu Thr
865 870 875 880

Val Lys Val Glu Gly Cys Pro Lys His Pro Lys Gly Ile Ile Ser Arg
885 890 895

Arg Asp Val Glu Lys Phe Leu Ser Lys Lys Arg Lys Phe Pro Lys Asn
900 905 910

Tyr Met Ser Gln Tyr Phe Lys Leu Leu Glu Lys Phe Gln Ile Ala Leu
915 920 925

Pro Ile Gly Glu Glu Tyr Leu Leu Val Pro Ser Ser Leu Ser Asp His
930 935 940

Arg Pro Val Ile Glu Leu Pro His Cys Glu Asn Ser Glu Ile Ile Ile
945 950 955 960

```
Arg Leu Tyr Glu Met Pro Tyr Phe Pro Met Gly Phe Trp Ser Arg Leu
                965                 970                 975

Ile Asn Arg Leu Leu Glu Ile Ser Pro Tyr Met Leu Ser Gly Arg Glu
            980                 985                 990

Arg Ala Leu Arg Pro Asn Arg Met  Tyr Trp Arg Gln Gly  Ile Tyr Leu
        995                 1000                 1005

Asn Trp  Ser Pro Glu Ala Tyr  Cys Leu Val Gly Ser  Glu Val Leu
    1010                 1015                 1020

Asp Asn  His Pro Glu Ser Phe  Leu Lys Ile Thr Val  Pro Ser Cys
    1025                 1030                 1035

Arg Lys  Gly Cys Ile Leu Leu  Gly Gln Val Val Asp  His Ile Asp
    1040                 1045                 1050

Ser Leu  Met Glu Glu Trp Phe  Pro Gly Leu Leu Glu  Ile Asp Ile
    1055                 1060                 1065

Cys Gly  Glu Gly Glu Thr Leu  Leu Lys Lys Trp Ala  Leu Tyr Ser
    1070                 1075                 1080

Phe Asn  Asp Gly Glu Glu His  Gln Lys Ile Leu Leu  Asp Asp Leu
    1085                 1090                 1095

Met Lys  Lys Ala Glu Glu Gly  Asp Leu Leu Val Asn  Pro Asp Gln
    1100                 1105                 1110

Pro Arg  Leu Thr Ile Pro Ile  Ser Gln Ile Ala Pro  Asp Leu Ile
    1115                 1120                 1125

Leu Ala  Asp Leu Pro Arg Asn  Ile Met Leu Asn Asn  Asp Glu Leu
    1130                 1135                 1140

Glu Phe  Glu Gln Ala Pro Glu  Phe Leu Leu Gly Asp  Gly Ser Phe
    1145                 1150                 1155

Gly Ser  Val Tyr Arg Ala Ala  Tyr Glu Gly Glu Glu  Val Ala Val
    1160                 1165                 1170

Lys Ile  Phe Asn Lys His Thr  Ser Leu Arg Leu Leu  Arg Gln Glu
    1175                 1180                 1185

Leu Val  Val Leu Cys His Leu  His His Pro Ser Leu  Ile Ser Leu
    1190                 1195                 1200

Leu Ala  Ala Gly Ile Arg Pro  Arg Met Leu Val Met  Glu Leu Ala
    1205                 1210                 1215

Ser Lys  Gly Ser Leu Asp Arg  Leu Leu Gln Gln Asp  Lys Ala Ser
    1220                 1225                 1230

Leu Thr  Arg Thr Leu Gln His  Arg Ile Ala Leu His  Val Ala Asp
    1235                 1240                 1245

Gly Leu  Arg Tyr Leu His Ser  Ala Met Ile Ile Tyr  Arg Asp Leu
    1250                 1255                 1260

Lys Pro  His Asn Val Leu Leu  Phe Thr Leu Tyr Pro  Asn Ala Ala
    1265                 1270                 1275

Ile Ile  Ala Lys Ile Ala Asp  Tyr Gly Ile Ala Gln  Tyr Cys Cys
    1280                 1285                 1290

Arg Met  Gly Ile Lys Thr Ser  Glu Gly Thr Pro Gly  Phe Arg Ala
    1295                 1300                 1305

Pro Glu  Val Ala Arg Gly Asn  Val Ile Tyr Asn Gln  Gln Ala Asp
    1310                 1315                 1320

Val Tyr  Ser Phe Gly Leu Leu  Leu Tyr Asp Ile Leu  Thr Thr Gly
    1325                 1330                 1335

Gly Arg  Ile Val Glu Gly Leu  Lys Phe Pro Asn Glu  Phe Asp Glu
    1340                 1345                 1350

Leu Glu  Ile Gln Gly Lys Leu  Pro Asp Pro Val Lys  Glu Tyr Gly
```

```
    1355                1360                1365

Cys Ala  Pro Trp Pro Met Val  Glu Lys Leu Ile Lys  Gln Cys Leu
    1370                1375                1380

Lys Glu  Asn Pro Gln Glu Arg  Pro Thr Ser Ala Gln  Val Phe Asp
    1385                1390                1395

Ile Leu  Asn Ser Ala Glu Leu  Val Cys Leu Thr Arg  Arg Ile Leu
    1400                1405                1410

Leu Pro  Lys Asn Val Ile Val  Glu Cys Met Val Ala  Thr His His
    1415                1420                1425

Asn Ser  Arg Asn Ala Ser Ile  Trp Leu Gly Cys Gly  His Thr Asp
    1430                1435                1440

Arg Gly  Gln Leu Ser Phe Leu  Asp Leu Asn Thr Glu  Gly Tyr Thr
    1445                1450                1455

Ser Glu  Glu Val Ala Asp Ser  Arg Ile Leu Cys Leu  Ala Leu Val
    1460                1465                1470

His Leu  Pro Val Glu Lys Glu  Ser Trp Ile Val Ser  Gly Thr Gln
    1475                1480                1485

Ser Gly  Thr Leu Leu Val Ile  Asn Thr Glu Asp Gly  Lys Lys Arg
    1490                1495                1500

His Thr  Leu Glu Lys Met Thr  Asp Ser Val Thr Cys  Leu Tyr Cys
    1505                1510                1515

Asn Ser  Phe Ser Lys Gln Ser  Lys Gln Lys Asn Phe  Leu Leu Val
    1520                1525                1530

Gly Thr  Ala Asp Gly Lys Leu  Ala Ile Phe Glu Asp  Lys Thr Val
    1535                1540                1545

Lys Leu  Lys Gly Ala Ala Pro  Leu Lys Ile Leu Asn  Ile Gly Asn
    1550                1555                1560

Val Ser  Thr Pro Leu Met Cys  Leu Ser Glu Ser Thr  Asn Ser Thr
    1565                1570                1575

Glu Arg  Asn Val Met Trp Gly  Gly Cys Gly Thr Lys  Ile Phe Ser
    1580                1585                1590

Phe Ser  Asn Asp Phe Thr Ile  Gln Lys Leu Ile Glu  Thr Arg Thr
    1595                1600                1605

Ser Gln  Leu Phe Ser Tyr Ala  Ala Phe Ser Asp Ser  Asn Ile Ile
    1610                1615                1620

Thr Val  Val Val Asp Thr Ala  Leu Tyr Ile Ala Lys  Gln Asn Ser
    1625                1630                1635

Pro Val  Val Glu Val Trp Asp  Lys Lys Thr Glu Lys  Leu Cys Gly
    1640                1645                1650

Leu Ile  Asp Cys Val His Phe  Leu Arg Glu Val Met  Val Lys Glu
    1655                1660                1665

Asn Lys  Glu Ser Lys His Lys  Met Ser Tyr Ser Gly  Arg Val Lys
    1670                1675                1680

Thr Leu  Cys Leu Gln Lys Asn  Thr Ala Leu Trp Ile  Gly Thr Gly
    1685                1690                1695

Gly Gly  His Ile Leu Leu Leu  Asp Leu Ser Thr Arg  Arg Leu Ile
    1700                1705                1710

Arg Val  Ile Tyr Asn Phe Cys  Asn Ser Val Arg Val  Met Met Thr
    1715                1720                1725

Ala Gln  Leu Gly Ser Leu Lys  Asn Val Met Leu Val  Leu Gly Tyr
    1730                1735                1740

Asn Arg  Lys Asn Thr Glu Gly  Thr Gln Lys Gln Lys  Glu Ile Gln
    1745                1750                1755
```

-continued

```
Ser Cys  Leu Thr Val Trp Asp  Ile Asn Leu Pro His  Glu Val Gln
    1760                 1765                 1770

Asn Leu  Glu Lys His Ile Glu  Val Arg Lys Glu Leu  Ala Glu Lys
    1775                 1780                 1785

Met Arg  Arg Thr Ser Val Glu
    1790                 1795


<210> SEQ ID NO 5
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Ala Asn Trp Leu Ala Ala Ser Ile Tyr Leu Asp Gly Lys Lys Lys
1               5                   10                  15


<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Leu Gly Arg Asp Lys Tyr Lys Thr Leu Arg Gln Ile Arg Gln
1               5                   10                  15
```